US012758150B2

(12) United States Patent
Rao et al.

(10) Patent No.: US 12,758,150 B2
(45) Date of Patent: Oct. 13, 2026

(54) SYSTEMS, DEVICES, AND METHODS FOR ANALYTE MONITORING

(71) Applicant: ABBOTT DIABETES CARE INC., Alameda, CA (US)

(72) Inventors: Vivek S. Rao, Alameda, CA (US); Matthew Simmons, Pleasanton, CA (US); Louis G. Pace, San Carlos, CA (US); Jean-Pierre Cole, Tracy, CA (US); Peter G. Robinson, Alamo, CA (US); Peter Voit, Dublin, CA (US); Steven T. Mitchell, Pleasant Hill, CA (US)

(73) Assignee: ABBOTT DIABETES CARE INC., Alameda, CA (US)

( * ) Notice: Subject to any disclaimer, the term of this patent is extended or adjusted under 35 U.S.C. 154(b) by 828 days.

(21) Appl. No.: 17/477,053

(22) Filed: Sep. 16, 2021

(65) Prior Publication Data

US 2022/0202367 A1 Jun. 30, 2022

Related U.S. Application Data

(60) Provisional application No. 63/132,651, filed on Dec. 31, 2020.

(51) Int. Cl.
*A61B 5/145* (2006.01)
*A61B 5/00* (2006.01)

(52) U.S. Cl.
CPC ........ *A61B 5/6849* (2013.01); *A61B 5/14503* (2013.01)

(58) Field of Classification Search
CPC ... A61B 5/145; A61B 5/14503; A61B 5/6849; A61B 5/14532
See application file for complete search history.

(56) References Cited

U.S. PATENT DOCUMENTS 2,402,306 A 6/1946 Turkel
2,752,918 A 7/1956 Uytenbogaart
(Continued)

FOREIGN PATENT DOCUMENTS

AU 2003259741 2/2004
CA 2291105 12/1998
(Continued)

OTHER PUBLICATIONS

Inter Partes Review of U.S. Pat. No. 10,945,649, Case No. IPR2022-00605.

(Continued)

*Primary Examiner* — Alex M Valvis
(74) *Attorney, Agent, or Firm* — ONE LLP

(57) ABSTRACT

An analyte measurement device including an electronics housing including a shell having an upper surface with a first aperture defined therein; a mount mated to the shell and having an underside with a second aperture defined therein aligned with the first aperture; a collar disposed between the shell and the mount and including: a third aperture aligned with the first aperture and the second aperture, and a plurality of tabs on an outer periphery of the collar; a circuit board disposed within the electronics housing and including a plurality of electronic modules, wherein the circuit board is mounted within the electronics housing on the plurality of tabs on the outer periphery; and an analyte sensor including a tail portion extending through the first aperture and the second aperture and configured to measure an analyte level and a flag portion including a plurality of electrical contacts coupled with the circuit board, and a neck portion interconnecting the tail portion and the flag portion. An assembly for delivery of an analyte sensor is also disclosed.

20 Claims, 101 Drawing Sheets

(56) References Cited

U.S. PATENT DOCUMENTS

| | | | |
|---|---|---|---|
| 3,123,790 | A | 3/1964 | Tyler |
| 3,132,123 | A | 5/1964 | Harris, Jr. et al. |
| 3,173,200 | A | 3/1965 | Dunmire et al. |
| 3,211,001 | A | 10/1965 | Petit |
| 3,260,656 | A | 7/1966 | Ross, Jr. |
| 3,517,670 | A | 6/1970 | Speelman |
| 3,522,807 | A | 8/1970 | Millenbach |
| 3,581,062 | A | 5/1971 | Aston |
| 3,653,841 | A | 4/1972 | Klein |
| 3,670,727 | A | 6/1972 | Reiterman |
| 3,719,564 | A | 3/1973 | Lilly, Jr. et al. |
| 3,776,832 | A | 12/1973 | Oswin et al. |
| 3,837,339 | A | 9/1974 | Aisenberg et al. |
| 3,926,760 | A | 12/1975 | Allen et al. |
| 3,949,388 | A | 4/1976 | Fuller |
| 3,960,497 | A | 6/1976 | Acord et al. |
| 3,972,320 | A | 8/1976 | Kalman |
| 3,979,274 | A | 9/1976 | Newman |
| 4,008,717 | A | 2/1977 | Kowarski |
| 4,016,866 | A | 4/1977 | Lawton |
| 4,033,330 | A | 7/1977 | Willis et al. |
| 4,036,749 | A | 7/1977 | Anderson |
| 4,055,175 | A | 10/1977 | Clemens et al. |
| 4,059,406 | A | 11/1977 | Fleet |
| 4,076,596 | A | 2/1978 | Connery et al. |
| 4,098,574 | A | 7/1978 | Dappen |
| 4,100,048 | A | 7/1978 | Pompei et al. |
| 4,120,292 | A | 10/1978 | LeBlanc, Jr. et al. |
| 4,129,128 | A | 12/1978 | McFarlane |
| 4,151,845 | A | 5/1979 | Clemens |
| 4,168,205 | A | 9/1979 | Danninger et al. |
| 4,172,770 | A | 10/1979 | Semersky et al. |
| 4,178,916 | A | 12/1979 | McNamara |
| 4,203,446 | A | 5/1980 | Hofert et al. |
| 4,206,755 | A | 6/1980 | Klein |
| 4,224,125 | A | 9/1980 | Nakamura et al. |
| 4,240,438 | A | 12/1980 | Updike et al. |
| 4,240,889 | A | 12/1980 | Yoda et al. |
| 4,245,634 | A | 1/1981 | Albisser et al. |
| 4,247,297 | A | 1/1981 | Berti et al. |
| 4,294,258 | A | 10/1981 | Bernard |
| 4,305,401 | A | 12/1981 | Reissmueller et al. |
| 4,308,981 | A | 1/1982 | Miura |
| 4,327,725 | A | 5/1982 | Cortese et al. |
| 4,340,458 | A | 7/1982 | Lerner et al. |
| 4,344,438 | A | 8/1982 | Schultz |
| 4,349,728 | A | 9/1982 | Phillips et al. |
| 4,352,960 | A | 10/1982 | Dormer et al. |
| 4,353,888 | A | 10/1982 | Sefton |
| 4,356,074 | A | 10/1982 | Johnson |
| 4,365,637 | A | 12/1982 | Johnson |
| 4,366,033 | A | 12/1982 | Richter et al. |
| 4,373,527 | A | 2/1983 | Fischell |
| 4,375,399 | A | 3/1983 | Havas et al. |
| 4,384,586 | A | 5/1983 | Christiansen |
| 4,390,621 | A | 6/1983 | Bauer |
| 4,392,849 | A | 7/1983 | Petre et al. |
| 4,401,122 | A | 8/1983 | Clark, Jr. |
| 4,404,066 | A | 9/1983 | Johnson |
| 4,418,148 | A | 11/1983 | Oberhardt |
| 4,425,920 | A | 1/1984 | Bourland et al. |
| 4,427,004 | A | 1/1984 | Miller et al. |
| 4,427,770 | A | 1/1984 | Chen et al. |
| 4,431,004 | A | 2/1984 | Bessman et al. |
| 4,436,094 | A | 3/1984 | Cerami |
| 4,440,175 | A | 4/1984 | Wilkins |
| 4,441,968 | A | 4/1984 | Emmer et al. |
| 4,450,842 | A | 5/1984 | Zick et al. |
| 4,458,686 | A | 7/1984 | Clark, Jr. |
| 4,461,691 | A | 7/1984 | Frank |
| 4,464,170 | A | 8/1984 | Clemens et al. |
| 4,469,110 | A | 9/1984 | Slama |
| 4,477,314 | A | 10/1984 | Richter et al. |
| 4,478,976 | A | 10/1984 | Goertz et al. |
| 4,484,987 | A | 11/1984 | Gough |
| 4,494,950 | A | 1/1985 | Fischell |
| 4,509,531 | A | 4/1985 | Ward |
| 4,522,690 | A | 6/1985 | Venkatasetty |
| 4,524,114 | A | 6/1985 | Samuels et al. |
| 4,526,661 | A | 7/1985 | Steckhan et al. |
| 4,527,240 | A | 7/1985 | Kvitash |
| 4,534,356 | A | 8/1985 | Papadakis |
| 4,538,616 | A | 9/1985 | Rogoff |
| 4,543,955 | A | 10/1985 | Schroeppel |
| 4,545,382 | A | 10/1985 | Higgins et al. |
| 4,552,840 | A | 11/1985 | Riffer |
| 4,553,541 | A | 11/1985 | Burns |
| 4,560,534 | A | 12/1985 | Kung et al. |
| 4,571,292 | A | 2/1986 | Liu et al. |
| 4,573,994 | A | 3/1986 | Fischell et al. |
| 4,581,336 | A | 4/1986 | Malloy et al. |
| 4,592,745 | A | 6/1986 | Rex et al. |
| 4,595,011 | A | 6/1986 | Phillips |
| 4,619,754 | A | 10/1986 | Niki et al. |
| 4,619,793 | A | 10/1986 | Lee |
| 4,622,966 | A | 11/1986 | Beard |
| 4,627,445 | A | 12/1986 | Garcia et al. |
| 4,627,842 | A | 12/1986 | Katz |
| 4,627,908 | A | 12/1986 | Miller |
| 4,633,878 | A | 1/1987 | Bombardieri |
| 4,637,403 | A | 1/1987 | Garcia et al. |
| 4,639,062 | A | 1/1987 | Taniguchi et al. |
| 4,650,547 | A | 3/1987 | Gough |
| 4,654,197 | A | 3/1987 | Lilja et al. |
| 4,655,880 | A | 4/1987 | Liu |
| 4,655,885 | A | 4/1987 | Hill et al. |
| 4,663,824 | A | 5/1987 | Kenmochi |
| 4,665,906 | A | 5/1987 | Jervis |
| 4,671,288 | A | 6/1987 | Gough |
| 4,675,346 | A | 6/1987 | Lin et al. |
| 4,679,562 | A | 7/1987 | Luksha |
| 4,680,268 | A | 7/1987 | Clark, Jr. |
| 4,682,602 | A | 7/1987 | Prohaska |
| 4,684,245 | A | 8/1987 | Goldring |
| 4,684,537 | A | 8/1987 | Graetzel et al. |
| 4,685,463 | A | 8/1987 | Williams |
| 4,685,466 | A | 8/1987 | Rau |
| 4,690,675 | A | 9/1987 | Katz |
| 4,698,057 | A | 10/1987 | Joishy |
| 4,703,324 | A | 10/1987 | White |
| 4,703,756 | A | 11/1987 | Gough et al. |
| 4,711,245 | A | 12/1987 | Higgins et al. |
| 4,711,247 | A | 12/1987 | Fishman |
| 4,717,673 | A | 1/1988 | Wrighton et al. |
| 4,721,601 | A | 1/1988 | Wrighton et al. |
| 4,721,677 | A | 1/1988 | Clark, Jr. |
| 4,726,378 | A | 2/1988 | Kaplan |
| 4,726,716 | A | 2/1988 | McGuire |
| 4,729,672 | A | 3/1988 | Takagi |
| 4,731,726 | A | 3/1988 | Allen, III |
| 4,749,985 | A | 6/1988 | Corsberg |
| 4,755,173 | A | 7/1988 | Konopka |
| 4,757,022 | A | 7/1988 | Shults et al. |
| 4,758,323 | A | 7/1988 | Davis et al. |
| 4,759,371 | A | 7/1988 | Franetzki |
| 4,759,828 | A | 7/1988 | Young et al. |
| 4,764,416 | A | 8/1988 | Ueyama et al. |
| 4,776,944 | A | 10/1988 | Janata et al. |
| 4,777,953 | A | 10/1988 | Ash et al. |
| 4,779,618 | A | 10/1988 | Mund et al. |
| 4,781,683 | A | 11/1988 | Wozniak et al. |
| 4,781,798 | A | 11/1988 | Gough |
| 4,784,736 | A | 11/1988 | Lonsdale et al. |
| 4,785,868 | A | 11/1988 | Koenig, Jr. |
| 4,795,707 | A | 1/1989 | Niiyama et al. |
| 4,796,634 | A | 1/1989 | Huntsman et al. |
| 4,805,624 | A | 2/1989 | Yao et al. |
| 4,813,424 | A | 3/1989 | Wilkins |
| 4,815,469 | A | 3/1989 | Cohen et al. |
| 4,817,603 | A | 4/1989 | Turner et al. |
| 4,818,994 | A | 4/1989 | Orth et al. |
| 4,820,399 | A | 4/1989 | Senda et al. |
| 4,822,337 | A | 4/1989 | Newhouse et al. |
| 4,830,959 | A | 5/1989 | McNeil et al. |

(56) References Cited

U.S. PATENT DOCUMENTS 4,832,797 A 5/1989 Vadgama et al.
RE32,947 E 6/1989 Dormer et al.
4,840,893 A 6/1989 Hill et al.
4,847,785 A 7/1989 Stephens
4,848,351 A 7/1989 Finch
4,852,025 A 7/1989 Herpichböhm
4,854,322 A 8/1989 Ash et al.
4,856,648 A 8/1989 Krueger
4,865,038 A 9/1989 Rich et al.
4,871,351 A 10/1989 Feingold
4,871,440 A 10/1989 Nagata et al.
4,874,500 A 10/1989 Madou et al.
4,890,620 A 1/1990 Gough
4,894,137 A 1/1990 Takizawa et al.
4,895,147 A 1/1990 Bodicky et al.
4,897,162 A 1/1990 Lewandowski et al.
4,897,173 A 1/1990 Nankai et al.
4,909,908 A 3/1990 Ross et al.
4,911,794 A 3/1990 Parce et al.
4,917,800 A 4/1990 Lonsdale et al.
4,919,141 A 4/1990 Zier et al.
4,919,767 A 4/1990 Vadgama et al.
4,921,199 A 5/1990 Villaveces
4,923,586 A 5/1990 Katayama et al.
4,924,879 A 5/1990 O'Brien
4,925,268 A 5/1990 Iyer et al.
4,927,516 A 5/1990 Yamaguchi et al.
4,934,369 A 6/1990 Maxwell
4,935,105 A 6/1990 Churchouse
4,935,345 A 6/1990 Guibeau et al.
4,938,860 A 7/1990 Wogoman
4,944,299 A 7/1990 Silvian
4,950,378 A 8/1990 Nagara
4,953,552 A 9/1990 DeMarzo
4,954,129 A 9/1990 Giuliani et al.
4,969,468 A 11/1990 Byers et al.
4,970,145 A 11/1990 Bennetto et al.
4,974,929 A 12/1990 Curry
4,985,142 A 1/1991 Laycock et al.
4,986,271 A 1/1991 Wilkins
4,988,341 A 1/1991 Columbus et al.
4,994,167 A 2/1991 Shults et al.
4,995,402 A 2/1991 Smith et al.
5,000,180 A 3/1991 Kuypers et al.
5,001,054 A 3/1991 Wagner
5,002,054 A 3/1991 Ash et al.
5,006,110 A 4/1991 Garrison et al.
5,013,161 A 5/1991 Zaragoza et al.
5,019,974 A 5/1991 Beckers
5,035,860 A 7/1991 Kleingeld et al.
5,036,860 A 8/1991 Leigh et al.
5,047,044 A 9/1991 Smith et al.
5,050,612 A 9/1991 Matsumura
5,051,688 A 9/1991 Murase et al.
5,055,171 A 10/1991 Peck
5,058,592 A 10/1991 Whisler
5,067,957 A 11/1991 Jervis
5,068,536 A 11/1991 Rosenthal
5,070,535 A 12/1991 Hochmair et al.
5,082,550 A 1/1992 Rishpon et al.
5,082,786 A 1/1992 Nakamoto
5,086,246 A 2/1992 Dymond et al.
5,089,112 A 2/1992 Skotheim et al.
5,095,904 A 3/1992 Seligman et al.
5,101,814 A 4/1992 Palti
5,106,365 A 4/1992 Hernandez
5,108,564 A 4/1992 Szuminsky et al.
5,108,889 A 4/1992 Smith et al.
5,109,850 A 5/1992 Blanco et al.
5,120,420 A 6/1992 Nankai et al.
5,122,925 A 6/1992 Inpyn
5,124,661 A 6/1992 Zellin et al.
5,126,034 A 6/1992 Carter et al.
5,133,856 A 7/1992 Yamaguchi et al.
5,135,003 A 8/1992 Souma
5,135,004 A 8/1992 Adams et al.
5,140,985 A 8/1992 Schroeder et al.
5,141,868 A 8/1992 Shanks et al.
5,161,532 A 11/1992 Joseph
5,162,407 A 11/1992 Turner
5,165,407 A 11/1992 Wilson et al.
5,173,165 A 12/1992 Schmid et al.
5,174,291 A 12/1992 Schoonen et al.
5,190,041 A 3/1993 Palti
5,190,546 A 3/1993 Jervis
5,192,416 A 3/1993 Wang et al.
5,193,545 A 3/1993 Marsoner et al.
5,198,367 A 3/1993 Aizawa et al.
5,202,261 A 4/1993 Musho et al.
5,204,264 A 4/1993 Kaminer et al.
5,205,297 A 4/1993 Montecalvo et al.
5,205,920 A 4/1993 Oyama et al.
5,208,154 A 5/1993 Weaver et al.
5,209,229 A 5/1993 Gilli
5,217,595 A 6/1993 Smith et al.
5,228,449 A 7/1993 Christ et al.
5,229,282 A 7/1993 Yoshioka et al.
5,231,988 A 8/1993 Wernicke et al.
5,234,835 A 8/1993 Nestor et al.
5,238,729 A 8/1993 Debe
5,243,696 A 9/1993 Carr et al.
5,245,314 A 9/1993 Kah et al.
5,246,867 A 9/1993 Lakowicz et al.
5,250,439 A 10/1993 Musho et al.
5,251,126 A 10/1993 Kahn et al.
5,262,035 A 11/1993 Gregg et al.
5,262,305 A 11/1993 Heller et al.
5,264,103 A 11/1993 Yoshioka et al.
5,264,104 A 11/1993 Gregg et al.
5,264,105 A 11/1993 Gregg et al.
5,264,106 A 11/1993 McAleer et al.
5,267,963 A 12/1993 Bachynsky
5,271,815 A 12/1993 Wong
5,279,294 A 1/1994 Anderson
5,284,156 A 2/1994 Schramm et al.
5,285,792 A 2/1994 Sjoquist et al.
5,286,362 A 2/1994 Hoenes et al.
5,286,364 A 2/1994 Yacynych et al.
5,288,636 A 2/1994 Pollmann et al.
5,289,497 A 2/1994 Jackobson et al.
5,293,546 A 3/1994 Tadros et al.
5,293,877 A 3/1994 O'Hara et al.
5,299,571 A 4/1994 Mastrototaro
5,305,008 A 4/1994 Turner et al.
5,318,583 A 6/1994 Rabenau et al.
5,320,098 A 6/1994 Davidson
5,320,715 A 6/1994 Berg
5,320,725 A 6/1994 Gregg et al.
5,322,063 A 6/1994 Allen et al.
5,333,615 A 8/1994 Craelius et al.
5,337,747 A 8/1994 Neftel
5,340,722 A 8/1994 Wolfbeis et al.
5,342,789 A 8/1994 Chick et al.
5,352,348 A 10/1994 Young et al.
5,356,420 A 10/1994 Czernecki et al.
5,356,786 A 10/1994 Heller et al.
5,360,404 A 11/1994 Novacek et al.
5,368,028 A 11/1994 Palti
5,372,133 A 12/1994 Hogen Esch
5,372,427 A 12/1994 Padovani et al.
5,376,251 A 12/1994 Kaneko et al.
5,378,628 A 1/1995 Gratzel et al.
5,379,238 A 1/1995 Stark
5,384,547 A 1/1995 Lynk et al.
5,387,327 A 2/1995 Khan
5,390,670 A 2/1995 Centa et al.
5,390,671 A 2/1995 Lord et al.
5,391,250 A 2/1995 Cheney, II et al.
5,394,877 A 3/1995 Orr et al.
5,395,504 A 3/1995 Saurer et al.
5,400,782 A 3/1995 Beaubiah
5,400,794 A 3/1995 Gorman
5,402,780 A 4/1995 Faasse, Jr.
5,407,431 A 4/1995 Botich et al.

(56) References Cited

U.S. PATENT DOCUMENTS 5,408,999 A 4/1995 Singh et al.
5,410,326 A 4/1995 Goldstein
5,411,647 A 5/1995 Johnson et al.
5,425,361 A 6/1995 Fenzlein et al.
5,425,868 A 6/1995 Pedersen
5,431,160 A 7/1995 Wilkins
5,431,921 A 7/1995 Thombre
5,437,999 A 8/1995 Diebold et al.
5,438,983 A 8/1995 Falcone
5,462,051 A 10/1995 Oka et al.
5,462,645 A 10/1995 Albery et al.
5,469,846 A 11/1995 Khan
5,472,317 A 12/1995 Field et al.
5,482,473 A 1/1996 Lord et al.
5,484,403 A 1/1996 Yoakum et al.
5,489,414 A 2/1996 Schreiber et al.
5,491,474 A 2/1996 Suni et al.
5,494,562 A 2/1996 Maley et al.
5,496,453 A 3/1996 Uenoyama et al.
5,497,772 A 3/1996 Schulman et al.
5,499,243 A 3/1996 Hall
5,507,288 A 4/1996 Bocker et al.
5,509,410 A 4/1996 Hill et al.
5,514,718 A 5/1996 Lewis et al.
5,516,832 A 5/1996 Kennan et al.
5,527,288 A 6/1996 Gross et al.
5,531,878 A 7/1996 Vadgama et al.
5,532,686 A 7/1996 Urbas et al.
5,533,977 A 7/1996 Metcalf et al.
5,536,259 A 7/1996 Utterberg
5,543,326 A 8/1996 Heller et al.
5,544,196 A 8/1996 Tiedmann, Jr. et al.
5,545,191 A 8/1996 Mann et al.
5,549,568 A 8/1996 Sheilds
5,551,427 A 9/1996 Altman
5,555,190 A 9/1996 Derby et al.
5,558,638 A 9/1996 Evers et al.
5,560,357 A 10/1996 Faupei et al.
5,562,713 A 10/1996 Silvian
5,564,434 A 10/1996 Halperin et al.
5,565,085 A 10/1996 Ikeda et al.
5,567,302 A 10/1996 Song et al.
5,568,806 A 10/1996 Cheney, II et al.
5,569,186 A 10/1996 Lord et al.
5,571,022 A 11/1996 Schaarschmidt
5,575,563 A 11/1996 Chiu et al.
5,581,206 A 12/1996 Chevallier et al.
5,582,184 A 12/1996 Erickson et al.
5,582,697 A 12/1996 Ikeda et al.
5,582,698 A 12/1996 Flaherty et al.
5,584,813 A 12/1996 Livingston et al.
5,586,553 A 12/1996 Halili et al.
5,589,326 A 12/1996 Deng et al.
5,593,852 A 1/1997 Heller et al.
5,596,150 A 1/1997 Arndt et al.
5,597,378 A 1/1997 Jervis
5,600,301 A 2/1997 Robinson, III
5,601,435 A 2/1997 Quy
5,609,575 A 3/1997 Larson et al.
5,613,978 A 3/1997 Harding
5,617,851 A 4/1997 Lipkovker
5,623,933 A 4/1997 Amano et al.
5,626,566 A 5/1997 Petersen et al.
5,628,310 A 5/1997 Rao et al.
5,628,324 A 5/1997 Sarbach
5,628,890 A 5/1997 Carter et al.
5,632,557 A 5/1997 Simons
5,634,468 A 6/1997 Platt et al.
5,636,640 A 6/1997 Staehlin
5,638,832 A 6/1997 Singer et al.
5,640,954 A 6/1997 Pfeiffer et al.
5,651,869 A 7/1997 Yoshioka et al.
5,653,239 A 8/1997 Pompei et al.
5,659,454 A 8/1997 Vermesse
5,660,163 A 8/1997 Schulman et al.
5,665,071 A 9/1997 Wyrick
5,665,222 A 9/1997 Heller et al.
5,669,543 A 9/1997 Ueno
5,669,890 A 9/1997 Grimm
5,670,031 A 9/1997 Hintsche et al.
5,673,322 A 9/1997 Pepe et al.
5,680,858 A 10/1997 Hansen et al.
5,682,233 A 10/1997 Brinda
5,695,623 A 12/1997 Michel et al.
5,707,502 A 1/1998 McCaffrey et al.
5,708,247 A 1/1998 McAleer et al.
5,711,001 A 1/1998 Bussan et al.
5,711,297 A 1/1998 Iliff et al.
5,711,861 A 1/1998 Ward et al.
5,711,862 A 1/1998 Sakoda et al.
5,724,030 A 3/1998 Urbas et al.
5,726,646 A 3/1998 Bane et al.
5,733,044 A 3/1998 Rose et al.
5,733,259 A 3/1998 Valcke et al.
5,733,262 A 3/1998 Paul
5,733,313 A 3/1998 Barreras, Sr. et al.
5,735,285 A 4/1998 Albert et al.
5,738,220 A 4/1998 Geszler
5,741,211 A 4/1998 Renirie et al.
5,743,262 A 4/1998 Lepper, Jr. et al.
5,746,217 A 5/1998 Erickson et al.
5,746,697 A 5/1998 Swedlow et al.
5,748,103 A 5/1998 Flach et al.
5,749,656 A 5/1998 Boehm et al.
5,749,907 A 5/1998 Mann
5,758,290 A 5/1998 Nealon et al.
5,766,131 A 6/1998 Kondo et al.
5,770,028 A 6/1998 Maley et al.
5,771,001 A 6/1998 Cobb
5,771,891 A 6/1998 Gozani
5,772,586 A 6/1998 Heinonen et al.
5,778,879 A 7/1998 Ota et al.
5,779,665 A 7/1998 Mastrototaro et al.
5,786,439 A 7/1998 Van Antwerp et al.
5,791,344 A 8/1998 Schulman et al.
5,798,961 A 8/1998 Heyden et al.
5,800,420 A 9/1998 Gross et al.
5,804,047 A 9/1998 Karube et al.
5,807,375 A 9/1998 Gross et al.
5,814,020 A 9/1998 Gross
5,820,551 A 10/1998 Hill et al.
5,820,570 A 10/1998 Erickson et al.
5,820,622 A 10/1998 Gross et al.
5,822,715 A 10/1998 Worthington et al.
5,823,802 A 10/1998 Bartley
5,827,184 A 10/1998 Netherly et al.
5,830,064 A 11/1998 Bradish et al.
5,833,603 A 11/1998 Kovacs et al.
5,840,020 A 11/1998 Heinonen et al.
5,842,983 A 12/1998 Abel et al.
5,851,197 A 12/1998 Marano et al.
5,856,758 A 1/1999 Joffe et al.
5,858,001 A 1/1999 Tsals et al.
5,865,804 A 2/1999 Bachynsky
5,871,494 A 2/1999 Simons et al.
5,875,186 A 2/1999 Belanger et al.
5,879,311 A 3/1999 Duchon et al.
5,885,211 A 3/1999 Eppstein et al.
5,891,049 A 4/1999 Cyrus et al.
5,899,855 A 5/1999 Brown
5,899,856 A 5/1999 Schoendorfer et al.
5,914,026 A 6/1999 Blubaugh, Jr. et al.
5,918,603 A 7/1999 Brown
5,919,141 A 7/1999 Money et al.
5,921,963 A 7/1999 Erez et al.
5,924,979 A 7/1999 Swedlow et al.
5,925,021 A 7/1999 Castellano et al.
5,931,814 A 8/1999 Alex et al.
5,931,868 A 8/1999 Gross
5,935,224 A 8/1999 Svancarek et al.
5,938,679 A 8/1999 Freeman et al.
5,942,979 A 8/1999 Luppino
5,948,006 A 9/1999 Mann
5,951,485 A 9/1999 Cyrus et al.

(56) References Cited

U.S. PATENT DOCUMENTS

| | | | |
|---|---|---|---|
| 5,951,492 | A | 9/1999 | Douglas et al. |
| 5,951,521 | A | 9/1999 | Mastrototaro et al. |
| 5,951,582 | A | 9/1999 | Thorne et al. |
| 5,954,643 | A | 9/1999 | Van Antwerp |
| 5,954,685 | A | 9/1999 | Tierny |
| 5,957,854 | A | 9/1999 | Besson et al. |
| 5,961,451 | A | 10/1999 | Reber et al. |
| 5,964,718 | A | 10/1999 | Duchon et al. |
| 5,964,993 | A | 10/1999 | Blubaugh, Jr. et al. |
| 5,965,380 | A | 10/1999 | Heller et al. |
| 5,971,922 | A | 10/1999 | Arita et al. |
| 5,971,941 | A | 10/1999 | Simons et al. |
| 5,972,199 | A | 10/1999 | Heller et al. |
| 5,987,353 | A | 11/1999 | Khatchatrian et al. |
| 5,993,411 | A | 11/1999 | Choi |
| 5,995,860 | A | 11/1999 | Sun et al. |
| 5,997,501 | A | 12/1999 | Gross et al. |
| 6,001,067 | A | 12/1999 | Shults et al. |
| 6,004,278 | A | 12/1999 | Botich et al. |
| 6,017,335 | A | 1/2000 | Burnham |
| 6,022,315 | A | 2/2000 | Iliff |
| 6,022,368 | A | 2/2000 | Gavronsky et al. |
| 6,024,699 | A | 2/2000 | Surwit et al. |
| 6,026,321 | A | 2/2000 | Miyata et al. |
| 6,027,459 | A | 2/2000 | Shain et al. |
| 6,028,413 | A | 2/2000 | Brockmann |
| 6,032,064 | A | 2/2000 | Devlin et al. |
| 6,036,924 | A | 3/2000 | Simons et al. |
| 6,048,352 | A | 4/2000 | Douglas et al. |
| 6,049,727 | A | 4/2000 | Crothall |
| 6,052,565 | A | 4/2000 | Ishikura et al. |
| 6,054,194 | A | 4/2000 | Kane |
| 6,056,718 | A | 5/2000 | Funderburk et al. |
| 6,059,946 | A | 5/2000 | Yukawa et al. |
| 6,066,243 | A | 5/2000 | Anderson et al. |
| 6,068,399 | A | 5/2000 | Tseng |
| 6,071,294 | A | 6/2000 | Simons et al. |
| 6,071,391 | A | 6/2000 | Gotoh et al. |
| 6,083,710 | A | 7/2000 | Heller et al. |
| 6,085,342 | A | 7/2000 | Marholev et al. |
| 6,088,605 | A | 7/2000 | Griffith et al. |
| 6,088,608 | A | 7/2000 | Schulman et al. |
| 6,091,975 | A | 7/2000 | Daddona et al. |
| 6,091,976 | A | 7/2000 | Pfeiffer et al. |
| 6,091,987 | A | 7/2000 | Thompson |
| 6,093,172 | A | 7/2000 | Funderburk et al. |
| 6,096,364 | A | 8/2000 | Bok et al. |
| 6,097,480 | A | 8/2000 | Kaplan |
| 6,099,484 | A | 8/2000 | Douglas et al. |
| 6,102,896 | A | 8/2000 | Roser |
| 6,103,033 | A | 8/2000 | Say et al. |
| 6,106,484 | A | 8/2000 | Terwilliger |
| 6,117,290 | A | 9/2000 | Say et al. |
| 6,119,028 | A | 9/2000 | Schulman et al. |
| 6,120,676 | A | 9/2000 | Heller et al. |
| 6,121,009 | A | 9/2000 | Heller et al. |
| 6,121,611 | A | 9/2000 | Lindsay et al. |
| 6,122,351 | A | 9/2000 | Schlueter, Jr. et al. |
| 6,129,666 | A | 10/2000 | DeLuca et al. |
| 6,130,623 | A | 10/2000 | MacLellan et al. |
| 6,132,449 | A | 10/2000 | Lum et al. |
| 6,134,461 | A | 10/2000 | Say et al. |
| 6,141,573 | A | 10/2000 | Kurnik et al. |
| 6,143,164 | A | 11/2000 | Heller et al. |
| 6,144,837 | A | 11/2000 | Quy |
| 6,144,871 | A | 11/2000 | Saito et al. |
| 6,144,922 | A | 11/2000 | Douglas et al. |
| 6,149,626 | A | 11/2000 | Bachynsky et al. |
| 6,157,850 | A | 12/2000 | Diab et al. |
| 6,159,147 | A | 12/2000 | Lichter et al. |
| 6,159,181 | A | 12/2000 | Crossman et al. |
| 6,161,095 | A | 12/2000 | Brown |
| 6,162,611 | A | 12/2000 | Heller et al. |
| 6,168,606 | B1 | 1/2001 | Levin et al. |
| 6,175,752 | B1 | 1/2001 | Say et al. |
| 6,186,982 | B1 | 2/2001 | Gross et al. |
| 6,192,891 | B1 | 2/2001 | Gravel et al. |
| 6,197,040 | B1 | 3/2001 | LeVaughn et al. |
| 6,198,946 | B1 | 3/2001 | Shin et al. |
| 6,200,265 | B1 | 3/2001 | Walsh et al. |
| 6,203,495 | B1 | 3/2001 | Bardy et al. |
| 6,212,416 | B1 | 4/2001 | Ward et al. |
| 6,213,972 | B1 | 4/2001 | Butterfield et al. |
| 6,219,574 | B1 | 4/2001 | Cormier et al. |
| 6,223,283 | B1 | 4/2001 | Chaiken et al. |
| 6,231,531 | B1 | 5/2001 | Lum et al. |
| 6,233,471 | B1 | 5/2001 | Berner et al. |
| 6,237,394 | B1 | 5/2001 | Harris et al. |
| 6,248,067 | B1 | 6/2001 | Causey, III et al. |
| 6,254,536 | B1 | 7/2001 | DeVito |
| 6,254,586 | B1 | 7/2001 | Mann et al. |
| 6,264,810 | B1 | 7/2001 | Stol et al. |
| 6,270,455 | B1 | 8/2001 | Brown |
| 6,275,717 | B1 | 8/2001 | Gross et al. |
| 6,283,761 | B1 | 9/2001 | Joao |
| 6,283,982 | B1 | 9/2001 | Levaughn et al. |
| 6,284,478 | B1 | 9/2001 | Heller et al. |
| 6,291,200 | B1 | 9/2001 | LeJeune et al. |
| 6,293,925 | B1 | 9/2001 | Safabash et al. |
| 6,294,997 | B1 | 9/2001 | Paratore et al. |
| 6,295,506 | B1 | 9/2001 | Heinonen et al. |
| 6,298,255 | B1 | 10/2001 | Cordero et al. |
| 6,299,347 | B1 | 10/2001 | Pompei |
| 6,299,757 | B1 | 10/2001 | Feldman et al. |
| 6,302,866 | B1 | 10/2001 | Marggi |
| 6,304,766 | B1 | 10/2001 | Colvin, Jr. |
| 6,306,104 | B1 | 10/2001 | Cunningham et al. |
| 6,306,141 | B1 | 10/2001 | Jervis |
| 6,309,884 | B1 | 10/2001 | Cooper et al. |
| 6,314,317 | B1 | 11/2001 | Willis |
| 6,329,161 | B1 | 12/2001 | Heller et al. |
| 6,331,244 | B1 | 12/2001 | Lewis et al. |
| 6,336,269 | B1 | 1/2002 | Eldridge et al. |
| 6,338,790 | B1 | 1/2002 | Feldman et al. |
| 6,341,232 | B1 | 1/2002 | Conn et al. |
| 6,348,640 | B1 | 2/2002 | Navot et al. |
| 6,359,270 | B1 | 3/2002 | Bridson |
| 6,359,444 | B1 | 3/2002 | Grimes |
| 6,360,888 | B1 | 3/2002 | McIvor et al. |
| 6,364,890 | B1 | 4/2002 | Lum et al. |
| 6,366,794 | B1 | 4/2002 | Moussy et al. |
| 6,368,141 | B1 | 4/2002 | Van Antwerp et al. |
| 6,368,274 | B1 | 4/2002 | Van Antwerp et al. |
| 6,368,339 | B1 | 4/2002 | Amplatz |
| 6,377,828 | B1 | 4/2002 | Chaiken et al. |
| 6,377,829 | B1 | 4/2002 | Al-Ali |
| 6,377,894 | B1 | 4/2002 | Deweese et al. |
| 6,379,301 | B1 | 4/2002 | Worthington et al. |
| 6,387,048 | B1 | 5/2002 | Schulman et al. |
| 6,400,974 | B1 | 6/2002 | Lesho |
| 6,405,066 | B1 | 6/2002 | Essenpreis et al. |
| 6,409,740 | B1 | 6/2002 | Kuhr et al. |
| 6,413,393 | B1 | 7/2002 | Van Antwerp et al. |
| 6,416,471 | B1 | 7/2002 | Kumar et al. |
| 6,418,332 | B1 | 7/2002 | Mastrototaro et al. |
| 6,418,346 | B1 | 7/2002 | Nelson et al. |
| 6,424,847 | B1 | 7/2002 | Mastrototaro et al. |
| 6,427,088 | B1 | 7/2002 | Bowman, IV et al. |
| 6,433,743 | B1 | 8/2002 | Massy et al. |
| 6,435,017 | B1 | 8/2002 | Nowicki, Jr. et al. |
| 6,437,679 | B1 | 8/2002 | Roques |
| 6,438,414 | B1 | 8/2002 | Conn et al. |
| 6,440,068 | B1 | 8/2002 | Brown et al. |
| 6,442,413 | B1 | 8/2002 | Silver |
| 6,445,374 | B2 | 9/2002 | Albert et al. |
| 6,451,025 | B1 | 9/2002 | Jervis |
| 6,458,109 | B1 | 10/2002 | Henley et al. |
| 6,461,496 | B1 | 10/2002 | Feldman et al. |
| 6,471,689 | B1 | 10/2002 | Joseph et al. |
| 6,472,220 | B1 | 10/2002 | Simons et al. |
| 6,478,736 | B1 | 11/2002 | Mault |
| 6,482,176 | B1 | 11/2002 | Wich |
| 6,484,045 | B1 | 11/2002 | Holker et al. |
| 6,484,046 | B1 | 11/2002 | Say et al. |

(56) References Cited

U.S. PATENT DOCUMENTS 6,493,069 B1 12/2002 Nagashimada et al.
6,494,830 B1 12/2002 Wessel
6,496,729 B2 12/2002 Thompson
6,497,655 B1 12/2002 Linberg et al.
6,503,381 B1 1/2003 Gotoh et al.
6,510,344 B1 1/2003 Halpern
6,514,460 B1 2/2003 Fendrock
6,514,689 B2 2/2003 Han et al.
6,514,718 B2 2/2003 Heller et al.
6,520,326 B2 2/2003 McIvor et al.
6,522,927 B1 2/2003 Bishay et al.
6,533,805 B1 3/2003 Jervis
6,537,242 B1 3/2003 Palmer
6,540,891 B1 4/2003 Stewart et al.
6,544,212 B2 4/2003 Galley et al.
6,546,268 B1 4/2003 Ishikawa et al.
6,549,796 B2 4/2003 Sohrab
6,551,494 B1 4/2003 Heller et al.
6,551,496 B1 4/2003 Moles et al.
6,554,795 B2 4/2003 Bagaoisan et al.
6,554,798 B1 4/2003 Mann et al.
6,558,320 B1 5/2003 Causey, III et al.
6,558,321 B1 5/2003 Burd et al.
6,558,351 B1 5/2003 Steil et al.
6,560,471 B1 5/2003 Heller et al.
6,561,975 B1 5/2003 Pool et al.
6,561,978 B1 5/2003 Conn et al.
6,562,001 B2 5/2003 Lebel et al.
6,564,105 B2 5/2003 Starkweather et al.
6,565,509 B1 5/2003 Say et al.
6,571,128 B2 5/2003 Lebel et al.
6,572,542 B1 6/2003 Houben et al.
6,572,566 B2 6/2003 Effenhauser
6,574,490 B2 6/2003 Abbink et al.
6,574,510 B2 6/2003 Von Arx et al.
6,575,895 B1 6/2003 Blair
6,576,101 B1 6/2003 Heller et al.
6,577,899 B2 6/2003 Lebel et al.
6,579,231 B1 6/2003 Phipps
6,579,690 B1 6/2003 Bonnecaze et al.
6,584,335 B1 6/2003 Haar et al.
6,585,644 B2 7/2003 Lebel et al.
6,589,229 B1 7/2003 Connelly et al.
6,591,125 B1 7/2003 Buse et al.
6,592,745 B1 7/2003 Feldman et al.
6,595,919 B2 7/2003 Berner et al.
6,600,997 B2 7/2003 Deweese et al.
6,602,268 B2 8/2003 Kuhr et al.
6,603,995 B1 8/2003 Carter
6,604,050 B2 8/2003 Trippel et al.
6,605,200 B1 8/2003 Mao et al.
6,605,201 B1 8/2003 Mao et al.
6,607,509 B2 8/2003 Bobroff et al.
6,607,543 B2 8/2003 Purcell et al.
6,608,562 B1 8/2003 Kimura et al.
6,610,012 B2 8/2003 Mault
6,611,206 B2 8/2003 Eshelman et al.
6,613,015 B2 9/2003 Sandstrom et al.
6,616,819 B1 9/2003 Liamos et al.
6,618,934 B1 9/2003 Feldman et al.
6,627,154 B1 9/2003 Goodman et al.
6,631,281 B1 10/2003 Kastle
6,633,772 B2 10/2003 Ford et al.
6,635,014 B2 10/2003 Starkweather et al.
6,635,167 B1 10/2003 Batman et al.
6,637,611 B2 10/2003 Luch
6,641,533 B2 11/2003 Causey, III et al.
6,645,359 B1 11/2003 Bhullar et al.
6,648,821 B2 11/2003 Lebel et al.
6,650,471 B2 11/2003 Doi
6,654,625 B1 11/2003 Say et al.
6,656,114 B1 12/2003 Poulson et al.
6,658,396 B1 12/2003 Tang et al.
6,659,948 B2 12/2003 Lebel et al.
6,662,439 B1 12/2003 Bhullar
6,666,849 B1 12/2003 Marshall et al.
6,668,196 B1 12/2003 Villegas et al.
6,671,534 B2 12/2003 Putz
6,675,030 B2 1/2004 Ciurczak et al.
6,676,290 B1 1/2004 Lu
6,676,816 B2 1/2004 Mao et al.
6,682,546 B2 1/2004 Amplatz
6,687,546 B2 2/2004 Lebel et al.
6,689,056 B1 2/2004 Kilcoyne et al.
6,694,191 B2 2/2004 Starkweather et al.
6,695,860 B1 2/2004 Ward et al.
6,698,269 B2 3/2004 Baber et al.
6,699,188 B2 3/2004 Wessel
6,702,857 B2 3/2004 Brauker et al.
6,706,159 B2 3/2004 Moerman et al.
6,721,582 B2 4/2004 Trepagnier et al.
6,730,025 B1 5/2004 Platt
6,730,072 B2 5/2004 Shawgo et al.
6,730,200 B1 5/2004 Stewart et al.
6,731,976 B2 5/2004 Penn et al.
6,733,446 B2 5/2004 Lebel et al.
6,735,183 B2 5/2004 O'Toole et al.
6,735,479 B2 5/2004 Fabian et al.
6,736,957 B1 5/2004 Forrow et al.
6,740,075 B2 5/2004 Lebel et al.
6,741,877 B1 5/2004 Shults et al.
6,743,635 B2 6/2004 Neel et al.
6,746,582 B2 6/2004 Heller et al.
6,748,445 B1 6/2004 Darcey et al.
6,749,740 B2 6/2004 Liamos et al.
6,758,810 B2 7/2004 Lebel et al.
6,758,835 B2 7/2004 Close et al.
6,764,581 B1 7/2004 Forrow et al.
6,767,440 B1 7/2004 Bhullar et al.
6,770,030 B1 8/2004 Schaupp et al.
6,773,671 B1 8/2004 Lewis et al.
6,781,522 B2 8/2004 Sleva et al.
6,790,178 B1 9/2004 Mault et al.
6,804,558 B2 10/2004 Haller et al.
6,804,561 B2 10/2004 Stover
6,809,653 B1 10/2004 Mann et al.
6,810,290 B2 10/2004 Lebel et al.
6,811,533 B2 11/2004 Lebel et al.
6,811,534 B2 11/2004 Bowman, IV et al.
6,813,519 B2 11/2004 Lebel et al.
6,814,844 B2 11/2004 Bhullar et al.
6,830,551 B1 12/2004 Uchigaki et al.
6,837,858 B2 1/2005 Cunningham et al.
6,837,885 B2 1/2005 Koblish et al.
6,837,988 B2 1/2005 Leong et al.
6,849,052 B2 2/2005 Uchigaki et al.
6,850,790 B2 2/2005 Berner et al.
6,850,859 B1 2/2005 Schuh
6,854,882 B2 2/2005 Chen
6,862,465 B2 3/2005 Shults et al.
6,873,268 B2 3/2005 Lebel et al.
6,878,112 B2 4/2005 Linberg et al.
6,881,551 B2 4/2005 Heller et al.
6,892,085 B2 5/2005 Mclvor et al.
6,893,545 B2 5/2005 Gotoh et al.
6,895,263 B2 5/2005 Shin et al.
6,895,265 B2 5/2005 Silver
6,923,763 B1 8/2005 Kovatchev et al.
6,923,764 B2 8/2005 Aceti et al.
6,925,393 B1 8/2005 Kalatz et al.
6,931,327 B2 8/2005 Goode, Jr. et al.
6,932,892 B2 8/2005 Chen
6,932,894 B2 8/2005 Mao et al.
6,936,006 B2 8/2005 Sabra
6,937,222 B2 8/2005 Numao
6,940,403 B2 9/2005 Kail, IV
6,941,163 B2 9/2005 Ford et al.
6,942,518 B2 9/2005 Liamos et al.
6,950,708 B2 9/2005 Bowman IV et al.
6,954,662 B2 10/2005 Freger et al.
6,958,705 B2 10/2005 Lebel et al.
6,959,211 B2 10/2005 Rule et al.
6,960,192 B1 11/2005 Flaherty et al.
6,968,294 B2 11/2005 Gutta et al.

(56) References Cited

U.S. PATENT DOCUMENTS 6,971,274 B2 12/2005 Olin
6,971,999 B2 12/2005 Py et al.
6,973,706 B2 12/2005 Say et al.
6,974,437 B2 12/2005 Lebel et al.
6,975,893 B2 12/2005 Say et al.
6,983,867 B1 1/2006 Fugere
6,990,366 B2 1/2006 Say et al.
6,997,907 B2 2/2006 Safabash et al.
6,998,247 B2 2/2006 Monfre et al.
6,999,854 B2 2/2006 Roth
7,003,336 B2 2/2006 Holker et al.
7,003,340 B2 2/2006 Say et al.
7,003,341 B2 2/2006 Say et al.
7,005,857 B2 2/2006 Stiene et al.
7,009,511 B2 3/2006 Mazar et al.
7,010,356 B2 3/2006 Jog et al.
7,015,817 B2 3/2006 Copley et al.
7,016,713 B2 3/2006 Gardner et al.
7,020,508 B2 3/2006 Stivoric et al.
7,022,072 B2 4/2006 Fox et al.
7,022,219 B2 4/2006 Mansouri et al.
7,024,236 B2 4/2006 Ford et al.
7,024,245 B2 4/2006 Lebel et al.
7,025,743 B2 4/2006 Mann et al.
7,025,774 B2 4/2006 Freeman et al.
7,027,848 B2 4/2006 Robinson et al.
7,027,859 B1 4/2006 McNichols et al.
7,027,931 B1 4/2006 Jones et al.
7,029,444 B2 4/2006 Shin et al.
7,041,057 B1 5/2006 Faupel et al.
7,041,068 B2 5/2006 Freeman et al.
7,041,468 B2 5/2006 Drucker et al.
7,043,305 B2 5/2006 Kenknight et al.
7,046,153 B2 5/2006 Oja et al.
7,052,483 B2 5/2006 Wojcik
7,056,302 B2 6/2006 Douglas
7,058,453 B2 6/2006 Nelson et al.
7,060,031 B2 6/2006 Webb et al.
7,073,246 B2 7/2006 Bhullar et al.
7,074,307 B2 7/2006 Simpson et al.
7,081,195 B2 7/2006 Simpson et al.
7,082,334 B2 7/2006 Boute et al.
7,097,637 B2 8/2006 Triplett et al.
7,098,803 B2 8/2006 Mann et al.
7,108,778 B2 9/2006 Simpson et al.
7,110,803 B2 9/2006 Shults et al.
7,113,821 B1 9/2006 Sun et al.
7,118,667 B2 10/2006 Lee
7,120,483 B2 10/2006 Russel et al.
7,123,950 B2 10/2006 Mannheimer
7,124,027 B1 10/2006 Ernst et al.
7,125,382 B2 10/2006 Zhou et al.
7,131,984 B2 11/2006 Sato et al.
7,134,999 B2 11/2006 Brauker et al.
7,136,689 B2 11/2006 Shults et al.
7,144,384 B2 12/2006 Gorman et al.
7,146,202 B2 12/2006 Ward et al.
7,154,398 B2 12/2006 Chen et al.
7,155,290 B2 12/2006 Von Arx et al.
7,167,818 B2 1/2007 Brown
7,169,600 B2 1/2007 Hoss et al.
7,171,274 B2 1/2007 Starkweather et al.
7,174,199 B2 2/2007 Berner et al.
7,179,226 B2 2/2007 Crothall et al.
7,183,102 B2 2/2007 Monfre et al.
7,190,988 B2 3/2007 Say et al.
7,192,450 B2 3/2007 Brauker et al.
7,198,606 B2 4/2007 Boecker et al.
7,203,549 B2 4/2007 Schommer et al.
7,207,974 B2 4/2007 Safabash et al.
7,220,387 B2 5/2007 Flaherty et al.
7,223,276 B2 5/2007 List et al.
7,225,535 B2 6/2007 Feldman et al.
7,226,442 B2 6/2007 Sheppard et al.
7,226,978 B2 6/2007 Tapsak et al.
7,228,162 B2 6/2007 Ward et al.
7,228,182 B2 6/2007 Healy et al.
7,237,712 B2 7/2007 DeRocco et al.
7,267,665 B2 9/2007 Steil et al.
7,276,029 B2 10/2007 Goode, Jr. et al.
7,276,146 B2 10/2007 Wilsey
7,276,147 B2 10/2007 Wilsey
7,278,983 B2 10/2007 Ireland et al.
7,286,894 B1 10/2007 Grant et al.
7,287,318 B2 10/2007 Bhullar et al.
7,291,497 B2 11/2007 Holmes et al.
7,295,867 B2 11/2007 Berner et al.
7,297,151 B2 11/2007 Boecker et al.
7,299,082 B2 11/2007 Feldman et al.
7,310,544 B2 12/2007 Brister et al.
7,318,816 B2 1/2008 Bobroff et al.
7,324,012 B2 1/2008 Mann et al.
7,324,850 B2 1/2008 Persen et al.
7,329,239 B2 2/2008 Safabash et al.
7,335,294 B2 2/2008 Heller et al.
7,340,287 B2 3/2008 Mason et al.
7,340,309 B2 3/2008 Miazga et al.
7,344,500 B2 3/2008 Talbot et al.
7,347,819 B2 3/2008 Lebel et al.
7,354,420 B2 4/2008 Steil et al.
7,364,592 B2 4/2008 Carr-Brendel et al.
7,366,556 B2 4/2008 Brister et al.
7,379,765 B2 5/2008 Petisce et al.
7,381,184 B2 6/2008 Funderburk et al.
7,384,397 B2 6/2008 Zhang et al.
7,386,937 B2 6/2008 Bhullar et al.
7,387,010 B2 6/2008 Sunshine et al.
7,399,277 B2 7/2008 Saidara et al.
7,400,111 B2 7/2008 Batman et al.
7,401,111 B1 7/2008 Batman et al.
7,402,153 B2 7/2008 Steil et al.
7,404,796 B2 7/2008 Ginsberg
7,407,493 B2 8/2008 Cane
7,408,132 B2 8/2008 Wambsganss et al.
7,416,541 B2 8/2008 Yuzhakov et al.
7,419,573 B2 9/2008 Gundel
7,424,318 B2 9/2008 Brister et al.
7,429,255 B2 9/2008 Thompson
7,433,727 B2 10/2008 Ward
7,448,996 B2 11/2008 Khanuja et al.
7,455,663 B2 11/2008 Bikovsky
7,460,898 B2 12/2008 Brister et al.
7,462,264 B2 12/2008 Heller et al.
7,467,003 B2 12/2008 Brister et al.
7,468,125 B2 12/2008 Kraft et al.
7,471,972 B2 12/2008 Rhodes et al.
7,476,827 B1 1/2009 Bhullar et al.
7,481,819 B2 1/2009 Koeppel et al.
7,492,254 B2 2/2009 Bandy et al.
7,494,465 B2 2/2009 Brister et al.
7,497,827 B2 3/2009 Brister et al.
7,499,002 B2 3/2009 Blasko et al.
7,519,408 B2 4/2009 Rasdal et al.
7,545,272 B2 6/2009 Goodnow et al.
7,547,281 B2 6/2009 Hayes et al.
7,565,197 B2 7/2009 Haubrich et al.
7,568,619 B2 8/2009 Todd et al.
7,569,030 B2 8/2009 Lebel et al.
7,574,266 B2 8/2009 Dudding et al.
7,582,059 B2 9/2009 Funderburk et al.
7,583,990 B2 9/2009 Goode, Jr. et al.
7,585,287 B2 9/2009 Bresina et al.
7,591,801 B2 9/2009 Brauker et al.
7,599,726 B2 10/2009 Goode, Jr. et al.
7,602,310 B2 10/2009 Mann et al.
7,604,178 B2 10/2009 Stewart
7,604,592 B2 10/2009 Freeman et al.
7,613,491 B2 11/2009 Boock et al.
7,615,007 B2 11/2009 Shults et al.
7,618,369 B2 11/2009 Hayter et al.
7,632,228 B2 12/2009 Brauker et al.
7,635,594 B2 12/2009 Holmes et al.
7,637,868 B2 12/2009 Saint et al.
7,640,048 B2 12/2009 Dobbles et al.

(56) References Cited

U.S. PATENT DOCUMENTS 7,643,798 B2 1/2010 Ljung
7,651,596 B2 1/2010 Petisce et al.
7,651,845 B2 1/2010 Doyle, III et al.
7,653,425 B2 1/2010 Hayter et al.
7,654,956 B2 2/2010 Brister et al.
7,657,297 B2 2/2010 Simpson et al.
7,659,823 B1 2/2010 Killian et al.
7,660,615 B2 2/2010 VanAntwerp et al.
7,666,149 B2 2/2010 Simons et al.
7,668,596 B2 2/2010 Von Arx et al.
7,682,338 B2 3/2010 Griffin
7,697,967 B2 4/2010 Stafford
7,699,775 B2 4/2010 Desai et al.
7,699,807 B2 4/2010 Faust et al.
7,701,052 B2 4/2010 Borland et al.
7,711,402 B2 5/2010 Shults et al.
7,713,574 B2 5/2010 Brister et al.
7,715,893 B2 5/2010 Kamath et al.
7,727,147 B1 6/2010 Osorio et al.
7,729,737 B2 6/2010 Ward
7,731,657 B2 6/2010 Stafford
7,731,691 B2 6/2010 Cote et al.
7,736,310 B2 6/2010 Taub et al.
7,736,344 B2 6/2010 Moberg et al.
7,741,734 B2 6/2010 Joannopoulos et al.
7,763,042 B2 7/2010 Iio et al.
7,766,829 B2 8/2010 Sloan et al.
7,768,387 B2 8/2010 Fennell et al.
7,771,352 B2 8/2010 Shults et al.
7,774,145 B2 8/2010 Brauker et al.
7,775,444 B2 8/2010 DeRocco et al.
7,778,680 B2 8/2010 Goode, Jr. et al.
7,779,332 B2 8/2010 Karr et al.
7,780,827 B1 8/2010 Bhullar et al.
7,782,192 B2 8/2010 Jeckelmann et al.
7,783,333 B2 8/2010 Brister et al.
7,791,467 B2 9/2010 Mazar et al.
7,792,562 B2 9/2010 Shults et al.
7,811,231 B2 10/2010 Jin et al.
7,813,809 B2 10/2010 Strother et al.
7,822,454 B1 10/2010 Alden et al.
7,826,981 B2 11/2010 Goode, Jr. et al.
7,831,310 B2 11/2010 Lebel et al.
7,833,151 B2 11/2010 Khait et al.
7,833,170 B2 11/2010 Matsumoto et al.
7,837,633 B2 11/2010 Conway et al.
7,842,046 B1 11/2010 Nakao
7,846,132 B2 12/2010 Gravesen et al.
7,850,652 B2 12/2010 Liniger et al.
7,860,574 B2 12/2010 Von Arx et al.
7,866,026 B1 1/2011 Wang et al.
7,867,244 B2 1/2011 Lathrop et al.
7,873,299 B2 1/2011 Berner et al.
7,882,611 B2 2/2011 Shah et al.
7,883,464 B2 2/2011 Stafford
7,883,473 B2 2/2011 LeVaughn et al.
7,885,697 B2 2/2011 Brister et al.
7,889,069 B2 2/2011 Fifolt et al.
7,896,844 B2 3/2011 Thalmann et al.
7,899,511 B2 3/2011 Shults et al.
7,899,545 B2 3/2011 John
7,905,833 B2 3/2011 Brister et al.
7,912,655 B2 3/2011 Power et al.
7,912,674 B2 3/2011 Killoren Clark et al.
7,914,450 B2 3/2011 Goode, Jr. et al.
7,914,460 B2 3/2011 Melker et al.
7,916,013 B2 3/2011 Stevenson
7,920,906 B2 4/2011 Goode, Jr. et al.
7,920,907 B2 4/2011 McGarraugh et al.
7,938,797 B2 5/2011 Estes
7,941,200 B2 5/2011 Weinart et al.
7,946,984 B2 5/2011 Brister et al.
7,946,985 B2 5/2011 Mastrototaro et al.
7,955,258 B2 6/2011 Goscha et al.
7,955,297 B2 6/2011 Radmer et al.
7,970,448 B2 6/2011 Shults et al.
7,970,449 B2 6/2011 Ward
7,972,296 B2 7/2011 Braig et al.
7,974,672 B2 7/2011 Shults et al.
7,976,467 B2 7/2011 Young et al.
7,978,063 B2 7/2011 Baldus et al.
7,985,203 B2 7/2011 Haueter et al.
7,985,222 B2 7/2011 Gall et al.
7,996,158 B2 8/2011 Hayter et al.
7,999,674 B2 8/2011 Kamen
8,000,918 B2 8/2011 Fjield et al.
8,005,524 B2 8/2011 Brauker et al.
8,010,174 B2 8/2011 Goode, Jr. et al.
8,010,256 B2 8/2011 Oowada
8,016,774 B2 9/2011 Freeman et al.
8,028,837 B2 10/2011 Gerstle et al.
8,029,441 B2 10/2011 Mazza et al.
8,029,442 B2 10/2011 Funderburk et al.
8,072,310 B1 12/2011 Everhart
8,090,445 B2 1/2012 Ginggen
8,093,991 B2 1/2012 Stevenson et al.
8,094,009 B2 1/2012 Allen et al.
8,098,159 B2 1/2012 Batra et al.
8,098,160 B2 1/2012 Howarth et al.
8,098,161 B2 1/2012 Lavedas
8,098,201 B2 1/2012 Choi et al.
8,098,208 B2 1/2012 Ficker et al.
8,102,021 B2 1/2012 Degani
8,102,154 B2 1/2012 Bishop et al.
8,102,263 B2 1/2012 Yeo et al.
8,102,789 B2 1/2012 Rosar et al.
8,103,241 B2 1/2012 Young et al.
8,103,325 B2 1/2012 Swedlow et al.
8,103,471 B2 1/2012 Hayter
8,111,042 B2 2/2012 Bennett
8,112,240 B2 2/2012 Fennell
8,115,488 B2 2/2012 McDowell
8,116,681 B2 2/2012 Baarman
8,116,683 B2 2/2012 Baarman
8,117,481 B2 2/2012 Anselmi et al.
8,120,493 B2 2/2012 Burr
8,124,452 B2 2/2012 Sheats
8,130,093 B2 3/2012 Mazar et al.
8,131,351 B2 3/2012 Kalgren et al.
8,131,365 B2 3/2012 Zhang et al.
8,131,565 B2 3/2012 Docks et al.
8,132,037 B2 3/2012 Fehr et al.
8,135,352 B2 3/2012 Langsweirdt et al.
8,136,735 B2 3/2012 Arai et al.
8,138,925 B2 3/2012 Downie et al.
8,140,160 B2 3/2012 Pless et al.
8,140,168 B2 3/2012 Olson et al.
8,140,299 B2 3/2012 Siess
8,140,312 B2 3/2012 Hayter et al.
8,150,321 B2 4/2012 Winter et al.
8,150,516 B2 4/2012 Levine et al.
8,160,670 B2 4/2012 Quyang et al.
8,160,900 B2 4/2012 Taub et al.
8,172,805 B2 5/2012 Mogensen et al.
8,175,673 B2 5/2012 Say et al.
8,179,266 B2 5/2012 Hermle
8,180,423 B2 5/2012 Mang et al.
8,192,394 B2 6/2012 Estes et al.
8,216,138 B1 7/2012 McGaraugh et al.
8,221,332 B2 7/2012 Robbins et al.
8,224,410 B2 7/2012 Hadvary et al.
8,239,166 B2 8/2012 Hayter et al.
8,255,026 B1 8/2012 Al-Ali
8,260,558 B2 9/2012 Hayter et al.
8,262,618 B2 9/2012 Scheurer
8,282,549 B2 10/2012 Brauker et al.
8,333,714 B2 12/2012 Stafford
8,346,335 B2 1/2013 Harper et al.
8,346,337 B2 1/2013 Heller et al.
8,373,544 B2 2/2013 Pitt-Plady
8,374,668 B1 2/2013 Hayter et al.
8,376,945 B2 2/2013 Hayter et al.
8,377,271 B2 2/2013 Mao et al.
8,382,671 B2 2/2013 Anthony et al.

(56) References Cited

U.S. PATENT DOCUMENTS 8,398,664 B2 3/2013 Lamps et al.
8,409,093 B2 4/2013 Bugler
8,409,145 B2 4/2013 Raymond et al.
8,439,838 B2 5/2013 Mogensen et al.
8,444,560 B2 5/2013 Hayter et al.
8,461,985 B2 6/2013 Fennell et al.
8,469,986 B2 6/2013 Schraga
8,512,243 B2 8/2013 Stafford
8,515,518 B2 8/2013 Ouyang et al.
8,515,519 B2 8/2013 Brister et al.
8,538,512 B1 9/2013 Bibian et al.
8,545,403 B2 10/2013 Peyser et al.
8,560,038 B2 10/2013 Hayter et al.
8,562,567 B2 10/2013 Gundberg
8,571,808 B2 10/2013 Hayter
8,583,205 B2 11/2013 Budiman et al.
8,585,591 B2 11/2013 Sloan et al.
8,597,570 B2 12/2013 Terashima et al.
8,600,681 B2 12/2013 Hayter et al.
8,602,991 B2 12/2013 Stafford
8,612,163 B2 12/2013 Hayter et al.
8,615,282 B2 12/2013 Brister et al.
8,617,069 B2 12/2013 Bernstein et al.
8,617,071 B2 12/2013 Say et al.
8,622,903 B2 1/2014 Jin et al.
8,628,498 B2 1/2014 Safabach et al.
8,641,674 B2 2/2014 Bobroff et al.
8,652,043 B2 2/2014 Drucker et al.
8,682,408 B2 3/2014 Boock et al.
8,682,615 B2 3/2014 Hayter et al.
8,684,930 B2 4/2014 Feldman et al.
8,692,655 B2 4/2014 Zimman et al.
8,710,993 B2 4/2014 Hayter et al.
8,747,363 B2 6/2014 Nielsen et al.
8,750,955 B2 6/2014 Brister et al.
8,771,183 B2 7/2014 Sloan
8,797,163 B2 8/2014 Finkenzeller
8,808,515 B2 8/2014 Feldman et al.
8,834,366 B2 9/2014 Hayter et al.
8,845,536 B2 9/2014 Brauker et al.
8,870,822 B2 10/2014 Thalmann et al.
8,880,138 B2 11/2014 Cho
8,945,056 B2 2/2015 Iio et al.
8,961,413 B2 2/2015 Teller et al.
9,007,781 B2 4/2015 Moein et al.
9,014,774 B2 4/2015 Mao et al.
9,031,630 B2 5/2015 Hoss et al.
9,060,719 B2 6/2015 Hayter et al.
9,060,805 B2 6/2015 Goodnow et al.
9,066,697 B2 6/2015 Peyser et al.
9,101,302 B2 8/2015 Mace et al.
9,186,098 B2 11/2015 Lee et al.
9,215,992 B2 12/2015 Donnay et al.
9,241,631 B2 1/2016 Valdes et al.
9,259,175 B2 2/2016 Stafford
9,289,179 B2 3/2016 Hayter et al.
9,295,786 B2 3/2016 Gottlieb et al.
9,357,951 B2 6/2016 Simpson et al.
9,398,872 B2 7/2016 Hayter et al.
9,402,544 B2 8/2016 Yee et al.
9,402,570 B2 8/2016 Pace et al.
9,439,586 B2 9/2016 Bugler
9,451,910 B2 9/2016 Brister et al.
9,474,479 B2 10/2016 Pusey et al.
9,480,421 B2 11/2016 Stafford
9,483,608 B2 11/2016 Hayter et al.
9,504,471 B2 11/2016 Vaitekunas et al.
9,558,325 B2 1/2017 Hayter et al.
9,566,384 B2 2/2017 Gymn et al.
9,636,068 B2 5/2017 Yee et al.
9,668,682 B2 6/2017 Brister et al.
9,743,876 B2 8/2017 Gelfand et al.
9,808,574 B2 11/2017 Yodfat et al.
9,814,414 B2 11/2017 Brister et al.
10,213,139 B2 2/2019 Rao et al.
10,292,632 B2 5/2019 Lee et al.
10,342,489 B2 7/2019 Stafford
10,772,547 B1 9/2020 Lee et al.
10,820,842 B2 11/2020 Harper
10,827,954 B2 11/2020 Hoss et al.
10,874,338 B2 12/2020 Stafford
10,881,340 B2 1/2021 Curry et al.
10,881,341 B1 1/2021 Curry et al.
10,945,647 B2 3/2021 Mazza et al.
10,945,649 B2 3/2021 Lee et al.
10,952,653 B2 3/2021 Harper
10,959,654 B2 3/2021 Curry et al.
10,966,644 B2 4/2021 Stafford
10,973,443 B2 4/2021 Funderburk et al.
10,980,461 B2 4/2021 Simpson et al.
11,000,213 B2 5/2021 Kamath et al.
11,000,216 B2 5/2021 Curry et al.
11,006,870 B2 5/2021 Yee et al.
11,006,871 B2 5/2021 Yee et al.
11,013,440 B2 5/2021 Lee et al.
11,051,724 B2 7/2021 Pace et al.
11,064,917 B2 7/2021 Simpson et al.
11,116,430 B2 9/2021 Funderburk et al.
11,141,084 B2 10/2021 Funderburk et al.
11,166,656 B2 11/2021 Yee et al.
11,179,068 B2 11/2021 Pace et al.
11,197,625 B1 * 12/2021 Schleicher ............. A61B 5/681
11,202,591 B2 12/2021 Yee et al.
11,213,229 B2 1/2022 Yee et al.
11,246,519 B2 2/2022 Donnay et al.
11,266,335 B2 3/2022 Donnay et al.
11,298,056 B2 4/2022 Harper
11,298,058 B2 4/2022 Stafford
11,510,625 B2 11/2022 Gray et al.
2001/0016682 A1 8/2001 Berner et al.
2001/0034479 A1 10/2001 Ring et al.
2001/0037060 A1 11/2001 Thompson et al.
2001/0037366 A1 11/2001 Webb et al.
2001/0039387 A1 11/2001 Rutynowski et al.
2001/0044608 A1 11/2001 Odell et al.
2001/0047127 A1 11/2001 New et al.
2001/0056262 A1 12/2001 Cabiri et al.
2002/0002344 A1 1/2002 Douglas et al.
2002/0010390 A1 1/2002 Guice et al.
2002/0013522 A1 1/2002 Lav et al.
2002/0013538 A1 1/2002 Teller
2002/0016534 A1 2/2002 Trepagnier et al.
2002/0016568 A1 2/2002 Lebel et al.
2002/0019022 A1 2/2002 Dunn et al.
2002/0019584 A1 2/2002 Schulze et al.
2002/0019586 A1 2/2002 Teller et al.
2002/0019606 A1 2/2002 Lebel et al.
2002/0022855 A1 2/2002 Bobroff et al.
2002/0023852 A1 2/2002 McIvor et al.
2002/0029058 A1 3/2002 LeVaughn et al.
2002/0032386 A1 3/2002 Sackner et al.
2002/0039026 A1 4/2002 Stroth et al.
2002/0042090 A1 4/2002 Heller et al.
2002/0045808 A1 4/2002 Ford et al.
2002/0049482 A1 4/2002 Fabian et al.
2002/0050250 A1 5/2002 Peterson et al.
2002/0055711 A1 5/2002 Lavi et al.
2002/0057993 A1 5/2002 Maisey et al.
2002/0065454 A1 5/2002 Lebel et al.
2002/0066764 A1 6/2002 Perry et al.
2002/0072720 A1 6/2002 Hague et al.
2002/0072784 A1 6/2002 Sheppard et al.
2002/0074162 A1 6/2002 Su et al.
2002/0076966 A1 6/2002 Carron et al.
2002/0077599 A1 6/2002 Wojcik
2002/0082487 A1 6/2002 Kollias et al.
2002/0084196 A1 7/2002 Liamos et al.
2002/0091796 A1 7/2002 Higginson et al.
2002/0093969 A1 7/2002 Lin et al.
2002/0095076 A1 7/2002 Krausman et al.
2002/0103499 A1 8/2002 Perez et al.
2002/0106709 A1 8/2002 Potts et al.
2002/0111832 A1 8/2002 Judge
2002/0117639 A1 8/2002 Paolini et al.

(56) References Cited

U.S. PATENT DOCUMENTS

2002/0118528 A1 8/2002 Su et al.
2002/0119711 A1 8/2002 VanAntwerp et al.
2002/0120186 A1 8/2002 Keimel
2002/0124017 A1 9/2002 Mault
2002/0128594 A1 9/2002 Das et al.
2002/0130042 A1 9/2002 Moerman et al.
2002/0133066 A1 9/2002 Miller et al.
2002/0147135 A1 10/2002 Schnell
2002/0150959 A1 10/2002 Lejeune et al.
2002/0151770 A1 10/2002 Noll et al.
2002/0151796 A1 10/2002 Koulik
2002/0151816 A1 10/2002 Rich et al.
2002/0154050 A1 10/2002 Krupp et al.
2002/0161288 A1 10/2002 Shin et al.
2002/0161290 A1 10/2002 Chance
2002/0161338 A1 10/2002 Peterson
2002/0164836 A1 11/2002 Ho
2002/0165462 A1 11/2002 Westbrook et al.
2002/0169369 A1 11/2002 Ward et al.
2002/0169439 A1 11/2002 Flaherty
2002/0169635 A1 11/2002 Shillingburg
2002/0183604 A1 12/2002 Gowda et al.
2002/0185128 A1 12/2002 Theobald
2002/0185130 A1 12/2002 Wright et al.
2002/0188748 A1 12/2002 Blackwell et al.
2002/0197522 A1 12/2002 Lawrence et al.
2002/0198444 A1 12/2002 Ughigaki et al.
2002/0198543 A1 12/2002 Burdulis et al.
2003/0004403 A1 1/2003 Drinan et al.
2003/0020477 A1 1/2003 Goldstein
2003/0023189 A1 1/2003 Kuo
2003/0023317 A1 1/2003 Brauker et al.
2003/0023461 A1 1/2003 Quintanilla et al.
2003/0028089 A1 2/2003 Galley et al.
2003/0028184 A1 2/2003 Lebel et al.
2003/0032077 A1 2/2003 Itoh et al.
2003/0032867 A1 2/2003 Crothall et al.
2003/0032874 A1 2/2003 Rhodes et al.
2003/0042137 A1 3/2003 Mao et al.
2003/0050546 A1 3/2003 Desai et al.
2003/0054428 A1 3/2003 Monfre et al.
2003/0055380 A1 3/2003 Flaherty
2003/0060692 A1 3/2003 Ruchti et al.
2003/0060753 A1 3/2003 Starkweather et al.
2003/0065308 A1 4/2003 Lebel et al.
2003/0069509 A1 4/2003 Matzinger et al.
2003/0069510 A1 4/2003 Semler
2003/0076792 A1 4/2003 Theimer
2003/0077642 A1 4/2003 Fritsch et al.
2003/0078481 A1 4/2003 McIvor et al.
2003/0078560 A1 4/2003 Miller et al.
2003/0083686 A1 5/2003 Freeman et al.
2003/0088166 A1 5/2003 Say et al.
2003/0097092 A1 5/2003 Flaherty
2003/0100040 A1 5/2003 Bonnecaze et al.
2003/0100821 A1 5/2003 Heller et al.
2003/0109775 A1 6/2003 O'Neil et al.
2003/0114897 A1 6/2003 Von Arx et al.
2003/0114898 A1 6/2003 Von Arx et al.
2003/0119457 A1 6/2003 Standke
2003/0125612 A1 7/2003 Fox et al.
2003/0130616 A1 7/2003 Steil et al.
2003/0134347 A1 7/2003 Heller et al.
2003/0135127 A1 7/2003 Sackner et al.
2003/0135333 A1 7/2003 Aceti et al.
2003/0144579 A1 7/2003 Buss
2003/0144581 A1 7/2003 Conn et al.
2003/0144608 A1 7/2003 Kojima et al.
2003/0153900 A1 8/2003 Aceti et al.
2003/0155656 A1 8/2003 Chiu et al.
2003/0168338 A1 9/2003 Gao et al.
2003/0176933 A1 9/2003 Lebel et al.
2003/0187338 A1 10/2003 Say et al.
2003/0188427 A1 10/2003 Say et al.
2003/0199744 A1 10/2003 Buse et al.
2003/0199790 A1 10/2003 Boecker et al.
2003/0199910 A1 10/2003 Boecker et al.
2003/0204290 A1 10/2003 Sadler et al.
2003/0208113 A1 11/2003 Mault et al.
2003/0208114 A1 11/2003 Ackerman
2003/0212317 A1 11/2003 Kovatchev et al.
2003/0212379 A1 11/2003 Bylund et al.
2003/0212579 A1 11/2003 Brown et al.
2003/0216621 A1 11/2003 Alpert et al.
2003/0216630 A1 11/2003 Jersey-Willuhn et al.
2003/0217966 A1 11/2003 Tapsak et al.
2003/0225361 A1 12/2003 Sabra
2003/0225373 A1 12/2003 Bobroff et al.
2003/0236489 A1 12/2003 Jacobson et al.
2004/0002682 A1 1/2004 Kovelman et al.
2004/0010207 A1 * 1/2004 Flaherty ................ A61B 5/157
600/573
2004/0011671 A1 1/2004 Shults et al.
2004/0015131 A1 1/2004 Flaherty et al.
2004/0017300 A1 1/2004 Kotzin et al.
2004/0030226 A1 2/2004 Quy
2004/0030531 A1 2/2004 Miller et al.
2004/0030581 A1 2/2004 Levin et al.
2004/0034289 A1 2/2004 Teller et al.
2004/0039255 A1 2/2004 Simonsen et al.
2004/0039298 A1 2/2004 Abreu
2004/0040840 A1 3/2004 Mao et al.
2004/0045879 A1 3/2004 Shults et al.
2004/0054263 A1 3/2004 Moerman et al.
2004/0060818 A1 4/2004 Feldman et al.
2004/0061232 A1 4/2004 Shah et al.
2004/0063435 A1 4/2004 Sakamoto et al.
2004/0064068 A1 4/2004 DeNuzzio et al.
2004/0064133 A1 4/2004 Miller et al.
2004/0072357 A1 4/2004 Steine et al.
2004/0073266 A1 4/2004 Haefner et al.
2004/0078215 A1 4/2004 Dahlin et al.
2004/0096959 A1 5/2004 Steine et al.
2004/0100376 A1 5/2004 Lye et al.
2004/0105411 A1 6/2004 Boatwright et al.
2004/0106858 A1 6/2004 Say et al.
2004/0106859 A1 6/2004 Say et al.
2004/0106860 A1 6/2004 Say et al.
2004/0111017 A1 6/2004 Say et al.
2004/0116847 A1 6/2004 Wall
2004/0116865 A1 6/2004 Bengtsson
2004/0116866 A1 6/2004 Gorman et al.
2004/0117204 A1 6/2004 Mazar et al.
2004/0119169 A1 6/2004 Hanawa
2004/0122353 A1 6/2004 Shahmirian et al.
2004/0122489 A1 6/2004 Mazar et al.
2004/0133089 A1 7/2004 Kilcoyne et al.
2004/0133164 A1 7/2004 Funderburk et al.
2004/0133390 A1 7/2004 Osorio et al.
2004/0135571 A1 7/2004 Uutela et al.
2004/0135684 A1 7/2004 Steinthal et al.
2004/0138544 A1 7/2004 Ward et al.
2004/0138588 A1 7/2004 Saikley et al.
2004/0138688 A1 7/2004 Giraud
2004/0140211 A1 7/2004 Broy et al.
2004/0142403 A1 7/2004 Hetzel et al.
2004/0146909 A1 7/2004 Duong et al.
2004/0147872 A1 7/2004 Thompson
2004/0147996 A1 7/2004 Miazga et al.
2004/0152366 A1 8/2004 Schultz et al.
2004/0152622 A1 8/2004 Keith et al.
2004/0158207 A1 8/2004 Hunn et al.
2004/0162521 A1 8/2004 Bengtsson et al.
2004/0162678 A1 8/2004 Hetzel et al.
2004/0167801 A1 8/2004 Say et al.
2004/0171910 A1 9/2004 Moore-Steele
2004/0171921 A1 9/2004 Say et al.
2004/0176672 A1 9/2004 Silver et al.
2004/0186362 A1 9/2004 Brauker et al.
2004/0186365 A1 9/2004 Jin et al.
2004/0193020 A1 9/2004 Chiba et al.
2004/0193025 A1 9/2004 Steil et al.
2004/0193090 A1 9/2004 Lebel et al.
2004/0197846 A1 10/2004 Hockersmith et al.

(56) References Cited

U.S. PATENT DOCUMENTS

2004/0199056 A1 10/2004 Husemann et al.
2004/0199059 A1 10/2004 Brauker et al.
2004/0204673 A1 10/2004 Flaherty
2004/0204687 A1 10/2004 Mogensen et al.
2004/0204744 A1 10/2004 Penner et al.
2004/0204868 A1 10/2004 Maynard et al.
2004/0206625 A1 10/2004 Bhullar et al.
2004/0206916 A1 10/2004 Colvin, Jr. et al.
2004/0210122 A1 10/2004 Sleburg
2004/0221057 A1 11/2004 Darcey et al.
2004/0223876 A1 11/2004 Kirollos et al.
2004/0223985 A1 11/2004 Dunfield et al.
2004/0225199 A1 11/2004 Evanyk et al.
2004/0225262 A1 11/2004 Fathallah et al.
2004/0225338 A1 11/2004 Lebel et al.
2004/0236200 A1 11/2004 Say et al.
2004/0236251 A1 11/2004 Roe et al.
2004/0240426 A1 12/2004 Wu et al.
2004/0249253 A1 12/2004 Racchini et al.
2004/0249999 A1 12/2004 Connolly et al.
2004/0254433 A1 12/2004 Bandis et al.
2004/0254434 A1 12/2004 Goodnow et al.
2004/0258564 A1 12/2004 Charlton
2004/0260224 A1 12/2004 Binder et al.
2004/0267300 A1 12/2004 Mace
2005/0001024 A1 1/2005 Kusaka et al.
2005/0003470 A1 1/2005 Nelson et al.
2005/0004439 A1 1/2005 Shin et al.
2005/0004494 A1 1/2005 Perez et al.
2005/0006122 A1 1/2005 Burnette
2005/0010269 A1 1/2005 Lebel et al.
2005/0017864 A1 1/2005 Tsoukalis
2005/0027177 A1 2/2005 Shin et al.
2005/0027180 A1 2/2005 Goode, Jr. et al.
2005/0027181 A1 2/2005 Goode, Jr. et al.
2005/0027462 A1 2/2005 Goode, Jr. et al.
2005/0027463 A1 2/2005 Goode, Jr. et al.
2005/0031689 A1 2/2005 Shults et al.
2005/0033132 A1 2/2005 Shults et al.
2005/0038332 A1 2/2005 Saidara et al.
2005/0038465 A1 2/2005 Shraga
2005/0038680 A1 2/2005 McMahon
2005/0043598 A1 2/2005 Goode, Jr. et al.
2005/0049179 A1 3/2005 Davidson et al.
2005/0051427 A1 3/2005 Brauker et al.
2005/0051440 A1 3/2005 Simpson et al.
2005/0056552 A1 3/2005 Simpson et al.
2005/0065464 A1 3/2005 Talbot et al.
2005/0070774 A1 3/2005 Addison et al.
2005/0070819 A1 3/2005 Poux et al.
2005/0085872 A1 4/2005 Yanagihara et al.
2005/0090607 A1 4/2005 Tapsak et al.
2005/0090850 A1 4/2005 Thoes et al.
2005/0096511 A1 5/2005 Fox et al.
2005/0096512 A1 5/2005 Fox et al.
2005/0096516 A1 5/2005 Soykan et al.
2005/0096520 A1 5/2005 Maekawa et al.
2005/0096587 A1 5/2005 Santini, Jr. et al.
2005/0101912 A1 5/2005 Faust et al.
2005/0101932 A1 5/2005 Cote et al.
2005/0103624 A1 5/2005 Bhullar et al.
2005/0104457 A1 5/2005 Jordan et al.
2005/0106713 A1 5/2005 Phan et al.
2005/0112169 A1 5/2005 Brauker et al.
2005/0112544 A1 5/2005 Xu et al.
2005/0113648 A1 5/2005 Yang et al.
2005/0113653 A1 5/2005 Fox et al.
2005/0113886 A1 5/2005 Fischell et al.
2005/0114068 A1 5/2005 Chey et al.
2005/0115832 A1 6/2005 Simpson et al.
2005/0116683 A1 6/2005 Cheng et al.
2005/0121322 A1 6/2005 Say et al.
2005/0131346 A1 6/2005 Douglas
2005/0131347 A1 6/2005 Marano-Ford et al.
2005/0134731 A1 6/2005 Lee et al.
2005/0137488 A1 6/2005 Henry et al.
2005/0137530 A1 6/2005 Campbell et al.
2005/0143635 A1 6/2005 Kamath et al.
2005/0149066 A1 7/2005 Stafford
2005/0151976 A1 7/2005 Toma
2005/0154271 A1 7/2005 Rasdal et al.
2005/0154410 A1 7/2005 Conway et al.
2005/0159678 A1 7/2005 Taniike et al.
2005/0161346 A1 7/2005 Simpson et al.
2005/0165404 A1 7/2005 Miller
2005/0171442 A1 8/2005 Shirasaki et al.
2005/0173245 A1 8/2005 Feldman et al.
2005/0176136 A1 8/2005 Burd et al.
2005/0177398 A1 8/2005 Watanabe et al.
2005/0181010 A1 8/2005 Hunter et al.
2005/0182306 A1 8/2005 Sloan
2005/0182358 A1 8/2005 Heit et al.
2005/0187442 A1 8/2005 Cho et al.
2005/0187720 A1 8/2005 Goode, Jr. et al.
2005/0192494 A1 9/2005 Ginsberg
2005/0192557 A1 9/2005 Brauker et al.
2005/0195930 A1 9/2005 Spital et al.
2005/0197554 A1 9/2005 Polcha
2005/0197793 A1 9/2005 Baker, Jr.
2005/0199494 A1 9/2005 Say et al.
2005/0203360 A1 9/2005 Brauker et al.
2005/0204134 A1 9/2005 Von Arx et al.
2005/0214892 A1 9/2005 Kovatchev et al.
2005/0215871 A1 9/2005 Feldman et al.
2005/0221504 A1 10/2005 Petruno et al.
2005/0222518 A1 10/2005 Dib
2005/0222599 A1 10/2005 Czernecki et al.
2005/0236277 A9 10/2005 Imran et al.
2005/0236361 A1 10/2005 Ufer et al.
2005/0239154 A1 10/2005 Feldman et al.
2005/0239156 A1 10/2005 Drucker et al.
2005/0241957 A1 11/2005 Mao et al.
2005/0245795 A1 11/2005 Goode, Jr. et al.
2005/0245799 A1 11/2005 Brauker et al.
2005/0245839 A1 11/2005 Stivoric et al.
2005/0245844 A1 11/2005 Mace et al.
2005/0245904 A1 11/2005 Estes et al.
2005/0247319 A1 11/2005 Berger
2005/0251033 A1 11/2005 Scarantino et al.
2005/0261563 A1 11/2005 Zhou et al.
2005/0267325 A1 12/2005 Bouchier et al.
2005/0267327 A1 12/2005 Iizuka et al.
2005/0269214 A1 12/2005 Lee
2005/0277164 A1 12/2005 Drucker et al.
2005/0277912 A1 12/2005 John
2005/0281234 A1 12/2005 Kawamura et al.
2005/0283114 A1 12/2005 Bresina et al.
2005/0283208 A1 12/2005 Von Arx et al.
2005/0283209 A1 12/2005 Katoozi et al.
2005/0284758 A1 12/2005 Funke et al.
2005/0287620 A1 12/2005 Heller et al.
2006/0001538 A1 1/2006 Kraft et al.
2006/0001551 A1 1/2006 Kraft et al.
2006/0004270 A1 1/2006 Bedard et al.
2006/0004272 A1 1/2006 Shah et al.
2006/0004303 A1 1/2006 Weidenhaupt et al.
2006/0006141 A1 1/2006 Ufer et al.
2006/0009727 A1 1/2006 O'Mahony et al.
2006/0010098 A1 1/2006 Goodnow et al.
2006/0012464 A1 1/2006 Nitzan et al.
2006/0015020 A1 1/2006 Neale et al.
2006/0015024 A1 1/2006 Brister et al.
2006/0016700 A1 1/2006 Brister et al.
2006/0019327 A1 1/2006 Brister et al.
2006/0020186 A1 1/2006 Brister et al.
2006/0020187 A1 1/2006 Brister et al.
2006/0020188 A1 1/2006 Kamath et al.
2006/0020189 A1 1/2006 Brister et al.
2006/0020190 A1 1/2006 Kamath et al.
2006/0020191 A1 1/2006 Brister et al.
2006/0020192 A1 1/2006 Brister et al.
2006/0020300 A1 1/2006 Nghiem et al.
2006/0025662 A1 2/2006 Buse et al.
2006/0025663 A1 2/2006 Talbot et al.

(56) References Cited

U.S. PATENT DOCUMENTS

| | | | |
|---|---|---|---|
| 2006/0029177 | A1 | 2/2006 | Cranford, Jr. et al. |
| 2006/0030789 | A1 | 2/2006 | Allen |
| 2006/0031094 | A1 | 2/2006 | Cohen et al. |
| 2006/0036139 | A1 | 2/2006 | Brister et al. |
| 2006/0036140 | A1 | 2/2006 | Brister et al. |
| 2006/0036141 | A1 | 2/2006 | Kamath et al. |
| 2006/0036142 | A1 | 2/2006 | Brister et al. |
| 2006/0036143 | A1 | 2/2006 | Brister et al. |
| 2006/0036144 | A1 | 2/2006 | Brister et al. |
| 2006/0036145 | A1 | 2/2006 | Brister et al. |
| 2006/0040402 | A1 | 2/2006 | Brauker et al. |
| 2006/0040793 | A1 | 2/2006 | Martens et al. |
| 2006/0041276 | A1 | 2/2006 | Chan |
| 2006/0042080 | A1 | 3/2006 | Say et al. |
| 2006/0047220 | A1 | 3/2006 | Sakata et al. |
| 2006/0049359 | A1 | 3/2006 | Busta et al. |
| 2006/0058588 | A1 | 3/2006 | Zdeblick |
| 2006/0064035 | A1 | 3/2006 | Wang et al. |
| 2006/0068208 | A1 | 3/2006 | Tapsak et al. |
| 2006/0079740 | A1 | 4/2006 | Silver et al. |
| 2006/0081469 | A1 | 4/2006 | Lee |
| 2006/0086624 | A1 | 4/2006 | Tapsak et al. |
| 2006/0091006 | A1 | 5/2006 | Wang et al. |
| 2006/0094944 | A1 | 5/2006 | Chuang |
| 2006/0095014 | A1 | 5/2006 | Ethelfeld |
| 2006/0116607 | A1 | 6/2006 | Nakamura et al. |
| 2006/0129173 | A1 | 6/2006 | Wilkinson |
| 2006/0129733 | A1 | 6/2006 | Solbelman |
| 2006/0135908 | A1 | 6/2006 | Liniger et al. |
| 2006/0142651 | A1 | 6/2006 | Brister et al. |
| 2006/0154642 | A1 | 7/2006 | Scannell |
| 2006/0155180 | A1 | 7/2006 | Brister et al. |
| 2006/0155210 | A1 | 7/2006 | Beckman et al. |
| 2006/0155317 | A1 | 7/2006 | List |
| 2006/0161194 | A1 | 7/2006 | Freeman et al. |
| 2006/0161664 | A1 | 7/2006 | Motoyama |
| 2006/0166629 | A1 | 7/2006 | Reggiardo |
| 2006/0173260 | A1 | 8/2006 | Gaoni et al. |
| 2006/0173406 | A1 | 8/2006 | Hayes et al. |
| 2006/0173444 | A1 | 8/2006 | Choy et al. |
| 2006/0181695 | A1 | 8/2006 | Sage, Jr. |
| 2006/0183984 | A1 | 8/2006 | Dobbles et al. |
| 2006/0183985 | A1 | 8/2006 | Brister et al. |
| 2006/0189851 | A1 | 8/2006 | Tvig et al. |
| 2006/0189863 | A1 | 8/2006 | Peyser et al. |
| 2006/0189939 | A1 | 8/2006 | Gonnelli et al. |
| 2006/0193375 | A1 | 8/2006 | Lee et al. |
| 2006/0195029 | A1 | 8/2006 | Shults et al. |
| 2006/0195133 | A1 | 8/2006 | Freeman et al. |
| 2006/0200020 | A1 | 9/2006 | Brister et al. |
| 2006/0200022 | A1 | 9/2006 | Brauker et al. |
| 2006/0200181 | A1 | 9/2006 | Fukuzawa et al. |
| 2006/0200970 | A1 | 9/2006 | Brister et al. |
| 2006/0200981 | A1 | 9/2006 | Bhullar et al. |
| 2006/0200982 | A1 | 9/2006 | Bhullar et al. |
| 2006/0202805 | A1 | 9/2006 | Schulman et al. |
| 2006/0202859 | A1 | 9/2006 | Mastrototaro et al. |
| 2006/0211921 | A1 | 9/2006 | Brauker et al. |
| 2006/0220839 | A1 | 10/2006 | Fifolt et al. |
| 2006/0222566 | A1 | 10/2006 | Brauker et al. |
| 2006/0222866 | A1 | 10/2006 | Nakamura et al. |
| 2006/0224108 | A1 | 10/2006 | Brauker et al. |
| 2006/0224109 | A1 | 10/2006 | Steil et al. |
| 2006/0224141 | A1 | 10/2006 | Rush et al. |
| 2006/0224171 | A1 | 10/2006 | Sakata et al. |
| 2006/0226985 | A1 | 10/2006 | Goodnow et al. |
| 2006/0229512 | A1 | 10/2006 | Petisce et al. |
| 2006/0233839 | A1 | 10/2006 | Jacquet |
| 2006/0247508 | A1 | 11/2006 | Fennell |
| 2006/0247710 | A1 | 11/2006 | Goetz et al. |
| 2006/0247895 | A1 | 11/2006 | Liamos et al. |
| 2006/0248398 | A1 | 11/2006 | Neel et al. |
| 2006/0253085 | A1 | 11/2006 | Geismar et al. |
| 2006/0253086 | A1 | 11/2006 | Moberg et al. |
| 2006/0258929 | A1 | 11/2006 | Goode, Jr. et al. |
| 2006/0258939 | A1 | 11/2006 | Pesach et al. |
| 2006/0258959 | A1 | 11/2006 | Sode |
| 2006/0264785 | A1 | 11/2006 | Dring et al. |
| 2006/0264888 | A1 | 11/2006 | Moberg et al. |
| 2006/0270922 | A1 | 11/2006 | Brauker et al. |
| 2006/0270923 | A1 | 11/2006 | Brauker et al. |
| 2006/0271013 | A1 | 11/2006 | Triplett et al. |
| 2006/0272652 | A1 | 12/2006 | Stocker et al. |
| 2006/0273759 | A1 | 12/2006 | Reggiardo |
| 2006/0276714 | A1 | 12/2006 | Holt et al. |
| 2006/0276724 | A1 | 12/2006 | Freeman et al. |
| 2006/0276771 | A1 | 12/2006 | Galley et al. |
| 2006/0281985 | A1 | 12/2006 | Ward et al. |
| 2006/0282042 | A1 | 12/2006 | Walters et al. |
| 2006/0287591 | A1 | 12/2006 | Ocvirk et al. |
| 2006/0287691 | A1 | 12/2006 | Drew |
| 2006/0290496 | A1 | 12/2006 | Peeters et al. |
| 2006/0293607 | A1 | 12/2006 | Alt et al. |
| 2007/0007133 | A1 | 1/2007 | Mang et al. |
| 2007/0010950 | A1 | 1/2007 | Abensour et al. |
| 2007/0016129 | A1 | 1/2007 | Liniger et al. |
| 2007/0016381 | A1 | 1/2007 | Kamath et al. |
| 2007/0017983 | A1 | 1/2007 | Frank et al. |
| 2007/0027381 | A1 | 2/2007 | Stafford |
| 2007/0027384 | A1 | 2/2007 | Brister et al. |
| 2007/0027385 | A1 | 2/2007 | Brister et al. |
| 2007/0027507 | A1 | 2/2007 | Burdett et al. |
| 2007/0030154 | A1 | 2/2007 | Aiki et al. |
| 2007/0032706 | A1 | 2/2007 | Kamath et al. |
| 2007/0032717 | A1 | 2/2007 | Brister et al. |
| 2007/0032718 | A1 | 2/2007 | Shults et al. |
| 2007/0033074 | A1 | 2/2007 | Nitzan et al. |
| 2007/0038044 | A1 * | 2/2007 | Dobbles ............. A61B 5/14546 600/316 |
| 2007/0045902 | A1 | 3/2007 | Brauker et al. |
| 2007/0049865 | A1 | 3/2007 | Radmer et al. |
| 2007/0055799 | A1 | 3/2007 | Koehler et al. |
| 2007/0056858 | A1 | 3/2007 | Chen et al. |
| 2007/0059196 | A1 | 3/2007 | Brister et al. |
| 2007/0060801 | A1 | 3/2007 | Neinast |
| 2007/0060814 | A1 | 3/2007 | Stafford |
| 2007/0060869 | A1 | 3/2007 | Tolle et al. |
| 2007/0066873 | A1 | 3/2007 | Kamath et al. |
| 2007/0068807 | A1 | 3/2007 | Feldman et al. |
| 2007/0071681 | A1 | 3/2007 | Gadkar et al. |
| 2007/0073129 | A1 | 3/2007 | Shah et al. |
| 2007/0078320 | A1 | 4/2007 | Stafford |
| 2007/0078321 | A1 | 4/2007 | Mazza et al. |
| 2007/0078322 | A1 | 4/2007 | Stafford |
| 2007/0078323 | A1 | 4/2007 | Reggiardo et al. |
| 2007/0088377 | A1 | 4/2007 | Levaughn et al. |
| 2007/0090511 | A1 | 4/2007 | Borland et al. |
| 2007/0093704 | A1 | 4/2007 | Brister et al. |
| 2007/0093754 | A1 | 4/2007 | Mogensen et al. |
| 2007/0093786 | A1 | 4/2007 | Goldsmith et al. |
| 2007/0095661 | A1 | 5/2007 | Wang et al. |
| 2007/0100218 | A1 | 5/2007 | Sweitzer et al. |
| 2007/0100222 | A1 | 5/2007 | Mastrototaro et al. |
| 2007/0106133 | A1 | 5/2007 | Satchwell et al. |
| 2007/0106135 | A1 | 5/2007 | Sloan et al. |
| 2007/0108048 | A1 | 5/2007 | Wang et al. |
| 2007/0110124 | A1 | 5/2007 | Shiraki et al. |
| 2007/0111196 | A1 | 5/2007 | Alarcon et al. |
| 2007/0123819 | A1 | 5/2007 | Mernoe et al. |
| 2007/0124002 | A1 | 5/2007 | Estes et al. |
| 2007/0129621 | A1 | 6/2007 | Kellogg et al. |
| 2007/0135696 | A1 | 6/2007 | Ward |
| 2007/0135774 | A1 | 6/2007 | Turner et al. |
| 2007/0149873 | A1 | 6/2007 | Say et al. |
| 2007/0149875 | A1 | 6/2007 | Ouyang et al. |
| 2007/0153705 | A1 | 7/2007 | Rosar et al. |
| 2007/0156033 | A1 | 7/2007 | Causey, III et al. |
| 2007/0156094 | A1 | 7/2007 | Safabash et al. |
| 2007/0163880 | A1 | 7/2007 | Woo et al. |
| 2007/0168224 | A1 | 7/2007 | Letzt et al. |
| 2007/0173706 | A1 | 7/2007 | Neinast et al. |
| 2007/0173709 | A1 | 7/2007 | Petisce et al. |
| 2007/0173710 | A1 | 7/2007 | Petisce et al. |
| 2007/0173711 | A1 | 7/2007 | Shah et al. |

(56) References Cited

U.S. PATENT DOCUMENTS

| | | | |
|---|---|---|---|
| 2007/0173741 | A1 | 7/2007 | Deshmukh et al. |
| 2007/0173761 | A1 | 7/2007 | Kanderian, Jr. et al. |
| 2007/0179349 | A1 | 8/2007 | Hoyme et al. |
| 2007/0179352 | A1 | 8/2007 | Randlov et al. |
| 2007/0179406 | A1 | 8/2007 | DeNuzzio et al. |
| 2007/0191701 | A1 | 8/2007 | Feldman et al. |
| 2007/0191702 | A1 | 8/2007 | Yodfat et al. |
| 2007/0197889 | A1 | 8/2007 | Brister et al. |
| 2007/0199818 | A1 | 8/2007 | Petyt et al. |
| 2007/0202562 | A1 | 8/2007 | Curry et al. |
| 2007/0203407 | A1 | 8/2007 | Hoss et al. |
| 2007/0203539 | A1 | 8/2007 | Stone et al. |
| 2007/0203966 | A1 | 8/2007 | Brauker et al. |
| 2007/0208244 | A1 | 9/2007 | Brauker et al. |
| 2007/0208245 | A1 | 9/2007 | Brauker et al. |
| 2007/0208246 | A1 | 9/2007 | Brauker et al. |
| 2007/0213611 | A1 | 9/2007 | Simpson et al. |
| 2007/0219480 | A1 | 9/2007 | Kamen et al. |
| 2007/0219496 | A1 | 9/2007 | Kamen et al. |
| 2007/0222609 | A1 | 9/2007 | Duron et al. |
| 2007/0227911 | A1 | 10/2007 | Wang et al. |
| 2007/0228071 | A1 | 10/2007 | Kamen et al. |
| 2007/0231846 | A1 | 10/2007 | Cosentino et al. |
| 2007/0232877 | A1 | 10/2007 | He |
| 2007/0232878 | A1 | 10/2007 | Kovatchev et al. |
| 2007/0232879 | A1 | 10/2007 | Brister et al. |
| 2007/0232880 | A1 | 10/2007 | Siddiqui et al. |
| 2007/0233013 | A1 | 10/2007 | Schoenberg et al. |
| 2007/0235331 | A1 | 10/2007 | Simpson et al. |
| 2007/0244368 | A1 | 10/2007 | Bayloff et al. |
| 2007/0244379 | A1 | 10/2007 | Boock et al. |
| 2007/0244383 | A1 | 10/2007 | Talbot et al. |
| 2007/0244398 | A1 | 10/2007 | Lo et al. |
| 2007/0249922 | A1 | 10/2007 | Peyser et al. |
| 2007/0253021 | A1 | 11/2007 | Mehta et al. |
| 2007/0255116 | A1 | 11/2007 | Mehta et al. |
| 2007/0255125 | A1 | 11/2007 | Moberg et al. |
| 2007/0255302 | A1 | 11/2007 | Koeppel et al. |
| 2007/0255321 | A1 | 11/2007 | Gerber et al. |
| 2007/0255348 | A1 | 11/2007 | Holtzclaw |
| 2007/0255531 | A1 | 11/2007 | Drew |
| 2007/0258395 | A1 | 11/2007 | Jollota et al. |
| 2007/0270672 | A1 | 11/2007 | Hayter |
| 2007/0282299 | A1 | 12/2007 | Hellwig |
| 2007/0285238 | A1 | 12/2007 | Batra |
| 2008/0004512 | A1 | 1/2008 | Funderburk et al. |
| 2008/0004515 | A1 | 1/2008 | Jennewine et al. |
| 2008/0004573 | A1 | 1/2008 | Kaufmann et al. |
| 2008/0004601 | A1 | 1/2008 | Jennewine et al. |
| 2008/0004904 | A1 | 1/2008 | Tran |
| 2008/0009304 | A1 | 1/2008 | Fry |
| 2008/0009692 | A1 | 1/2008 | Stafford |
| 2008/0009805 | A1 | 1/2008 | Ethelfeld |
| 2008/0017522 | A1 | 1/2008 | Heller et al. |
| 2008/0018433 | A1 | 1/2008 | Pitt-Pladdy |
| 2008/0021543 | A1 | 1/2008 | Shrivastava |
| 2008/0021666 | A1 | 1/2008 | Goode, Jr. et al. |
| 2008/0027296 | A1 | 1/2008 | Hadvary et al. |
| 2008/0027474 | A1 | 1/2008 | Curry et al. |
| 2008/0029391 | A1 | 2/2008 | Mao et al. |
| 2008/0030369 | A1 | 2/2008 | Mann et al. |
| 2008/0031941 | A1 | 2/2008 | Pettersson |
| 2008/0033254 | A1 | 2/2008 | Kamath et al. |
| 2008/0033268 | A1 | 2/2008 | Stafford |
| 2008/0033273 | A1 | 2/2008 | Zhou et al. |
| 2008/0033318 | A1 | 2/2008 | Mace et al. |
| 2008/0039702 | A1 | 2/2008 | Hayter et al. |
| 2008/0045824 | A1 | 2/2008 | Tapsak et al. |
| 2008/0046038 | A1 | 2/2008 | Hill et al. |
| 2008/0055070 | A1 | 3/2008 | Bange et al. |
| 2008/0057484 | A1 | 3/2008 | Miyata et al. |
| 2008/0058625 | A1 | 3/2008 | McGarraugh et al. |
| 2008/0058626 | A1 | 3/2008 | Miyata et al. |
| 2008/0058678 | A1 | 3/2008 | Miyata et al. |
| 2008/0058773 | A1 | 3/2008 | John |
| 2008/0058830 | A1 | 3/2008 | Cole et al. |
| 2008/0059227 | A1 | 3/2008 | Clapp |
| 2008/0060955 | A1 | 3/2008 | Goodnow |
| 2008/0061961 | A1 | 3/2008 | John |
| 2008/0062055 | A1 | 3/2008 | Cunningham et al. |
| 2008/0064437 | A1 | 3/2008 | Chambers et al. |
| 2008/0064937 | A1 | 3/2008 | McGarraugh et al. |
| 2008/0064941 | A1 | 3/2008 | Funderburk et al. |
| 2008/0064943 | A1 | 3/2008 | Talbot et al. |
| 2008/0064944 | A1 | 3/2008 | VanAntwerp et al. |
| 2008/0065646 | A1 | 3/2008 | Zhang et al. |
| 2008/0066305 | A1 | 3/2008 | Wang et al. |
| 2008/0067627 | A1 | 3/2008 | Boeck et al. |
| 2008/0071156 | A1 | 3/2008 | Brister et al. |
| 2008/0071157 | A1 | 3/2008 | McGarraugh et al. |
| 2008/0071158 | A1 | 3/2008 | McGarraugh et al. |
| 2008/0071328 | A1 | 3/2008 | Haubrich et al. |
| 2008/0071580 | A1 | 3/2008 | Marcus |
| 2008/0081977 | A1 | 4/2008 | Hayter et al. |
| 2008/0083617 | A1 | 4/2008 | Simpson et al. |
| 2008/0086042 | A1 | 4/2008 | Brister et al. |
| 2008/0086044 | A1 | 4/2008 | Brister et al. |
| 2008/0086273 | A1 | 4/2008 | Shults et al. |
| 2008/0092638 | A1 | 4/2008 | Brenneman et al. |
| 2008/0092911 | A1 | 4/2008 | Schulman et al. |
| 2008/0097246 | A1 | 4/2008 | Stafford |
| 2008/0097289 | A1 | 4/2008 | Steil et al. |
| 2008/0097908 | A1 | 4/2008 | Dicks et al. |
| 2008/0099332 | A1 | 5/2008 | Scott et al. |
| 2008/0102441 | A1 | 5/2008 | Chen et al. |
| 2008/0108942 | A1 | 5/2008 | Brister et al. |
| 2008/0112848 | A1 | 5/2008 | Huffstodt et al. |
| 2008/0114228 | A1 | 5/2008 | Mccluskey et al. |
| 2008/0114280 | A1 | 5/2008 | Stafford |
| 2008/0119705 | A1 | 5/2008 | Patel et al. |
| 2008/0119707 | A1 | 5/2008 | Stafford |
| 2008/0119710 | A1 | 5/2008 | Reggiardo et al. |
| 2008/0125636 | A1 | 5/2008 | Ward et al. |
| 2008/0127052 | A1 | 5/2008 | Rostoker |
| 2008/0129486 | A1 | 6/2008 | Jeckelmann et al. |
| 2008/0133059 | A1 | 6/2008 | Trippel et al. |
| 2008/0133702 | A1 | 6/2008 | Sharma et al. |
| 2008/0139910 | A1 | 6/2008 | Mastrototaro et al. |
| 2008/0146904 | A1 | 6/2008 | Hunn |
| 2008/0148873 | A1 | 6/2008 | Wang |
| 2008/0154205 | A1 | 6/2008 | Wojcik |
| 2008/0154286 | A1 | 6/2008 | Abbott et al. |
| 2008/0154513 | A1 | 6/2008 | Kovatchev et al. |
| 2008/0161664 | A1 | 7/2008 | Mastrototaro et al. |
| 2008/0161666 | A1 | 7/2008 | Feldman et al. |
| 2008/0167543 | A1 | 7/2008 | Say et al. |
| 2008/0167572 | A1 | 7/2008 | Stivoric et al. |
| 2008/0167578 | A1 | 7/2008 | Bryer et al. |
| 2008/0172205 | A1 | 7/2008 | Breton et al. |
| 2008/0177149 | A1 | 7/2008 | Weinart et al. |
| 2008/0177165 | A1 | 7/2008 | Blomquist et al. |
| 2008/0179187 | A1 | 7/2008 | Ouyang |
| 2008/0182537 | A1 | 7/2008 | Manku et al. |
| 2008/0183060 | A1 | 7/2008 | Steil et al. |
| 2008/0183061 | A1 | 7/2008 | Goode, Jr. et al. |
| 2008/0183399 | A1 | 7/2008 | Goode, Jr. et al. |
| 2008/0188731 | A1 | 8/2008 | Brister et al. |
| 2008/0188796 | A1 | 8/2008 | Steil et al. |
| 2008/0189051 | A1 | 8/2008 | Goode, Jr. et al. |
| 2008/0194926 | A1 | 8/2008 | Goh et al. |
| 2008/0194934 | A1 | 8/2008 | Ray et al. |
| 2008/0194935 | A1 | 8/2008 | Brister et al. |
| 2008/0194936 | A1 | 8/2008 | Goode, Jr. et al. |
| 2008/0194937 | A1 | 8/2008 | Goode, Jr. et al. |
| 2008/0194938 | A1 | 8/2008 | Brister et al. |
| 2008/0195049 | A1 | 8/2008 | Thalmann et al. |
| 2008/0195232 | A1 | 8/2008 | Carr-Brendel et al. |
| 2008/0195967 | A1 | 8/2008 | Goode, Jr. et al. |
| 2008/0197024 | A1 | 8/2008 | Simpson et al. |
| 2008/0200788 | A1 | 8/2008 | Brister et al. |
| 2008/0200789 | A1 | 8/2008 | Brister et al. |
| 2008/0200791 | A1 | 8/2008 | Simpson et al. |
| 2008/0200897 | A1 | 8/2008 | Hoss et al. |
| 2008/0201325 | A1 | 8/2008 | Doniger et al. |

(56) References Cited

U.S. PATENT DOCUMENTS

2008/0208025 A1 8/2008 Shults et al.
2008/0208026 A1 8/2008 Noujaim et al.
2008/0208113 A1 8/2008 Damiano et al.
2008/0214481 A1 9/2008 Challoner et al.
2008/0214900 A1 9/2008 Fennell et al.
2008/0214910 A1 9/2008 Buck
2008/0214915 A1 9/2008 Brister et al.
2008/0214918 A1 9/2008 Brister et al.
2008/0215035 A1 9/2008 Yodfat et al.
2008/0228051 A1 9/2008 Shults et al.
2008/0228054 A1 9/2008 Shults et al.
2008/0234561 A1 9/2008 Roesicke et al.
2008/0234992 A1 9/2008 Ray et al.
2008/0235469 A1 9/2008 Drew
2008/0242961 A1 10/2008 Brister et al.
2008/0242962 A1 10/2008 Roesicke et al.
2008/0242963 A1 10/2008 Essenpreis et al.
2008/0243051 A1 10/2008 DeStefano
2008/0252459 A1 10/2008 Butler et al.
2008/0254544 A1 10/2008 Modzelewski et al.
2008/0255434 A1 10/2008 Hayter et al.
2008/0255437 A1 10/2008 Hayter
2008/0255438 A1 10/2008 Saidara et al.
2008/0255440 A1 10/2008 Eilerson et al.
2008/0255808 A1 10/2008 Hayter
2008/0256048 A1 10/2008 Hayter
2008/0262300 A1 10/2008 Reynolds et al.
2008/0262469 A1 10/2008 Brister et al.
2008/0267823 A1 10/2008 Wang et al.
2008/0269584 A1 10/2008 Shekalim
2008/0269673 A1 10/2008 Butoi et al.
2008/0269683 A1 10/2008 Bikovsky
2008/0269687 A1 10/2008 Chong et al.
2008/0269714 A1 10/2008 Mastrototaro et al.
2008/0275313 A1 11/2008 Brister et al.
2008/0275327 A1 11/2008 Faarbaek et al.
2008/0278333 A1 11/2008 Fennell et al.
2008/0281178 A1 11/2008 Chuang et al.
2008/0281179 A1 11/2008 Fennell et al.
2008/0283396 A1 11/2008 Wang et al.
2008/0287755 A1 11/2008 Sass et al.
2008/0287761 A1 11/2008 Hayter
2008/0287762 A1 11/2008 Hayter
2008/0287763 A1 11/2008 Hayter
2008/0287764 A1 11/2008 Rasdal et al.
2008/0287765 A1 11/2008 Rasdal et al.
2008/0287766 A1 11/2008 Rasdal et al.
2008/0288180 A1 11/2008 Hayter
2008/0288204 A1 11/2008 Hayter et al.
2008/0294024 A1 11/2008 Cosentino et al.
2008/0294096 A1 11/2008 Uber et al.
2008/0296155 A1 12/2008 Shults et al.
2008/0300476 A1 12/2008 Stafford
2008/0300572 A1 12/2008 Rankers et al.
2008/0306368 A1 12/2008 Goode, Jr. et al.
2008/0306434 A1 12/2008 Dobbles et al.
2008/0306435 A1 12/2008 Kamath et al.
2008/0306444 A1 12/2008 Brister et al.
2008/0308523 A1 12/2008 Krulevitch et al.
2008/0312518 A1 12/2008 Jina et al.
2008/0312601 A1 12/2008 Cane
2008/0312841 A1 12/2008 Hayter
2008/0312842 A1 12/2008 Hayter
2008/0312844 A1 12/2008 Hayter et al.
2008/0312845 A1 12/2008 Hayter et al.
2008/0312859 A1 12/2008 Skyggebjerg et al.
2008/0319085 A1 12/2008 Wright et al.
2008/0319295 A1 12/2008 Bernstein et al.
2008/0319296 A1 12/2008 Bernstein et al.
2008/0319414 A1 12/2008 Yodfat et al.
2008/0319416 A1 12/2008 Yodfat et al.
2009/0005659 A1 1/2009 Kollias et al.
2009/0005665 A1 1/2009 Hayter et al.
2009/0005666 A1 1/2009 Shin et al.
2009/0005729 A1 1/2009 Hendrixson et al.
2009/0006034 A1 1/2009 Hayter et al.
2009/0006061 A1 1/2009 Thukral et al.
2009/0006133 A1 1/2009 Weinart et al.
2009/0012376 A1 1/2009 Agus
2009/0012377 A1 1/2009 Jennewine et al.
2009/0012379 A1 1/2009 Goode, Jr. et al.
2009/0018424 A1 1/2009 Kamath et al.
2009/0018425 A1 1/2009 Ouyang et al.
2009/0020502 A1 1/2009 Bhullar et al.
2009/0028824 A1 1/2009 Chiang et al.
2009/0030293 A1 1/2009 Cooper et al.
2009/0030294 A1 1/2009 Petisce et al.
2009/0033482 A1 2/2009 Hayter et al.
2009/0036747 A1 2/2009 Hayter et al.
2009/0036758 A1 2/2009 Brauker et al.
2009/0036760 A1 2/2009 Hayter
2009/0036763 A1 2/2009 Brauker et al.
2009/0036915 A1 2/2009 Karbowniczek et al.
2009/0040022 A1 2/2009 Finkenzeller
2009/0043181 A1 2/2009 Brauker et al.
2009/0043182 A1 2/2009 Brauker et al.
2009/0043525 A1 2/2009 Brauker et al.
2009/0043541 A1 2/2009 Brauker et al.
2009/0043542 A1 2/2009 Brauker et al.
2009/0045055 A1 2/2009 Rhodes et al.
2009/0048499 A1 2/2009 Glejbol
2009/0048503 A1 2/2009 Dalal et al.
2009/0048563 A1 2/2009 Ethelfeld et al.
2009/0054737 A1 2/2009 Magar et al.
2009/0054745 A1 2/2009 Jennewine et al.
2009/0054747 A1 2/2009 Fennell
2009/0054748 A1 2/2009 Feldman et al.
2009/0054753 A1 2/2009 Robinson et al.
2009/0054866 A1 2/2009 Teisen-Simony et al.
2009/0055149 A1 2/2009 Hayter et al.
2009/0058635 A1 3/2009 LaLonde et al.
2009/0062633 A1 3/2009 Brauker et al.
2009/0062635 A1 3/2009 Brauker et al.
2009/0062767 A1 3/2009 Van Antwerp et al.
2009/0063187 A1 3/2009 Johnson et al.
2009/0063402 A1 3/2009 Hayter
2009/0069658 A1 3/2009 Say et al.
2009/0069750 A1 3/2009 Schraga
2009/0076356 A1 3/2009 Simpson et al.
2009/0076359 A1 3/2009 Peyser
2009/0076360 A1 3/2009 Brister et al.
2009/0076361 A1 3/2009 Kamath et al.
2009/0082693 A1 3/2009 Stafford
2009/0085768 A1 4/2009 Patel et al.
2009/0085873 A1 4/2009 Betts et al.
2009/0088614 A1 4/2009 Taub
2009/0088787 A1 4/2009 Koike et al.
2009/0093687 A1 4/2009 Telfort et al.
2009/0099436 A1 4/2009 Brister et al.
2009/0099521 A1 4/2009 Gravesen et al.
2009/0102678 A1 4/2009 Mazza et al.
2009/0105554 A1 4/2009 Stahmann et al.
2009/0105560 A1 4/2009 Solomon
2009/0105568 A1 4/2009 Bugler
2009/0105569 A1 4/2009 Stafford
2009/0105570 A1 4/2009 Sloan et al.
2009/0105571 A1 4/2009 Fennell et al.
2009/0105636 A1 4/2009 Hayter et al.
2009/0108992 A1 4/2009 Shafer
2009/0112123 A1 4/2009 Freeman et al.
2009/0112478 A1 4/2009 Mueller, Jr. et al.
2009/0118592 A1 5/2009 Klitgaard
2009/0124877 A1 5/2009 Goode, Jr. et al.
2009/0124878 A1 5/2009 Goode, Jr. et al.
2009/0124879 A1 5/2009 Brister et al.
2009/0124964 A1 5/2009 Leach et al.
2009/0124979 A1 5/2009 Raymond et al.
2009/0131768 A1 5/2009 Simpson et al.
2009/0131769 A1 5/2009 Leach et al.
2009/0131776 A1 5/2009 Simpson et al.
2009/0131777 A1 5/2009 Simpson et al.
2009/0131860 A1 5/2009 Nielsen
2009/0137886 A1 5/2009 Shariati et al.
2009/0137887 A1 5/2009 Shariati et al.

(56) References Cited

U.S. PATENT DOCUMENTS

| | | | |
|---|---|---|---|
| 2009/0143659 | A1 | 6/2009 | Li et al. |
| 2009/0143660 | A1 | 6/2009 | Brister et al. |
| 2009/0149728 | A1 | 6/2009 | Van Antwerp et al. |
| 2009/0150186 | A1 | 6/2009 | Cohen et al. |
| 2009/0150454 | A1 | 6/2009 | Gejdos et al. |
| 2009/0156919 | A1 | 6/2009 | Brister et al. |
| 2009/0156924 | A1 | 6/2009 | Shariati et al. |
| 2009/0163790 | A1 | 6/2009 | Brister et al. |
| 2009/0163791 | A1 | 6/2009 | Brister et al. |
| 2009/0163855 | A1 | 6/2009 | Shin et al. |
| 2009/0164190 | A1 | 6/2009 | Hayter |
| 2009/0164239 | A1 | 6/2009 | Hayter et al. |
| 2009/0164251 | A1 | 6/2009 | Hayter |
| 2009/0171182 | A1 | 7/2009 | Stafford |
| 2009/0177068 | A1 | 7/2009 | Stivoric et al. |
| 2009/0178459 | A1 | 7/2009 | Li et al. |
| 2009/0182217 | A1 | 7/2009 | Li et al. |
| 2009/0189738 | A1 | 7/2009 | Hermle |
| 2009/0192366 | A1 | 7/2009 | Mensinger et al. |
| 2009/0192380 | A1 | 7/2009 | Shariati et al. |
| 2009/0192722 | A1 | 7/2009 | Shariati et al. |
| 2009/0192724 | A1 | 7/2009 | Brauker et al. |
| 2009/0192745 | A1 | 7/2009 | Kamath et al. |
| 2009/0192751 | A1 | 7/2009 | Kamath et al. |
| 2009/0198118 | A1 | 8/2009 | Hayter et al. |
| 2009/0198186 | A1 | 8/2009 | Mernoe et al. |
| 2009/0198215 | A1 | 8/2009 | Chong et al. |
| 2009/0203981 | A1 | 8/2009 | Brauker et al. |
| 2009/0204340 | A1 | 8/2009 | Feldman et al. |
| 2009/0204341 | A1 | 8/2009 | Brauker et al. |
| 2009/0210249 | A1 | 8/2009 | Rasch-Menges et al. |
| 2009/0212766 | A1 | 8/2009 | Olson et al. |
| 2009/0216100 | A1 | 8/2009 | Ebner et al. |
| 2009/0216103 | A1 | 8/2009 | Brister et al. |
| 2009/0216215 | A1 | 8/2009 | Thalmann et al. |
| 2009/0234200 | A1 | 9/2009 | Husheer |
| 2009/0240120 | A1 | 9/2009 | Mensinger et al. |
| 2009/0240121 | A1 | 9/2009 | Bickoff |
| 2009/0240128 | A1 | 9/2009 | Mensinger et al. |
| 2009/0240193 | A1 | 9/2009 | Mensinger et al. |
| 2009/0242399 | A1 | 10/2009 | Kamath et al. |
| 2009/0242425 | A1 | 10/2009 | Kamath et al. |
| 2009/0247855 | A1 | 10/2009 | Boock et al. |
| 2009/0247856 | A1 | 10/2009 | Boock et al. |
| 2009/0247857 | A1 | 10/2009 | Harper et al. |
| 2009/0247931 | A1 | 10/2009 | Damgaard-Sorenson |
| 2009/0253973 | A1 | 10/2009 | Bashan et al. |
| 2009/0259118 | A1 | 10/2009 | Feldman et al. |
| 2009/0259201 | A1 | 10/2009 | Hwang et al. |
| 2009/0259202 | A1 | 10/2009 | Leeflang et al. |
| 2009/0267765 | A1 | 10/2009 | Greene et al. |
| 2009/0270765 | A1 | 10/2009 | Ghesquire et al. |
| 2009/0277242 | A1 | 11/2009 | Crane et al. |
| 2009/0281406 | A1 | 11/2009 | McGarraugh et al. |
| 2009/0287073 | A1 | 11/2009 | Boock et al. |
| 2009/0287074 | A1 | 11/2009 | Shults et al. |
| 2009/0289796 | A1 | 11/2009 | Blumberg |
| 2009/0292184 | A1 | 11/2009 | Funderburk et al. |
| 2009/0292185 | A1 | 11/2009 | Funderburk et al. |
| 2009/0294277 | A1 | 12/2009 | Thomas et al. |
| 2009/0298182 | A1 | 12/2009 | Schulat et al. |
| 2009/0299152 | A1 | 12/2009 | Taub et al. |
| 2009/0299155 | A1 | 12/2009 | Yang et al. |
| 2009/0299156 | A1 | 12/2009 | Simpson et al. |
| 2009/0299162 | A1 | 12/2009 | Brauker et al. |
| 2009/0299167 | A1 | 12/2009 | Seymour |
| 2009/0299276 | A1 | 12/2009 | Brauker et al. |
| 2009/0299301 | A1 | 12/2009 | Gottlieb et al. |
| 2010/0004597 | A1 | 1/2010 | Gryn et al. |
| 2010/0010324 | A1 | 1/2010 | Brauker et al. |
| 2010/0010329 | A1 | 1/2010 | Taub et al. |
| 2010/0010331 | A1 | 1/2010 | Brauker et al. |
| 2010/0010332 | A1 | 1/2010 | Brauker et al. |
| 2010/0014626 | A1 | 1/2010 | Fennell et al. |
| 2010/0016687 | A1 | 1/2010 | Brauker et al. |
| 2010/0016698 | A1 | 1/2010 | Rasdal et al. |
| 2010/0022855 | A1 | 1/2010 | Brauker et al. |
| 2010/0022863 | A1 | 1/2010 | Mogensen et al. |
| 2010/0022988 | A1 | 1/2010 | Wochner et al. |
| 2010/0025238 | A1 | 2/2010 | Gottlieb et al. |
| 2010/0030038 | A1 | 2/2010 | Brauker et al. |
| 2010/0030053 | A1 | 2/2010 | Goode, Jr. et al. |
| 2010/0030111 | A1 | 2/2010 | Perriere |
| 2010/0030484 | A1 | 2/2010 | Brauker et al. |
| 2010/0030485 | A1 | 2/2010 | Brauker et al. |
| 2010/0036215 | A1 | 2/2010 | Goode, Jr. et al. |
| 2010/0036216 | A1 | 2/2010 | Goode, Jr. et al. |
| 2010/0036222 | A1 | 2/2010 | Goode, Jr. et al. |
| 2010/0036223 | A1 | 2/2010 | Goode, Jr. et al. |
| 2010/0036225 | A1 | 2/2010 | Goode, Jr. et al. |
| 2010/0036281 | A1 | 2/2010 | Doi |
| 2010/0041971 | A1 | 2/2010 | Goode, Jr. et al. |
| 2010/0045465 | A1 | 2/2010 | Brauker et al. |
| 2010/0049014 | A1 | 2/2010 | Funderburk et al. |
| 2010/0049024 | A1 | 2/2010 | Saint et al. |
| 2010/0049129 | A1 | 2/2010 | Yokoi et al. |
| 2010/0057040 | A1 | 3/2010 | Hayter |
| 2010/0057041 | A1 | 3/2010 | Hayter |
| 2010/0057042 | A1 | 3/2010 | Hayter |
| 2010/0057044 | A1 | 3/2010 | Hayter |
| 2010/0057057 | A1 | 3/2010 | Hayter et al. |
| 2010/0063373 | A1 | 3/2010 | Kamath et al. |
| 2010/0069728 | A1 | 3/2010 | Funderburk et al. |
| 2010/0076283 | A1 | 3/2010 | Simpson et al. |
| 2010/0076379 | A1 | 3/2010 | Matusch |
| 2010/0081905 | A1 | 4/2010 | Bommakanti et al. |
| 2010/0081906 | A1 | 4/2010 | Hayter et al. |
| 2010/0081908 | A1 | 4/2010 | Dobbles et al. |
| 2010/0081910 | A1 | 4/2010 | Brister et al. |
| 2010/0081953 | A1 | 4/2010 | Syeda-Mahmood et al. |
| 2010/0087724 | A1 | 4/2010 | Brauker et al. |
| 2010/0094251 | A1 | 4/2010 | Estes et al. |
| 2010/0096259 | A1 | 4/2010 | Zhang et al. |
| 2010/0099970 | A1 | 4/2010 | Shults et al. |
| 2010/0099971 | A1 | 4/2010 | Shults et al. |
| 2010/0100113 | A1 | 4/2010 | Iio et al. |
| 2010/0105999 | A1 | 4/2010 | Dixon et al. |
| 2010/0106088 | A1 | 4/2010 | Yodfat et al. |
| 2010/0113897 | A1 | 5/2010 | Brenneman et al. |
| 2010/0119693 | A1 | 5/2010 | Tapsak et al. |
| 2010/0119881 | A1 | 5/2010 | Patel et al. |
| 2010/0121167 | A1 | 5/2010 | McGarraugh et al. |
| 2010/0121169 | A1 | 5/2010 | Petisce et al. |
| 2010/0137695 | A1 | 6/2010 | Yodfat et al. |
| 2010/0141656 | A1 | 6/2010 | Krieftewirth |
| 2010/0145229 | A1 | 6/2010 | Perez et al. |
| 2010/0145377 | A1 | 6/2010 | Lai et al. |
| 2010/0146300 | A1 | 6/2010 | Brown |
| 2010/0152548 | A1 | 6/2010 | Koski |
| 2010/0152554 | A1 | 6/2010 | Steine et al. |
| 2010/0152674 | A1 | 6/2010 | Kavazov et al. |
| 2010/0160757 | A1 | 6/2010 | Weinart et al. |
| 2010/0160759 | A1 | 6/2010 | Celentano et al. |
| 2010/0160760 | A1 | 6/2010 | Shults et al. |
| 2010/0161269 | A1 | 6/2010 | Kamath et al. |
| 2010/0168538 | A1 | 7/2010 | Keenan et al. |
| 2010/0168540 | A1 | 7/2010 | Kamath et al. |
| 2010/0168541 | A1 | 7/2010 | Kamath et al. |
| 2010/0168542 | A1 | 7/2010 | Kamath et al. |
| 2010/0168543 | A1 | 7/2010 | Kamath et al. |
| 2010/0168544 | A1 | 7/2010 | Kamath et al. |
| 2010/0168545 | A1 | 7/2010 | Kamath et al. |
| 2010/0168546 | A1 | 7/2010 | Kamath et al. |
| 2010/0168547 | A1 | 7/2010 | Kamath et al. |
| 2010/0168660 | A1 | 7/2010 | Galley et al. |
| 2010/0168677 | A1 | 7/2010 | Gabriel et al. |
| 2010/0174157 | A1 | 7/2010 | Brister et al. |
| 2010/0174158 | A1 | 7/2010 | Kamath et al. |
| 2010/0174163 | A1 | 7/2010 | Brister et al. |
| 2010/0174164 | A1 | 7/2010 | Brister et al. |
| 2010/0174165 | A1 | 7/2010 | Brister et al. |
| 2010/0174166 | A1 | 7/2010 | Brister et al. |
| 2010/0174167 | A1 | 7/2010 | Kamath et al. |
| 2010/0174168 | A1 | 7/2010 | Goode, Jr. et al. |

(56) References Cited

U.S. PATENT DOCUMENTS

| | | | |
|---|---|---|---|
| 2010/0174266 | A1 | 7/2010 | Estes |
| 2010/0179399 | A1 | 7/2010 | Goode, Jr. et al. |
| 2010/0179400 | A1 | 7/2010 | Brauker et al. |
| 2010/0179401 | A1 | 7/2010 | Rasdal et al. |
| 2010/0179402 | A1 | 7/2010 | Goode, Jr. et al. |
| 2010/0179404 | A1 | 7/2010 | Kamath et al. |
| 2010/0179405 | A1 | 7/2010 | Goode, Jr. et al. |
| 2010/0179407 | A1 | 7/2010 | Goode, Jr. et al. |
| 2010/0179408 | A1 | 7/2010 | Kamath et al. |
| 2010/0179409 | A1 | 7/2010 | Kamath et al. |
| 2010/0185065 | A1 | 7/2010 | Goode, Jr. et al. |
| 2010/0185069 | A1 | 7/2010 | Brister et al. |
| 2010/0185070 | A1 | 7/2010 | Brister et al. |
| 2010/0185071 | A1 | 7/2010 | Simpson et al. |
| 2010/0185072 | A1 | 7/2010 | Goode, Jr. et al. |
| 2010/0185073 | A1 | 7/2010 | Goode, Jr. et al. |
| 2010/0185074 | A1 | 7/2010 | Goode, Jr. et al. |
| 2010/0185075 | A1 | 7/2010 | Brister et al. |
| 2010/0185175 | A1 | 7/2010 | Kamen et al. |
| 2010/0190435 | A1 | 7/2010 | Cook et al. |
| 2010/0191082 | A1 | 7/2010 | Brister et al. |
| 2010/0191087 | A1 | 7/2010 | Talbot et al. |
| 2010/0191472 | A1 | 7/2010 | Doniger et al. |
| 2010/0198033 | A1 | 8/2010 | Krulevitch et al. |
| 2010/0198034 | A1 | 8/2010 | Thomas et al. |
| 2010/0198035 | A1 | 8/2010 | Kamath et al. |
| 2010/0198036 | A1 | 8/2010 | Kamath et al. |
| 2010/0198042 | A1 | 8/2010 | Sloan et al. |
| 2010/0198142 | A1 | 8/2010 | Sloan et al. |
| 2010/0198314 | A1 | 8/2010 | Wei |
| 2010/0204557 | A1 | 8/2010 | Kiaie et al. |
| 2010/0204653 | A1 | 8/2010 | Gryn et al. |
| 2010/0212583 | A1 | 8/2010 | Brister et al. |
| 2010/0213057 | A1 | 8/2010 | Feldman et al. |
| 2010/0213080 | A1 | 8/2010 | Celentano et al. |
| 2010/0214104 | A1 | 8/2010 | Goode, Jr. et al. |
| 2010/0217105 | A1 | 8/2010 | Yodfat et al. |
| 2010/0217557 | A1 | 8/2010 | Kamath et al. |
| 2010/0223013 | A1 | 9/2010 | Kamath et al. |
| 2010/0223022 | A1 | 9/2010 | Kamath et al. |
| 2010/0223023 | A1 | 9/2010 | Kamath et al. |
| 2010/0228109 | A1 | 9/2010 | Kamath et al. |
| 2010/0228111 | A1 | 9/2010 | Friman et al. |
| 2010/0228497 | A1 | 9/2010 | Kamath et al. |
| 2010/0230285 | A1 | 9/2010 | Hoss et al. |
| 2010/0235439 | A1 | 9/2010 | Goodnow et al. |
| 2010/0240975 | A1 | 9/2010 | Goode, Jr. et al. |
| 2010/0240976 | A1 | 9/2010 | Goode, Jr. et al. |
| 2010/0256471 | A1 | 10/2010 | Say et al. |
| 2010/0259543 | A1 | 10/2010 | Tarassenko et al. |
| 2010/0261987 | A1 | 10/2010 | Kamath et al. |
| 2010/0262183 | A1 | 10/2010 | Abbott et al. |
| 2010/0262201 | A1 | 10/2010 | He et al. |
| 2010/0267161 | A1 | 10/2010 | Wu et al. |
| 2010/0274107 | A1 | 10/2010 | Boock et al. |
| 2010/0274111 | A1 | 10/2010 | Say et al. |
| 2010/0274515 | A1 | 10/2010 | Hoss et al. |
| 2010/0275108 | A1 | 10/2010 | Sloan et al. |
| 2010/0280341 | A1 | 11/2010 | Boock et al. |
| 2010/0286496 | A1 | 11/2010 | Simpson et al. |
| 2010/0298684 | A1 | 11/2010 | Leach et al. |
| 2010/0312176 | A1 | 12/2010 | Lauer et al. |
| 2010/0313105 | A1 | 12/2010 | Nekoomaram et al. |
| 2010/0317952 | A1 | 12/2010 | Budiman et al. |
| 2010/0324392 | A1 | 12/2010 | Yee et al. |
| 2010/0324403 | A1 | 12/2010 | Brister et al. |
| 2010/0325868 | A1 | 12/2010 | Wang et al. |
| 2010/0326842 | A1 | 12/2010 | Mazza et al. |
| 2010/0331642 | A1 | 12/2010 | Bruce et al. |
| 2010/0331644 | A1 | 12/2010 | Neale et al. |
| 2010/0331647 | A1 | 12/2010 | Shah et al. |
| 2010/0331648 | A1 | 12/2010 | Kamath et al. |
| 2010/0331651 | A1 | 12/2010 | Groll |
| 2010/0331653 | A1 | 12/2010 | Stafford |
| 2010/0331656 | A1 | 12/2010 | Mensinger et al. |
| 2010/0331657 | A1 | 12/2010 | Mensinger et al. |
| 2011/0004085 | A1 | 1/2011 | Mensinger et al. |
| 2011/0004276 | A1 | 1/2011 | Blair et al. |
| 2011/0009727 | A1 | 1/2011 | Mensinger et al. |
| 2011/0015509 | A1 | 1/2011 | Peyser |
| 2011/0016691 | A1 | 1/2011 | Alden et al. |
| 2011/0021889 | A1 | 1/2011 | Hoss et al. |
| 2011/0022411 | A1 | 1/2011 | Hjelm et al. |
| 2011/0024043 | A1 | 2/2011 | Boock et al. |
| 2011/0024307 | A1 | 2/2011 | Simpson et al. |
| 2011/0027127 | A1 | 2/2011 | Simpson et al. |
| 2011/0027453 | A1 | 2/2011 | Boock et al. |
| 2011/0027458 | A1 | 2/2011 | Boock et al. |
| 2011/0028815 | A1 | 2/2011 | Simpson et al. |
| 2011/0028816 | A1 | 2/2011 | Simpson et al. |
| 2011/0031986 | A1 | 2/2011 | Bhat et al. |
| 2011/0040163 | A1 | 2/2011 | Telson et al. |
| 2011/0040256 | A1 | 2/2011 | Bobroff et al. |
| 2011/0040263 | A1 | 2/2011 | Hordum et al. |
| 2011/0046456 | A1 | 2/2011 | Hordum et al. |
| 2011/0046467 | A1 | 2/2011 | Simpson et al. |
| 2011/0046977 | A1 | 2/2011 | Goodnow et al. |
| 2011/0054275 | A1 | 3/2011 | Stafford |
| 2011/0054282 | A1 | 3/2011 | Nekoomaram et al. |
| 2011/0060196 | A1 | 3/2011 | Stafford |
| 2011/0060530 | A1 | 3/2011 | Fennell |
| 2011/0070633 | A1 | 3/2011 | Matsumoto et al. |
| 2011/0073475 | A1 | 3/2011 | Kastanos et al. |
| 2011/0077469 | A1 | 3/2011 | Blocker et al. |
| 2011/0077490 | A1 | 3/2011 | Simpson et al. |
| 2011/0077494 | A1 | 3/2011 | Doniger et al. |
| 2011/0077659 | A1 | 3/2011 | Mandecki et al. |
| 2011/0081726 | A1 | 4/2011 | Berman et al. |
| 2011/0082484 | A1 | 4/2011 | Saravia et al. |
| 2011/0087196 | A1 | 4/2011 | Hunn et al. |
| 2011/0097090 | A1 | 4/2011 | Cao |
| 2011/0106126 | A1 | 5/2011 | Love et al. |
| 2011/0112696 | A1 | 5/2011 | Yodfat et al. |
| 2011/0118579 | A1 | 5/2011 | Goode, Jr. et al. |
| 2011/0118580 | A1 | 5/2011 | Goode, Jr. et al. |
| 2011/0123971 | A1 | 5/2011 | Berkowitz et al. |
| 2011/0124992 | A1 | 5/2011 | Brauker et al. |
| 2011/0124997 | A1 | 5/2011 | Goode, Jr. et al. |
| 2011/0125040 | A1 | 5/2011 | Crawford et al. |
| 2011/0125410 | A1 | 5/2011 | Goode, Jr. et al. |
| 2011/0130970 | A1 | 6/2011 | Goode, Jr. et al. |
| 2011/0130971 | A1 | 6/2011 | Goode, Jr. et al. |
| 2011/0130998 | A1 | 6/2011 | Goode, Jr. et al. |
| 2011/0137257 | A1 | 6/2011 | Gymn et al. |
| 2011/0137571 | A1 | 6/2011 | Power et al. |
| 2011/0144465 | A1 | 6/2011 | Shults et al. |
| 2011/0148905 | A1 | 6/2011 | Simmons et al. |
| 2011/0152637 | A1 | 6/2011 | Kateraas et al. |
| 2011/0152778 | A1 | 6/2011 | Gyrn |
| 2011/0172510 | A1 | 7/2011 | Chickering, III et al. |
| 2011/0178378 | A1 | 7/2011 | Brister et al. |
| 2011/0178461 | A1 | 7/2011 | Chong et al. |
| 2011/0184258 | A1 | 7/2011 | Stafford |
| 2011/0184482 | A1 | 7/2011 | Eberman et al. |
| 2011/0184752 | A1 | 7/2011 | Ray et al. |
| 2011/0190603 | A1 | 8/2011 | Stafford |
| 2011/0190614 | A1 | 8/2011 | Brister et al. |
| 2011/0191044 | A1 | 8/2011 | Stafford |
| 2011/0193704 | A1 | 8/2011 | Harper et al. |
| 2011/0201910 | A1 | 8/2011 | Rasdal et al. |
| 2011/0201911 | A1 | 8/2011 | Johnson et al. |
| 2011/0208027 | A1 | 8/2011 | Wagner et al. |
| 2011/0213225 | A1 | 9/2011 | Bernstein et al. |
| 2011/0218414 | A1 | 9/2011 | Kamath et al. |
| 2011/0218490 | A1 | 9/2011 | Ocvirk et al. |
| 2011/0230741 | A1 | 9/2011 | Liang et al. |
| 2011/0231107 | A1 | 9/2011 | Brauker et al. |
| 2011/0231140 | A1 | 9/2011 | Goode, Jr. et al. |
| 2011/0231141 | A1 | 9/2011 | Goode, Jr. et al. |
| 2011/0231142 | A1 | 9/2011 | Goode, Jr. et al. |
| 2011/0253533 | A1 | 10/2011 | Shults et al. |
| 2011/0257495 | A1 | 10/2011 | Hoss et al. |
| 2011/0257521 | A1 | 10/2011 | Fraden |
| 2011/0257895 | A1 | 10/2011 | Brauker et al. |

(56) References Cited

U.S. PATENT DOCUMENTS

2011/0263958 A1 10/2011 Brauker et al.
2011/0263959 A1 10/2011 Young et al.
2011/0264378 A1 10/2011 Breton et al.
2011/0270062 A1 11/2011 Goode, Jr. et al.
2011/0270158 A1 11/2011 Brauker et al.
2011/0275919 A1 11/2011 Petisce et al.
2011/0282327 A1 11/2011 Kellogg et al.
2011/0287528 A1 11/2011 Fern et al.
2011/0288574 A1 11/2011 Curry et al.
2011/0289497 A1 11/2011 Kiaie et al.
2011/0290645 A1 12/2011 Brister et al.
2011/0313543 A1 12/2011 Brauker et al.
2011/0319729 A1 12/2011 Donnay et al.
2011/0319733 A1 12/2011 Stafford
2011/0319738 A1 12/2011 Woodruff et al.
2011/0319739 A1 12/2011 Kamath et al.
2011/0320130 A1 12/2011 Valdes et al.
2012/0010642 A1 1/2012 Lee et al.
2012/0035445 A1 2/2012 Boock et al.
2012/0040101 A1 2/2012 Tapsak et al.
2012/0046534 A1 2/2012 Simpson et al.
2012/0078071 A1 3/2012 Bohm et al.
2012/0088995 A1 4/2012 Fennell et al.
2012/0095406 A1 4/2012 Gyrn et al.
2012/0108934 A1 5/2012 Valdes et al.
2012/0108983 A1 5/2012 Banet et al.
2012/0116322 A1 5/2012 Brink et al.
2012/0123385 A1 5/2012 Edwards et al.
2012/0143135 A1 6/2012 Cole et al.
2012/0165626 A1 6/2012 Irina et al.
2012/0165640 A1 6/2012 Galley et al.
2012/0173200 A1 7/2012 Breton et al.
2012/0179113 A1 7/2012 Yokota et al.
2012/0184909 A1 7/2012 Gyrn et al.
2012/0190943 A1 7/2012 Donnay et al.
2012/0190989 A1 7/2012 Kaiser et al.
2012/0197098 A1 8/2012 Donnay et al.
2012/0197222 A1 8/2012 Donnay et al.
2012/0245447 A1 9/2012 Karan et al.
2012/0265042 A1 10/2012 Neinast et al.
2012/0296327 A1 11/2012 Hutchins et al.
2012/0303043 A1 11/2012 Donnay et al.
2013/0035575 A1 2/2013 Mayou et al.
2013/0047981 A1 2/2013 Bacon
2013/0109940 A1 5/2013 Yang et al.
2013/0111248 A1 5/2013 Ghesquiere et al.
2013/0150691 A1 6/2013 Pace et al.
2013/0184547 A1 7/2013 Taub et al.
2013/0199312 A1 8/2013 Wilmer et al.
2013/0225959 A1 8/2013 Bugler
2013/0235166 A1 9/2013 Jones et al.
2013/0253289 A1 9/2013 Hadvary et al.
2013/0267811 A1 10/2013 Pryor et al.
2013/0317323 A1 11/2013 Fujiwara et al.
2014/0031655 A1 1/2014 Stafford
2014/0121480 A1 5/2014 Budiman et al.
2014/0148667 A1 5/2014 Boock et al.
2014/0171771 A1 6/2014 Feldman et al.
2014/0188053 A1 7/2014 Lundquist
2014/0228760 A1 8/2014 Ethelfeld
2014/0275907 A1 9/2014 Feldman et al.
2015/0005601 A1 1/2015 Hoss et al.
2015/0018643 A1 1/2015 Cole et al.
2015/0025338 A1 1/2015 Lee et al.
2015/0073238 A1 3/2015 Matsumoto et al.
2015/0105644 A1 4/2015 Yang et al.
2015/0141776 A1 5/2015 Hadvary et al.
2015/0164545 A1 6/2015 Gyrn
2015/0173661 A1 6/2015 Myles
2015/0241407 A1 8/2015 Ou et al.
2015/0326072 A1 11/2015 Petras et al.
2016/0058342 A1 3/2016 Maiz-Aguinaga et al.
2016/0058470 A1 3/2016 Peterson et al.
2016/0058474 A1 3/2016 Peterson et al.
2016/0128615 A1 5/2016 Curry et al.
2016/0157759 A1 6/2016 Yang
2016/0256106 A1 9/2016 Krasnow et al.
2016/0331283 A1 11/2016 Rao et al.
2016/0331284 A1 11/2016 Pace
2016/0338733 A1 11/2016 Shah et al.
2016/0338734 A1 11/2016 Shah et al.
2016/0354555 A1 12/2016 Gibson et al.
2017/0112533 A1 4/2017 Schoonmaker et al.
2017/0112534 A1 4/2017 Schoonmaker et al.
2017/0127985 A1 5/2017 Thompson et al.
2017/0128011 A1 5/2017 Frey et al.
2017/0165451 A1 6/2017 Frey et al.
2017/0188908 A1 7/2017 Hoss et al.
2017/0188910 A1 7/2017 Halac et al.
2017/0188912 A1 7/2017 Halac et al.
2017/0216536 A1 8/2017 Scott
2017/0265791 A1 9/2017 Pace et al.
2017/0290533 A1 10/2017 Antonio et al.
2017/0290534 A1 10/2017 Antonio et al.
2017/0290535 A1 10/2017 Rao et al.
2017/0290546 A1 10/2017 Antonio et al.
2017/0319137 A1 11/2017 Tsubouchi et al.
2017/0367630 A1 12/2017 Arita et al.
2017/0368268 A1 12/2017 Chopra
2018/0116572 A1 5/2018 Simpson et al.
2018/0125464 A1 5/2018 Kolb et al.
2018/0235520 A1 8/2018 Rao et al.
2018/0360493 A1 12/2018 Baker et al.
2018/0368771 A1 12/2018 Gray et al.
2019/0076073 A1 3/2019 Donnay et al.
2019/0133501 A1 5/2019 Rao et al.
2019/0133638 A1 5/2019 Ii et al.
2019/0298240 A1 10/2019 Lee et al.
2020/0077928 A1 3/2020 Brister et al.
2020/0100712 A1 4/2020 Stafford
2020/0113494 A1 4/2020 Akiyama
2020/0178899 A1 6/2020 Chae et al.
2020/0196919 A1 6/2020 Rao et al.
2020/0397356 A1 12/2020 Yee et al.
2021/0030969 A1 2/2021 Huang et al.
2021/0113124 A1 4/2021 Yee et al.
2021/0161437 A1 6/2021 Thomas et al.
2021/0177315 A1 6/2021 Thomas et al.
2021/0204841 A1 7/2021 Thomas et al.
2021/0204843 A1 7/2021 Mazza et al.
2021/0378592 A1 12/2021 Rodriguez et al.
2022/0007973 A1 1/2022 Rao et al.
2022/0079475 A1 3/2022 Cole et al.
2022/0125480 A1 4/2022 Rao et al.
2022/0273240 A1 9/2022 Hopcroft
2023/0108476 A1 4/2023 Rao
2024/0293615 A1 9/2024 Lanigan

FOREIGN PATENT DOCUMENTS

CA 2468577 6/2003
CA 2495648 2/2004
CA 2143172 7/2005
CA 2498682 9/2005
CA 2555749 9/2005
CA 2632709 6/2007
CA 2396613 3/2008
CA 2678336 5/2008
CA 2615575 6/2008
CA 2626349 9/2008
CA 2701374 4/2009
CA 2413148 8/2010
CA 2728831 7/2011
CA 2766693 A1 9/2011
CA 2617965 10/2011
CA 2766685 A1 12/2011
CA 3050721 7/2018
CN 1202872 5/2005
CN 101163440 4/2008
CN 101268932 9/2008
CN 101296650 10/2008
CN 201370857 12/2009
DE 44 01 400 7/1995
DE 201 10 059 8/2002

(56) References Cited

FOREIGN PATENT DOCUMENTS

| | | | |
|---|---|---|---|
| DE | 101 17 285 | | 11/2002 |
| DE | 10 2008 053 216 | | 5/2010 |
| EP | 0 010 375 | | 4/1980 |
| EP | 0 026 995 | | 4/1981 |
| EP | 0 048 090 | | 3/1982 |
| EP | 0 078 636 | | 5/1983 |
| EP | 0 096 288 | | 12/1983 |
| EP | 0 098 592 | | 1/1984 |
| EP | 0 125 139 | | 11/1984 |
| EP | 0 127 958 | | 12/1984 |
| EP | 0 136 362 | | 4/1985 |
| EP | 0 170 375 | | 2/1986 |
| EP | 0 177 743 | | 4/1986 |
| EP | 0 080 304 | | 5/1986 |
| EP | 0 184 909 | | 6/1986 |
| EP | 0 206 218 | | 12/1986 |
| EP | 0 230 472 | | 8/1987 |
| EP | 0 241 309 | | 10/1987 |
| EP | 0 245 073 | | 11/1987 |
| EP | 0 255 291 | | 2/1988 |
| EP | 0 278 647 | | 8/1988 |
| EP | 0 319 277 | A1 | 6/1989 |
| EP | 0 320 109 | | 6/1989 |
| EP | 0 353 328 | | 2/1990 |
| EP | 0 359 831 | | 3/1990 |
| EP | 0 368 209 | | 5/1990 |
| EP | 0 390 390 | | 10/1990 |
| EP | 0 396 788 | | 11/1990 |
| EP | 0 400 918 | | 12/1990 |
| EP | 0 453 283 | | 10/1991 |
| EP | 0 470 290 | | 2/1992 |
| EP | 0 567 725 | | 11/1993 |
| EP | 0 286 118 | | 1/1995 |
| EP | 0 680 727 | | 11/1995 |
| EP | 0 724 859 | | 8/1996 |
| EP | 0 805 574 | | 11/1997 |
| EP | 1 897 488 | | 12/1999 |
| EP | 0 973 289 | | 1/2000 |
| EP | 0 678 308 | | 5/2000 |
| EP | 1 048 264 | | 11/2000 |
| EP | 1 177 802 | | 2/2002 |
| EP | 0 729 366 | | 7/2002 |
| EP | 1 292 218 | | 3/2003 |
| EP | 1 077 634 | | 7/2003 |
| EP | 1 092 390 | | 7/2004 |
| EP | 1 568 309 | | 8/2005 |
| EP | 1 630 898 | | 3/2006 |
| EP | 1 666 091 | | 6/2006 |
| EP | 1 669 020 | | 6/2006 |
| EP | 1 703 697 | | 9/2006 |
| EP | 1 704 889 | | 9/2006 |
| EP | 1 704 893 | | 9/2006 |
| EP | 1 729 128 | | 12/2006 |
| EP | 0 987 982 | | 1/2007 |
| EP | 1 956 371 | | 8/2008 |
| EP | 1 972 270 | | 9/2008 |
| EP | 2 031 534 | | 3/2009 |
| EP | 2 060 284 | | 5/2009 |
| EP | 1 897 487 | | 11/2009 |
| EP | 1 897 492 | | 11/2009 |
| EP | 2 113 864 | | 11/2009 |
| EP | 1 681 992 | | 4/2010 |
| EP | 2 201 969 | | 6/2010 |
| EP | 1 448 489 | | 8/2010 |
| EP | 1 971 396 | | 8/2010 |
| EP | 1 725 163 | | 12/2010 |
| EP | 2 260 757 | | 12/2010 |
| EP | 1 413 245 | | 6/2011 |
| EP | 2 327 362 | | 6/2011 |
| EP | 2 327 984 | | 6/2011 |
| EP | 2 335 587 | | 6/2011 |
| EP | 2 153 382 | | 2/2012 |
| EP | 2 284 773 | | 2/2012 |
| EP | 1 789 116 | B1 | 5/2013 |
| EP | 3 251 597 | B1 | 11/2019 |
| EP | 3 632 314 | | 4/2020 |
| EP | 3 632 315 | A1 | 4/2020 |
| EP | 3 851 045 | A1 | 7/2021 |
| EP | 3 730 044 | B1 | 12/2021 |
| EP | 3 730 045 | B1 | 3/2022 |
| EP | 3 766 408 | B1 | 4/2022 |
| EP | 3 928 688 | B1 | 6/2022 |
| EP | 4 111 949 | B1 | 7/2023 |
| EP | 3 300 658 | | 1/2024 |
| EP | 4 344 633 | | 4/2024 |
| EP | 4 203 819 | | 7/2024 |
| GB | 1 394 171 | | 5/1975 |
| GB | 1 599 241 | | 9/1981 |
| GB | 2 073 891 | | 10/1981 |
| GB | 2 067 764 | | 1/1984 |
| GB | 2 154 003 | | 8/1985 |
| GB | 2 204 408 | | 11/1988 |
| GB | 2 254 436 | | 10/1992 |
| GB | 2 409 951 | | 7/2005 |
| JP | 54-041191 | | 4/1979 |
| JP | 55-010581 | | 1/1980 |
| JP | 55-010583 | | 1/1980 |
| JP | 55-010584 | | 1/1980 |
| JP | 55-012406 | | 1/1980 |
| JP | 56-163447 | | 10/1981 |
| JP | 57-070448 | | 4/1982 |
| JP | 60-173457 | | 9/1985 |
| JP | 60-173458 | | 9/1985 |
| JP | 60-173459 | | 9/1985 |
| JP | 62-085855 | | 4/1987 |
| JP | 62-114747 | | 5/1987 |
| JP | 63-058149 | | 3/1988 |
| JP | 63-128252 | | 5/1988 |
| JP | 63-139246 | | 6/1988 |
| JP | 63-294799 | | 12/1988 |
| JP | 63-317757 | | 12/1988 |
| JP | 63-317758 | | 12/1988 |
| JP | 01-114746 | | 5/1989 |
| JP | 01-114747 | | 5/1989 |
| JP | 01-124060 | | 5/1989 |
| JP | 01-134244 | | 5/1989 |
| JP | 01-156658 | | 6/1989 |
| JP | 02-062958 | | 3/1990 |
| JP | 02-120655 | | 5/1990 |
| JP | 02-287145 | | 11/1990 |
| JP | 02-310457 | | 12/1990 |
| JP | 03-020752 | | 1/1991 |
| JP | 03-026956 | | 2/1991 |
| JP | 03-028752 | | 2/1991 |
| JP | 03-500940 | | 2/1991 |
| JP | 03-194458 | | 8/1991 |
| JP | 03-202764 | | 9/1991 |
| JP | 05-072171 | | 3/1993 |
| JP | 05-196595 | | 8/1993 |
| JP | 06-190050 | | 7/1994 |
| JP | 07-055757 | | 3/1995 |
| JP | 07-072585 | | 3/1995 |
| JP | 07-182462 | | 7/1995 |
| JP | 07-311196 | | 11/1995 |
| JP | 08-285814 | | 11/1996 |
| JP | 08-285815 | | 11/1996 |
| JP | 09-021778 | | 1/1997 |
| JP | 09-101280 | | 4/1997 |
| JP | 09-285459 | | 4/1997 |
| JP | 10-170471 | | 6/1998 |
| JP | 10-305016 | | 11/1998 |
| JP | 11-506629 | | 6/1999 |
| JP | 11-225359 | | 8/1999 |
| JP | 2003-144417 | | 5/2003 |
| JP | 2004-033438 | | 2/2004 |
| JP | 2004-214014 | | 7/2004 |
| JP | 2004-520103 | | 7/2004 |
| JP | 2004-520898 | | 7/2004 |
| JP | 2004-358016 | | 12/2004 |
| JP | 2006-021031 | | 1/2006 |
| JP | 2006-280464 | | 10/2006 |
| JP | 2006-527036 | | 11/2006 |
| JP | 2007-510499 | | 4/2007 |
| JP | 2007-152037 | | 6/2007 |

(56) References Cited

FOREIGN PATENT DOCUMENTS

| | | | |
|---|---|---|---|
| JP | 2008-506468 | | 3/2008 |
| KR | 10-2017-0068694 | | 6/2017 |
| SU | 1281988 | | 1/1987 |
| WO | WO 89/05119 | | 6/1989 |
| WO | WO 89/08713 | | 9/1989 |
| WO | WO 90/05300 | | 5/1990 |
| WO | WO 90/05910 | | 5/1990 |
| WO | WO 91/01680 | | 2/1991 |
| WO | WO 91/04704 | | 4/1991 |
| WO | WO 91/15993 | | 10/1991 |
| WO | WO 92/13271 | | 8/1992 |
| WO | WO 94/02062 | | 9/1994 |
| WO | WO 95/28878 | | 2/1995 |
| WO | WO 96/25089 | | 8/1996 |
| WO | WO 96/35370 | | 11/1996 |
| WO | WO 96/39977 | | 12/1996 |
| WO | WO 97/02847 | | 1/1997 |
| WO | WO 97/19344 | | 5/1997 |
| WO | WO 97/21457 | | 6/1997 |
| WO | WO 97/33513 | | 9/1997 |
| WO | WO 97/42882 | | 11/1997 |
| WO | WO 97/42883 | | 11/1997 |
| WO | WO 97/42886 | | 11/1997 |
| WO | WO 97/42888 | | 11/1997 |
| WO | WO 97/43962 | | 11/1997 |
| WO | WO 98/04902 | | 2/1998 |
| WO | WO 98/35053 | | 8/1998 |
| WO | WO 98/56293 | | 12/1998 |
| WO | WO 99/27849 | | 6/1999 |
| WO | WO 99/28736 | | 6/1999 |
| WO | WO 99/33504 | | 7/1999 |
| WO | WO 99/56613 | | 11/1999 |
| WO | WO 00/40159 | | 7/2000 |
| WO | WO 00/49940 | | 8/2000 |
| WO | WO 00/59370 | | 10/2000 |
| WO | WO 00/60350 | | 10/2000 |
| WO | WO 00/74753 | | 12/2000 |
| WO | WO 00/78992 | | 12/2000 |
| WO | WO 01/52727 | A1 | 7/2001 |
| WO | WO 01/52935 | | 7/2001 |
| WO | WO 01/54753 | | 8/2001 |
| WO | WO 01/58348 | | 8/2001 |
| WO | WO 02/15778 | | 2/2002 |
| WO | WO 02/16905 | | 2/2002 |
| WO | WO 02/50534 | | 6/2002 |
| WO | WO 02/058537 | | 8/2002 |
| WO | WO 02/100457 | | 12/2002 |
| WO | WO 03/026728 | | 4/2003 |
| WO | WO 03/028784 | | 4/2003 |
| WO | WO 03/056319 | | 7/2003 |
| WO | WO 03/057027 | | 7/2003 |
| WO | WO 03/072164 | | 9/2003 |
| WO | WO 03/073936 | | 9/2003 |
| WO | WO 03/076893 | | 9/2003 |
| WO | WO 03/082091 | | 10/2003 |
| WO | WO 03/085372 | | 10/2003 |
| WO | WO 2004/006982 | | 1/2004 |
| WO | WO 2004/015539 | | 2/2004 |
| WO | WO 2004/028337 | | 4/2004 |
| WO | WO 2004/030726 | | 4/2004 |
| WO | WO 2004/034024 | | 4/2004 |
| WO | WO 2004/047445 | | 6/2004 |
| WO | WO 2004/049237 | | 6/2004 |
| WO | WO 2004/054445 | | 7/2004 |
| WO | WO 2004/060436 | | 7/2004 |
| WO | WO 2004/061420 | | 7/2004 |
| WO | WO 2004/090503 | | 10/2004 |
| WO | WO 2004/098405 | | 11/2004 |
| WO | WO 2004/098682 | A2 | 11/2004 |
| WO | WO 2004/098683 | | 11/2004 |
| WO | WO 2004/098684 | | 11/2004 |
| WO | WO 2004/098685 | | 11/2004 |
| WO | WO 2004/107971 | | 12/2004 |
| WO | WO 2004/112602 | | 12/2004 |
| WO | WO 2005/011779 | A1 | 2/2005 |
| WO | WO 2005/018450 | | 3/2005 |
| WO | WO 2005/037184 | | 4/2005 |
| WO | WO 2005/041766 | | 5/2005 |
| WO | WO 2005/044116 | | 5/2005 |
| WO | WO 2005/045744 | | 5/2005 |
| WO | WO 2005/046780 | | 5/2005 |
| WO | WO 2005/051170 | | 6/2005 |
| WO | WO 2005/057175 | | 6/2005 |
| WO | WO 2005/065538 | | 7/2005 |
| WO | WO 2005/084534 | | 9/2005 |
| WO | WO 2005/089103 | | 9/2005 |
| WO | WO 2005/092177 | | 10/2005 |
| WO | WO 2005/121785 | | 12/2005 |
| WO | WO 2005/123186 | | 12/2005 |
| WO | WO 2006/001024 | | 1/2006 |
| WO | WO 2006/015922 | | 2/2006 |
| WO | WO 2006/017358 | | 2/2006 |
| WO | WO 2006/020212 | | 2/2006 |
| WO | WO 2006/024671 | | 3/2006 |
| WO | WO 2006/026741 | | 3/2006 |
| WO | WO 2006/032653 | | 3/2006 |
| WO | WO 2006/036145 | | 4/2006 |
| WO | WO 2006/040083 | | 4/2006 |
| WO | WO 2006/042811 | | 4/2006 |
| WO | WO 2006/061354 | | 6/2006 |
| WO | WO 2006/064397 | | 6/2006 |
| WO | WO 2006/072035 | | 7/2006 |
| WO | WO 2006/079114 | | 7/2006 |
| WO | WO 2006/086423 | | 8/2006 |
| WO | WO 2006/094513 | | 9/2006 |
| WO | WO 2006/108809 | | 10/2006 |
| WO | WO 2006/110742 | | 10/2006 |
| WO | WO 2006/114297 | | 11/2006 |
| WO | WO 2006/118947 | | 11/2006 |
| WO | WO 2006/121921 | | 11/2006 |
| WO | WO 2006/124099 | | 11/2006 |
| WO | WO 2007/002189 | | 1/2007 |
| WO | WO 2007/007459 | | 1/2007 |
| WO | WO 2007/016399 | | 2/2007 |
| WO | WO 2007/019289 | | 2/2007 |
| WO | WO 2007/027788 | | 3/2007 |
| WO | WO 2007/041069 | | 4/2007 |
| WO | WO 2007/041070 | | 4/2007 |
| WO | WO 2007/041248 | | 4/2007 |
| WO | WO 2007/053832 | | 5/2007 |
| WO | WO 2007/056638 | | 5/2007 |
| WO | WO 2007/065285 | | 6/2007 |
| WO | WO 2007/089738 | | 8/2007 |
| WO | WO 2007/092618 | | 8/2007 |
| WO | WO 2007/097754 | | 8/2007 |
| WO | WO 2007/101223 | | 9/2007 |
| WO | WO 2007/120363 | | 10/2007 |
| WO | WO 2007/126444 | | 11/2007 |
| WO | WO 2007/140783 | | 12/2007 |
| WO | WO 2007/143225 | | 12/2007 |
| WO | WO 2007/149319 | | 12/2007 |
| WO | WO 2008/001366 | | 1/2008 |
| WO | WO 2008/014792 | | 2/2008 |
| WO | WO 2008/021913 | | 2/2008 |
| WO | WO 2008/031106 | | 3/2008 |
| WO | WO 2008/031110 | | 3/2008 |
| WO | WO 2008/039944 | | 4/2008 |
| WO | WO 2008/042760 | | 4/2008 |
| WO | WO 2008/048452 | | 4/2008 |
| WO | WO 2008/051920 | | 5/2008 |
| WO | WO 2008/051924 | | 5/2008 |
| WO | WO 2008/052374 | | 5/2008 |
| WO | WO 2008/061552 | | 5/2008 |
| WO | WO 2008/062099 | | 5/2008 |
| WO | WO 2008/065646 | | 6/2008 |
| WO | WO 2008/073813 | | 6/2008 |
| WO | WO 2008/086541 | | 7/2008 |
| WO | WO 2008/103620 | | 8/2008 |
| WO | WO 2008/114223 | | 9/2008 |
| WO | WO 2008/115409 | | 9/2008 |
| WO | WO 2008/128210 | | 10/2008 |
| WO | WO 2008/129532 | | 10/2008 |
| WO | WO 2008/130896 | | 10/2008 |
| WO | WO 2008/130897 | | 10/2008 |

(56) References Cited

FOREIGN PATENT DOCUMENTS

| | | | |
|---|---|---|---|
| WO | WO 2008/130898 | 10/2008 | |
| WO | WO 2008/133702 | 11/2008 | |
| WO | WO 2008/138006 | 11/2008 | |
| WO | WO 2008/143943 | 11/2008 | |
| WO | WO 2008/144445 | 11/2008 | |
| WO | WO 2008/147921 | 12/2008 | |
| WO | WO 2008/147921 A1 | 12/2008 | |
| WO | WO 2008/150917 | 12/2008 | |
| WO | WO 2008/153693 | 12/2008 | |
| WO | WO 2008/155377 | 12/2008 | |
| WO | WO 2008/157821 | 12/2008 | |
| WO | WO 2009/007287 | 1/2009 | |
| WO | WO 2009/010396 | 1/2009 | |
| WO | WO 2009/016635 | 2/2009 | |
| WO | WO 2009/016638 | 2/2009 | |
| WO | WO 2009/018058 | 2/2009 | |
| WO | WO 2009/035773 | 3/2009 | |
| WO | WO 2009/039013 | 3/2009 | |
| WO | WO 2009/062674 | 5/2009 | |
| WO | WO 2009/062675 | 5/2009 | |
| WO | WO 2009/066288 A1 | 5/2009 | |
| WO | WO 2009/068661 | 6/2009 | |
| WO | WO 2009/086216 | 7/2009 | |
| WO | WO 2009/096992 | 8/2009 | |
| WO | WO 2009/097594 | 8/2009 | |
| WO | WO 2010/062898 | 6/2010 | |
| WO | WO 2010/077329 | 7/2010 | |
| WO | WO 2010/091005 | 8/2010 | |
| WO | WO 2010/099507 | 9/2010 | |
| WO | WO 2010/112521 | 10/2010 | |
| WO | WO 2010/141922 | 12/2010 | |
| WO | WO 2011/000528 | 1/2011 | |
| WO | WO 2011/002815 | 1/2011 | |
| WO | WO 2011/015659 | 2/2011 | |
| WO | WO 2011/022418 | 2/2011 | |
| WO | WO 2011/025549 | 3/2011 | |
| WO | WO 2011/104616 | 9/2011 | |
| WO | WO 2011/119896 | 9/2011 | |
| WO | WO 2011/119898 A1 | 9/2011 | |
| WO | WO 2012/103429 | 8/2012 | |
| WO | WO 2013/090215 | 6/2013 | |
| WO | WO 2016/183493 | 11/2016 | |
| WO | WO 2017/027749 | 2/2017 | |
| WO | WO 2017/116915 | 7/2017 | |
| WO | WO 2017/134227 | 8/2017 | |
| WO | WO 2018/136898 A1 | 7/2018 | |
| WO | WO 2018/166963 | 9/2018 | |
| WO | WO 2019/005627 A1 | 1/2019 | |
| WO | WO 2019/236850 A1 | 12/2019 | |
| WO | WO 2019/236859 A1 | 12/2019 | |
| WO | WO-2019236876 A1 * | 12/2019 | ............ A61L 2/206 |
| WO | WO 01/17875 A1 | 3/2021 | |
| WO | WO 2022/046416 | 3/2022 | |
| WO | WO 2022/060677 | 3/2022 | |

OTHER PUBLICATIONS

Inter Partes Review of U.S. Pat. No. 11,013,440, Case No. IPR2022-00637.
Opposition of EP2393418.
Opposition of EP2549918.
Opposition of EP2645324.
Opposition of EP3730044.
Opposition of EP3730045.
Opposition of EP3766408.
WO, PCT/US21/50672 ISR and Written Opinion, Jan. 5, 2022.
AU, 2007309066 Examiner's Report, Jul. 12, 2012.
AU, 2007309066 Examiner's Report, Aug. 16, 2013.
AU, 2008265541 Examiner's Report, Oct. 15, 2012.
AU, 2008265541 Examiner's Report, Nov. 29, 2013.
AU, 2010286917 Examiner's Report, Sep. 8, 2014.
AU, 2011230596 Examiner's Report, Feb. 28, 2014.
AU, 2011269796 Examiner's Report, Apr. 3, 2014.
AU, 2016201703 Examiner's Report, Mar. 22, 2017.
AU, 2017254903 Examiner's Report, Dec. 11, 2018.
AU, 2018200899 Examiner's Report, Dec. 6, 2018.
CA, 2,765,712 Examiner's Report, Apr. 10, 2017.
CA, 2,765,712 Examiner's Report, Mar. 27, 2018.
CA, 2,872,576 Examiner's Report, Feb. 17, 2015.
CA, 2,872,576 Examiner's Report, Feb. 19, 2016.
CA, 3,182,961 Examiner's Report, Mar. 29, 2023.
CN, 200780045373.9 Notice of Allowance, May 18, 2011.
CN, 200780045373.9 Office Action, Apr. 14, 2010.
CN, 201080027344.1 Office Action, Jun. 5, 2014.
CN, 201080027344.1 Office Action, Feb. 6, 2015.
CN, 201080006480.2 Office Action, May 6, 2013.
CN, 201080006480.2 Office Action, Dec. 11, 2013.
CN, 201080006481.7 Office Action, Dec. 2, 2014.
CN, 201180002616.7 Office Action, Apr. 24, 2014.
CN, 201180002617.1 Office Action, Jul. 3, 2014.
CN, 20160144860.1 Office Action, Mar. 23, 2018.
CN, 20160144860.1 Office Action, Dec. 10, 2018.
CN, 20160144860.1 Office Action, May 23, 2019.
CN, 201980082748.1 First Office Action, Jan. 10, 2023.
EP, 06804122.7 Decision to Refuse the Application, Feb. 25, 2013.
EP, 06804122.7 Examination Report, Nov. 30, 2011.
EP, 06804122.7 Examination Report, Jan. 25, 2011.
EP, 06815715.5 Extended Search Report, Oct. 30, 2009.
EP, 06851063.5 Extended Search Report, Sep. 21, 2009.
EP, 07842173.2 Examination Report, Mar. 21, 2013.
EP, 07842173.2 Extended Search Report, Dec. 29, 2010.
EP, 07842180.7 Examination Report, Oct. 23, 2012.
EP, 07842180.7 Examination Report, Dec. 14, 2011.
EP, 07842180.7 Examination Report, Feb. 23, 2011.
EP, 07842180.7 Extended Search Report, Sep. 28, 2009.
EP, 07843396.8 Extended Search Report, Dec. 22, 2010.
EP, 10739015.5 Extended Search Report, May 10, 2013.
EP, 10739031.2 Extended Search Report, May 7, 2013.
EP, 10739031.2 Examination Report, Oct. 28, 2016.
EP, 10739031.2 Notice of Opposition, Dec. 20, 2018.
EP, 10739031.2 Reply to Notice of Opposition, May 21, 2019.
EP, 10739031.2 Reply to Notice of Opposition Reply, Aug. 8, 2019.
EP, 10739031.2 Summons to Attend Oral Proceedings, Sep. 17, 2019.
EP, 10739031.2 Written Submissions, Dec. 3, 2019.
EP, 10739031.2 Response to Written Submissions, Jan. 24, 2020.
EP, 10739031.2 Summons to Attend Oral Proceedings, May 20, 2020.
EP, 10739031.2 Written Submissions, Nov. 20, 2020.
EP, 10739031.2 Response to Written Submissions, Jan. 7, 2021.
EP, 10739031.2 Decision and Grounds for Revoking Patent, Jun. 9, 2021.
EP, 10739031.2 Grounds of Appeal, Oct. 19, 2021.
EP, 10739031.2 Response to Grounds of Appeal, Mar. 1, 2022.
EP, 10739031.2 Response to Response to Grounds of Appeal, Jul. 29, 2022.
EP, 10739031.2 Response to Response to Response to Grounds of Appeal, Jan. 18, 2023.
EP, 10812438.9 Extended Search Report, Dec. 10, 2013.
EP, 11760268.0 Decision of the Oral Proceedings, Sep. 27, 2022.
EP, 11760268.0 Minutes of Oral Proceedings, Aug. 11, 2022.
EP, 11760268.0 Communication from Board of Appeals, Mar. 31, 2022.
EP, 11760268.0 Response to Written Submissions, Jan. 14, 2020.
EP, 11760268.0 Response to Notice of Appeal, Sep. 5, 2019.
EP, 11760268.0 Statement of Grounds of Appeal, Apr. 23, 2019.
EP, 11760268.0 Grounds of Appeal, Apr. 18, 2019.
EP, 11760268.0 Notice of Appeal Abbott Diabetes Care Inc, Feb. 25, 2019.
EP, 11760268.0 Notice of Appeal Dexcom, Feb. 22, 2019.
EP, 11760268.0 Interlocutory Decision, Dec. 13, 2018.
EP, 11760268.0 Response to Summons to Attend Oral Proceedings, Sep. 13, 2018.
EP, 11760268.0 Letter Regarding the Opposition Procedure, Sep. 12, 2018.

(56) References Cited

OTHER PUBLICATIONS

EP, 11760268.0 Summons to Attend Oral Proceedings, Mar. 22, 2018.
EP, 11760268.0 Comments on Reply to Notice of Opposition, Dec. 27, 2017.
EP, 11760268.0 Reply to Notice of Opposition, Sep. 4, 2017.
EP, 11760268.0 Notice of Opposition, Mar. 29, 2017.
EP, 11760268.0 Extended Search Report, Apr. 14, 2014.
EP, 13000104.3 Extended Search Report, Mar. 12, 2013.
EP, 13000105.0 Examination Report, Oct. 18, 2016.
EP, 13000105.0 Minutes of the Oral Proceedings, Oct. 18, 2016.
EP, 13000105.0 Notice of Opposition, Jan. 4, 2019.
EP, 14179905.6 Summons to Attend Oral Proceedings, Apr. 10, 2017.
EP, 14179905.6 Notice of Opposition, May 19, 2016.
EP, 14179905.6 Extended Search Report, Dec. 23, 2014.
EP, 15002441.2 Extended Search Report, Dec. 18, 2015.
EP, 15184320.8 Examination Report, Apr. 18, 2017.
EP, 16176370.1 Extended Search Report, Dec. 7, 2016.
EP, 16793637.6 Extended Search Report, Oct. 9, 2018.
EP, 17182379.2 Extended Search Report, Feb. 21, 2018.
EP, 17201183.5 Extended Search Report, May 7, 2018.
EP, 17201183.5 Examination Report, May 7, 2019.
EP, 18192278.2 Extended Search Report, Mar. 13, 2019.
EP, 18208224.8 Extended Search Report, Oct. 11, 2019.
EP, 18741791.0 Extended Search Report, Sep. 23, 2020.
EP, 19151577.4 Extended Search Report, Aug. 16, 2019.
EP, 19151577.4 Examination Report, May 27, 2022.
EP, 19184881.1 Extended Search Report, Dec. 4, 2019.
EP, 20177703.4 Response to Notice of Opposition, Jun. 29, 2023.
EP, 20177703.4 Notice of Intervention, Jun. 23, 2023.
EP, 20177703.4 Reply to Opposition, Feb. 22, 2023.
EP, 20177703.4 Grounds of Opposition, Sep. 28, 2022.
EP, 20177703.4 Notice of Opposition, Sep. 28, 2022.
EP, 20177703.4 Examination Report, Jun. 25, 2021.
EP, 20177703.4 Extended Search Report, Sep. 25, 2020.
EP, 20177712.5 Notice of Intervention, Jun. 23, 2023.
EP, 20177712.5 Reply to Opposition, May 23, 2023.
EP, 20177712.5 Grounds of Opposition Gulde & Partner Patent, Dec. 22, 2022.
EP, 20177712.5 Grounds of Opposition Dexcom, Dec. 22, 2022.
EP, 20177712.5 Notice of Opposition Gulde & Partner Patent, Dec. 22, 2022.
EP, 20177712.5 Notice of Opposition Dexcom, Dec. 22, 2022.
EP, 20177712.5 Extended Search Report, Sep. 30, 2020.
EP, 20195922.8 Reply to Opposition, Jun. 20, 2023.
EP, 20195922.8 Notice of Intervention, Jun. 13, 2023.
EP, 20195922.8 Grounds of Opposition Dexcom, Jan. 26, 2023.
EP, 20195922.8 Notice of Opposition Dexcom, Jan. 26, 2023.
EP, 20195922.8 Extended Search Report, Dec. 16, 2020.
EP, 21152231.3 Extended Search Report, May 11, 2021.
EP, 21192910.4 Extended Search Report, Jan. 31, 2022.
EP, 21211041.5 Extended Search Report, Mar. 3, 2022.
EP, 22168031.7 Extended Search Report, Aug. 17, 2022.
EP, 22169853.3 Extended Search Report, Sep. 2, 2022.
IL, 198329 Office Action, Mar. 5, 2012.
JP, 2009-534798 Office Action, Sep. 25, 2012.
JP, 2012-526736 Office Action, Apr. 15, 2014.
JP, 2012-526736 Office Action, Dec. 16, 2014.
JP, 2013-501503 Office Action, Mar. 3, 2015.
JP, 2015-159805 Office Action, Aug. 9, 2016.
JP, 2016-44196 Office Action, Apr. 11, 2017.
JP, 2021-531135 Office Action, Feb. 22, 2023.
MX, MX/a/2009/004398 Office Action, Sep. 24, 2012.
MY, PI2021004760 Examination Report, Mar. 30, 2022.
MY, PI2021005830 Examination Report, Sep. 30, 2022.
MY, PI2021005830 Examination Report, Aug. 29, 2022.
MY, PI2022007295 Examination Report, Jul. 11, 2023.
NL, 2009963 Search Report, Aug. 12, 2013.
US, Final Written Decision, IPR No. 2022-00605, Jul. 10, 2023.
US, Institution Decision, IPR No. 2022-00605, Jul. 27, 2022.
US, Patent Owner's Preliminary Sur-Reply, IPR No. 2022-00605, Jun. 28, 2022.
US, Petitioner's Preliminary Reply to Patent Owner's Preliminary Response, IPR No. 2022-00605, Jun. 21, 2022.
US, Patent Owner's Preliminary Response, IPR No. 2022-00605, May 24, 2022.
US, Petition for Inter Partes Review of U.S. Pat. No. 10,945,649, IPR No. 2022-00605, Feb. 15, 2022.
US, Institution Decision, IPR No. 2022-00637, Jul. 27, 2022.
US, Patent Owner's Preliminary Sur-Reply, IPR No. 2022-00637, Jun. 28, 2022.
US, Petitioner's Preliminary Reply to Patent Owner's Preliminary Response, IPR No. 2022-00637, Jun. 21, 2022.
US, Patent Owner's Preliminary Response, IPR No. 2022-00637, Jun. 9, 2022.
US, Petition fFor Inter Partes Review of U.S. Pat. No. 11,013,440, IPR No. 2022-00637, Feb. 8, 2022.
US, Reexamination Serial No. 95/002,162 Request to Review Order Denying Request for Reexamination, Dec. 13, 2012.
US, Reexamination Serial No. 95/002,162 Order Denying Request for Reexamination, Nov. 13, 2012.
US, Request for Reexamination Serial No. 95/002,162 of U.S. Pat. No. 8,175,673, Sep. 7, 2012.
US, Reexamination Serial No. 95/002,113 Request to Review Order Denying Request for Reexamination, Dec. 13, 2012.
US, Reexamination Serial No. 95/002,113 Order Denying Request for Reexamination, Nov. 13, 2012.
US, Request for Reexamination Serial No. 95/002,113 of U.S. Pat. No. 6,990,366, Aug. 30, 2012.
US, Reexamination Serial No. 90/011,730 Notice of Intent to Issue Ex Parte Reexamination Certificate, Apr. 5, 2012.
US, Reexamination Serial No. 90/011,730 Office Action, Jan. 11, 2012.
US, Reexamination Serial No. 90/011,730 Order Granting Request for Reexamination, Aug. 24, 2011.
US, Request for Reexamination Serial No. 90/011,730 of U.S. Pat. No. 6,990,366, Jun. 3, 2011.
US, Reexamination Serial No. 90/010,791 Ex Parte Reexamination Certificate, May 17, 2011.
US, Reexamination Serial No. 90/010,791 Office Action, Dec. 17, 2010.
US, Reexamination Serial No. 90/010,791 Office Action, May 28, 2010.
US, Reexamination Serial No. 90/010,791 Order Granting Request for Reexamination, Feb. 22, 2010.
US, Request for Reexamination Serial No. 90/010,791 of U.S. Pat. No. 6,990,366, Dec. 22, 2009.
US, Reexamination Serial No. 90/009,328 Notice of Intent to Issue Ex Parte Reexamination Certificate, Nov. 20, 2009.
US, Reexamination Serial No. 90/009,328 Office Action, Sep. 30, 2009.
US, Reexamination Serial No. 90/009,328 Office Action, Aug. 4, 2009.
US, Reexamination Serial No. 90/009,328 Order Granting Request for Reexamination, Dec. 9, 2008.
US, Request for Reexamination Serial No. 90/009,328 of U.S. Pat. No. 6,990,366, Nov. 10, 2008.
US, Reexamination Serial No. 90/009,104 Notice of Intent to Issue Ex Parte Reexamination Certificate, Nov. 20, 2009.
US, Reexamination Serial No. 90/009,104 Office Action, Sep. 30, 2009.
US, Reexamination Serial No. 90/009,104 Office Action, Aug. 4, 2009.
US, Reexamination Serial No. 90/009,104 Office Action, Oct. 16, 2008.
US, Reexamination Serial No. 90/009,104 Order Granting Request for Reexamination, Jun. 5, 2008.
US, Request for Reexamination Serial No. 90/009,104 of U.S. Pat. No. 6,990,366, Apr. 8, 2008.
US, Reexamination Serial No. 90/008,457 Notice of Intent to Issue Ex Parte Reexamination Certificate, Mar. 13, 2008.

(56) References Cited

OTHER PUBLICATIONS

US, Reexamination Serial No. 90/008,457 Order Granting Request for Reexamination, Feb. 23, 2007.
US, Request for Reexamination Serial No. 90/008,457 of U.S. Pat. No. 6,990,366, Jan. 23, 2007.
US, Request for Reexamination Serial No. 90/008,172 of U.S. Pat. No. 6,990,366, Aug. 16, 2006.
US, Reexamination Serial No. 90/007,910 Patent Board Decision, May 17, 2013.
US, Reexamination Serial No. 90/007,910 Decision on Appeal, Jan. 18, 2011.
US, Reexamination Serial No. 90/007,910 Advisory Action, Jul. 30, 2009.
US, Reexamination Serial No. 90/007,910 Advisory Action, Feb. 6, 2009.
US, Reexamination Serial No. 90/007,910 Examiner's Answer to Appeal Brief, Nov. 19, 2009.
US, Reexamination Serial No. 90/007,910 Office Action, Oct. 2, 2008.
US, Reexamination Serial No. 90/007,910 Office Action, Feb. 13, 2008.
US, Reexamination Serial No. 90/007,910 Order Granting Request for Reexamination, Mar. 27, 2006.
US, Request for Reexamination Serial No. 90/007,910 of U.S. Pat. No. 6,175,752, Feb. 1, 2006.
US, Reexamination Serial No. 90/009,270 Order Denying Request for Reexamination, Dec. 1, 2008.
US, Request for Reexamination Serial No. 90/009,270 of U.S. Pat. No. 6,175,752, Sep. 8, 2008.
US, Reexamination Serial No. 90/009,497 Notice of Intent to Issue Reexamination Certificate, Aug. 23, 2010.
US, Reexamination Serial No. 90/009,497 Order Granting Request, Jul. 30, 2009.
US, Request for Reexamination Serial No. 90/009,497 of U.S. Pat. No. 6,175,752, Jun. 17, 2009.
WO, PCT/US2006/037312 ISR and Written Opinion, Apr. 17, 2007.
WO, PCT/US2006/037928 ISR and Written Opinion, Jul. 11, 2008.
WO, PCT/US2006/062690 ISR and Written Opinion, Jan. 2, 2008.
WO, PCT/US2007/078065 ISR and Written Opinion, Apr. 11, 2008.
WO, PCT/US2007/078073 ISR and Written Opinion, Apr. 11, 2008.
WO, PCT/US2007/079774 ISR and Written Opinion, Apr. 1, 2008.
WO, PCT/US2007/082114 ISR and Written Opinion, May 9, 2008.
WO, PCT/US2010/002401 ISR and Written Opinion, Nov. 12, 2010.
WO, PCT/US2010/022860 ISR and Written Opinion, Mar. 23, 2010.
WO, PCT/US2010/022928 ISR and Written Opinion, Mar. 21, 2010.
WO, PCT/US2010/047381 ISR and Written Opinion, Oct. 15, 2010.
WO, PCT/US2010/050772 ISR and Written Opinion, Dec. 3, 2010.
WO, PCT/US2010/050888 ISR and Written Opinion, Nov. 29, 2010.
WO, PCT/US2010/051861 ISR and Written Opinion, Nov. 30, 2010.
WO, PCT/US2011/029881 ISR and Written Opinion, May 20, 2011.
WO, PCT/US2011/029883 ISR and Written Opinion, Jun. 2, 2011.
WO, PCT/US2011/029884 ISR and Written Opinion, Jun. 1, 2011.
WO, PCT/US2012/062551 ISR and Written Opinion, Jan. 2, 2013.
WO, PCT/US2012/068839 ISR and Written Opinion, Feb. 22, 2013.
WO, PCT/US2013/052397 ISR and Written Opinion, Dec. 2, 2013.
WO, PCT/US2016/032485 ISR and Written Opinion, Sep. 12, 2016.
WO, PCT/US2018/014745 ISR and Written Opinion, Jun. 4, 2018.
WO, PCT/US2019/035843 ISR and Written Opinion, Sep. 18, 2019.
WO, PCT/US2021/040541 ISR and Written Opinion, Dec. 20, 2021.
WO, PCT/US2021/045576 ISR and Written Opinion, Jan. 27, 2022.
WO, PCT/US2021/048086 ISR and Written Opinion, Feb. 28, 2022.
WO, PCT/US2022/037291 ISR and Written Opinion, Nov. 22, 2022.
WO, PCT/US2022/037291 Invitation to Pay Additional Fees, Sep. 29, 2022.
WO, PCT/US2023/010054 ISR and Written Opinion, May 15, 2023.
WO, PCT/U82023/010054 Invitation to Pay Additional Fees, Mar. 24, 2023.
Abruna, H. D., et al., "Rectifying Interfaces Using Two-Layer Films of Electrochemically Polymerized Vinylpyridine and Vinylbipyridine Complexes of Ruthenium and Iron on Electrodes", Journal of the American Chemical Society, 1981, vol. 103, No. 1, pp. 1-5.
Accu-Chek Compact Plus Owner's Booklet, 2008, pp. 1-100.
Accu-Chek Softclix Plus Lancet Device retrieved from https://web.archive.org/web/20061018055737/http://www.accu-check.com/us/rewrite/content/en_US/2.1.7.1:10/article/ACCM_general_article_3303.htm, 2006, pp. 1-2.
Affidavit of Richard Paragas signed on May 18, 2016, pp. 1-4.
Affidavit of Paul Neale signed on May 18, 2016, pp. 1-2.
Ahson, S., et al., "RFID Handbook: Applications, Technology, Security, and Privacy", 2008, Chapter 4, Far-Field Tag Antenna Design Methodology, and Chapter 13, RFID Tags for Metallic Object Identification, pp. 71 and 253-254.
Albery, W.J., et al., "Amperometric Enzyme Electrodes Part II: Conducting Salts as Electrode Materials for the Oxidation of Glucose Oxidase", Journal of ElectroAnalytical Chemistry, 1985, vol. 194, pp. 223-235.
Albery, W.J., et al., "Amperometric Enzyme Electrodes", Philosophical Transactions of the Royal Society of London, 1987, vol. 316, pp. 107-119.
Alcock, S J, et al., "Continuous analyte monitoring to aid clinical practice," IEEE Engineering in Medicine & BioloXY Magazine, 1994, vol. 13. pp. 319-25.
Ambade, V. N., et al., "Methods for Estimation of Blood Glucose: A Comparative Evaluation", Medical Journal Armed Forces India, 1998, vol. 54, No. 2, pp. 131-133.
Anderson, L. B., et al., "Thin-Layer Electrochemistry: Steady-State Methods of Studying Rate Processes", Journal of ElectroAnalytical Chemistry, 1965, vol. 10, pp. 295-305.
Application Note AN048, Antenna Part No. FR05-S1-N-0-102, Compact Reach Xtend™, Bluetooth®, 802.11b/g WLAN Chip Antenna, 2008, pp. 1-13.
Application Note AVR2023-AT86RF231 PCB reference design for antenna diversity, Atmel Corporation, 2008, pp. 1-15.
Application Note nRF9E5 RF and antenna layout, Nordic Semiconductor, 2006, pp. 1-13.
Armour, J. C., et al., "Application of Chronic Intravascular Blood Glucose Sensor in Dogs," Diabetes, 1990, vol. 39, pp. 1519-1526.
ASTM International, Designation D2240-05, 2010, pp. 1-13.
Aussedat, B., et al., "A User-Friendly Method for Calibrating a Subcutaneous Glucose Sensor-Based Hypoglycemic Alarm", Biosensors & Bioelectronics, 1997, vol. 12, No. 11, pp. 1061-1071.
Bartlett, P. N., et al., "Covalent Binding of Electron Relays to Glucose Oxidase", Journal of the Chemical Society, Chemical Communications, 1987, pp. 1603-1604.
Bartlett, P. N., et al., "Modification of Glucose Oxidase by Tetrathiafulvalene", Journal of the Chemical Society, Chemical Communications, 1990, pp. 1135-1136.
Benkič, K., et al., "Using RSSI value for distance estimation in Wireless sensor networks based on ZigBee", 15th International Conference on Systems, Signals and Image Processing, Bratislava, Slovakia, 2008, pp. 1-4.
Bennion, N., et al., "Alternate Site Glucose Testing: A Crossover Design", Diabetes Technology & Therapeutics, 2002, vol. 4, No. 1, pp. 25-33.
Bindra, D.S., et al., "Pulsed Amperometric Detection of Glucose in Biological Fluids at a Surface-Modified Gold Electrode", American Chemical Society, 1989, vol. 61, No. 22, pp. 2566-2570.
Bindra, D.S., et al., "Design and in Vitro Studies of a Needle-Type Glucose Sensor for Subcutaneous Monitoring," Anal. Chem., 1991, vol. 63, No. 17, pp. 1692-1696.
Biosensors: Fundamentals and Applications, Turner et al., Eds., 1987, pp. 1-786.

(56) References Cited

OTHER PUBLICATIONS

Blank, T. B., et al., "Clinical Results From a Non-Invasive Blood Glucose Monitor", Optical Diagnostics and Sensing of Biological Fluids and Glucose and Cholesterol Monitoring II, Proceedings of SPIE, 2002, vol. 4624, pp. 1-10.
"Bluetooth Antenna Design", National Semiconductor Application Note, 2005, pp. 1-16.
Bluetooth Core Specification 4.0, Jun. 30, 2010, Master Table of Contents & Compliance Requirements, pp. 1-89.
Bobbioni-Harsch, E. et al., "Lifespan of subcutaneous glucose sensors and their performances during dynamic glycaemia changes in rats," J. Biomed. Eng., 1993, vol. 15, pp. 457-463.
Bonnett, A. H., et al., "Squirrel-Cage Rotor Options for AC Induction Motors", IEEE Transactions on Industry Applications, 2001, vol. 37, No. 4, pp. 1197-1209.
Brandt, J., et al., "Covalent Attachment of Proteins to Polysaccharide Carriers by Means of Benzoquinone", Biochimica et Biophysica Acta, 1975, vol. 386, pp. 196-202.
Brooks, S. L., et al., "Development of an On-Line Glucose Sensor for Fermentation Monitoring", Biosensors, 1987/88, vol. 3, pp. 45-56.
Brownlee, M., et al., "A Glucose-Controlled Insulin-Delivery System: Semisynthetic Insulin Bound to Lectin", Science, 1979, vol. 206, pp. 1190-1191.
Bühling, K. J., et al., "Optimal timing for postprandial glucose measurement in pregnant women with diabetes and a non-diabetic pregnant population evaluated by the Continuous Glucose Monitoring System (CGMS®)", Journal of Perinatal Medicine, 2005, vol. 33, No. 2, pp. 125-131.
Callaway, Jr., E. H., "Wireless Sensor Networks: Architectures and Protocols", 2004, Chapter 8, Antennas and the Definition of RF Performance, pp. 201-202.
Cass, A.E.G et al., "Ferrocene-Mediated Enzyme Electrode for Amperometric Determination of Glucose," Anal. Chem., 1984, vol. 56, No. 4, pp. 667-671.
Cass, A.E.G et al., "Ferricinium Ion as an Electron Acceptor for Oxido-Reductases", Journal of ElectroAnalytical Chemistry, 1985, vol. 190, pp. 117-127.
Castner, J. F., et al., "Mass Transport and Reaction Kinetic Parameters Determined Electrochemically for Immobilized Glucose Oxidase", Biochemistry, 1984, vol. 23, No. 10, pp. 2203-2210.
U.S. Appl. No. 60/424,099, filed Nov. 5, 2002.
Cheyne, E.H., et al., "Performance of a Continuous Glucose Monitoring System During Controlled Hypoglycaemia in Healthy Volunteers", Diabetes Technology & Therapeutics, 2002, vol. 4, No. 5, pp. 607-613.
Choleau, C., et al., "Calibration of a Subcutaneous Amperometric Glucose Sensor Implanted for 7 Days in Diabetic Patients Part 2. Superiority of the One-Point Calibration Method", Biosensor & Bioelectronics, 2002, vol. 17, No. 8, pp. 647-654.
Choleau, C., et al., "Calibration of a Subcutaneous Amperometric Glucose Sensor Part 1. Effect of Measurement Uncertainties on the Determination of Sensor Sensitivity and Background Current", Biosensor & Bioelectronics, 2002, vol. 17, No. 8, pp. 641-646.
Claremont, D. J., et al., "Biosensors for Continuous In Vivo Glucose Monitoring", Proceedings of the Annual International Conference of the IEEE Engineering in Medicine and Biology Society, 1988, vol. 10, pp. 1-2.
Clark Jr., L. C., et al., "Electrode Systems for Continuous Monitoring in Cardiovascular Surgery", Annals New York Academy of Sciences, 1962, pp. 29-45.
Clark Jr., L. C., et al., "Differential Anodic Enzyme Polarography for the Measurement of Glucose", Oxygen Transport to Tissue: Instrumentation, Methods, and Physiology, 1973, pp. 127-133.
Clark Jr., L. C., et al., "Long-term Stability of Electroenzymatic Glucose Sensors Implanted in Mice", American Society of Artificial Internal Organs Transactions, 1988, vol. XXXIV, pp. 259-265.
Clarke, W. L., et al., "Evaluating Clinical Accuracy of Systems for Self-Monitoring of Blood Glucose", Diabetes Care, 1987, vol. 10, No. 5, pp. 622-628.
Clarke, W., et al., "Statistical Tools to Analyze Continuous Glucose Monitor Data", Diabetes Technology & Therapeutics, 2009, vol. 11, Suppl. 1, pp. S-45-S-54.
Cleo™ 90 Infusion Set, 510(k) Summary of Safety and Effectiveness, Aug. 10, 2004, pp. 1-618.
Cleo® 90 Infusion Set Training Guide, 2011, 1 page.
Compact Plus Blood Glucose Meter retrieved from https://web.archive.org/web/20090316065810/http://www.accu-check.com/us/rewrite/content/en_US/2.1.9:0/article/ACCM_general_article_5136.htm, 2009, pp. 1-3.
Complaint *Abbott Diabetes Care Inc*. v. *Dexcom, Inc*. U.S. District Court Delaware C.A. No. 05-590 filed Aug. 11, 2005.
Complaint, Amended, *Abbott Diabetes Care Inc*. v. *Dexcom, Inc*. U.S. District Court Delaware C.A. No. 05-590 filed Jun. 27, 2006.
Complaint *Abbott Diabetes Care Inc*. v. *Dexcom, Inc*. U.S. District Court Delaware C.A. No. 06-514 filed Aug. 17, 2006.
Cox, M., "An Overview of Continuous Glucose Monitoring Systems", Journal of Pediatric Health Care, 2009, vol. 23, No. 5, pp. 344-347.
Csöregi, E., et al., "Design and Optimization of a Selective Subcutaneously Implantable Glucose Electrode Based on 'Wired' Glucose Oxidase", Analytical Chemistry, 1995, vol. 67, No. 7, pp. 1240-1244.
Csöregi, E., et al., "Design, Characterization, and One-Point in Vivo Calibration of a Subcutaneously Implanted Glucose Electrode", Analytical Chemistry, 1994, vol. 66 No. 19, pp. 3131-3138.
Csöregi, E., et al., "On-Line Glucose Monitoring by Using Microdialysis Sampling and Amperometric Detection Based on 'Wired' Glucose Oxidase in Carbon Paste", Mikrochimica Acta, 1995, vol. 121, pp. 31-40.
Cullen, M.T., et al., "The Changing Presentations of Diabetic Ketoacidosis During Pregnancy", Amer. J. Perinatol, 1996, vol. 13, No. 7, pp. 449-451 (abstract only).
In Vivo Glucose Sensing, Cunningham et al., Eds., 2010, Chemical Analysis, vol. 174, pp. 1-466.
Darley, J., "Is your user experience as good as your technology?", 2019, retrieved from https://www.massdevice.com/is-your-user-experience-as-good-as-your-technology/, pp. 1-16.
Davis, G., "Electromechanical Techniques for the Development of Amperometric Biosensors", Biosensors, 1985, vol. 1, pp. 161-178.
De Block, C., et al., "Minimally-Invasive and Non-Invasive Continuous Glucose Monitoring Systems: Indications, Advantages, Limitations and Clinical Aspects", Current Diabetes Reviews, 2008, vol. 4, No. 3, pp. 159-168.
IPR2022-00605 (Ex. 2001) Declaration of Michael Cima, Ph.D dated May 24, 2022, pp. 1-70.
IPR2022-00637 (Ex. 2001) Declaration of Michael Cima, Ph.D dated Jun. 9, 2022, pp. 1-79.
IPR2022-00605 (Ex. 1003) Declaration of Gary D. Fletcher, Ph.D dated Feb. 15, 2022, pp. 1-122.
IPR2022-00605 (Ex. 1003) Corrected Declaration of Gary D. Fletcher, Ph.D dated Feb. 18, 2022, pp. 1-124.
IPR2022-00637 (Ex. 1035) Second Declaration of Gary D. Fletcher, Ph.D dated Feb. 28, 2022, pp. 1-136.
Decuir, J., "Bluetooth 4.0: Low Energy", IEEE SCV Consultants' Network of Silicon Valley, 2012, pp. 1-68.
Degani, Y., et al., "Direct Electrical Communication Between Chemically Modified Enzymes and Metal Electrodes. 1. Electron Transfer from Glucose Oxidase to Metal Electrodes via Electron Relays, Bound Covalently to the Enzyme", The Journal of Physical Chemistry, 1987, vol. 91, No. 6, pp. 1285-1289.
Degani, Y., et al., "Direct Electrical Communication Between Chemically Modified Enzymes and Metal Electrodes. 2. Methods for Bonding Electron-Transfer Relays to Glucose Oxidase and D-Amino-Acid Oxidase", Journal of the American Chemical Society, 1988, vol. 110, No. 8, pp. 2615-2620.
Degani, Y., et al., "Electrical Communication Between Redox Centers of Glucose Oxidase and Electrodes via Electrostatically and Covalently Bound Redox Polymers", Journal of the American Chemical Society, 1989, vol. 111, pp. 2357-2358.
Dehez, B., et al., "Development of a Spherical Induction Motor With Two Degrees of Freedom", IEEE Transactions on Magnetics, 2006, vol. 42, No. 8, pp. 2077-2089.

(56) References Cited

OTHER PUBLICATIONS

Delve Talks: Jake Leach, Dexcom, retrieved from https://www.delve.com/podcasts/delve-talks-jake-leach-dexcom, 2019, pp. 1-9.
Dementyev, A., et al., "Power Consumption Analysis of Bluetooth Low Energy, ZigBee and ANT Sensor Nodes in a Cyclic Sleep Scenario", IEEE International Wireless Symposium (IWS), 2013, Beijing, China, pp. 1-4.
Denisevich, P., et al., "Unidirectional Current Flow and Charge State Trapping at Redox Polymer Interfaces on Bilayer Electrodes: Principles, Experimental Demonstration, and Theory", Journal of the American Chemical Society, 1981, vol. 103, pp. 4727-4737.
"Dexcom CEO tells investors not to fear new competition from Abbott's Freestyle Libre", 2017, retrieved from https://www.mobihealthnews.com/content/dexcom-ceo-tells-investors-not-fear-new-competition-abbotts-freestyle-libre, pp. 1-3.
Dexcom G5 Mobile System User Guide, 2020, pp. 1-410.
Dexcom G6, Winner Health & Wellness Award, Core77 Design Awards, 2019, retrieved from https://designawards.core77.com/health-wellness/85111/Dexcom-G6, pp. 1-8.
DexCom™ STS™ Continuous Glucose Monitoring System User's Guide, 2006, pp. 1-57.
Dexcom STS®-7 Continuous Glucose Monitoring System User's Guide, 2007, pp. 1-74.
Dicks, J.M., et al., "Ferrocene Modified Polypyrrole with Immobilised Glucose Oxidase and its Application in Amperometric Glucose Microbiosensors", Annales de Biologie Clinique, 1989, vol. 47, pp. 607-619.
Diem, P., et al., "Clinical Performance of a Continuous Viscometric Affinity Sensor for Glucose", Diabetes Technology & Therapeutics, 2004, vol. 6, pp. 790-799.
ECMA International Standard ECMA-340, Near Field Communication Interface and Protocol (NFCIP-1), 2nd Edition, 2004, pp. 1-65.
El-Khatib, F. H, et al., "Adaptive Closed-Loop Control Provides Blood-Glucose Regulation Using Subcutaneous Insulin and Glucagon Infusion in Diabetic Swine", Journal of Diabetes Science and Technology, 2007, vol. 1, No. 2, pp. 181-192.
Ellis, C. D., et al., "Selectivity and Directed Charge Transfer through an Electroactive Metallopolymer Film", Journal of the American Chemical Society, 1981, vol. 103, No. 25, pp. 7480-7483.
Engstrom, R. C., "Electrochemical Pretreatment of Glassy Carbon Electrodes", Analytical Chemistry, 1982, vol. 54, No. 13, pp. 2310-2314.
Engstrom, R. C., et al., "Characterization of Electrochemically Pretreated Glassy Carbon Electrodes", Analytical Chemistry, 1984, vol. 56, No. 2, pp. 136-141.
Facchinetti, A., et al., "A New Index to Optimally Design and Compare Continuous Glucose Monitoring Glucose Prediction Algorithms", Diabetes Technology & Therapeutics, 2011, vol. 13, No. 2, pp. 111-119.
Feldman, B., et al., "Electron Transfer Kinetics at Redox Polymer/Solution Interfaces Using Microelectrodes and Twin Electrode Thin Layer Cells", Journal of ElectroAnalytical Chemistry, 1985, vol. 194, pp. 63-81.
Feldman, B., et al., "A Continuous Glucose Sensor Based on Wired Enzyme™ Technology—Results from a 3-Day Trial in Patients with Type 1 Diabetes", Diabetes Technology & Therapeutics, 2003, vol. 5, No. 5, pp. 769-779.
Feldman, B., et al., "Correlation of Glucose Concentrations in Interstitial Fluid and Venous Blood During Periods of Rapid Glucose Change", Abbott Diabetes Care, Inc. Freestyle Navigator Continuous Glucose Monitor Pamphlet, 2004.
File History of U.S. Pat. No. 10,292,632.
File History of U.S. Pat. No. 10,945,649.
File History of U.S. Pat. No. 11,013,440.
File Wrapper of U.S. Appl. No. 60/587,787.
File Wrapper of U.S. Appl. No. 10/633,367.
File Wrapper of U.S. Appl. No. 12/250,760.
Fischer, H., et al., "Intramolecular Electron Transfer Medicated by 4,4'-Bypyridine and Related Bridging Groups", Journal of the American Chemical Society, 1976, vol. 98, No. 18, pp. 5512-5517.
Foulds, N. C., et al., "Enzyme Entrapment in Electrically Conducting Polymers: Immobilisation of Glucose Oxidase in Polypyrrole and its Application in Amperometric Glucose Sensors", Journal of the Chemical Society, Faraday Transactions 1, 1986, vol. 82, pp. 1259-1264.
Foulds, N. C., et al., "Immobilization of Glucose Oxidase in Ferrocene-Modified Pyrrole Polymers", Analytical Chemistry, 1988, vol. 60, No. 22, pp. 2473-2478.
Freedman, D., et al., Statistics: Second Edition, 1991, Chapter 5, p. 74.
Freestyle Navigator Continuous Glucose Monitor FDA Premarket Approval (PMA), May 2022, pp. 1-6.
Freestyle Navigator Summary of Safety and Effectiveness Data, 2008, pp. 1-27.
Freestyle Navigator User's Guide, 2008, pp. 1-195.
Frenzel, L. E., "Printed-Circuit-Board Antennas", retrieved from https://www.electronicdesign.com/technologies/boards/article/21751417/printedcircuitboard-antennasprint/3266, Electronic Design, 2005, pp. 1-4.
Frew, J. E., et al., "Electron-Transfer Biosensors", Philosophical Transactions of the Royal Society of London, 1987, vol. 316, pp. 95-106.
Fujipoly Silver ZEBRA® Connector Data Sheet FSDS 01-34, Version 5, 2006, pp. 1-7.
Garg, S., et al., "Improvement in Glycemic Excursions with a Transcutaneous, Real-Time Continuous Glucose Sensor", Diabetes Care, 2006, vol. 29, No. 1, pp. 44-50.
Garibotto, J., et al., "An Innovative Application of Shape Memory Alloy Technology Yields a Novel Therapeutic Approach to Diabetes Management", Insulet Corporation, 2006, p. A41.
Gilligan, B. J., et al., "Evaluation of a Subcutaneous Glucose Sensor out to 3 Months in a Dog Model", Diabetes Care, 1994, vol. 17, No. 8, pp. 882-887.
Gonzales, W. V., et al., "The Progress of Glucose Monitoring—A Review of Invasive to Minimally and Non-Invasive Techniques, Devices and Sensors", Sensors, 2019, vol. 19, No. 800, pp. 1-45.
Gonzalez, O. L., et al., "Low-Cost Wireless Sensors—Designer Reference Manual", Freescale Semiconductor, 2007, pp. 1-146.
Gorton, L., et al., "Selective Detection in Flow Analysis Based on the Combination of Immobilized Enzymes and Chemically Modified Electrodes", Analytica Chimica Acta, 1991, vol. 250, pp. 203-248.
Gregg, B. A., et al., "Cross-Linked Redox Gels Containing Glucose Oxidase for Amperometric Biosensor Applications," Analytical Chemistry, 1990, vol. 62, No. 3, pp. 258-263.
Gregg, B. A., et al., "Redox Polymer Films Containing Enzymes. 1. A Redox-Conducting Epoxy Cement: Synthesis, Characterization, and Electrocatalytic Oxidation of Hydroquinone", Journal of Physical Chemistry, 1991, vol. 95, No. 15, pp. 5970-5975.
Gregg, T. H., "How Continuous Glucose Monitoring is Transforming Diabetes Treatment", Qualcomm Life Connect, 2013, pp. 1-33.
Guardian® RT Continuous Glucose Monitoring System REF MMT-7900 User Guide, 2005, pp. 1-128.
Guerci, B., et al., "Clinical Performance of CGMS in Type 1 Diabetic Patients Treated by Continuous Subcutaneous Insulin Infusion Using Insulin Analogs", Diabetes Care, 2003, vol. 26, No. 3, pp. 582-589.
Guerra, S., et al., "A Dynamic Risk Measure from Continuous Glucose Monitoring Data", Diabetes Technology & Therapeutics, 2011, vol. 13, No. 8, pp. 843-852.
Güler, N. F., et al., "Theory and Applications of Biotelemetry", Journal of Medical Systems, 2002, vol. 26, No. 2, pp. 159-178.
Gunasingham, et al., "Electrochemically Modulated Optrode for Glucose", Biosensors & Bioelectronics, 1992, vol. 7, pp. 353-359.
Hale, P. D., et al., "A New Class of Amperometric Biosensor Incorporating a Polymeric Electron-Transfer Mediator", Journal of the American Chemical Society, 1989, vol. 111, No. 9, pp. 3482-3484.
Hao, Y., "Wireless body sensor networks for health-monitoring applications", Physiol. Meas., 2008, vol. 29, R27-R56.

(56) References Cited

OTHER PUBLICATIONS

Harrison, D. J et al., "Characterization of Perfluorosulfonic Acid Polymer Coated Enzyme Electrodes and a Miniaturized Integrated Potentiostat for Glucose Analysis in Whole Blood," Anal. Chem., 1988, vol. 60, No. 19, pp. 2002-2007.
Hawkridge, F. M., et al., "Indirect Coulometric Titration of Biological Electron Transport Components", Analytical Chemistry, 1973, vol. 45, No. 7, pp. 1021-1027.
Heftman, G., "Chip Antenna Reduces Cell-Phone Dimensions", Microwaves & RF, 1999, p. 182.
Heise, T., et al., "Hypoglycemia Warning Signal and Glucose Sensors: Requirements and Concepts", Diabetes Technology & Therapeutics, 2003, vol. 5, No. 4, pp. 563-571.
Heller, A., "Electrical Connection of Enzyme Redox Centers to Electrodes," J. Phys. Chem., 1992, vol. 96, No. 9, pp. 3579-3587.
Heller, A., "Electrical Wiring of Redox Enzymes," Acc. Chem. Res., 1990, vol. 23, No. 5, pp. 129-134.
Heller, A., et al., "Amperometric Biosensors Based on Three-Dimensional Hydrogel-Forming Epoxy Networks", Sensors and Actuators B, 1993, vol. 13-14, pp. 180-183.
Heller, A., "Implanted Electrochemical Glucose Sensors for the Management of Diabetes", Annnu. Rev. Biomed. Eng., 1999, vol. 1, pp. 153-175.
Hirsch, I. B., "Introduction: History of Glucose Monitoring", Clinical Compendia, 2018, vol. 2018, No. 1, 1 page.
Hoel, P. G., Elementary Statistics: Fourth Edition, 1976, Chapter 5, pp. 113-114.
Howe, D., "Comparing the Dexcom G6 to the G5", 2018, retrieved from https://beyondtype1.org/comparing-the-dexcom-g6-to-the-g5/, pp. 1-10.
Huang, Y., et al., "Antennas from Theory to Practice", 2008, Chapter 8, Antenna Diversity, pp. 322-325.
Ianniello, R. M., et al., "Immobilized Enzyme Chemically Modified Electrode as an Amperometric Sensor", Analytical Chemistry, 1981, vol. 53, No. 13, pp. 2090-2095.
Ianniello, R. M., et al., "Differential Pulse Voltammetric Study of Direct Electron Transfer in Glucose Oxidase Chemically Modified Graphite Electrodes", Analytical Chemistry, 1982, vol. 54, No. 7, pp. 1098-1101.
Ikeda, T., et al., "Kinetics of Outer-Sphere Electron Transfers Between Metal Complexes in Solutions and Polymeric Films on Modified Electrodes", Journal of the American Chemical Society, 1981, vol. 103, No. 25, pp. 7422-7425.
Ikeda, T., et al., "Glucose Oxidase-Immobilized Benzoquinone-Carbon Paste Electrode as a Glucose Sensor", Agricultural and Biological Chemistry, 1985, vol. 49, No. 2, pp. 541-543.
Ikeda, T., et al., "Artificial Pancreas—Investigation of the Stability of Glucose Sensors Using a Telemetry System" (English language translation of abstract), Jpn. J. Artif. Organs, 1990, vol. 19, No. 2, pp. 889-892.
"In Vitro Diagnostic Products for Human Use", Federal Register, 1974, vol. 39, No. 126, pp. 24136-24147.
Isermann, R., "Supervision, Fault-Detection and Fault-Diagnosis Methods—An Introduction", Control Engineering Practice, 1997, vol. 5, No. 5, pp. 639-652.
Isermann, R., et al., "Trends in the Application of Model-Based Fault Detection and Diagnosis of Technical Processes", Control Engineering Practice, 1997, vol. 5, No. 5, pp. 709-719.
Jain, A.K., et al., "Wound Rotor Induction Generator With Sensorless Control and Integrated Active Filter for Feeding Nonlinear Loads in a Stand-Alone Grid", IEEE Transactions on Industrial Electronics, 2008, vol. 55, No. 1, pp. 218-228.
James, Jr., et al., "Handbook of Microstrip Antennas", 1969, pp. 1038-1047.
Johnson, J. M., et al., "Potential-Dependent Enzymatic Activity in an Enzyme Thin-Layer Cell", Analytical Chemistry, 1982, vol. 54, No. 8, pp. 1377-1383.
Johnson, K. W., "Reproducible Electrodeposition of Biomolecules for the Fabrication of Miniature Electroenzymatic Biosensors", Sensors and Actuators B, 1991, vol. 5, pp. 85-89.
Johnson, K. W., et al., "In vivo evaluation of an electroenzymatic glucose sensor implanted in subcutaneous tissue," Biosensors and Bioelectronics, 1992, vol. 7, pp. 709-714.
Johnson, P. C., "Peripheral Circulation", John Wiley & Sons, 1978, p. 198.
Jönsson, G., et al., "An Amperometric Glucose Sensor Made by Modification of a Graphite Electrode Surface With Immobilized Glucose Oxidase and Adsorbed Mediator", Biosensors, 1985, vol. 1, pp. 355-368.
Josowicz, M., et al., "Electrochemical Pretreatment of Thin Film Platinum Electrodes", Journal of the Electrochemical Society, 1988, vol. 135, No. 1, pp. 112-115.
Jovanovic, L., "The Role of Continuous Glucose Monitoring in Gestational Diabetes Mellitus", Diabetes Technology & Therapeutics, 2000, vol. 2, Supplement 1, pp. S-67-S-71.
Jungheim, K., et al., "How Rapid Does Glucose Concentration Change in Daily Life of Patients with Type 1 Diabetes?", 2002, p. 250.
Jungheim, K., et al., "Risky Delay of Hypoglycemia Detection by Glucose Monitoring at the Arm", Diabetes Care, 2001, vol. 24, No. 7, pp. 1303-1304.
Kal, S., "Basic Electronics - Devices, Circuits and IT Fundamentals", 2006, Chapter 13, Microcomputers and Microprocessors, p. 412.
Kaplan, S. M., "Wiley Electrical and Electronics Engineering Dictionary", IEEE Press, 2004, pp. 141, 142, 548, 549.
Katakis, I., et al., "L-α-Glycerophosphate and $_L$-Lactate Electrodes Based on the Electrochemical 'Wiring' of Oxidases", Analytical Chemistry, 1992, vol. 64, No. 9, pp. 1008-1013.
Katakis, I., et al., "Electrostatic Control of the Electron Transfer Enabling Binding of Recombinant Glucose Oxidase and Redox Polyelectrolytes", Journal of the American Chemical Society, 1994, vol. 116, No. 8, pp. 3617-3618.
Kenausis, G., et al., "'Wiring' of Glucose Oxidase and Lactate Oxidase Within a Hydrogel Made with Poly(vinyl pyridine) complexed with [Os(4,4'-dimethoxy-2,2'-bipyridine) $_2$Cl] $^{+/2+}$", Journal of the Chemical Society, Faraday Transactions, 1996, vol. 92, No. 20, pp. 4131-4136.
Klonoff, D. C., "A Review of Continuous Glucose Monitoring Technology", Diabetes Technology & Therapeutics, 2005, vol. 7, No. 5, pp. 770-775.
Kondepati, V., et al., "Recent Progress in Analytical Instrumentation for Glycemic Control in Diabetic and Critically Ill Patients", Analytical Bioanalytical Chemistry, 2007, vol. 388, pp. 545-563.
Koudelka, M., et al., "In-Vivo Behaviour of Hypodermically Implanted Microfabricated Glucose Sensors", Biosensors & Bioelectronics, 1991, vol. 6, pp. 31-36.
Kovatchev, B. P., et al., "Evaluating the Accuracy of Continuous Glucose-Monitoring Sensors", Diabetes Care, 2004, vol. 27, No. 8, pp. 1922-1928.
Kulys, J., et al., "Mediatorless Peroxidase Electrode and Preparation of Bienzyme Sensors", Bioelectrochemistry and Bioenergetics, 1990, vol. 24, pp. 305-311.
Lager, W., et al., "Implantable Electrocatalytic Glucose Sensor", Hormone Metabolic Research, 1994, vol. 26, pp. 526-530.
León, L. P., et al., "Continuous-Flow Analysis for Glucose in Serum, with Use of Hexokinase and Glucose-6-Phosphate Dehydrogenase Co-Immobilized in Tubular Form", Clinical Chemistry, 1980, vol. 26, No. 1, pp. 123-129.
Lindner, E., et al., "Flexible (Kapton-Based) Microsensor Arrays of High Stability for Cardiovascular Applications", Journal of the Chemical Society, Faraday Transactions, 1993, vol. 89, No. 2, pp. 361-367.
Lo, B., et al., "Key Technical Challenges and Current Implementations of Body Sensor Networks", Body Sensor Networks, 2005, pp. 1-5.
Lodwig, V., et al., "Continuous Glucose Monitoring with Glucose Sensors: Calibration and Assessment Criteria", Diabetes Technology & Therapeutics, 2003, vol. 5, No. 4, pp. 573-587.
Lortz, J., et al., "What is Bluetooth? We Explain The Newest Short-Range Connectivity Technology", Smart Computing Learning Series, Wireless Computing, 2002, vol. 8, Issue 5, pp. 72-74.

(56) References Cited

OTHER PUBLICATIONS

Loy, M., et al., "ISM-Band and Short Range Device Antennas", Texas Instruments Application Report, 2005, pp. 1-38.
Maidan, R. et al., "Elimination of Electroaxidizable Interferant-Produced Currents in Amperometric Biosensors," Analytical Chemistry, 1992, vol. 64, No. 23, pp. 2889-2896.
Malin, S. F., et al., "Noninvasive Prediction of Glucose by Near-Infrared Diffuse Reflectance Spectoscopy", Clinical Chemistry, 1999, vol. 45, No. 9, pp. 1651-1658.
Mastrototaro, J.J., et al., "An Electroenzymatic Glucose Sensor Fabricated on a Flexible Substrate," Sensors and Biosensors B Chemical, 1991, B5, pp. 139-144.
Mauras, N., et al., "Lack of Accuracy of Continuous Sensors in Healthy, Nondiabetic Children: Results of the Diabetes Research in Children Network (DirecNet) Accuracy Study", Journal of Pediatrics, 2004, pp. 770-775.
Mcgarraugh, G., et al., "Glucose Measurements Using Blood Extracted from the Forearm and the Finger", TheraSense, Inc., 2001, 16 Pages.
Mcgarraugh, G., et al., "Physiological Influences on Off-Finger Glucose Testing", Diabetes Technology & Therapeutics, 2001, vol. 3, No. 3, pp. 367-376.
Mckean, B., et al., "A Telemetry-Instrumentation System for Chronically Implanted Glucose and Oxygen Sensors," IEEE Transactions on Biomedical Engineering, 1988, vol. 35, No. 7, pp. 526-532.
Mcneil, C. J., et al., "Thermostable Reduced Nicotinamide Adenine Dinucleotide Oxidase: Application to Amperometric Enzyme Assay", Analytical Chemistry, 1989, vol. 61, No. 1, pp. 25-29.
Medtronic Guardian® REAL-Time Continuous Glucose Monitoring System User Guide, 2006, pp. 1-181.
Medtronic Guardian® REAL-Time Continuous Glucose Monitoring System User Guide, 2006, pp. 1-184.
Medtronic MiniMed Sen-Serter® User Guide, 2006, pp. 1-96.
IPR2022-00605 (Ex. 1027) The Merriam-Webster Dictionary, Merriam Webster, Incorporated (2005), pp. 66, 403, and 415.
Microchip Technology Inc., MRF24J40MA Data Sheet, 2008, pp. 1-30.
IPR2022-00605 (Ex. 2008) MiniMed® Glucose Sensor, Ref MMT-7002, Instructions for Use, May 1999, pp. 1-4.
Minimed Technologies, "Tape Tips and Other Infusion Site Information", 1995.
Minimed Quick-set™ retrieved from https://web.archive.org/web/20010412224824/http://www.minimed.com/patientfam/pf_ipt_pumpinfusion_quickset.shtml, Apr. 12, 2001, pp. 1-2.
Minimed Sof-set Micro QR® Sof-set Ultimate QR® retrieved from https://web.archive.org/web/20010412225617/http://www.minimed.com/patientfam/pf_ipt_pumpinfusion_sofset.shtml, Apr. 12, 2001, pp. 1-2.
Miyawaki, O., et al., "Electrochemical and Glucose Oxidase Coenzyme Activity of Flavin Adenine Dinucleotide Covalently Attached to Glassy Carbon at the Adenine Amino Group", Biochimica et Biophysica Acta, 1985, vol. 838, pp. 60-68.
Moatti-Sirat, D., et al., "Evaluating In Vitro and In Vivo the Interference of Ascorbate and Acetaminophen on Glucose Detection by a Needle-Type Glucose Sensor", Biosensors & Bioelectronics, 1992, vol. 7, pp. 345-352.
Moatti-Sirat, D., et al., "Reduction of Acetaminophen Interference in Glucose Sensors by a Composite Nafion Membrane: Demonstration in Rats and Man", Diabetologia, 1994, vol. 37, pp. 610-616.
Moatti-Sirat, D., et al., "Towards Continuous Glucose Monitoring: In Vivo Evaluation of a Miniaturized Glucose Sensor Implanted for Several Days in Rat Subcutaneous Tissue," Diabetolocia, 1992, vol. 35, No. 3 (1 page—Abstract only).
IPR2022-00605 (Ex. 2003) "Monitoring Your Blood Sugar", retrieved from https://www.cdc.gov/diabetes/managing/managing-blood-sugar/bloodglucosemonitoring.html, 2021, pp. 1-3.
Moore, B., "The Potential Use of Radio Frequency Identification Devices for Active Monitoring of Blood Glucose Levels", Journal of Diabetes Science and Technology, 2009, vol. 3, No. 1, pp. 180-183.
Morak, J., et al., "Design and Evaluation of a Telemonitoring Concept Based on NFC-Enabled Mobile Phones and Sensor Devices", IEEE Transactions on Information Technology in Biomedicine, 2012, vol. 16, No. 1, pp. 17-23.
Morbiducci, U., et al., "Improved Usability of the Minimal Model of Insulin Sensitivity Based on an Automated Approach and Genetic algorithms for Parameter Estimation", Clinical Science, vol. 112, 2007, pp. 257-263.
Mougiakakou, S. G., et al., "A Real Time Simulation Model of Glucose-Insulin Metabolism for Type 1 Diabetes Patients", Proceedings of the 2005 IEEE, 2005, pp. 298-301.
Movassaghi, S., et al., "Wireless Technologies for Body Area Networks: Characteristics and Challenges", 2012 International Symposium on Communications and Information Technologies (ISCIT), 2012, Gold Coast, QLD, Australia, pp. 42-47.
"Murata Puts Antenna on a Chip", Passives, 1999, vol. 44, 1 page.
Nagy, G., et al., "A New Type of Enzyme Electrode: The Ascorbic Acid Eliminator Electrode", Life Sciences, 1982, vol. 31, No. 23, pp. 2611-2616.
Nakamura, S., et al., "Effect of Periodate Oxidation on the Structure and Properties of Glucose Oxidase", Biochimica et Biophysica Acta., 1976, vol. 445, pp. 294-308.
Narasimham, K., et al., "p-Benzoquinone Activation of Metal Oxide Electrodes for Attachment of Enzymes", Enzyme and Microbial Technology, 1985, vol. 7, pp. 283-286.
Ohara, T. J., et al., "Glucose Electrodes Based on Cross-Linked $[Os(bpy)_2Cl]^{+/2+}$ Complexed Poly(1-vinylimadazole) Films," Analytical Chemistry, 1993, vol. 65, No. 23, pp. 3512-3516.
Ohara, T. J., et al., "'Wired' Enzyme Electrodes for Amperometric Determination of Glucose or Lactate in the Presence of Interfering Substances", Analytical Chemistry, 1994, vol. 66, No. 15, pp. 2451-2457.
Ohara, T. J., "Osmium Bipyridyl Redox Polymers Used in Enzyme Electrodes", Platinum Metals Review, 1995, vol. 39, No. 2, pp. 54-62.
Olievier, C. N., et al., "In Vivo Measurement of Carbon Dioxide Tension with a Miniature Electrodes", Pflugers Archiv: European Journal of Physiology, 1978, vol. 373, pp. 269-272.
OmniPod Insulet UST400 User Manual, 2011, pp. 1-190.
Opinion of the Court, Supreme Court of the United States, No. 04-1350, *KSR International co.*, Petitioner v. *Teleflex Inc. et al.*, Apr. 30, 2007.
Osmonics, Poretics® Polycarbonate Membrane; Product Leaflet; Engineering Purity, 2002, pp. 1-2.
Paddock, R. M., et al., "Electrocatalytic Reduction of Hydrogen Peroxide via Direct Electron Transfer From Pyrolytic Graphite Electrodes to Irreversibly Adsorbed Cyctochrome C Peroxidase", Journal of ElectroAnalytical Chemistry, 1989, vol. 260, pp. 487-494.
Palleschi, G., et al., "A Study of Interferences in Glucose Measurements in Blood by Hydrogen Peroxide Based Glucose Probes", Analytical Biochemistry, 1986, vol. 159, pp. 114-121.
Pankratov, I., et al., "Sol-Gel Derived Renewable-Surface Biosensors", Journal of ElectroAnalytical Chemistry, 1995, vol. 393, pp. 35-41.
Parker, R., et al., "Robust Ho Glucose Control in Diabetes Using a Physiological Model", AIChE Journal, 2000, vol. 46, No. 12, 2000, pp. 2537-2549.
Passey, R. B., et al., "Evaluation and Comparison of 10 Glucose Methods and the Reference Method Recommendation in the Proposed Product Class Standard (1974)", Clinical Chemistry, 1977, vol. 23, No. 1, pp. 131-139.
Pathak, C., et al., "Rapid Photopolymerization of Immunoprotective Gels in Contact with Cells and Tissue", Journal of the American Chemical Society, 1992, vol. 114, No. 21, pp. 8311-8312.
Patton, S. R., et al., "Continuous Glucose Monitoring Versus Self-monitoring of Blood Glucose in Children with Type 1 Diabetes—Are there Pros and Cons for Both?", US Endocrinol., 2012, vol. 8, No. 1, pp. 27-29.
Pickup, J., "Developing Glucose Sensors for In Vivo Use", Tibtech, 1993, vol. 11, pp. 285-291.

(56) References Cited

OTHER PUBLICATIONS

Pickup, J., et al., "Implantable Glucose Sensors: Choosing the Appropriate Sensing Strategy", Biosensors, 1987/88, vol. 3, pp. 335-346.
Pickup, J. C., et al., "In Vivo Molecular Sensing In Diabetes Mellitus: An Implantable Glucose Sensor With Direct Electron Transfer," Diabetologia, 1989, vol. 32, No. 3, pp. 213-217.
Pickup, J., et al., "Potentially-Implantable, Amperometric Glucose Sensors with Mediated Electron Transfer: Improving the Operating Stability", Biosensors, 1989, vol. 4, pp. 109-119.
Pishko, M. V., et al., "Amperometric Glucose Microelectrodes Prepared Through Immobilization of Glucose Oxidase in Redox Hydrogels," Anal. Chem., 1991, vol. 63, No. 20, pp. 2268-2272.
Poitout, V., et al., "A Glucose Monitoring System for On Line Estimation in Man of Blood Glucose Concentration Using a Miniaturized Glucose Sensor Implanted in the Subcutaneous Tissue and a Wearable Control Unit", Diabetologia, 1993, vol. 36, pp. 658-663.
Poitout, V., et al., "Calibration in Dogs of a Subcutaneous Miniaturized Glucose Sensor Using a Glucose Meter for Blood Glucose Determination", Biosensors & Bioelectronics, 1992, vol. 7, pp. 587-592.
Poitout, V., et al., "In Vitro and in Vivo Evaluation in Dogs of a Miniaturized Glucose Sensor," ASAIO Transactions, 1991, vol. 37, No. 3 (1 page—Abstract only).
Pollak, A., et al., "Enzyme Immobilization by Condensation Copolymerization into Cross-Linked Polyacrylamide Gels", Journal of the American Chemical Society, 1980, vol. 102, No. 20, pp. 6324-6336.
Quinn, C. P., et al., "Kinetics of Glucose Delivery to Subcutaneous Tissue in Rats Measured with 0.3-mm Amperometric Microsensors", The American Physiological Society, 1995, E155-E161.
Ratner, B. D., "Reducing Capsular Thickness and Enhancing Angeiogenesis Around Implant Drug Release Systems", Journal of Controlled Release, 2002, vol. 78, pp. 211-218.
Reach, G., et al., "Can Continuous Glucose Monitoring Be Used for the Treatment of Diabetes?", Analytical Chemistry, 1992, vol. 64, No. 6, pp. 381-386.
Rebrin, K., et al., "Automated Feedback Control of Subcutaneous Glucose Concentration in Diabetic Dogs," Diabetologia, 1989, vol. 32, No. 8, pp. 573-576.
Repas, R., "Sensor Sense: RFID for smart position sensing", retrieved from https://www/machinedesign/com/automation-iiot/article/21818777/sensor-sense-rfid-for-smart-position-sensing, 2010, pp. 1-2.
Rodriguez, N., et al., "Flexible Communication and Control Protocol for Injectable Neuromuscular Interfaces", IEEE Transactions on Biomedical Circuits and Systems, 2007, vol. 1, No. 1, pp. 19-27.
Roe, J. N., et al., "Bloodless Glucose Measurements", Critical Review in Therapeutic Drug Carrier Systems, vol. 15, Issue 3, 1998, pp. 199-241.
IPR2022-00605 (Ex. 1024) "Rotor," Dictionary of Mechanical Engineering, Fourth Ed., G.H.F. Nayler, Society of Automotive Engineers, Inc., 1996, p. 328.
IPR2022-00605 (Ex. 1025) "Rotor," Random House Kernerman Webster's College Dictionary, K Dictionaries Ltd. (2010), available at https://www.thefreedictionary.com/rotor.
IPR2022-00605 (Ex. 1026) "Rotate," Random House Kernerman Webster's College Dictionary, K Dictionaries Ltd. (2010), available at https://www.thefreedictionary.com/rotate.
Sakakida, M., et al., "Ferrocene-mediated needle-type glucose sensor covered with newly designed biocompatible membrane," Sensors and Actuators B, 1993, vols. 13-14, pp. 319-322.
Sakakida, M., et al., "Development of ferrocene-mediated needle-type glucose sensor as a measure of true subcutaneous tissue glucose concentrations", Artif Organs Today, 1992, vol. 2, No. 2, pp. 145-458.
Salditt, P., "Trends in Medical Device Design and Manufacturing", SMTA News and Journal of Surface Mount Technology, 2004, vol. 17, pp. 19-24.
Salehi, C., et al., "A Telemetry-Instrumentation System for Long-Term Implantable Glucose and Oxygen Sensors", Analytical Letters, 1996, vol. 29, No. 13, pp. 2289-2308.
Samuels, G. J., et al., "An Electrode-Supported Oxidation Catalyst Based on Ruthenium (IV). pH "Encapsulation" in a Polymer Film", Journal of the American Chemical Society, 1981, vol. 103, No. 2, pp. 307-312.
Sandham, W., et al., "Blood Glucose Prediction for Diabetes Therapy Using a Recurrent Artificial Neural Network", 9$^{th}$ European Signal Processing Conference, 1998, Rhodes, Greece, pp. 1-4.
Sasso, S. V., et al., "Electropolymerized 1,2-Diaminobenzene as a Means to Prevent Interferences and Fouling and to Stabilize Immobilized Enzyme in Electrochemical Biosensors", Analytical Chemistry, 1990, vol. 62, No. 11, pp. 1111-1117.
IPR2022-00605 (Ex. 1013) Scheduling Order in *Abbott Diabetes Care Inc., et al.* v. *Dexcom, Inc.*, 1:21-cv-00977 (D. Del.), dated Dec. 2, 2021.
Scheller, F., et al., "Enzyme Electrodes and Their Application", Philosophical Transactions of The Royal Society of London B, 1987, vol. 316, pp. 85-94.
Schmehl, R. H., et al., "The Effect of Redox Site Concentration on the Rate of Mediated Oxidation of Solution Substrates by a Redox Copolymer Film", Journal of ElectroAnalytical Chemistry, 1983, vol. 152, pp. 97-109.
Schmidt, F. J., et al., "Calibration of a Wearable Glucose Sensor", The International Journal of Artificial Organs, 1992, vol. 15, No. 1, pp. 55-61.
Schmidtke, D. W., et al., "Accuracy of the One-Point In Vivo Calibration of "Wired" Glucose Oxidase Electrodes Implanted in Jugular Veins of Rats in Periods of Rapid Rise and Decline of the Glucose Concentration", Analytical Chemistry, 1998, vol. 70, No. 10, pp. 2149-2155.
Schmidtke, D. W., et al., "Measurement and Modeling of the Transient Difference Between Blood and Subcutaneous Glucose Concentrations in the Rat After Injection of Insulin", Proceedings of the National Academy of Sciences, 1998, vol. 95, pp. 294-299.
Schoepke, E., "Chip Antenna Layout Considerations for 802.11 Applications", Johanson Technology, 2006, retrieved from https://www.johansontechnology.com/chip-antenna-layout-considerations-for-802-11-applications, pp. 1-7.
Sharawi, M. S., "Use of low-cost patch antennas in modern wireless technology", IEEE Potentials, 2006, pp. 35-38 and 47.
Shaw, G. W., et al., "In Vitro Testing of a Simply Constructed, Highly Stable Glucose Sensor Suitable for Implantation in Diabetic Patients", Biosensors & Bioelectronics, 1991, vol. 6, pp. 401-406.
Shichiri, M., et al., "Glycaemic Control in Pancreatectomized Dogs with a Wearable Artificial Endocrine Pancreas," Diabetologia, 1983, vol. 24, No. 3, pp. 179-18.
Shichiri, M., et al., "Membrane Design for Extending the Long-Life of an Implantable Glucose Sensor", Diabetes Nutrition and Metabolism, 1989, vol. 2, pp. 309-313.
Shichiri, M., et al., "Needle-type Glucose Sensor for Wearable Artificial Endocrine Pancreas", Implantable Sensors for Closed-Loop Prosthetic Systems, Chapter 15, 1985, pp. 197-210.
Shichiri, M., et al., "Telemetry Glucose Monitoring Device with Needle-type Glucose Sensor: A Useful Tool for Blood Glucose Monitoring in Diabetic Individuals," Diabetes Care, 1986, vol. 9, No. 3, pp. 298-301.
Shichiri, M., et al., "In Vivo Characteristics of Needle-Type Glucose Sensor—Measurement of Subcutaneous Glucose Concentrations in Human Volunteers," Horm Metab Res Suppl. 1988, vol. 20, pp. 17-20.
Shichiri, M., et al., "Wearable Artificial Endocrine Pancreas With Needle-Type Glucose Sensor," The Lancet, 1982, vol. 2, No. 8308, pp. 1129-1131.
Shults, M., "A Telemetry-Instrumentation System for Monitoring Multiple Subcutaneously Implanted Glucose Sensors," IEEE Transactions on Biomedical Engineering, 1994, vol. 41, No. 10, pp. 937-942.
Sittampalam, G., et al., "Surface-Modified Electrochemical Detector for Liquid Chromatography", Analytical Chemistry, 1983, vol. 55, No. 9, pp. 1608-1610.

(56) References Cited

OTHER PUBLICATIONS

Soegijoko, S., et al., "External Artificial Pancreas: A New Control Unit Using Microprocessor", Hormone and Metabolic Research Supplement Series, 1982, vol. 12, pp. 165-169.
Sparacino, G., et al., "Glucose Concentration Can Be Predicted Ahead in Time from Continuous Glucose Monitoring Sensor Time-Series", IEEE Transactions on Biomedical Engineering, 2007, vol. 54, No. 5, pp. 931-937.
Sprules, S. D., et al., "Evaluation of a New Disposable Screen-Printed Sensor Strip for the Measurement of NADH and Its Modification to Produce a Lactate Biosensor Employing Microliter Volumes", Electroanalysis, 1996, vol. 8, No. 6, pp. 539-543.
Sternberg, F., et al., "Calibration Problems of Subcutaneous Glucosensors when Applied "In-Situ" in Man", Hormone and Metabolic Research, 1994, vol. 26, pp. 523-526.
Sternberg, R., et al., "Covalent Enzyme Coupling on Cellulose Acetate Membranes for Glucose Sensor Development", Analytical Chemistry, 1988, vol. 60, No. 24, pp. 2781-2786.
Sternberg, R., et al., "Study and Development of Multilayer Needle-type Enzyme-based Glucose Microsensors," Biosensors, 1988, vol. 4, pp. 27-40.
Suekane, M., et al., "Immobilization of Glucose Isomerase", Zettschrift fur Allgemeine Mikrobiologie, 1982, vol. 22, No. 8, pp. 565-576.
Tajima, S., et al., "Simultaneous Determination of Glucose and 1,5-Anydroglucitol", Chemical Abstracts, 1989, vol. 111, No. 25, p. 394.
Tarasevich, M. R., "Bioelectrocatalysis", Comprehensive Treatise of Electrochemistry, 1985, vol. 10, pp. 231-295.
Tatsuma, T., et al., "Enzyme Monolayer- and Bilayer-Modified Tin Oxide Electrodes for the Determination of Hydrogen Peroxide and Glucose", Analytical Chemistry, 1989, vol. 61, No. 21, pp. 2352-2355.
Taylor, C., et al., ""Wiring" of Glucose Oxidase Within a Hydrogel Made with Polyvinyl Imidazole Complexed with [(Os-4,4'-dimethoxy-2,2'-bipyridine)Cl]$^{+/2+}$", Journal of ElectroAnalytical Chemistry, 1995, vol. 396, pp. 511-515.
Thompson, M., et al., "In Vivo Probes: Problems and Perspectives", Clinical Biochemistry, 1986, vol. 19, pp. 255-261.
Tierney, M. J., et al., "Effect of Acetaminophen on the Accuracy of Glucose Measurements Obtained with the GlucoWatch Biographer", Diabetes Technology & Therapeutics, 2000, vol. 2, No. 2, pp. 199-207.
Townsend, K., et al., "Getting Started with Bluetooth Low Energy—Chapter 1", 2014, pp. 1-26.
Trojanowicz, M., et al., "Enzyme Entrapped Polypyrrole Modified Electrode for Flow-Injection Determination of Glucose", Biosensors & Bioelectronics, 1990, vol. 5, pp. 149-156.
Tsalikian, e., et al., "Accuracy of the GlucoWatch G2® Biographer and the Continuous Glucose Monintoring System During Hypoglycemia: Experience of the Diabetes Research in Children Network", Diabetes Care, 2004, vol. 27, No. 3, pp. 722-726.
Tung, S., "Layers of Security for Active RFID Tags", RFID Handbook: Applications, Technology, Security, and Privacy, Edited by Ehson, et al., Chapter 33, 2008, pp. 1-28.
Turner, A.P.F., et al., "Diabetes Mellitus: Biosensors for Research and Management", Biosensors, 1985, vol. 1, pp. 85-115.
Turner, R.F.B., et al., "A Biocompatible Enzyme Electrode for Continuous in vivo Glucose Monitoring in Whole Blood", Sensors and Actuators B, 1990, vol. 1, pp. 561-564.
Tuzhi, P., et al., "Constant Potential Pretreatment of Carbon Fiber Electrodes for in Vivo Electrochemistry", Analytical Letters, 1991, vol. 24, No. 6, pp. 935-945.
Umana, M., "Protein-Modified Electrochemically Active Biomaterial Surface", U.S. Army Research Office, Analytical and Chemical Sciences Research Triangle Institute, 1988, pp. 1-9.
United States Court of Appeals for the Federal Circuit, No. 06-1402, *Leapfrog Enterprises, Inc.* v. *Fisher-Price, Inc. and Mattel, Inc.*, May 9, 2007.
Updike, S. J., et al., "Principles of Long-term Fully Implanted Sensors with Emphasis on Radiotelemetric Monitoring of Blood Glucose from inside a Subcutaneous Foreign Body Capsule (FBC)", Biosensors in the Body: Continuous In vivo Monitoring, Chapter 4, 1997, pp. 117-137.
Updike, S. J., et al., "A Subcutaneous Glucose Sensor With Improved Longevity, Dynamic Range, and Stability of Calibration", Diabetes Care, 2000, vol. 23, pp. 208-214.
Urban, G., et al., "Miniaturized Thin-Film Biosensors Using Covalently Immobilized Glucose Oxidase", Biosensors & Bioelectronics, 1991, vol. 6, pp. 555-562.
Velho, G., et al., "In Vitro and In Vivo Stability of Electrode Potentials in Needle-Type Glucose Sensors", Diabetes, 1989, vol. 38, No. 2, pp. 164-171.
Velho, G. et al., "Strategies for Calibrating a Subcutaneous Glucose Sensor," Biomed. Biochim. Acta, 1989, 48 (11112), pp. 957-964.
Von Woedtke, T., et al., "In Situ Calibration of Implanted Electrochemical Glucose Sensors", Biomedica Biochimica Acta, 1989, vol. 48, pp. 943-952.
Vreeke, M. S., et al., "Hydrogen Peroxide Electrodes Based on Electrical Connection of Redox Centers of Various Peroxidases to Electrodes through a Three-Dimensional Electron-Relaying Polymer Network", Diagnostic Biosensors Polymers, Chapter 15, 1993, pp. 180-193.
Vreeke, M., et al., "Hydrogen Peroxide and β-Nicotinamide Adenine Dinucleotide Sensing Amperometric Electrodes Based on Electrical Connection of Horseradish Peroxidase Redox Centers to Electrodes through a Three-Dimensional Electron Relaying Polymer Network", Analytical Chemistry, 1992, vol. 64, No. 24, pp. 3084-3090.
Wang, D. L., et al., "Miniaturized Flexible Amperometric Lactate Probe", Analytical Chemistry, 1993, vol. 65, No. 8, pp. 1069-1073.
Wang, J., et al., "Activation of Glassy Carbon Electrodes by Alternating Current Electrochemical Treatment", Analytica Chimica Acta, 1985, vol. 167, pp. 325-334.
Wang, J., et al., "Amperometric Biosensing of Organic Peroxides with Peroxidase-Modified Electrodes", Analytica Chimica Acta, 1991, vol. 254, pp. 81-88.
Wang, J., et al., "Screen-Printable Sol-Gel Enzyme-Containing Carbon Inks", Analytical Chemistry, 1996, vol. 68, No. 15, pp. 2705-2708.
Wang, J., et al., "Sol-Gel-Derived Metal-Dispersed Carbon Composite Amperometric Biosensors", Electroanalysis, 1997, vol. 9, No. 1, pp. 52-55.
Wang, X.H., et al., "Bluetooth: Opening a blue sky for healthcare", Mobile Information Systems, 2006, vol. 2, pp. 151-167.
Ward, W. K., et al., "Rise in Background Current Over Time in a Subcutaneous Glucose Sensor in the Rabbit: Relevance to Calibration and Accuracy", Biosensors & Bioelectronics, 2000, vol. 15, pp. 53-61.
Waterhouse, R., "Printed Antennas for Wireless Communications," 2007, pp. 116-129 and 284-289.
Williams, D. L., et al., "Electrochemical-Enzymatic Analysis of Blood Glucose and Lactate", Analytical Chemistry, 1970, vol. 42, No. 1, pp. 118-121.
Wilson, G. S., et al., "Progress Toward the Development of an Implantable Sensor for Glucose," Clinical Chemistry, 1992, vol. 38, No. 9, pp. 1613-1617.
Wong, Kl, "Planar Antennas for Wireless Communications," 2003, Chapter 1, Introduction and Overview, pp. 4-17, 38-45, and 218-221.
Yabuki, S., et al., "Electro-Conductive Enzyme Membrane", Journal of the Chemical Society, Chemical Communications, 1989, pp. 945-946.
Yang, L., et al., "Determination of Oxidase Enzyme Substrates Using Cross-Flow Thin-Layer Amperometry", Electroanalysis, 1996, vol. 8, No. 8-9, pp. 716-721.
Yao, S. J., et al., "The Interference of Ascorbate and Urea in Low-Potential Electrochemical Glucose Sensing", Proceedings of the Twelfth Annual International Conference of the IEEE Engineering in Medicine and Biology Society, 1990, vol. 12, Part 2, pp. 487-489.
Yao, T., "A Chemically-Modified Enzyme Membrane Electrode as an Amperometric Glucose Sensor", Analytica Chimica Acta, 1983, vol. 148, pp. 27-33.

(56) References Cited

OTHER PUBLICATIONS

Ye, L. et al., "High Current Density "Wired" Quinoprotein Glucose Dehydrogenase Electroade," Anal. Chem., 1993, vol. 65, No. 3, pp. 238-241.
Yildiz, A., et al., "Evaluation of an Improved Thin-Layer Electrode", Analytical Chemistry, 1968, vol. 40, No. 7, pp. 1018-1024.
Zamzow, K., et al., "New Wearable Continuous Blood Glucose Monitor (BGM) and Artificial Pancreas (AP)", Diabetes, 1990, vol. 39, pp. 5A-20.
Z-Carbon Connector, retrieved from http://www.zaxisconnector.com/SS_zc.shtml, 2004, 2 pages.
Zhang, Y., et al., "Application of Cell Culture Toxicity Tests to the Development of Implantable Biosensors", Biosensors & Bioelectronics, 1991, vol. 6, pp. 653-661.
Zhang, Y., et al., "Elimination of the Acetaminophen Interference in an Implantable Glucose Sensor", Analytical Chemistry, 1994, vol. 66, No. 7, pp. 1183-1188.
Zhu, J., et al., "Fabrication and Characterization of Glucose Sensors Based on a Microarray $H_2O_2$ electrode", Biosensors & Bioelectronics, 1994, vol. 9, pp. 295-300.
Zisser, H. C., "The OmniPod Insulin Management System: the Latest Innovation in Insulin Pump Therapy", Diabetes Ther, 2010, vol. 1, No. 1, pp. 10-24.
Z-Silver Connector, retrieved from http://www.zaxisconnector.com/SS_zs.shtml, 2004, 2 pages.
CA, 2,617,192 Examiner's Report, Oct. 22, 2012.
CA, 2,984,939 Examiner's Report, Aug. 7, 2024.
CA, 2,984,939 Examiner's Report, Nov. 15, 2023.
CA, 3,120,335 Examiner's Report, May 27, 2024.
CA, 3,120,335 Examiner's Report, Mar. 31, 2023.
CA, 3,182,961 Examiner's Report, Dec. 6, 2023.
CN, 200780039416.2 Second Office Action, Apr. 25, 2012.
CN, 200780039416.2 First Office Action, Mar. 30, 2011.
CN, 200880005149.1 Notice of Allowance, Jun. 21, 2013.
CN, 200880005149.1 Fourth Office Action, Dec. 3, 2012.
CN, 200880005149.1 Third Office Action, Feb. 16, 2012.
CN, 200880005149.1 Second Office Action, Aug. 17, 2011.
CN, 200880005149.1 First Office Action, Jul. 29, 2010.
CN, 200880005388.7 Second Office Action, May 16, 2012.
CN, 200880005388.7 First Office Action, Jul. 25, 2011.
CN, 201980082748.1 Final Office Action, Nov. 27, 2023.
CN, 201980082748.1 Second Office Action, Jul. 10, 2023.
DE, Complaint in Litigation of EP 3300658, Mar. 20, 2024.
EP, 06788869.3 Examination Report, Sep. 25, 2012.
EP, 06788869.3 Extended Search Report, Mar. 18, 2010.
EP, 06813967.4 Extended Search Report, Mar. 4, 2010.
EP, 07854298.2 Extended Search Report, Mar. 29, 2010.
EP, 08730066.1 Extended Search Report, Oct. 5, 2012.
EP, 10739031.2 Decision of Oral Proceedings, Jun. 11, 2024.
EP, 10739031.2 Minutes of Oral Proceedings, May 10, 2024.
EP, 10739031.2 Communication from Board of Appeals, Feb. 21, 2024.
EP, 10739031.2 Summons to Attend Oral Proceedings, Oct. 26, 2023.
EP, 17182379.2 Grounds of Opposition, Jul. 12, 2024.
EP, 17182379.2 Notice of Opposition, Jul. 12, 2024.
EP, 17182379.2 Reply to Examination Report, Apr. 9, 2021.
EP, 17182379.2 Reply to Search Report, Oct. 3, 2018.
EP, 19900891.3 Extended Search Report, Sep. 26, 2022.
EP, 20177703.4 Summons to Attend Oral Proceedings, Apr. 29, 2024.
EP, 20177703.4 Reply to Reply to Reply to Notice of Opposition ADC, Dec. 18, 2023.
EP, 20177703.4 Reply to Notice of Intervention, Nov. 17, 2023.
EP, 20177712.5 Response to Summons to Attend Oral Proceedings, Aug. 30, 2024.
EP, 20177712.5 Summons to Attend Oral Proceedings, Jul. 2, 2024.
EP, 20177712.5 Response to Written Submissions Dexcom, Feb. 26, 2024.
EP, 20177712.5 Written Submissions ADC, Jan. 26, 2024.
EP, 20177712.5 Reply to Reply to Reply to Notice of Opposition ADC, Dec. 18, 2023.
EP, 20177712.5 Reply to Notice of Intervention, Nov. 17, 2023.
EP, 20177712.5 Reply to Reply to Notice of Opposition Dexcom, Sep. 27, 2023.
EP, 20177712.5 Reply to Reply to Notice of Opposition Gulde & Partner Patent, Aug. 30, 2023.
EP, 20195922.8 Grounds of Appeal, Sep. 6, 2024.
EP, 20195922.8 Notice of Appeal, Jul. 4, 2024.
EP, 20195922.8 Written Submissions Dexcom, May 9, 2024.
EP, 20195922.8 Decision Revoking the European Patent, May 8, 2024.
EP, 20195922.8 Minutes of the Oral Proceedings, May 8, 2024.
EP, 20195922.8 Written Submissions Dexcom, Mar. 15, 2024.
EP, 20195922.8 Response to Summons to Attend Oral Proceedings, Feb. 15, 2024.
EP, 20195922.8 Written Submissions Dexcom, Dec. 12, 2023.
EP, 20195922.8 Written Submissions ADC, Oct. 23, 2023.
EP, 20195922.8 Summons to Attend Oral Proceedings, Sep. 21, 2023.
EP, 20195922.8 Reply to Notice of Intervention, Aug. 29, 2023.
EP, 20195922.8 Reply to Reply to Notice of Opposition, Aug. 21, 2023.
EP, 21211041.5 Reply to Notice of Opposition, Jul. 17, 2024.
EP, 21211041.5 Grounds of Opposition Dexcom, Mar. 28, 2024.
EP, 21211041.5 Notice of Opposition Dexcom, Mar. 28, 2024.
EP, 23166498.8 Examination Report, Sep. 2, 2024.
EP, 23166498.8 Extended Search Report, Nov. 17, 2023.
EP, 23190032.5 Extended Search Report, Nov. 17, 2023.
EP, 24152079.0 Extended Search Report, Sep. 4, 2024.
EP, 24152079.0 Partial Search Report, Jun. 14, 2024.
GB, Claim No. HP-2021-000025 Approved Judgement, Oct. 18, 2023.
JP, 2009-534799 Final Office Action, Feb. 19, 2013.
JP, 2009-534799 Office Action, Sep. 27, 2011.
EP, 2021-531135 Office Action, Aug. 9, 2023.
MX, MX/a/2009/004322 Office Action, Mar. 11, 2013.
MX, MX/a/2009/004322 Office Action, Sep. 19, 2012.
MX, MX/a/2021/007294 Office Action, Aug. 20, 2024.
MY, PI2023005466 Examination Report, Dec. 28, 2023.
RU, 2009119430 Office Action, Jun. 5, 2011.
RU, 2009134334 Office Action, Feb. 7, 2012.
RU, 2009135048 Office Action, Dec. 20, 2011.
UP, First Expert Opinion of Dr Michael Schoemaker of Litigation of EP 3977921, Jun. 11, 2024.
US, Notice of Filing Date Accorded to Petition and Time for Filing Patent Owner Preliminary Response, IPR No. 2024-00860, Mar. 23, 2024.
US, Declaration of Dr. Cameron Riviere, Ph.D., IPR No. 2024-00860, May 9, 2024.
US, Petition for Inter Partes Review of U.S. Pat. No. 11,510,625, IPR No. 2024-00860, May 9, 2024.
US, Decision Denying Institution of Inter Partes Review, IPR No. 2024-00520, Aug. 8, 2024.
US, Patent Owner's Authorized Sur-Reply to Petitioner's Reply to Patent Owner's Preliminary Response, IPR No. 2024-00520, Jun. 11, 2024.
US, Petitioner's Authorized Reply to Patent Owner's Preliminary Response, IPR No. 2024-00520, May 31, 2024.
US, Patent Owner's Preliminary Response, IPR No. 2024-00520, May 8, 2024.
US, Patent Owner's Exhibit List, IPR No. 2024-00520, Mar. 25, 2024.
US, Telephonic Hearing, IPR No. 2024-00520, Mar. 13, 2024.
US, Petitioner's Explanation of Material Differences Between the Petition in IPR2024-00520 and Previously Filed Petitions in IPR2023-01396 and IPR2023-01397, IPR No. 2024-00520, Jan. 31, 2024.
US, Third Declaration of Gary Fletcher, Ph.D., IPR No. 2024-00520, Jan. 31, 2024.
US, Petition For Inter Partes Review of U.S. Pat. No. 11,266,335, IPR No. 2024-00520, Jan. 31, 2024.
US, Order, IPR No. 2023-01409, May 30, 2024.
US, Notice of Stipulation, IPR No. 2023-01409, May 29, 2024.

(56) References Cited

OTHER PUBLICATIONS

US, Patent Owner's Objections to Petitioner's Exhibits to the Petition, IPR No. 2023-01409, Apr. 29, 2024.
US, Patent Owner's Request for Rehearing by the Director, IPR 2023-01409, Apr. 29, 2024.
US, Email of Peter McAndrews, IPR 2023-01409, Apr. 29, 2024.
US, Decision Granting Institution of Inter Partes Review, IPR No. 2023-01409, Apr. 15, 2024.
US, Scheduling Order, IPR 2023-01409, Apr. 15, 2024.
US, Order Conduct of the Proceeding 37 C.F.R. § 42.5, IPR No. 2023-01409, Feb. 6, 2024.
US, Petitioner's Updated Exhibit List, IPR No. 2023-01409, Feb. 5, 2024.
US, Telephonic Conference Call, IPR No. 2023-01409, Feb. 2, 2024.
US, Patent Owner's Updated Mandatory Notices, IPR No. 2023-01409, Feb. 2, 2024.
US, Email of Andrew M. Mason, IPR 2023-01409, Jan. 30, 2024.
US, Patent Owner's Preliminary Response, IPR No. 2023-01409, Jan. 18, 2024.
US, Notice of Filing Date Accorded to Petition and Time for Filing Patent Owner Preliminary Response, IPR No. 2023-01409, Oct. 18, 2023.
US, Petition For Inter Partes Review of U.S. Pat. No. 11,202,591, IPR No. 2023-01409, Oct. 11, 2023.
US, Decision Denying Institution of Inter Partes Review, IPR No. 2023-01397, Apr. 16, 2024.
US, Patent Owner's Updated Exhibit List, IPR No. 2023-01397, Mar. 25, 2024.
US, Telephonic Hearing, IPR No. 2023-01397, Mar. 13, 2024.
US, Petitioner's Updated Mandatory Notices Pursuant to 37 C.F.R. § 42.8(a)(3), IPR No. 2023-01397, Feb. 19, 2024.
US, Patent Owner's Updated Mandatory Notices, IPR No. 2023-01397, Feb. 2, 2024.
US, Patent Owner's Preliminary Response, IPR No. 2023-01397, Jan. 18, 2024.
Patent Owner's Response to Petitioner's Explanation of Material Differences Between Petitions, IPR Nos. 2023-01396 and 2023-01397, Jan. 18, 2024.
US, Petitioner's Explanation of Material Differences Between Petitions, IPR No. 2023-01397, Oct. 6, 2023.
US, Declaration of Gary D. Fletcher, Ph.D, IPR No. 2023-01396 and IPR No. 2023-01397, Oct. 6, 2023.
US, Petition For Inter Partes Review of U.S. Pat. No. 11,266,335, IPR No. 2023-01397, Oct. 6, 2023.
US, Petitioner's Request for Rehearing of Decision Denying Institution, IPR No. 2023-01396, May 16, 2024.
US, Decision Denying Institution of Inter Partes Review, IPR No. 2023-01396, Apr. 16, 2024.
US, Patent Owner's Updated Exhibit List, IPR No. 2023-01396, Mar. 25, 2024.
US, Telephonic Hearing, IPR No. 2023-01396, Mar. 13, 2024.
US, Petitioner's Updated Mandatory Notices Pursuant to 37 C.F.R. § 42.8(a)(3), IPR No. 2023-01396, Feb. 19, 2024.
US, Patent Owner's Preliminary Response, IPR No. 2023-01396, Jan. 18, 2024.
US, Notice of Filing Date Accorded to Petition and Time for Filing Patent Owner Preliminary Response, IPR No. 2023-01396, Oct. 18, 2023.
US, Petitioner's Explanation of Material Differences Between Petitions, IPR No. 2023-01396, Oct. 6, 2023.
US, Petition for Inter Partes Review of U.S. Pat. No. 11,266,335, IPR No. 2023-01396, Oct. 6, 2023.
US, Notice of Final Written Decision re Inter Partes Review of the '649 Patent, IPR No. 2022-00605, Jul. 13, 2023.
US, Reexamination Serial No. 90/019,329 Notification of Concurrent Proceedings, May 15, 2024.
US, Petition Under 37 CFR § 1.181 and/or § 1.182 to Terminate Reexamination No. 90/019,329, Apr. 26, 2024.
US, Reexamination Serial No. 90/019,329 Order Granting Request for Reexamination of U.S. Pat. No. 11,013,440, Jan. 30, 2024.
US, Reexamination Serial No. 90/019,329 Declaration of Gary D. Fletcher, Ph.D, Dec. 11, 2023.
US, Request for Ex Parte Reexamination Under 35.U.S.C. §§ 302-307 and 37 C.F.R. § 1.510 of U.S. Pat. No. 11,013,440, Dec. 11, 2023.
US, Reexamination Serial No. 90/019,331 Decision Granting Petition, Aug. 26, 2024.
US, Reexamination Serial No. 90/019,331 Petition to Withdraw From Issue and Reopen the Proceeding, Jul. 26, 2024.
US, Reexamination Serial No. 90/019,331 Notice of Intent to Issue Ex Parte Reexamination Certificate, Jul. 10, 2024.
US, Reexamination Serial No. 90/019,331 Notification of Concurrent Proceedings, May 15, 2024.
US, Reexamination Serial No. 90/019,331 Order Granting Request for Reexamination of U.S. Pat. No. 11,000,216, Jan. 23, 2024.
US, Request for Ex Parte Reexamination Under 35.U.S.C. §§ 302-307 and 37 C.F.R. § 1.510 of U.S. Pat. No. 11,000,216, Dec. 11, 2023.
US, Reexamination Serial No. 90/019,307 Order Granting Request for Reexamination of U.S. Pat. No. 10,973,443, Dec. 22, 2023.
US, Request for Ex Parte Reexamination Under 35.U.S.C. §§ 302-307 and 37 C.F.R. § 1.510 of U.S. Pat. No. 10,973,443, Nov. 27, 2023.
US, Reexamination Serial No. 90/019,330 Decision Granting Petition and Vacating a Reexamination Certificate, Aug. 26, 2024.
US, Ex Parte Reexamination Certificate of U.S. Pat. No. 10,959,654, Aug. 5, 2024.
US, Reexamination Serial No. 90/019,330 Petition to Withdraw From Issue and Reopen the Proceeding, Jul. 26, 2024.
US, Reexamination Serial No. 90/019,330 Notice of Intent to Issue Ex Parte Reexamination Certificate of U.S. Pat. No. 10,959,654, Jul. 1, 2024.
US, Reexamination Serial No. 90/019,330 Notification of Concurrent Proceedings, May 15, 2024.
US, Reexamination Serial No. 90/019,330 Order Granting Request for Reexamination of U.S. Pat. No. 10,959,654, Jan. 23, 2024.
US, Reexamination Serial No. 90/019,330 Declaration of John Mastrototaro, Ph.D, Dec. 11, 2023.
US, Request for Ex Parte Reexamination Under 35.U.S.C. §§ 302-307 and 37 C.F.R. § 1.510 of U.S. Pat. No. 10,959,654, Dec. 11, 2023.
WO, PCT/US2006/029541 ISR and Written Opinion, Apr. 24, 2007.
WO, PCT/US2006/033885 ISR and Written Opinion, Aug. 3, 2007.
WO, PCT/US2007/082121 ISR and Written Opinion, May 9, 2008.
WO, PCT/US2008/054165 ISR and Written Opinion, Jun. 5, 2008.
WO, PCT/US2008/054186 ISR and Written Opinion, Aug. 8, 2008.
WO, PCT/US2008/065154 Isr and Written Opinion, Aug. 3, 2008.
WO, PCT/US2008/067791 ISR and Written Opinion, Sep. 30, 2008.
WO, PCT/US2010/047065 ISR and Written Opinion, Dec. 21, 2010.
WO, PCT/US2010/047414 ISR and Written Opinion, Dec. 27, 2010.
WO, PCT/US2010/047415 ISR and Written Opinion, Oct. 25, 2010.
WO, PCT/US24/11756 ISR and Written Opinion, Jun. 28, 2024.
WO, PCT/US24/11756 Invitation to Pay Additional Fees, May 7, 2024.
WO, PCT/US24/16127 Invitation to Pay Additional Fees, Jun. 4, 2024.
WO, PCT/US24/18665 ISR and Written Opinion, Jun. 21, 2024.
"27 Winners Announced at the 19$^{th}$ Annual Medical Design Excellence Awards (MDEA) Award Ceremony", UBM Americas, 2017, 4 pages.
"55 Chosen as Winners in Annual Big Innovation Awards", 2018, retrieved from https://www.bintelligence.com/posts/55-chosen-as-winners-in-annual-big-innovation-awards, 2 pages.
2017 Good Design Award, retrieved from https://www.g-mark.org/gallery/winners/9dda01a3-803d-11ed-af7e-0242ac130002, 9 pages.
"2019 Top 10 Innovations", The Scientist, retrieved from https://www.the-scientist.com/2019-top-10-innovations-66738, 7 pages.
Abbott 2023 Annual Report, retrieved from https://www.abbottinvestor.com/static-files/6cb09c09-2422-40e0-a24b-6545ffcf5267, pp. 1-82.

(56) References Cited

OTHER PUBLICATIONS

Abbott Clinical Trials Competitor and Ecosystem Players, 2020, 28 pages.
"Abbott's Freestyle Libre® Is Named Best Medical Technology in Last 50 Years By The Galien Foundation", 2022, PRNewswire, 1 page.
"Abbott's Freestyle® Libre 2 ICGM Cleared in U.S. for Adults and Children With Diabetes, Achieving Highest Level of Accuracy and Performance Standards", retrieved from https://abbott.mediaroom.com/2020-06-15-Abbotts-FreeStyle-R-Libre-2-iCGM-Cleared-in-U-S-for-Adults-and-Children-with-Diabetes-Achieving-Highest-Level-of-Accuracy-and-Performance—tandards#:~:text=FDA%20clears%20Abbott's%20FreeStyle%20Libre,high%20or%20low%20without%20scanning, on Jul. 7, 2024, 3 pages.
"Abbott's Freestyle Libre® 3 Receives U.S. FDA Clearance—Features World's Smallest, Thinnest and Most Accurate 14-Day Glucose Sensor", 2022, PRNewswire, 3 pages.
"Abbott's Freestyle Libre Flash Glucose Monitoring System Wins the IMSTA Most Innovative Product Multi-National Award 2017", retrieved from https://www.ie.abbott/media-center/news/abbotts-freestyle-libre-flash-glucose-monitoring-system-wins-the-imsta-award-2017.html, 2 pages.
"Abbott's Freestyle Libre 14 Day Flash Glucose Monitoring System Now Approved in U.S.", 2018, PRNewswire, 2 pages.
"Abbott Receives CE Mark for Freestyle® Libre, A Revolutionary Glucose Monitoring System for People With Diabetes", 2014, 7 pages.
About the Edison Awards retrieved from https://edisonawards.com/about/, 2024, 3 pages.
Ahn, D., "Abbott's Euro approved wearable glucose monitor is different than anything on the market", 2014, retrieved from https://www.imedicalapps.com/2014/09/abbotts-wearable-glucose-monitor/, 6 pages.
"Alcove", Webster's New College Dictionary, 2001, p. 26.
Anderson, A. J., "Foundations of Computer Technology", 1994, pp. 55-57.
"BinaxNOW, FreeStyle Libre 2 win BIG innovation honors", 2021, retrieved from https://www.abbott.com/corpnewsroom/strategy-and-strength/binaxnow-freestyle-libre-win-big-innovation-honors.html, 6 pages.
Blum, A., "Freestyle Libre Glucose Monitoring System", Clinical Pharmacology Update, 2018, vol. 36, No. 2, pp. 203-204.
Boise, M., "Dexcom CEO Kevin Sayer Explains G6", 2018, retrieved from https://beyondtype1.org/dexcom-ceo-kevin-sayer-explains-g6/, 9 pages.
Breton, M. D., et al., "Optimum Subcutaneous Glucose Sampling and Fourier Analysis of Continuous Glucose Monitors", Journal of Diabetes Science and Technology, 2008, vol. 2, No. 3, pp. 495-500.
Cather, D. E., "CGM Frustrations Survey", 2020, 36 pages.
Certified U.S. Appl. No. 61/149,639, filed Feb. 3, 2009.
Certified Preliminary Amendment filed on Apr. 20, 2018 for U.S. Pat. No. 10,827,954, 7 pages.
Certified Excerpts of the File History of U.S. Pat. No. 10,973,443, 22 pages.
CES 2022 Innovation Award Honorees, retrieved from https://www.ces.tech/innovation-awards/honorees/2022/best-of/f/freestyle-libre-3-system.aspx, 1 page.
CGMs Changing Diabetes Management: Kevin Sayer, DIC Interview Transcript, 2019, retrieved from https://www.diabetesincontrol.com/cgms-changing-diabetes-management-kevin-sayer-dic-interview-transcript/, 10 pages.
2019 Chicago Innovation Award Winner Abbott Laboratories, retrieved from https://chicagoinnovation.com/winners/abbott-laboratories/, 4 pages.
Continuous Glucose Monitoring Systems Product Reference Guide, Diabetes Health, 2006-2007, pp. 50-51.
Das, S. D., et al., "Review—Electrochemistry and Other Emerging Technologies for Continuous Glucose Monitoring Devices", ECS Sensors Plus, 2022, 19 pages.
"Deciding When to Submit a 510(k) for a Change to an Existing Device, Guidance for Industry and Food and Drug Administration Staff", 2017, pp. 1-77.
"Deciding When to Submit a 510(k) for a Software Change to an Existing Device, Guidance for Industry and Food and Drug Administration Staff", 2017, pp. 1-31.
Design Concepts Project Status Update, Glucose Sensor Applicator Dexcom (project #2554), 2014, 5 pages.
Dexcom CEO—Prime Position in Our Market—Mad Money—CNBC.mp4, Transcript 2023 by Sonix, 2 pages.
DexCom (DXCM) 2017 Q4 Earnings Call Transcript, 2017, retrieved from https://docoh.com/transcript/1093557/2017Q4/DXCM, 11 pages.
DexCom (DXCM) Q1 2018 Results—Earnings Call Transcript, 2018, retrieved from https://seekingalpha.com/article/4168949-dexcom-dxcm-q1-2018-results-earnings-call-transcript, 4 pages.
Dexcom, Inc. NasdaqGS:DXCM Company Conference Presentation, 2019, 10 pages.
Dexcom, Inc. NasdaqGS:DXCM Company Conference Presentation, 2020, 9 pages.
Dexcom, Inc. NasdaqGS:DXCM Company Conference Presentation, 2021, 16 pages.
Dexcom G5 Quick Start Guide, 2020, pp. 1-31.
Dexcom G6 Continuous Glucose Monitoring System User Guide, 2022, 346 pages.
Dexcom G6 Start Here Set up Guide, 2019, pp. 1-8.
Dexcom G6 Start Here Set up Guide, 2022, pp. 18 pages.
Dexcom G6 Using Your G6 Guide, Mar. 2020, pp. 1-7.
"The Dexcom G7. The most accurate CGM system.[1]" retrieved from https://www.dexcom.com/g7-cgm-system on Jun. 27, 2024, 20 pages.
Dexcom G7 Continuous Glucose Monitoring (CGM) System Section 510(k) Approval, 2022, 10 pages.
Dexcom G7 Inserting Sensor Instructions for Use, 2021, pp. 1-2.
Dexcom G7, Start Here, Operational Manual, 2022, pp. 1-9 (English Abstract).
Dexcom G7, User Guide, 2022, p. 1-179 (English Abstract).
Dexcom G7 User Guide, 2024, p. i-186.
Dexcom Seven® Plus Continuous Glucose Monitoring System User's Guide, 2011, pp. 1-144.
DexCom™ STS™ Continuous Glucose Monitoring System Summary of Safety and Effectiveness Data, 2006, 20 pages.
DexCom™ STS™ Sensor Instructions for Use, 2006, pp. 1-6.
Dexcom STS-7 Continuous Glucose Monitoring System FDA Premarket Approval (PMA), 2007, pp. 1-7.
Dexcom STS®-7 Continuous Glucose Monitoring System Summary of Safety and Effectiveness Data, 2007, 14 pages.
Diglas, J., et al., "Reduced pain perception with Pen Mate™, an automatic needle insertion device for use with an insulin pen", Practical Diabetes International, 1999, vol. 16, No. 2, pp. 39-41.
"Does Dexcom Really Have a Future If It Can't Match Abbott's Scale", 2019, retrieved from https://www.sprucepointcap.com/reports/dxcm_research_thesis_3-21-2019.pdf, p. 46.
Edison Awards Announces 2016 Gold, Silver, and Bronze Awards Winners, Edison Awards, 9 pages.
Edison Best New Product Awards™ 2021 Winners retrieved from https://edisonawards.com/2021-winners/, 19 pages.
Edison Best New Product Awards™ 2022 Winners retrieved from https://edisonawards.com/2022-winners/, 52 pages.
Email chain from Sophie Hood, oldest email dated Jan. 24, 2023, 5 pages.
Email from Christopher M Dougherty dated Dec. 17, 2019, 68 pages.
Email from John Shaw of Shaw & Keller dated May 16, 2023, 2 pages.
Englert, K., et al., "Skin and Adhesive Issues With Continuous Glucose Monitors: A Sticky Situation", Journal of Diabetes Science and Technology, 2014, vol. 8, No. 4, pp. 745-751.
European Standard, ISO 11607-1, Packaging for terminally sterilized medical devices—Part 1: Requirements for materials, sterile barrier systems and packaging systems, 2006, 32 pages.
European Standard, ISO 13485, Medical devices—Quality management systems—Requirement for regulatory purposes, 2003, 69 pages.

(56) References Cited

OTHER PUBLICATIONS

European Standard, ISO 15197, In vitro diagnostic test systems—Requirements for blood glucose monitoring systems for self-testing in managing diabetes mellitus, 2003, 43 pages.
Explore the Monroe Street Market Community, retrieved from https://www.monroestreetmarket.com/floor-plans/apartment/B-231 on May 10, 2023, 2 pages.
"FDA authorizes first fully interoperable continuous glucose monitoring system, streamlines review pathway for similar devices", FDA News Release, 2018, retrieved from https://www.fda.gov/news-events/press-announcements/fda-authorizes-first-fully-interoperable-continuous-glucose-monitoring-system-streamlines-review, 3 pages.
U.S. Appl. No. 61/317,243.
U.S. Appl. No. 61/345,562.
U.S. Appl. No. 61/361,374.
U.S. Appl. No. 61/411,262.
U.S. Appl. No. 62/524,247.
Food and Drug Administration, HHS, 2009, Code of Federal Regulation § 820.30, Subpart C—Design Controls, pp. 147-148.
Freckmann, G., et al., "Performance Evaluation of Three Continuous Glucose Monitoring Systems: Comparison of Six Sensors per Subject in Parallel", Journal of Diabetes Science and Technology, 2013, vol. 7, No. 4, pp. 842-853.
Freestyle Libre Brochure, 2016, 10 pages.
Freestyle Libre Fact Sheet, 2016, retrieved from www.FreeStyleLibre.de, 2 pages.
Freestyle Libre FAQ, 2024, retrieved from https://www.freestyle.abbott/uk-en/support/faq/question-answer.html?q=UKFaqquestion-55#, 2 pages.
"FreeStyle Libre Honored by Prix Galien", 2019, 4 pages.
FreeStyle Libre In-Service Guide, 2021, 28 pages.
FreeStyle Libre 2 Get Started Guide, 2023, pp. 1-28.
Freestyle Libre 2 HCP Pulse Report, 2021, 13 pages.
"FreeStyle Libre 2—Zucker messen ohne stechen per Sensor und App", German Innovation Awards Gold Winner, 2020, retrieved from https://www.german-innovation-award.de/preistraeger/preis/gewinner/freestyle-libre-2-zucker-messen-ohne-stechen-per-sensor-und-app/#:~:text=Beschreibung%20Die%20kontinuierliche%20Glukosemessung%20mit, um%20die%20Glukosewerte%20kontinuierlich%20aufzuzeichnen, 1 page.
FreeStyle Libre 3 Get Started Guide, 2023, pp. 1-20.
FreeStyle Libre 3 User's Manual, 2022-2023, pp. iv-241.
Freestyle Libre Pro Flash Glucose Monitoring System Summary of Safety and Effectiveness Data, 2016, 31 pages.
FreeStyle Lite Blood Glucose Monitoring System Owner's Booklet, 2006, 15 pages.
FreeStyle Navigator Continuous Glucose Monitoring System FDA Premarket Approval (PMA), 2008, pp. 1-7.
The Galien Foundation is proud to announce the laureates of the best-of-the-best from the half century 1970-2020, The 2022 Galien Golden Jubilee Winners, retrieved from https://www.galienfoundation.org/galien-golden-jubilee, 3 pages.
Gough, D. A., et al., "Development of the Implantable Glucose Sensor: What Are the Prospects and Why Is It Taking So Long?", Diabetes, 1995, vol. 44, pp. 1005-1009.
Harris, J. M., et al., "Common Causes of Glucose Oxidase Instability in In Vivo Biosensing: A Brief Review", Journal of Diabetes Science and Technology. 2013, vol. 7, No. 4, pp. 1030-1038.
Hemmerich, K. J., et al., "Sterilization Methods Stand the Test of Time", 2004, retrieved from https://www.mddionline.com/sterilization/sterilization-methods-stand-test-time, pp. 1-8.
Hermanides, J., et al., "Current Application of Continuous Glucose Monitoring in the Treatment of Diabetes", Diabetes Care, 2011, vol. 34, Suppl. 2, pp. S197-S201.
Hirsch, I. B., "Realistic Expectations and Practical Use of Continuous Glucose Monitoring for the Endocrinologist", The Journal of Clinical Endocrinology & Metabolism, 2009, vol. 94, No. 7, pp. 2232-2238.
Hoss, U., et al., "Continuous glucose monitoring in the tissue: Do we really need to calibrate in-vivo?", Feb. 28, 2009, pp. 1-21.
Hoss, U., et al., "Continuous Glucose Monitoring in Subcutaneous Tissue Using Factory-Calibrated Sensors: A Pilot Study", Diabetes Technology & Therapeutics, 2010, vol. 12, No. 8, pp. 591-597.
Hoss, U., et al., "Feasibility of Factory Calibration for Subcutaneous Glucose Sensors in Subjects With Diabetes", Journal of Diabetes Science and Technology, 2014, vol. 8, No. 1, pp. 89-94.
"Housing", "recess", "release", and "retain", Merriam-Webster's Collegiate Dictionary, Tenth Edition, 1999, pp. 563, 975, 987, and 999.
"Housing" and "recess", The New Penguin English Dictionary, 2000, pp. 678 and 1167.
Hovorka, R., "Continuous glucose monitoring and closed-loop systems", Diabetic Medicine, 2005, vol. 23, pp. 1-12.
Hughes, M. D., "The Business of Self-Monitoring of Blood Glucose: A Market Profile", Journal of Diabetes Science and Technology, 2009, vol. 3, No. 5, pp. 1219-1223.
IEEE 100 The Authoritative Dictionary of IEEE Standards Terms, Seventh Edition, 2000, 3 pages.
Insert Molding, 1996, retrieved from https://www.mddionline.com/equipment/insert-molding, 4 pages.
International Diabetes Device 2022 Blue Book, Seagrove Partners, 142 pages.
International Standard, ISO 14971, Medical devices—Application of risk management to medical devices, 2007, 90 pages.
"An Interview with Kevin Sayer, President and CEO of Dexcom, About the New G6", 2021, 5 pages.
Joseph, J. I., et al., "Glucose Sensing in the Subcutaneous Tissue: Attempting to Correlate the Immune Response with Continuous Glucose Monitoring Accuracy", Diabetes Technology & Therapeutics, 2018, vol. 20, No. 5, pp. 321-324.
Klueh, U., et al., "Inflammation and Glucose Sensors: Use of Dexamethasone to Extend Glucose Sensor Function and Life Span in Vivo", Journal of Diabetes Science and Technology, 2007, vol. 1, No. 4, pp. 496-504.
Klueh, U., et al., "Blood-Induced Interference of Glucose Sensor Function in Vitro: Implications for in Vivo Sensor Function", Journal of Diabetes Science and Technology, 2007, vol. 1, No. 6, pp. 842-849.
Lomas, P., "Dexcom G7 Release: The Most Exciting New Features", 2024, retrieved from https://notjustapatch.com/dexcom-g7-features/, 13 pages.
Lovett, L., "What's next for Dexcom? CEO, CTO talk G6 for inpatient use, expanding CGMs for patients without diabetes", 2020, retrieved from https://www.mobihealthnews.com/news/whats-next-dexcom-ceo-cto-talk-g6-inpatient-use-expanding-cgms-patients-without-diabetes, 6 pages.
Medtronic Enlite Serter User Guide, 2014, 26 pages.
Medtronic MiniMed Guardian RT FDA Premarket Approval (PMA), 2005, pp. 1-6.
Medtronic MiniMed Guardian RT Summary of Safety and Effectiveness Data, 2005, 13 pages.
Medtronic MiniMed iPro2 User Guide, 2010, pp. 1-99.
Medtronic MiniMed Paradigm® Real-Time 522 and 722 Insulin Pumps User Guide, 2008, pp. 1-262.
Meltsner, M A, et al., "Observations on rotating needle insertions using a brachytherapy robot", Phys. Med. Biol., 2007, vol. 52, pp. 6027-6037.
Nichols, S. P., et al., "Biocompatible Materials for Continuous Glucose Monitoring Devices", Chem Rev., 2013, vol. 113, No. 4, pp. 2528-2549.
Occupational Safety and Health Admin., Labor, 2003, 29 CFR § 1910.1030 Bloodborne pathogens, pp. 260-273.
Ólafsdóttir, A. F., et al., "A Clinical Trial of the Accuracy and Treatment Experience of the Flash Glucose Monitor FreeStyle Libre in Adults with Type 1 Diabetes", Diabetes Technology & Therapeutics, 2017, vol. 19, No. 3, pp. 164-172.
Omnipod image, Exhibit 182 of ADC Reply Brief SJ, Daubert, Sep. 22, 2022, 2 pages.
OneTouch® Ultra™ Blood Glucose Monitoring System Owner's Booklet, 2000, 23 pages.
OneTouch Ultra2 Blood Glucose Monitoring System Owner's Booklet, 2005, 34 pages.
Order, Federal Communications Commission, 2006, pp. 1-8.

(56) References Cited

OTHER PUBLICATIONS

Panteleon, A. E., et al., "The Role of the Independent Variable to Glucose Sensor Calibration", Diabetes Technology & Therapeutics, 2003, vol. 5, No. 3, pp. 401-410.
Parker, S. P., ed., McGraw-Hill Dictionary of Mechanical and Design Engineering, 1984 (excerpted), pp. 1-4.
"Periphery", Cambridge Dictionary of American English, 2000, p. 631.
"Product Review: Abbott FreeStyle Libre Flash Glucose Monitor", DiabetesMine Team, 2021, retrieved from https://www.healthline.com/diabetesmine/abbott-freestyle-libre-review#bottom-line, 6 pages.
Program, 2$^{nd}$ International Conference on Advanced Technologies & Treatments for Diabetes, Athens, Greece, 2009, 3 pages.
"Real-World Data Show Abbott's Freestyle LibreR Systems And GLP-1 Medicines Work Better Together For People With Type 2 Diabetes", 2024, PRNewswire, 2 pages.
"Recess", Cambridge Dictionary of American English, 2000, pp. 710-711.
"Retract", The Chambers Dictionary, 1998, p. 1410.
"Retract", The New Oxford American Dictionary, 2001, p. 1455.
"Retract", Webster's Third New International Dictionary, 1993, pp. 1939-1940.
Rice, M. J., et al., "Continuous Measurement of Glucose: Facts and Challenges", Anesthesiology, 2012, vol. 116, No. 1, pp. 199-204.
Rigo, R. S., et al., "Cutaneous Reactions to Continuous Glucose Monitoring and Continuous Subcutaneous Insulin Infusion Devices in Type 1 Diabetes Mellitus", Journal of Diabetes Science and Technology, 2021, vol. 15, No. 4, pp. 786-791.
Rocchitta, G., et al., "Enzyme Biosensors for Biomedical Applications: Strategies for Safeguarding Analytical Performances in Biological Fields", Sensors, 2016. Vol. 16, No. 6, 21 pages.
Sclater, N., et al., eds., Mechanisms and Mechanical Devices Sourcebook, Fourth Edition, 2007, Chapter 12—Shaft Couplings and Connections, pp. 290-307.
Shenoi, B. A., ed., Introduction to Digital Signal Processing and Filter Design, 2006, "Introduction", Chapter 1, pp. 1-30.
Smith, S. S., ed., The Scientist and Engineer's Guide to Digital Signal Processing, Second Edition, 1997-1999, "Digital Signal Processors", Chapter 28, pp. 503-534.
"Submission and Review of Sterility Information in Premarket Notification (510(k)) Submissions for Devices Labeled as Sterile, Guidance for Industry and Food and Drug Administration Staff", 2016, pp. 1-11.
Tegnestedt, C., et al., "Levels and sources of sound in the intensive care unit—an observational study of three room types", Acta Anaesthiesiologica Scandinavica, 2013, pp. 1-10.
"Transcutaneous", Webster's Third New International Dictionary, 2002, pp. 2426.
Tsumura, R., et al., "Histological Evaluation of Tissue Damage Caused by Rotational Needle Insertion", Proceedings of the Annual International Conference of the IEEE Engineering in Medicine and Biology Society, 2016, pp. 5120-5123.
Van Den Boom, L., et al., "Changes in the utilization of blood glucose test strips among patients using intermittent-scanning continuous glucose monitoring in Germany", Diabetes, Obesity and Metabolism, 2020, vol. 22, pp. 922-928.
Watkin, J., "An Introduction to Flash Glucose Monitoring", 2013, 14 pages.
Xu, J., et al., "Anti-Biofouling Strategies for Long-Term Continuous Use of Implantable Sensors", Chemosensors, 2020, vol. 20 No. 3, 29 pages.
AU, 2019404908 Examiner's Report, Feb. 17, 2025.
CA, 3,050,721 Examiner's Report, Nov. 8, 2024.
CN, 202211091194.1 Notification of Filing Divisional Application, Mar. 27, 2025.
EP, 17182379.2 Reply to Opposition, Feb. 27, 2025.
EP, 19151577.4 Examination Report, Oct. 7, 2024.
EP, 20177703.4 Response to Withdrawals, Jan. 7, 2025.
EP, 20177703.4 Withdrawal of Intervention, Dec. 27, 2024.
EP, 20177703.4 Withdrawal of Opposition, Dec. 27, 2024.
EP, 20177703.4 Written Submissions Dexcom, Nov. 22, 2024.
EP, 20177712.5 Summons to Attend Oral Proceedings, Oct. 1, 2024.
EP, 20195922.8 Withdrawal of Intervention, Dec. 27, 2024.
EP, 20195922.8 Withdrawal of Opposition, Dec. 27, 2024.
EP, 21211041.5 Grounds of Appeal, Apr. 23, 2025.
EP, 21211041.5 Withdrawal of Opposition, Dec. 27, 2024.
EP, 21211041.5 Notice of Appeal, Dec. 17, 2024.
EP, 21211041.5 Minutes of Oral Proceedings, Dec. 13, 2024.
EP, 21211041.5 Response to Summons to Attend Oral Proceedings Dexcom, Nov. 12, 2024.
EP, 21211041.5 Response to Summons to Attend Oral Proceedings, Nov. 12, 2024.
EP, 21211041.5 Summons to Attend Oral Proceedings, Sep. 23, 2024.
EP, 24152079.0 Examination Report, Dec. 2, 2024.
EP, 24183336.7 Extended Search Report, Oct. 11, 2024.
EP, 24187206.8 Extended Search Report, Oct. 9, 2024.
EP, 24194029.5 Extended Search Report, Nov. 18, 2024.
EP, 24201435.5 Extended Search Report, Jan. 27, 2025.
JP, 2023-516522 Office Action, Mar. 5, 2025.
JP, 2024-31538 Office Action, Oct. 16, 2024.
MX, MX/a/2021/007294 Second Office Action, Feb. 19, 2025.
MY, PI2021003022 Examination Report, Mar. 5, 2025.
MY, PI2022002786 Examination Report, Jan. 8, 2025.
UP, Second Expert Opinion of Dr Michael Schoemaker in Litigation of EP 3977921, Nov. 8, 2024.
US, Decision Denying Institution of Inter Partes Review, IPR No. 2024-00860, Nov. 20, 2024.
US, Patent Owner's Response to Petitioner's Explanation of Parallel Petitions Challenging U.S. Pat. No. 11,510,325, IPR No. 2024-00860, Aug. 23, 2024.
US, Patent Owner Preliminary Response Pursuant to 37 C.F.R. § 42.107, IPR No. 2024-00860, Aug. 23, 2024.
US, Declaration of Julia Castellano, IPR No. 2024-00860.
US, Declaration of Scott E. Davis, IPR No. 2024-00860, Jun. 5, 2024.
US, Petitioner's Explanation Of Parallel Petitions Challenging U.S. Pat. No. 11,510,325, IPR No. 2024-00860, May 9, 2024.
US, Termination Due to Settlement After Institution of Trial, IPR No. 2023-01409, Jan. 7, 2025.
US, Joint Motion to Treat Settlement Agreement as Business Confidential Information. IPR No. 2023-01409, Jan. 3, 2025.
US, Joint Motion to Terminate Proceeding Under 35 U.S.C. § 317(a), IPR No. 2023-01409, Jan. 3, 2025.
US, Order Setting Oral Argument, IPR No. 2023-01409, Dec. 11, 2024.
US, Patent Owner's Sur-Reply, IPR No. 2023-01409, Dec. 10, 2024.
US, Deposition of Gary D. Fletcher, Ph.D., IPR No. 2023-01409, Dec. 4, 2024.
US, Patent Owner's Request For Oral Argument, IPR No. 2023-01409, Dec. 3, 2024.
US, Petitioner's Request for Oral Argument, IPR No. 2023-01409, Dec. 3, 2024.
US, Patent Owner's Objections to Petitioner's Exhibits Submitted With Its Reply, IPR No. 2023-01409, Nov. 1, 2024.
US, Petitioner's Updated Exhibit List, IPR No. 2023-01409, Oct. 25, 2024.
US, Second Declaration of Gary Fletcher, Ph.D., IPR No. 2023-01409, Oct. 25, 2024.
US, Petitioner's Reply to Patent Owner's Response, IPR No. 2023-01409, Oct. 25, 2024.
US, Deposition of Karl R. Leinsing, MSME, PE, IPR No. 2023-01409, Oct. 17, 2024.
US, Conference Call Before the Patent Trial and Appeal Board • Before Judge Cynthia Hardman, IPR No. 2023-01409, Oct. 17, 2024.
US, Notice of Joint Stipulation to Modify Schedule, IPR No. 2023-01409, Sep. 26, 2024.
US, Declaration of Karl R. Leinsing, MSME, PE, IPR No. 2023-01409, Jul. 19, 2024.
US, Patent Owner's Response, IPR No. 2023-01409, Jul. 19, 2024.

(56) References Cited

OTHER PUBLICATIONS

US, Deposition of Gary Fletcher, Ph.D., IPR No. 2023-01409, Jun. 26, 2024.
US, Decision Denying Patent Owner's Request on Rehearing of Decision Denying Institution, IPR No. 2023-01396, Aug. 9, 2024.
US, Reexamination No. 90/019,307 Office Action, Mar. 18, 2025.
US, Reexamination No. 90/019,307 Decision on Petition, Feb. 13, 2025.
US, Reexamination No. 90/019,307 Petition Under 37 CFR § 1.181 to Terminate, Aug. 15, 2024.
US, Reexamination No. 90/019,307 Decision on Petitions, Aug. 7, 2024.
US, Reexamination No. 90/019,307 Petition Under 37 CFR § 1.59 to Expunge Application Papers, Aug. 1, 2024.
US, Reexamination No. 90/019,307 Petition Under 37 CFR § 1.59 to Expunge Application Papers, Jun. 12, 2024.
US, Reexamination Serial No. 90/019,307 Notification of Concurrent Proceedings, May 15, 2024.
US, Reexamination No. 90/019,307 Petition Under 37 CFR §§ 1.182 and/or § 1.183 to Allow Filing and Consideration of Response to Patent Owner's Extraordinary Petition to Suspend, Mar. 19, 2024.
US, Reexamination No. 90/019,307 Petition Under 37 CFR § 1.181 and/or § 1.183 to Suspend, Mar. 1, 2024.
US, Reexamination Serial No. 90/019,329 Decision on Petition Under 37 C.F.R. § 1.181, Mar. 18, 2025.
US, Ex Parte Reexamination Certificate of U.S. Pat. No. 11,013,440, Oct. 30, 2024.
US, Reexamination Serial No. 90/019,329 Notice of Intent to Issue Ex Parte Reexamination Certificate, Oct. 8, 2024.
US, Reexamination Serial No. 90/019,329 Decision on Petition Under 37 C.F.R. § 1.59, Sep. 16, 2024.
US, Reexamination Serial No. 90/019,329 Statutory disclaimer per Manual of Patent Examining Procedure (MPEP) 1490, Sep. 3, 2024.
US, Reexamination Serial No. 90/019,329 Petition Under 37 C.F.R. § 1.182 to Seal Document Versions Filed via IDS and Substitute Redacted Document Versions Therfor, Aug. 1, 2024.
US, Reexamination No. 90/019,329 Petition Under 37 CFR § 1.59 to Expunge Application Papers, Aug. 1, 2024.
US, Reexamination No. 90/019,329 Ex Parte Reexamination Interview Summary, Jul. 25, 2024.
US, Reexamination Serial No. 90/019,329 Decision on Petition Under 37 C.F.R. § 1.59, Jul. 22, 2024.
US, Reexamination No. 90/019,329 Decision Sua Sponte Vacating Notice of Intent to Issue Ex Parte Reexamination Certificate, Jul. 3, 2024.
US, Reexamination No. 90/019,329 Petition Under 37 CFR § 1.59 to Expunge Application Papers, Jun. 12, 2024.
US, Ex Parte Reexamination Certificate of U.S. Pat. No. 11,000,216, Nov. 14, 2024.
US, Reexamination Serial No. 90/019,331 Notice of Intent to Issue Ex Parte Reexamination Certificate, Oct. 15, 2024.
US, Reexamination Serial No. 90/019,331 Decision on Petition Under 37 C.F.R. § 1.59, Sep. 16, 2024.
US, Reexamination Serial No. 90/019,331 Petition Under 37 C.F.R. § 1.182 to Seal Document Versions Filed via IDS and Substitute Redacted Document Versions Therfor, Aug. 1, 2024.
US, Reexamination No. 90/019,331 Petition Under 37 CFR § 1.59 to Expunge Application Papers, Aug. 1, 2024.
US, Reexamination Serial No. 90/019,331 Decision on Petition Under 37 C.F.R. § 1.59, Jul. 16, 2024.
US, Reexamination No. 90/019,331 Petition Under 37 CFR § 1.59 to Expunge Application Papers, Jun. 12, 2024.
US, Ex Parte Reexamination Certificate of U.S. Pat. No. 10,959,654, Nov. 5, 2024.
US, Reexamination Serial No. 90/019,330 Notice of Intent to Issue Ex Parte Reexamination Certificate, Oct. 7, 2024.
US, Reexamination Serial No. 90/019,330 Decision on Petition Under 37 C.F.R. § 1.59, Sep. 16, 2024.
US, Reexamination Serial No. 90/019,330 Petition Under 37 C.F.R. § 1.182 to Seal Document Versions Filed via IDS and Substitute Redacted Document Versions Therfor, Aug. 1, 2024.
US, ReexaminationNo. 90/019,330 Petition Under 37 CFR § 1.59 to Expunge Application Papers, Aug. 1, 2024.
US, Reexamination Serial No. 90/019,330 Decision on Petition Under 37 C.F.R. § 1.59, Jul. 16, 2024.
US, Reexamination No. 90/019,330 Petition Under 37 CFR § 1.59 to Expunge Application Papers, Jun. 12, 2024.
WO, PCT/US24/16127 ISR and Written Opinion, Sep. 11, 2024.
WO, PCT/US25/13698 Invitation to Pay Additional Fees, Apr. 15, 2025.
Abbott Patent Marking Diabetes, 2024, retrieved from https://www.abbott.com/patents/diabetes-patents.html, 6 pages.
ACCU-CHEK® Softclix Lancet Device retrieved from file:///C:/Users/afredericks/Downloads/softclix-user-manual.pdf, 2007, 2 pages.
Using your ACCU-CHEK® Multiclix Lancet Device, 2005, retrieved from https://www.northcoastmed.com/wp-content/uploads/2023/03/multiclix_userguide.pdf, 2 pages.
"The Advantages of the Cleo® 90 Infusion Set Are Clear", 2019, retrieved from https://web.archive.org/web/20220816002119/https:/smiths-medical.com/-/media/M/Smiths-medical_com//Files/Import-Files/Product-Literature/IN193873GB-092019_LR.pdf, 2 pages.
American National Standard, ANSI/AAMI HE75:2009, Human factors engineering—Design of medical devices, 2010, 465 pages.
Automated Retractable VanishPoint Syringe 510(k) Safety and Effectiveness Summary, 1998, 5 pages.
"Bluetooth rival unveiled by Nokia", 2006, retrieved from news.bbc.co.uk/1/hi/technology/5403564.stm, 2 pages.
Breton, M., et al., "Fully Integrated Artificial Pancreas in Type 1 Diabetes: Modular Closed-Loop Glucose Control Maintains Near Normoglycemia", Diabetes, 2012, vol. 61, No. 9, pp. 2230-2237.
Burge, M. R., et al., "Continuous Glucose Monitoring: The Future of Diabetes Management", Diabetes Spectrum, 2008, vol. 21, No. 2, pp. 112-119.
Clancy, N. T., et al., "A new device for assessing changes in skin viscoelasticity using indentation and optical measurement", Skin Research and Technology, 2010, vol. 16, pp. 210-228.
Cleo® 90 Infusion Set 510(k) Premarket Notification, 2004, 1 page.
Dexcom G5 Mobile System User Guide, 2015, pp. 1-260.
Dexcom G6 Continuous Glucose Monitoring (CGM) System Section 510(k) Approval, 2022, 7 pages.
Dexcom STS Continuous Monitors FDA Premarket Approval (PMA), 2006, 2 pages.
U.S. Appl. No. 61/569,287.
Freestyle Navigator Answers to Frequently Asked Questions, 2007, retrieved from https://web.archive.org/web/20080917183534/http:/www.freestylenavigator.com/ab_nav/url/content/en_US/3 0.10.10:1 O/general_content/General_ContenL0000004.htm, 2 pages.
"The Future is Bright for Veteran-centric Rehabilitation Research Publications", Journal of Rehabilitation Research & Development (JRRD), 2013, retrieved from https://www.rehab.research.va.gov/jrrd/index.html, 2 pages.
International Standard, IEC 62366, Medical devices—Application of usability engineering to medical devices, 2007, 214 pages.
Kaye, R., et al., "Medical Device Use-Safety: Incorporating Human Factors Engineering into Risk Management", 2000, retrieved from https://www.qualysinnova.com/download/files/MD-Use-Safety.pdf, pp. 1-33.
Mazze, R. S., et al., "Evaluating the Accuracy, Reliability, and Clinical Applicability of Continuous Glucose Monitoring (CGM): Is CGM Ready for Real Time?", Diabetes Technology & Therapeutics, 2009, vol. 11, No. 1., pp. 11-18.
Medtronic MiniMed Guardian® REAL-Time Components, 2007, retrieved from https://web.archive.org/20071013095335/http:/www.medtronicdiabetes.com/products/guardian/components.html, 2 pages.
Medtronic MiniMed Guardian® REAL-Time Features, 2007, retrieved from https://web.archive.org/20071025084715/http:/www.medtronicdiabetes.com/products/guardian/features.html, 2 pages.
Medtronic MiniMed One-press Serter User Guide, 2015, 26 pages.
Medtronic MiniMed Paradigm® 512 and 712 Insulin Pumps User Guide, 2005, pp. 1-136.

(56) References Cited

OTHER PUBLICATIONS

Microlet® 2 Lancing Device, 2008, retrieved from https://image.tigermedical.com/Manuals/BAY6606-20141216010820833.pdf, 1 page.
Piper, H. G., et al., "Real-Time Continuous Glucose Monitoring in Pediatric Patients During and After Cardiac Surgery", Pediatrics, 2006, vol. 118, No. 3, pp. 1176-1184.
Rabiee, A., et al., "Numerical and Clinical Accuracy of a Continuous Glucose Monitoring System during Intravenous Insulin Therapy in the Surgical and Burn Intensive Care Units", Journal of Diabetes Science and Technology, 2009, vol. 3, No. 4, pp. 951-959.
Sacks, A. H., et al., "Skin blood flow changes and tissue deformations produced by cylindrical indentors", Journal of Rehabilitation Research and Development, 1985, vol. 22, No. 3, pp. 1-6.
Schneider, M., et al., "Evaluating the use of the Cleo® 90 infusion set for patients on a palliative care unit", International Journal of Palliative Nursing, 2009, vol. 15, No. 8, pp. 372-376.
CA, 3,228,738 Examiner's Report, May 8, 2025.
CN, 202180063087.5 First Office Action, Aug. 14, 2025.
EP, 17182379.2 Written Submissions, Aug. 6, 2025.
EP, 17182379.2 Summons to Attend Oral Proceedings, Jul. 4, 2025.
EP, 17182379.2 Reply to Reply to Opposition, May 16, 2025.
EP, 19900891.3 Examination Report, May 8, 2025.
EP, 20177712.5 Response to Summons to Attend Oral Proceedings, Aug. 21, 2025.
EP, 23190032.5 Examination Report, May 19, 2025.
EP, 24218309.3 Extended Search Report, Jul. 9, 2025.
EP, 24220160.6 Extended Search Report, Jun. 17, 2025.
JP, 2023-514023 Office Action, Apr. 16, 2025.
JP, 2023-514024 Office Action, Apr. 30, 2025.
JP, 2023-532327 Office Action, Jul. 23, 2025.
US, Reexamination No. 90/019,307 Final Office Action, Jul. 8, 2025.
WO, PCT/US25/13698 ISR and Written Opinion, Jun. 5, 2025.
WO, PCT/US25/27260 Invitation to Pay Additional Fees, Jul. 24, 2025.
CA, 3,254, 151 Examiner's Report, Dec. 24, 2025.
EP, 17182379.2 Decision Revoking the European Patent, Nov. 24, 2025.
EP, 17182379.2 Minutes of the Oral Proceedings, Nov. 24, 2025.
EP, 18741791.0 Examination Report, Sep. 12, 2025.
EP, 19151577.4 Examination Report, Sep. 3, 2025.
EP, 20177712.5 Notice of Appeal, Jan. 28, 2026.
EP, 20177712.5 Decision Revoking the European Patent, Nov. 28, 2025.
EP, 20177712.5 Minutes of the Oral Proceedings, Nov. 28, 2025.
EP, 20177712.5 Written Submissions Gulde, Aug. 21, 2025.
EP, 21192910.4 Reply to Notices of Opposition, Jan. 22, 2026.
EP, 21192910.4 Notice of Intervention Sen Earon, Nov. 14, 2025.
EP, 21192910.4 Notice of Opposition Stolmar, Sep. 10, 2025.
EP, 21192910.4 Notice of Opposition Strawman, Sep. 10, 2025.
EP, 21211041.5 Summons to Attend Oral Proceedings, Dec. 15, 2025.
EP, 21772864.1 Examination Report, Dec. 9, 2025.
EP, 22754227.1 Examination Report, Jan. 2, 2026.
EP, 23166498.8 Examination Report, Dec. 10, 2025.
EP, 23190032.5 Examination Report, Dec. 10, 2025.
EP, 24187206.8 Examination Report, Jan. 2, 2023.
EP, 24194029.5 Examination Report, Aug. 26, 2025.
EP, 24201435.5 Examination Report, Oct. 28, 2025.
GB, Case No. CA-2025-000284 Approved Judgement, Dec. 18, 2025.
JP, 2023-514023 Final Office Action, Aug. 20, 2025.
JP, 2025-026588 Office Action, Aug. 27, 2025.
JP, 2025-117332 Office Action, Nov. 19, 2025.
MX, MX/a/2021/007294 Third Office Action, Sep. 10, 2025.
UP, Order in Litigation of EP 3960072, Feb. 6, 2026.
WO, PCT/US25/27260 ISR and Written Opinion, Sep. 16, 2025.

* cited by examiner

FIG. 7D
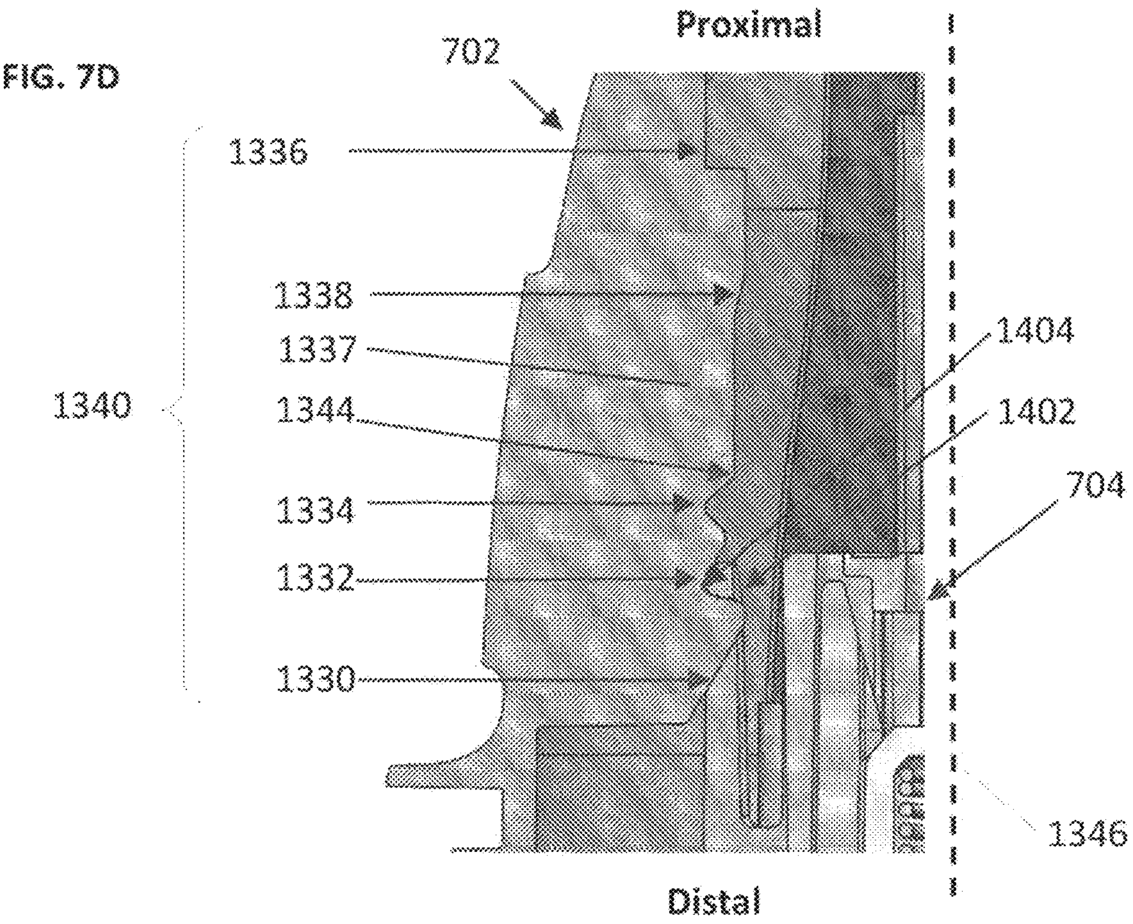
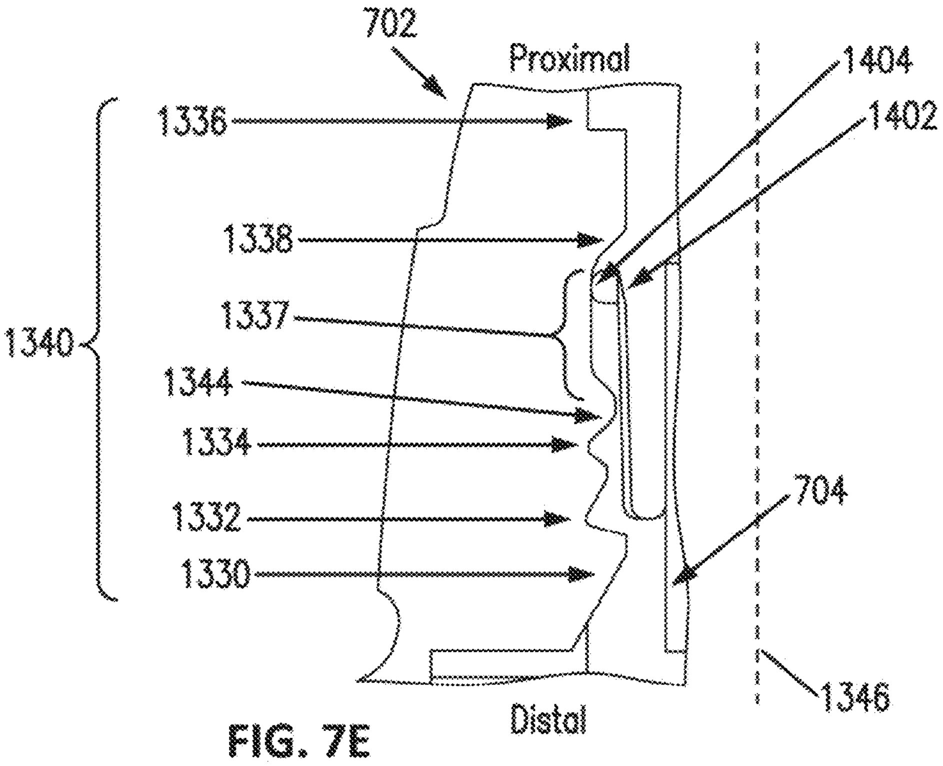
FIG. 7E

2600

2600

SYSTEMS, DEVICES, AND METHODS FOR ANALYTE MONITORING

CROSS-REFERENCE TO RELATED APPLICATIONS

This application claims priority to U.S. Provisional Application No. 63/132,651, filed Dec. 31, 2020, which is herein expressly incorporated by reference in its entirety for all purposes.

FIELD

The subject matter described herein relates generally to systems, devices, and methods for in vivo analyte monitoring.

BACKGROUND

The detection and/or monitoring of analyte levels, such as glucose, ketones, lactate, oxygen, hemoglobin AIC, or the like, can be vitally important to the overall health of a person, particularly for an individual having diabetes. Patients suffering from diabetes mellitus can experience complications including loss of consciousness, cardiovascular disease, retinopathy, neuropathy, and nephropathy. Persons with diabetes are generally required to monitor their glucose levels to ensure that they are being maintained within a clinically safe range, and may also use this information to determine if and/or when insulin is needed to reduce glucose levels in their bodies, or when additional glucose is needed to raise the level of glucose in their bodies.

Growing clinical data demonstrates a strong correlation between the frequency of glucose monitoring and glycemic control. Despite such correlation, however, many individuals diagnosed with a diabetic condition do not monitor their glucose levels as frequently as they should due to a combination of factors including convenience, testing discretion, pain associated with glucose testing, and cost.

To increase patient adherence to a plan of frequent glucose monitoring, in vivo analyte monitoring systems can be utilized, in which a sensor control device may be worn on the body of an individual who requires analyte monitoring. To increase comfort and convenience for the individual, the sensor control device may have a small form-factor, and can be assembled and applied by the individual with a sensor applicator. The application process includes inserting a sensor that senses a user's analyte level in a bodily fluid located in the human body, using an applicator or insertion mechanism, such that the sensor comes into contact with a bodily fluid. The sensor control device may also be configured to transmit analyte data to another device, from which the individual or her health care provider ("HCP") can review the data and make therapy decisions. Furthermore, the benefits of analyte monitoring systems are not limited to persons with diabetes. For instance, analyte monitoring systems can provide useful information and insights to individuals interested in improving their health and wellness. As one example, to improve their sports performance, athletes can utilize a sensor control device worn on the body to collect data relating to one or more analytes such as, for example, glucose and/or lactate.

While current sensors can be convenient for users, they are also susceptible to malfunctions due to improper insertion. These malfunctions can be caused by user error, lack of proper training, poor user coordination, overly complicated procedures, and other issues. This can be particularly true for analyte monitoring systems having sensors used to measure an analyte level in an interstitial fluid ("ISF"), and which are inserted using sharps (also known as "introducers" or "needles"). Some prior art systems, for example, may rely too much on the precision assembly and deployment of a sensor control device and an applicator by the individual user. Other prior art systems may utilize sharp insertion and retraction mechanisms that are susceptible to premature withdrawal before the sensor can be properly implanted. In addition, some prior art systems may utilize sharps that are not optimally configured to create an insertion path without creating trauma to surrounding tissue. These challenges and others described herein can lead to improperly inserted or damaged sensors, and consequently, a failure to properly monitor the patient's analyte level.

Thus, a need exists for more reliable sensor insertion devices, systems and methods, that are easy to use by the patient and less prone to error. Additionally, a need exists for sensor insertion deices, systems, and methods that provide moisture control and extended shelf stability. Furthermore, a need exists for sensor control devices housing electronic circuitry to measure and transmit analyte data in a small form-factor.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings.

To achieve these and other advantages and in accordance with the purpose of the disclosed subject matter, as embodied and broadly described, the disclosed subject matter is directed to an analyte measurement device. The analyte measurement device can include an electronics housing including a shell having an upper surface with a first aperture defined therein; a mount mated to the shell and having an underside with a second aperture defined therein aligned with the first aperture; a collar disposed between the shell and the mount and including: a third aperture aligned with the first aperture and the second aperture, and a plurality of tabs on an outer periphery of the collar; a circuit board disposed within the electronics housing and including a plurality of electronic modules, wherein the circuit board is mounted within the electronics housing on the plurality of tabs on the outer periphery; and an analyte sensor including a tail portion extending through the first aperture and the second aperture and configured to measure an analyte level and a flag portion including a plurality of electrical contacts coupled with the circuit board, and a neck portion interconnecting the tail portion and the flag portion. The plurality of tabs can include three tabs.

The foldable circuit board can include a first portion foldable over a second portion, the second portion mounted on the mount and the first portion mounted on the plurality of tabs on the outer periphery. The circuit board can include a battery. The circuit board can include battery aperture to position the battery and to eliminate electrical interference between the battery and the circuit board.

The collar can include a collar channel on an upper surface mated with an annular ridge defined on an inner surface of the shell, and an annular lip on a bottom surface received within a channel defined on an inner surface of the mount, and a seal on the upper surface of the collar. The seal can be an elastomeric seal.

The analyte measurement device can include a sharp hub including a sharp extending through the first, second, and third apertures and a mating surface mated with the seal. The mating surface can include a ledge.

In accordance with the disclosed subject matter, an assembly for delivery of an analyte sensor is provided. The assembly can include a sensor control device including: an electronics housing including a shell and a mount mounted to the shell; a circuit board disposed within the electronics housing and including a plurality of electronic modules; an analyte sensor including a tail portion extending through an aperture in the mount and configured to measure an analyte level and a flag portion including a plurality of electrical contacts connected to the circuit board, and a neck portion interconnecting the tail portion and the flag portion; a sensor cap having a first end, a second end, and an inner chamber, wherein the inner chamber receives the tail portion of the analyte sensor and wherein the first end is removably coupled to the mount to seal the inner chamber; and an applicator for delivery of the analyte sensor including: a housing defining an interior space; a sensor carrier within the interior space and releasably securing the sensor control device within an interior of the applicator; an applicator cap removably coupled to the housing and including: a desiccant including a plurality of retention snaps, one or more retention clips engaged to the plurality of retention snaps to retain the desiccant in the cap and to limit rotation of the desiccant, and a cap post engaged with an engagement feature on the second end of the sensor cap.

The desiccant can include an internal bore and the engagement feature on the second end of the sensor cap passes through the internal bore of the desiccant and engages the applicator cap. The desiccant can be substantially cylindrical in shape.

The sensor control device can comprise an elastomeric plug arranged at the second end of the sensor cap. The elastomeric plug can include a seal bead in an interference fit arrangement with the sensor cap. The elastomeric plug can define the engagement feature of the sensor cap.

The applicator for delivery of the analyte sensor can include a sharp carrier coupled to a sharp extending through the aperture in the mount, the sharp configured to penetrate a user's skin to position the analyte sensor into contact with bodily fluid, a sensor carrier to releasably hold the sensor control device within the interior space, and a spring biasing the sharp carrier to move upward within the housing.

The spring can include a spring having a spring constant of about 0.12. The spring can have a wire diameter of about 0.65 millimeters, an inner diameter of about 9.6 millimeter, and an outer diameter of about 11.1 millimeters. The spring can have a maximum solid strength of about 11 millimeters.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIGS. 7D and 7E are side cross-sectional views depicting a locking rib portion of an example embodiment of a housing with a portion of a sheath.

DETAILED DESCRIPTION

Figure 1:
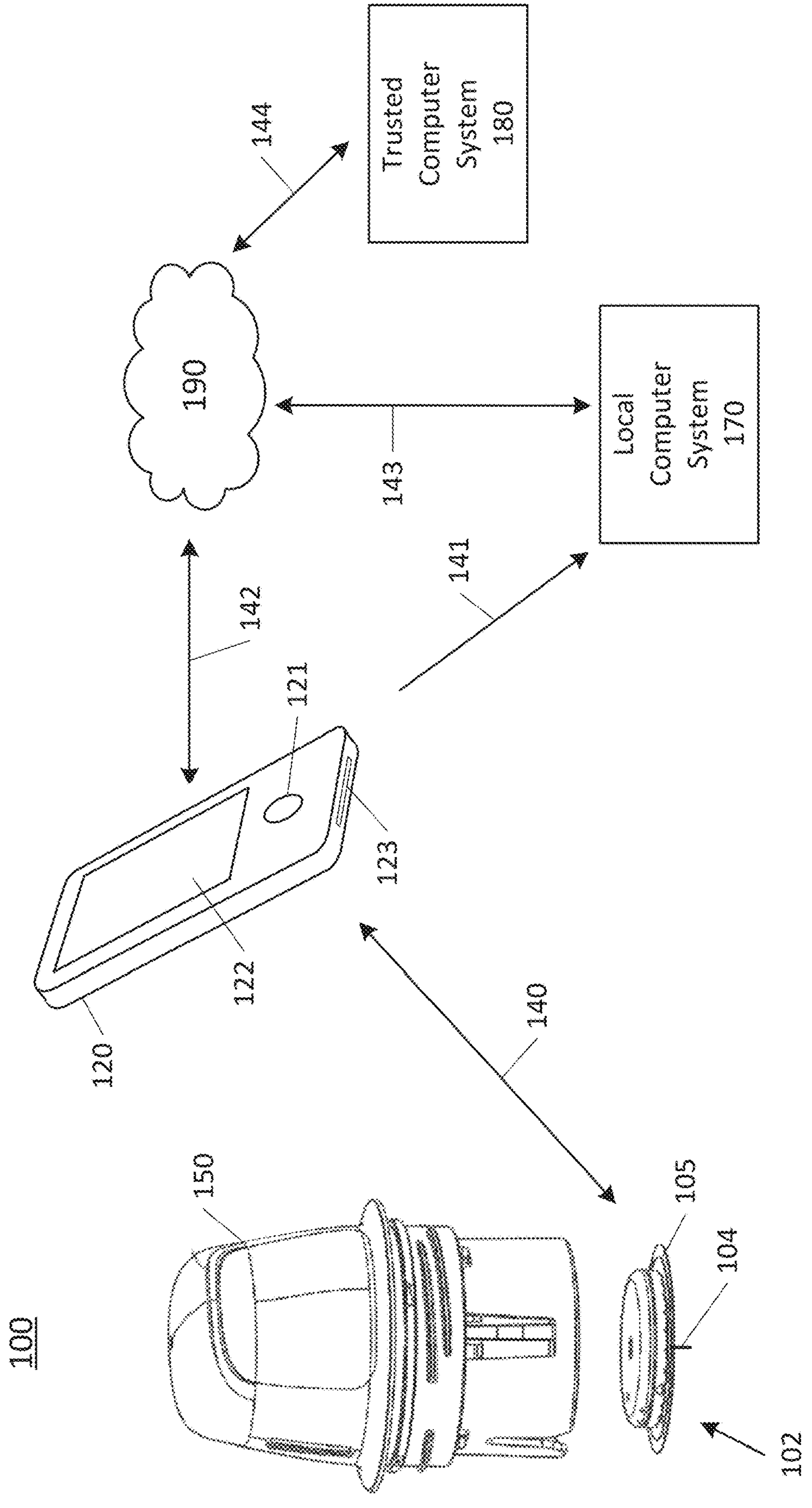
FIG. 1 is a system overview of a sensor applicator, reader device, monitoring system, network, and remote system.

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms “a,” “an,” and “the” include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

Generally, embodiments of the present disclosure include systems, devices, and methods for the use of analyte sensor insertion applicators for use with in vivo analyte monitoring systems. An applicator can be provided to the user in a sterile package with an electronics housing of the sensor control device contained therein. According to some embodiments, a structure separate from the applicator, such as a container, can also be provided to the user as a sterile package with a sensor module and a sharp module contained therein. The user can couple the sensor module to the electronics housing, and can couple the sharp to the applicator with an assembly process that involves the insertion of the applicator into the container in a specified manner. In other embodiments, the applicator, sensor control device, sensor module, and sharp module can be provided in a single package. The applicator can be used to position the sensor control device on a human body with a sensor in contact with the wearer’s bodily fluid. The embodiments provided herein are improvements to reduce the likelihood that a sensor is improperly inserted or damaged, or elicits an adverse physiological response. Other improvements and advantages are provided as well. The various configurations of these devices are described in detail by way of the embodiments which are only examples.

Furthermore, many embodiments include in vivo analyte sensors structurally configured so that at least a portion of the sensor is, or can be, positioned in the body of a user to obtain information about at least one analyte of the body. It should be noted, however, that the embodiments disclosed herein can be used with in vivo analyte monitoring systems that incorporate in vitro capability, as well as purely in vitro or ex vivo analyte monitoring systems, including systems that are entirely non-invasive.

Furthermore, for each and every embodiment of a method disclosed herein, systems and devices capable of performing each of those embodiments are covered within the scope of the present disclosure. For example, embodiments of sensor control devices are disclosed and these devices can have one or more sensors, analyte monitoring circuits (e.g., an analog circuit), memories (e.g., for storing instructions), power sources, communication circuits, transmitters, receivers, processors and/or controllers (e.g., for executing instructions) that can perform any and all method steps or facilitate the execution of any and all method steps. These sensor control device embodiments can be used and can be capable of use to implement those steps performed by a sensor control device from any and all of the methods described herein.

As mentioned, a number of embodiments of systems, devices, and methods are described herein that provide for the improved assembly and use of sensor insertion devices for use with in vivo analyte monitoring systems. In particular, several embodiments of the present disclosure are designed to improve the method of sensor insertion with respect to in vivo analyte monitoring systems and, in particular, to prevent the premature retraction of an insertion sharp during a sensor insertion process. Some embodiments, for example, include a sensor insertion mechanism with an increased firing velocity and a delayed sharp retraction. In other embodiments, the sharp retraction mechanism can be motion-actuated such that the sharp is not retracted until the user pulls the applicator away from the skin. Consequently, these embodiments can reduce the likelihood of prematurely withdrawing an insertion sharp during a sensor insertion process; decrease the likelihood of improper sensor insertion; and decrease the likelihood of damaging a sensor during the sensor insertion process, to name a few advantages. Several embodiments of the present disclosure also provide for improved insertion sharp modules. In addition, several embodiments of the present disclosure are designed to prevent undesirable axial and/or rotational movement of applicator components during sensor insertion. Accordingly, these embodiments can reduce the likelihood of instability of a positioned sensor, irritation at the insertion site, and damage to surrounding tissue, to name a few advantages. In addition, to mitigate inaccurate sensor readings which can be caused by trauma at the insertion site, several embodiments of the present disclosure can reduce the end-depth penetration of the needle relative to the sensor tip during insertion.

Before describing these aspects of the embodiments in detail, however, it is first desirable to describe examples of devices that can be present within, for example, an in vivo analyte monitoring system, as well as examples of their operation, all of which can be used with the embodiments described herein.

There are various types of in vivo analyte monitoring systems. "Continuous Analyte Monitoring" systems (or "Continuous Glucose Monitoring" systems), for example, can transmit data from a sensor control device to a reader device continuously without prompting, e.g., automatically according to a schedule. "Flash Analyte Monitoring" systems (or "Flash Glucose Monitoring" systems or simply "Flash" systems), as another example, can transfer data from a sensor control device in response to a scan or request for data by a reader device, such as with a Near Field Communication (NFC) or Radio Frequency Identification (RFID) protocol. In vivo analyte monitoring systems can also operate without the need for finger stick calibration.

In vivo analyte monitoring systems can be differentiated from "in vitro" systems that contact a biological sample outside of the body (or "ex vivo") and that typically include a meter device that has a port for receiving an analyte test strip carrying bodily fluid of the user, which can be analyzed to determine the user's blood sugar level.

In vivo monitoring systems can include a sensor that, while positioned in vivo, makes contact with the bodily fluid of the user and senses the analyte levels contained therein. The sensor can be part of the sensor control device that resides on the body of the user and contains the electronics and power supply that enable and control the analyte sensing. The sensor control device, and variations thereof, can also be referred to as a "sensor control unit," an "on-body electronics" device or unit, an "on-body" device or unit, or a "sensor data communication" device or unit, to name a few.

In vivo monitoring systems can also include a device that receives sensed analyte data from the sensor control device and processes and/or displays that sensed analyte data, in any number of forms, to the user. This device, and variations thereof, can be referred to as a "handheld reader device," "reader device" (or simply a "reader"), "handheld electronics" (or simply a "handheld"), a "portable data processing" device or unit, a "data receiver," a "receiver" device or unit (or simply a "receiver"), or a "remote" device or unit, to name a few. Other devices such as personal computers have also been utilized with or incorporated into in vivo and in vitro monitoring systems.

Exemplary In Vivo Analyte Monitoring System

FIG. 1 is a conceptual diagram depicting an example embodiment of an analyte monitoring system 100 that includes a sensor applicator 150, a sensor control device 102, and a reader device 120. Here, sensor applicator 150 can be used to deliver sensor control device 102 to a monitoring location on a user's skin where a sensor 104 is maintained in position for a period of time by an adhesive patch 105. Sensor control device 102 is further described in FIGS. 2B and 2C, and can communicate with reader device 120 via a communication path 140 using a wired or wireless technique. Example wireless protocols include Bluetooth, Bluetooth Low Energy (BLE, BTLE, Bluetooth SMART, etc.), Near Field Communication (NFC) and others. Users can monitor applications installed in memory on reader device 120 using screen 122 and input 121 and the device battery can be recharged using power port 123. More detail about reader device 120 is set forth with respect to FIG. 2A below. Reader device 120 can communicate with local computer system 170 via a communication path 141 using a wired or wireless technique. Local computer system 170 can include one or more of a laptop, desktop, tablet, phablet, smartphone, set-top box, video game console, or other computing device and wireless communication can include any of a number of applicable wireless networking protocols including Bluetooth, Bluetooth Low Energy (BTLE), Wi-Fi or others. Local computer system 170 can communicate via communications path 143 with a network 190 similar to how reader device 120 can communicate via a communications path 142 with network 190, by wired or wireless technique as described previously. Network 190 can be any of a number of networks, such as private networks and public networks, local area or wide area networks, and so forth. A trusted computer system 180 can include a server and can provide authentication services and secured data storage and can communicate via communications path 144 with network 190 by wired or wireless technique.

Exemplary Reader Device

Figure 2A:
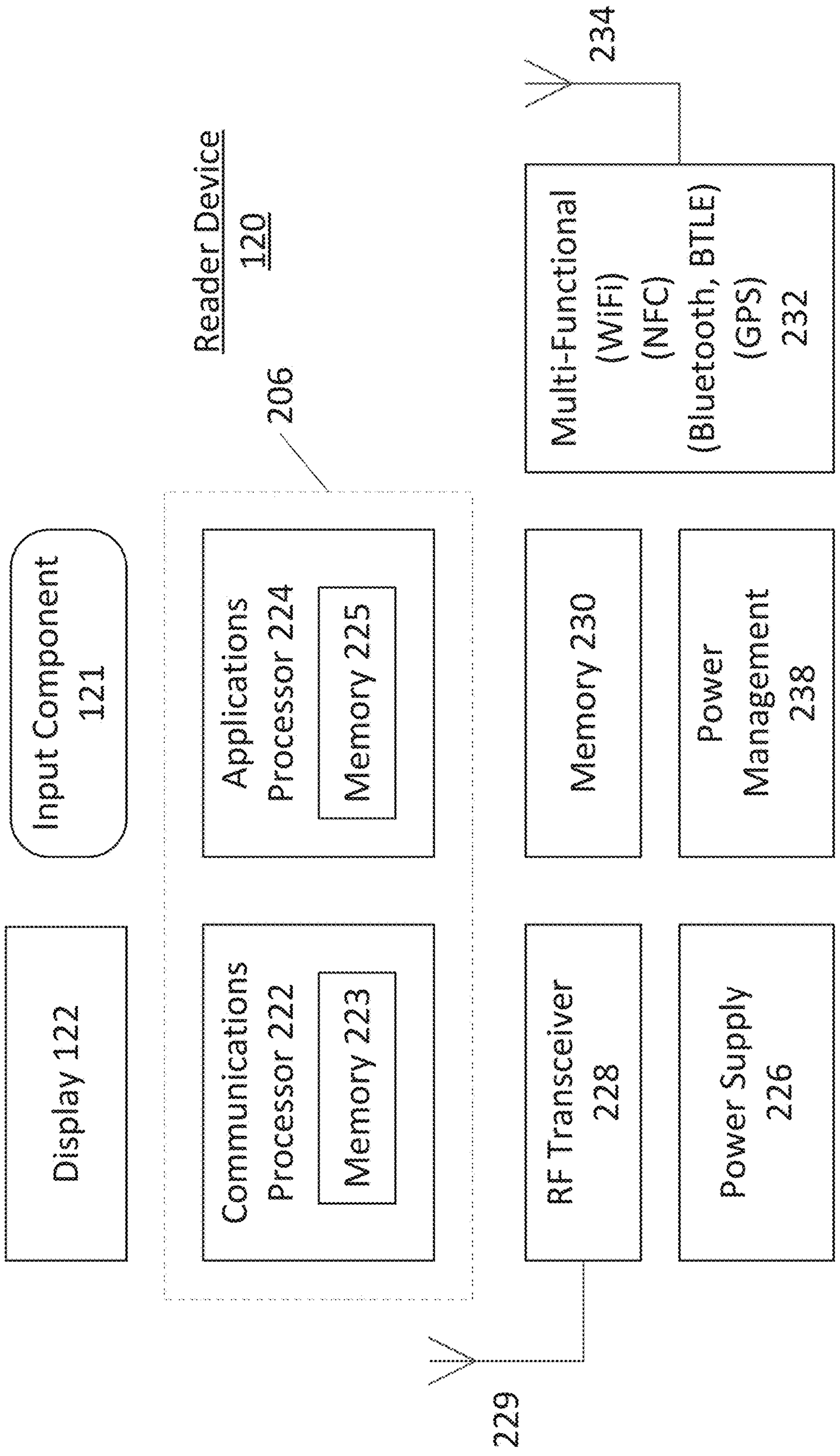
FIG. 2A is a block diagram depicting an example embodiment of a reader device.

FIG. 2A is a block diagram depicting an example embodiment of a reader device configured as a smartphone. Here, reader device 120 can include a display 122, input component 121, and a processing core 206 including a communications processor 222 coupled with memory 223 and an applications processor 224 coupled with memory 225. Also included can be separate memory 230, RF transceiver 228 with antenna 229, and power supply 226 with power management module 238. Further included can be a multi-functional transceiver 232 which can communicate over Wi-Fi, NFC, Bluetooth, BTLE, and GPS with an antenna 234. As understood by one of skill in the art, these components are electrically and communicatively coupled in a manner to make a functional device.

Exemplary Sensor Control Devices

Figure 2B:
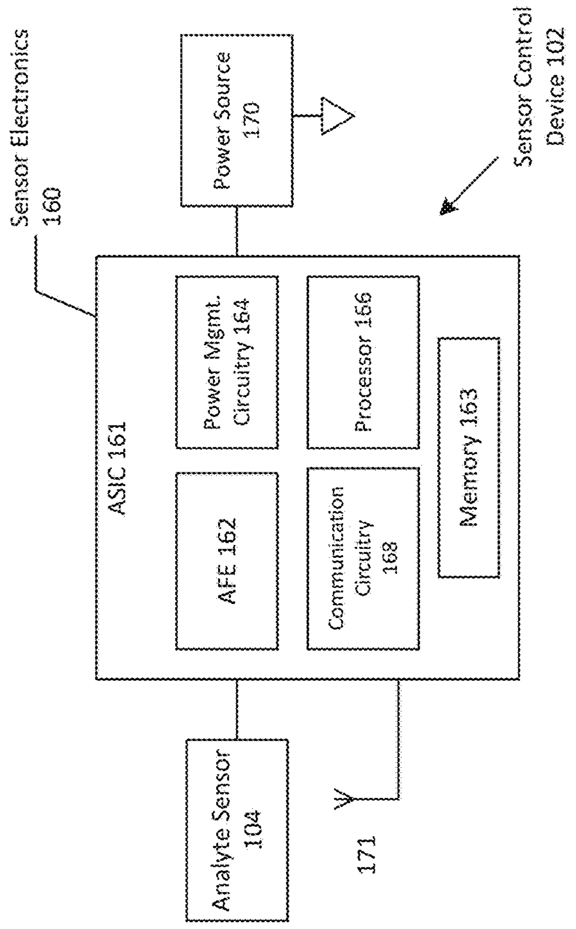
FIGS. 2B and 2C are block diagrams depicting example embodiments of sensor control devices.
Figure 2C:
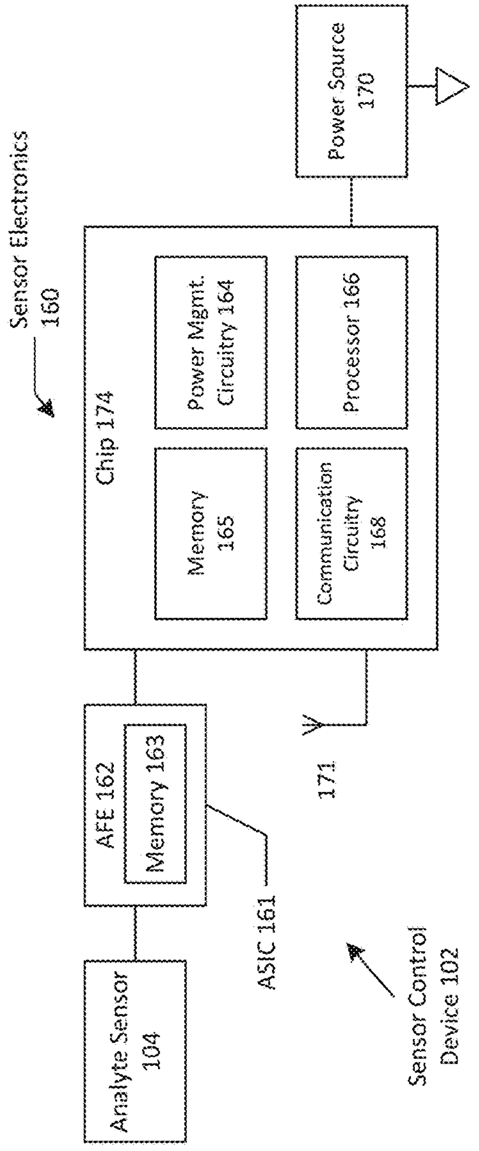

FIGS. 2B and 2C are block diagrams depicting example embodiments of sensor control device 102 having analyte sensor 104 and sensor electronics 160 (including analyte monitoring circuitry) that can have the majority of the processing capability for rendering end-result data suitable for display to the user. In FIG. 2B, a single semiconductor chip 161 is depicted that can be a custom application specific integrated circuit (ASIC). Shown within ASIC 161 are certain high-level functional units, including an analog front end (AFE) 162, power management (or control) circuitry 164, processor 166, and communication circuitry 168 (which can be implemented as a transmitter, receiver, transceiver, passive circuit, or otherwise according to the communication protocol). In this embodiment, both AFE 162 and processor 166 are used as analyte monitoring circuitry, but in other embodiments either circuit can perform the analyte monitoring function. Processor 166 can include one or more processors, microprocessors, controllers, and/or microcontrollers, each of which can be a discrete chip or distributed amongst (and a portion of) a number of different chips.

A memory 163 is also included within ASIC 161 and can be shared by the various functional units present within ASIC 161, or can be distributed amongst two or more of them. Memory 163 can also be a separate chip. Memory 163 can be volatile and/or non-volatile memory. In this embodiment, ASIC 161 is coupled with power source 170, which can be a coin cell battery, or the like. AFE 162 interfaces with in vivo analyte sensor 104 and receives measurement data therefrom and outputs the data to processor 166 in digital form, which in turn processes the data to arrive at the end-result glucose discrete and trend values, etc. This data can then be provided to communication circuitry 168 for sending, by way of antenna 171, to reader device 120 (not shown), for example, where minimal further processing is needed by the resident software application to display the data.

FIG. 2C is similar to FIG. 2B but instead includes two discrete semiconductor chips 162 and 174, which can be packaged together or separately. Here, AFE 162 is resident on ASIC 161. Processor 166 is integrated with power management circuitry 164 and communication circuitry 168 on chip 174. AFE 162 includes memory 163 and chip 174 includes memory 165, which can be isolated or distributed within. In one example embodiment, AFE 162 is combined with power management circuitry 164 and processor 166 on one chip, while communication circuitry 168 is on a separate chip. In another example embodiment, both AFE 162 and communication circuitry 168 are on one chip, and processor 166 and power management circuitry 164 are on another chip. It should be noted that other chip combinations are possible, including three or more chips, each bearing responsibility for the separate functions described, or sharing one or more functions for fail-safe redundancy.

Exemplary Assembly Processes for Sensor Control Devices

The components of sensor control device 102 can be acquired by a user in multiple packages requiring final assembly by the user before delivery to an appropriate user location. FIGS. 3A-3D depict an example embodiment of an assembly process for sensor control device 102 by a user, including preparation of separate components before coupling the components in order to ready the sensor for delivery. FIGS. 3E-3F depict an example embodiment of delivery of sensor control device 102 to an appropriate user location by selecting the appropriate delivery location and applying device 102 to the location.

Figure 3A:
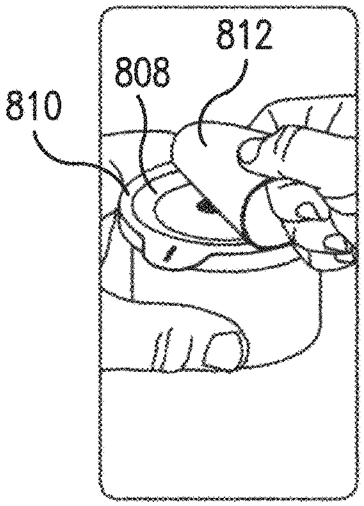
FIG. 3A is a proximal perspective view depicting an example embodiment of a user preparing a tray for an assembly.

FIG. 3A is a proximal perspective view depicting an example embodiment of a user preparing a container 810, configured here as a tray (although other packages can be used), for an assembly process. The user can accomplish this preparation by removing lid 812 from tray 810 to expose platform 808, for instance by peeling a non-adhered portion of lid 812 away from tray 810 such that adhered portions of lid 812 are removed. Removal of lid 812 can be appropriate in various embodiments so long as platform 808 is adequately exposed within tray 810. Lid 812 can then be placed aside.

Figure 3B:
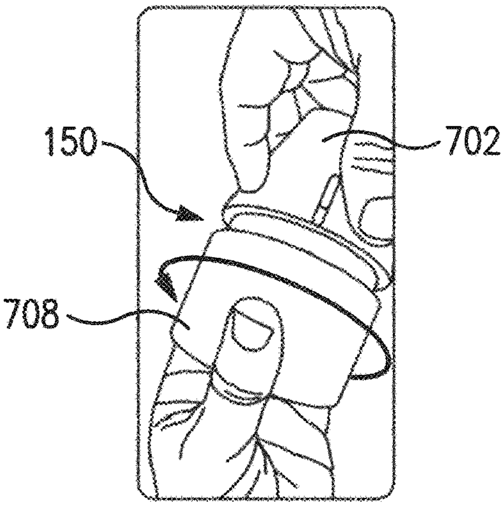
FIG. 3B is a side view depicting an example embodiment of a user preparing an applicator device for an assembly.
Figure 3C:
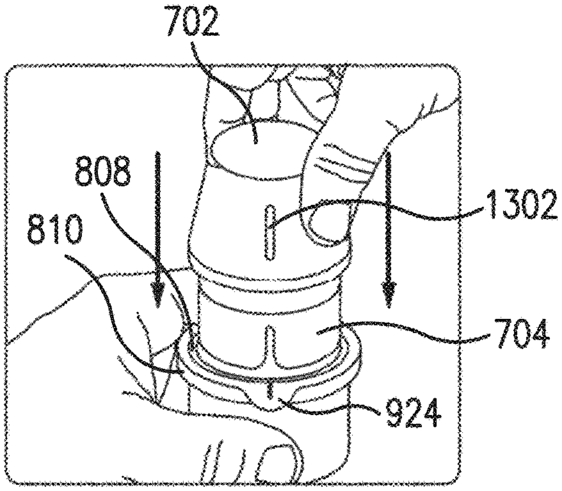
FIG. 3C is a proximal perspective view depicting an example embodiment of a user inserting an applicator device into a tray during an assembly.

FIG. 3B is a side view depicting an example embodiment of a user preparing an applicator device 150 for assembly. Applicator device 150 can be provided in a sterile package sealed by a cap 708. Preparation of applicator device 150 can include uncoupling housing 702 from cap 708 to expose sheath 704 (FIG. 3C). This can be accomplished by unscrewing (or otherwise uncoupling) cap 708 from housing 702. Cap 708 can then be placed aside.

FIG. 3C is a proximal perspective view depicting an example embodiment of a user inserting an applicator device 150 into a tray 810 during an assembly. Initially, the user can insert sheath 704 into platform 808 inside tray 810 after aligning housing orienting feature 1302 (or slot or recess) and tray orienting feature 924 (an abutment or detent). Inserting sheath 704 into platform 808 temporarily unlocks sheath 704 relative to housing 702 and also temporarily unlocks platform 808 relative to tray 810. At this stage, removal of applicator device 150 from tray 810 will result in the same state prior to initial insertion of applicator device 150 into tray 810 (i.e., the process can be reversed or aborted at this point and then repeated without consequence).

Sheath 704 can maintain position within platform 808 with respect to housing 702 while housing 702 is distally advanced, coupling with platform 808 to distally advance platform 808 with respect to tray 810. This step unlocks and collapses platform 808 within tray 810. Sheath 704 can contact and disengage locking features (not shown) within tray 810 that unlock sheath 704 with respect to housing 702 and prevent sheath 704 from moving (relatively) while housing 702 continues to distally advance platform 808. At the end of advancement of housing 702 and platform 808, sheath 704 is permanently unlocked relative to housing 702. A sharp and sensor (not shown) within tray 810 can be coupled with an electronics housing (not shown) within housing 702 at the end of the distal advancement of housing 702. Operation and interaction of the applicator device 150 and tray 810 are further described below.

Figure 3D:
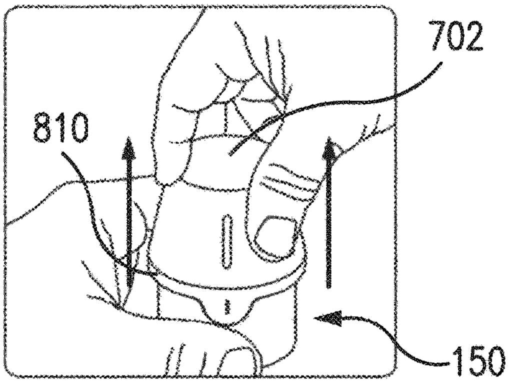
FIG. 3D is a proximal perspective view depicting an example embodiment of a user removing an applicator device from a tray during an assembly.
Figure 3E:
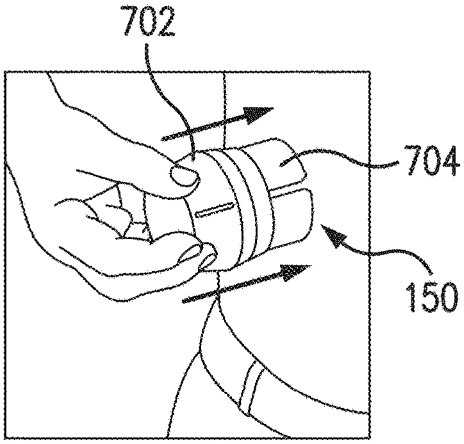
FIG. 3E is a proximal perspective view depicting an example embodiment of a patient applying a sensor using an applicator device.
Figure 3F:
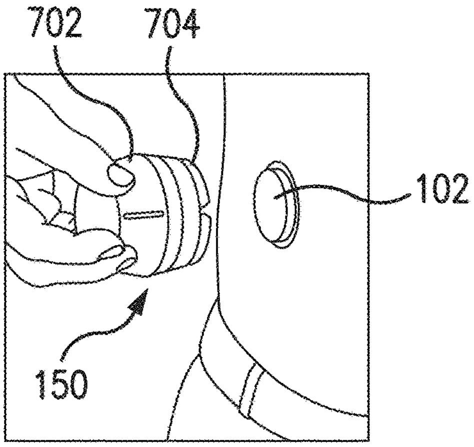
FIG. 3F is a proximal perspective view depicting an example embodiment of a patient with an applied sensor and a used applicator device.

FIG. 3D is a proximal perspective view depicting an example embodiment of a user removing an applicator device 150 from a tray 810 during an assembly. A user can remove applicator 150 from tray 810 by proximally advancing housing 702 with respect to tray 810 or other motions having the same end effect of uncoupling applicator 150 and tray 810. The applicator device 150 is removed with sensor control device 102 (not shown) fully assembled (sharp, sensor, electronics) therein and positioned for delivery.

FIG. 3E is a proximal perspective view depicting an example embodiment of a patient applying sensor control device 102 using applicator device 150 to a target area of skin, for instance, on an abdomen or other appropriate location. Advancing housing 702 distally collapses sheath 704 within housing 702 and applies the sensor to the target location such that an adhesive layer on the bottom side of sensor control device 102 adheres to the skin. The sharp is automatically retracted when housing 702 is fully advanced, while the sensor (not shown) is left in position to measure analyte levels.

FIG. 3F is a proximal perspective view depicting an example embodiment of a patient with sensor control device 102 in an applied position. The user can then remove applicator 150 from the application site.

System 100, described with respect to FIGS. 3A-3F and elsewhere herein, can provide a reduced or eliminated chance of accidental breakage, permanent deformation, or incorrect assembly of applicator components compared to prior art systems. Since applicator housing 702 directly engages platform 808 while sheath 704 unlocks, rather than indirect engagement via sheath 704, relative angularity between sheath 704 and housing 702 will not result in breakage or permanent deformation of the arms or other components. The potential for relatively high forces (such as in conventional devices) during assembly will be reduced, which in turn reduces the chance of unsuccessful user assembly.

Exemplary Sensor Applicator Devices

Figure 4A:
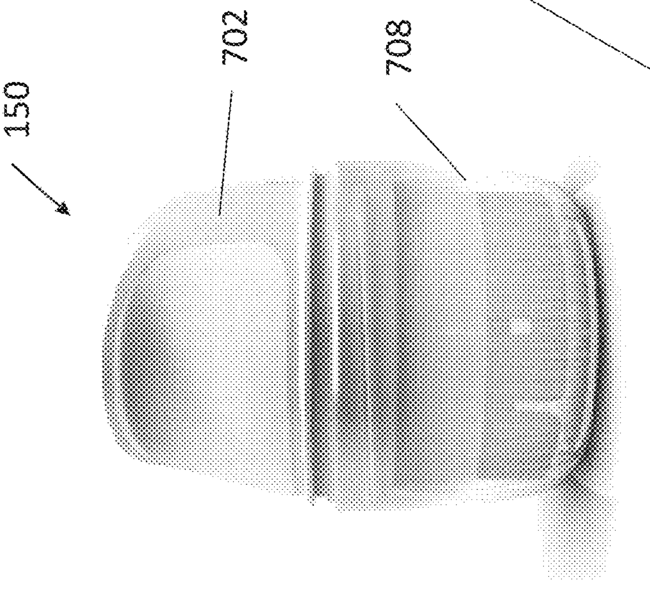
FIG. 4A is a side view depicting an example embodiment of an applicator device coupled with a cap.
Figure 4B:
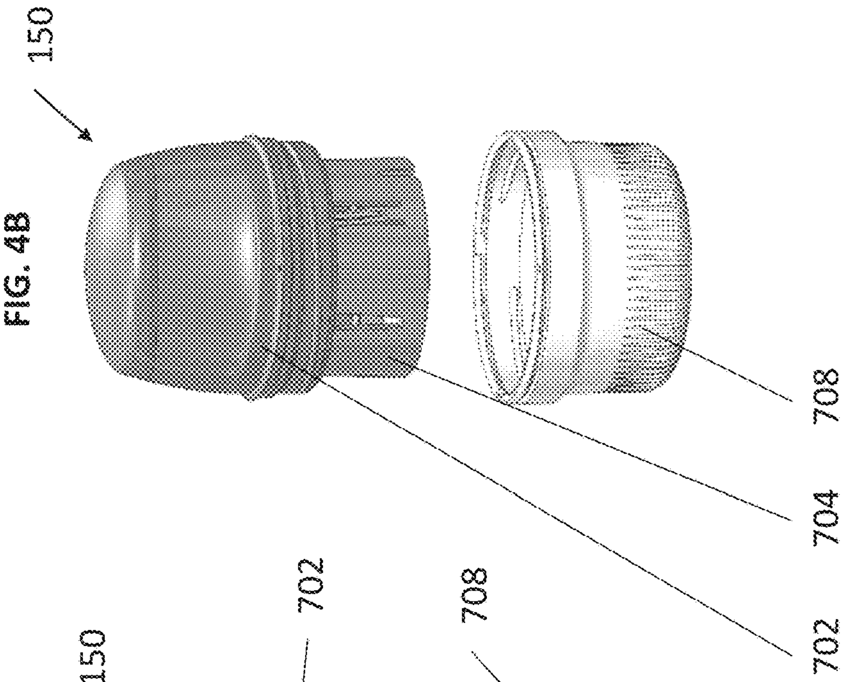
FIG. 4B is a side perspective view depicting an example embodiment of an applicator device and cap decoupled.
Figure 4C:
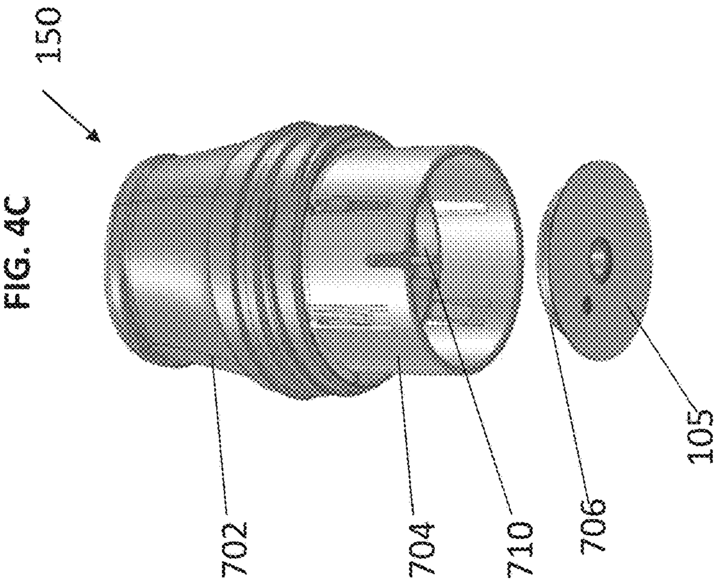
FIG. 4C is a perspective view depicting an example embodiment of a distal end of an applicator device and electronics housing.

FIG. 4A is a side view depicting an example embodiment of an applicator device 150 coupled with screw cap 708. This is an example of how applicator 150 is shipped to and received by a user, prior to assembly by the user with a sensor. FIG. 4B is a side perspective view depicting applicator 150 and cap 708 after being decoupled. FIG. 4C is a perspective view depicting an example embodiment of a distal end of an applicator device 150 with electronics housing 706 and adhesive patch 105 removed from the position they would have retained within sensor carrier 710 of sheath 704, when cap 708 is in place.

Figure 4E:
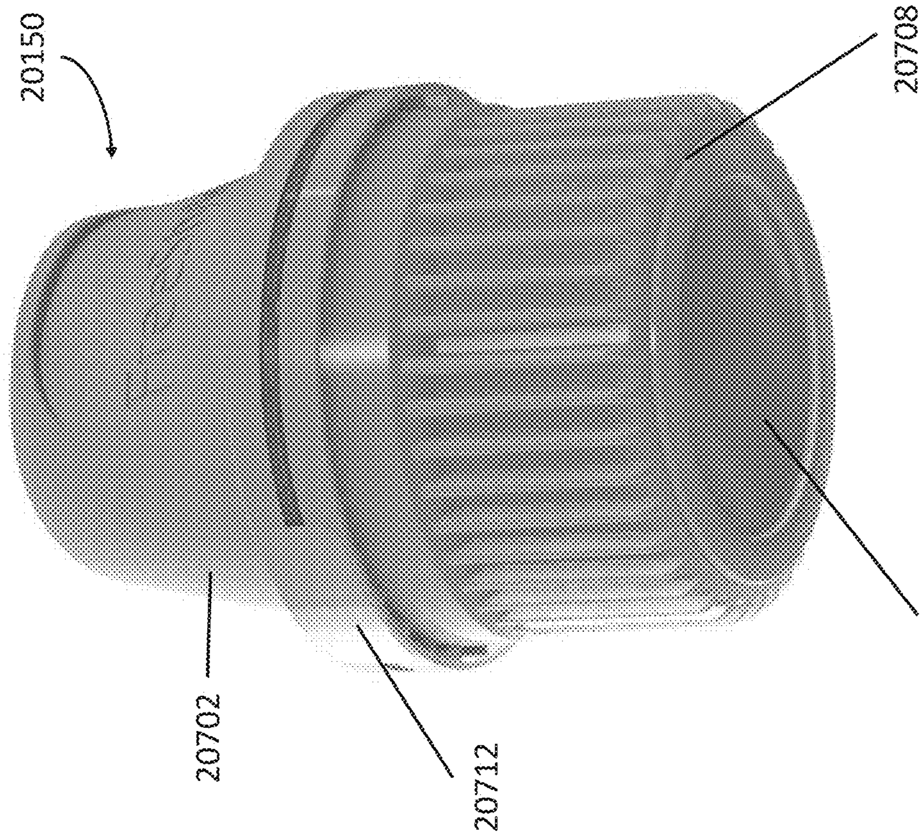
FIG. 4E is a bottom perspective view of the applicator device of FIG. 4D.
Figure 4D:
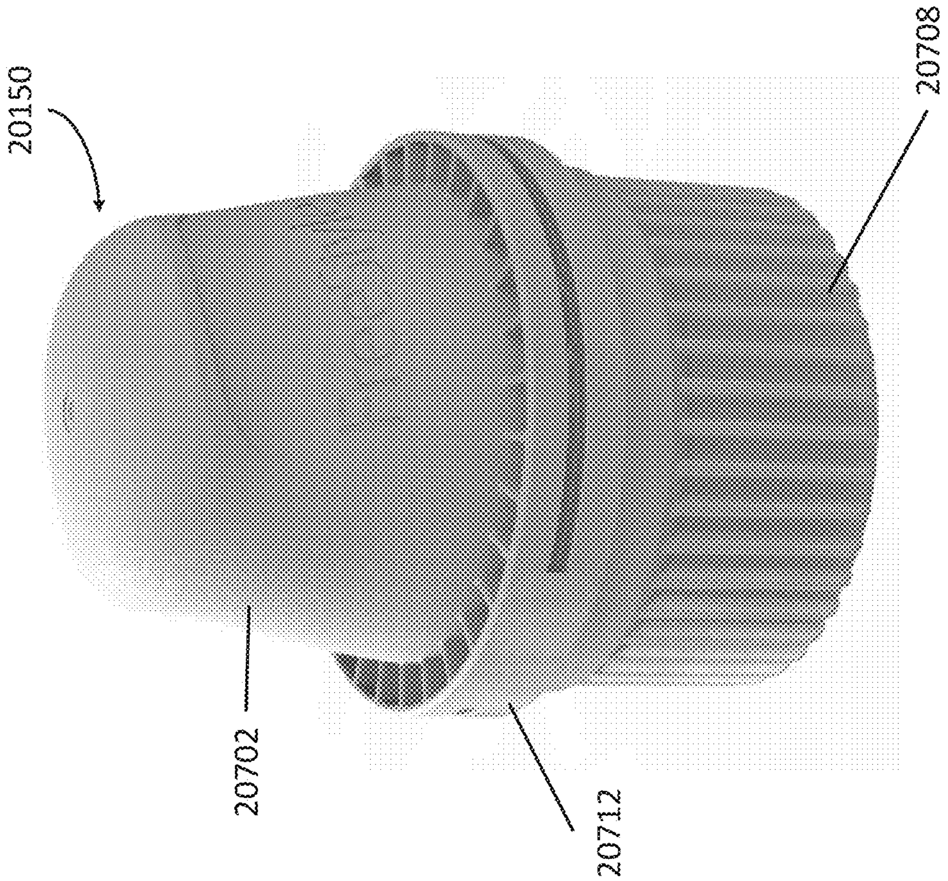
FIG. 4D is a top perspective view of an exemplary applicator device in accordance with the disclosed subject matter.
Figure 4F:
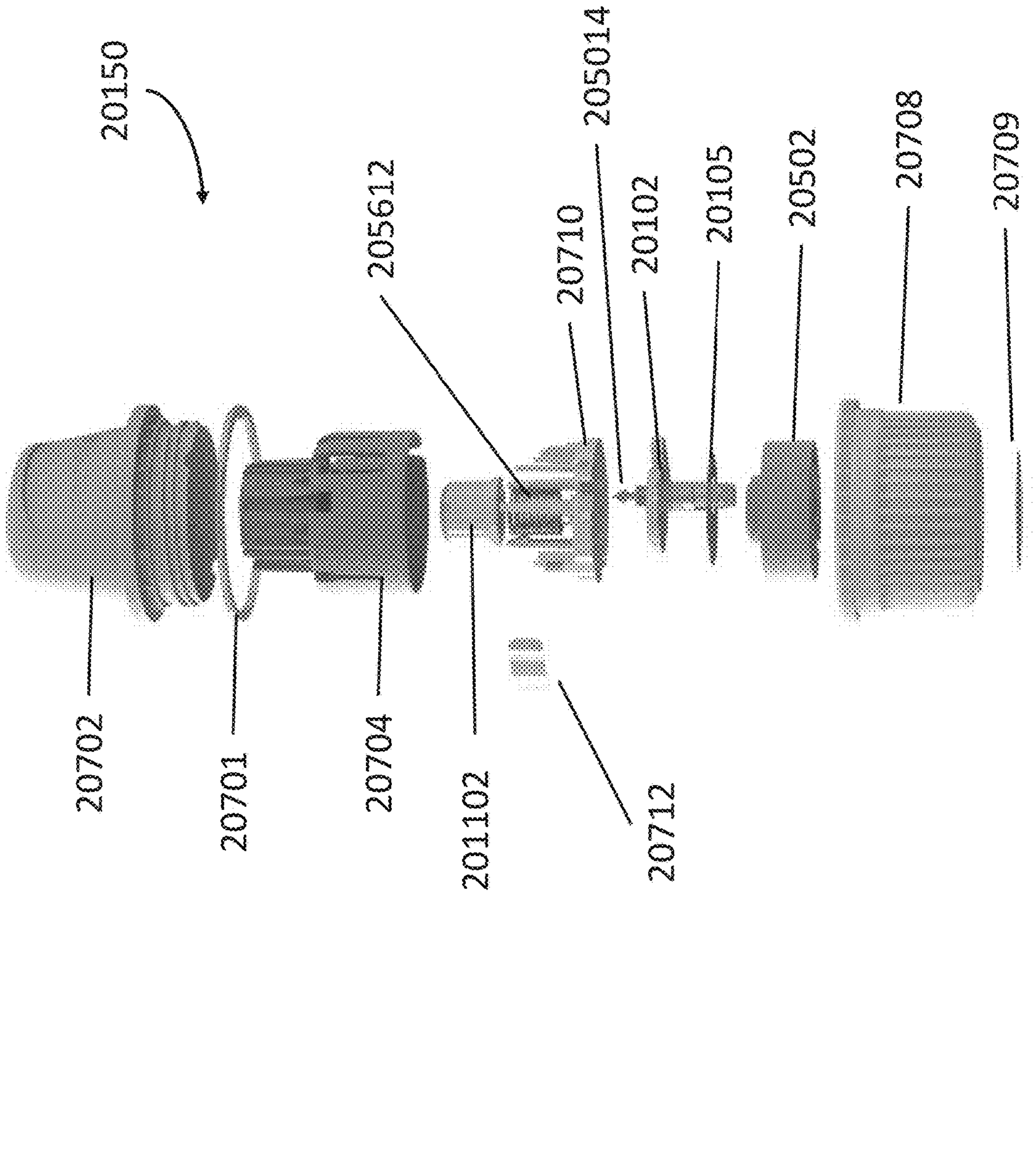
FIG. 4F is an exploded view of the applicator device of FIG. 4D.
Figure 4G:
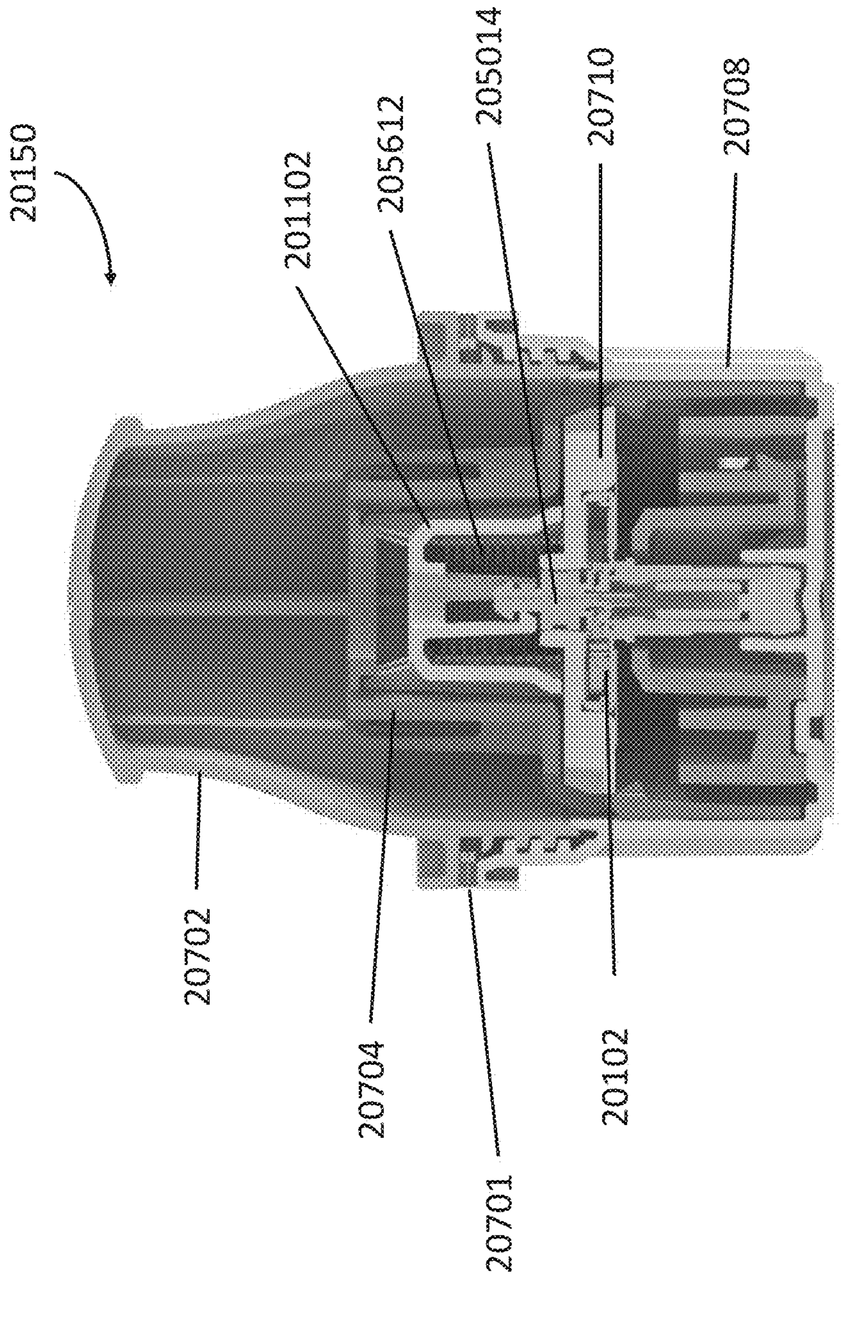
FIG. 4G is a side cutaway view of the applicator device of FIG. 4D.

Referring to FIG. 4D-G for purpose of illustration and not limitation, the applicator device 20150 can be provided to a user as a single integrated assembly. FIGS. 4D and 4E provide perspective top and bottom views, respectively, of the applicator device 20150, FIG. 4F provides an exploded view of the applicator device 20150 and FIG. 4G provides a side cut-away view. The perspective views illustrate how applicator 20150 is shipped to and received by a user. The exploded and cut-away views illustrate the components of the applicator device 20150. The applicator device 20150 can include a housing 20702, gasket 20701, sheath 20704, sharp carrier 201102, spring 205612, sensor carrier 20710 (also referred to as a "puck carrier"), sharp hub 205014, sensor control device (also referred to as a "puck") 20102, adhesive patch 20105, desiccant 20502, cap 20708, serial label 20709, and tamper evidence feature 20712. As received by a user, only the housing 20702, cap 20708, tamper evidence feature 20712, and label 20709 are visible. The tamper evidence feature 20712 can be, for example, a sticker coupled to each of the housing 20702 and the cap 20708, and tamper evidence feature 20712 can be damaged, for example, irreparably, by uncoupling housing 20702 and cap 20708, thereby indicating to a user that the housing 20702 and cap 20708 have been previously uncoupled. These features are described in greater detail below.

Exemplary Tray and Sensor Module Assembly

Figure 5:
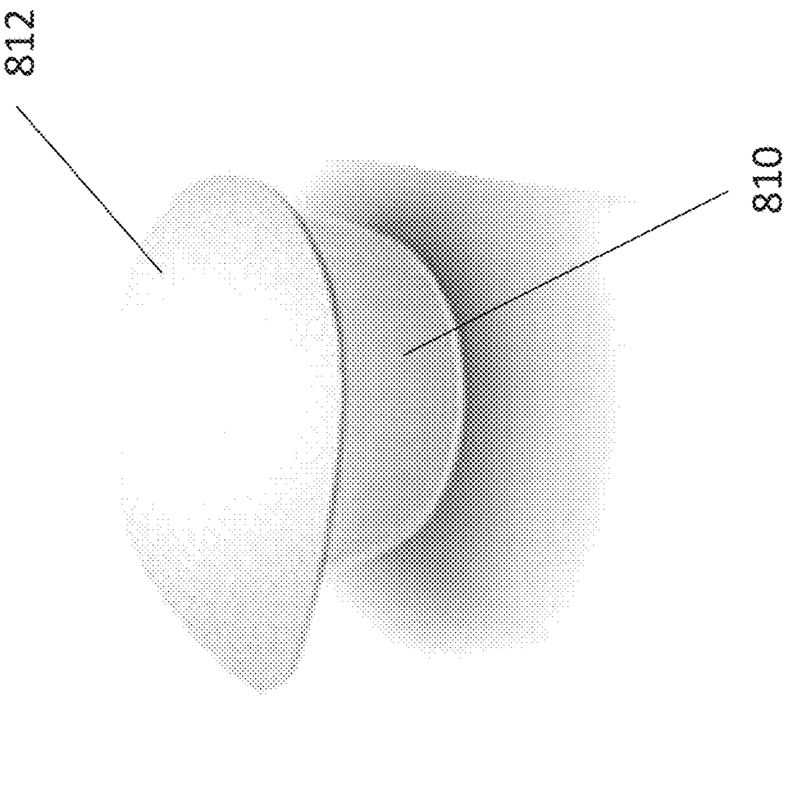
FIG. 5 is a proximal perspective view depicting an example embodiment of a tray with sterilization lid coupled.

FIG. 5 is a proximal perspective view depicting an example embodiment of a tray 810 with sterilization lid 812 removably coupled thereto, which may be representative of how the package is shipped to and received by a user prior to assembly.

Figure 6A:
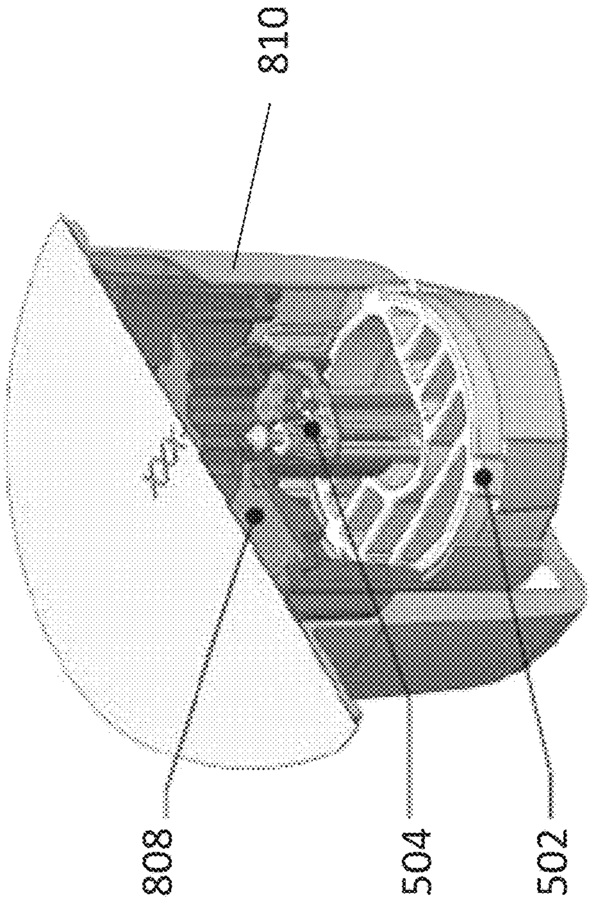
FIG. 6A is a proximal perspective cutaway view depicting an example embodiment of a tray with sensor delivery components.

FIG. 6A is a proximal perspective cutaway view depicting sensor delivery components within tray 810. Platform 808 is slidably coupled within tray 810. Desiccant 502 is stationary with respect to tray 810. Sensor module 504 is mounted within tray 810.

Figure 6B:
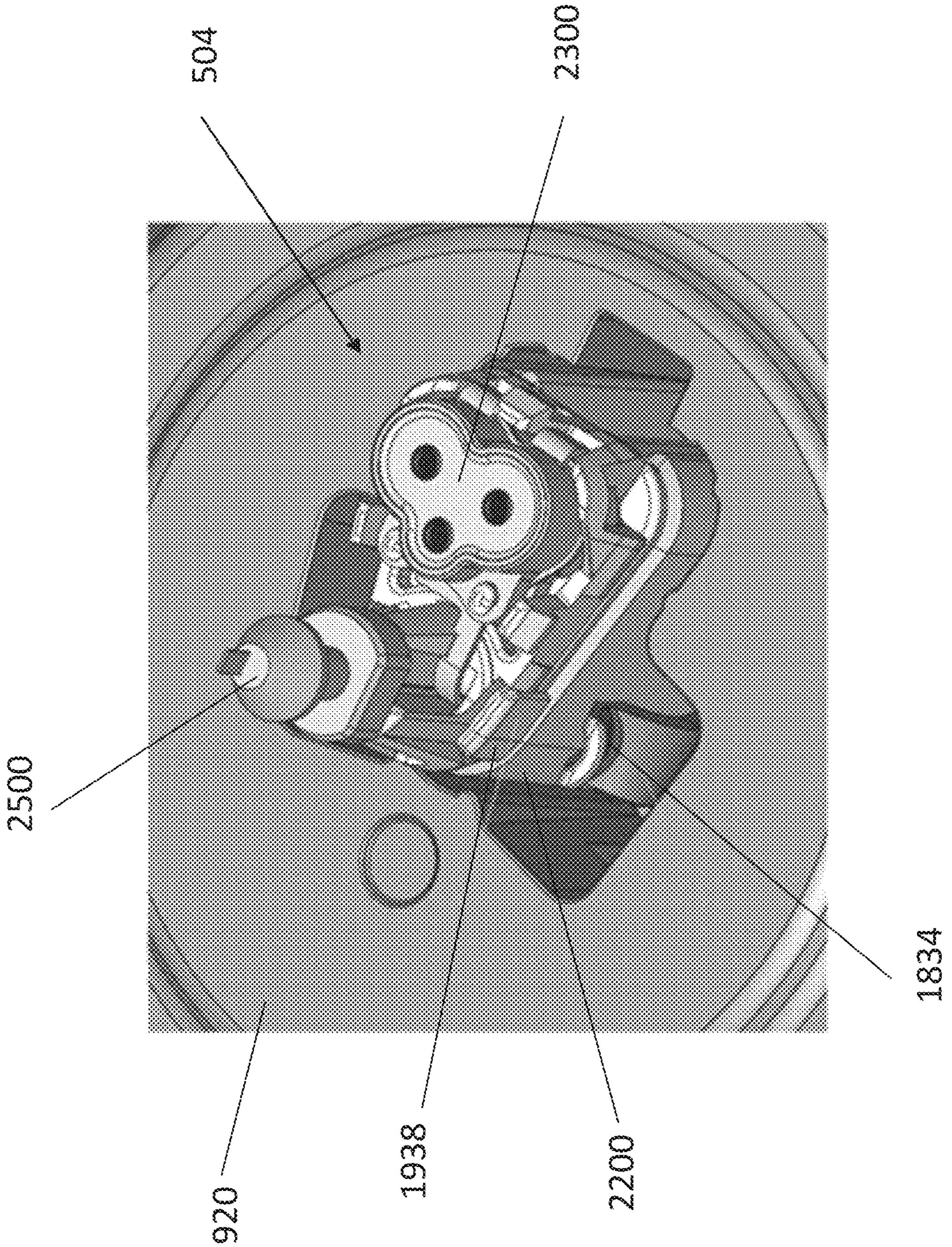
FIG. 6B is a proximal perspective view depicting sensor delivery components.

FIG. 6B is a proximal perspective view depicting sensor module 504 in greater detail. Here, retention arm extensions 1834 of platform 808 releasably secure sensor module 504 in position. Module 2200 is coupled with connector 2300, sharp module 2500 and sensor (not shown) such that during assembly they can be removed together as sensor module 504.

Exemplary Applicator Housings and Caps

Figure 7A:
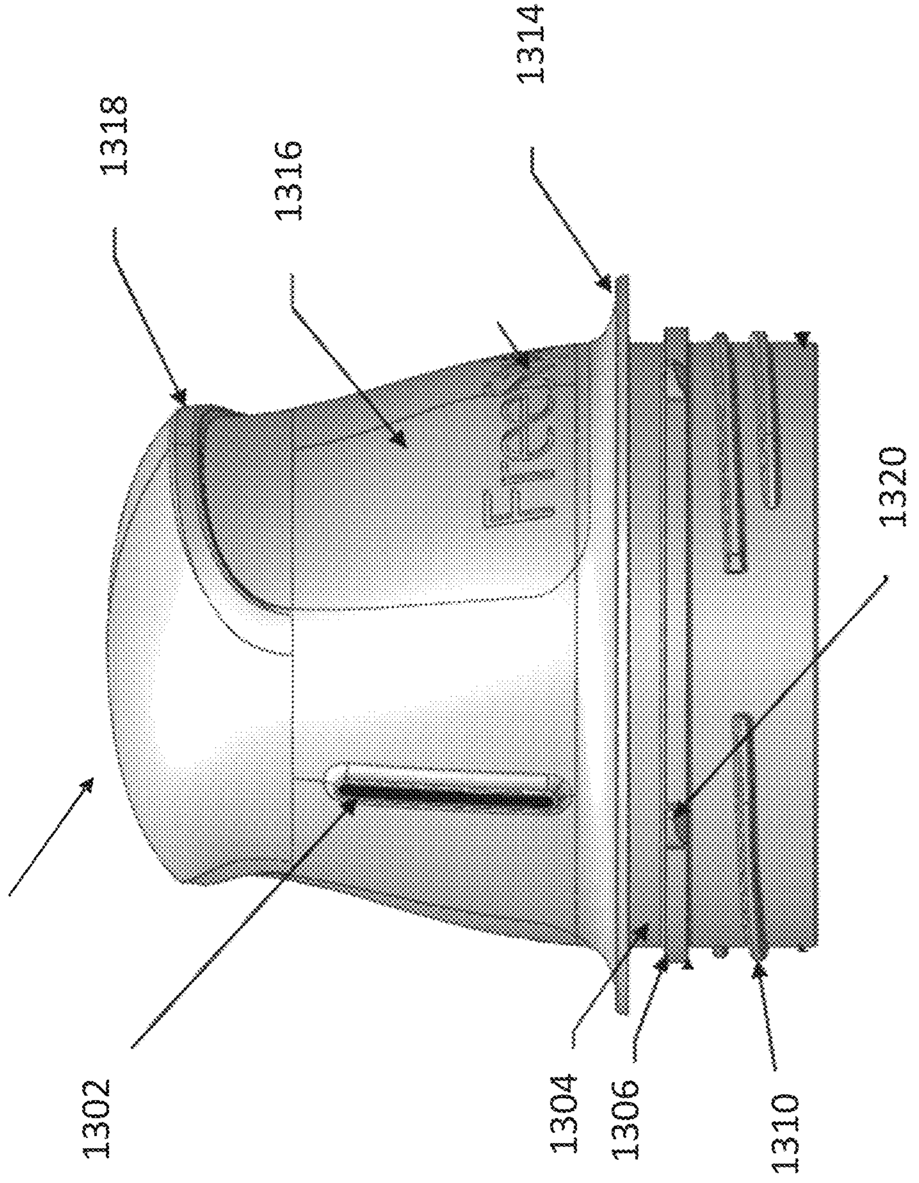
FIG. 7A is side view depicting an example embodiment of a housing.

FIG. 7A is side view depicting an example embodiment of the applicator housing 702 that can include an internal cavity with support structures for applicator function. A user can push housing 702 in a distal direction to activate the applicator assembly process and then also to cause delivery of sensor control device 102, after which the cavity of housing 702 can act as a receptacle for a sharp. In the example embodiment, various features are shown including housing orienting feature 1302 for orienting the device during assembly and use. Tamper ring groove 1304 can be a recess located around an outer circumference of housing 702, distal to a tamper ring protector 1314 and proximal to a tamper ring retainer 1306. Tamper ring groove 1304 can retain a tamper ring so users can identify whether the device has been tampered with or otherwise used. Housing threads 1310 can secure housing 702 to complimentary threads on cap 708 (FIGS. 4A and 4B) by aligning with complimentary cap threads and rotating in a clockwise or counterclockwise direction. A side grip zone 1316 of housing 702 can provide an exterior surface location where a user can grip housing 702 in order to use it. Grip overhang 1318 is a slightly raised ridge with respect to side grip zone 1316 which can aid in ease of removal of housing 702 from cap 708. A shark tooth 1320 can be a raised section with a flat side located on a clockwise edge to shear off a tamper ring (not shown), and hold tamper ring in place after a user has unscrewed cap 708 and housing 702. In the example embodiment four shark teeth 1320 are used, although more or less can be used as desired.

Figure 7B:
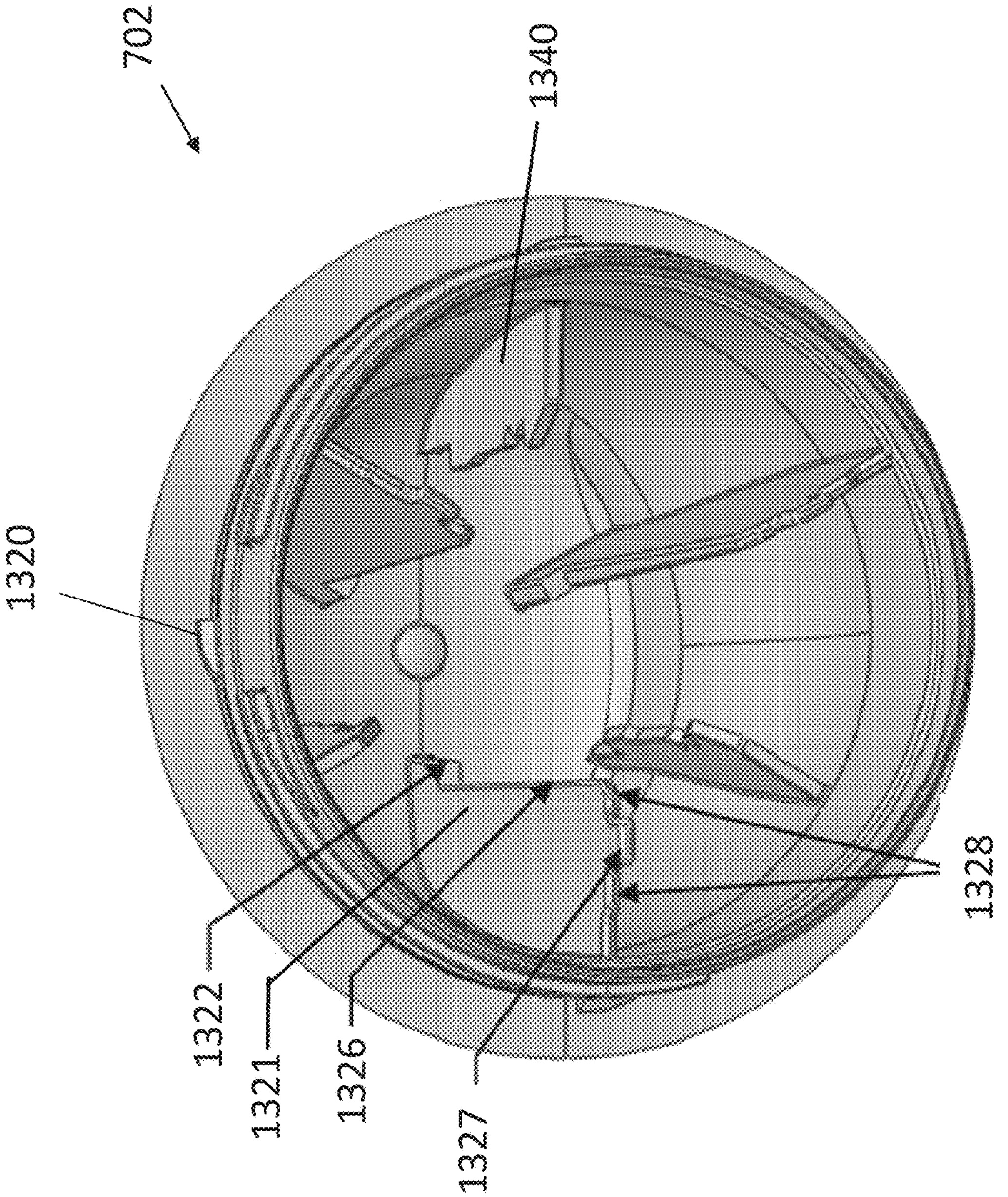
FIG. 7B is a perspective view depicting an example embodiment of a distal end of a housing.

FIG. 7B is a perspective view depicting a distal end of housing 702. Here, three housing guide structures (or "guide ribs") 1321 are located at 120 degree angles with respect to each other and at 60 degree angles with respect to locking structures (or "locking ribs") 1340, of which there are also three at 120 degree angles with respect to each other. Other angular orientations, either symmetric or asymmetric, can be used, as well as any number of one or more structures 1321 and 1340. Here, each structure 1321 and 1340 is configured as a planar rib, although other shapes can be used. Each guide rib 1321 includes a guide edge (also called a "sheath guide rail") 1326 that can pass along a surface of sheath 704 (e.g., guide rail 1418 described with respect to FIG. 8A). An insertion hard stop 1322 can be a flat, distally facing surface of housing guide rib 1321 located near a proximal end of housing guide rib 1321. Insertion hard stop 1322 provides a surface for a sensor carrier travel limiter face 1420 of a sheath 704 (FIG. 8B) to abut during use, preventing sensor carrier travel limiter face 1420 from moving any further in a proximal direction. A carrier interface post 1327 passes through an aperture 1510 (FIG. 9A) of sensor carrier 710 during an assembly. A sensor carrier interface 1328 can be a rounded, distally facing surface of housing guide ribs 1321 which interfaces with sensor carrier 710.

Figure 7C:
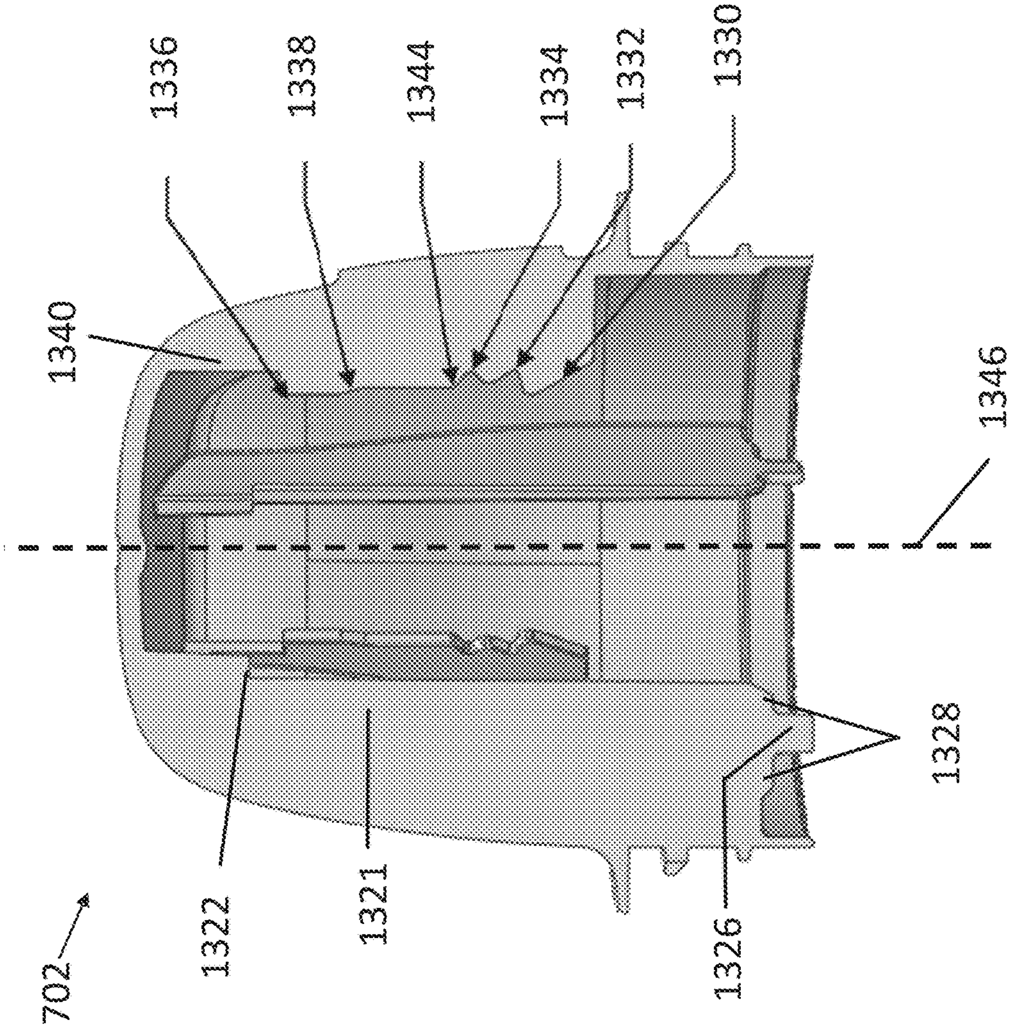
FIG. 7C is a side cross-sectional view depicting an example embodiment of a housing.

FIG. 7C is a side cross-section depicting an example embodiment of a housing. In the example embodiment, side cross-sectional profiles of housing guide rib 1321 and locking rib 1340 are shown. Locking rib 1340 includes sheath snap lead-in feature 1330 near a distal end of locking rib 1340 which flares outward from central axis 1346 of housing 702 distally. Each sheath snap lead-in feature 1330 causes detent snap round 1404 of detent snap 1402 of sheath 704 as shown in FIG. 8C to bend inward toward central axis 1346 as sheath 704 moves towards the proximal end of housing 702. Once past a distal point of sheath snap lead-in feature 1330, detent snap 1402 of sheath 704 is locked into place in locked groove 1332. As such, detent snap 1402 cannot be easily moved in a distal direction due to a surface with a near perpendicular plane to central axis 1346, shown as detent snap flat 1406 in FIG. 8C.

As housing 702 moves further in a distal direction toward the skin surface, and as sheath 704 advances toward the proximal end of housing 702, detent snaps 1402 shift into the unlocked grooves 1334, and applicator 150 is in an "armed" position, ready for use. When the user further applies force to the proximal end of housing 702, while sheath 704 is pressed against the skin, detent snap 1402 passes over firing detent 1344. This begins a firing sequence (as described, for example, with respect to FIGS. 12A-12D) due to release of stored energy in the deflected detent snaps 1402, which travel in a proximal direction relative to the skin surface, toward sheath stopping ramp 1338 which is slightly flared outward with respect to central axis 1346 and slows sheath 704 movement during the firing sequence. The next groove encountered by detent snap 1402 after unlocked groove 1334 is final lockout groove 1336 which detent snap 1402 enters at the end of the stroke or pushing sequence performed by the user. Final lockout recess 1336 can be a proximally-facing surface that is perpendicular to central axis 1346 which, after detent snap 1402 passes, engages a detent snap flat 1406 and prevents reuse of the device by securely holding sheath 704 in place with respect to housing 702. Insertion hard stop 1322 of housing guide rib 1321 prevents sheath 704 from advancing proximally with respect to housing 702 by engaging sensor carrier travel limiter face 1420.

FIGS. 7D and 7E are close-up side views of an example embodiment of locking rib 1340 of applicator housing 702, as detent snap 1402 of sheath 704 moves toward the proximal end of housing 702. FIG. 7D shows sheath 704 in a "locked" state, in which detent round 1404 of detent snap 1402 has already passed over sheath snap lead-in feature 1330 and is positioned in locked groove 1332 of locking rib 1340. As force is applied to the proximal end of housing 702, detent round 1404 is advanced proximally into unlocked groove 1334, placing applicator 150 into an "armed" position. When force is further applied to the proximal end of housing 702, applicator 150 is "fired," as detent round 1404 is advanced proximally from the unlocked groove 1334 and passes over firing detent 1344. Thereafter, sheath 704 is further advanced proximally such that detent round 1404 is slidably advanced over firing surface 1337, as shown in FIG. 7E. In this embodiment, firing surface 1337 is substantially parallel to central axis 1346. As sheath 704 continues to advance proximally, detent round 1404 reaches sheath stopping ramp 1338 which slows the movement of sheath 704. Upon detent round 1404 reaching final lockout recess 1336, detent snap flat 1406 (not shown) is engaged and securely holds sheath 704 in place with respect to housing 702.

Figure 7F:
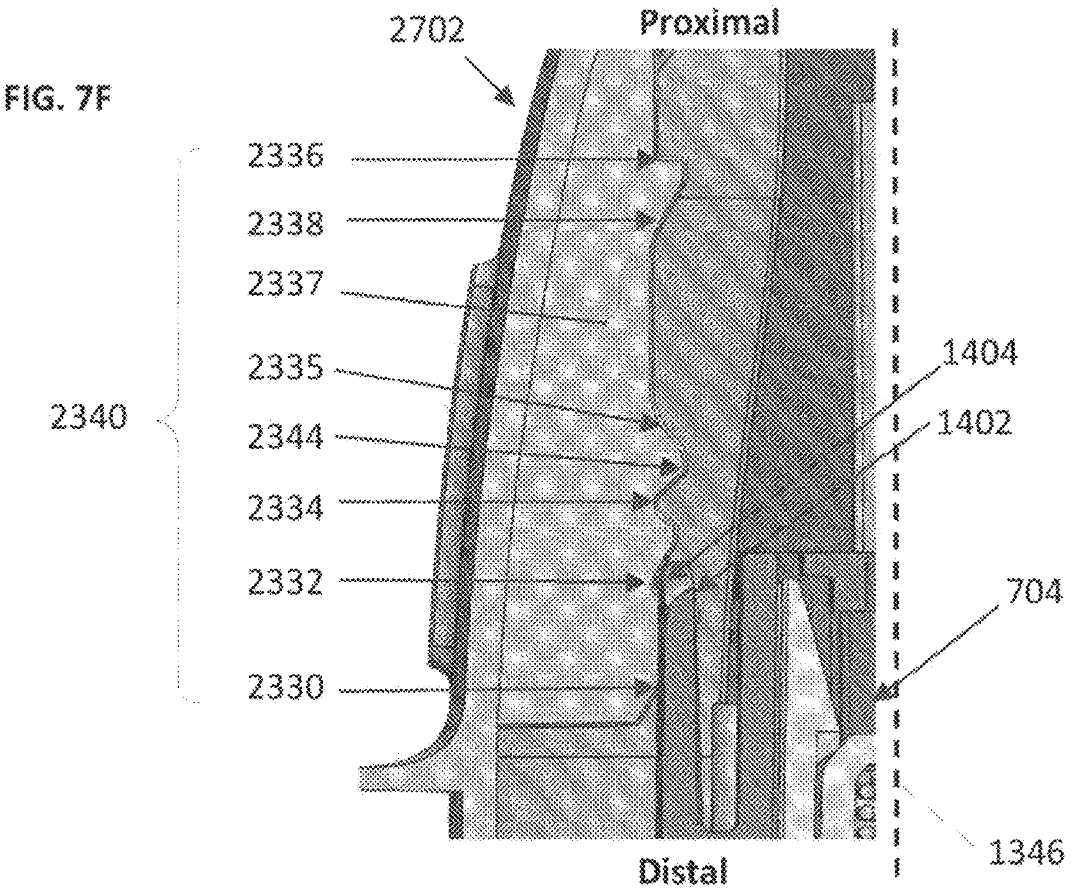
FIGS. 7F and 7G are side cross-sectional views depicting a locking rib portion of another example embodiment of a housing and a portion of a sheath.
Figure 7G:
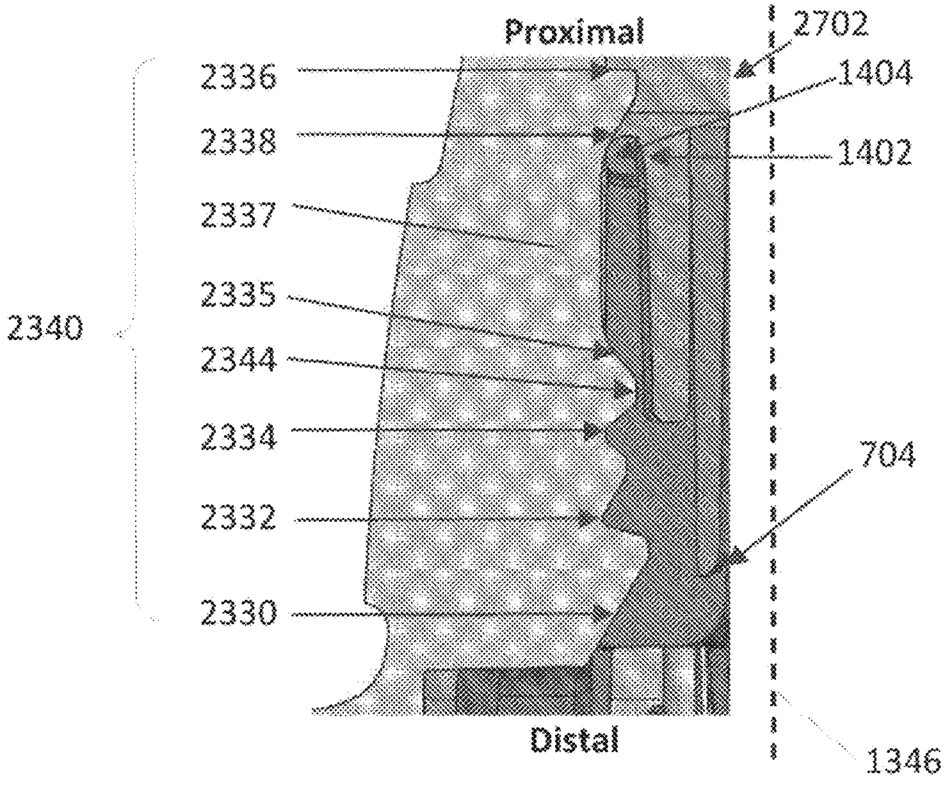

FIGS. 7F and 7G are close-up side views of an alternative embodiment of locking rib 2340 that is designed to improve the firing velocity of the sharp from the sensor applicator. Here, locking rib 2340 includes an inward detent ramp 2335 to reduce friction between sheath 704 and housing 2702 during firing. Locking rib 2340 also includes a sheath stopping ramp 2338 at the proximal end of firing surface 2337. In FIG. 7F, sheath 704 is initially shown in a "locked" state, in which detent round 1404 of detent snap 1402 has already passed over sheath snap lead-in feature 2330, and is positioned in locked groove 2332. As force is applied to the proximal end of housing 2702, detent round 1404 is advanced into unlocked groove 2334, placing applicator 150 into the "armed" position. When force is further applied to the proximal end of housing 2702, applicator 150 is "fired," as detent round 1404 passes over firing detent 2344.

As shown in FIG. 7G, detent round 1404 then advances toward the proximal end of housing 2702 in a "free flight" state, in which detent round 1404 passes over inward detent ramp 2335. While advancing proximally in the "free flight" state, detent round 1404 can be in non-continuous, or have no contact with, inward detent ramp 2335 and firing surface 2337. In this regard, detent round 1404 can be easily and quickly advanced, as there is little to no frictional force between detent round 1404 and inward detent ramp 2335 and firing surface 2337, and as such, improves upon the firing velocity of the sharp from the applicator. Sheath stopping ramp 2338, which is positioned proximally further along the locking rib 2340 relative to the embodiment shown in FIGS. 7D and 7E, provides an edge portion to frictionally engage the detent round 1404 and slow the movement of sheath 704. The sheath stopping ramp 2338 can have a sloped shape and provide for increasing frictional contact as the detent round 1404 advances in a proximal direction. Finally, upon detent round 1404 reaching final lockout recess 2336, detent snap flat 1406 (not shown) is engaged and securely holds sheath 704 in place with respect to housing 2702. Lockout recess 2336 prevents detent round 1404 and sheath 704 from backwards, or distal movement. This embodiment reflects a higher firing velocity relative to the embodiment depicted in FIGS. 7D and 7E, which also assists in prevention of a premature withdrawal of sharp.

Figure 7I:
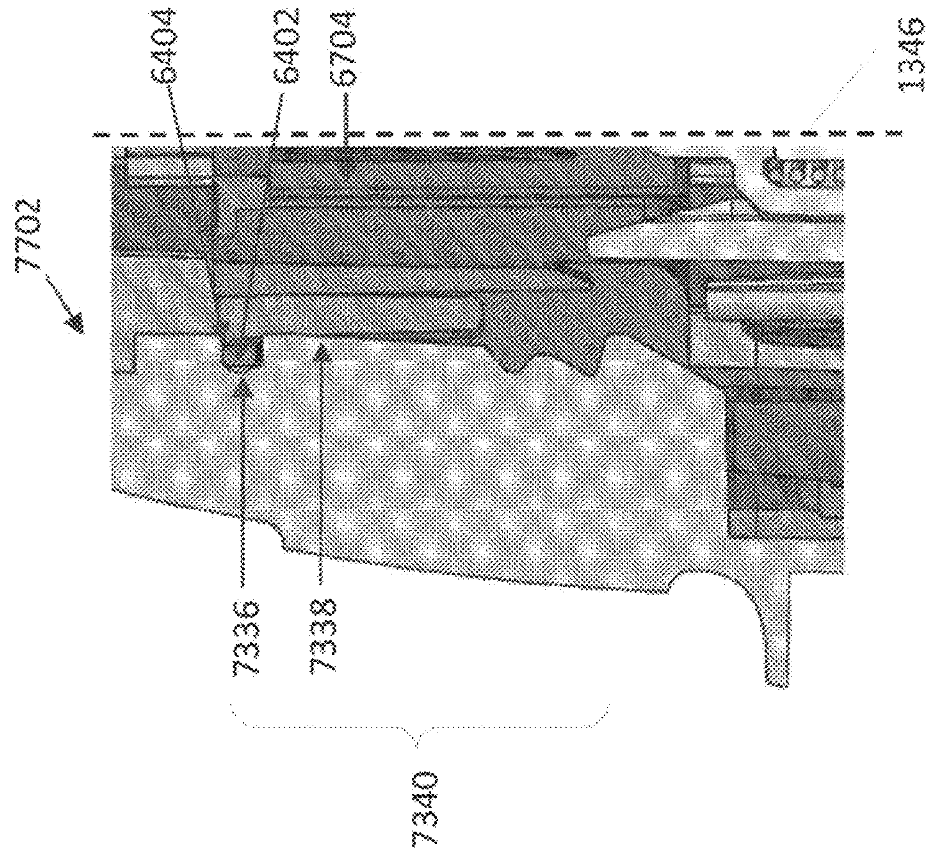
FIG. 7I is a side cross-sectional view depicting a locking rib portion of another example embodiment of a housing and a portion of a sheath.
Figure 7H:
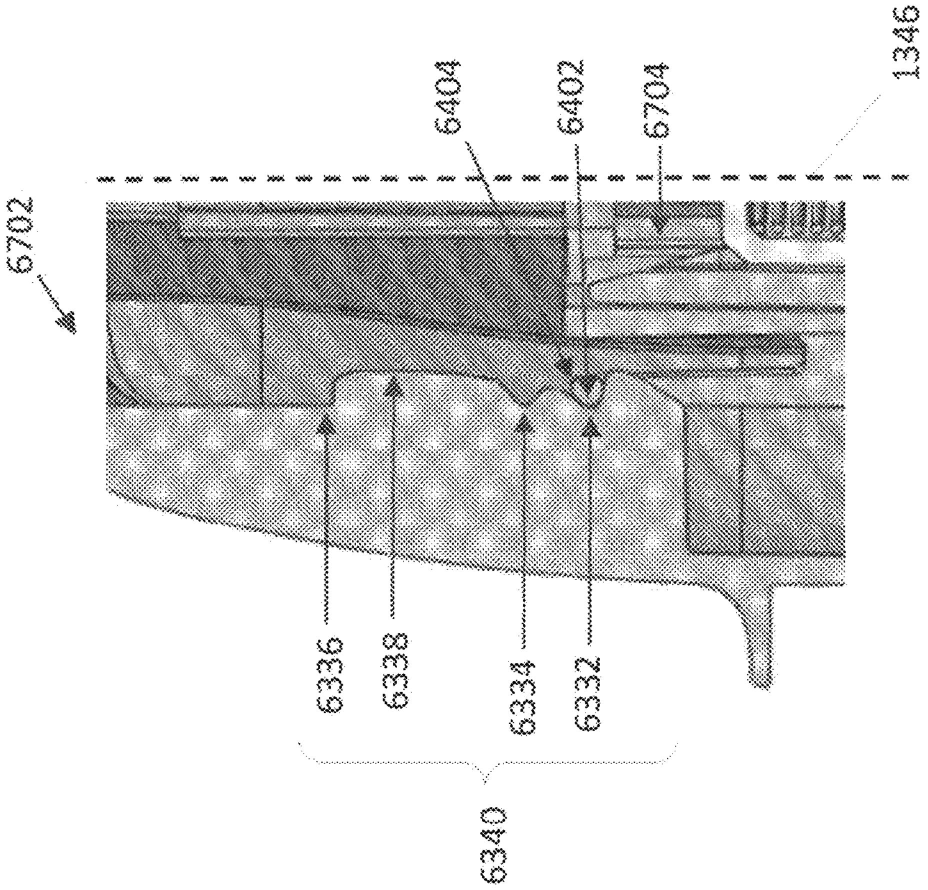
FIG. 7H is a side cross-sectional view depicting a locking rib portion of another example embodiment of a housing and a portion of a sheath.

FIG. 7H is a close-up side view of an alternative embodiment of locking rib 6340 designed to maintain a downward force on sheath 6704 during firing which, in turn, can prevent sheath 6704 from unwanted movement during the sensor insertion process. Here, sheath 6704 is shown in a "locked" state, in which detent round 6404 of detent snap 6402 is positioned in locked groove 6332. As force is applied to the proximal end of housing 6702, detent round 6404 is advanced into unlocked groove 6334, placing applicator in the "armed" position. When force is further applied to the proximal end of housing 6702, applicator is "fired," and detent round 6404 advances over sloped firing surface 6338 toward the proximal end of housing 6702. Sloped firing surface 6338 can be angled toward central axis 1346 such that the resulting downward force upon sheath 6704 increases as detent round 6404 advances in a proximal direction. In the depicted embodiment, detent round 6404 is in continuous contact with sloped firing surface 6338. Lockout recess 6336 prevents detent round 6404 and sheath 6704 from backwards, or distal movement. This embodiment reflects a slower firing velocity relative to the previously described embodiments, and can be used, for example, with the motion-actuated sharp retraction process that is described with respect to FIGS. 14A-14C and 15A-15B.

FIG. 7I is a close-up side view of still another alternative embodiment of locking rib 7340, also designed to maintain a downward force on sheath 6704 during firing which, in turn, can prevent sheath 6704 from unwanted movement during a sensor insertion process. Here, sheath 6704 is shown in a "fired" state, in which detent round 6404 of detent snap 6402 is positioned in a two-way lockout recess 7336. Upon detent round 6404 advancing into two-way lockout recess 7336, sheath 6704 can be prevented from further movement in either a proximal or distal direction. This can reduce unwanted movement of sheath 6704 during the sensor insertion process. Furthermore, in some embodiments, as described with respect to FIGS. 14A-14C and 15A-15B, two-way lockout recess 7336 can provide for the immobilization of sheath 6704 during a motion-actuated sharp retraction process. As can be seen in FIG. 7I, sloped firing surface 7338 is angled toward central axis 1346 such that a resulting downward force upon sheath 6704 increases as detent round 6404 advances in a proximal direction. In the depicted embodiment, detent round 6404 is in continuous contact with sloped firing surface 7338. This embodiment reflects a slower firing velocity and can be used, for example, with the motion-actuated sharp retraction process that is described with respect to FIGS. 14A-14C and 15A-15B.

Figure 7J:
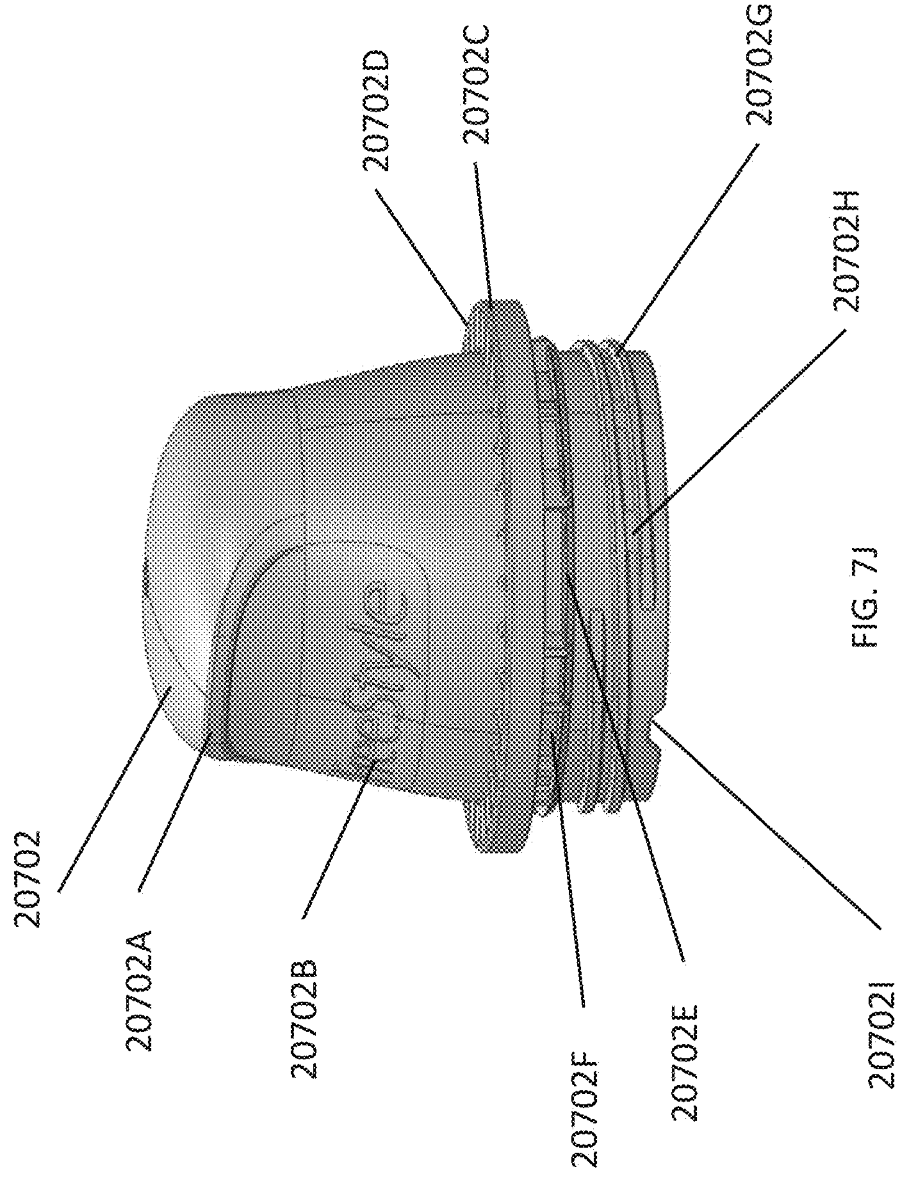
FIG. 7J is a side view of an exemplary housing in accordance with the disclosed subject matter.
Figure 7K:
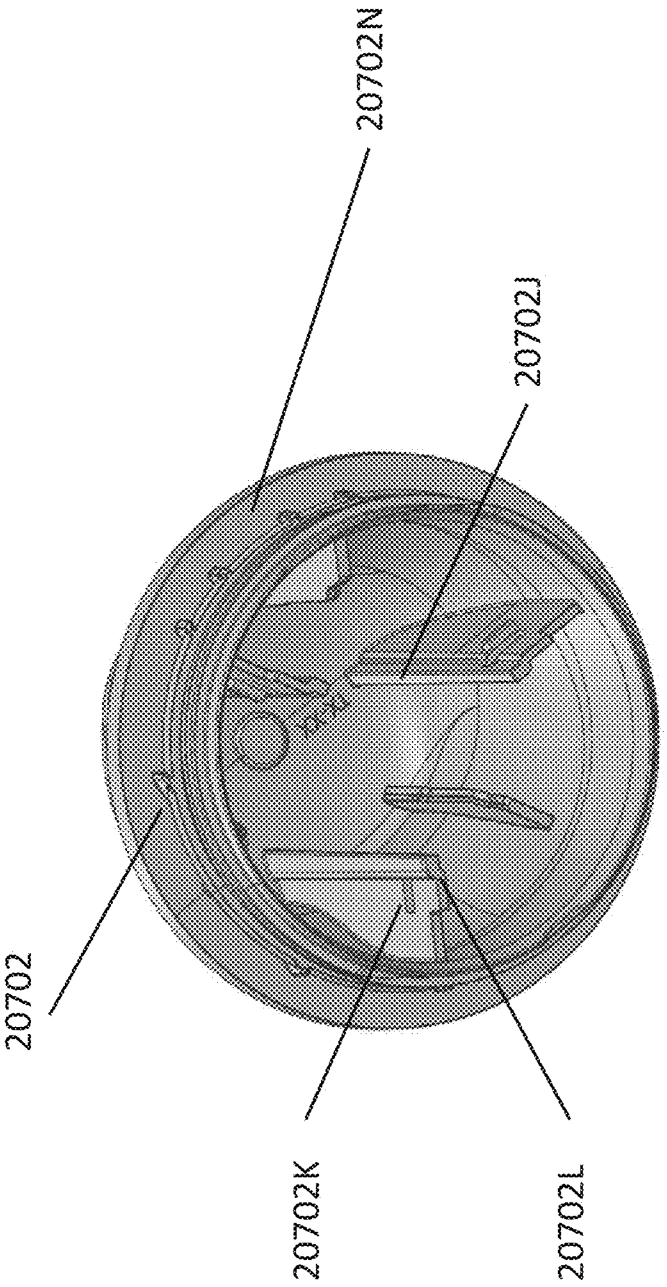
FIG. 7K is a bottom perspective view of the housing of FIG. 7J.
Figure 7L:
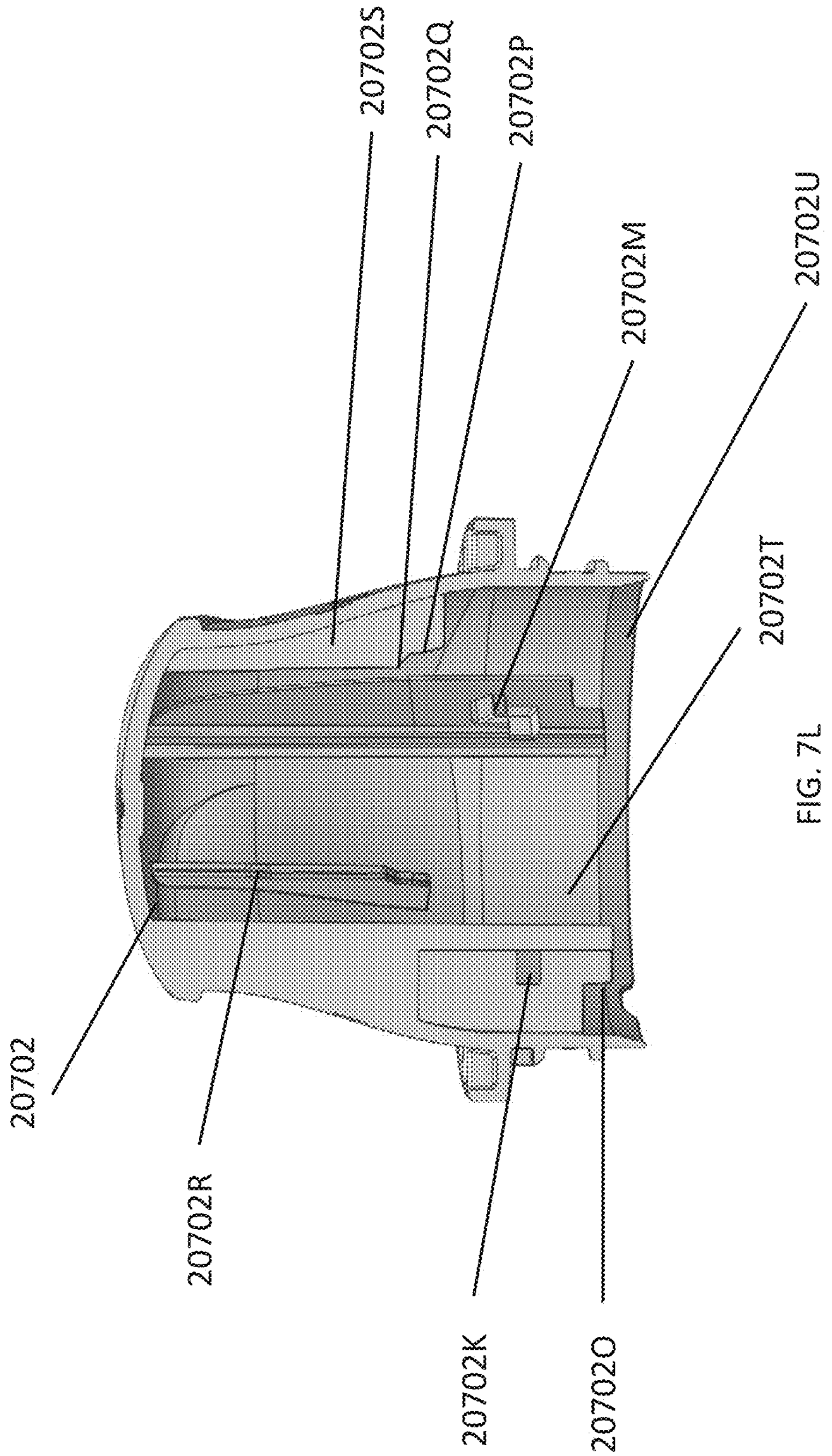
FIG. 7L is a side cutaway view of the housing of FIG. 7J.
Figure 7M:
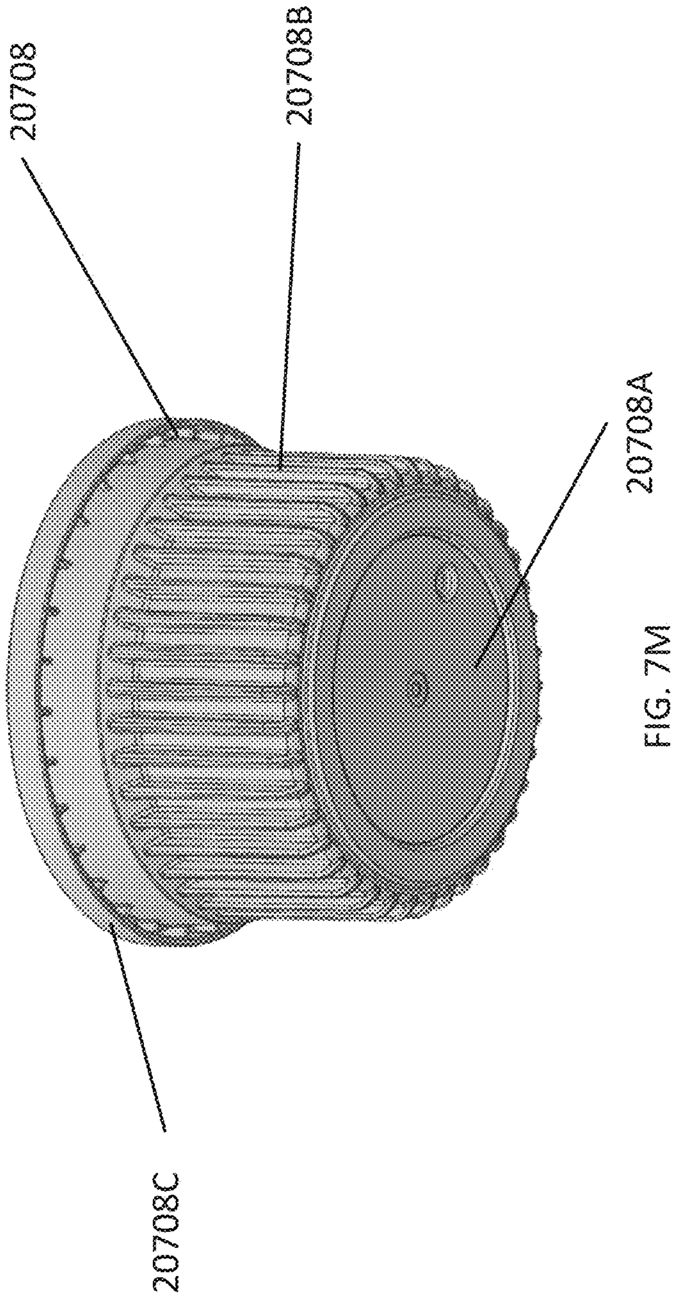
FIG. 7M is bottom perspective view of a cap in accordance with the disclosed subject matter.
Figure 7N:
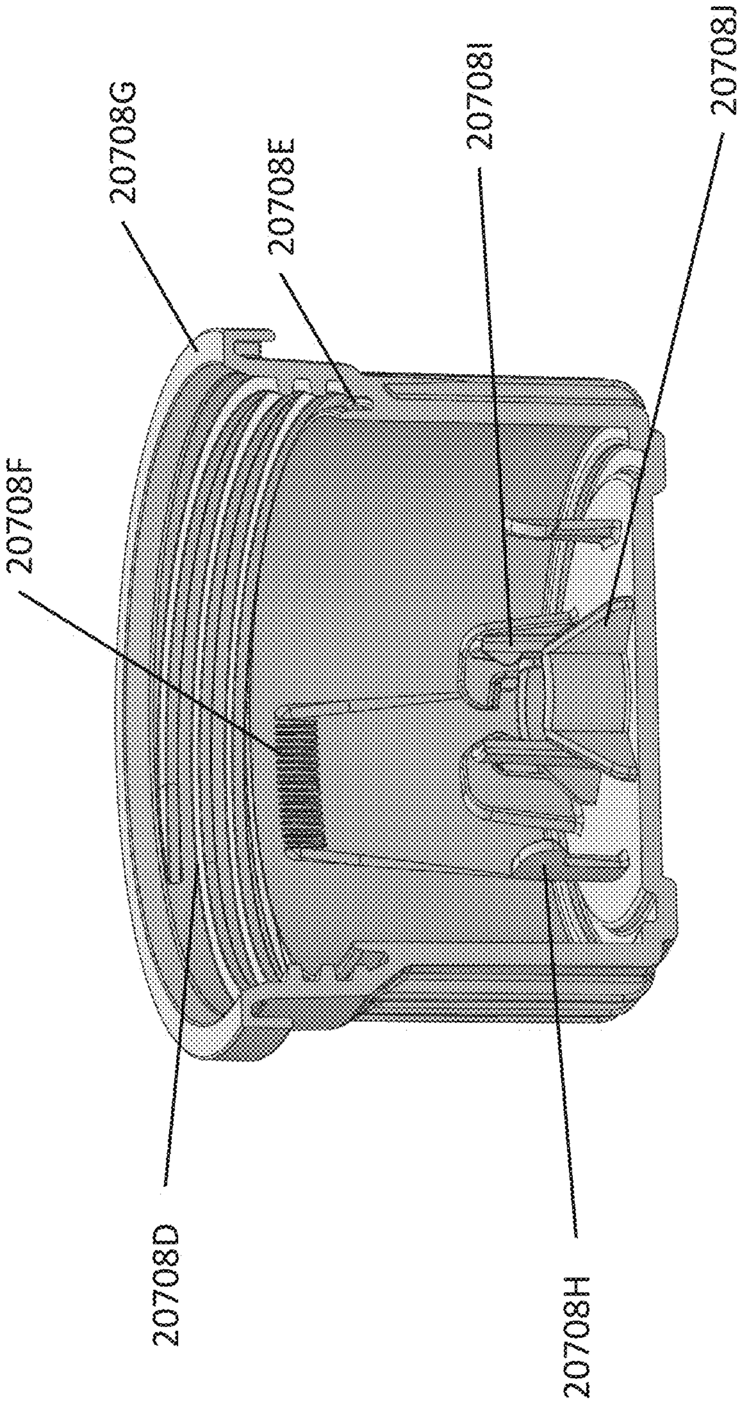
FIG. 7N is a side cutaway view of the cap of FIG. 7M.

Referring to FIGS. 7J-7L, for purpose of illustration and not limitation, a housing 20702 in accordance with the disclosed subject matter is provided. Housing 20702 can be made of cyclic olefin copolymer, or other suitable materials, such as Polycarbonate or high density poly ethylene (HDPE). Housing 20702 can include one or more of the features described herein with regard to housings, wherein similar features can operate as described herein. For example, housing 20702 can include a grip overhang 20702A that can enable a user to securely grip housing 20702. The housing 20702 can have additional grip overhangs 20702A, for example, two grip overhands 20702A on opposite sides of the housing 20702. The housing 20702 can include a side grip zone 20702B disposed below the grip overhand 20702A. The side grip zone 20702B can be textured for improved gripping by a user. The housing 20702 can have additional side grip zones 20702B, for example, two side grip zones 20702B on opposite sides of the housing 20702, each disposed below a grip overhang 20702A.

The housing 20702 can include a housing skirt 20702C, which can provide a surface for tamper evidence feature 20712. The housing skirt 20702C can be supported by a plurality of skirt stiffening ribs 20702D. The skirt stiffening ribs 20702D can provide support for the housing skirt 20702C and can help protect the applicator device 20150 during a shock event, such as a drop. Additionally, the skirt stiffening ribs 20702D can be used to support the housing 20702 during manufacturing. The housing skirt 20702C and skirt stiffening ribs 20702D can provide stiffness against forces due to gasket compression, and can help maintain gasket 20701 compression through shelf life. The housing 20702 can include a gasket retention ring 20702E and a plurality of gasket retention pockets 20702F, which can hold the gasket 20701 relative the housing 20702. For example, the gasket retention ring 20702E can prevent lateral movement of the gasket 20701 and the gasket retention pockets 20702E can prevent rotation of the gasket 20701. The housing 20702 can include a plurality of gasket retention pockets, for example, 14 gasket retention pockets 20702E. Gasket sealing face 20702N that can seal against the gasket 20701. Housing 20702 can additionally or alternatively have an applicator cap sealing lip 20702U that can interface with the cap 20708, as described in greater detail below. Housing 20702 can have inner surface 20702T that can receive the sheath 20704.

Housing 20702 can include threads 20702G configure to engage with threads 20708D disposed on cap 20708. The threads can include radial limiting features 20702H, which can limit radial deformation of the cap 20702G during a shock event, such as a drop. Housing 20702 can include a plurality of radial limiting features 20702H, for example, 6 radial limiting features 20702H. The radial limiting features 20702H can be protrusions from the housing and can close a gap with the threads 20708D disposed on cap 20708. This can limit oval deformation of the cap 20702H during a shock event, such as a drop. Preventing oval deformation of cap 20702H can, in turn, ensure that lock arms 20704J of sheath 20704 stay locked between the cap 20702 and the sensor carrier 20710 to limit movement of the sheath 20704 prior to removing cap 20702H (as described in greater detail below). Housing 20702 can further include a clearance notch 20702I for clearance of the sheath arms during firing.

The interior of housing 20702 can include a plurality of sensor carrier attachment features for receiving, aligning, and limiting movement of the sensor carrier 20710. For example, housing 20703 can include sheath guide rails 20702I, which can help to align and guide sheath 20704 as the sheath 20704 moves relative the housing 20702. Housing 20702 can include sensor carrier attach slots 20702K, which can engage and hold the sensor carrier 20710, and sensor carrier hard stops 20702L, that can limit axial movement of the sensor carrier 20710 relative the housing 20702. Housing 20702 can include sensor carrier biasing feature 20702M that can remove slop between the sensor carrier 20710 and the housing 20702 after assembly and sensor carrier radial limiting feature 20702O that can keep the sensor carrier radially aligned relative the housing 20702. Flat horizontal faces between sensor carrier attach slots 20702K and sensor carrier radial limiting feature 20702O can be used to stop the sheath 20704 at the end of a stroke. Corresponding features on the sheath 20704 can interact with these faces. The sensor carrier biasing feature 20702M can further limit rotation of the sensor carrier 20710 relative the housing 20702. Housing 20702 can include one or more of each of the sheath guide rails 20702I, sensor carrier attach slots 20702K, sensor carrier hard stops 20702L, sensor carrier radial limiting feature 20702O, and sensor carrier biasing feature 20702M, for example, three of each.

The interior of housing 20702 can further include a plurality sheath ribs 20702S for engaging the sheath 20704 for insertion, as described herein. Housing 20702 can include one or more of sheath ribs 20702S, for example, three. Each sheath rib 20702S can include a sheath snap lead in feature 20702P configured to initially lead in the detent snap 20704A of sheath 20704 into the correct location. The housing 20702 can include a firing detent 20702Q. After the detent snap 20704A of sheath 20704 passes the firing detent 20702Q, the firing sequence can be initiated, and the sheath 20704 can travel toward the sheath stopping ramp 20702R. The sheath stopping ramp 20702 can slow the sheath 20704 at the end of firing.

Referring to FIGS. 7M-7Q and 7S-X for purpose of illustration, an exemplary cap 20708 is provided. Cap 20708 can include one or more of the features described herein with regard to caps, wherein similar features can operate as described herein. Cap 20708 can be made of high density polyethylene (HDPE) or any other suitable materials, such as Polypropylene or low-density polyethylene (LDPE). Cap 20708 can include a label surface 20708A configured to receive label 20709. Cap 20708 can include ribs 20708B which can provide strength and provide an improved gripping surface for a user. The cap 20708 can include tamper label ring 20708C, which can receive the tamper evidence feature 20712. The cap 20708 can also include a gasket sealing surface 20708G, configured to engage gasket 20701.

Internally, cap 20708 can include threads 20708D, which can engage threads 20702G disposed on the housing 20702. Cap 20708 can also include seal interface 20708E which can be configured to receive the applicator cap sealing lip 20702U to create a seal between the housing 20702 and the cap 20708.

Figure 7O:
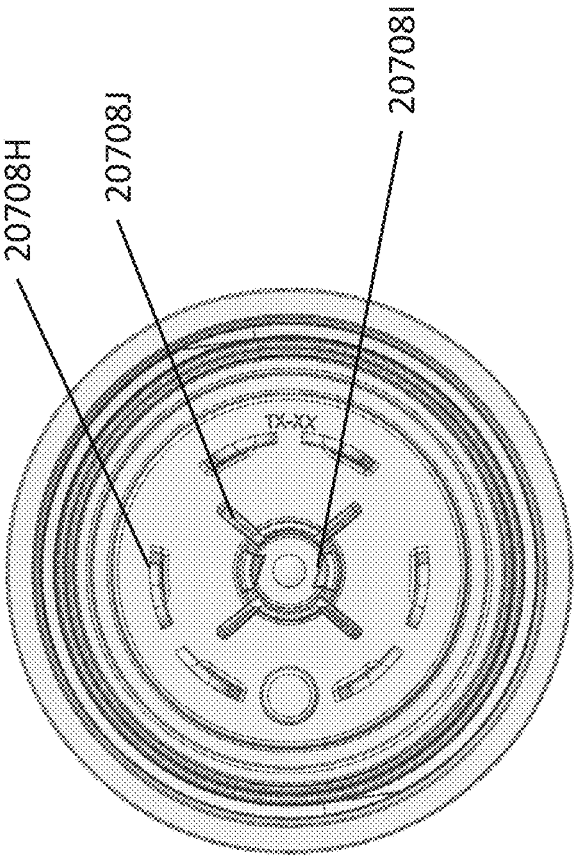
FIG. 7O is a top view of the cap of FIG. 7M.
Figure 7P:
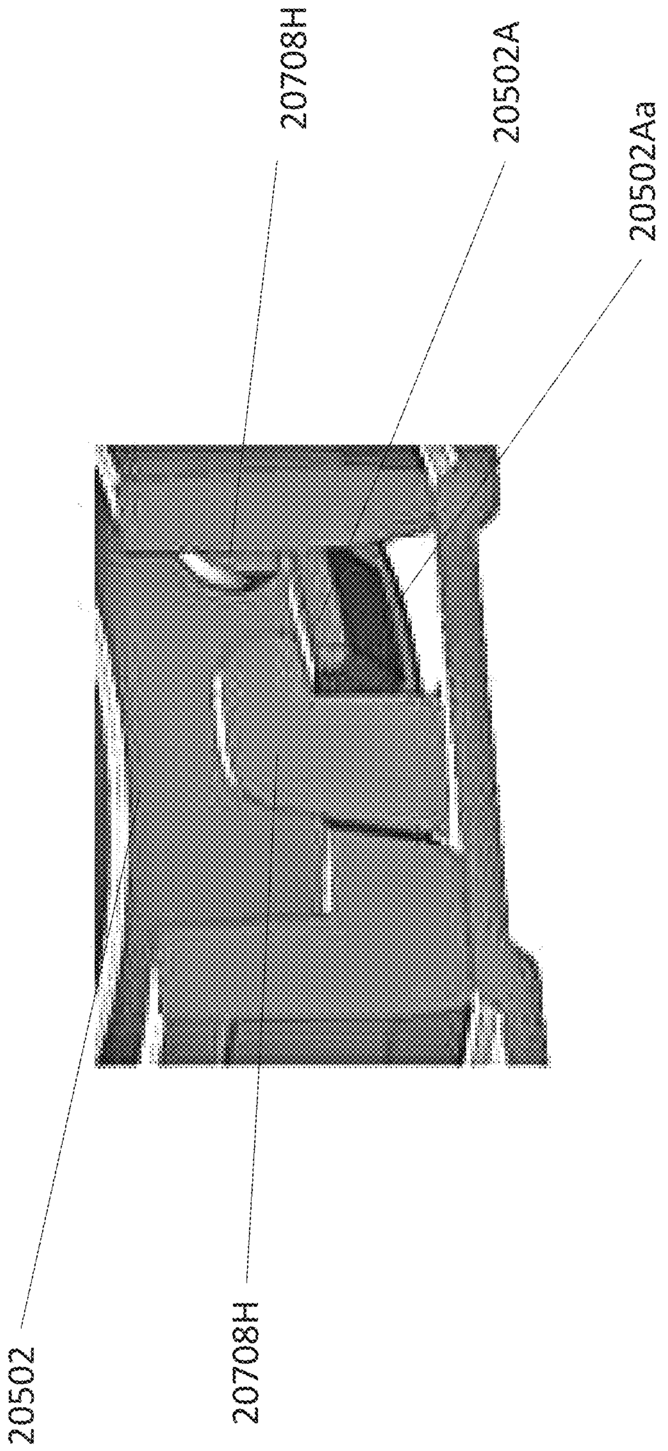
FIG. 7P is a cutaway view of a desiccant in a cap in accordance with the disclosed subject matter.
Figure 7R:
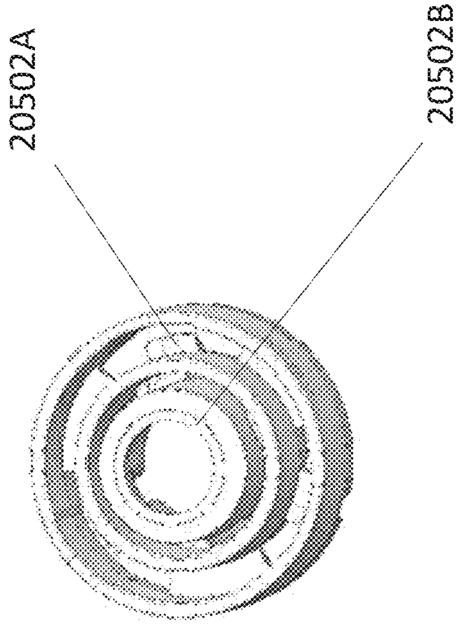
FIG. 7Q-R are bottom and top perspective views of an exemplary desiccant in accordance with the disclosed subject matter.
Figure 7Q:
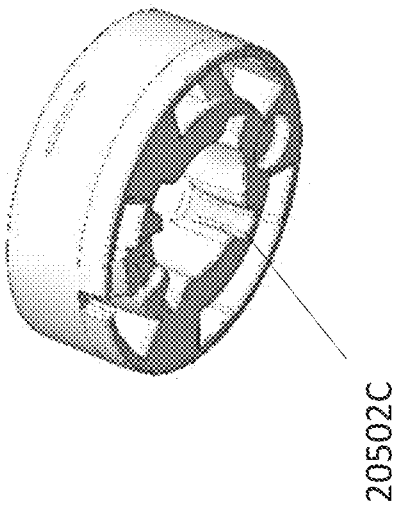
Figure 7S:
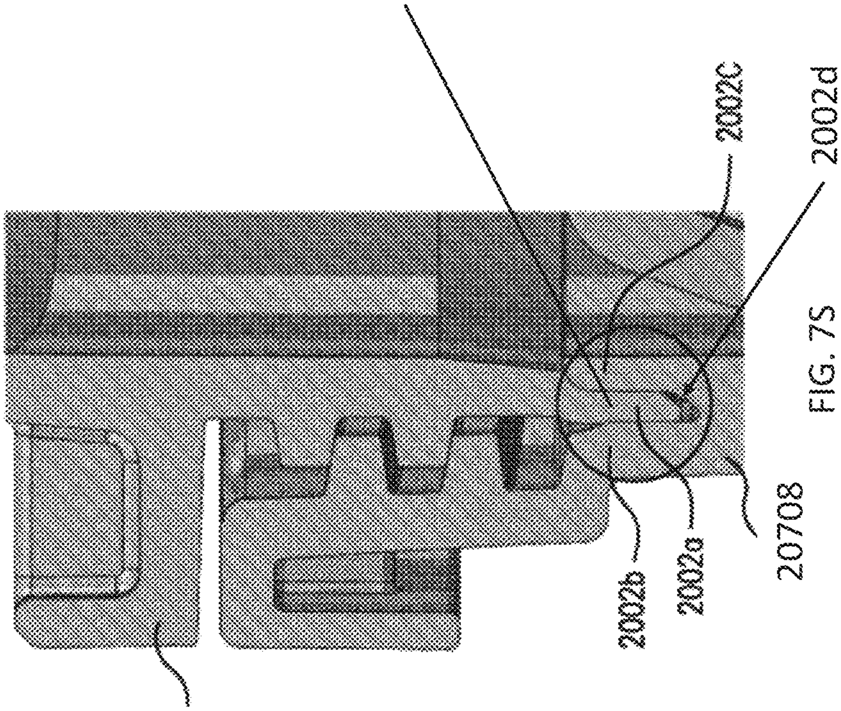
FIGS. 7S-T are enlarged cross-sectional side views of the interface between the housing and cap in accordance with the disclosed subject matter.
Figure 7T:
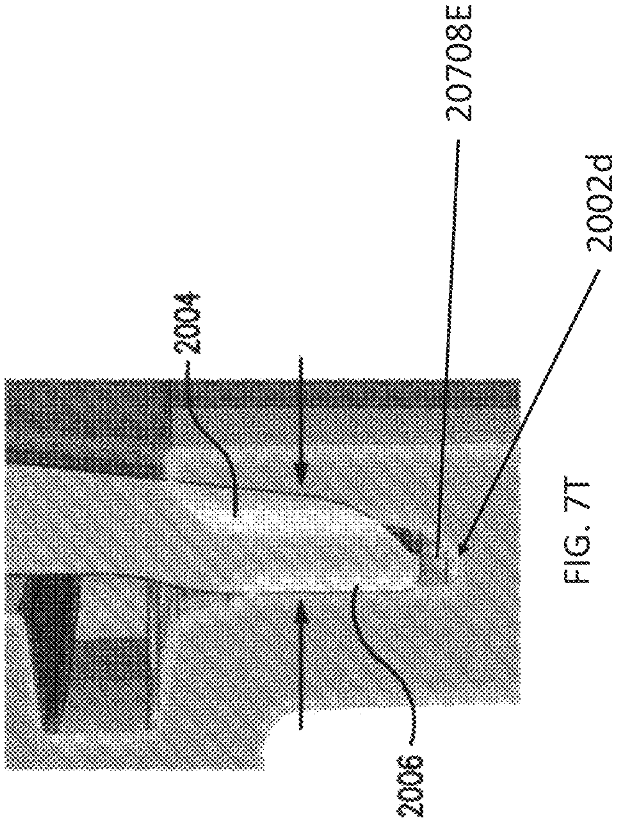
Figure 7U:
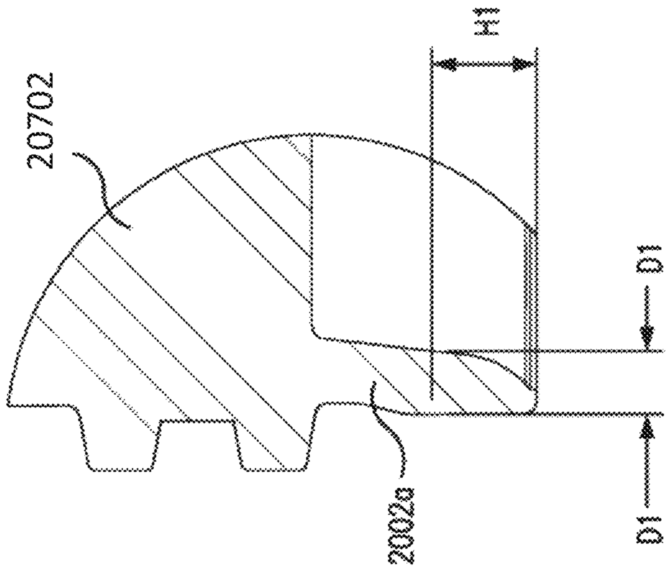
FIGS. 7U-V are enlarged cross-sectional side views of the housing and cap, respectively, in accordance with the disclosed subject matter.
Figure 7V:
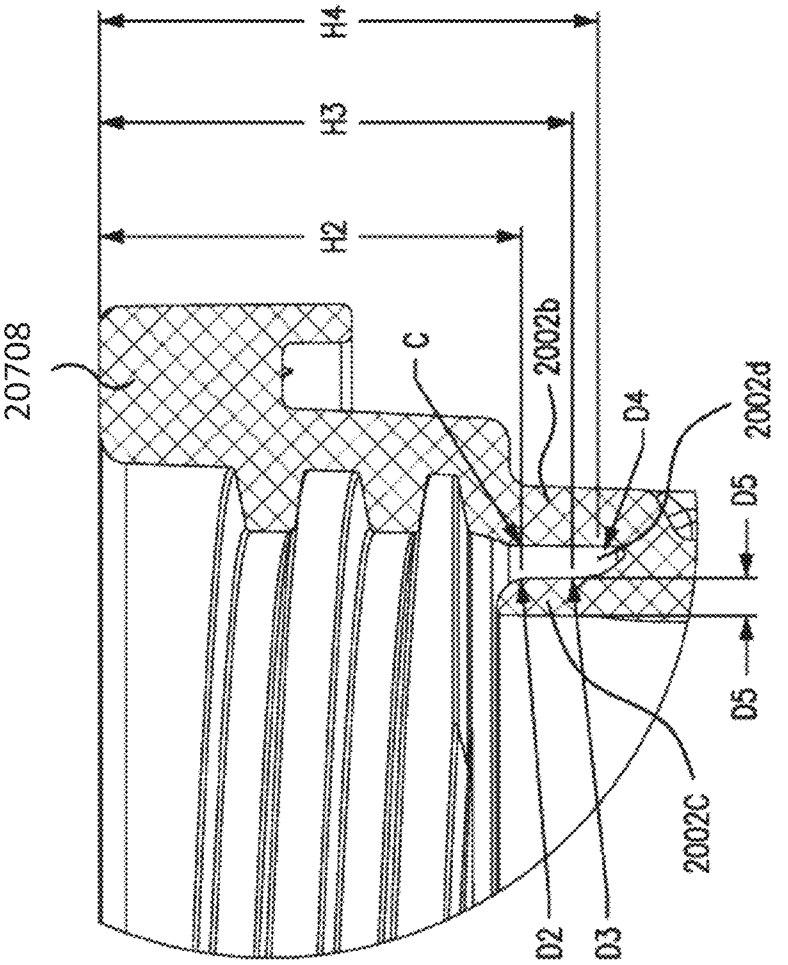

FIGS. 7S-V show an enlarged cross-sectional side view of the interface between housing 20702 and cap 20708. As illustrated, applicator cap sealing lip 20702U of housing 20702 includes a first axial extension 2002*a* and seal interface 20708E of cap 20708 provides a cavity 2002*d* matable with the first axial extension 2002*a*. In the illustrated embodiment, the diameter of cavity 2002*d* formed from second axial extension 2002*b* and third axial extension 2002*c* of the cap 20708 is sized to receive the diameter of first axial extension 2002*a* of housing 20702 within cavity 2002*d*. For example, as shown in FIG. 7U, axial extension 2002*a* can have thickness D1 at height H1, as measured from distal edge of axial extension 2002*a*. Similarly, second axial extension 2002*c* can have a thickness D5 at height H3, as measured from proximal edge of cap 20708; cavity 2002*d* can have a thickness D2, D3, and D4 at heights H2, H3, and H4, respectively, as measured from proximal edge of cap 20708. In certain embodiments, D1 can measure 1 mm with a tolerance of +/−0.03 mm, D2, D3, D4 can have any suitable dimensions, H1 can measure 1.66 mm with a tolerance of +/−0.1 mm, H2 can measure 8.25 mm with a tolerance of +/−0.1 mm, H3 can measure 9.25 mm with a tolerance of +/−0.1 mm, H4 can measure 9.75 mm with a tolerance of +/−0.1 mm. In other embodiments, however, the reverse can be employed, where the diameter of first axial extension 2002*a* can be sized to receive the diameter of the second axial extension 2002*b*, without departing from the scope of the disclosure.

In each embodiment, two radial seals 2004, 2006 can be defined or otherwise provided at the interface between first and second axial extensions 2002*a, b* and radial seals 2004 and 2006 can help prevent migration of fluids or contaminants across the interface in either axial direction. Moreover, the dual radial seals described herein can accommodate tolerance and thermal variations combined with stress relaxation via a redundant sealing strategy. In the illustrated embodiment, dual radial seals 2004, 2006 utilize a "wedge" effect for effective sealing between first axial extension 2002*a* and second axial extension 2002*b*.

Cap 20708 can include one or more sets of crush ribs 20708F (see FIG. 7N), for example, two sets of crush ribs 20708F. The crush ribs 20708F can be configured to engage the sharp edge 20704N of lock arm 20704J during a shock event, for example a drop, as described in greater detail below (see e.g., FIG. 8N).

In accordance with the disclosed subject matter, cap 20708 can include one or more desiccant retention clips 20708H to retain the desiccant 20502 in the cap 20708 and limit rotation of the desiccant 20502 (see e.g., FIG. 7P). Cap 20708 can include any number of desiccant retention clips 20708H. For example, cap 20708 can include one, two, three, four, five, six, or more desiccant retention clips 20708H. As can be seen in FIG. 7O, cap 20708 can include three pairs of two desiccant retention clips 20708H each. Each pair of desiccant retention clips 20708H may correspond to a desiccant retention snap 20502A (see e.g., FIG. 7R) on desiccant 20502 (see e.g., FIG. 7P). As can be seen in FIG. 7P, desiccant 20502 can include a plurality of desiccant retention snaps 20502A and each desiccant retention snap 20502A may snap down into a pair of desiccant retention clip 20708H. For example, desiccant retention snap 20502A can include angled surface 20502Aa to radially expand clips 20708H when the desiccant is pressed down onto the cap until desiccant retention snap 20502A locks in place within desiccant retention clips 20708H. Desiccant retention clips 20708H can hold desiccant 20502 within cap 20708 to limit distal and rotational movement of desiccant 20502. As can be seen in FIG. 7Q, desiccant 20502 can include catch pockets (not shown) to angularly position desiccant 20502 relative to desiccant retention clips 20708H. In some embodiments, as can be seen in FIG. 7Q desiccant 20502 can be cylindrical in shape.

In accordance with disclosed subject matter, cap 20708 can include a ratchet 207081 to engage the sensor cap and remove the sensor cap when the cap 20708 is removed from the housing 20702, as described in greater detail below. According to some embodiments, ratchet 207081 can be provided in a cap 20708 without the use or presence of the desiccant retention clips 20708H described earlier. In other embodiments, ratchet 207081 and desiccant retention clips 20708H can be provided together with cap 20708. Cap 20708 can include a plurality of ribs 20708J to provide strength. Correspondingly, as can be seen in FIGS. 4G and 7Q-R, internal bore 20502B of desiccant 20502 can be sized and dimensioned to allow sufficient clearance for sensor cap to pass through and engage with ratchet 207081 of cap 20708; desiccant 20502 can include a plurality of rib pockets 20502C to provide clearance for plurality of ribs 20708J of cap 20708.

Figure 7X:
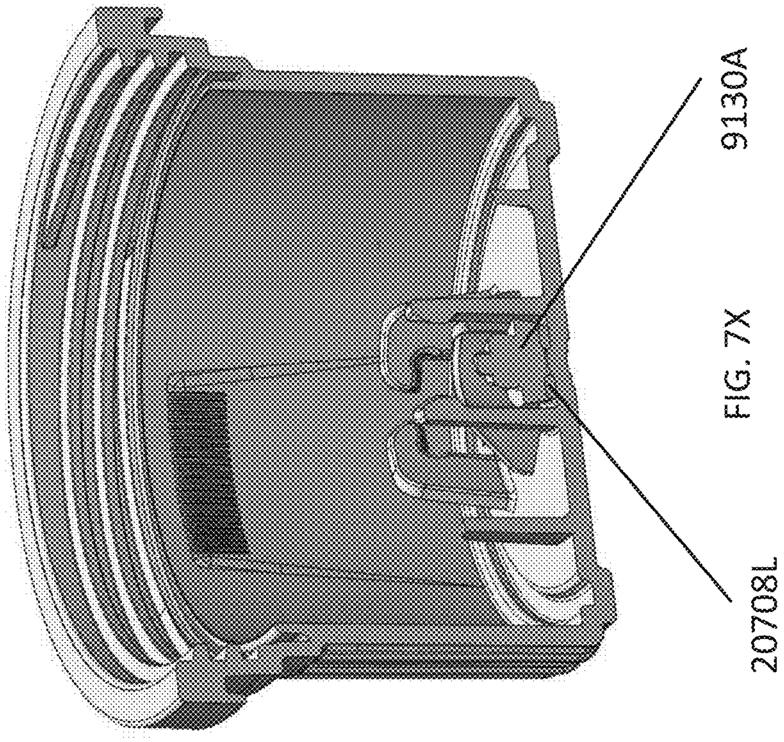
FIGS. 7W-X are side cutaway views of the cap of FIG. 7M.
Figure 7W:
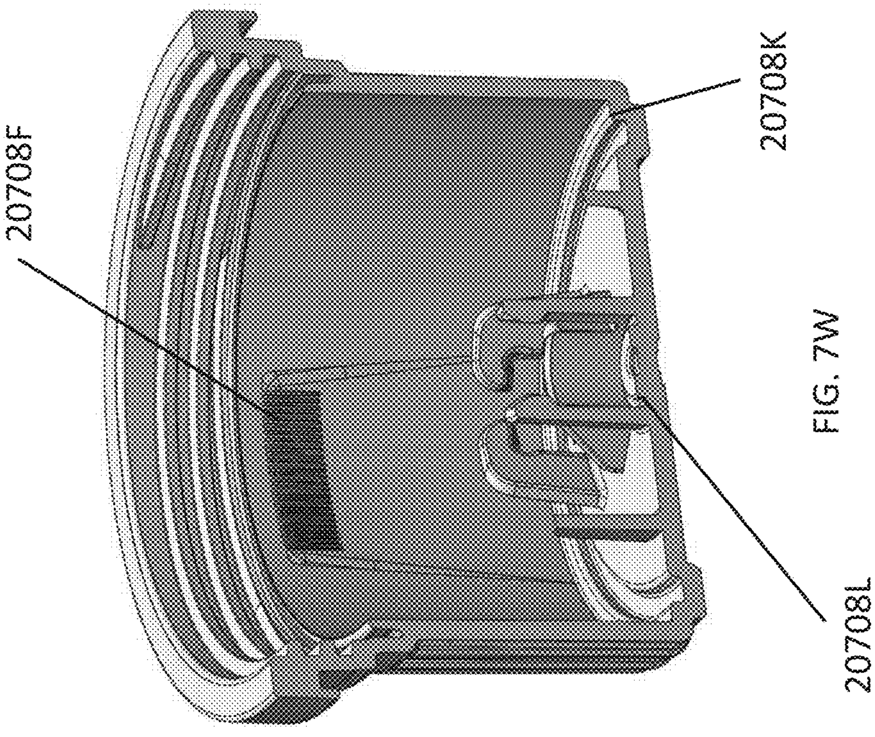
Figure 7Y:
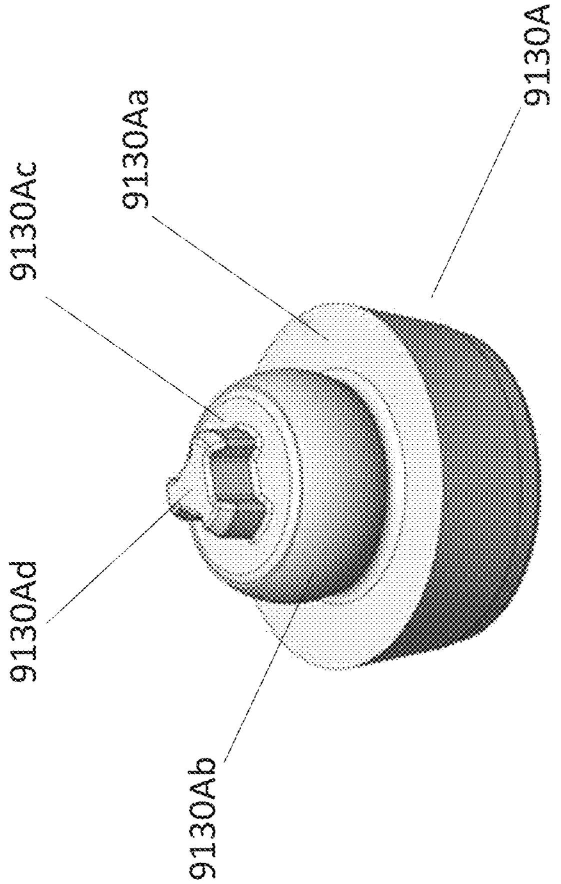
FIG. 7Y is a top perspective view of an exemplary elastomeric plug, according to one or more embodiments.
Figure 7Z:
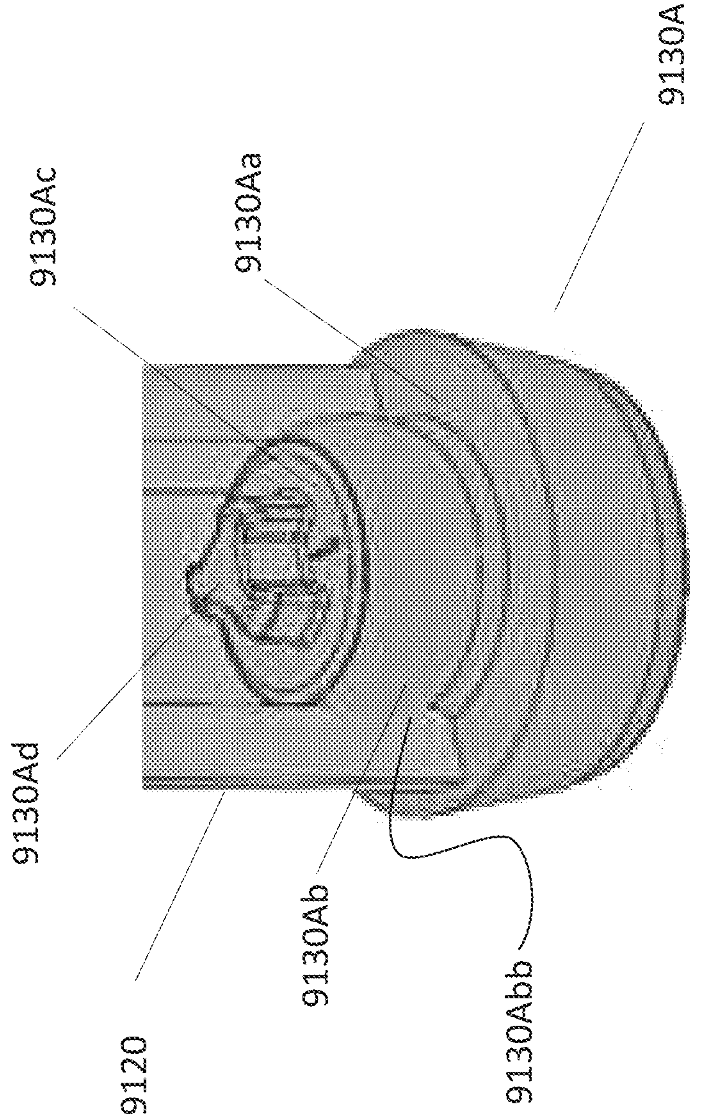
FIG. 7Z is a partial cross-sectional perspective view of an exemplary sensor cap and elastomeric plug, according to one or more embodiments.

Referring to FIGS. 7W and 7X for purpose of illustration and not limitation, in accordance with the disclosed subject matter, cap 20708 can include one or more surfaces to engage other elements in the applicator device 20150 to provide support or limit movement in the case of a shock event, for example, a drop. For example, the cap can include a sheath support surface 20708K, configured to support the sheath 20704 during a shock event. The sheath support surface 20708K can limit distal movement of the sheath 20704 during a shock event. This can lead to less stress on the sensor carrier 20710 and the sensor control device 20102 and can reduce the risk of the sensor control device 20102 dislodging form the sensor carrier 20710. Additionally, or alternatively, the cap 20708 can include a raised ridge 20708L. The raised ridge 20708L can interface with a plug, such as an elastomeric plug 9130A (which can, in some embodiments, be coupled to a desiccant cap 9130 and in other embodiments, as can be seen in FIG. 7Z, couple to sensor cap 9120). In some embodiments, the elastomeric plug can include liquid silicone rubber. The raised ridge 20708L can thereby also support the sharp carrier 201102, sensor carrier 20710, sensor control device 20102, and accordingly, can prevent dislodging of the sensor control device 20102 from the sensor carrier 20710 during a shock event. Furthermore, additional support on the elastomeric plug 9130A and other features can increase the stress on various seals in the applicator device 20150, and thereby improve the seals prior to removing the cap 20708 from the housing. For example, as can be seen in FIG. 7Y, elastomeric plug 9130A may include stop surface 9130Aa, seal bead 9130Ab, intermediate surface 9130Ac, and top surface 9130Ad. As can be seen in FIG. 7Y, top surface 9130Ad can include a triangular surface with squares or rectangular corners instead of pointed vertices. As can be seen in FIG. 7Z, seal bead 9130Ab may be inserted in sensor cap 9120 until stop surface 9130Aa (as shown in cross-sectional view of FIG. 33) mates to the bottom of surface of sensor cap 9120. Seal bead 9130Ab may generally be barrel shaped (i.e., cylindrical shape with a thicker middle portion that tapers towards the top and bottom of seal bead 9130Ab) and configured to create an interference fit 9130Abb between the seal bead 9130Ab and the inner diameter of sensor cap 9120 which creates a sterile barrier and to seal inner chamber 9124.

Exemplary Applicator Sheaths

Figure 8A:
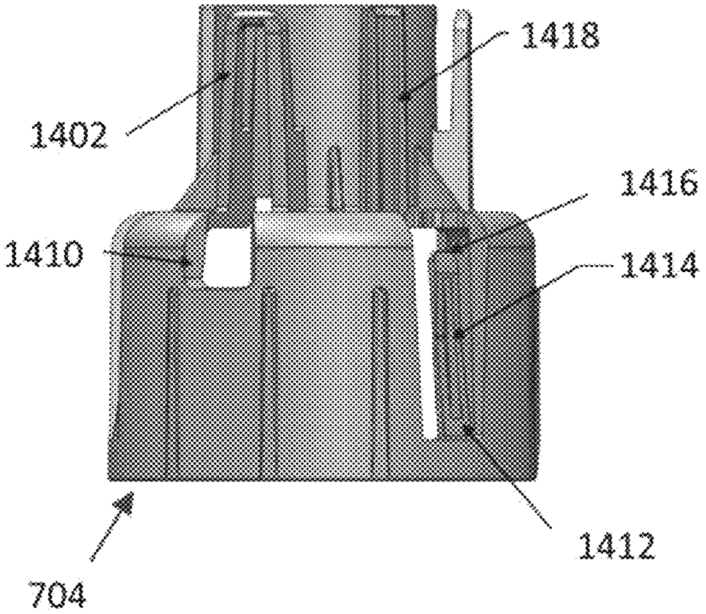
FIG. 8A is a side view depicting an example embodiment of a sheath.
Figure 8B:
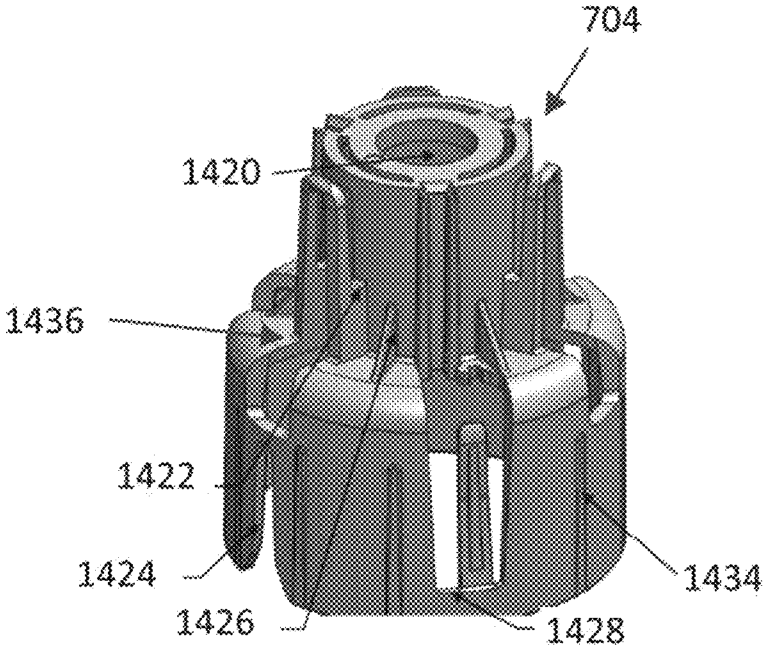
FIG. 8B is a perspective view depicting an example embodiment of a proximal end of a sheath.

FIGS. 8A and 8B are a side view and perspective view, respectively, depicting an example embodiment of sheath 704. In this example embodiment, sheath 704 can stage sensor control device 102 above a user's skin surface prior to application. Sheath 704 can also contain features that help retain a sharp in a position for proper application of a sensor, determine the force required for sensor application, and guide sheath 704 relative to housing 702 during application. Detent snaps 1402 are near a proximal end of sheath 704, described further with respect to FIG. 8C below. Sheath 704 can have a generally cylindrical cross section with a first radius in a proximal section (closer to top of figure) that is shorter than a second radius in a distal section (closer to bottom of figure). Also shown are a plurality of detent clearances 1410, three in the example embodiment. Sheath 704 can include one or more detent clearances 1410, each of which can be a cutout with room for sheath snap lead-in feature 1330 to pass distally into until a distal surface of locking rib 1340 contacts a proximal surface of detent clearance 1410.

Guide rails 1418 are disposed between sensor carrier traveler limiter face 1420 at a proximal end of sheath 704 and a cutout around lock arms 1412. Each guide rail 1418 can be a channel between two ridges where the guide edge 1326 of housing guide rib 1321 can slide distally with respect to sheath 704.

Lock arms 1412 are disposed near a distal end of sheath 704 and can include an attached distal end and a free proximal end, which can include lock arm interface 1416. Lock arms 1412 can lock sensor carrier 710 to sheath 704 when lock arm interface 1416 of lock arms 1412 engage lock interface 1502 of sensor carrier 710. Lock arm strengthening ribs 1414 can be disposed near a central location of each lock arm 1412 and can act as a strengthening point for an otherwise weak point of each lock arm 1412 to prevent lock arm 1412 from bending excessively or breaking.

Detent snap stiffening features 1422 can be located along the distal section of detent snaps 1402 and can provide reinforcement to detent snaps 1402. Alignment notch 1424 can be a cutout near the distal end of sheath 704, which provides an opening for user alignment with sheath orientation feature of platform 808. Stiffening ribs 1426 can include buttresses, that are triangularly shaped here, which provide support for detent base 1436. Housing guide rail clearance 1428 can be a cutout for a distal surface of housing guide rib 1321 to slide during use.

FIG. 8C is a close-up perspective view depicting an example embodiment of detent snap 1402 of sheath 704. Detent snap 1402 can include a detent snap bridge 1408 located near or at its proximal end. Detent snap 1402 can also include a detent snap flat 1406 on a distal side of detent snap bridge 1408. An outer surface of detent snap bridge 1408 can include detent snap rounds 1404 which are rounded surfaces that allow for easier movement of detent snap bridge 1408 across interior surfaces of housing 702 such as, for example, locking rib 1340.

Figure 8D:
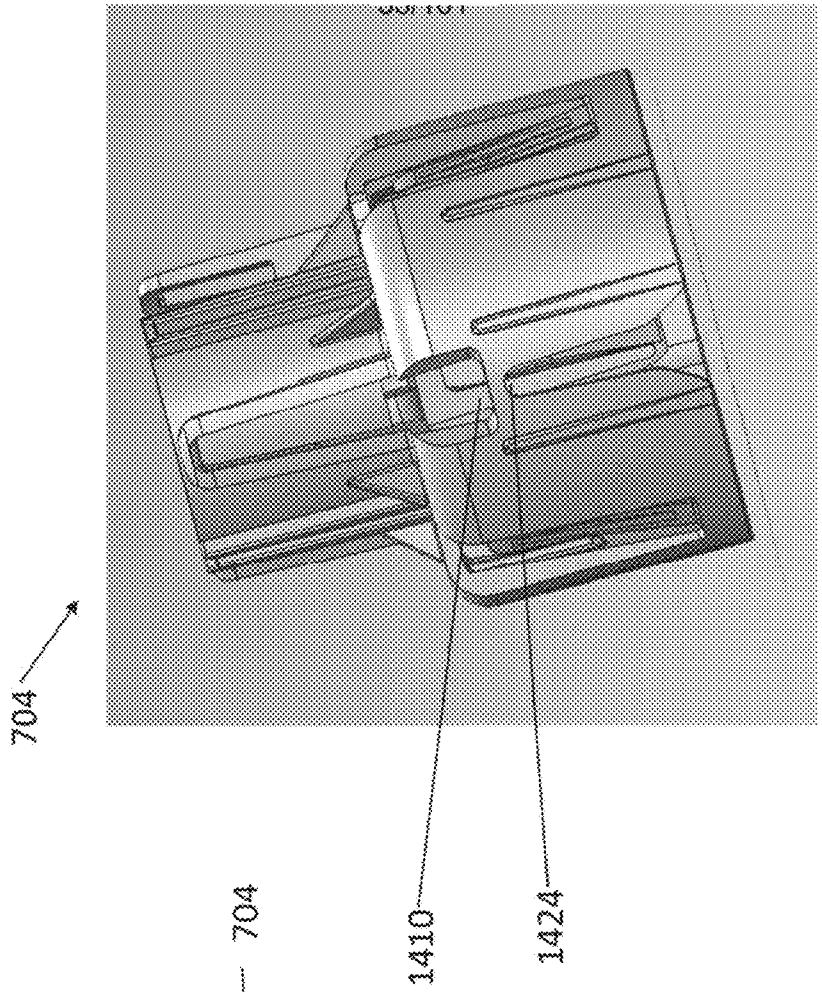
FIG. 8D is a side view depicting an example embodiment of features of a sheath.
Figure 8C:
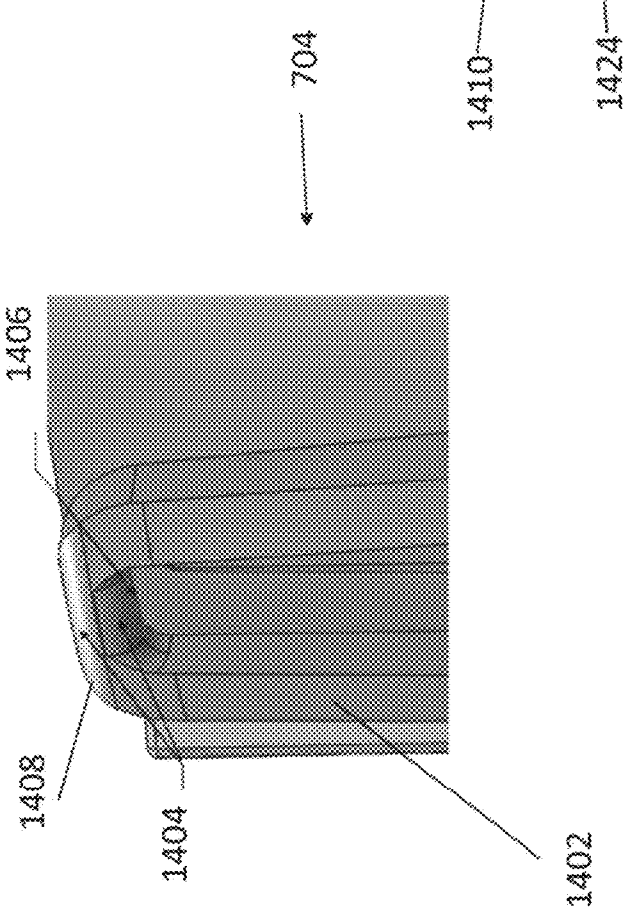
FIG. 8C is a close-up perspective view depicting an example embodiment of a distal side of a detent snap of a sheath.

FIG. 8D is a side view depicting an example embodiment of sheath 704. Here, alignment notch 1424 can be relatively close to detent clearance 1410. Detent clearance 1410 is in a relatively proximal location on distal portion of sheath 704.

Figure 8E:
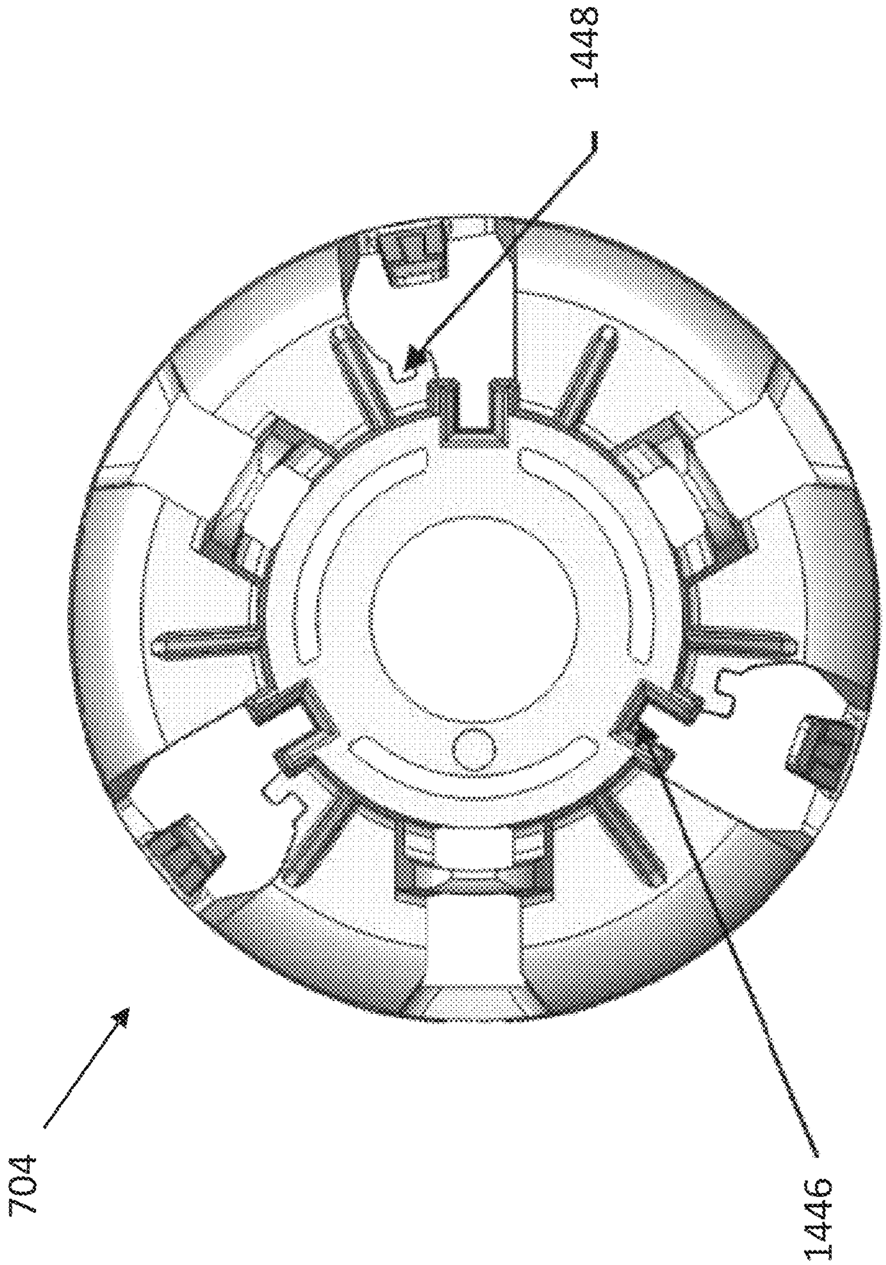
FIG. 8E is an end view of an example embodiment of a proximal end of a sheath.

FIG. 8E is an end view depicting an example embodiment of a proximal end of sheath 704. Here, a back wall for guide rails 1446 can provide a channel to slidably couple with housing guide rib 1321 of housing 702. Sheath rotation limiter 1448 can be notches which reduce or prevent rotation of the sheath 704.

Figure 8G:
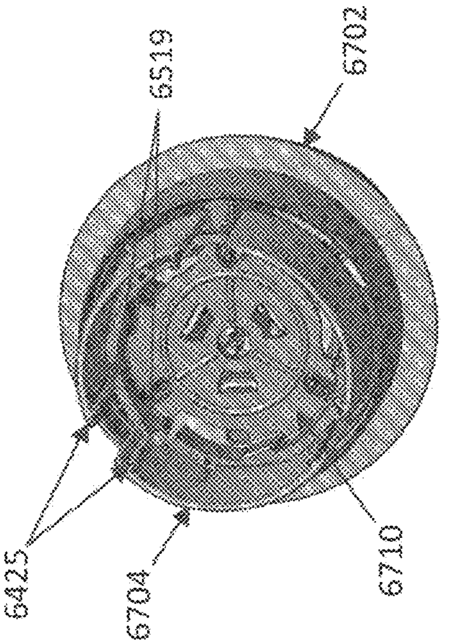
FIGS. 8F to 8H are perspective views depicting another example embodiment of a sheath in various stages of assembly with other applicator components.
Figure 8H:
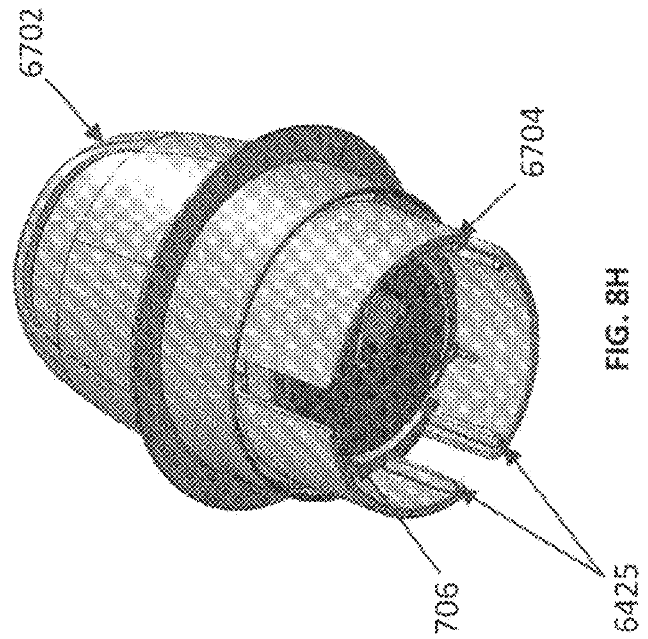
Figure 8F:
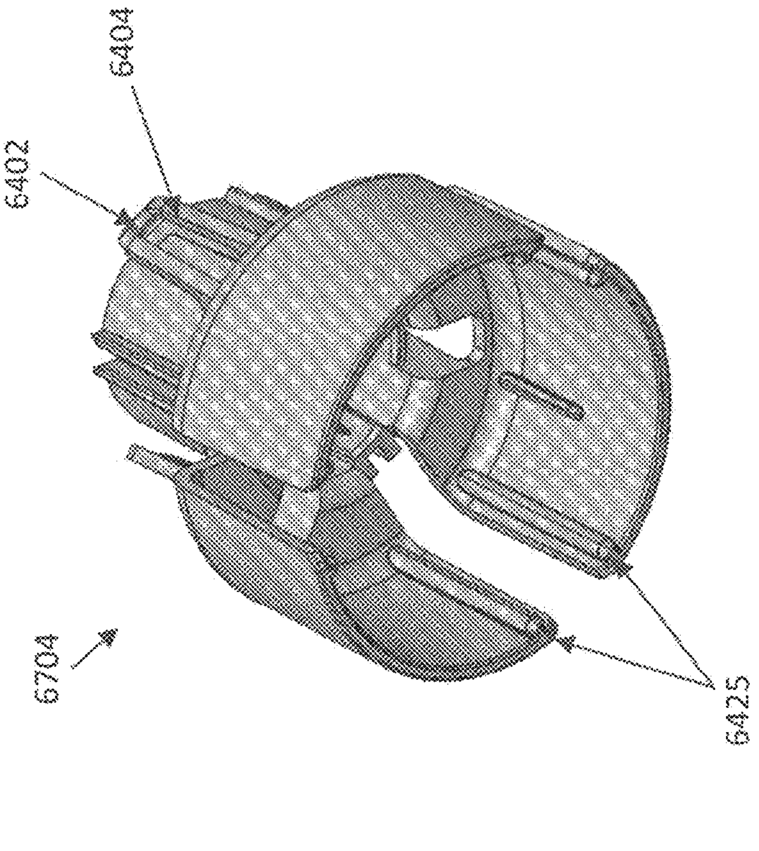
Figure 8I:
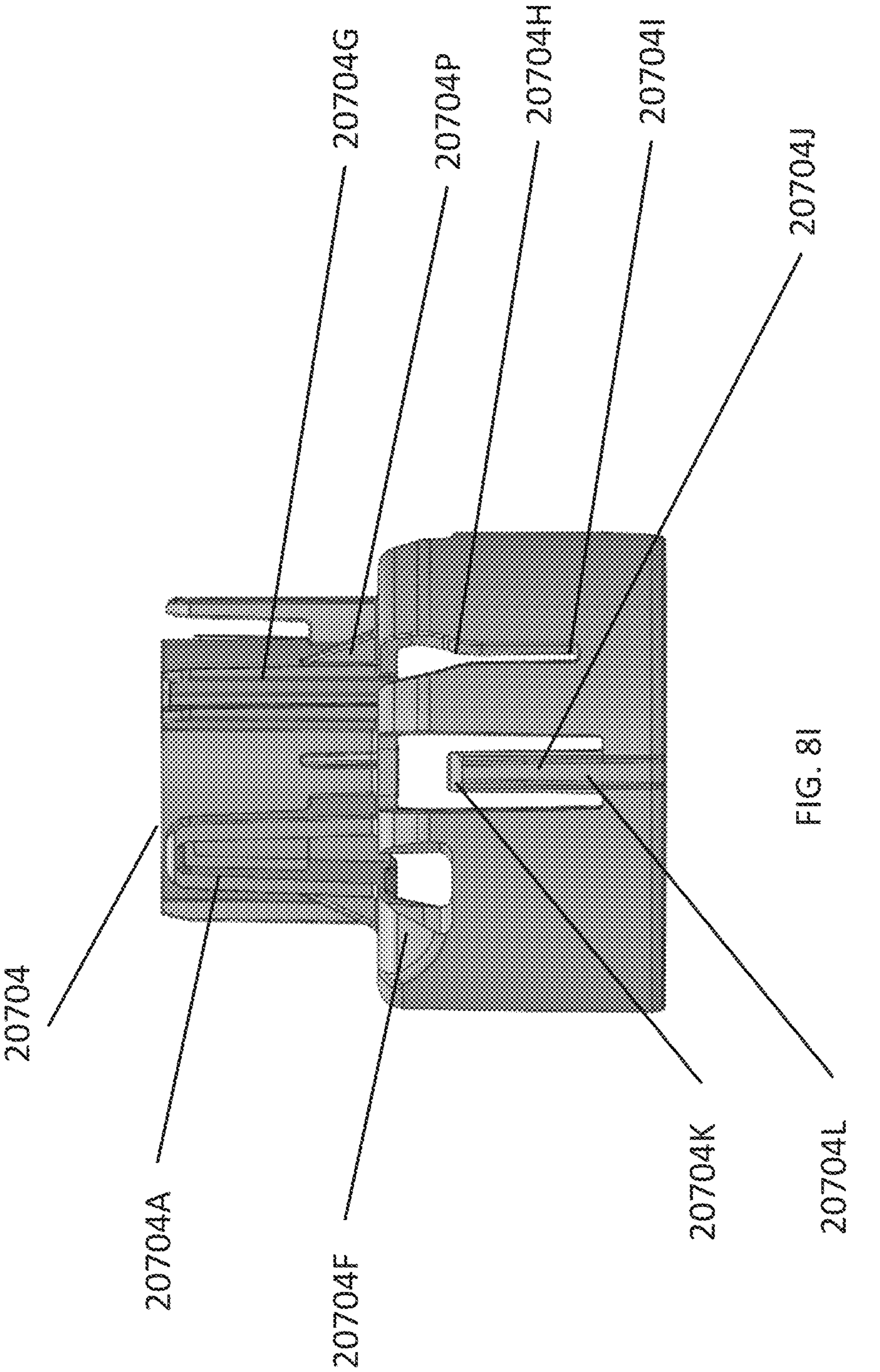
FIG. 8I is a side view of a sheath in accordance with the disclosed subject matter.

FIGS. 8F-8H are perspective views of an alternative example embodiment of sheath 6704 in various stages of assembly with other components of the applicator. As shown in FIG. 8F, sheath 6704 can have many of the same features as sheath 704, previously described with respect to FIGS. 8A-8C. Sheath 6704, for example, can include one or more detent snaps 6404 having one or more detent rounds 6402 attached thereto. Sheath 6704, however, can be shorter in overall length as compared to sheath 702. In addition, sheath 6704 can include one or more inner sheath ribs 6425 disposed on the inner surface of sheath 6704, and which protrude in an inward direction towards the central axis of sheath 6704.

Turning to FIG. 8G, sheath 6704 is shown in perspective view in a stage of assembly with applicator housing 6702 and sensor carrier 6710. One or more inner sheath ribs 6425 of sheath 6704 can interface with one or more corresponding rib notches 6519 in sensor carrier 6710. The fitted interface between corresponding ribs 6425 and notches 6519 can help maintain axial alignment of the sheath 6704 and sensor carrier 6710 during the sensor insertion process. Furthermore, the interface between ribs 6425 and notches 6519 can reduce lateral and rotational movement between the applicator components, which can, in turn, reduce the chance of improper sensor insertion.

Turning to FIG. 8H, sheath 6704 is shown in perspective view in a stage of assembly with applicator housing 6702 and sensor electronics housing 706, which has been inserted into sensor carrier 6710. Inner sheath ribs 6425 are also shown.

It should be noted that although six inner sheath ribs 6425 and six corresponding rib notches 6519 are depicted, any number of ribs and notches are fully within the scope of the present disclosure. Moreover, while ribs 6425 are depicted with a rounded surface edge, in other embodiments, ribs 6425 can have a rectangular or triangular shape, and rib notches 6519 can have a corresponding receiving shape for interfacing with ribs 6425. In addition, although ribs 6425 are depicted as being disposed on an inner circumferential surface of sheath 6704, ribs 6425 can also be disposed on any other surface of sheath 6704, or portion thereof, that comes into contact with sensor carrier 6710.

Figure 8J:
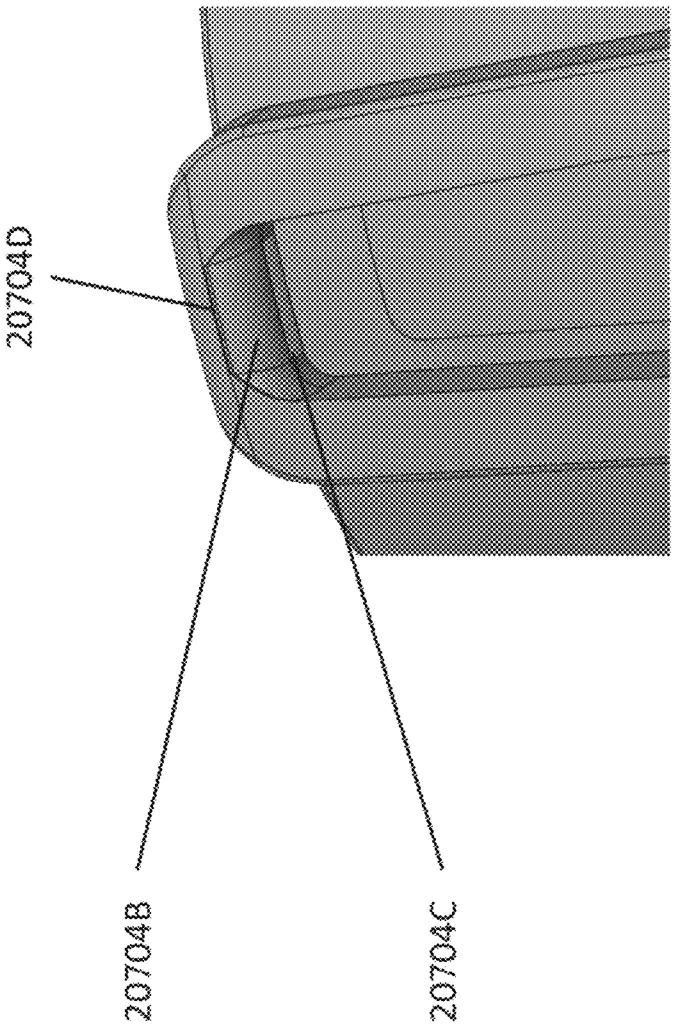
FIG. 8J is a close-up view of a detent snap of the sheath of FIG. 8I.
Figure 8K:
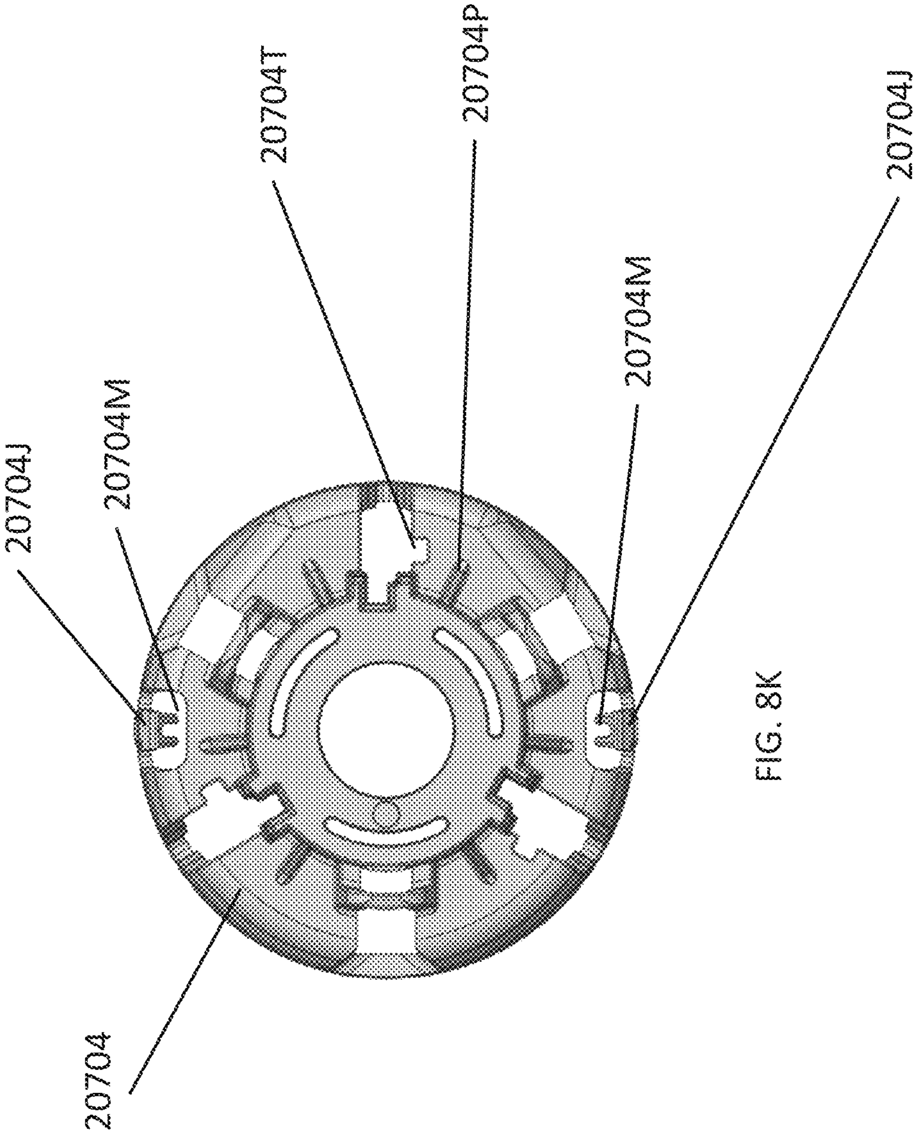
FIG. 8K is a top view of the sheath of FIG. 8I.
Figure 8L:
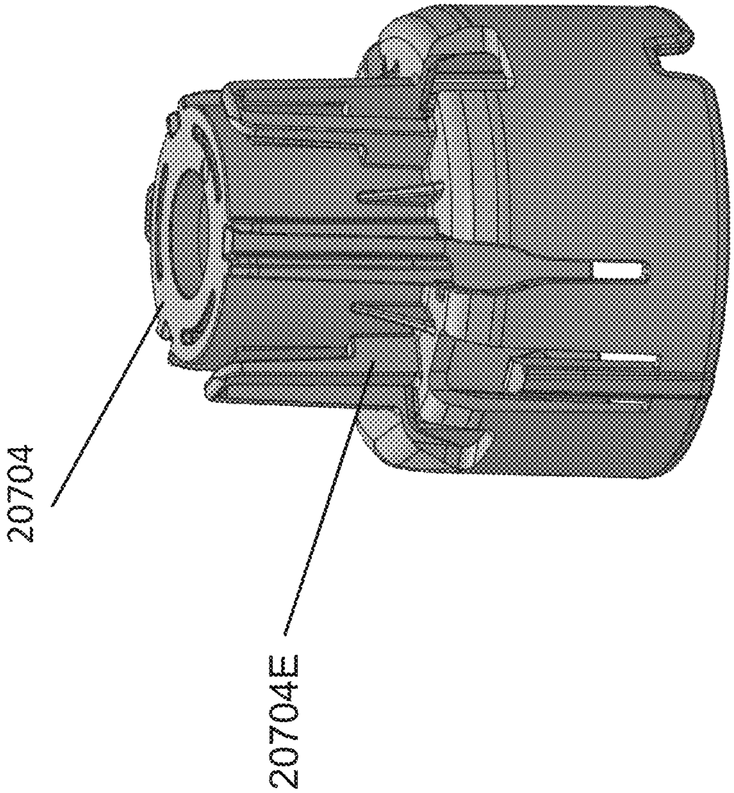
FIG. 8L is a perspective view of the sheath of FIG. 8I.
Figure 8M:
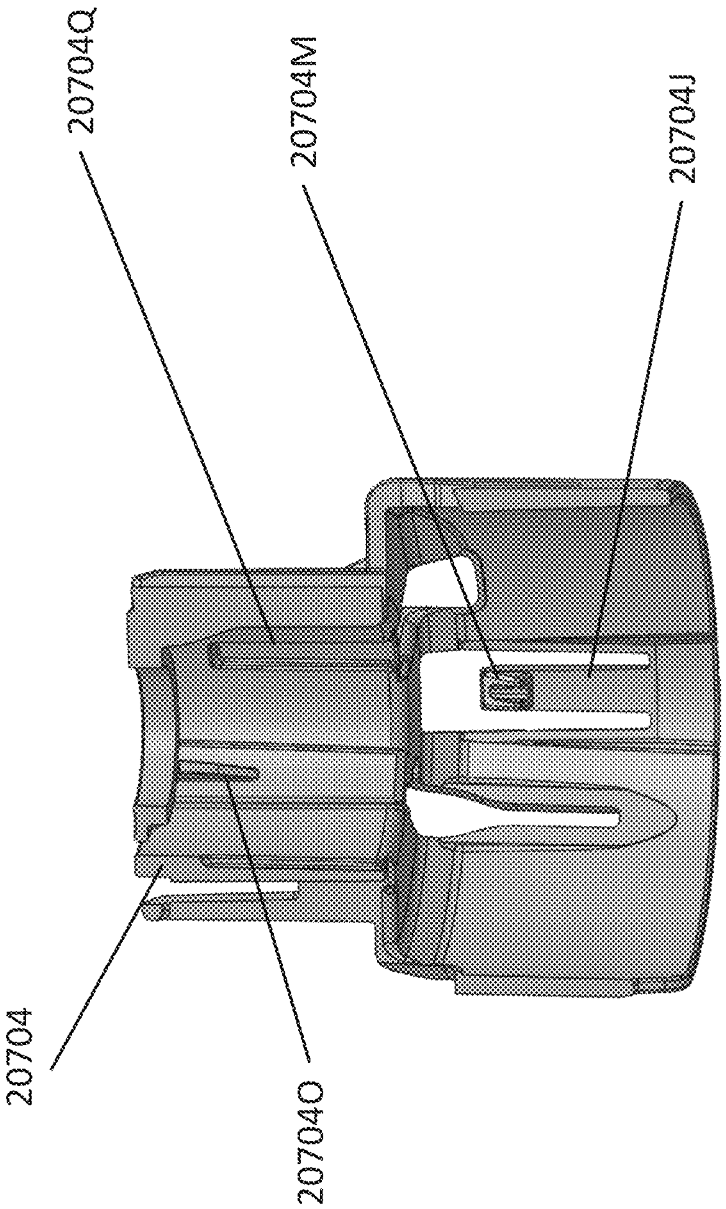
FIG. 8M is a side cutaway view of the sheath of FIG. 8I.
Figure 8N:
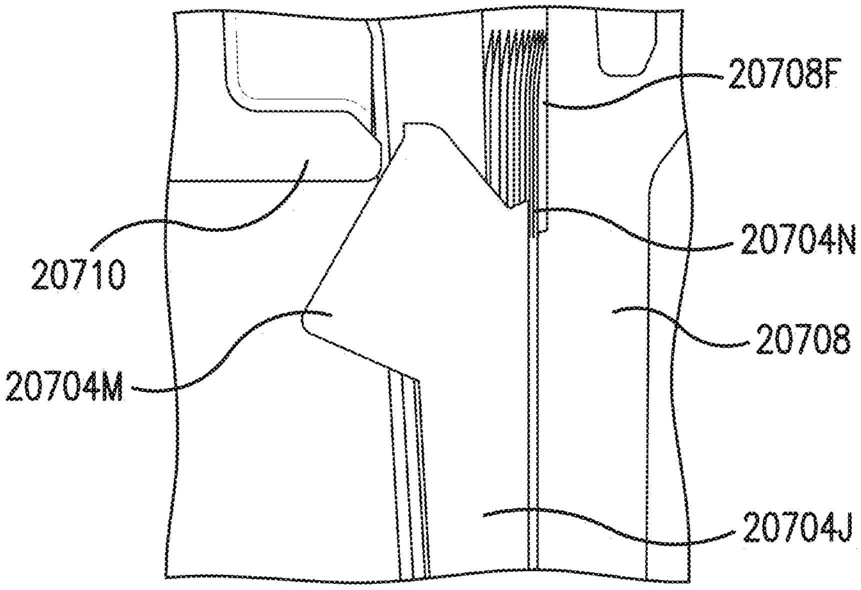
FIG. 8N is a close-up view a lock arm of the sheath of FIG. 8I and the lock arm's engagement with a cap and a sensor carrier, in accordance with the disclosed subject matter.
Figure 8O:
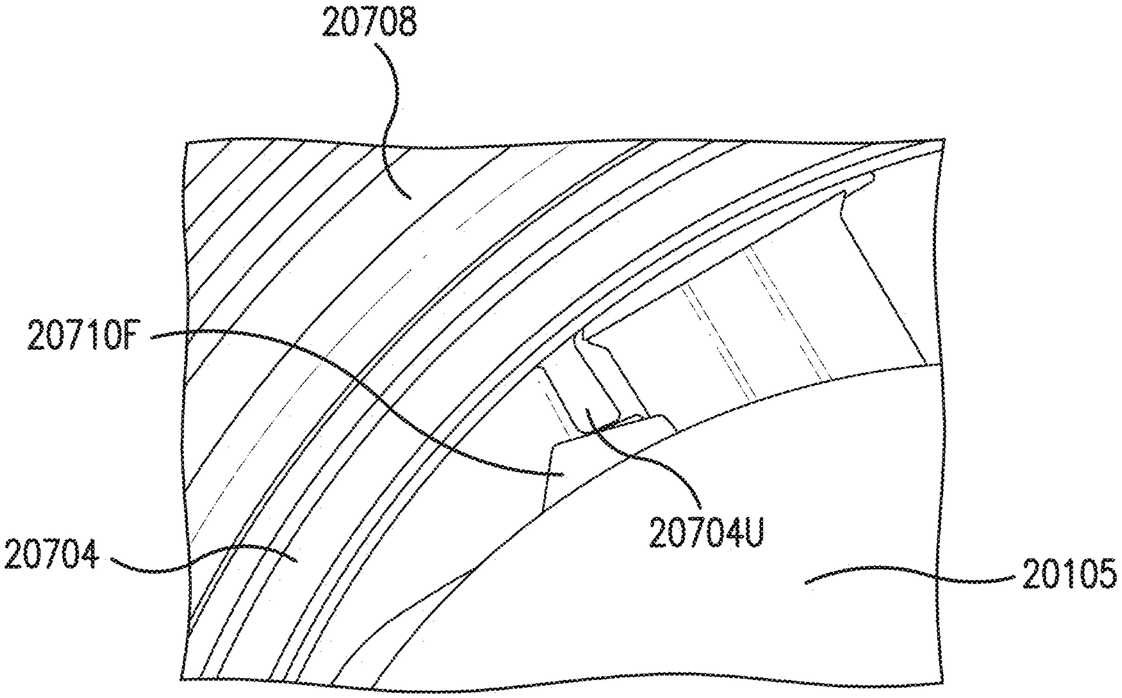
FIG. 8O is a close-up view of a rib of the sheath of FIG. 8I and the rib's engagement with a sensor carrier, in accordance with the disclosed subject matter.

Referring to FIGS. 8I-8O, for purpose of illustration and not limitation, a sheath 20704 is provide, in accordance with the disclosed subject matter. Sheath 20704 can be made of Delrin or other suitable materials, for example, other low friction polymers. Sheath 20704 can include one or more of the features described herein with regard to sheaths, wherein similar features can operate as described herein. For example, sheath 20704 can include detent snaps 20704A having a free proximal end, configured to engage the sheath ribs 20702S during firing. FIG. 8J shows a close up of the free proximal end of detent snap 20704A. The detent snaps 20704A can include a round portion 20704B, for engagement with the sheath ribs 20702S and a flat portion 20704C for final lockout on housing 20704 after use. The round portion 20704B can include a parting line mismatch 20704D that can prevent a force spike during firing. The detent snaps 20704A can be coupled to the sheath 20704 at an enlarged distal portion 20704E, which can provide support to the detent snap 20704. Sheath 20704 can include a plurality of detent snaps 20704A, for example, three. The sheath 20704 can include one or more, for example, three, housing clearances 20704F, which can allow the sheath 20704 to clear the housing 20702 at the end of firing. In accordance with the disclosed subject matter, sheath 20704 can further include a plurality of stiffening ribs 20704P (e.g., six) which can stiffen the sheath 20704.

Sheath 20704 can include a plurality of guides 20704G for engaging the sheath guide rails 20702J of the housing 20702. Sheath 20704 can further include a slot 20704H including a stop 20704J at a distal end of the slot 20704H configured to engage the sheath guide rails 20702J of the sheath 20702 to limit further proximal movement of the sheath 20704 relative the housing 20702 at the end of firing. Sheath 20704 can also include a clearance 20704T for clearing the sensor carrier biasing feature 20702I disposed on the sheath guide rails 20702J of the housing 20702.

In accordance with the disclosed subject matter, sheath 20704 can include lock arms 20704J. Lock arms 20704J can be configured to engage the sensor carrier 20710 and limit movement of the sensor carrier 20710 or sheath 20704 prior to firing. The lock arms 20704J can include a free proximal end 20704K and an attached distal end 20704L. The free proximal end 20704K can include a lock arm interface 20704M disposed on an inner surface of the lock arm 20704J. The lock arm interface 20704M can engage a lock ledge 20710N on the sensor carrier 20710. For example, when cap 20708 is coupled to housing 20702, the cap 20708 can urge the lock arm 20704J inwardly, and can cause the lock arm interface 20704M to engage the sensor carrier 20710. That is, the lock arms 20704J can wedge between the cap 20708 and the sensor carrier 20710. Accordingly, the lock arm 20704J can limit proximal movement of the sheath 20704 when the cap 20708 is coupled to the housing 20702. Such engagement can limit movement of the sheath 20704 during a shock event, such as a drop. The lock arm interface 20704M can have a triangle shape when viewed in side view (e.g., FIG. 8N) and a “U” shape when viewed in top view (e.g., FIG. 8K). The shape of the lock arm interface 20704M can provide benefits during manufacturing. For example, the shape of the lock arm interface 20704M can allow the sheath 20704 to be force ejected from a mold during manufacturing of the sheath 20704. Force ejecting the sheath 20704 can allow for a more a simplified manufacture process, for example, using a one-piece mold, and can eliminate parting lines created from two-piece molds. Parting lines can result in an unsmooth surface which can catch on the sensor carrier 20710 during firing and can result in potential spikes in firing force. Accordingly, using force ejection and a one-piece mold can create a smoother lock arm interface 20704M and prevent potential spikes in firing force due to parting lines.

The proximal free end of the lock arm 20704J can further include a sharp edge 20704N on an outer surface. The sharp edge 20704N can be configured to engage crush ribs 20708F disposed on the cap 20708 during a shock event. The sharp edge 20704N can dig into the crush ribs 20708F and permanently deform the crush ribs 20708F, which can absorb energy during a shock event, and prevent sheath 20704 collapse. The shape lock arm interface 20704M can also be beneficial for drop protection. The ramp can force the lock arm 20704J to move radially as the sheath 20704 collapsed during a drop. This can force the sharp edge 20704N to dig into the crush ribs 20708F and can help to stop the sheath 20704 from collapsing. Sheath 20704 can include a plurality of lock arms 20704J, for example, two lock arms 20704J.

Additionally or alternatively, sheath 20704 can include rib 20704U configured to engage a lock interface 20710F on a sensor retention arm 20710B on the sensor carrier 20710. The rib 20704U can prevent the sensor retention arm 20710B from flexing outwardly, for example, during a shock event, and therefore can prevent movement of the sensor control device 20102 during a shock event. Rib 20704U can have a height (i.e., in the longitudinal direction) selected such that even if the sheath 20704 moves proximally or distally during a shock event, the rib 20704U will continue to engage lock interface 20710F on a sensor retention arm 20710B on the sensor carrier 20710 and prevent the sensor control device 20102 from dislodging from the sensor carrier 20710.

The sheath 20704 can include a noise damper 20704O. The noise damper 20704O can be configured to engage the sharp carrier 201102 as the sharp carrier 201102 is retracted to slow movement of the sharp carrier 201102 and can thereby reduce noise produce by the sharp carrier 201102 engaging the sheath 20704. In exemplary embodiments, the noise damper 20704O includes an angled ramp extending from the inner surface of sheath 20704, but other suitable configurations can be used.

In accordance with the disclosed subject matter, sheath 20704 can include a slot 20704Q configured to receive sharp carrier retention feature 20710L disposed on the sensor carrier 20710 and to thereby permit partial retraction of the sharp carrier 201102 during deployment (as described in greater detail below). The sheath 20704 can also include cap lead-in 20704R, alignment notch 20704S and skin interface 20704T.

Exemplary Sensor Carriers

Figure 9A:
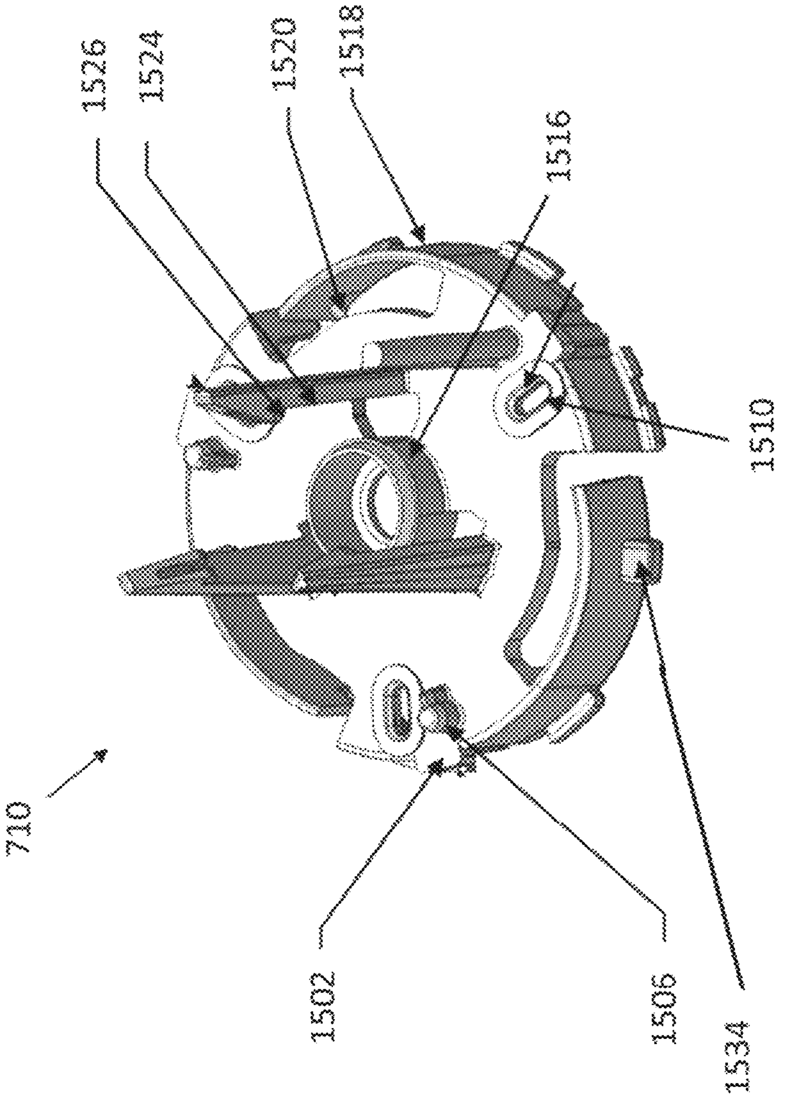
FIG. 9A is a proximal perspective view depicting an example embodiment of a sensor carrier.

FIG. 9A is a proximal perspective view depicting an example embodiment of sensor carrier 710 that can retain sensor electronics within applicator 150. It can also retain sharp carrier 1102 with sharp module 2500. In this example embodiment, sensor carrier 710 generally has a hollow round flat cylindrical shape, and can include one or more deflectable sharp carrier lock arms 1524 (e.g., three) extending proximally from a proximal surface surrounding a centrally located spring alignment ridge 1516 for maintaining alignment of spring 1104. Each lock arm 1524 has a detent or retention feature 1526 located at or near its proximal end. Shock lock 1534 can be a tab located on an outer circumference of sensor carrier 710 extending outward and can lock sensor carrier 710 for added safety prior to firing. Rotation limiter 1506 can be a proximally extending relatively short protrusion on a proximal surface of sensor carrier 710 which limits rotation of carrier 710. Sharp carrier lock arms 1524 can interface with sharp carrier 1102 as described with reference to FIGS. 10A-10E below.

Figure 9B:
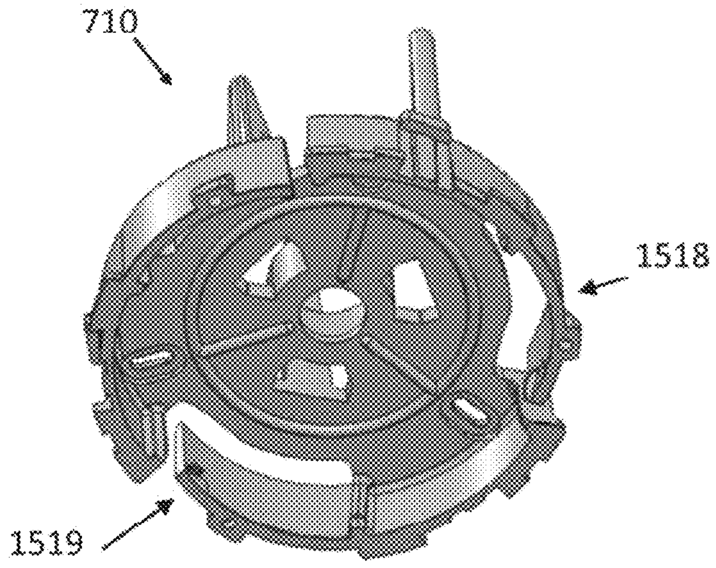
FIG. 9B is a distal perspective view depicting an example embodiment of a sensor carrier.

FIG. 9B is a distal perspective view of sensor carrier 710. Here, one or more sensor electronics retention spring arms 1518 (e.g., three) are normally biased towards the position shown and include a detent 1519 that can pass over the distal surface of electronics housing 706 of device 102 when housed within recess or cavity 1521. In certain embodiments, after sensor control device 102 has been adhered to the skin with applicator 150, the user pulls applicator 150 in a proximal direction, i.e., away from the skin. The adhesive force retains sensor control device 102 on the skin and overcomes the lateral force applied by spring arms 1518. As a result, spring arms 1518 deflect radially outwardly and disengage detents 1519 from sensor control device 102 thereby releasing sensor control device 102 from applicator 150.

Figure 9C:
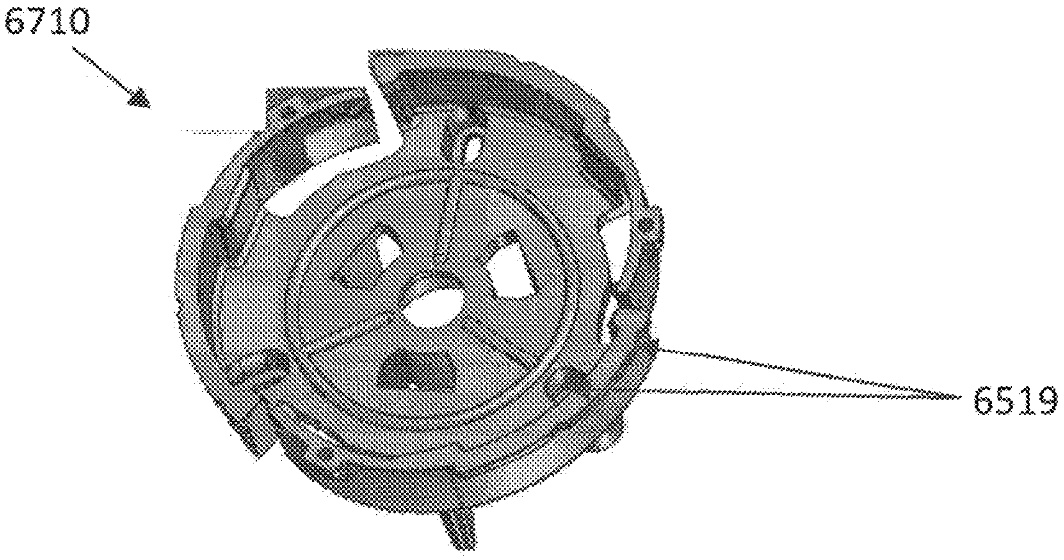
FIG. 9C is a distal perspective view depicting another example embodiment of a sensor carrier.

FIG. 9C is a perspective view of an alternative example embodiment of sensor carrier 6710. As shown in FIG. 9C, sensor carrier 6710 can have many of the same features as sensor carrier 710, previously described with respect to FIGS. 9A-9B. In addition, sensor carrier 6710 also includes one or more notch ribs 6519 disposed along an outer circumferential surface. As best seen in FIGS. 8F-8H, notch ribs 6519 are configured to interface with inner sheath ribs 6425 in order to maintain axial alignment of the sheath and sensor carrier, and reduce lateral and rotational movement between applicator components during the sensor insertion process.

Figure 9D:
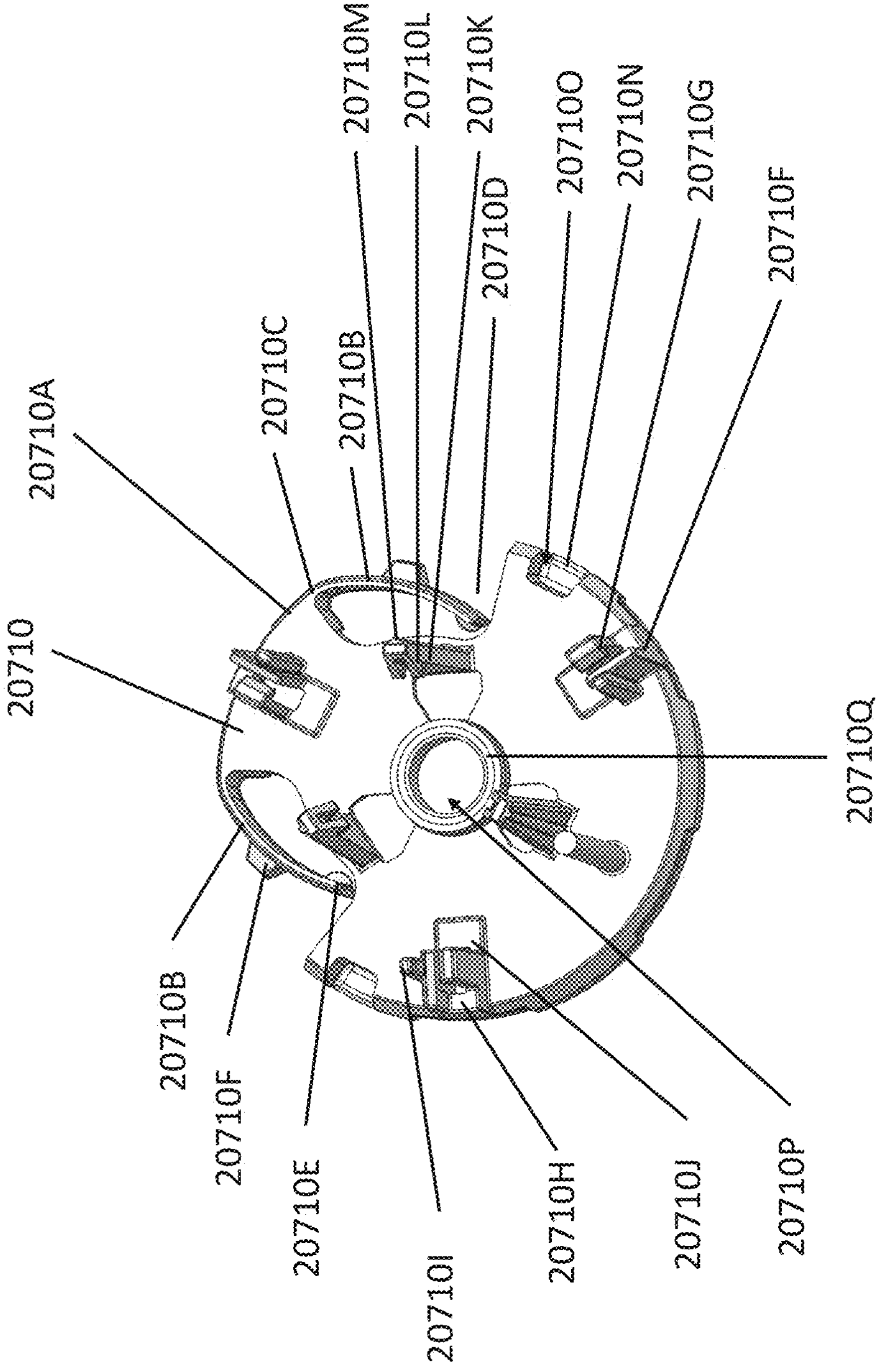
FIG. 9D is a top perspective view of a sensor carrier in accordance with the disclosed subject matter.
Figure 9E:
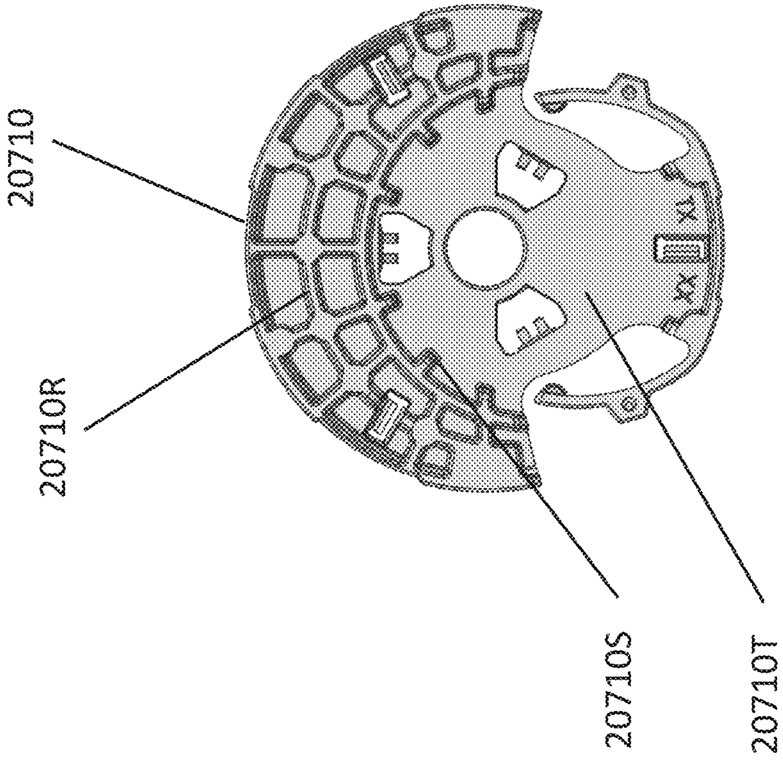
FIG. 9E is a bottom view of the sensor carrier of FIG. 9D.

Referring to FIGS. 9D and 9E, for purpose of illustration and not limitation, an exemplary sensor carrier 20710 is provided. Sensor carrier 20710 can include one or more of the features described herein with regard to sensor carriers, wherein similar features can operate as described herein. For example, sensor carrier 20710 can include a base 20710A and first and second retention arms 20710B. Each retention arm 20710B can include a first end portion 20710C coupled to the base 20710A and a free end portion 20710D. For example, each retention arm 20710B can be coupled to the base 20710A at a first half of the base 20710A and the free end portion 20710D can extend toward a second half of the base 20710A. Each retention arm 20710B can include a sensor retention feature 20710E disposed on an inner surface of the sensor retention arm 20710B. The sensor retention feature 20710E can be disposed on the free end portion 20710D. The sensor retention feature 20710E can be configured to retain the sensor control device 20102 within the housing 20702. The retention feature 20710E can include a conical surface and angular parting line, which can allow for release of the sensor control device 20102 upon delivery. Each retention arm 20710 can include a lock interface 20710F disposed on an outer surface of the retention arm 20710B. The lock interface 20710F can engage rib 20704U on the sheath 20704. As described hereinabove, the rib 20704U can prevent the sensor retention arm 20710B from flexing outwardly, for example, during a shock event, and therefore can keep retention feature 20710E engaged with the sensor control device 20102, and thereby prevent movement of the sensor control device 20102 during a shock event.

Sensor carrier 20710 can include a plurality of housing attachment features 20710F, for example three housing attachment features 20710F. The housing attachment features 20710F can be equally spaced on the sensor carrier 20710 and can extend upwardly from a top surface of the sensor carrier 20710. Each sensor housing attachment feature 20710F can include a housing snap 20710G, housing locator feature 20710H, biasing feature 20710I, and housing stop 20710J. The housing locator feature 20710H can locate the sensor carrier 20710 relative the housing 20702 when the two are to be coupled together. The housing snap 20710G can engage the sensor carrier attach slots 20702K on the housing 20702 to couple the sensor carrier 20710 to the housing 20702. The biasing feature 20710I can engage sensor carrier biasing feature 20702M on housing 20702 configured to remove slop between the sensor carrier 20710 and the housing 20702. Housing stop 20710) can engage sensor carrier hard stop 20702L on sheath guide rails 20702J on housing 20702 to locate the sensor carrier 20710 axially relative to the housing 20702.

Sensor carrier 20710 can further include a plurality of sharp carrier lock arms 20710K, for example three sharp carrier lock arms 20710K. The sharp carrier lock arms 20710K can be equally spaced on the sensor carrier 20710 and can extend upwardly form a top surface of the sensor carrier 20710. Each sharp carrier lock arm 20710K can include a sharp carrier retention feature 20710L and a rib 20710M. Rib 20710M can engage an inner surface of the sheath 20704, which can urge the sharp carrier lock arm 20710K inwardly and cause sharp carrier retention feature 20710L to retain sharp carrier 201102, as described in greater detail below. The carrier retention feature 20710L can have a triangle shape when viewed in side view and a "U" shape when viewed in top view.

In accordance with the disclosed subject matter, the sensor carrier 20710 can include a plurality of lock ledges 20710N configured to engage lock arm interface 20704M of the sheath 20704 as described herein above. For example, the sensor carrier 20710 can include two lock ledges 20710N. Sensor carrier 20710 can include recesses 207100 disposed proximate each lock ledge 20710N and configured to receive the lock arm interface 20704M during firing, to prevent the lock arm 20704J from engaging with housing 20702 during firing. Sensor carrier 20710 can include a hole 20710P extending through a middle of the base 20710A. The hole 20710P can guide and limit movement of sharp hub 205014 during insertion. Additionally, or alternatively, sensor carrier 20710 can include spring locator 20710Q.

A bottom surface of the sensor carrier 20710 can include stiffening ribs 20710R and sensor locator ribs 20710S, which can limit planar motion of the sensor control device 20102 relative the sensor carrier 20710. The bottom surface of the sensor carrier 20710 can include a sensor support surface 20710T configure to support the sensor control device 20102.

Exemplary Sharp Carriers

Figure 10A:
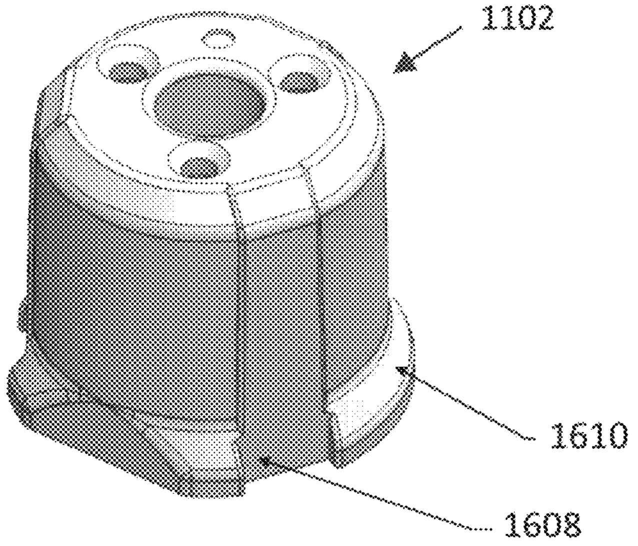
FIG. 10A is a perspective view of a sharp carrier in accordance with the disclosed subject matter.
Figure 10B:
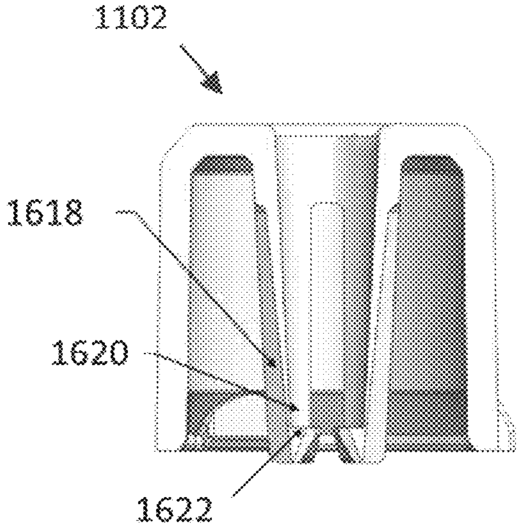
FIG. 10B is a side cutaway view of the sharp carrier of FIG. 10A.

FIGS. 10A and 10B are a proximal perspective view and a side cross-sectional view, respectively, depicting an example embodiment of sharp carrier 1102. Sharp carrier 1102 can grasp and retain sharp module 2500 within applicator 150. It can also automatically retract as a result of one or more springs changing from a preloaded, compressed state to an expanded state during an insertion process, as described with respect to FIGS. 40A-40F. Near a distal end of sharp carrier 1102 can be anti-rotation slots 1608 which prevent sharp carrier 1102 from rotating when located within a central area of sharp carrier lock arms 1524 (as shown in FIG. 9A). Anti-rotation slots 1608 can be located between sections of sharp carrier base chamfer 1610, which can ensure full retraction of sharp carrier 1102 through sheath 704 upon retraction of sharp carrier 1102 at the end of the deployment procedure.

Figure 17A:
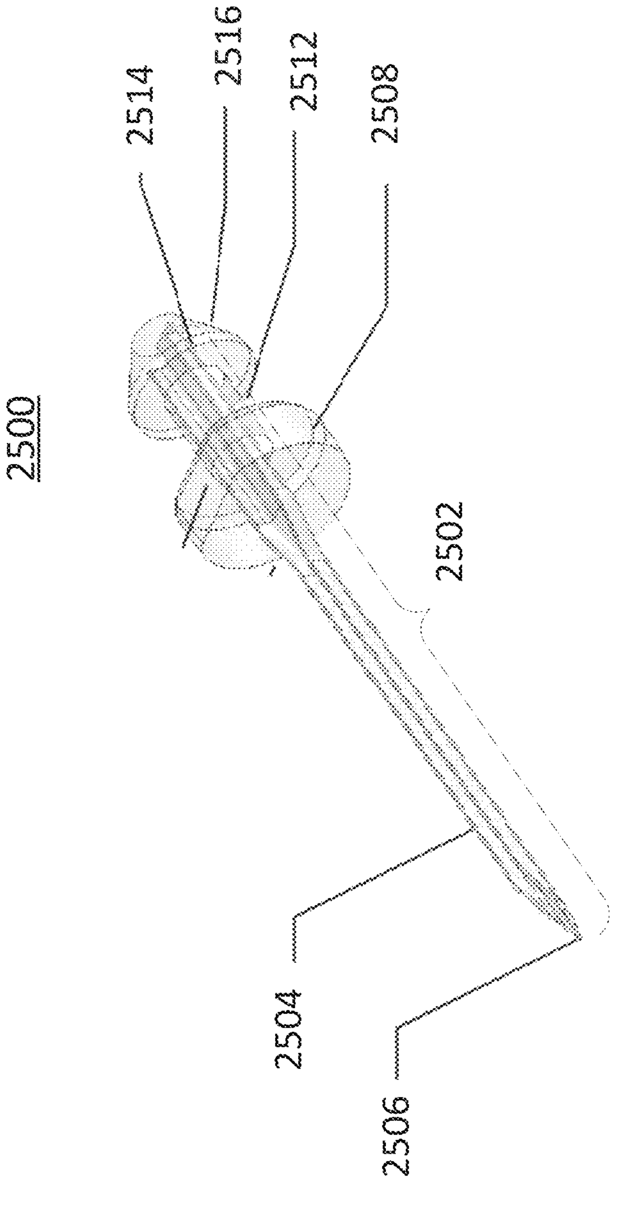
FIG. 17A is a perspective view depicting an example embodiment of a sharp module.

As shown in FIG. 10B, sharp retention arms 1618 can be located in an interior of sharp carrier 1102 about a central axis and can include a sharp retention clip 1620 at a distal end of each arm 1618. Sharp retention clip 1620 can have a proximal surface which can be nearly perpendicular to the central axis and can abut a distally facing surface of sharp hub 2516 (FIG. 17A).

Figure 10C:
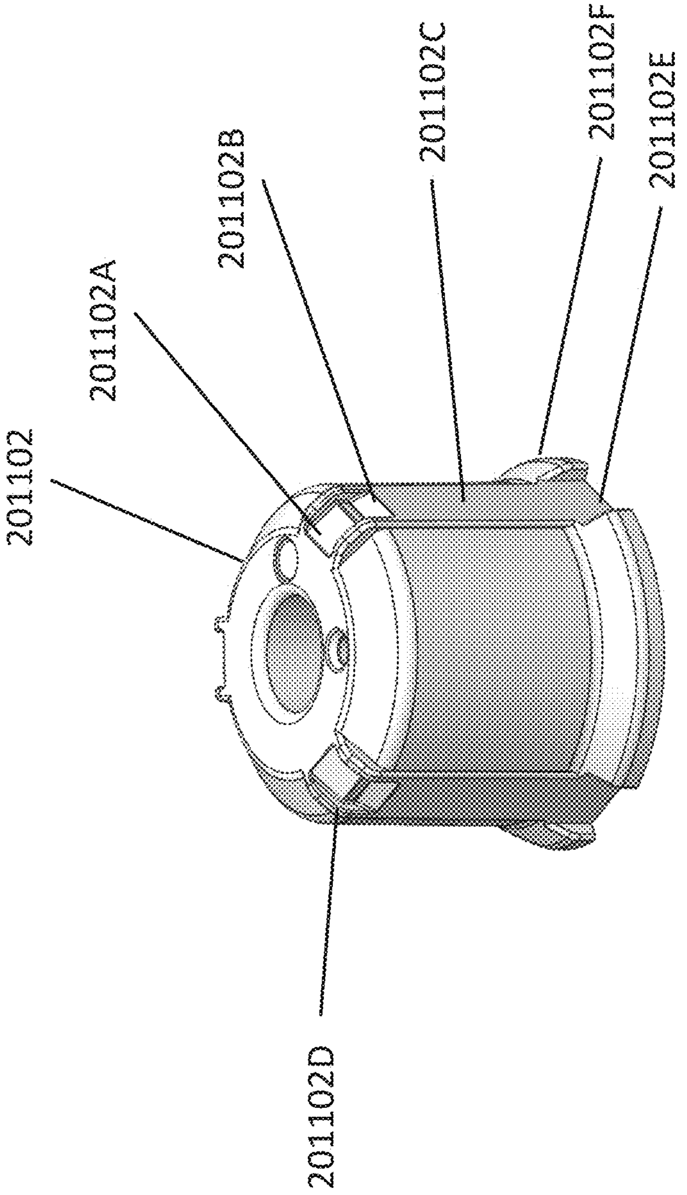
FIG. 10C is a perspective view of a sharp carrier in accordance with the disclosed subject matter.
Figure 10D:
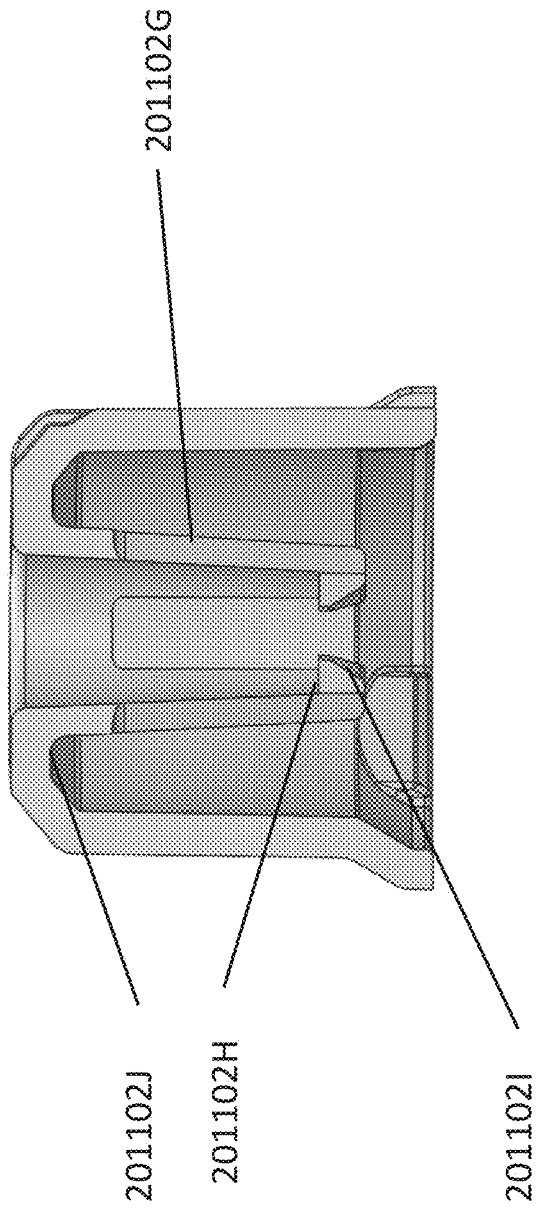
FIG. 10D is a side cutaway view of the sharp carrier of FIG. 10C.

Referring to FIGS. 10C and 10D, for purpose of illustration and not limitation, an exemplary sharp carrier 201102 is provided. Sharp carrier 201102 can include one or more features described herein with regard to sharp carriers, wherein similar features can operate as describe herein. For example, sharp carrier 201102 can include a series of features for engaging with the three sharp carrier lock arms 20710K of the sensor carrier 20710. The features can include a pre-partial-retraction retention face 201102A and a post-partial-retraction retention face 201102B. The pre-partial retraction retention face 201102A can engage the sharp carrier retention feature 20710L prior to partial retraction, for example, during shipping and storage. Post-partial-retraction retention face 201102B can engage the sharp carrier retention feature 20710L after partial retraction. For example, as the sheath 20704 initially move proximally relative to the sensor carrier 20710, the rib 20710M of the retention arm 20710L can engage slot 20704Q of sheath 20704, which can allow the retention arm 20710L to move radially outward and allow sharp carrier retention feature 20710L to clear the pre-partial retraction retention face 201102A and engage the post-partial retraction retention face 201102B. A height between the end of the pre-partial-retraction face 201102A and the start of the post-partial-retraction face 201102B can be the distance of the partial retraction. A running face 201102C can be disposed below the post-partial-retraction retention face 201102B and can slide against the retention arm 20710L as the sharp carrier 201102 is retracted. Alignment walls 201102D can help to keep the sharp carrier 201102 aligned with the sensor carrier 20704 during partial retraction. Sharp carrier 201102 can include a chamfer 201102F, which can include anti-rotation slots 201102E to engage the retention arms 20710L on the sensor carrier 20710.

Internally, sharp carrier 201102 can include sharp retention arms 201102G including lead-in face 201102I and sharp hub contact face 201102H. The retention arms 201102G can receive and hold sharp hub 205014. Spring stop 201102J can engage retraction spring 205612.

Spring 205612 can include any type of spring known in the art, such as a helical spring. For example, according to certain embodiments, spring 205612 may include a helical spring constructed of stainless steel. Spring 205612 may include a spring constant of any suitable range, and a wire diameter, an inner diameter, an outer diameter, and a maximum solid strength of any suitable dimension. For example, the spring constant can be about 0.12, the wire diameter can be about 0.65 millimeters, the inner diameter can be about 9.6 millimeter, the outer diameter can be about 11.1 millimeters, and the maximum solid strength can be 11 millimeters. It is noted that each of the parameter values listed above may be provided independently without requiring a particular embodiment of the spring to fulfill all of the listed parameter values. For example, a spring 205612 may be provided having a spring constant of about 0.12 while having different dimensions to those listed above, or a spring 205612 may have a different wire diameter while having the other highlighted dimensions.

Exemplary Sensor Modules

Figure 11B:
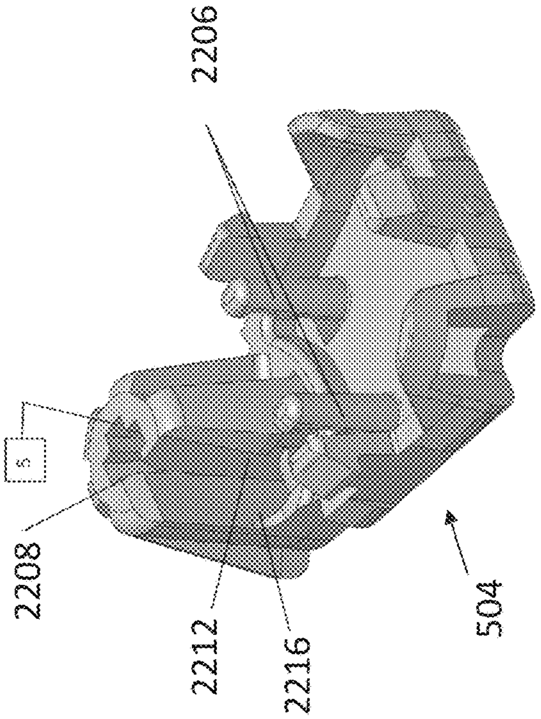
FIGS. 11A to 11B are top and bottom perspective views, respectively, depicting an example embodiment of a sensor module.
Figure 11A:
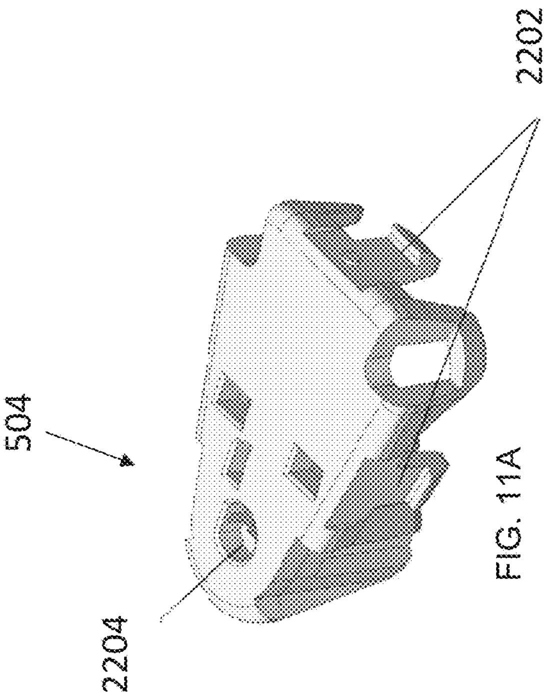

FIGS. 11A and 11B are a top perspective view and a bottom perspective view, respectively, depicting an example embodiment of sensor module 504. Module 504 can hold a connector 2300 (FIGS. 12A and 12B) and a sensor 104 (FIG. 13). Module 504 is capable of being securely coupled with electronics housing 706. One or more deflectable arms or module snaps 2202 can snap into the corresponding features 2010 of housing 706. A sharp slot 2208 can provide a location for sharp tip 2502 to pass through and sharp shaft 2504 to temporarily reside. A sensor ledge 2212 can define a sensor position in a horizontal plane, prevent a sensor from lifting connector 2300 off of posts and maintain sensor 104 parallel to a plane of connector seals. It can also define sensor bend geometry and minimum bend radius. It can limit sensor travel in a vertical direction and prevent a tower from protruding above an electronics housing surface and define a sensor tail length below a patch surface. A sensor wall 2216 can constrain a sensor and define a sensor bend geometry and minimum bend radius.

Figure 12A:
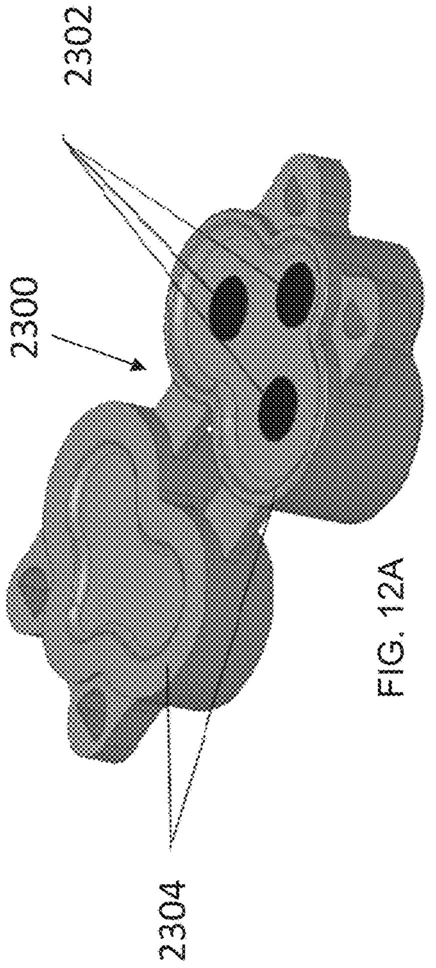
FIGS. 12A and 12B are perspective and compressed views, respectively, depicting an example embodiment of a sensor connector.
Figure 12B:
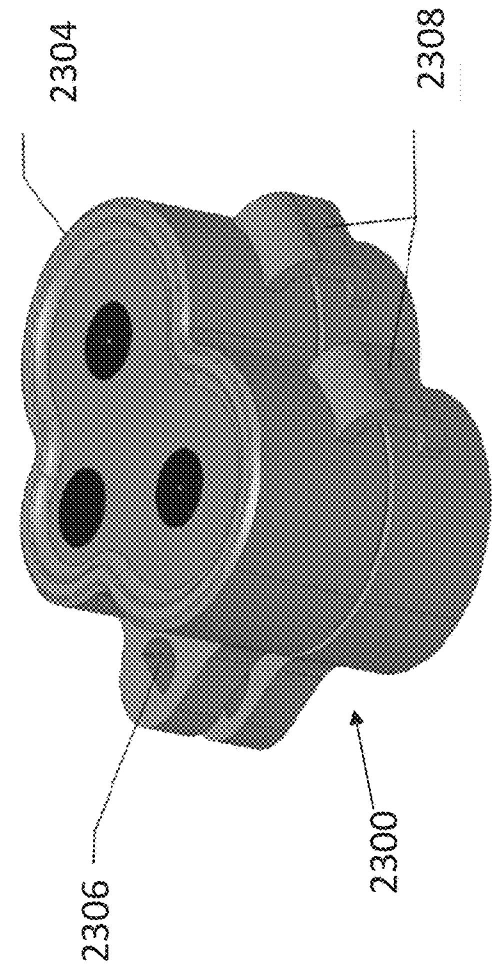
Figure 13:
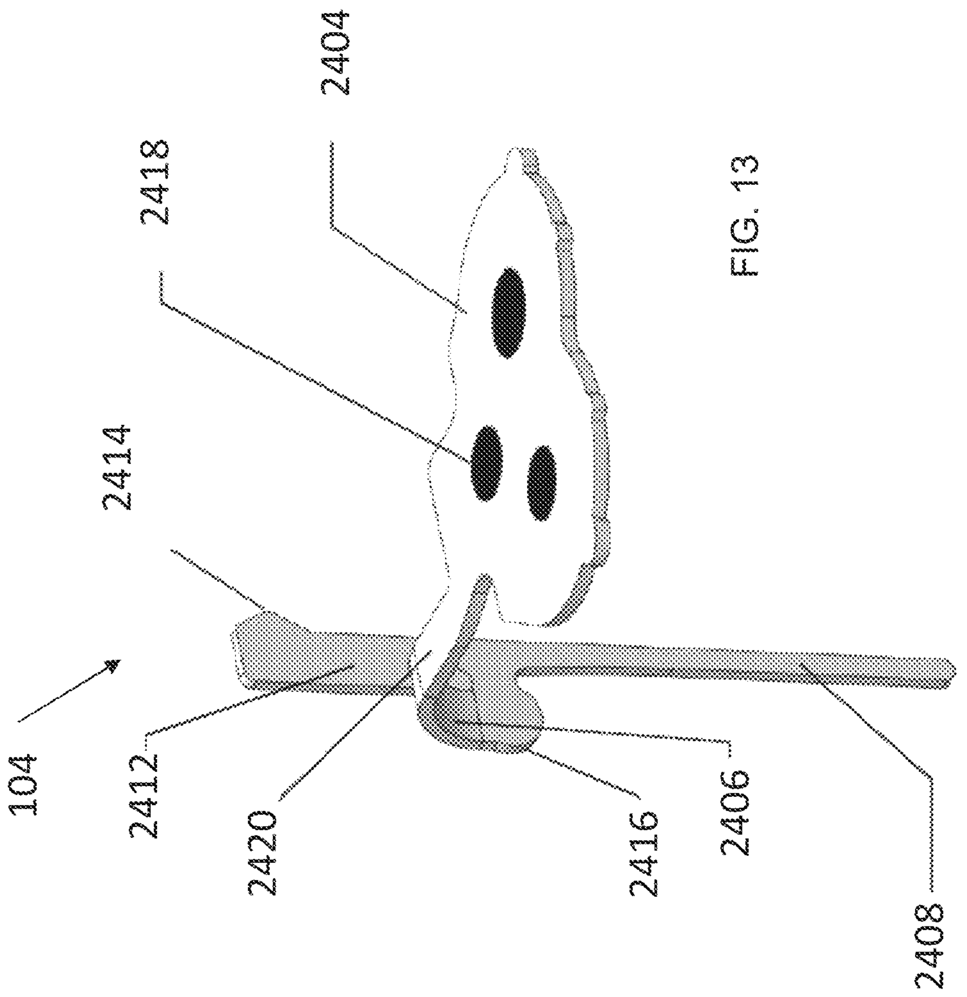
FIG. 13 is a perspective view depicting an example embodiment of a sensor.

FIGS. 12A and 12B are perspective views depicting an example embodiment of connector 2300 in an open state and a closed state, respectively. Connector 2300 can be made of silicone rubber that encapsulates compliant carbon impregnated polymer modules that serve as electrical conductive contacts 2302 between sensor 104 and electrical circuitry contacts for the electronics within housing 706. The connector can also serve as a moisture barrier for sensor 104 when assembled in a compressed state after transfer from a container to an applicator and after application to a user's skin. A plurality of seal surfaces 2304 can provide a watertight seal for electrical contacts and sensor contacts. One or more hinges 2208 can connect two distal and proximal portions of connector 2300.

FIG. 13 is a perspective view depicting an example embodiment of sensor 104. A neck 2406 can be a zone which allows folding of the sensor, for example ninety degrees. A membrane on tail 2408 can cover an active analyte sensing element of the sensor 104. Tail 2408 can be the portion of sensor 104 that resides under a user's skin after insertion. A flag 2404 can contain contacts and a sealing surface. A biasing tower 2412 can be a tab that biases the tail 2408 into sharp slot 2208. A bias fulcrum 2414 can be an offshoot of biasing tower 2412 that contacts an inner surface of a needle to bias a tail into a slot. A bias adjuster 2416 can reduce a localized bending of a tail connection and prevent sensor trace damage. Contacts 2418 can electrically couple the active portion of the sensor to connector 2300. A service loop 2420 can translate an electrical path from a vertical direction ninety degrees and engage with sensor ledge 2212 (FIG. 11B).

Figure 14B:
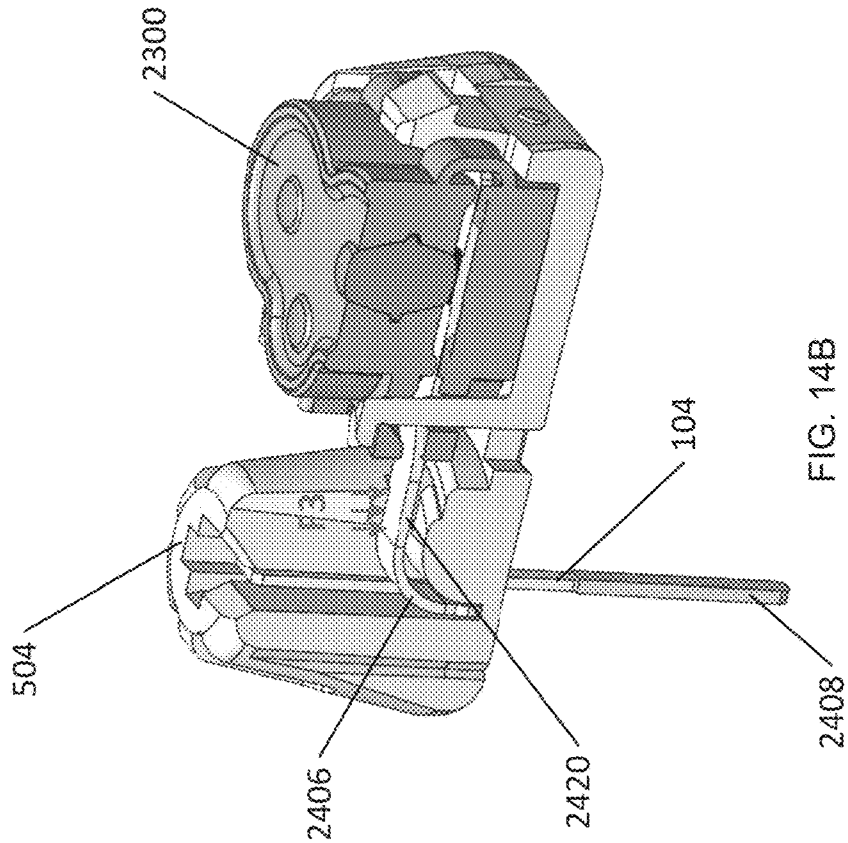
FIGS. 14A and 14B are bottom and top perspective views, respectively, of an example embodiment of a sensor module assembly.
Figure 14A:
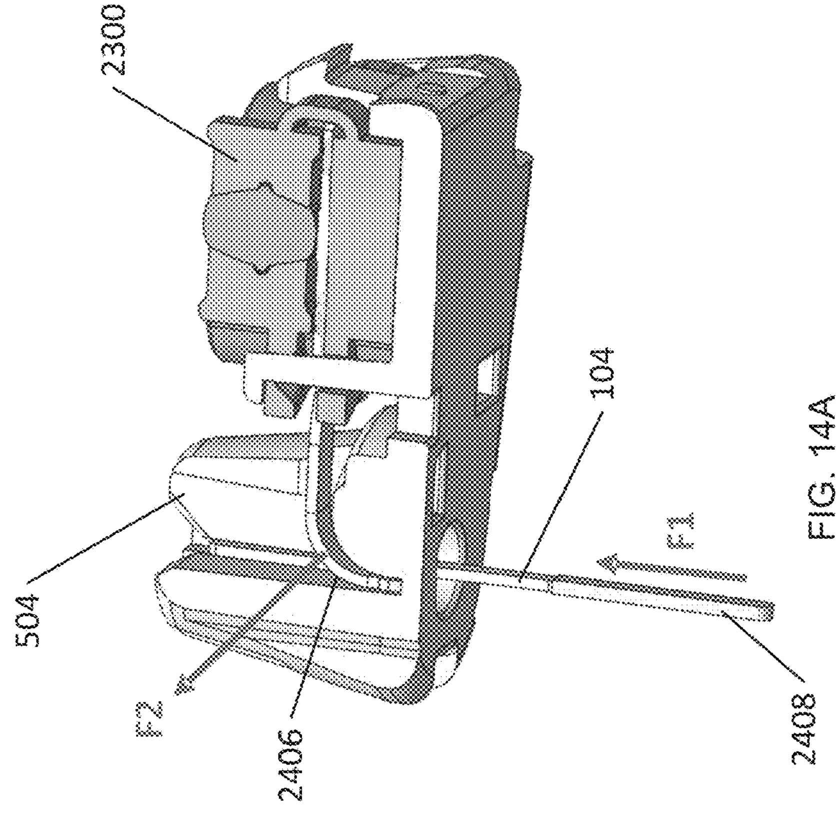

FIGS. 14A and 14B are bottom and top perspective views, respectively, depicting an example embodiment of a sensor module assembly comprising sensor module 504, connector 2300, and sensor 104. According to one aspect of the aforementioned embodiments, during or after insertion, sensor 104 can be subject to axial forces pushing up in a proximal direction against sensor 104 and into the sensor module 504, as shown by force, F1, of FIG. 14A. According to some embodiments, this can result in an adverse force, F2, being applied to neck 2406 of sensor 104 and, consequently, result in adverse forces, F3, being translated to service loop 2420 of sensor 104. In some embodiments, for example, axial forces, F1, can occur as a result of a sensor insertion mechanism in which the sensor is designed to push itself through the tissue, a sharp retraction mechanism during insertion, or due to a physiological reaction created by tissue surrounding sensor 104 (e.g., after insertion).

Figure 15B:
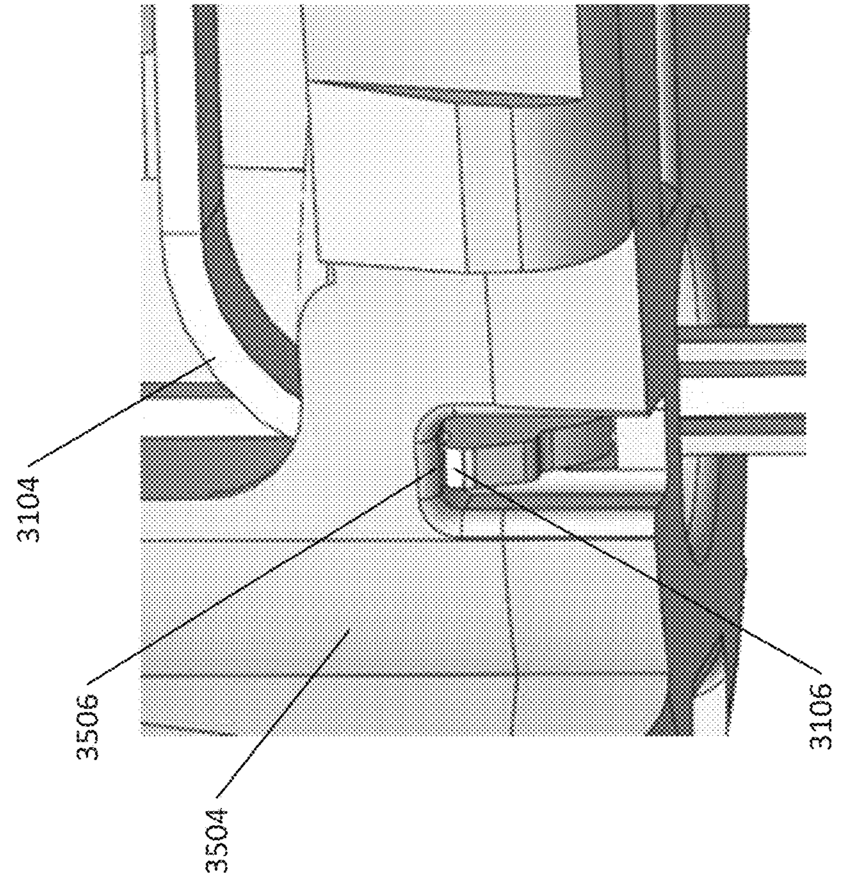
FIGS. 15A and 15B are close-up partial views of an example embodiment of a sensor module assembly.
Figure 15A:
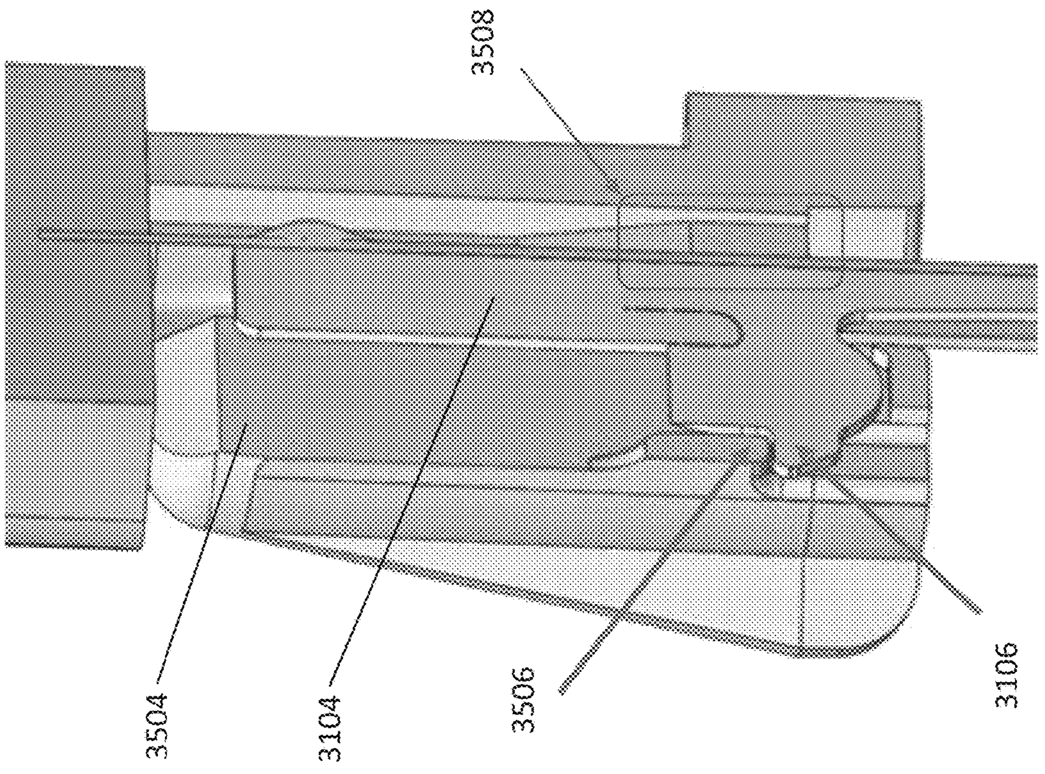

FIGS. 15A and 15B are close-up partial views of an example embodiment of a sensor module assembly having certain axial stiffening features. In a general sense, the embodiments described herein are directed to mitigating the effects of axial forces on the sensor as a result of insertion and/or retraction mechanisms, or from a physiological reaction to the sensor in the body. As can be seen in FIGS. 15A and 15B, according to one aspect of the embodiments, sensor 3104 comprises a proximal portion having a hook feature 3106 configured to engage a catch feature 3506 of the sensor module 3504. In some embodiments, sensor module 3504 can also include a clearance area 3508 to allow a distal portion of sensor 3104 to swing backwards during assembly to allow for the assembly of the hook feature 3106 of sensor 3104 over and into the catch feature 3506 of sensor module 3504.

According to another aspect of the embodiments, the hook and catch features 3106, 3506 operate in the following manner. Sensor 3104 includes a proximal sensor portion, coupled to sensor module 3504, as described above, and a distal sensor portion that is positioned beneath a skin surface in contact with a bodily fluid. As seen in FIGS. 15A and 15B, the proximal sensor portion includes a hook feature 3106 adjacent to the catch feature 3506 of sensor module 3504. During or after sensor insertion, one or more forces are exerted in a proximal direction along a longitudinal axis of sensor 3104. In response to the one or more forces, hook feature 3106 engages catch feature 3506 to prevent displacement of sensor 3104 in a proximal direction along the longitudinal axis.

According to another aspect of the embodiments, sensor 3104 can be assembled with sensor module 3504 in the following manner. Sensor 3104 is loaded into sensor module 3504 by displacing the proximal sensor portion in a lateral direction to bring the hook feature 3106 in proximity to the catch feature 3506 of sensor module 3504. More specifically, displacing the proximal sensor portion in a lateral direction causes the proximal sensor portion to move into clearance area 3508 of sensor module 3504.

Although FIGS. 15A and 15B depict hook feature 3106 as a part of sensor 3104, and catch feature 3506 as a part of sensor module 3504, those of skill in the art will appreciate that hook feature 3106 can instead be a part of sensor module 3504, and, likewise, catch feature 3506 can instead be a part of sensor 3106. Similarly, those of skill in the art will also recognize that other mechanisms (e.g., detent, latch, fastener, screw, etc.) implemented on sensor 3104 and sensor module 3504 to prevent axial displacement of sensor 3104 are possible and within the scope of the present disclosure.

Figure 15C:
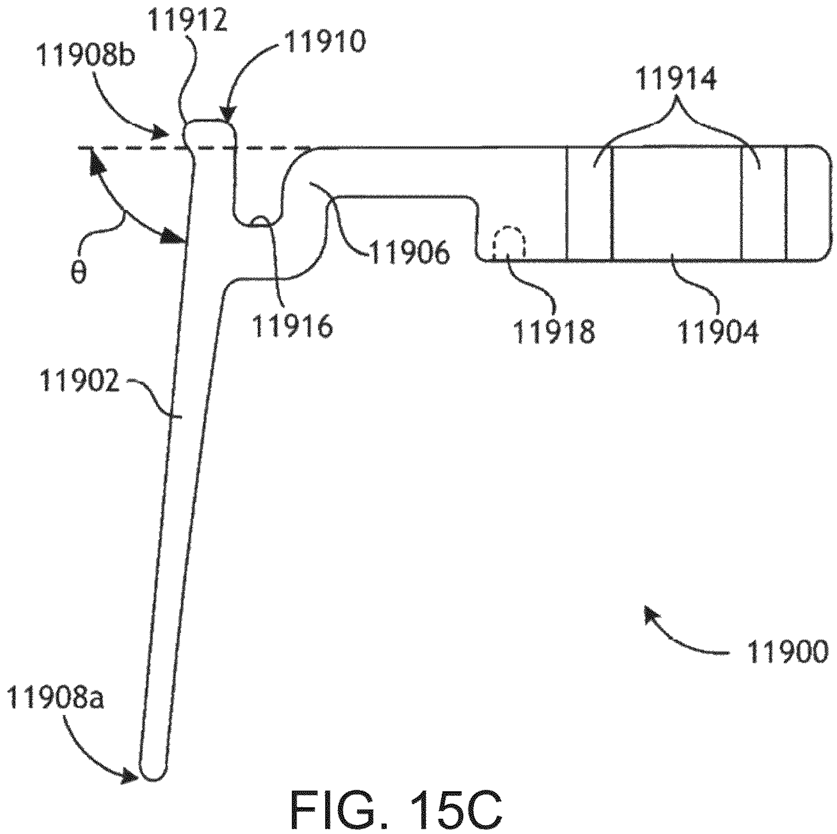
FIGS. 15C-G are side views of exemplary sensors, according to one or more embodiments of the disclosure.

FIG. 15C is a side view of an example sensor 11900, according to one or more embodiments of the disclosure. The sensor 11900 may be similar in some respects to any of the sensors described herein and, therefore, may be used in an analyte monitoring system to detect specific analyte concentrations. As illustrated, the sensor 11900 includes a tail 11902, a flag 11904, and a neck 11906 that interconnects the tail 11902 and the flag 11904. The tail 11902 includes an enzyme or other chemistry or biologic and, in some embodiments, a membrane may cover the chemistry. In use, the tail 11902 is transcutaneously received beneath a user's skin, and the chemistry included thereon helps facilitate analyte monitoring in the presence of bodily fluids.

The tail 11902 may be received within a hollow or recessed portion of a sharp (not shown) to at least partially circumscribe the tail 11902 of the sensor 11900. As illustrated, the tail 11902 may extend at an angle Q offset from horizontal. In some embodiments, the angle Q may be about 85°. Accordingly, in contrast to other sensor tails, the tail 11902 may not extend perpendicularly from the flag 11904, but instead at an angle offset from perpendicular. This may prove advantageous in helping maintain the tail 11902 within the recessed portion of the sharp.

The tail 11902 includes a first or bottom end 11908*a* and a second or top end 11908*b* opposite the bottom end 11908*a*. A tower 11910 may be provided at or near the top end 11908*b* and may extend vertically upward from the location where the neck 11906 interconnects the tail 11902 to the flag 11904. During operation, if the sharp moves laterally, the tower 11910 will help pivot the tail 11902 toward the sharp and otherwise stay within the recessed portion of the sharp. Moreover, in some embodiments, the tower 11910 may provide or otherwise define a protrusion 11912 that extends laterally therefrom. When the sensor 11900 is mated with the sharp and the tail 11902 extends within the recessed portion of the sharp, the protrusion 11912 may engage the inner surface of the recessed portion. In operation, the protrusion 11912 may help keep the tail 11902 within the recessed portion.

The flag 11904 may comprise a generally planar surface having one or more sensor contacts 11914 arranged thereon. The sensor contact(s) 11914 may be configured to align with a corresponding number of compliant carbon impregnated polymer modules encapsulated within a connector.

In some embodiments, as illustrated, the neck 11906 may provide or otherwise define a dip or bend 11916 extending between the flag 11904 and the tail 11902. The bend 11916 may prove advantageous in adding flexibility to the sensor 11900 and helping prevent bending of the neck 11906.

In some embodiments, a notch 11918 (shown in dashed lines) may optionally be defined in the flag near the neck 11906. The notch 11918 may add flexibility and tolerance to the sensor 11900 as the sensor 11900 is mounted to the mount. More specifically, the notch 11918 may help take up interference forces that may occur as the sensor 11900 is mounted within the mount.

In some embodiments, as illustrated in FIGS. 15D-15G, the neck can comprise or otherwise define a non-linear configuration such as a dip or bend 11920*a*-11920*d* with a plurality of turns, e.g., 11921*a*, 11921*b*, extending between the flag 11904 and the tail 11902. The bend 11920*a*-11920*d* can be advantageous in reducing in-place stiffness of the sensor 11900 by adding flexibility to the sensor 11900 in both a vertically-oriented and horizontally-oriented direction. The added flexibility can provide a multi-directional spring-like structure in the sensor 11900 that helps to limit deformation of the neck 11906 while ensuring that the tail 11902 and the flag 11904 can remain in their expected or fixed positions. The spring-like structure also increases compliance of the sensor 11900 while reducing stress on the overall structure.

Generally, the sensor can be understood as including a tail, a flag, and a neck aligned along a planar surface having a vertical axis and a horizontal axis. The spring-like structure can be created by various orientations of turns in the bend of the neck of a sensor. Between the tail and the flag, the neck can include at least two turns in relation to the vertical axis providing a spring-like structure. The at least two turns can provide, in relation to an axis of the planar surface shared by the tail, the flag, and the neck, overlapping layers of the structure of the neck, where the neck itself remains unbroken. These overlapping turns make up the spring-like structure. In some embodiments, the overlapping layers of the neck are vertically-oriented. In some embodiments, the overlapping layers of the neck are horizontally-oriented.

Figure 15D:
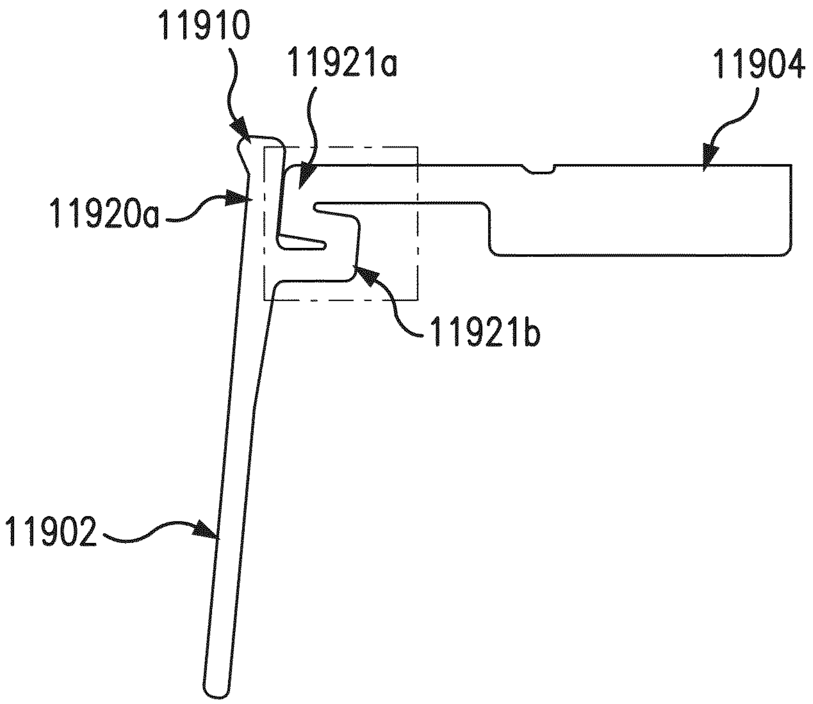

FIG. 15D illustrates one embodiment of a sensor 11900 including a neck between the flag 11904 and tail 11902 with a bend 11920*a* including turns 11921*a* and 11921*b*. In the illustrated embodiment, at least one turn 11921*a* abuts the top end of the tail or possibly the tower 11910 of the sensor 11900. This orientation can be advantageous in that it reduces the overall footprint of the sensor, even considering the additional material used to generate the bend 11920*a*. The arrangement can provide multiple overlapping, vertically-aligned horizontal layers between the turns.

Figure 15E:
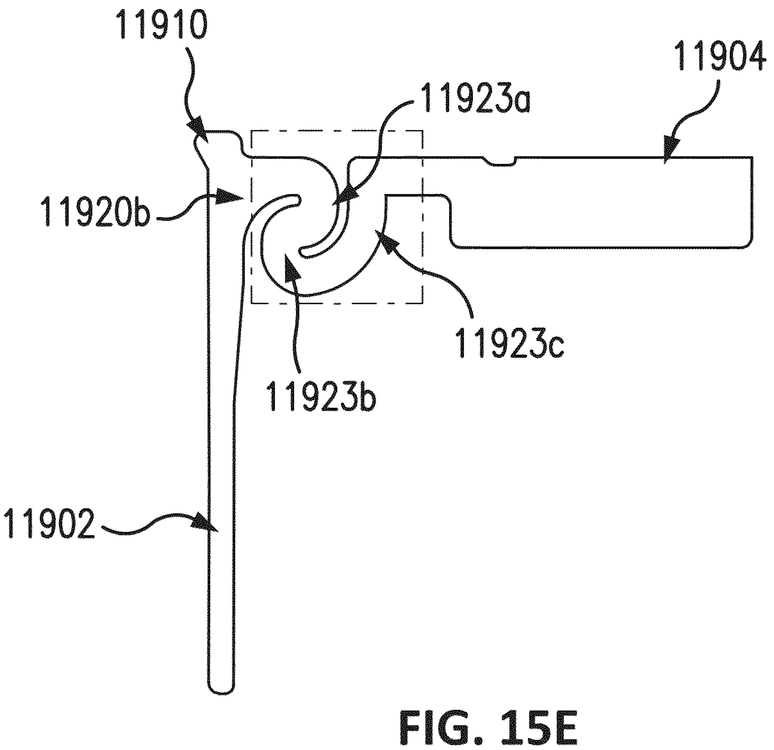

FIG. 15E illustrates another embodiment of a sensor 11900 including a neck between the flag 11904 and tail 11902 with a bend 11920*b* that generally forms a swirl pattern including at least turn turns 11923*a*, 11923*b*, and 11923*c*. In this embodiment, the turns again abut the top end of the tail or the tower 11910 of the sensor 11900. In addition to maintaining the overall footprint of the sensor, this orientation may provide for additional balancing of the horizontally-oriented and vertically-oriented stresses. The overlapping layers in this arrangement of turns are substantially balanced in along both the horizontal and vertical axes.

Figure 15F:
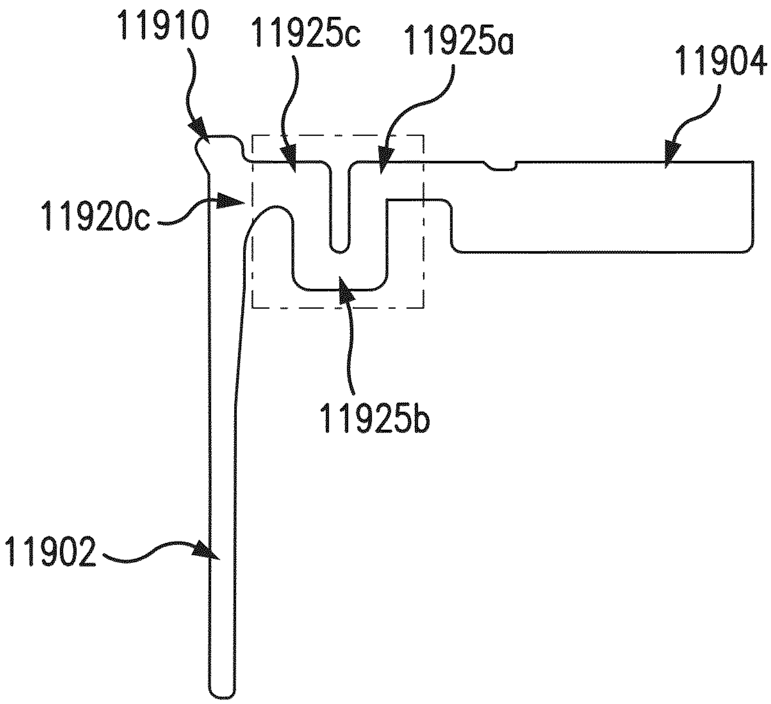

FIG. 15F illustrates another embodiment of a sensor 11900 including a neck between the flag 11904 and tail 11902 with a bend 11920*c* including turns 11925*a*, 11925*b*, and 11925*c*. In the illustrated embodiment, the turn 11925*c* connects a region of the tail 11902 near the top end of the tail or the tower 11910 of the sensor to the rest of the bend 11920*c*. In addition to reducing the overall footprint of the sensor, this orientation can be considered to provide additional flexibility in the horizontally-oriented axis. The arrangement can provide multiple overlapping, horizontally-aligned vertical layers between the turns.

Figure 15G:
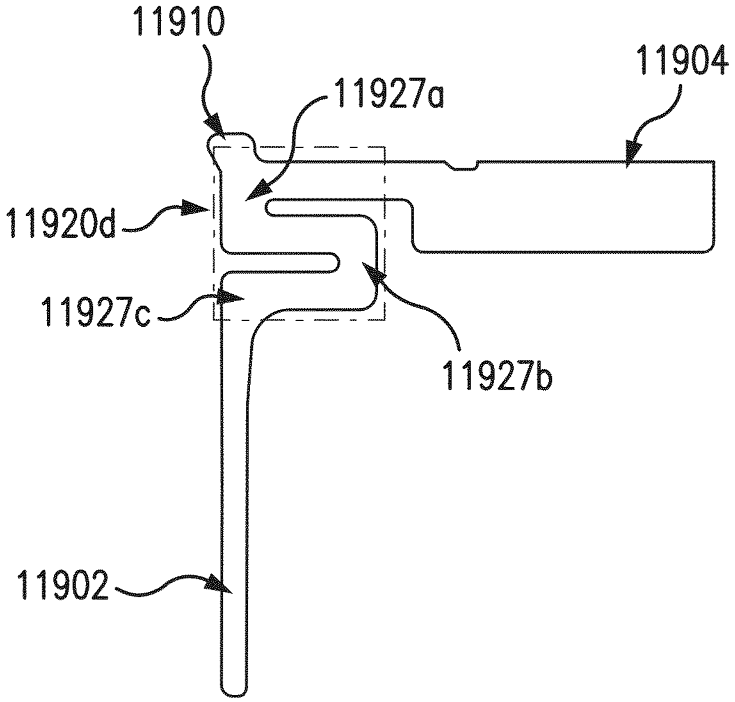

FIG. 15G illustrates another embodiment of a sensor 11900 including a neck between the flag 11904 and tail 11902 with a bend 11920*d* including turn 11927*a*, 11927*b*, and 11927*c*. In the illustrated embodiment, the bend 11920*d* occurs primarily in the tail 11902 of the sensor, connecting the tail 11902 and the tower 11910, while the stretch of the sensor between the tower 11910 and the flag 11904 is generally uninterrupted. The turn 11927*a* generally connects the tower 11910 to the rest of the bend 11920*d*, while the turn 11927*c* connects the tail 11902 to the rest of the bend 11920*d*. This orientation can be considered to provide additional flexibility in the vertically-oriented axis. The arrangement can provide multiple overlapping, horizontally-aligned vertical layers between the turns.

The turns of the neck can be created by folding the neck of the sensor from a larger neck structure, laser cutting the sensor from a sheet of the material comprising the sensor, printing the sensor having the configuration with turns, stamping the sensor from a sheet of material of which the sensor is composed, or other suitable manufacturing processes for providing precision bends in the neck.

Figure 16A:
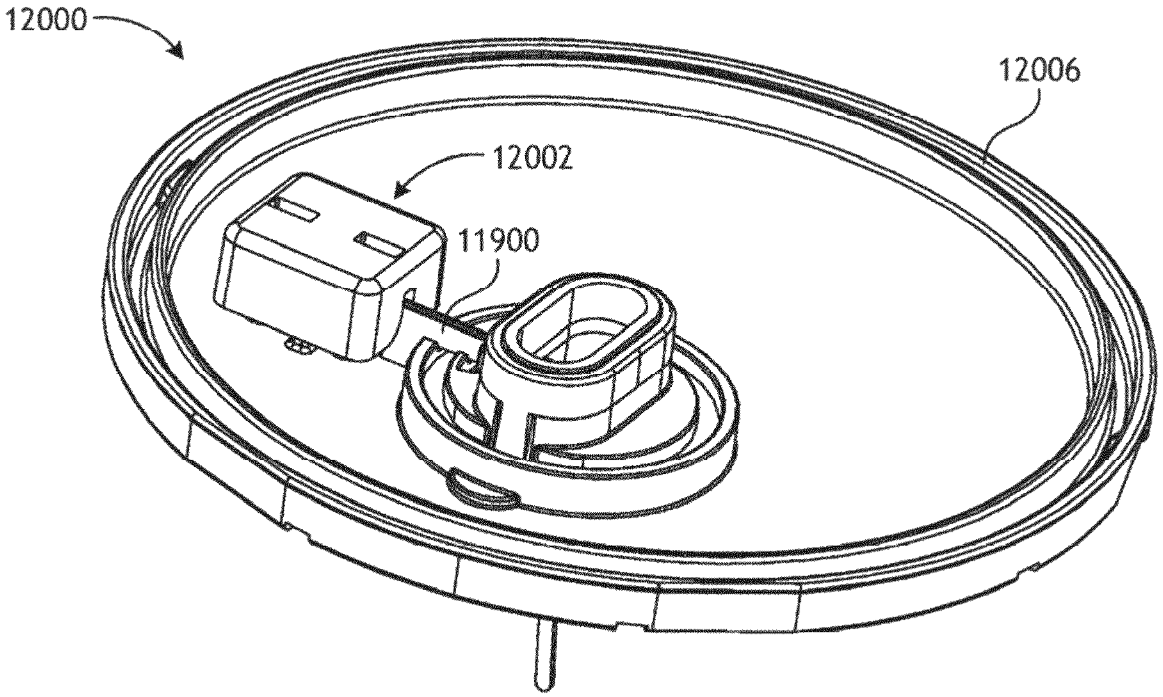
FIGS. 16A and 16B are isometric and partially exploded isometric views of an example connector assembly, according to one or more embodiments.
Figure 16B:
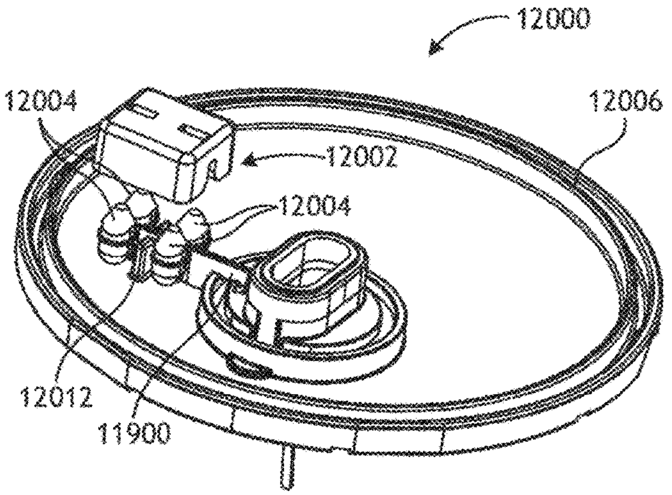

FIGS. 16A and 16B are isometric and partially exploded isometric views of an example connector assembly 12000, according to one or more embodiments. As illustrated, the connector assembly 12000 may include a connector 12002, and FIG. 17C is an isometric bottom view of the connector 12002. The connector 12002 may comprise an injection molded part used to help secure one or more compliant carbon impregnated polymer modules 12004 (four shown in FIG. 16B) to a mount 12006. More specifically, the connector 12002 may help secure the modules 12004 in place adjacent the sensor 11900 and in contact with the sensor contacts 11914 (FIG. 15C) provided on the flag 11904 (FIG. 15C). The modules 12004 may be made of a conductive material to provide conductive communication between the sensor 11900 and corresponding circuitry contacts (not shown) provided within the mount 12006.

Figure 16C:
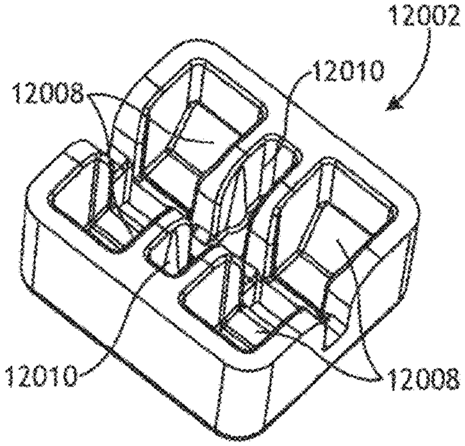
FIG. 16C is an isometric bottom view of the connector of FIGS. 16A-16B.

As best seen in FIG. 16C, the connector 12002 may define pockets 12008 sized to receive the modules 12004. Moreover, in some embodiments, the connector 12002 may further define one or more depressions 12010 configured to mate with one or more corresponding flanges 12012 (FIG. 16B) on the mount 12006. Mating the depressions 12010 with the flanges 12012 may secure the connector 12002 to the mount 12006 via an interference fit or the like. In other embodiments, the connector 12002 may be secured to the mount 12006 using an adhesive or via sonic welding.

Figure 16D:
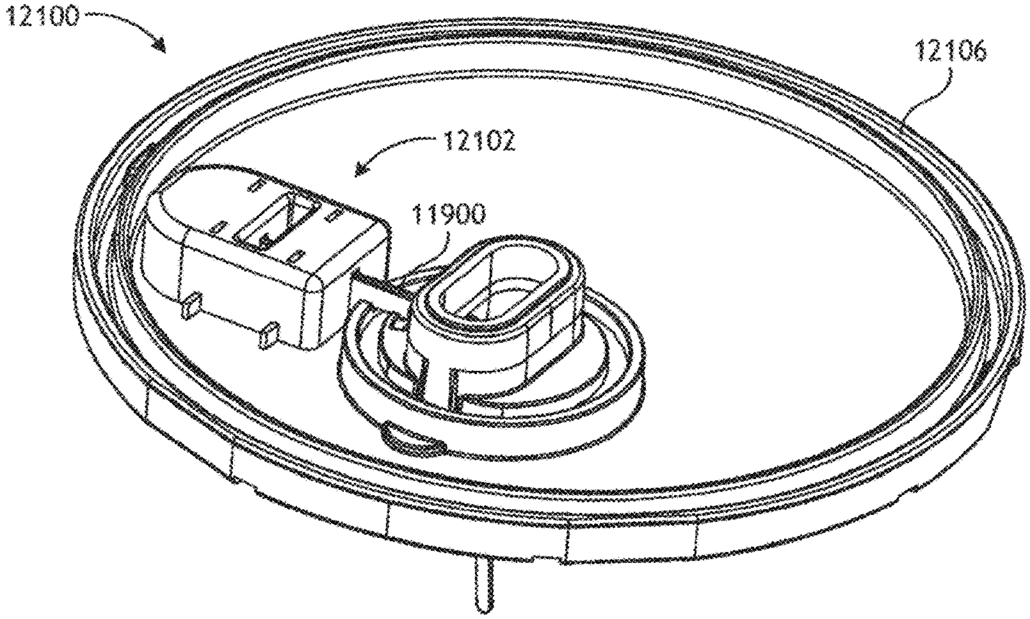
FIGS. 16D and 16E are isometric and partially exploded isometric views of another example connector assembly, according to one or more embodiments.
Figure 16E:
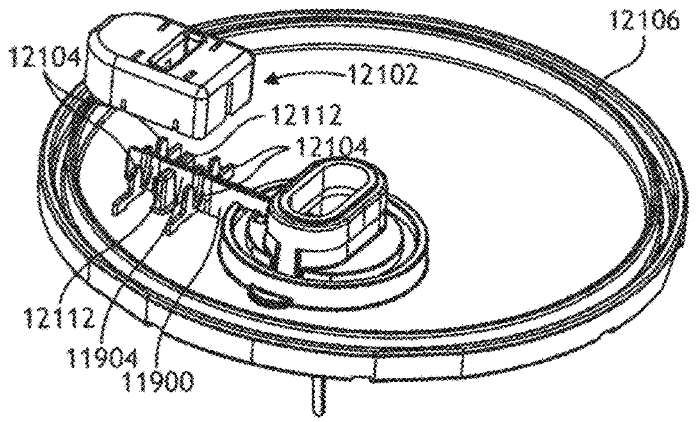
Figure 16F:
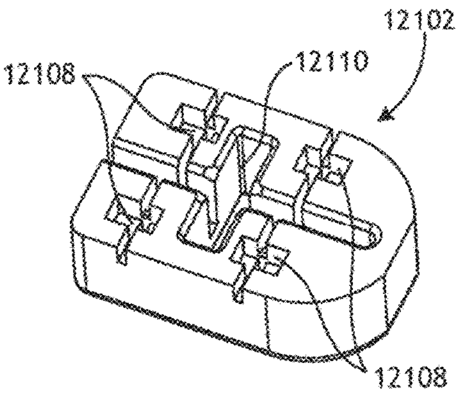
FIG. 16F is an isometric bottom view of the connector of FIGS. 16D-16E.

FIGS. 16D and 16E are isometric and partially exploded isometric views of another example connector assembly 12100, according to one or more embodiments. As illustrated, the connector assembly 12100 may include a connector 12102, and FIG. 16F is an isometric bottom view of the connector 12102. The connector 12102 may comprise an injection molded part used to help keep one or more compliant metal contacts 12104 (four shown in FIG. 16E) secured against the sensor 11900 on a mount 12106. More specifically, the connector 12102 may help secure the contacts 12104 in place adjacent the sensor 11900 and in contact with the sensor contacts 11914 (FIG. 15C) provided on the flag 11904. The contacts 12104 may be made of a stamped conductive material that provides conductive communication between the sensor 11900 and corresponding circuitry contacts (not shown) provided within the mount 12106. In some embodiments, for example, the contacts 12104 may be soldered to a PCB (not shown) arranged within the mount 12106.

As best seen in FIG. 16F, the connector 12102 may define pockets 12108 sized to receive the contacts 12104. Moreover, in some embodiments, the connector 12102 may further define one or more depressions 12110 configured to mate with one or more corresponding flanges 12112 (FIG. 120B) on the mount 12006. Mating the depressions 12110 with the flanges 12112 may help secure the connector 12102 to the mount 12106 via an interference fit or the like. In other embodiments, the connector 12102 may be secured to the mount 12106 using an adhesive or via sonic welding.

Exemplary Sharp Modules

FIG. 17A is a perspective view depicting an example embodiment of sharp module 2500 prior to assembly within sensor module 504 (FIG. 6B). Sharp 2502 can include a distal tip 2506 which can penetrate the skin while carrying sensor tail in a hollow or recess of sharp shaft 2504 to put the active surface of the sensor tail into contact with bodily fluid. A hub push cylinder 2508 can provide a surface for a sharp carrier to push during insertion. A hub small cylinder 2512 can provide a space for the extension of sharp hub contact faces 1622 (FIG. 10B). A hub snap pawl locating cylinder 2514 can provide a distal-facing surface of hub snap pawl 2516 for sharp hub contact faces 1622 to abut. A hub snap pawl 2516 can include a conical surface that opens clip 1620 during installation of sharp module 2500.

FIGS. 17B to 17H show example embodiments of sharp modules, in various stages of assembly, for use in the insertion of dermal analyte sensors. According to one aspect of the embodiments, angling the sensor and/or insertion sharp relative to a reference point can enable co-localization of the tip of the insertion needle and the tip of the sensor, and furthermore, can create a single contact point at the surface of the skin. As such, the sharp can create a leading edge at the surface of the skin to form an insertion path into the dermal layer for the sensor, as the sensor is inserted into a subject. In some embodiments, for example, the sharp and/or dermal sensor may be angled relative to a reference point (e.g., each other, surface of the skin, or the base of the applicator) for insertion, where the angle of the sharp differs from the angle of the sensor. For example, the reference point may be the skin surface to be breached for dermal insertion, or may be a reference or component of the sensor applicator set. In some embodiments, the sharp may be disposed at an angle relative to the sensor. For example, when designed so that that the sharp is angled relative to the sensor, the needle creates a leading edge for the sensor during operation of the applicator set. Furthermore, the needle design itself, and the positioning of the needle with respect to the sensor can be implemented in any desired configuration, including all of those configurations disclosed in U.S. Patent Publication No. 2014/0171771, which is incorporated by reference herein in its entirety for all purposes.

Furthermore, although many of the example embodiments described with respect to FIGS. 17B to 17J make reference to dermal analyte sensors and dermal insertion, it will be understood by those of skill in the art that any of the embodiments can be dimensioned and configured for use with analyte sensors that can be positioned beyond the dermal space, such as into (or even fully through) subcutaneous tissue (e.g., 3 mm to 10 mm beneath the surface of the skin depending on the location of the skin on the body).

Figure 17B:
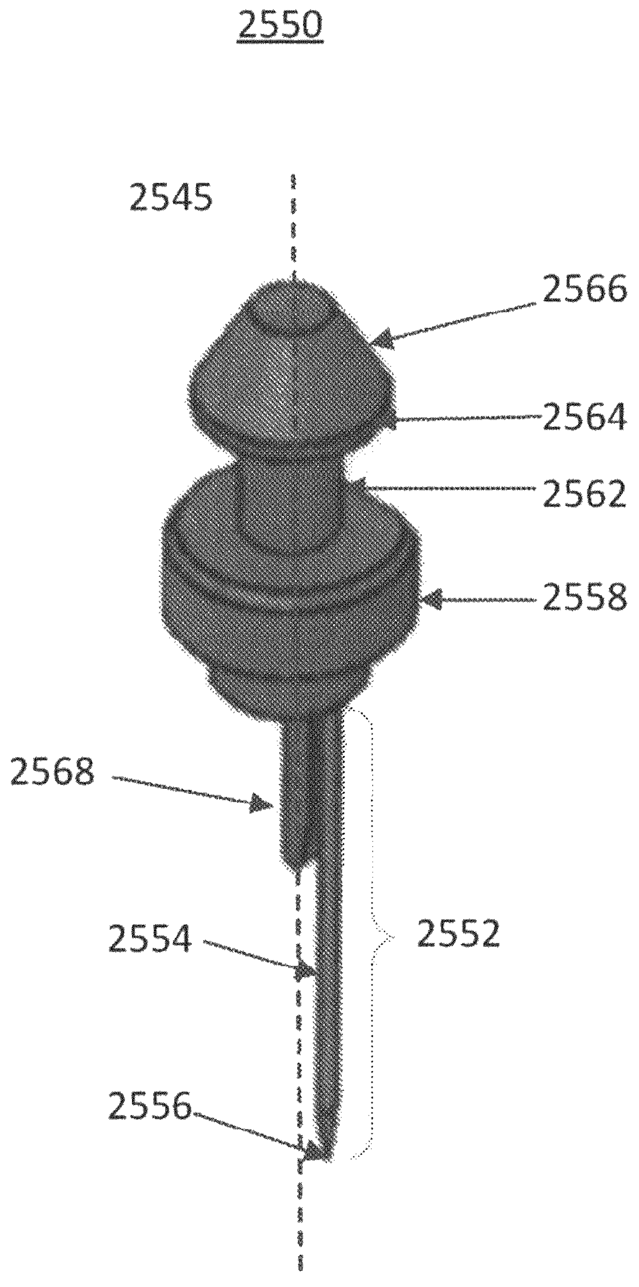
FIG. 17B is a perspective view of another example embodiment of a sharp module.

FIG. 17B is a perspective view depicting an example embodiment of a sharp module 2550 that can be used for the insertion of a dermal sensor. Sharp module 2550 is shown here prior to assembly with sensor module 504 (FIG. 6B), and can include components similar to those of the embodiment described with respect to FIG. 17A, including sharp 2552, sharp shaft 2554, sharp distal tip 2556, hub push cylinder 2558, hub small cylinder 2562, hub snap pawl 2566 and hub snap pawl locating cylinder 2564. Sharp 2552 can be positioned within sharp module 2550 at an off-center location relative to a longitudinal axis 2545 that extends through center of hub snap pawl 2566, hub small cylinder 2562 and hub push cylinder 2558. In addition, sharp module 2550 can include a sharp spacer 2568 that is parallel to and adjacent with a portion of sharp 2552. Sharp spacer 2568 can be positioned in between sensor 104 (not shown) and sharp 2552 along a proximal portion of sharp 2552, and can ensure that sensor 104 and sharp 2552 remain spaced apart at a proximal portion of sharp 2552. Sharp 2552 can be positioned in an off-center location during a molding process with hub components 2558, 2562, 2566, each of which may consist of a rigid plastic material.

Figure 17D:
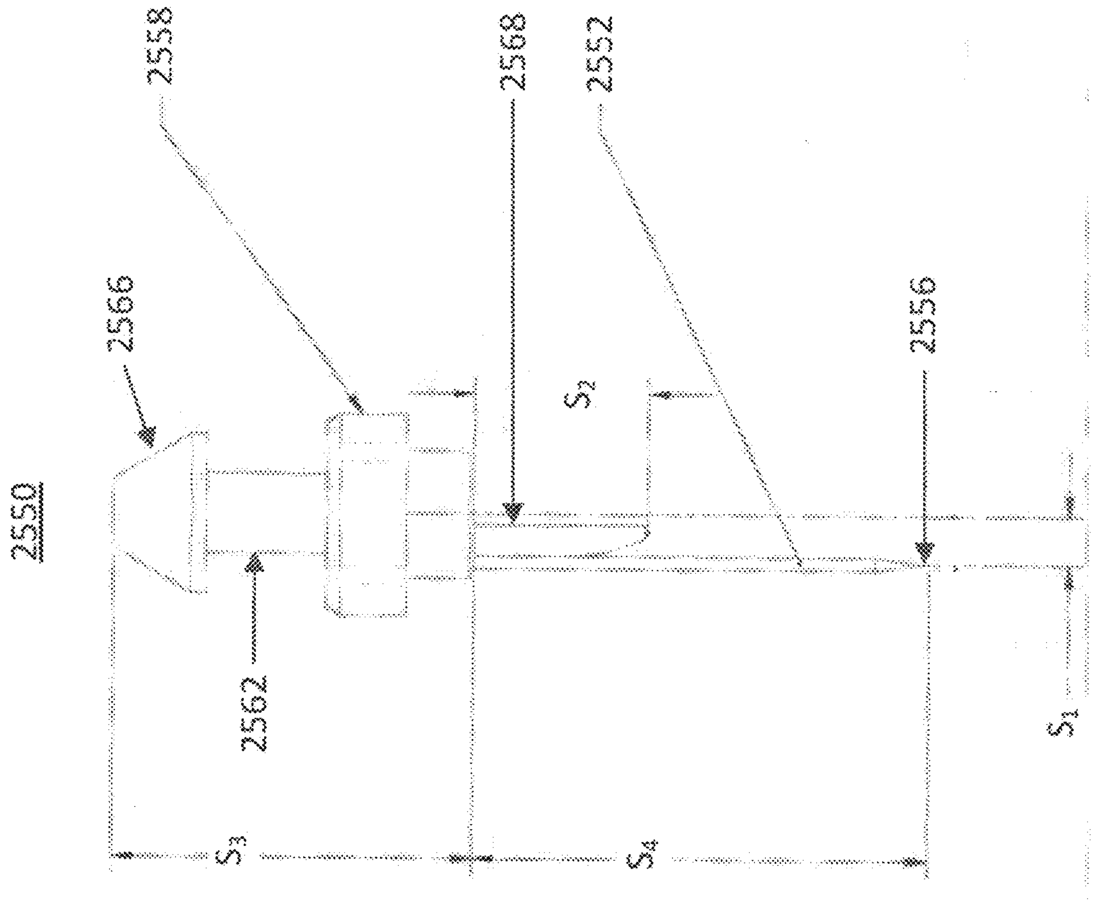
FIGS. 17C and 17D are schematic views depicting the sharp module of FIG. 17B.
Figure 17C:
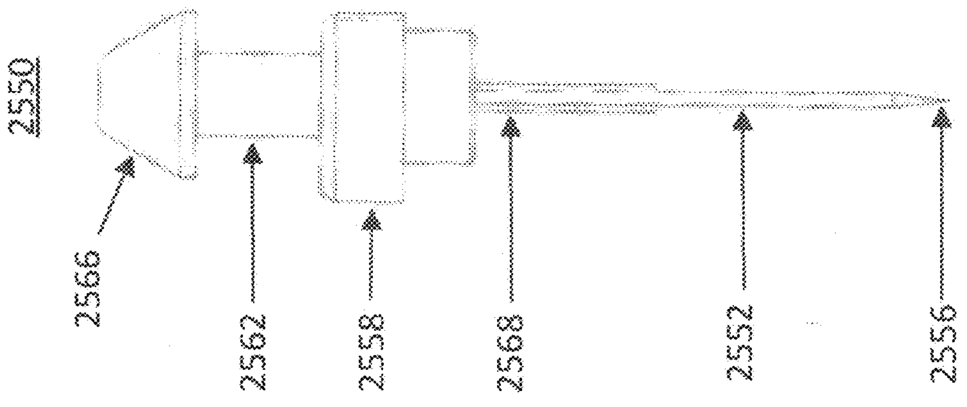

FIGS. 17C and 17D are two side views depicting sharp module 2550 prior to assembly with sensor module 504 (FIG. 6B), and include sharp 2552, spacer 2568, hub push cylinder 2558, hub small cylinder 2562 and hub snap pawl 2566. In some embodiments, the relative distances between the sharp 2552 and hub components can be positioned as follows. For example, distance, $S_1$, between the sharp 2552 and the radial center of hub can range from 0.50 mm to 1 mm (e.g., 0.89 mm). Height, $S_2$, of sharp spacer 2568 can range from 3 to 5 mm (e.g., 3.26 mm). Height, $S_3$, of hub can range from 5 to 10 mm (e.g., 6.77 mm). Length, $S_4$, of sharp 2552 can range from 1.5 mm to 25 mm (e.g., 8.55 mm), and may depend on the location of the insertion site on the subject.

Figure 17F:
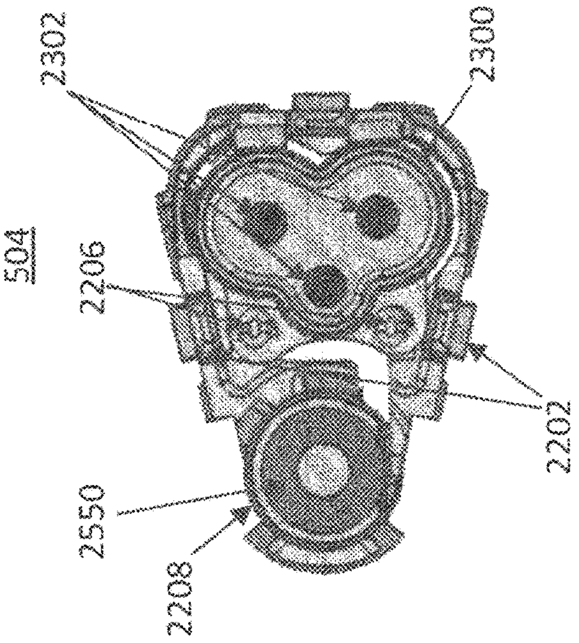
FIGS. 17E and 17F are a side schematic view and a top-down schematic view, respectively, of the sharp module of FIG. 17B, as assembled with a sensor module.
Figure 17E:
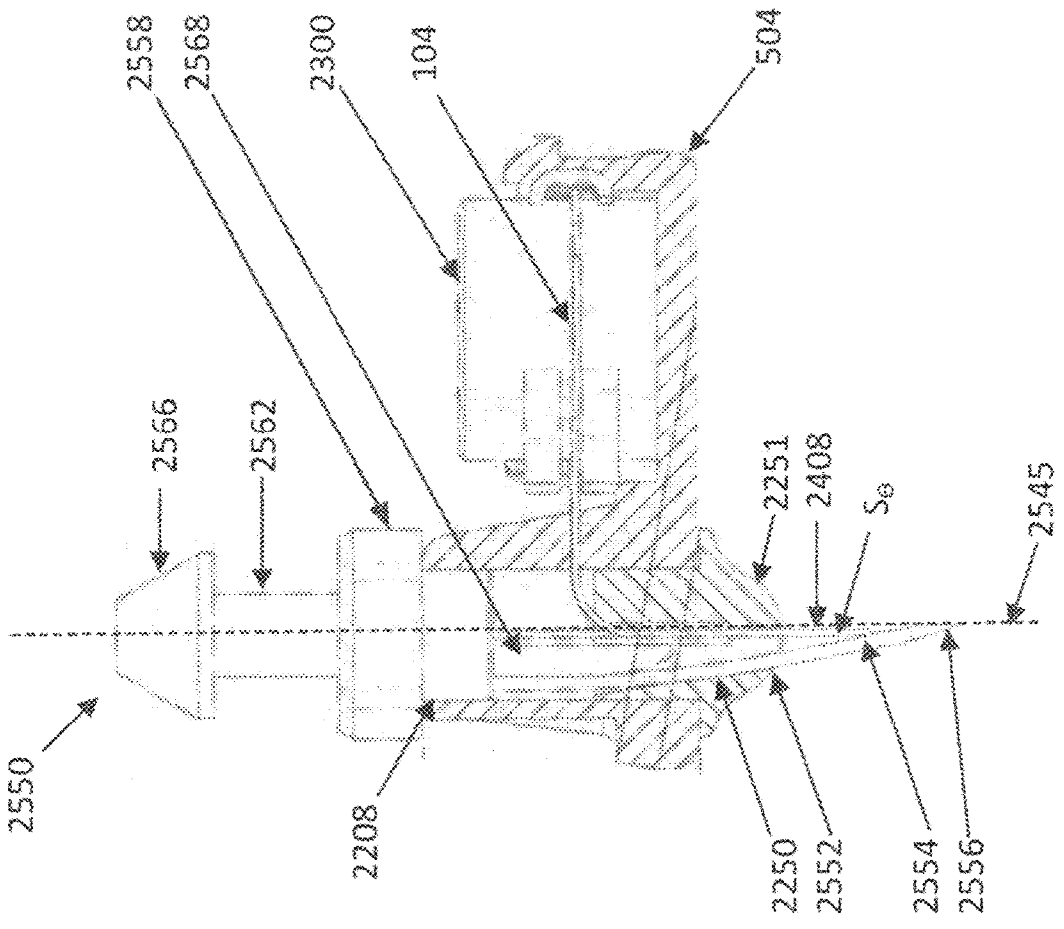
Figure 17H:
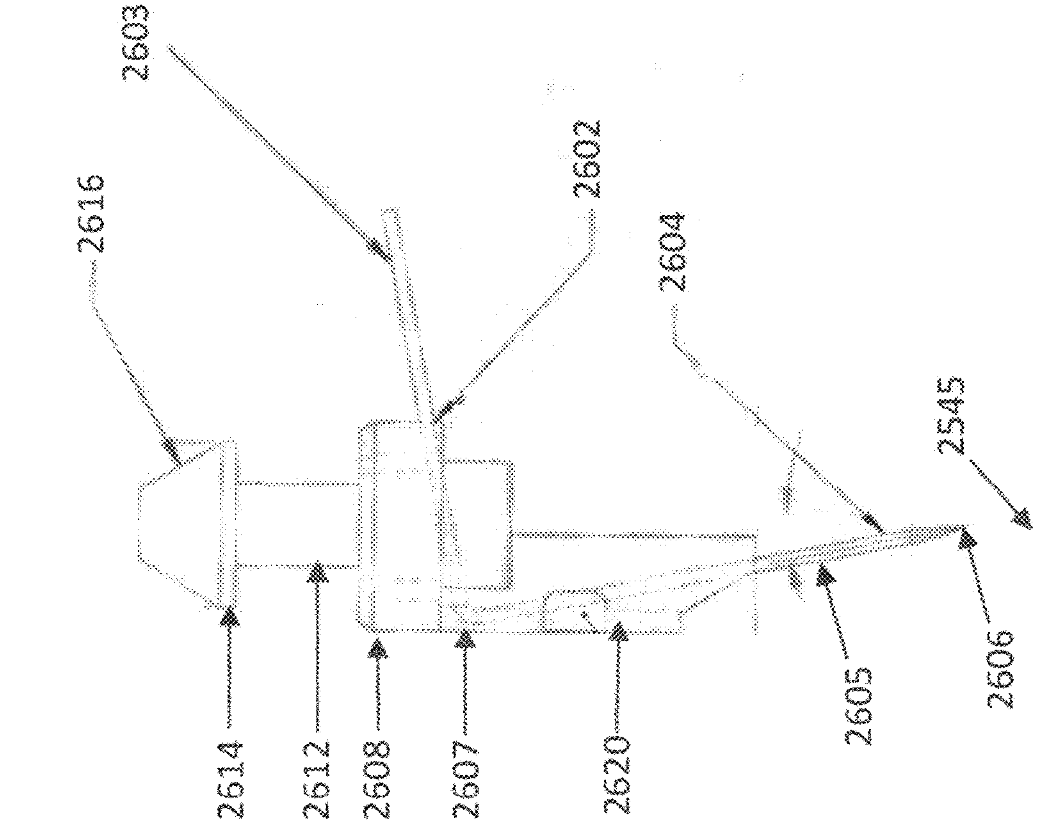
FIG. 17H is a side schematic view depicting the sharp module of FIG. 17G.

FIG. 17E depicts a side cross-sectional side view of sharp module 2550, including sharp 2552, sharp spacer 2568 and hub components (hub snap pawl 2566, hub small cylinder 2562, and hub push cylinder 2558), as assembled with sensor module 504. As can be seen in FIG. 17E, sharp 2552 is positioned within sharp slot 2208 of sensor module 504 that includes a curved interior surface 2250, located at a distal end. Curved interior surface 2250 of sensor module 504 can be in contact with a portion of sharp 2552 and cause a deflection such that sharp distal tip 2556 is oriented toward central longitudinal axis 2545. As best seen in FIG. 17H, sharp 2552 can be positioned such that the distal portion and central longitudinal axis 2545 form an acute angle, $S_\theta$, that can range between 5° and 20°. In some embodiments, for example, $S_\theta$, can range from 5° to 17°, or 7° to 15°, or 9° to 13°, e.g., 9°, 10°, 11°, 12°, or 13°

Referring still to FIG. 17E, near a distal end of sensor module 504 is protrusion 2251, which can enhance the perfusion of bodily fluid, such as dermal fluid. Although shown as a curved surface in FIG. 17E, protrusion 2251 can be shaped in any desired fashion. In addition, in some embodiments, multiple protrusions can be present. U.S. Patent Publication No. 2014/0275907, which is incorporated by reference herein in its entirety for all purposes, describes sensor devices having different protrusion configurations, each of which can be implemented with the embodiments described herein. Many of the embodiments described herein show the needle exiting from the protrusion, and in other embodiments, the needle can exit from the base of the sensor device adjacent the protrusion, and from that position extend over the tip of sensor 104.

Referring still to FIGS. 17E and 17F, sensor 104 can be a dermal sensor and can include sensor tail 2408, located at a distal end of sensor 104, and which can be positioned in a substantially parallel orientation to central longitudinal axis 2545. Distal end of sensor tail 2408 can be proximal to distal sharp tip 2556, either in a spaced relation with, at rest in, or at rest against a portion of sharp shaft 2554. As further depicted in FIG. 17E, sharp spacer 2568 provides a spaced relation between a proximal portion of sharp 2552 and sensor 104, such that the proximal portion of sharp 2552 and sensor 104 are not in contact. Sensor module 504 can further include sensor connector 2300 for housing a proximal portion of sensor 104 that is relatively perpendicular to a distal end of sensor 104.

FIG. 17F is a top-down cross-sectional view of sensor module 504. Sensor module 504 can include one or more sensor module snaps 2202 for coupling with a housing (not shown) of sensor control device 102. Sensor module 504 can also include sensor connector 2300, which can have sensor contacts 2302 for coupling with a proximal portion of sensor 104. Sensor connector 2300 can be made of silicone rubber that encapsulates compliant carbon impregnated polymer modules that serve as electrical conductive contacts 2302 between sensor 104 and electrical circuitry contacts for the electronics within sensor control device 102. The connector can also serve as a moisture barrier for sensor 104 when assembled in a compressed state after transfer from a container to an applicator and after application to a user's skin. Although three contacts 2302 are depicted, it should be understood that connector 2300 can have fewer contacts (e.g., two) or more contacts (e.g., four, five, six, etc.), depending on the particular type or configuration of sensor 104. Sensor connector 2300 can be further coupled with sensor module 504 by two connector posts 2206 positioned through a like number of apertures in connector 2300. Although two connector posts 2206 are depicted, it should be understood that any number of connector posts 2206 can be used to couple connector 2300 to sensor module 504.

Figure 17G:
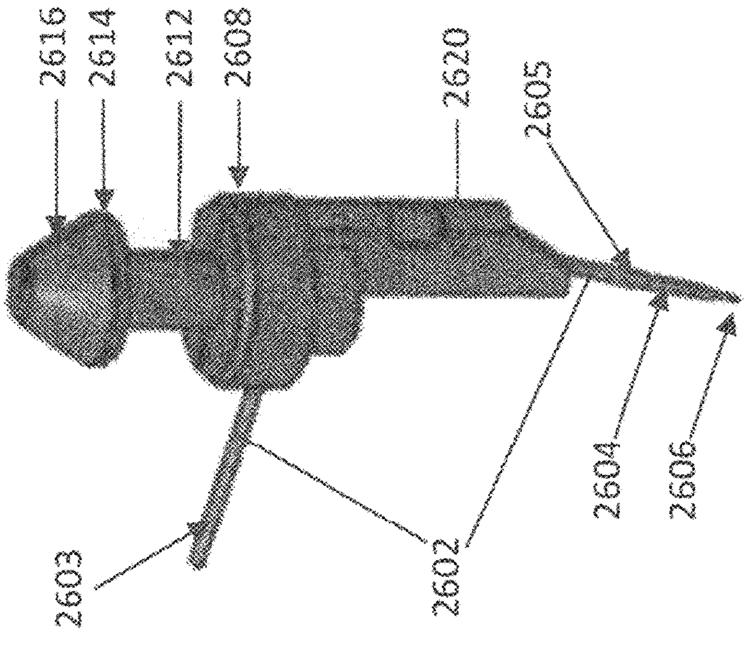
FIG. 17G is a perspective view of another example embodiment of a sharp module.

FIGS. 17G and 17H are, respectively, a perspective view and a side view of another example embodiment of sharp module 2600 that can be used for the insertion of a dermal sensor. Sharp module 2600 is shown here prior to assembly with sensor module 504 (FIG. 6B), and can include components similar to those of the embodiments described with respect to FIGS. 17A and 17B, including sharp 2602, sharp shaft 2604, sharp distal tip 2606, hub push cylinder 2608, hub small cylinder 2612, hub snap pawl 2616 and hub snap pawl locating cylinder 2614. In some embodiments, sharp 2602 can be a "pre-bent" needle that includes a proximal portion 2603 that originates from a point external to sharp module 2600 and intersects, at an angle, a central point of the hub (e.g., through hub push cylinder 2608). Sharp 2602 can also include a distal portion 2605 that extends in a distal direction, at an angle, from a point near a distal portion of hub toward the insertion point of the user's skin. As shown in FIG. 17H, sharp 2602 can include an angled portion 2607 located external to hub push cylinder 2608, which can have a substantially 90° angle between proximal portion 2603 and distal portion 2605 of sharp 2602. Sharp module 2600 can also include a bend fin guide 2620 for maintaining "pre-bent" sharp 2602 in position during assembly and/or use, and can prevent lateral or rotational movement of sharp 2602 relative to hub components. Proximal portion 2603 of sharp 2602 can be "trimmed" from the hub after molding process is completed, and prior to assembly of sharp module 2600 with sensor module 504.

Figure 17J:
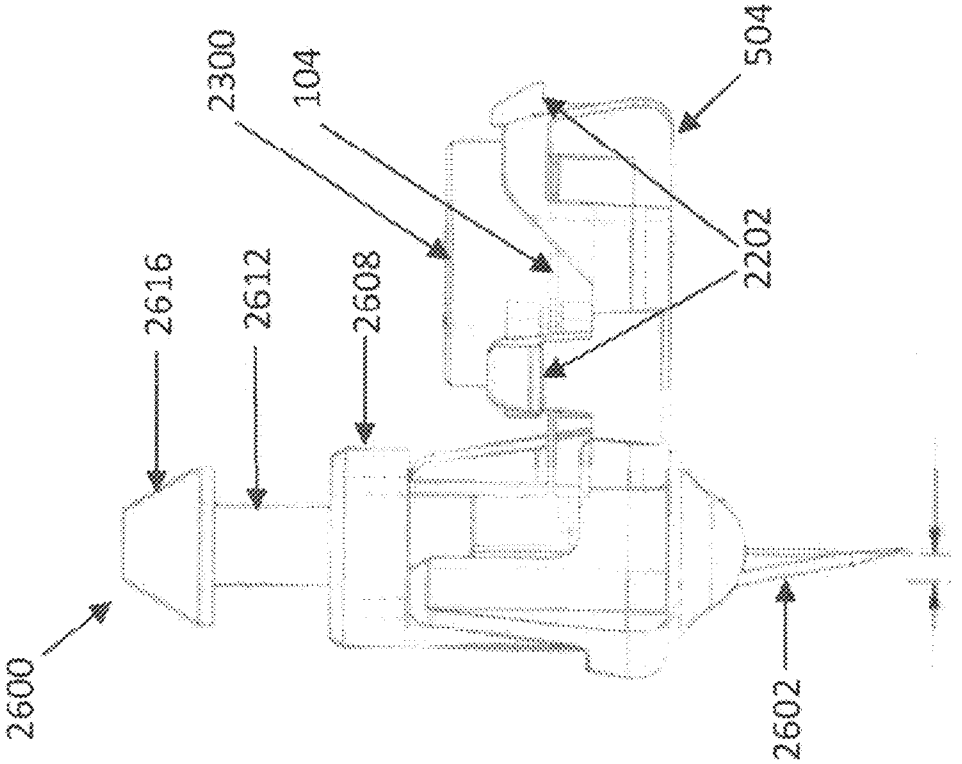
FIGS. 17I and 17J are a side cross-sectional view and a side view, respectively, of the sharp module of FIG. 17G, as assembled with a sensor module.
Figure 17I:
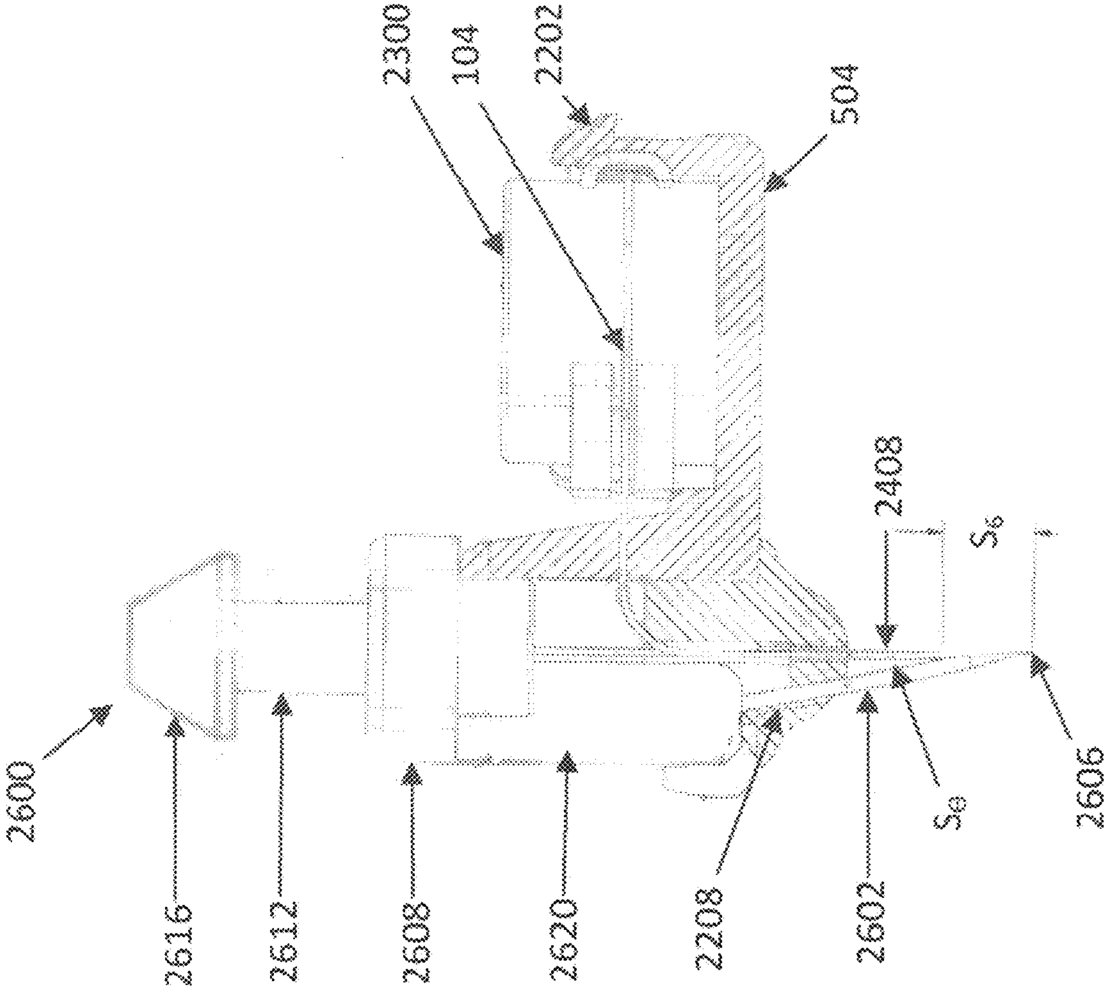

FIGS. 17I and 17J show, respectively, a side cross-sectional view and a side view of sharp module 2600 (including hub snap pawl 2616, hub small cylinder 2612, and hub push cylinder 2608), as assembled with sensor module 504. As can be seen in FIG. 17I, sensor module 504 includes sharp slot 2208, through which sharp 2602 can extend in an angled and distal direction. As described earlier, a proximal portion of sharp 2602 passes through bend fin guide 2620, which is coupled with a distal portion of sensor module 504. Sensor module 504 can also include sensor 104, which can be a dermal sensor. As seen in FIG. 17I, sharp 2602 and sensor tail 2408 can form an acute angle, $S_\theta$, at a point where their respective longitudinal axes converge. Angle $S_\theta$ can range between 5° and 20°. In some embodiments, for example, So, can range from 5° to 17°, or 7° to 15°, or 9° to 13°, e.g., 9°, 10°, 11°, 12°, or 13° In some embodiments, distal sharp tip 2606 is located at a distance, $S_6$, that is proximal to an end of sensor tail 2408. Distance, $S_6$, can range between 0.02 mm to 0.10 mm, e.g., 0.05 mm, 0.06 mm or 0.07 mm.

Referring still to FIGS. 17I and 17J, sensor module 504 can also include sensor connector 2300 for housing a proximal portion of sensor 104 that is relatively perpendicular to a distal end of sensor 104. Sensor module 504 can further include one or more sensor module snaps 2202 for coupling with a housing (not shown) of sensor control device 102. Sensor connector 2300 can include the same structures described with respect to FIG. 17F.

In the above embodiments, the sharp can be made of stainless steel or a like flexible material (e.g., material used to manufacture acupuncture needles), and dimensioned such that the applicator provides for insertion of at least a portion of the dermal sensor into the dermal layer, but not through the dermal layer of the skin. According to certain embodiments, the sharp has a cross sectional diameter (width) of from 0.1 mm to 0.5 mm. For example, the sharp may have a diameter of from 0.1 mm to 0.3 mm, such as from 0.15 mm to 0.25 mm, e.g., 0.16 mm to 0.22 mm in diameter. A given sharp may have a constant, i.e., uniform, width along its entire length, or may have a varying, i.e., changing, width along at least a portion of its length, such as the tip portion used to pierce the surface of the skin. For example, with respect to the embodiment shown in FIG. 17I, width of sharp 2602 can narrow along a distal portion between bend fin guide 1620 and distal sharp tip 2606.

A sharp can also have a length to insert a dermal sensor just into the dermal layer, and no more. Insertion depth may be controlled by the length of the sharp, the configuration of the base and/or other applicator components that limit insertion depth. A sharp may have a length between 1.5 mm and 25 mm. For example, the sharp may have a length of from 1 mm to 3 mm, from 3 mm to 5 mm, from 5 mm to 7 mm, from 7 mm to 9 mm, from 9 mm to 11 mm, from 11 mm to 13 mm, from 13 mm to 15 mm, from 15 mm to 17 mm, from 17 mm to 19 mm, from 19 mm to 21 mm, from 21 mm to 23 mm, from 23 mm to 25 mm, or a length greater than 25 mm. It will be appreciated that while a sharp may have a length up to 25 mm, in certain embodiments the full length of the sharp is not inserted into the subject because it would extend beyond the dermal space. Non-inserted sharp length may provide for handling and manipulation of the sharp in an applicator set. Therefore, while a sharp may have a length up to 25 mm, the insertion depth of the sharp in the skin on a subject in those certain embodiments will be limited to the dermal layer, e.g., about 1.5 mm to 4 mm, depending on the skin location, as described in greater detail below. However, in all of the embodiments disclosed herein, the sharp can be configured to extend beyond the dermal space, such as into (or even fully through) subcutaneous tissue (e.g., 3 mm to 10 mm beneath the surface of the skin depending on the location of the skin on the body). Additionally, in some example embodiments, the sharps described herein can include hollow or partially hollow insertion needles, having an internal space or lumen. In other embodiments, however, the sharps described herein can include solid insertion needles, which do not have an internal space and/or lumen. Furthermore, a sharp of the subject applicator sets can also be bladed or non-bladed.

Likewise, in the above embodiments, a dermal sensor is sized so that at least a portion of the sensor is positioned in the dermal layer and no more, and a portion extends outside the skin in the transcutaneously positioned embodiments. That is, a dermal sensor is dimensioned such that when the dermal sensor is entirely or substantially entirely inserted into the dermal layer, the distal-most portion of the sensor (the insertion portion or insertion length) is positioned within the dermis of the subject and no portion of the sensor is inserted beyond a dermal layer of the subject when the sensor is operably dermally positioned.

The dimensions (e.g., the length) of the sensor may be selected according to the body site of the subject in which the sensor is to be inserted, as the depth and thickness of the epidermis and dermis exhibit a degree of variability depending on skin location. For example, the epidermis is only about 0.05 mm thick on the eyelids, but about 1.5 mm thick on the palms and the soles of the feet. The dermis is the thickest of the three layers of skin and ranges from about 1.5 mm to 4 mm thick, depending on the skin location. For implantation of the distal end of the sensor into, but not through, the dermal layer of the subject, the length of the inserted portion of the dermal sensor should be greater than the thickness of the epidermis, but should not exceed the combined thickness of the epidermis and dermis. Methods may include determining an insertion site on a body of a user and determining the depth of the dermal layer at the site, and selecting the appropriately-sized applicator set for the site.

In certain aspects, the sensor is an elongate sensor having a longest dimension (or "length") of from 0.25 mm to 4 mm. The length of the sensor that is inserted, in the embodiments in which only a portion of a sensor is dermally inserted, ranges from 0.5 mm to 3 mm, such as from 1 mm to 2 mm, e.g., 1.5 mm. The dimensions of the sensor may also be expressed in terms of its aspect ratio. In certain embodiments, a dermal sensor has an aspect ratio of length to width (diameter) of about 30:1 to about 6:1. For example, the aspect ratio may be from about 25:1 to about 10:1, including 20:1 and 15:1. The inserted portion of a dermal sensor has sensing chemistry.

However, all of the embodiments disclosed herein can be configured such that at least a portion of the sensor is positioned beyond the dermal layer, such as into (or through) the subcutaneous tissue (or fat). For example, the sensor can be dimensioned such that when the sensor is entirely or substantially entirely inserted into the body, the distal-most portion of the sensor (the insertion portion or insertion length) is positioned within the subcutaneous tissue (beyond the dermis of the subject) and no portion of the sensor is inserted beyond the subcutaneous tissue of the subject when the sensor is operably positioned. As mentioned, the subcutaneous tissue is typically present in the region that is 3 mm to 10 mm beneath the outer skin surface, depending on the location of the skin on the body.

Exemplary Applicators and Sensor Control Devices for One Piece Architectures

Referring briefly again to FIGS. 1 and 3A-3G, for the two-piece architecture system, the sensor tray 202 and the sensor applicator 102 are provided to the user as separate packages, thus requiring the user to open each package and finally assemble the system. In some applications, the discrete, sealed packages allow the sensor tray 202 and the sensor applicator 102 to be sterilized in separate sterilization processes unique to the contents of each package and otherwise incompatible with the contents of the other. More specifically, the sensor tray 202, which includes the plug assembly 207, including the sensor 110 and the sharp 220, may be sterilized using radiation sterilization, such as electron beam (or "e-beam") irradiation. Radiation sterilization, however, can damage the electrical components arranged within the electronics housing of the sensor control device 102. Consequently, if the sensor applicator 102, which contains the electronics housing of the sensor control device 102, needs to be sterilized, it may be sterilized via another method, such as gaseous chemical sterilization using, for example, ethylene oxide. Gaseous chemical sterilization, however, can damage the enzymes or other chemistry and biologies included on the sensor 110. Because of this sterilization incompatibility, the sensor tray 202 and the sensor applicator 102 are commonly sterilized in separate sterilization processes and subsequently packaged separately, which requires the user to finally assemble the components for use.

According to embodiments of the present disclosure, the sensor control device 102 may be modified to provide a one-piece architecture that may be subjected to sterilization techniques specifically designed for a one-piece architecture sensor control device. A one-piece architecture allows the sensor applicator 150 and the sensor control device 102 to be shipped to the user in a single, sealed package that does not require any final user assembly steps. Rather, the user need only open one package and subsequently deliver the sensor control device 102 to the target monitoring location. The one-piece system architecture described herein may prove advantageous in eliminating component parts, various fabrication process steps, and user assembly steps. As a result, packaging and waste are reduced, and the potential for user error or contamination to the system is mitigated.

Figure 18A:
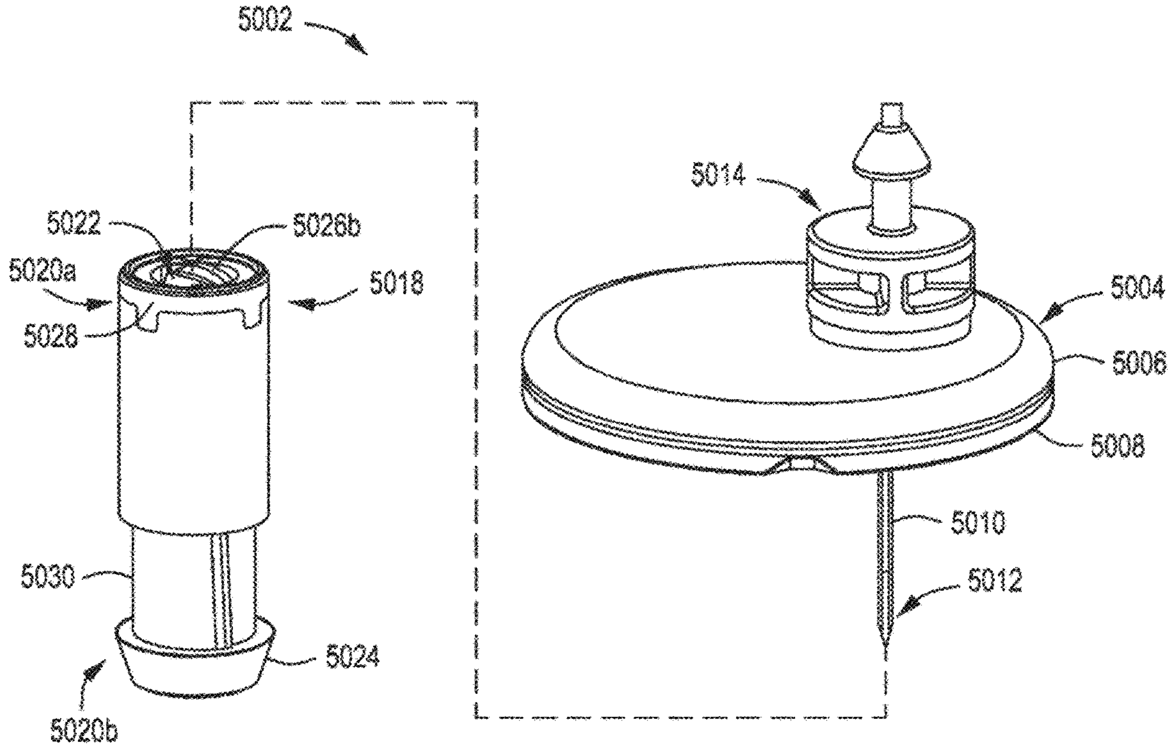
FIGS. 18A and 18B are isometric and side views, respectively, of another example sensor control device.
Figure 18B:
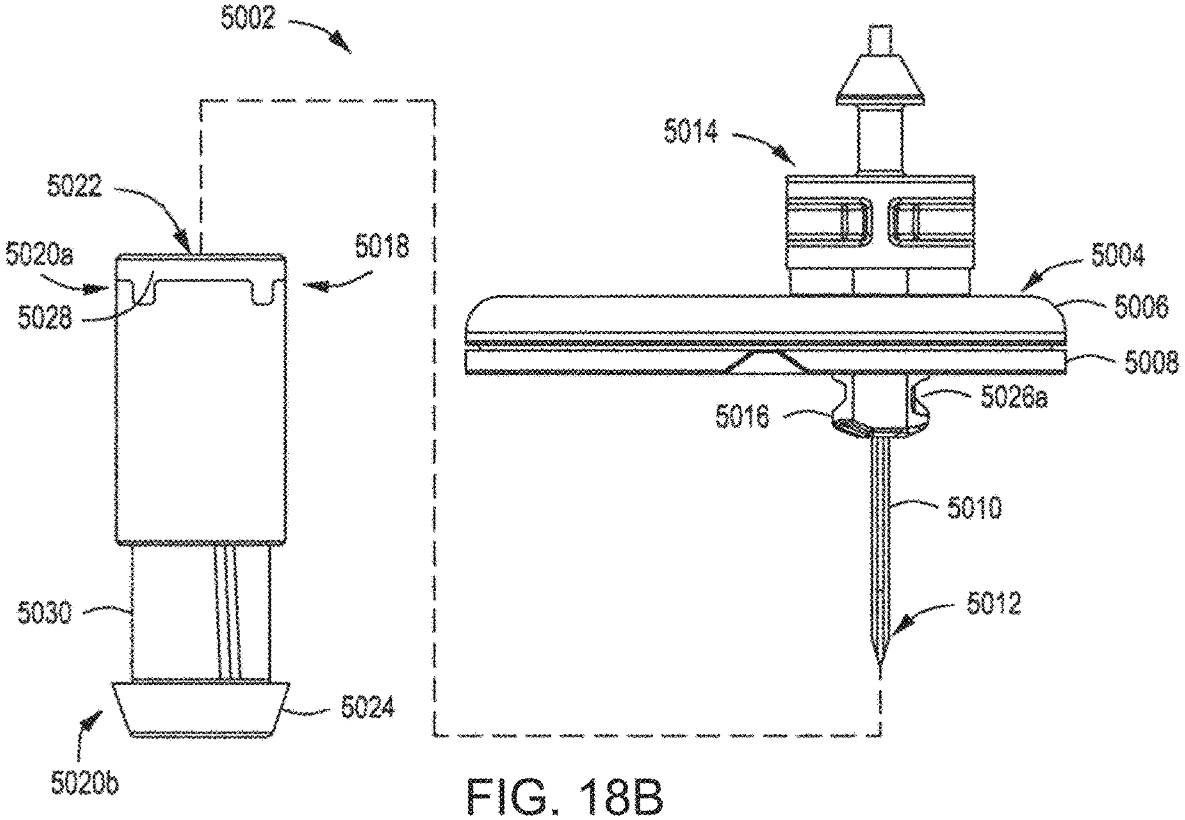

FIGS. 18A and 18B are isometric and side views, respectively, of another example sensor control device 5002, according to one or more embodiments of the present disclosure. The sensor control device 5002 may be similar in some respects to the sensor control device 102 of FIG. 1 and therefore may be best understood with reference thereto. Moreover, the sensor control device 5002 may replace the sensor control device 102 of FIG. 1 and, therefore, may be used in conjunction with the sensor applicator 102 of FIG. 1, which may deliver the sensor control device 5002 to a target monitoring location on a user's skin.

Unlike the sensor control device 102 of FIG. 1, however, the sensor control device 5002 may comprise a one-piece system architecture not requiring a user to open multiple packages and finally assemble the sensor control device 5002 prior to application. Rather, upon receipt by the user, the sensor control device 5002 may already be fully assembled and properly positioned within the sensor applicator 150 (FIG. 1). To use the sensor control device 5002, the user need only open one barrier (e.g., the applicator cap 708 of FIG. 3B) before promptly delivering the sensor control device 5002 to the target monitoring location for use.

As illustrated, the sensor control device 5002 includes an electronics housing 5004 that is generally disc-shaped and may have a circular cross-section. In other embodiments, however, the electronics housing 5004 may exhibit other cross-sectional shapes, such as ovoid or polygonal, without departing from the scope of the disclosure. The electronics housing 5004 may be configured to house or otherwise contain various electrical components used to operate the sensor control device 5002. In at least one embodiment, an adhesive patch (not shown) may be arranged at the bottom of the electronics housing 5004. The adhesive patch may be similar to the adhesive patch 105 of FIG. 1, and may thus help adhere the sensor control device 5002 to the user's skin for use.

As illustrated, the sensor control device 5002 includes an electronics housing 5004 that includes a shell 5006 and a mount 5008 that is matable with the shell 5006. The shell 5006 may be secured to the mount 5008 via a variety of ways, such as a snap fit engagement, an interference fit, sonic welding, one or more mechanical fasteners (e.g., screws), a gasket, an adhesive, or any combination thereof. In some cases, the shell 5006 may be secured to the mount 5008 such that a sealed interface is generated therebetween.

The sensor control device 5002 may further include a sensor 5010 (partially visible) and a sharp 5012 (partially visible), used to help deliver the sensor 5010 transcutaneously under a user's skin during application of the sensor control device 5002. As illustrated, corresponding portions of the sensor 5010 and the sharp 5012 extend distally from the bottom of the electronics housing 5004 (e.g., the mount 5008). The sharp 5012 may include a sharp hub 5014 configured to secure and carry the sharp 5012. As best seen in FIG. 18B, the sharp hub 5014 may include or otherwise define a mating member 5016. To couple the sharp 5012 to the sensor control device 5002, the sharp 5012 may be advanced axially through the electronics housing 5004 until the sharp hub 5014 engages an upper surface of the shell 5006 and the mating member 5016 extends distally from the bottom of the mount 5008. As the sharp 5012 penetrates the electronics housing 5004, the exposed portion of the sensor 5010 may be received within a hollow or recessed (arcuate) portion of the sharp 5012. The remaining portion of the sensor 5010 is arranged within the interior of the electronics housing 5004.

The sensor control device 5002 may further include a sensor cap 5018, shown exploded or detached from the electronics housing 5004 in FIGS. 18A-18B. The sensor cap 5016 may be removably coupled to the sensor control device 5002 (e.g., the electronics housing 5004) at or near the bottom of the mount 5008. The sensor cap 5018 may help provide a sealed barrier that surrounds and protects the exposed portions of the sensor 5010 and the sharp 5012 from gaseous chemical sterilization. As illustrated, the sensor cap 5018 may comprise a generally cylindrical body having a first end 5020*a* and a second end 5020*b* opposite the first end 5020*a*. The first end 5020*a* may be open to provide access into an inner chamber 5022 defined within the body. In contrast, the second end 5020*b* may be closed and may provide or otherwise define an engagement feature 5024. As described herein, the engagement feature 5024 may help mate the sensor cap 5018 to the cap (e.g., the applicator cap 708 of FIG. 3B) of a sensor applicator (e.g., the sensor applicator 150 of FIGS. 1 and 3A-3G), and may help remove the sensor cap 5018 from the sensor control device 5002 upon removing the cap from the sensor applicator.

The sensor cap 5018 may be removably coupled to the electronics housing 5004 at or near the bottom of the mount 5008. More specifically, the sensor cap 5018 may be removably coupled to the mating member 5016, which extends distally from the bottom of the mount 5008. In at least one embodiment, for example, the mating member 5016 may define a set of external threads 5026*a* (FIG. 18B) matable with a set of internal threads 5026*b* (FIG. 18A) defined by the sensor cap 5018. In some embodiments, the external and internal threads 5026*a, b* may comprise a flat thread design (e.g., lack of helical curvature), which may prove advantageous in molding the parts. Alternatively, the external and internal threads 5026*a, b* may comprise a helical threaded engagement. Accordingly, the sensor cap 5018 may be threadably coupled to the sensor control device 5002 at the mating member 5016 of the sharp hub 5014. In other embodiments, the sensor cap 5018 may be removably coupled to the mating member 5016 via other types of engagements including, but not limited to, an interference or friction fit, or a frangible member or substance that may be broken with minimal separation force (e.g., axial or rotational force).

In some embodiments, the sensor cap 5018 may comprise a monolithic (singular) structure extending between the first and second ends 5020*a, b*. In other embodiments, however, the sensor cap 5018 may comprise two or more component parts. In the illustrated embodiment, for example, the sensor cap 5018 may include a seal ring 5028 positioned at the first end 5020*a* and a desiccant cap 5030 arranged at the second end 5020*b*. The seal ring 5028 may be configured to help seal the inner chamber 5022, as described in more detail below. In at least one embodiment, the seal ring 5028 may comprise an elastomeric O-ring. The desiccant cap 5030 may house or comprise a desiccant to help maintain preferred humidity levels within the inner chamber 5022. The desiccant cap 5030 may also define or otherwise provide the engagement feature 5024 of the sensor cap 5018.

Figure 19A:
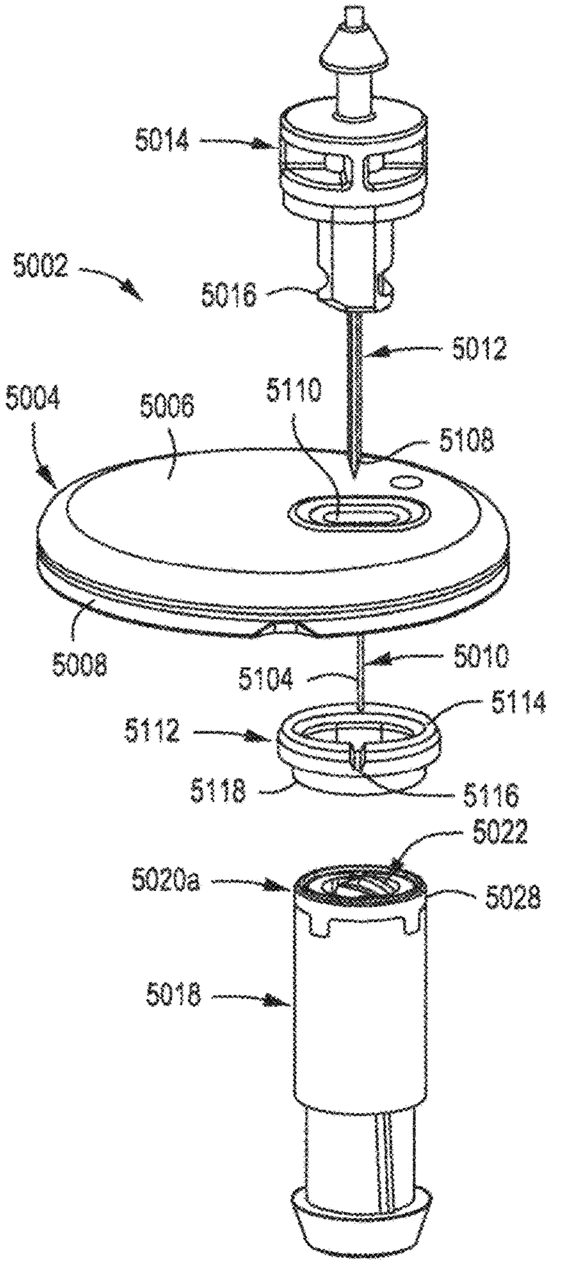
FIGS. 19A and 19B are exploded isometric top and bottom views, respectively of the sensor control device of FIGS. 18A-18B.
Figure 19B:
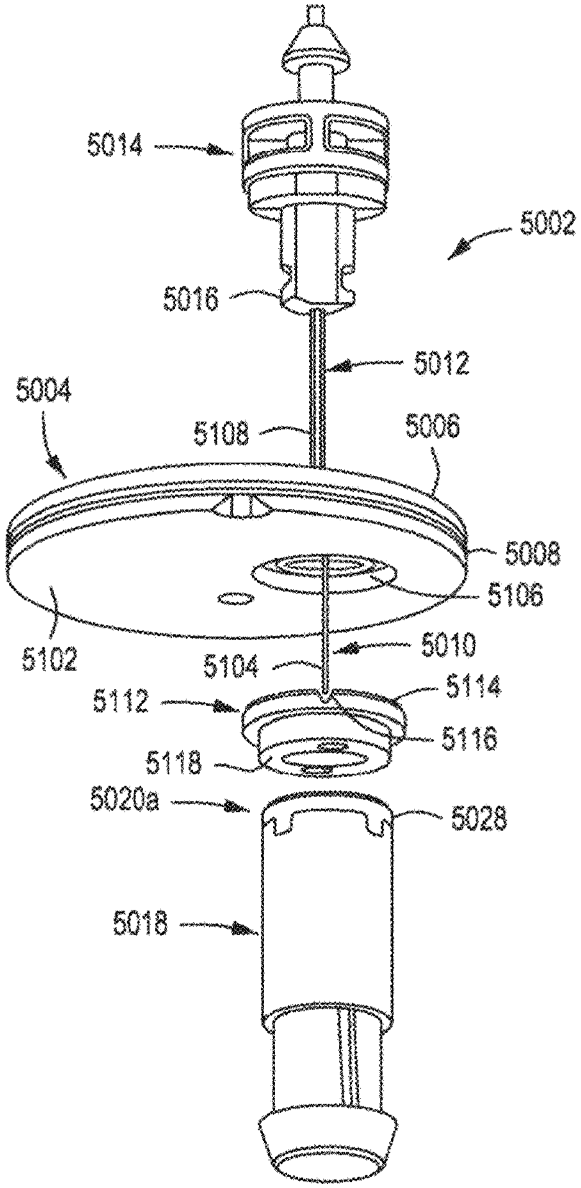
Figure 19C:
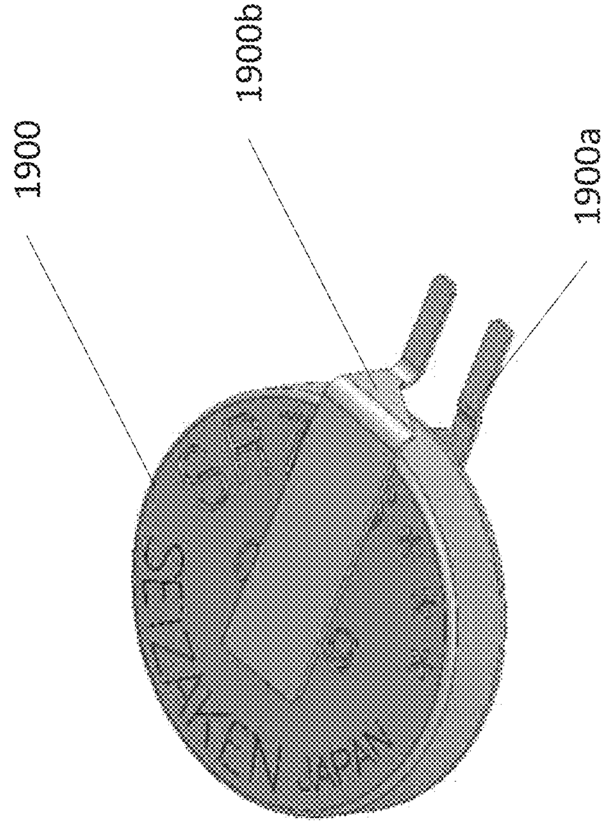
FIG. 19C is a top perspective view of a cell battery in accordance with the disclosed subject matter.

FIGS. 19A and 19B are exploded isometric top and bottom views, respectively, of the sensor control device 5002, according to one or more embodiments. The shell 5006 and the mount 5008 operate as opposing clamshell halves that enclose or otherwise substantially encapsulate various electronic components of the sensor control device 5002. More specifically, electronic components may include, but are not limited to, a printed circuit board (PCB), one or more resistors, transistors, capacitors, inductors, diodes, and switches. A data processing unit and a battery may be mounted to or otherwise interact with the PCB. The data processing unit may comprise, for example, an application specific integrated circuit (ASIC) configured to implement one or more functions or routines associated with operation of the sensor control device 5002. More specifically, the data processing unit may be configured to perform data processing functions, where such functions may include, but are not limited to, filtering and encoding of data signals, each of which corresponds to a sampled analyte level of the user. The data processing unit may also include or otherwise communicate with an antenna for communicating with the reader device 120 (FIG. 1). The battery may provide power to the sensor control device 5002 and, more particularly, to the electronic components of the PCB. For example, battery can be any battery known to a person of ordinary skill in the art, such as a coin cell battery or a button battery, as shown in FIG. 19C. In certain embodiments, battery 1900 may include silver oxide batteries. Battery 1900 may be laser welded to the PCB and located to ensure that outer diameter of battery remains within outer perimeter of PCB. In some embodiments, battery 1900 may be connected to PCB using negative battery tab 1900*a* and positive battery tab 1900*b*. For example, negative battery tab 1900*a* of battery 1900 may be substantially planar and in the same plane as negative terminal of battery 1900; while positive battery tab 1900*b* may include one or more bends so that one end of positive terminal 1900*b* is in contact with and in the same plane as positive battery terminal while a second end configured to couple to the PCB is in the same plane as the negative battery tab 1900*a*. Furthermore, battery 1900 may be positioned in a battery aperture on the PCB to eliminate electrical interference between negative battery tab 1900*a* and PCB. While not shown, the sensor control device 5002 may also include an adhesive patch that may be applied to the bottom 5102 (FIG. 19B) of the mount 5008, and may help adhere the sensor control device 5002 to the user's skin for use.

It will be understood by those of skill in the art that the battery assembly embodiments described herein, including the PCB and data processing unit, may be implemented in other medical devices, including sensor control devices having other types of housing and configurations relating thereto. In other words, the example embodiments of sensor control device 5002, comprising opposing clamshell halves, are intended to be non-limiting and merely illustrate one type of device that can be used with the battery assembly embodiments described herein.

The sensor control device 5002 may provide or otherwise include a sealed subassembly that includes, among other component parts, the shell 5006, the sensor 5010, the sharp 5012, and the sensor cap 5018. The sealed subassembly of the sensor control device 5002 may help isolate the sensor 5010 and the sharp 5012 within the inner chamber 5022 (FIG. 19A) of the sensor cap 5018 during a gaseous chemical sterilization process, which might otherwise adversely affect the chemistry provided on the sensor 5010.

The sensor 5010 may include a tail 5104 that extends out an aperture 5106 (FIG. 19B) defined in the mount 5008 to be transcutaneously received beneath a user's skin. The tail 5104 may have an enzyme or other chemistry included thereon to help facilitate analyte monitoring. The sharp 5012 may include a sharp tip 5108 extendable through an aperture 5110 (FIG. 19A) defined by the shell 5006, and the aperture 5110 may be coaxially aligned with the aperture 5106 of the mount 5008. As the sharp tip 5108 penetrates the electronics housing 5004, the tail 5104 of the sensor 5010 may be received within a hollow or recessed portion of the sharp tip 5108. The sharp tip 5108 may be configured to penetrate the skin while carrying the tail 5104 to put the active chemistry of the tail 5104 into contact with bodily fluids.

The sharp tip 5108 may be advanced through the electronics housing 5004 until the sharp hub 5014 engages an upper surface of the shell 5006 and the mating member 5016 extends out the aperture 5106 in the bottom 5102 of the mount 5008. In some embodiments, a seal member (not shown), such as an O-ring or seal ring, may interpose the sharp hub 5014 and the upper surface of the shell 5006 to help seal the interface between the two components. In some embodiments, the seal member may comprise a separate component part, but may alternatively form an integral part of the shell 5006, such as being a co-molded or overmolded component part.

The sealed subassembly may further include a collar 5112 that is positioned within the electronics housing 5004 and extends at least partially into the aperture 5106. The collar 5112 may be a generally annular structure that defines or otherwise provides an annular ridge 5114 on its top surface. In some embodiments, as illustrated, a groove 5116 may be defined in the annular ridge 5114 and may be configured to accommodate or otherwise receive a portion of the sensor 5010 extending laterally within the electronics housing 5004.

In assembling the sealed subassembly, a bottom 5118 of the collar 5112 may be exposed at the aperture 5106 and may sealingly engage the first end 5020*a* of the sensor cap 5018 and, more particularly, the seal ring 5028. In contrast, the annular ridge 5114 at the top of the collar 5112 may sealingly engage an inner surface (not shown) of the shell 5006. In at least one embodiment, a seal member (not shown) may interpose the annular ridge 5114 and the inner surface of the shell 5006 to form a sealed interface. In such embodiments, the seal member may also extend (flow) into the groove 5116 defined in the annular ridge 5114 and thereby seal about the sensor 5010 extending laterally within the electronics housing 5004. The seal member may comprise, for example, an adhesive, a gasket, or an ultrasonic weld, and may help isolate the enzymes and other chemistry included on the tail 5104.

Figure 20:
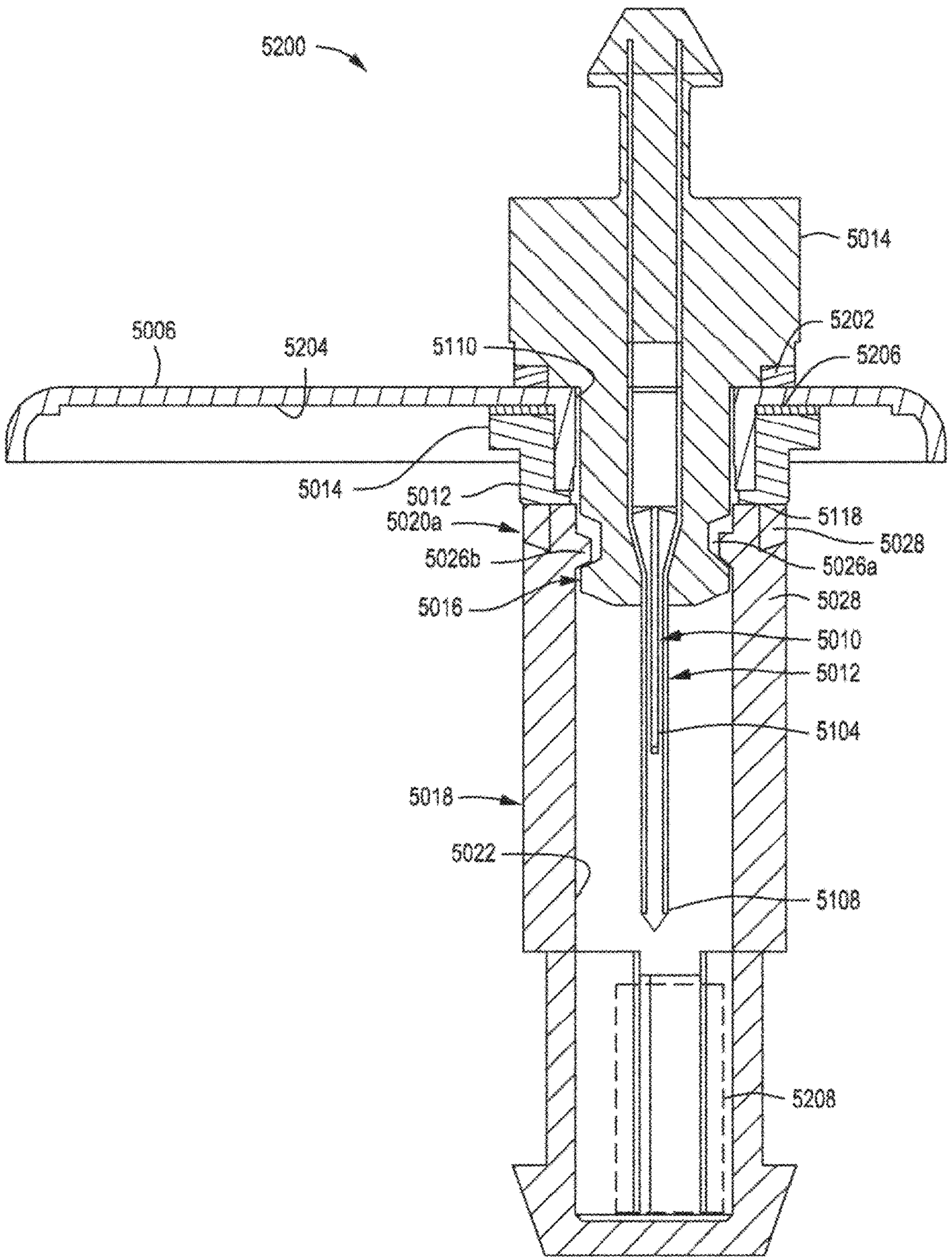
FIG. 20 is a cross-sectional side view of an assembled sealed subassembly, according to one or more embodiments.

FIG. 20 is a cross-sectional side view of an assembled sealed subassembly 5200, according to one or more embodiments. The sealed subassembly 5200 may form part of the sensor control device 5002 of FIGS. 18A-18B and 19A-20B and may include portions of the shell 5006, the sensor 5010, the sharp 5012, the sensor cap 5018, and the collar 5112. The sealed subassembly 5200 may be assembled in a variety of ways. In one assembly process, the sharp 5012 may be coupled to the sensor control device 5002 by extending the sharp tip 5108 through the aperture 5110 defined in the top of the shell 5006 and advancing the sharp 5012 through the shell 5006 until the sharp hub 5014 engages the top of the shell 5006 and the mating member 5016 extends distally from the shell 5006. In some embodiments, as mentioned above, a seal member 5202 (e.g., an O-ring or seal ring) may interpose the sharp hub 5014 and the upper surface of the shell 5006 to help seal the interface between the two components.

The collar 5112 may then be received over (about) the mating member 5016 and advanced toward an inner surface 5204 of the shell 5006 to enable the annular ridge 5114 to engage the inner surface 5204. A seal member 5206 may interpose the annular ridge 5114 and the inner surface 5204 and thereby form a sealed interface. The seal member 5206 may also extend (flow) into the groove 5116 (FIGS. 19A-20B) defined in the annular ridge 5114 and thereby seal about the sensor 5010 extending laterally within the electronics housing 5004 (FIGS. 19A-20B). In other embodiments, however, the collar 5112 may first be sealed to the inner surface 5204 of the shell 5006, following which the sharp 5012 and the sharp hub 5014 may be extended through the aperture 5110, as described above.

The sensor cap 5018 may be removably coupled to the sensor control device 5002 by threadably mating the internal threads 5026*b* of the sensor cap 5018 with the external threads 5026*a* of the mating member 5016. Tightening (rotating) the mated engagement between the sensor cap 5018 and the mating member 5016 may urge the first end 5020*a* of the sensor cap 5018 into sealed engagement with the bottom 5118 of the collar 5112. Moreover, tightening the mated engagement between the sensor cap 5018 and the mating member 5016 may also enhance the sealed interface between the sharp hub 5014 and the top of the shell 5006, and between the annular ridge 5114 and the inner surface 5204 of the shell 5006.

The inner chamber 5022 may be sized and otherwise configured to receive the tail 5104 and the sharp tip 5108. Moreover, the inner chamber 5022 may be sealed to isolate the tail 5104 and the sharp tip 5108 from substances that might adversely interact with the chemistry of the tail 5104. In some embodiments, a desiccant 5208 (shown in dashed lines) may be present within the inner chamber 5022 to maintain proper humidity levels.

Once properly assembled, the sealed subassembly 5200 may be subjected to any of the radiation sterilization processes mentioned herein to properly sterilize the sensor 5010 and the sharp 5012. This sterilization step may be undertaken apart from the remaining portions of the sensor control device (FIGS. 18A-18B and 19A-20B) to prevent damage to sensitive electrical components. The sealed subassembly 5200 may be subjected to radiation sterilization prior to or after coupling the sensor cap 5018 to the sharp hub 5014. When sterilized after coupling the sensor cap 5018 to the sharp hub 5014, the sensor cap 5018 may be made of a material that permits the propagation of radiation therethrough. In some embodiments, the sensor cap 5018 may be transparent or translucent, but can otherwise be opaque, without departing from the scope of the disclosure.

Figure 21B:
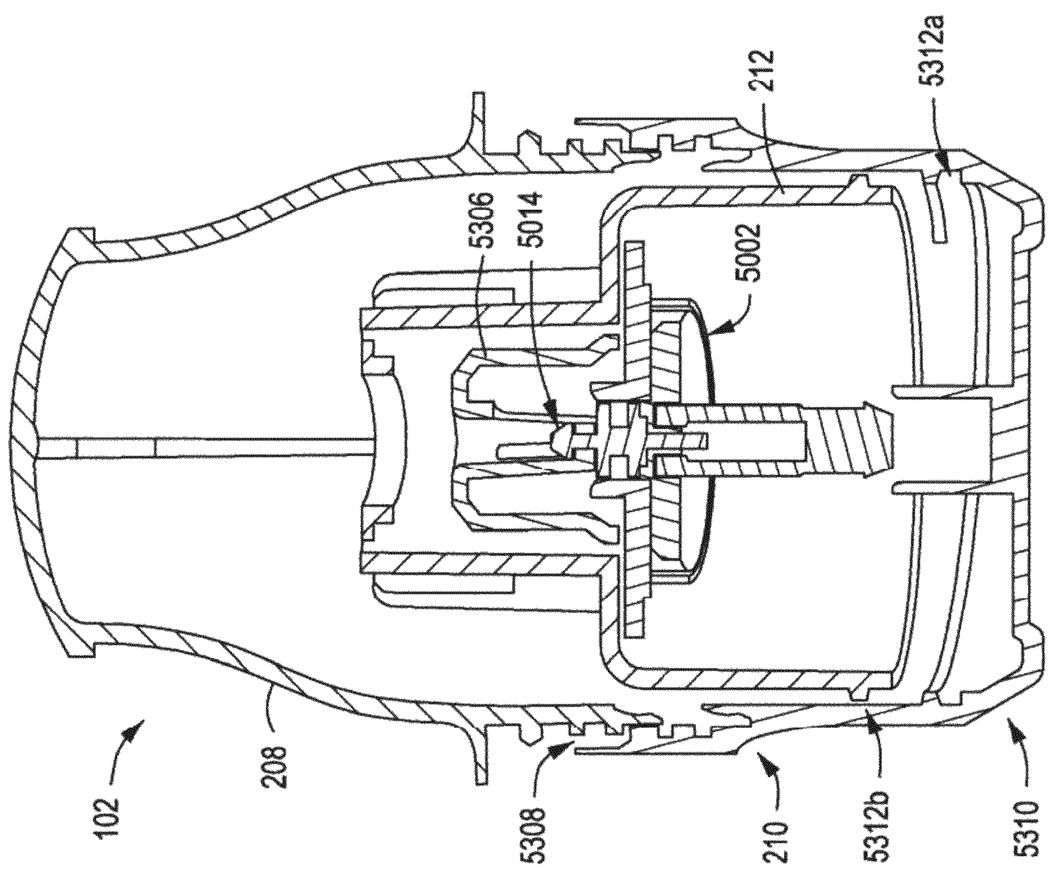
FIGS. 21A-21C are progressive cross-sectional side views showing assembly of the sensor applicator with the sensor control device of FIGS. 18A-18B.
Figure 21A:
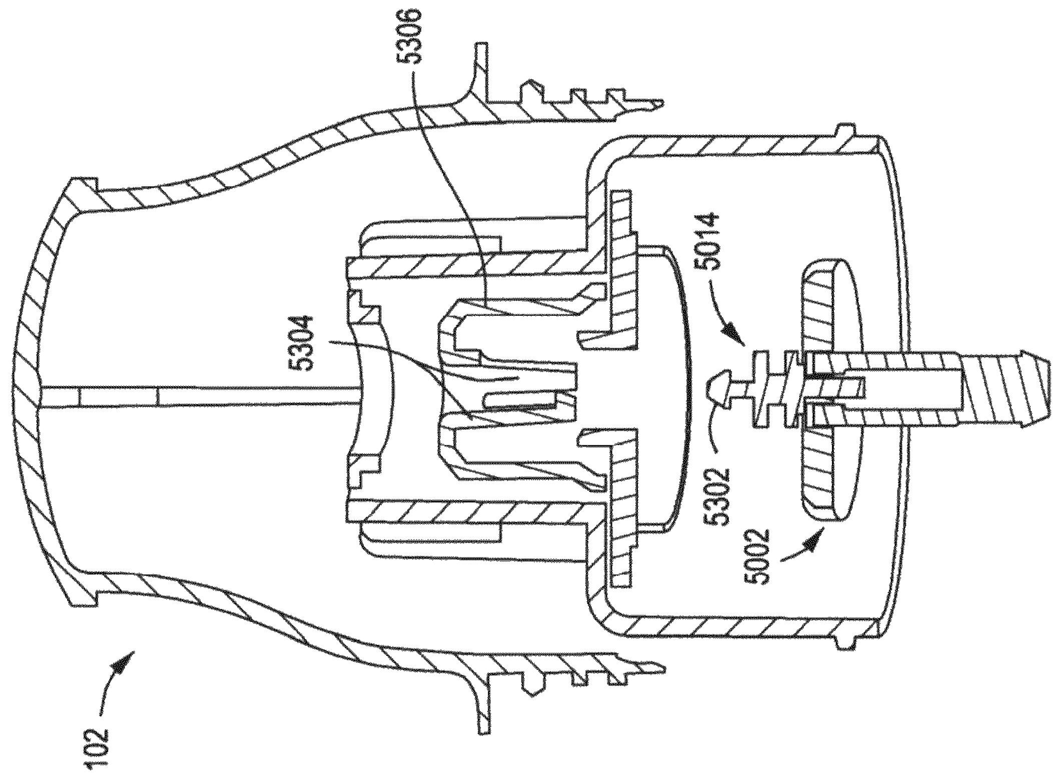
Figure 21C:
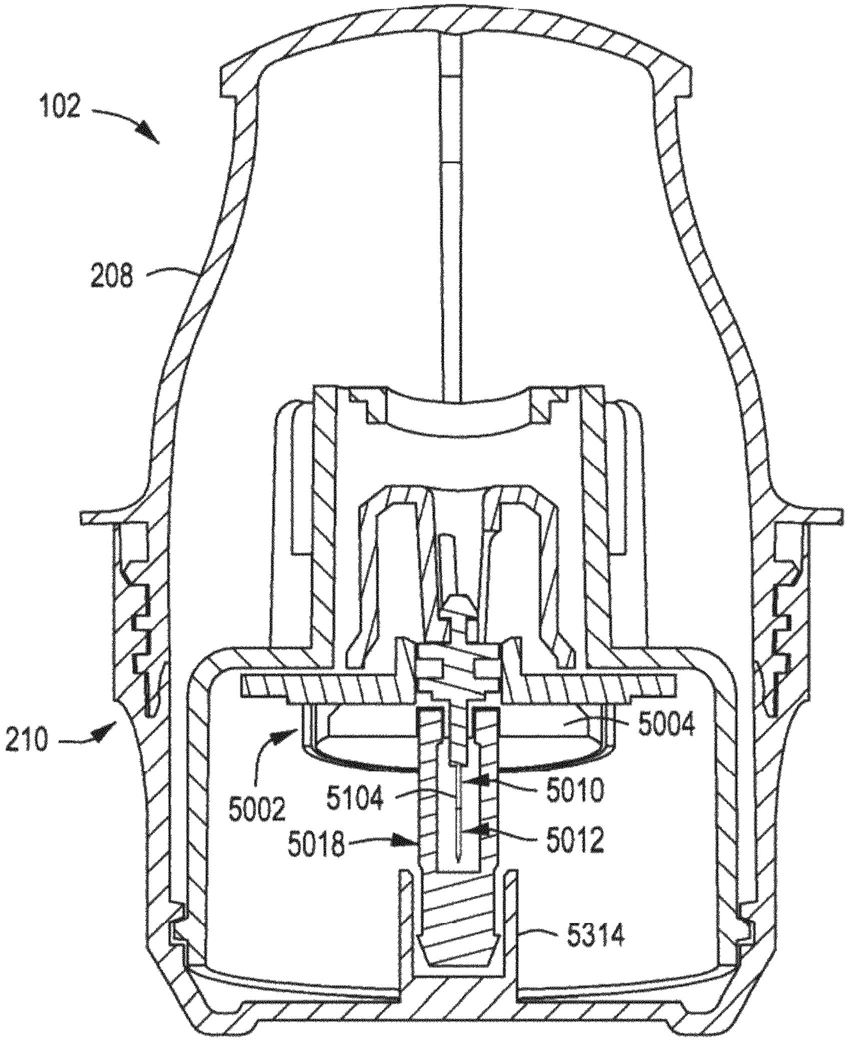

FIGS. 21A-21C are progressive cross-sectional side views showing assembly of the sensor applicator 102 with the sensor control device 5002, according to one or more embodiments. Once the sensor control device 5002 is fully assembled, it may then be loaded into the sensor applicator 102. With reference to FIG. 21A, the sharp hub 5014 may include or otherwise define a hub snap pawl 5302 configured to help couple the sensor control device 5002 to the sensor applicator 102. More specifically, the sensor control device 5002 may be advanced into the interior of the sensor applicator 102 and the hub snap pawl 5302 may be received by corresponding arms 5304 of a sharp carrier 5306 positioned within the sensor applicator 102.

In FIG. 21B, the sensor control device 5002 is shown received by the sharp carrier 5306 and, therefore, secured within the sensor applicator 102. Once the sensor control device 5002 is loaded into the sensor applicator 102, the applicator cap 210 may be coupled to the sensor applicator 102. In some embodiments, the applicator cap 210 and the housing 208 may have opposing, matable sets of threads 5308 that enable the applicator cap 210 to be screwed onto the housing 208 in a clockwise (or counter-clockwise) direction and thereby secure the applicator cap 210 to the sensor applicator 102.

As illustrated, the sheath 212 is also positioned within the sensor applicator 102, and the sensor applicator 102 may include a sheath locking mechanism 5310 configured to ensure that the sheath 212 does not prematurely collapse during a shock event. In the illustrated embodiment, the sheath locking mechanism 5310 may comprise a threaded engagement between the applicator cap 210 and the sheath 212. More specifically, one or more internal threads 5312*a* may be defined or otherwise provided on the inner surface of the applicator cap 210, and one or more external threads 53 12*b* may be defined or otherwise provided on the sheath 212. The internal and external threads 53 12*a, b* may be configured to threadably mate as the applicator cap 210 is threaded to the sensor applicator 102 at the threads 5308. The internal and external threads 5312*a, b* may have the same thread pitch as the threads 5308 that enable the applicator cap 210 to be screwed onto the housing 208.

In FIG. 21C, the applicator cap 210 is shown fully threaded (coupled) to the housing 208. As illustrated, the applicator cap 210 may further provide and otherwise define a cap post 5314 centrally located within the interior of the applicator cap 210 and extending proximally from the bottom thereof. The cap post 5314 may be configured to receive at least a portion of the sensor cap 5018 as the applicator cap 210 is screwed onto the housing 208.

With the sensor control device 5002 loaded within the sensor applicator 102 and the applicator cap 210 properly secured, the sensor control device 5002 may then be subjected to a gaseous chemical sterilization configured to sterilize the electronics housing 5004 and any other exposed portions of the sensor control device 5002. Since the distal portions of the sensor 5010 and the sharp 5012 are sealed within the sensor cap 5018, the chemicals used during the gaseous chemical sterilization process are unable to interact with the enzymes, chemistry, and biologies provided on the tail 5104, and other sensor components, such as membrane coatings that regulate analyte influx.

Figure 22A:
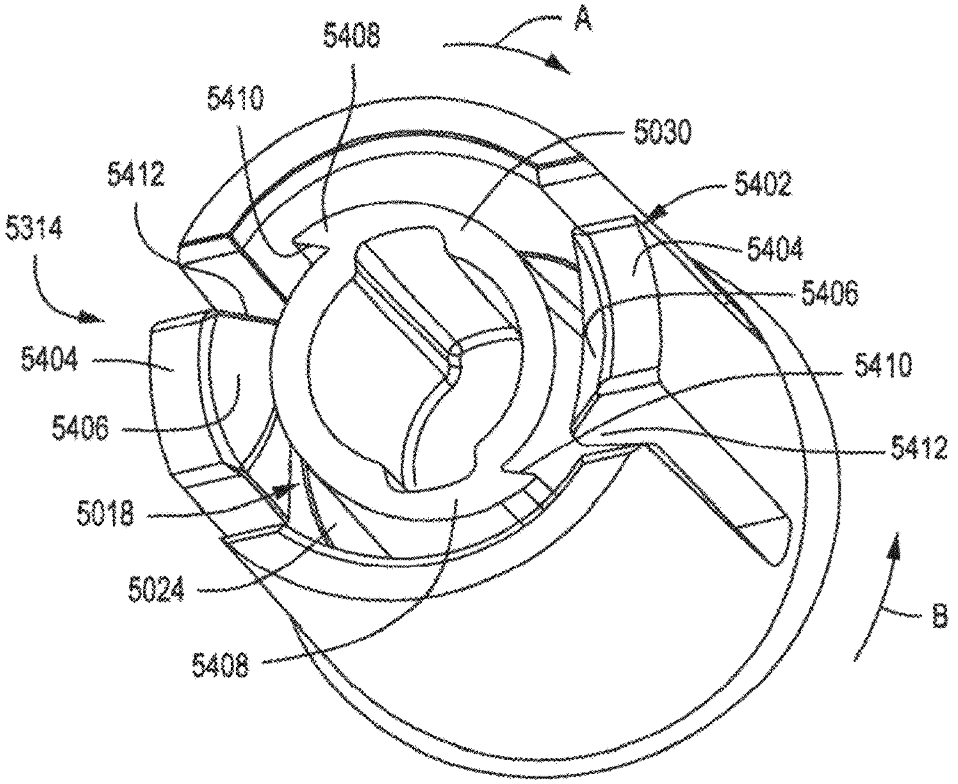
FIGS. 22A and 22B are perspective and top views, respectively, of the cap post of FIG. 21C, according to one or more additional embodiments.
Figure 22B:
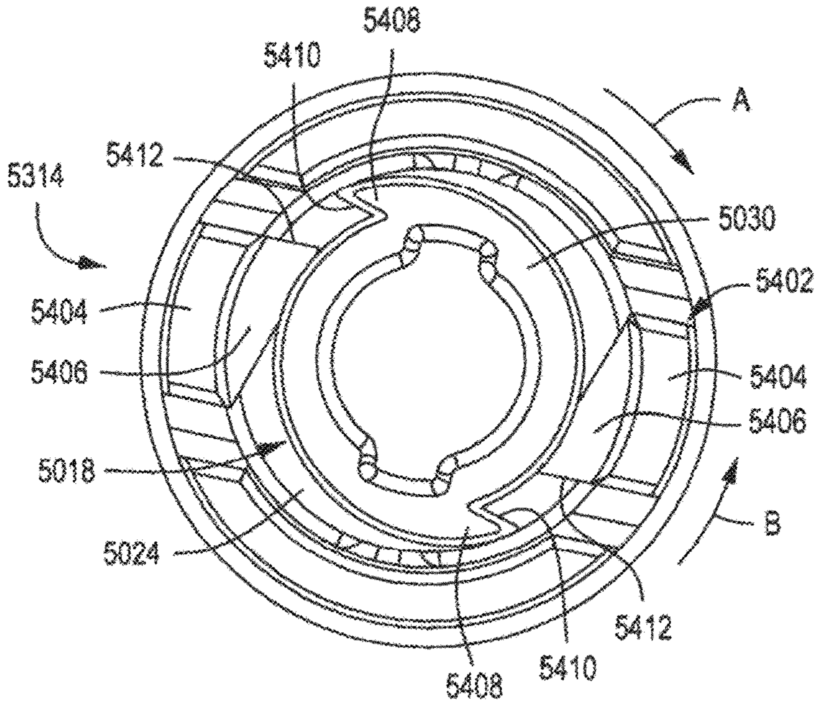

FIGS. 22A and 22B are perspective and top views, respectively, of the cap post 5314, according to one or more additional embodiments. In the illustrated depiction, a portion of the sensor cap 5018 is received within the cap post 5314 and, more specifically, the desiccant cap 5030 of the sensor cap 5018 is arranged within cap post 5314.

As illustrated, the cap post 5314 may define a receiver feature 5402 configured to receive the engagement feature 5024 of the sensor cap 5018 upon coupling (e.g., threading) the applicator cap 210 (FIG. 21C) to the sensor applicator 102 (FIGS. 21A-21C). Upon removing the applicator cap 210 from the sensor applicator 102, however, the receiver feature 5402 may prevent the engagement feature 5024 from reversing direction and thus prevent the sensor cap 5018 from separating from the cap post 5314. Instead, removing the applicator cap 210 from the sensor applicator 102 will simultaneously detach the sensor cap 5018 from the sensor control device 5002 (FIGS. 18A-18B and 21A-21C), and thereby expose the distal portions of the sensor 5010 (FIGS. 21A-21C) and the sharp 5012 (FIGS. 21A-21C).

Many design variations of the receiver feature 5402 may be employed, without departing from the scope of the disclosure. In the illustrated embodiment, the receiver feature 5402 includes one or more compliant members 5404 (two shown) that are expandable or flexible to receive the engagement feature 5024 (FIGS. 18A-18B). The engagement feature 5024 may comprise, for example, an enlarged head and the compliant member(s) 5404 may comprise a collet-type device that includes a plurality of compliant fingers configured to flex radially outward to receive the enlarged head.

The compliant member(s) 5404 may further provide or otherwise define corresponding ramped surfaces 5406 configured to interact with one or more opposing camming surfaces 5408 provided on the outer wall of the engagement feature 5024. The configuration and alignment of the ramped surface(s) 5406 and the opposing camming surface(s) 5408 is such that the applicator cap 210 is able to rotate relative to the sensor cap 5018 in a first direction A (e.g., clockwise), but the cap post 5314 binds against the sensor cap 5018 when the applicator cap 210 is rotated in a second direction B (e.g., counter clockwise). More particularly, as the applicator cap 210 (and thus the cap post 5314) rotates in the first direction A, the camming surfaces 5408 engage the ramped surfaces 5406, which urge the compliant members 5404 to flex or otherwise deflect radially outward and results in a ratcheting effect. Rotating the applicator cap 210 (and thus the cap post 5314) in the second direction B, however, will drive angled surfaces 5410 of the camming surfaces 5408 into opposing angled surfaces 5412 of the ramped surfaces 5406, which results in the sensor cap 5018 binding against the compliant member(s) 5404.

Figure 23:
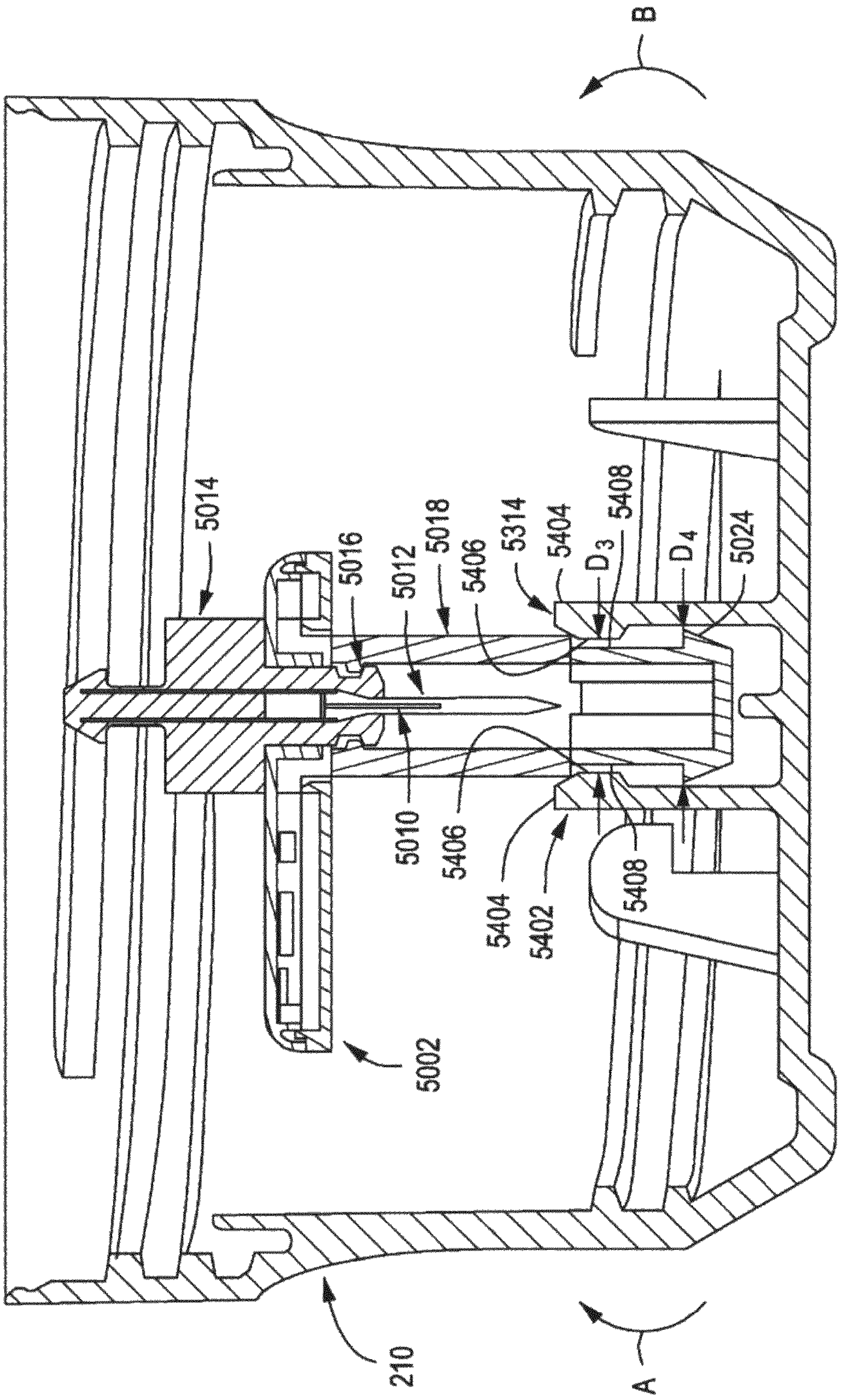
FIG. 23 is a cross-sectional side view of the sensor control device of FIGS. 18A-18B.

FIG. 23 is a cross-sectional side view of the sensor control device 5002 positioned within the applicator cap 210, according to one or more embodiments. As illustrated, the opening to the receiver feature 5402 exhibits a first diameter D3, while the engagement feature 5024 of the sensor cap 5018 exhibits a second diameter D4 that is larger than the first diameter D3 and greater than the outer diameter of the remaining portions of the sensor cap 5018. As the sensor cap 5018 is extended into the cap post 5314, the compliant member(s) 5404 of the receiver feature 5402 may flex (expand) radially outward to receive the engagement feature 5024. In some embodiments, as illustrated, the engagement feature 5024 may provide or otherwise define an angled or frustoconical outer surface that helps bias the compliant member(s) 5404 radially outward. Once the engagement feature 5024 bypasses the receiver feature 5402, the compliant member(s) 5404 are able to flex back to (or towards) their natural state and thus lock the sensor cap 5018 within the cap post 5314.

As the applicator cap 210 is threaded to (screwed onto) the housing 208 (FIGS. 21A-21C) in the first direction A, the cap post 5314 correspondingly rotates in the same direction and the sensor cap 5018 is progressively introduced into the cap post 5314. As the cap post 5314 rotates, the ramped surfaces 5406 of the compliant members 5404 ratchet against the opposing camming surfaces 5408 of the sensor cap 5018. This continues until the applicator cap 210 is fully threaded onto (screwed onto) the housing 208. In some embodiments, the ratcheting action may occur over two full revolutions of the applicator cap 210 before the applicator cap 210 reaches its final position.

To remove the applicator cap 210, the applicator cap 210 is rotated in the second direction B, which correspondingly rotates the cap post 5314 in the same direction and causes the camming surfaces 5408 (i.e., the angled surfaces 5410 of FIGS. 22A-22B) to bind against the ramped surfaces 5406 (i.e., the angled surfaces 5412 of FIGS. 22A-22B). Consequently, continued rotation of the applicator cap 210 in the second direction B causes the sensor cap 5018 to correspondingly rotate in the same direction and thereby unthread from the mating member 5016 to allow the sensor cap 5018 to detach from the sensor control device 5002. Detaching the sensor cap 5018 from the sensor control device 5002 exposes the distal portions of the sensor 5010 and the sharp 5012, and thus places the sensor control device 5002 in position for firing (use).

Figure 24B:
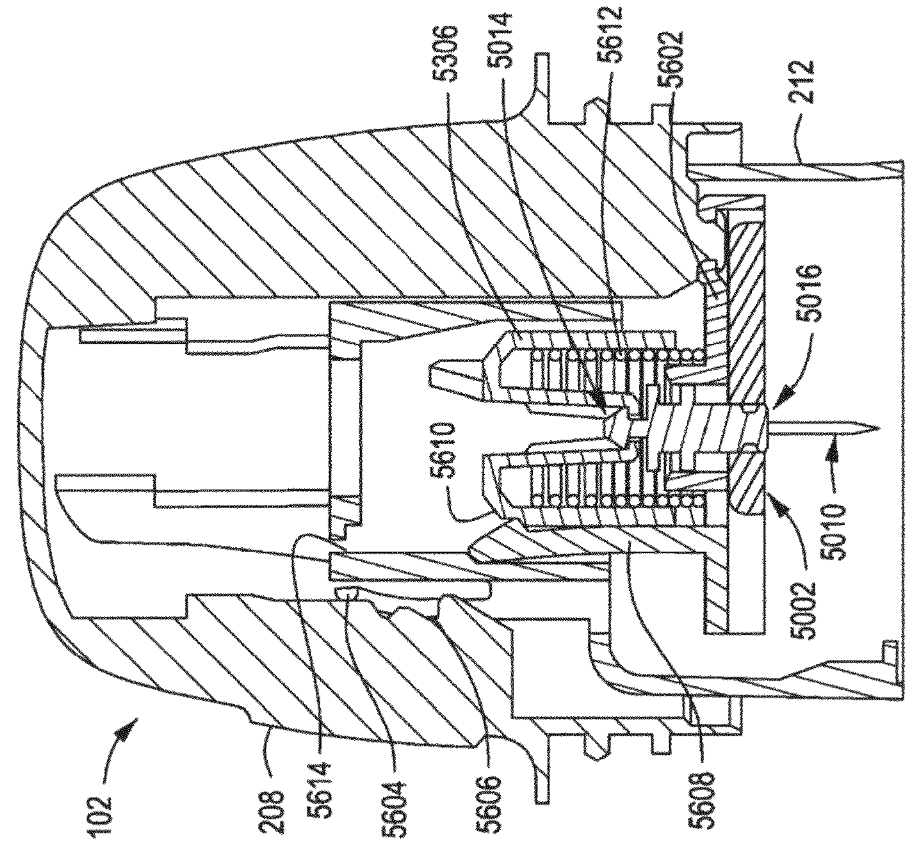
FIGS. 24A and 24B are cross-sectional side views of the sensor applicator ready to deploy the sensor control device to a target monitoring location.
Figure 24A:
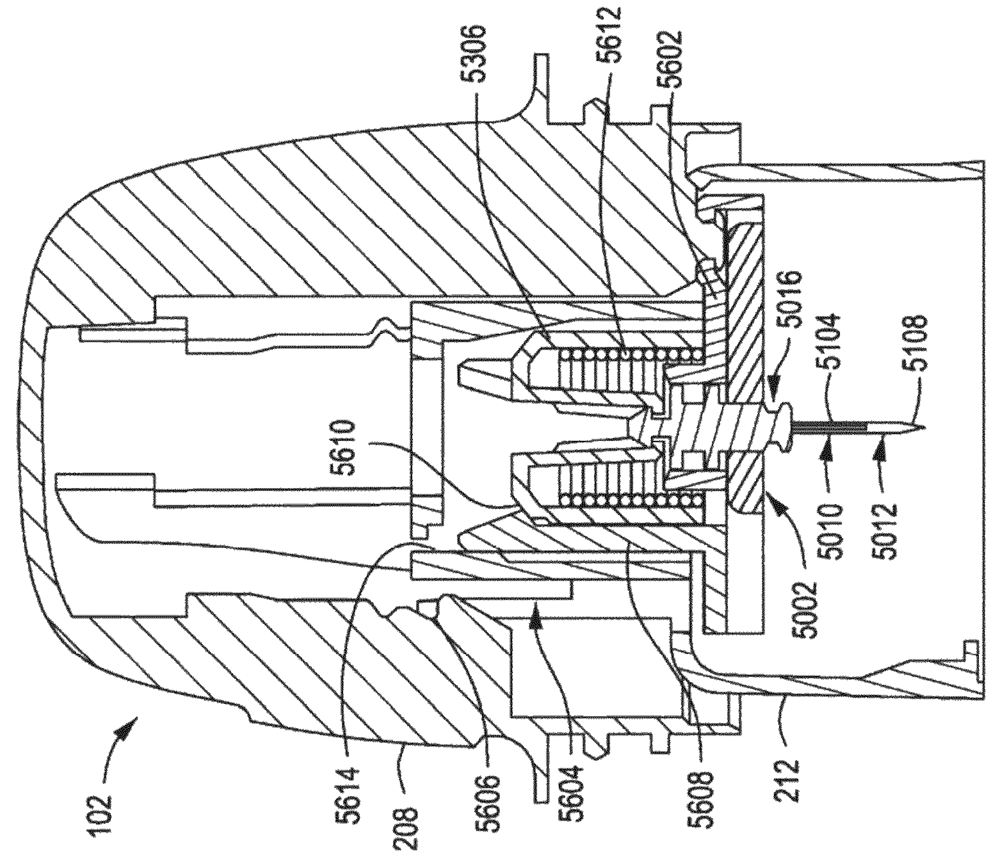

FIGS. 24A and 24B are cross-sectional side views of the sensor applicator 102 ready to deploy the sensor control device 5002 to a target monitoring location, according to one or more embodiments. More specifically, FIG. 24A depicts the sensor applicator 102 ready to deploy (fire) the sensor control device 5002, and FIG. 24B depicts the sensor applicator 102 in the process of deploying (firing) the sensor control device 5002. As illustrated, the applicator cap 210 (FIGS. 21A-21C and 23) has been removed, which correspondingly detaches (removes) the sensor cap 5018 (FIGS. 21A-21C and 23) and thereby exposes the tail 5104 of the sensor 5010 and the sharp tip 5108 of the sharp 5012, as described above. In conjunction with the sheath 212 and the sharp carrier 5306, the sensor applicator 102 also includes a sensor carrier 5602 (alternately referred to as a "puck"

carrier) that helps position and secure the sensor control device 5002 within the sensor applicator 102.

Referring first to FIG. 24A, as illustrated, the sheath 212 includes one or more sheath arms 5604 (one shown) configured to interact with a corresponding one or more detents 5606 (one shown) defined within the interior of the housing 208. The detent(s) 5606 are alternately referred to as "firing" detent(s). When the sensor control device 5002 is initially installed in the sensor applicator 102, the sheath arms 5604 may be received within the detents 5606, which places the sensor applicator 102 in firing position. In the firing position, the mating member 5016 extends distally beyond the bottom of the sensor control device 5002. As discussed below, the process of firing the sensor applicator 102 causes the mating member 5016 to retract so that it does not contact the user's skin.

The sensor carrier 5602 may also include one or more carrier arms 5608 (one shown) configured to interact with a corresponding one or more grooves 5610 (one shown) defined on the sharp carrier 5306. A spring 5612 may be arranged within a cavity defined by the sharp carrier 5306 and may passively bias the sharp carrier 5306 upward within the housing 208. When the carrier arm(s) 5608 are properly received within the groove(s) 5610, however, the sharp carrier 5306 is maintained in position and prevented from moving upward. The carrier arm(s) 5608 interpose the sheath 212 and the sharp carrier 5306, and a radial shoulder 5614 defined on the sheath 212 may be sized to maintain the carrier arm(s) 5608 engaged within the groove(s) 5610 and thereby maintain the sharp carrier 5306 in position.

In FIG. 24B, the sensor applicator 102 is in the process of firing. As discussed herein with reference to FIGS. 3F-3G, this may be accomplished by advancing the sensor applicator 102 toward a target monitoring location until the sheath 212 engages the skin of the user. Continued pressure on the sensor applicator 102 against the skin may cause the sheath arm(s) 5604 to disengage from the corresponding detent(s) 5606, which allows the sheath 212 to collapse into the housing 208. As the sheath 212 starts to collapse, the radial shoulder 5614 eventually moves out of radial engagement with the carrier arm(s) 5608, which allows the carrier arm(s) 5608 to disengage from the groove(s) 5610. The passive spring force of the spring 5612 is then free to push upward on the sharp carrier 5306 and thereby force the carrier arm(s) 5608 out of engagement with the groove(s) 5610, which allows the sharp carrier 5306 to move slightly upward within the housing 208. In some embodiments, fewer coils may be incorporated into the design of the spring 5612 to increase the spring force necessary to overcome the engagement between carrier arm(s) 5608 and the groove(s) 5610. In at least one embodiment, one or both of the carrier arm(s) 5608 and the groove(s) 5610 may be angled to help ease disengagement.

As the sharp carrier 5306 moves upward within the housing 208, the sharp hub 5014 may correspondingly move in the same direction, which may cause partial retraction of the mating member 5016 such that it becomes flush, substantially flush, or sub-flush with the bottom of the sensor control device 5002. As will be appreciated, this ensures that the mating member 5016 does not come into contact with the user's skin, which might otherwise adversely impact sensor insertion, cause excessive pain, or prevent the adhesive patch (not shown) positioned on the bottom of the sensor control device 5002 from properly adhering to the skin.

Figure 25A:
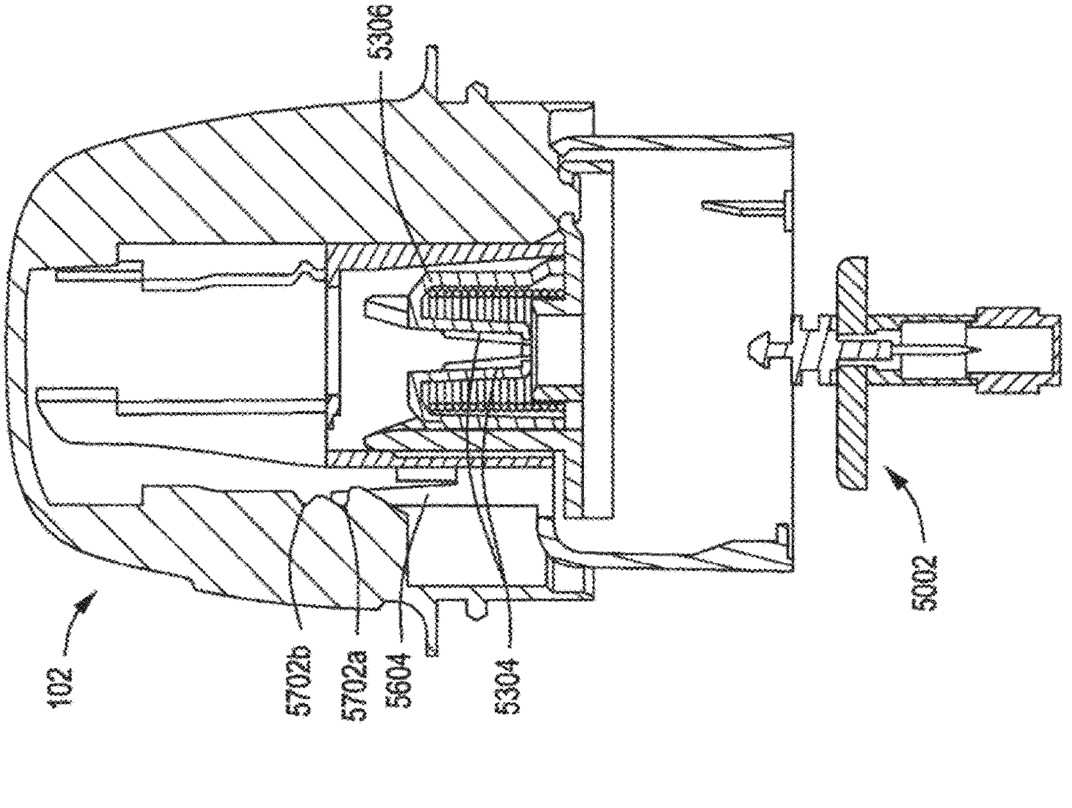
FIGS. 25A-25C are progressive cross-sectional side views showing assembly and disassembly of an example embodiment of the sensor applicator with the sensor control device of FIGS. 18A-18B.
Figure 25B:
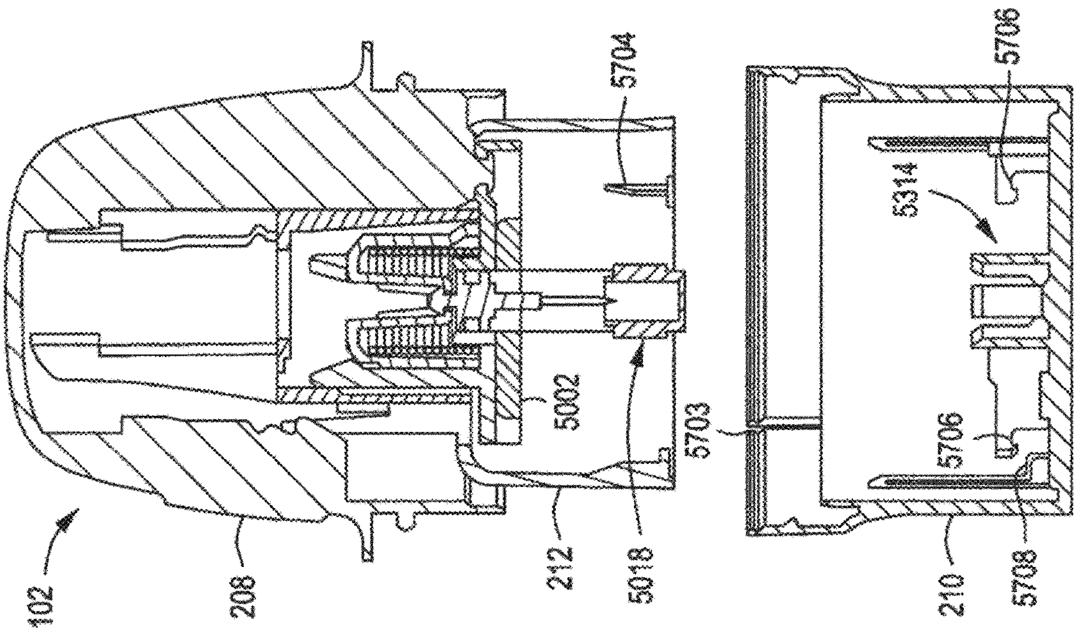
Figure 25C:
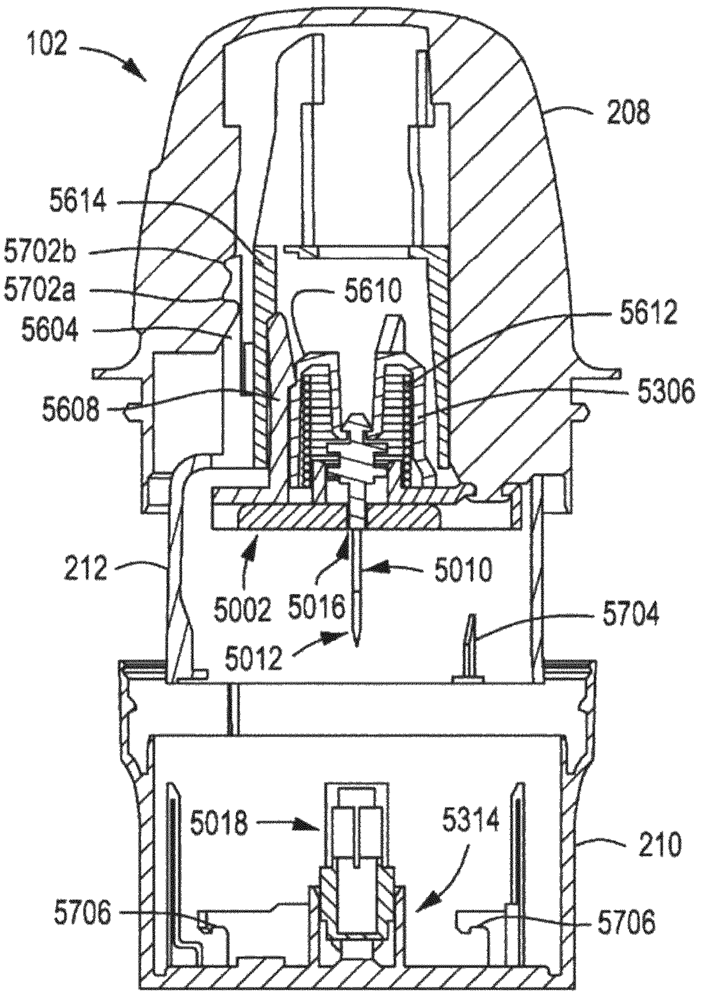

FIGS. 25A-25C are progressive cross-sectional side views showing assembly and disassembly of an alternative embodiment of the sensor applicator 102 with the sensor control device 5002, according to one or more additional embodiments. A fully assembled sensor control device 5002 may be loaded into the sensor applicator 102 by coupling the hub snap pawl 5302 into the arms 5304 of the sharp carrier 5306 positioned within the sensor applicator 102, as generally described above.

In the illustrated embodiment, the sheath arms 5604 of the sheath 212 may be configured to interact with a first detent 5702*a* and a second detent 5702*b* defined within the interior of the housing 208. The first detent 5702*a* may alternately be referred to a "locking" detent, and the second detent 5702*b* may alternately be referred to as a "firing" detent. When the sensor control device 5002 is initially installed in the sensor applicator 102, the sheath arms 5604 may be received within the first detent 5702*a*. As discussed below, the sheath 212 may be actuated to move the sheath arms 5604 to the second detent 5702*b*, which places the sensor applicator 102 in firing position.

In FIG. 25B, the applicator cap 210 is aligned with the housing 208 and advanced toward the housing 208 so that the sheath 212 is received within the applicator cap 210. Instead of rotating the applicator cap 210 relative to the housing 208, the threads of the applicator cap 210 may be snapped onto the corresponding threads of the housing 208 to couple the applicator cap 210 to the housing 208. Axial cuts or slots 5703 (one shown) defined in the applicator cap 210 may allow portions of the applicator cap 210 near its threading to flex outward to be snapped into engagement with the threading of the housing 208. As the applicator cap 210 is snapped to the housing 208, the sensor cap 5018 may correspondingly be snapped into the cap post 5314.

Similar to the embodiment of FIGS. 21A-21C, the sensor applicator 102 may include a sheath locking mechanism configured to ensure that the sheath 212 does not prematurely collapse during a shock event. In the illustrated embodiment, the sheath locking mechanism includes one or more ribs 5704 (one shown) defined near the base of the sheath 212 and configured to interact with one or more ribs 5706 (two shown) and a shoulder 5708 defined near the base of the applicator cap 210. The ribs 5704 may be configured to inter-lock between the ribs 5706 and the shoulder 5708 while attaching the applicator cap 210 to the housing 208. More specifically, once the applicator cap 210 is snapped onto the housing 208, the applicator cap 210 may be rotated (e.g., clockwise), which locates the ribs 5704 of the sheath 212 between the ribs 5706 and the shoulder 5708 of the applicator cap 210 and thereby "locks" the applicator cap 210 in place until the user reverse rotates the applicator cap 210 to remove the applicator cap 210 for use. Engagement of the ribs 5704 between the ribs 5706 and the shoulder 5708 of the applicator cap 210 may also prevent the sheath 212 from collapsing prematurely.

In FIG. 25C, the applicator cap 210 is removed from the housing 208. As with the embodiment of FIGS. 21A-21C, the applicator cap 210 can be removed by reverse rotating the applicator cap 210, which correspondingly rotates the cap post 5314 in the same direction and causes sensor cap 5018 to unthread from the mating member 5016, as generally described above. Moreover, detaching the sensor cap 5018 from the sensor control device 5002 exposes the distal portions of the sensor 5010 and the sharp 5012.

As the applicator cap 210 is unscrewed from the housing 208, the ribs 5704 defined on the sheath 212 may slidingly engage the tops of the ribs 5706 defined on the applicator cap 210. The tops of the ribs 5706 may provide corresponding ramped surfaces that result in an upward displacement of the sheath 212 as the applicator cap 210 is rotated, and moving the sheath 212 upward causes the sheath arms 5604 to flex out of engagement with the first detent 5702*a* to be received within the second detent 5702*b*. As the sheath 212 moves to the second detent 5702*b*, the radial shoulder 5614 moves out of radial engagement with the carrier arm(s) 5608, which allows the passive spring force of the spring 5612 to push upward on the sharp carrier 5306 and force the carrier arm(s) 5608 out of engagement with the groove(s) 5610. As the sharp carrier 5306 moves upward within the housing 208, the mating member 5016 may correspondingly retract until it becomes flush, substantially flush, or sub-flush with the bottom of the sensor control device 5002. At this point, the sensor applicator 102 in firing position. Accordingly, in this embodiment, removing the applicator cap 210 correspondingly causes the mating member 5016 to retract.

Figure 26A:
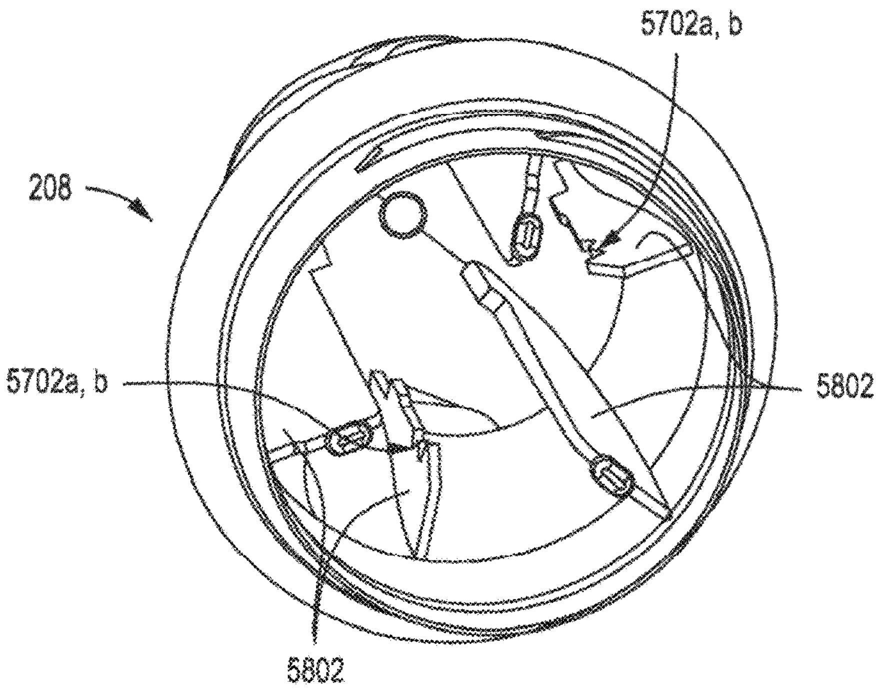
FIG. 26A is an isometric bottom view of the housing, according to one or more embodiments.

FIG. 26A is an isometric bottom view of the housing 208, according to one or more embodiments. As illustrated, one or more longitudinal ribs 5802 (four shown) may be defined within the interior of the housing 208. The ribs 5802 may be equidistantly or non-equidistantly spaced from each other and extend substantially parallel to centerline of the housing 208. The first and second detents 5702*a, b* may be defined on one or more of the longitudinal ribs 5802.

Figure 27A:
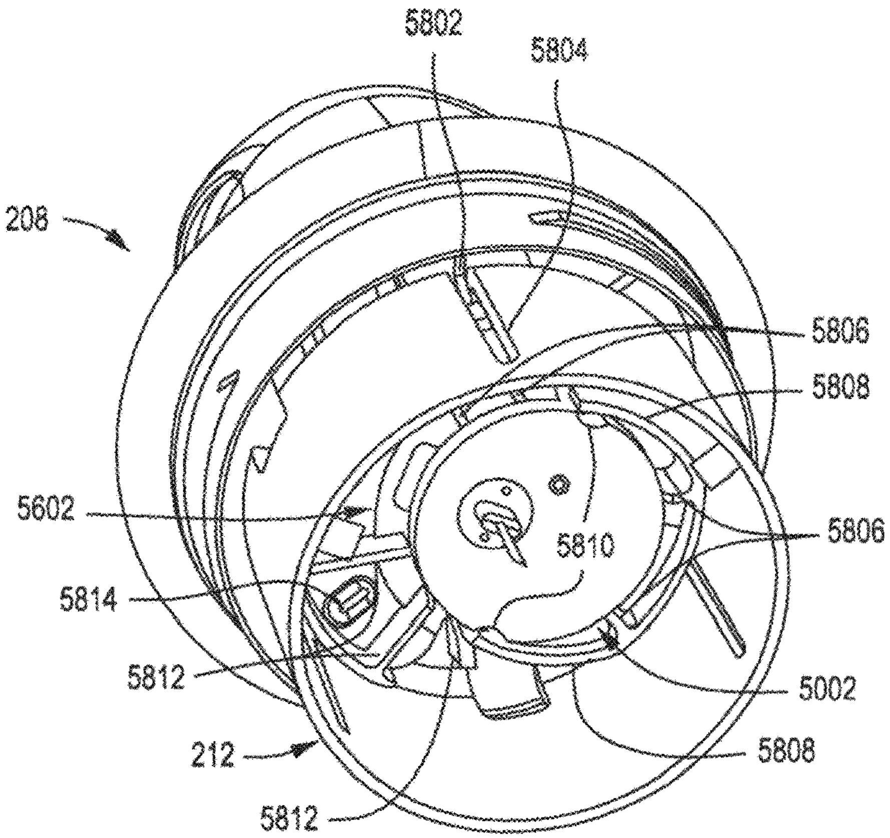
FIG. 27A is an isometric bottom view of the housing with the sheath and other components at least partially positioned therein.

FIG. 27A is an isometric bottom view of the housing 208 with the sheath 212 and other components at least partially positioned within the housing 208. As illustrated, the sheath 212 may provide or otherwise define one or more longitudinal slots 5804 configured to mate with the longitudinal ribs 5802 of the housing 208. As the sheath 212 collapses into the housing 208, as generally described above, the ribs 5802 may be received within the slots 5804 to help maintain the sheath 212 aligned with the housing during its movement. As will be appreciated, this may result in tighter circumferential and radial alignment within the same dimensional and tolerance restrictions of the housing 208.

In the illustrated embodiment, the sensor carrier 5602 may be configured to hold the sensor control device 5002 in place both axially (e.g., once the sensor cap 5018 is removed) and circumferentially. To accomplish this, the sensor carrier 5602 may include or otherwise define one or more support ribs 5806 and one or more flexible arms 5808. The support ribs 5806 extend radially inward to provide radial support to the sensor control device 5002. The flexible arms 5808 extend partially about the circumference of the sensor control device 5002 and the ends of the flexible arms 5808 may be received within corresponding grooves 5810 defined in the side of the sensor control device 5002. Accordingly, the flexible arms 5808 may be able to provide both axial and radial support to the sensor control device 5002. In at least one embodiment, the ends of the flexible arms 5808 may be biased into the grooves 5810 of the sensor control device 5002 and otherwise locked in place with corresponding sheath locking ribs 5812 provided by the sheath 212.

In some embodiments, the sensor carrier 5602 may be ultrasonically welded to the housing 208 at one or more points 5814. In other embodiments, however, the sensor carrier 5602 may alternatively be coupled to the housing 208 via a snap-fit engagement, without departing from the scope of the disclosure. This may help hold the sensor control device 5002 in place during transport and firing.

Figure 28:
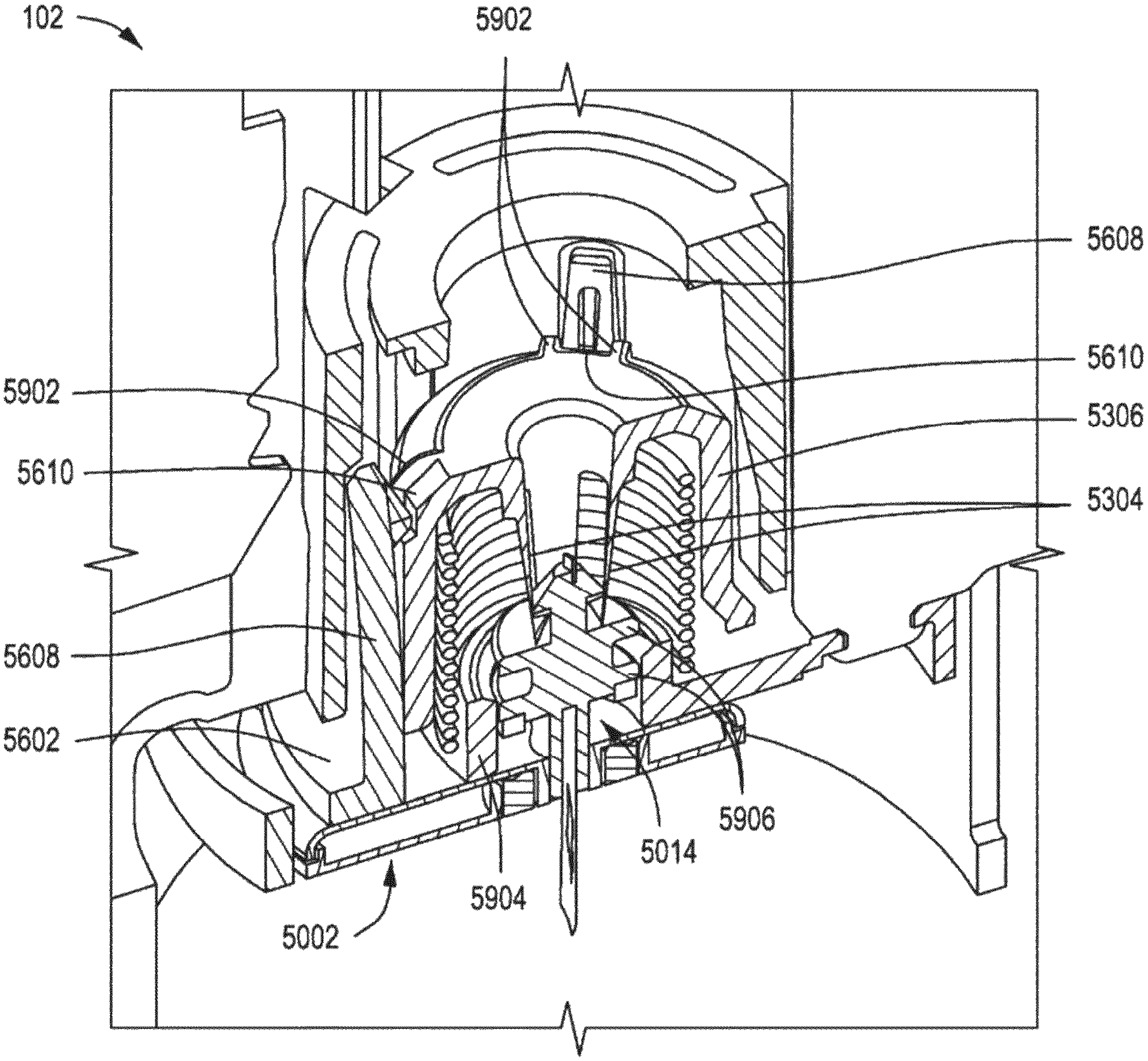
FIG. 28 is an enlarged cross-sectional side view of the sensor applicator with the sensor control device installed therein, according to one or more embodiments.

FIG. 28 is an enlarged cross-sectional side view of the sensor applicator 102 with the sensor control device 5002 installed therein, according to one or more embodiments. As discussed above, the sensor carrier 5602 may include one or more carrier arms 5608 (two shown) engageable with the sharp carrier 5306 at corresponding grooves 5610. In at least one embodiment, the grooves 5610 may be defined by pairs of protrusions 5902 defined on the sharp carrier 5306. Receiving the carrier arms 5608 within the grooves 5610 may help stabilize the sharp carrier 5306 from unwanted tilting during all stages of retraction (firing).

In the illustrated embodiment, the arms 5304 of the sharp carrier 5306 may be stiff enough to control, with greater refinement, radial and bi-axial motion of the sharp hub 5014. In some embodiments, for example, clearances between the sharp hub 5014 and the arms 5304 may be more restrictive in both axial directions as the relative control of the height of the sharp hub 5014 may be more critical to the design.

In the illustrated embodiment, the sensor carrier 5602 defines or otherwise provides a central boss 5904 sized to receive the sharp hub 5014. In some embodiments, as illustrated, the sharp hub 5014 may provide one or more radial ribs 5906 (two shown). In at least one embodiment, the inner diameter of the central boss 5904 helps provide radial and tilt support to the sharp hub 5014 during the life of sensor applicator 102 and through all phases of operation and assembly. Moreover, having multiple radial ribs 5906 increases the length-to-width ratio of the sharp hub 5014, which also improves support against tilting.

Figure 29A:
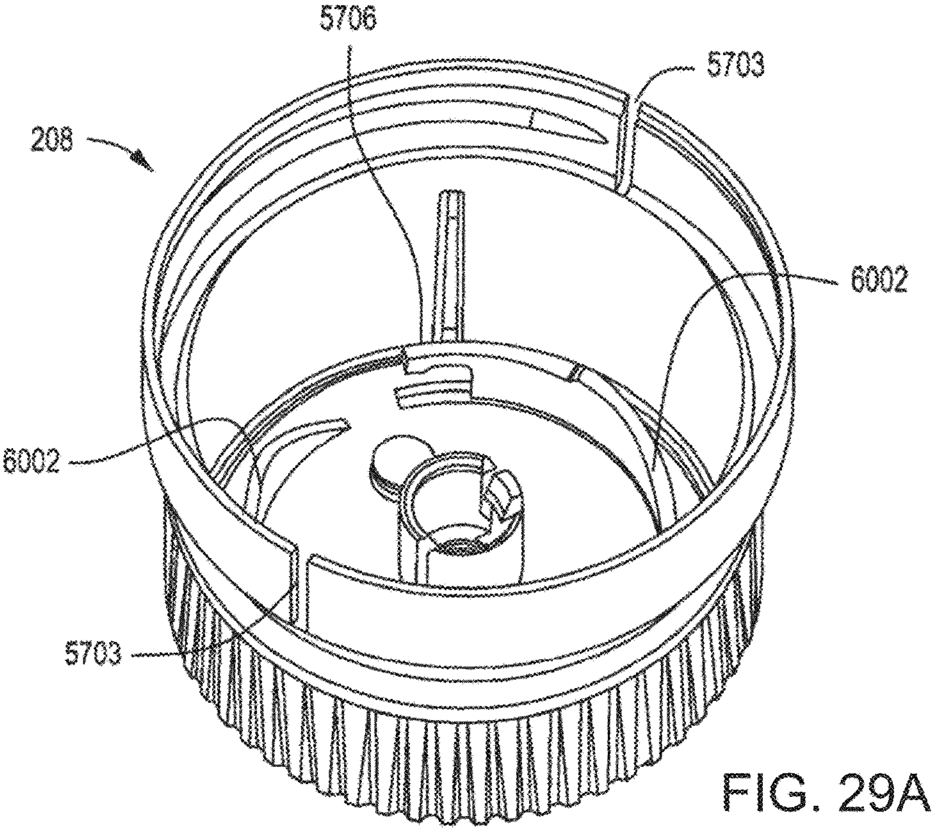
FIG. 29A is an isometric top view of the cap, according to one or more embodiments.

FIG. 29A is an isometric top view of the applicator cap 210, according to one or more embodiments. In the illustrated embodiment, two axial slots 5703 are depicted that separate upper portions of the applicator cap 210 near its threading. As mentioned above, the slots 5703 may help the applicator cap 210 flex outward to be snapped into engagement with the housing 208 (FIG. 25B). In contrast, the applicator cap 210 may be twisted (unthreaded) off the housing 208 by an end user.

FIG. 29A also depicts the ribs 5706 (one visible) defined by the applicator cap 210. By interlocking with the ribs 5704 (FIG. 25C) defined on the sheath 212 (FIG. 25C), the ribs 5706 may help lock the sheath 212 in all directions to prevent premature collapse during a shock or drop event. The sheath 212 may be unlocked when the user unscrews the applicator cap 210 from the housing, as generally described above. As mentioned herein, the top of each rib 5706 may provide a corresponding ramped surface 6002, and as the applicator cap 210 is rotated to unthread from the housing 208, the ribs 5704 defined on the sheath 212 may slidingly engage the ramped surfaces 6002, which results in the upward displacement of the sheath 212 into the housing 208.

In some embodiments, additional features may be provided within the interior of the applicator cap 210 to hold a desiccant component that maintains proper moisture levels through shelf life. Such additional features may be snaps, posts for press-fitting, heat-staking, ultrasonic welding, etc.

Figure 29B:
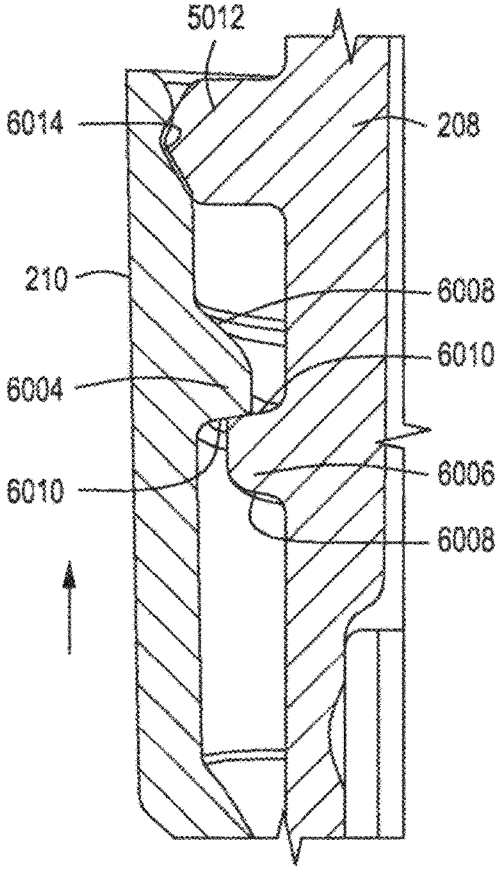
FIG. 29B is an enlarged cross-sectional view of the engagement between the cap and the housing, according to one or more embodiments.

FIG. 29B is an enlarged cross-sectional view of the engagement between the applicator cap 210 and the housing 208, according to one or more embodiments. As illustrated, the applicator cap 210 may define a set of inner threads 6004 and the housing 208 may define a set of outer threads 6006 engageable with the inner threads 6004. As mentioned herein, the applicator cap 210 may be snapped onto the housing 208, which may be accomplished by advancing the inner threads 6004 axially past the outer threads 6006 in the direction indicated by the arrow, which causes the applicator cap 210 to flex outward. To help ease this transition, as illustrated, corresponding surfaces 6008 of the inner and outer threads 6004, 6006 may be curved, angled, or chamfered. Corresponding flat surfaces 6010 may be provided on each thread 6004, 6006 and configured to matingly engage once the applicator cap 210 is properly snapped into place on the housing 208. The flat surfaces 6010 may slidingly engage one another as the user unthreads the applicator cap 210 from the housing 208.

The threaded engagement between the applicator cap 210 and the housing 208 results in a sealed engagement that protects the inner components against moisture, dust, etc. In some embodiments, the housing 208 may define or otherwise provide a stabilizing feature 6012 configured to be received within a corresponding groove 1914 defined on the applicator cap 210. The stabilizing feature 6012 may help stabilize and stiffen the applicator cap 210 once the applicator cap 210 is snapped onto the housing 208. This may prove advantageous in providing additional drop robustness to the sensor applicator 102. This may also help increase the removal torque of the applicator cap 210.

Figure 30A:
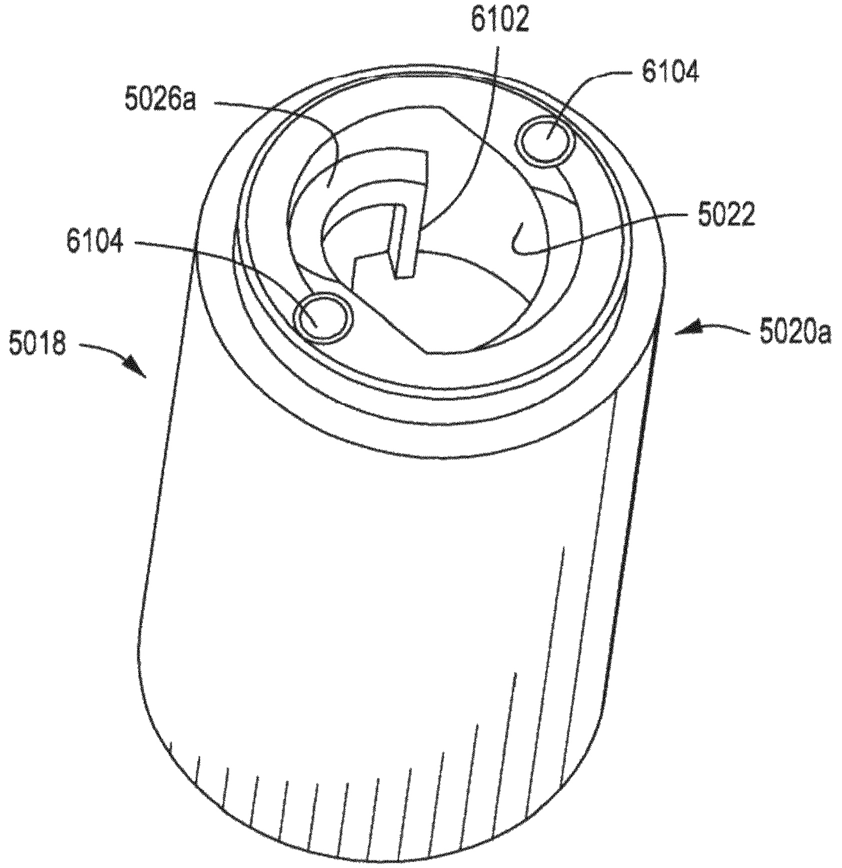
FIGS. 30A and 30B are isometric views of the sensor cap and the collar, respectively, according to one or more embodiments.
Figure 30B:
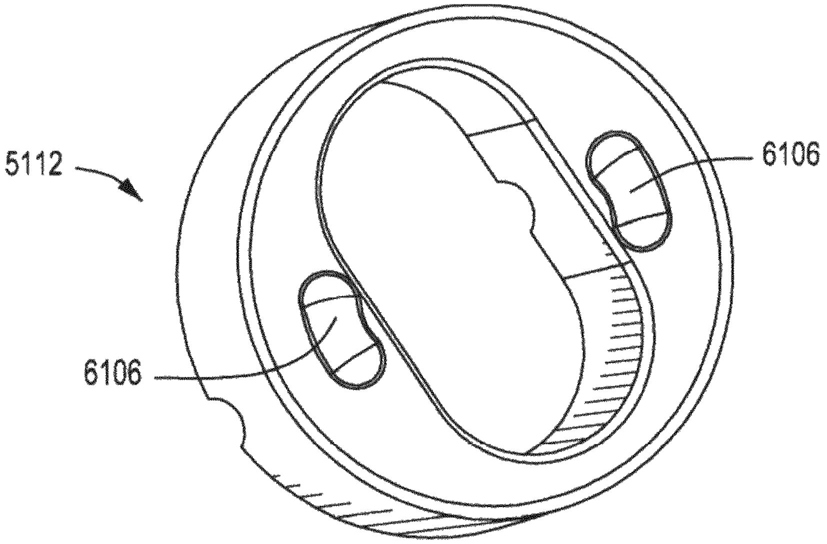

FIGS. 30A and 30B are isometric views of the sensor cap 5018 and the collar 5112, respectively, according to one or more embodiments. Referring to FIG. 30A, in some embodiments, the sensor cap 5018 may comprise an injection molded part. This may prove advantageous in molding the internal threads 5026*a* defined within the inner chamber 5022, as opposed to installing a threaded core or threading the inner chamber 5022. In some embodiments, one or more stop ribs 6102 (on visible) may be defined within the inner chamber 5022 to prevent over travel relative to mating member 5016 of the sharp hub 5014 (FIGS. 18A-18B).

Referring to both FIGS. 30A and 30B, in some embodiments, one or more protrusions 6104 (two shown) may be defined on the first end 5020*a* of the sensor cap 5018 and configured to mate with one or more corresponding indentations 6106 (two shown) defined on the collar 5112. In other embodiments, however, the protrusions 6104 may instead be defined on the collar 5112 and the indentations 6106 may be defined on the sensor cap 5018, without departing from the scope of the disclosure.

The matable protrusions 6104 and indentations 6106 may prove advantageous in rotationally locking the sensor cap 5018 to prevent unintended unscrewing of the sensor cap 5018 from the collar 5112 (and thus the sensor control device 5002) during the life of the sensor applicator 102 and through all phases of operation/assembly. In some embodiments, as illustrated, the indentations 6106 may be formed or otherwise defined in the general shape of a kidney bean. This may prove advantageous in allowing for some over-rotation of the sensor cap 5018 relative to the collar 5112. Alternatively, the same benefit may be achieved via a flat end threaded engagement between the two parts.

Embodiments disclosed herein include:

A. A sensor control device that includes an electronics housing, a sensor arranged within the electronics housing and having a tail extending from a bottom of the electronics housing, a sharp extending through the electronics housing and having a sharp tip extending from the bottom of the electronics housing, and a sensor cap removably coupled at the bottom of the electronics housing and defining a sealed inner chamber that receives the tail and the sharp.

B. An analyte monitoring system that includes a sensor applicator, a sensor control device positioned within the sensor applicator and including an electronics housing, a sensor arranged within the electronics housing and having a tail extending from a bottom of the electronics housing, a sharp extending through the electronics housing and having a sharp tip extending from the bottom of the electronics housing, and a sensor cap removably coupled at the bottom of the electronics housing and defining an engagement feature and a sealed inner chamber that receives the tail and the sharp. The analyte monitoring system may further include a cap coupled to the sensor applicator and providing a cap post defining a receiver feature that receives the engagement feature upon coupling the cap to the sensor applicator, wherein removing the cap from the sensor applicator detaches the sensor cap from the electronics housing and thereby exposes the tail and the sharp tip.

C. A method of preparing an analyte monitoring system that includes loading a sensor control device into a sensor applicator, the sensor control device including an electronics housing, a sensor arranged within the electronics housing and having a tail extending from a bottom of the electronics housing, a sharp extending through the electronics housing and having a sharp tip extending from the bottom of the electronics housing, and a sensor cap removably coupled at the bottom of the electronics housing and defining a sealed inner chamber that receives the tail and the sharp. The method further including securing a cap to the sensor applicator, sterilizing the sensor control device with gaseous chemical sterilization while the sensor control device is positioned within the sensor applicator, and isolating the tail and the sharp tip within the inner chamber from the gaseous chemical sterilization.

Each of embodiments A, B, and C may have one or more of the following additional elements in any combination: Element 1: wherein the sensor cap comprises a cylindrical body having a first end that is open to access the inner chamber, and a second end opposite the first end and providing an engagement feature engageable with a cap of a sensor applicator, wherein removing the cap from the sensor applicator correspondingly removes the sensor cap from the electronics housing and thereby exposes the tail and the sharp tip. Element 2: wherein the electronics housing includes a shell matable with a mount, the sensor control device further comprising a sharp and sensor locator defined on an inner surface of the shell, and a collar received about the sharp and sensor locator, wherein the sensor cap is removably coupled to the collar. Element 3: wherein the sensor cap is removably coupled to the collar by one or more of an interference fit, a threaded engagement, a frangible member, and a frangible substance. Element 4: wherein an annular ridge circumscribes the sharp and sensor locator and the collar provides a column and an annular shoulder extending radially outward from the column, and wherein a seal member interposes the annular shoulder and the annular ridge to form a sealed interface. Element 5: wherein the annular ridge defines a groove and a portion of the sensor is seated within the groove, and wherein the seal member extends into the groove to seal about the portion of the sensor. Element 6: wherein the seal member is a first seal member, the sensor control device further comprising a second seal member interposing the annular shoulder and a portion of the mount to form a sealed interface. Element 7: wherein the electronics housing includes a shell matable with a mount, the sensor control device further comprising a sharp hub that carries the sharp and is engageable with a top surface of the shell, and a mating member defined by the sharp hub and extending from the bottom of the electronics housing, wherein the sensor cap is removably coupled to the mating member. Element 8: further comprising a collar at least partially receivable within an aperture defined in the mount and sealingly engaging the sensor cap and an inner surface of the shell. Element 9: wherein a seal member interposes the collar and the inner surface of the shell to form a sealed interface. Element 10: wherein the collar defines a groove and a portion of the sensor is seated within the groove, and wherein the seal member extends into the groove to seal about the portion of the sensor.

Element 11: wherein the receiver feature comprises one or more compliant members that flex to receive the engagement feature, and wherein the one or more compliant members prevent the engagement feature from exiting the cap post upon removing the cap from the sensor applicator. Element 12: further comprising a ramped surface defined on at least one of the one or more compliant members, and one or more camming surfaces provided by the engagement feature and engageable with the ramped surface, wherein the ramped surface and the one or more camming surfaces allow the cap and the cap post to rotate relative to the sensor cap in a first direction, but prevent the cap and the cap post from rotating relative to the sensor cap in a second direction opposite the first direction. Element 13: wherein the electronics housing includes a shell matable with a mount, the sensor control device further comprising a sharp hub that carries the sharp and is engageable with a top surface of the shell, and a mating member defined by the sharp hub and extending from the bottom of the electronics housing, wherein the sensor cap is removably coupled to the mating member and rotating the cap in the second direction detaches the sensor cap from the mating member. Element 14: wherein the electronics housing includes a shell matable with a mount and the sensor control device further includes a sharp and sensor locator defined on an inner surface of the shell, and a collar received about the sharp and sensor locator, wherein the sensor cap is removably coupled to the collar.

Element 15: wherein the cap provides a cap post defining a receiver feature and the sensor cap defines an engagement feature, the method further comprising receiving the engagement feature with the receiver feature as the cap is secured to the sensor applicator. Element 16: further comprising removing the cap from the sensor applicator, and engaging the engagement feature on the receiver feature as the cap is being removed and thereby detaching the sensor cap from the electronics housing and exposing the tail and the sharp tip. Element 17: wherein loading the sensor control device into a sensor applicator is preceded by sterilizing the tail and the sharp tip with radiation sterilization, and sealing the tail and the sharp tip within the inner chamber.

By way of non-limiting example, exemplary combinations applicable to A, B, and C include: Element 2 with Element 3; Element 2 with Element 4; Element 4 with Element 5; Element 4 with Element 6; Element 7 with Element 8; Element 8 with Element 9; Element 9 with Element 10; Element 11 with Element 12; and Element 15 with Element 16.

Example Embodiments of Seal Arrangement for Analyte Monitoring Systems

Figure 31A:
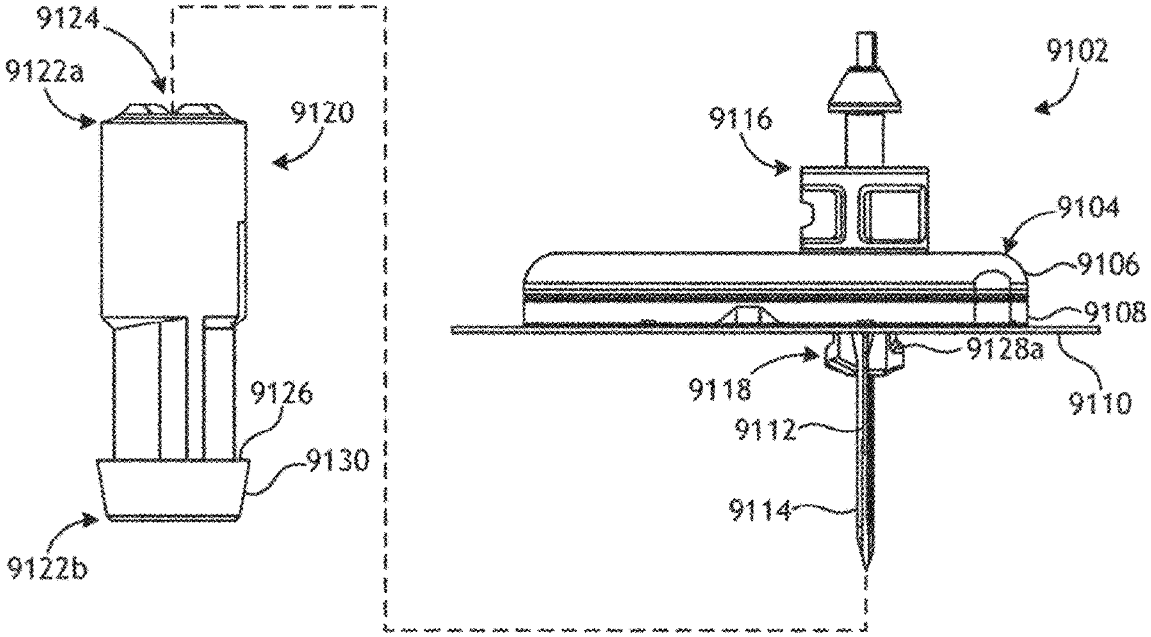
FIGS. 31A and 31B are side and isometric views, respectively, of an example sensor control device, according to one or more embodiments of the present disclosure.
Figure 31B:
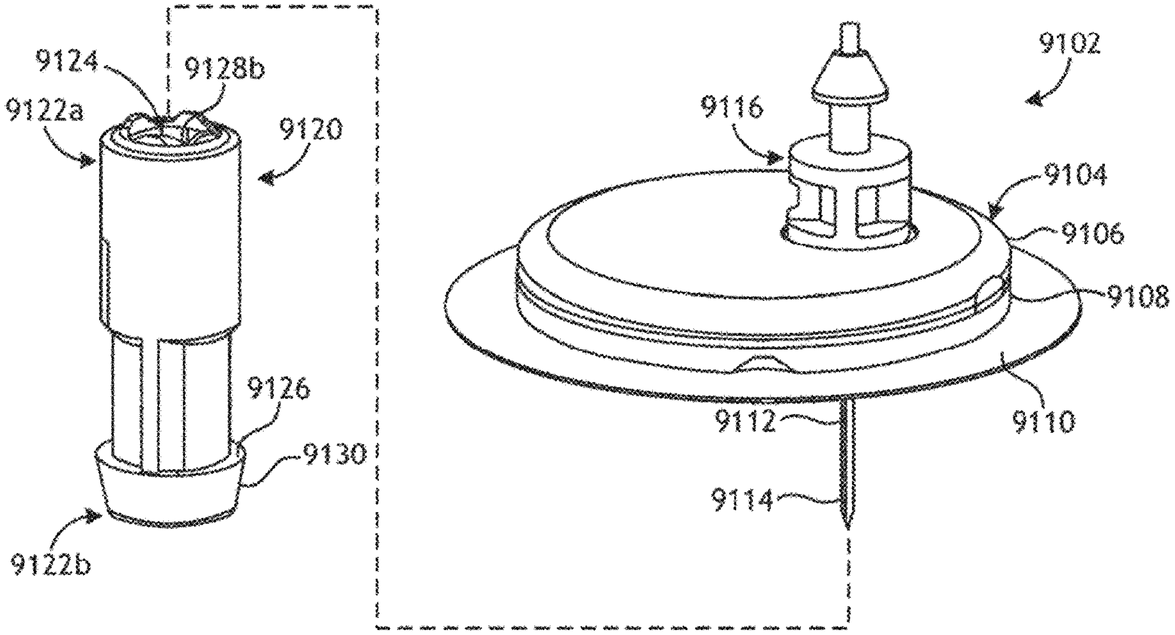

FIGS. 31A and 31B are side and isometric views, respectively, of an example sensor control device 9102, according to one or more embodiments of the present disclosure. The sensor control device 9102 may be similar in some respects to the sensor control device 102 of FIG. 1 and therefore may be best understood with reference thereto. Moreover, the sensor control device 9102 may replace the sensor control device 102 of FIG. 1 and, therefore, may be used in conjunction with the sensor applicator 102 of FIG. 1, which may deliver the sensor control device 9102 to a target monitoring location on a user's skin.

As illustrated, the sensor control device 9102 includes an electronics housing 9104, which may be generally disc-shaped and have a circular cross-section. In other embodiments, however, the electronics housing 9104 may exhibit other cross-sectional shapes, such as ovoid, oval, or polygonal, without departing from the scope of the disclosure. The electronics housing 9104 includes a shell 9106 and a mount 9108 that is matable with the shell 9106. The shell 9106 may be secured to the mount 9108 via a variety of ways, such as a snap fit engagement, an interference fit, sonic welding, laser welding, one or more mechanical fasteners (e.g., screws), a gasket, an adhesive, or any combination thereof. In some cases, the shell 9106 may be secured to the mount 9108 such that a sealed interface is generated therebetween. An adhesive patch 9110 may be positioned on and otherwise attached to the underside of the mount 9108. Similar to the adhesive patch 108 of FIG. 1, the adhesive patch 9110 may be configured to secure and maintain the sensor control device 9102 in position on the user's skin during operation.

The sensor control device 9102 may further include a sensor 9112 and a sharp 9114 used to help deliver the sensor 9112 transcutaneously under a user's skin during application of the sensor control device 9102. Corresponding portions of the sensor 9112 and the sharp 9114 extend distally from the bottom of the electronics housing 9104 (e.g., the mount 9108). A sharp hub 9116 may be overmolded onto the sharp 9114 and configured to secure and carry the sharp 9114. As best seen in FIG. 31A, the sharp hub 9116 may include or otherwise define a mating member 9118. In assembling the sharp 9114 to the sensor control device 9102, the sharp 9114 may be advanced axially through the electronics housing 9104 until the sharp hub 9116 engages an upper surface of the electronics housing 9104 or an internal component thereof and the mating member 9118 extends distally from the bottom of the mount 9108. As described herein below, in at least one embodiment, the sharp hub 9116 may sealingly engage an upper portion of a seal overmolded onto the mount 9108. As the sharp 9114 penetrates the electronics housing 9104, the exposed portion of the sensor 9112 may be received within a hollow or recessed (arcuate) portion of the sharp 9114. The remaining portion of the sensor 9112 is arranged within the interior of the electronics housing 9104.

The sensor control device 9102 may further include a sensor cap 9120, shown detached from the electronics housing 9104 in FIGS. 31A-31B. The sensor cap 9120 may help provide a sealed barrier that surrounds and protects exposed portions of the sensor 9112 and the sharp 9114. As illustrated, the sensor cap 9120 may comprise a generally cylindrical body having a first end 9122*a* and a second end 9122*b* opposite the first end 9122*a*. The first end 9122*a* may be open to provide access into an inner chamber 9124 defined within the body. In contrast, the second end 9122*b* may be closed and may provide or otherwise define an engagement feature 9126. As described in more detail below, the engagement feature 9126 may help mate the sensor cap 9120 to an applicator cap of a sensor applicator (e.g., the sensor applicator 102 of FIG. 1), and may help remove the sensor cap 9120 from the sensor control device 9102 upon removing the sensor cap from the sensor applicator.

The sensor cap 9120 may be removably coupled to the electronics housing 9104 at or near the bottom of the mount 9108. More specifically, the sensor cap 9120 may be removably coupled to the mating member 9118, which extends distally from the bottom of the mount 9108. In at least one embodiment, for example, the mating member 9118 may define a set of external threads 9128*a* (FIG. 31A) matable with a set of internal threads 9128*b* (FIG. 31B) defined within the inner chamber 9124 of the sensor cap 9120. In some embodiments, the external and internal threads 9128*a,b* may comprise a flat thread design (e.g., lack of helical curvature), but may alternatively comprise a helical threaded engagement. Accordingly, in at least one embodiment, the sensor cap 9120 may be threadably coupled to the sensor control device 9102 at the mating member 9118 of the sharp hub 9116. In other embodiments, the sensor cap 9120 may be removably coupled to the mating member 9118 via other types of engagements including, but not limited to, an interference or friction fit, or a frangible member or substance (e.g., wax, an adhesive, etc.) that may be broken with minimal separation force (e.g., axial or rotational force).

In some embodiments, the sensor cap 9120 may comprise a monolithic (singular) structure extending between the first and second ends 9122*a,b*. In other embodiments, however, the sensor cap 9120 may comprise two or more component parts. In the illustrated embodiment, for example, the body of the sensor cap 9120 may include a desiccant cap 9130 arranged at the second end 9122*b*. The desiccant cap 9130 may house or comprise a desiccant to help maintain preferred humidity levels within the inner chamber 9124. Moreover, the desiccant cap 9130 may also define or otherwise provide the engagement feature 9126 of the sensor cap 9120. In at least one embodiment, the desiccant cap 9130 may comprise an elastomeric plug inserted into the bottom end of the sensor cap 9120.

Figure 32A:
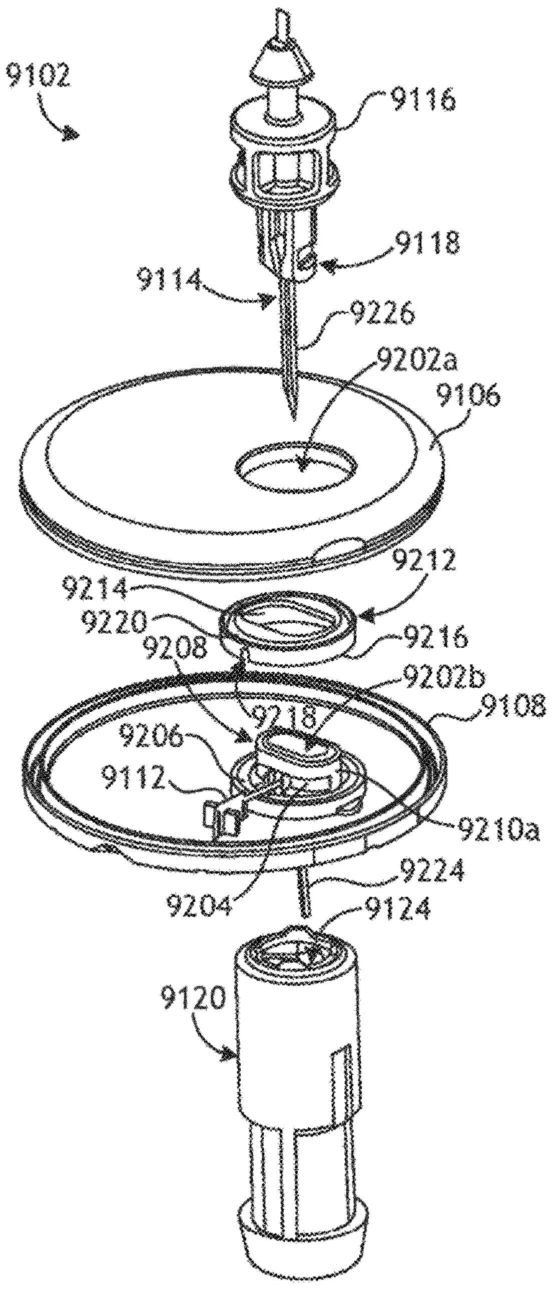
FIGS. 32A and 32B are exploded, isometric top and bottom views, respectively, of the sensor control device of FIG. 2, according to one or more embodiments.
Figure 32B:
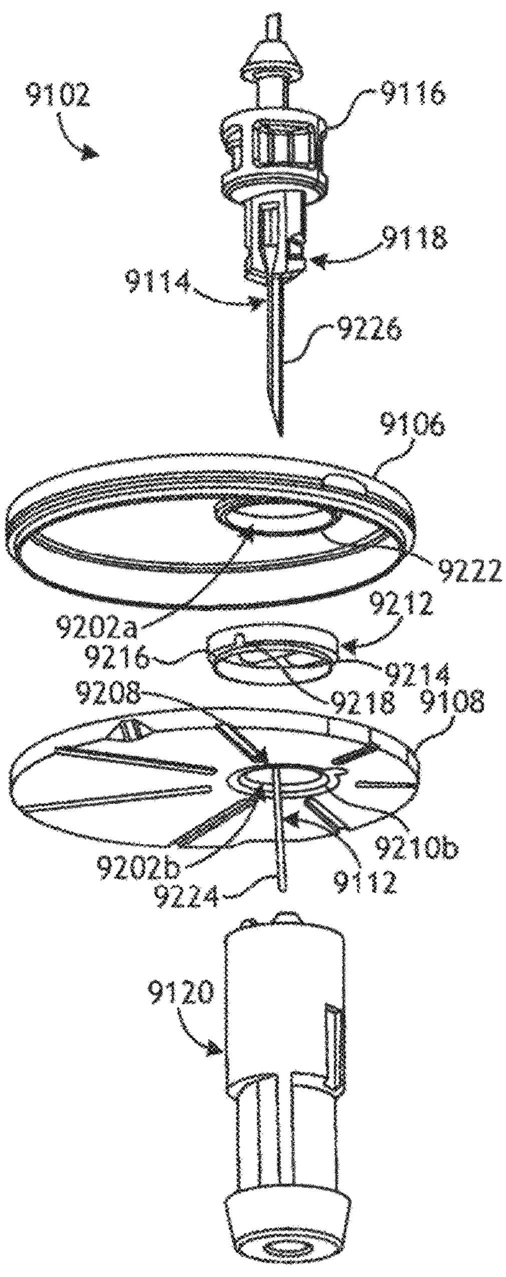

FIGS. 32A and 32B are exploded, isometric top and bottom views, respectively, of the sensor control device 9102, according to one or more embodiments. The shell 9106 and the mount 9108 operate as opposing clamshell halves that enclose or otherwise substantially encapsulate various electronic components (not shown) of the sensor control device 9102. Example electronic components that may be arranged between the shell 9106 and the mount 9108 include, but are not limited to, a battery, resistors, transistors, capacitors, inductors, diodes, and switches.

The shell 9106 may define a first aperture 9202*a* and the mount 9108 may define a second aperture 9202*b*, and the apertures 9202*a,b* may align when the shell 9106 is properly mounted to the mount 9108. As best seen in FIG. 32A, the mount 9108 may provide or otherwise define a pedestal 9204 that protrudes from the inner surface of the mount 9108 at the second aperture 9202*b*. The pedestal 9204 may define at least a portion of the second aperture 9202*b*. Moreover, a channel 9206 may be defined on the inner surface of the mount 9108 and may circumscribe the pedestal 9202. In the illustrated embodiment, the channel 9206 is circular in shape, but could alternatively be another shape, such as oval, ovoid, or polygonal.

The mount 9108 may comprise a molded part made of a rigid material, such as plastic or metal. In some embodiments, a seal 9208 may be overmolded onto the mount 9108 and may be made of an elastomer, rubber, a -polymer, or another pliable material suitable for facilitating a sealed interface. In embodiments where the mount 9108 is made of a plastic, the mount 9108 may be molded in a first "shot" of injection molding, and the seal 9208 may be overmolded onto the mount 9108 in a second "shot" of injection molding. Accordingly, the mount 9108 may be referred to or otherwise characterized as a "two-shot mount."

In the illustrated embodiment, the seal 9208 may be overmolded onto the mount 9108 at the pedestal 9204 and also on the bottom of the mount 9108. More specifically, the seal 9208 may define or otherwise provide a first seal element 9210*a* overmolded onto the pedestal 9204, and a second seal element 9210*b* (FIG. 32B) interconnected to (with) the first seal element 9210*a* and overmolded onto the mount 9108 at the bottom of the mount 9108. In some embodiments, one or both of the seal elements 9210*a,b* may help form corresponding portions (sections) of the second aperture 9202*b*. While the seal 9208 is described herein as being overmolded onto the mount 9108, it is also contemplated herein that one or both of the seal elements 9210*a,b* may comprise an elastomeric component part independent of the mount 9208, such as an O-ring or a gasket.

The sensor control device 9102 may further include a collar 9212 disposed between shell 9106 and mount 9208 and may be a generally annular structure that defines a central aperture 9214. The central aperture 9214 may be sized to receive the first seal element 9210*a* and may align with both the first and second apertures 9202*a,b* when the sensor control device 9102 is properly assembled. The shape of the central aperture 9214 may generally match the shape of the second aperture 9202*b* and the first seal element 9210*a*.

Figure 32C:
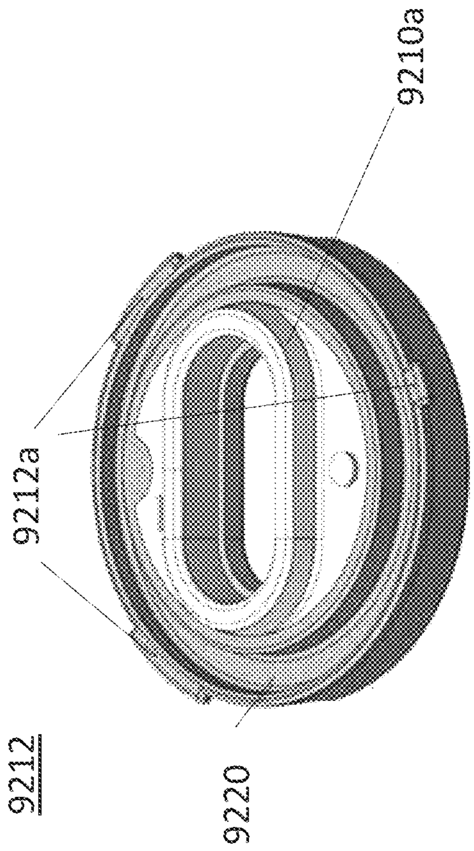
FIG. 32C is a top perspective view of the collar of FIG. 32A-B, according to one or more embodiments.
Figure 32E:
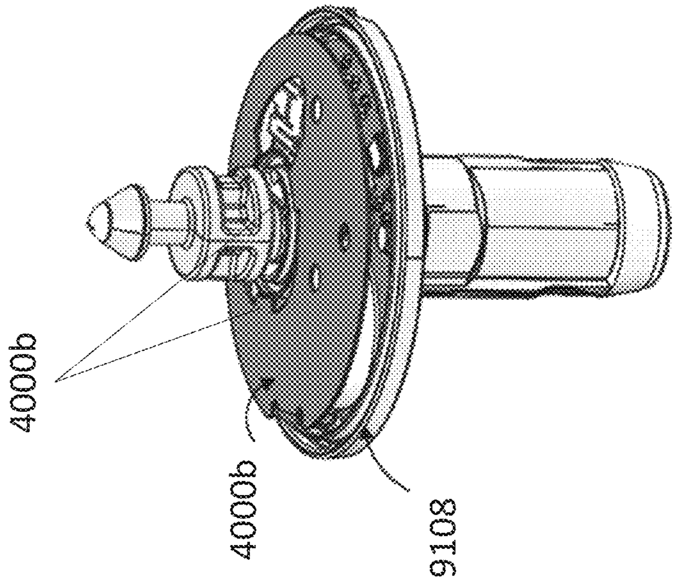
FIG. 32D-E are isometric top views of the sensor control device of FIG. 2 according to one or more embodiments.
Figure 32D:
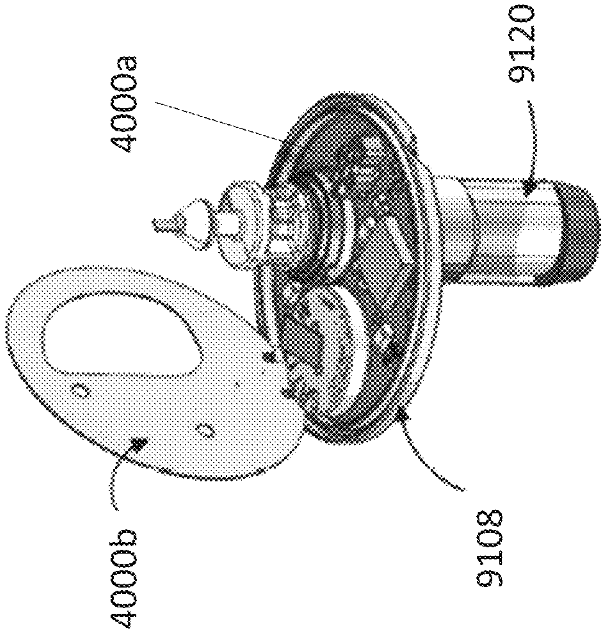

In some embodiments, the collar 9212 may define or otherwise provide an annular lip 9216 on its bottom surface. The annular lip 9216 may be sized and otherwise configured to mate with or be received into the channel 9206 defined on the inner surface of the mount 9108. In some embodiments, a groove 9218 may be defined on the annular lip 9216 and may be configured to accommodate or otherwise receive a portion of the sensor 9112 extending laterally within the mount 9108. In some embodiments, the collar 9212 may further define or otherwise provide a collar channel 9220 (FIG. 32A) on its upper surface sized to receive and otherwise mate with an annular ridge 9222 (FIG. 32B) defined on the inner surface of the shell 9106 when the sensor control device 9102 is properly assembled. In some embodiments, collar 9212 may further include a plurality of tabs 9212*a* (FIG. 32C) on its outer periphery. Tabs 9212*a* may be located on the same plane as the top surface of collar 9212 and create a shelf for a circuit board. In some embodiments, the circuit board can be foldable and/or a flexible PCB, as described in U.S. Provisional Application No. 63/081,223, filed Sep. 21, 2020, which is incorporated herein by reference in its entirety. For example, PCB 4000 can be mounted within the electronics housing on the plurality of tabs 9212*a*. As can be seen in FIG. 32D, after PCB 4000 has been loaded onto the sensor mount 9108, first portion 4000*a* of PCB may be located under tabs 9212*a* (not shown in FIG. 32D) and rest on the sensor mount 9108. Thereafter, second portion 4000*b* of PCB 4000 may be folded over first portion 4000*a* and mounted on the plurality of tabs 9212*a*. In some embodiments, tabs 9212*a* can be of the same size or of different sizes and may be equally spaced along the collar 9212's outer periphery. In some embodiments, tabs 9212*a* can extend from the top surface of the collar 9212, the bottom surface of the collar 9212, or an intermediate location of the collar 9212 therebetween. As shown in FIG. 32C, collar 9212 can include three tabs 9212*a* and tabs 9212*a* can be of different sizes, for example, with two tabs being the same size as each other and longer (i.e., as measured along the outer periphery of collar 9212) than a third tab. Additionally, tabs 9212*a* can be the same or different widths (i.e., measured as distance extending radially outwards). In some embodiments, as can be seen in FIG. 32E, PCB 4000 can include one or more tabs 4000*c* corresponding to tabs 9212*a* and mated with and fixed to tabs 9212*a*.

The sensor 9112 may include a tail 9224 that extends through the second aperture 9202*b* defined in the mount 9108 to be transcutaneously received beneath a user's skin. The tail 9224 may have an enzyme or other chemistry included thereon to help facilitate analyte monitoring. The sharp 9114 may include a sharp tip 9226 extendable through the first aperture 9202*a* defined by the shell 9106. As the sharp tip 9226 penetrates the electronics housing 9104, the tail 9224 of the sensor 9112 may be received within a hollow or recessed portion of the sharp tip 9226. The sharp tip 9226 may be configured to penetrate the skin while carrying the tail 9224 to put the active chemistry of the tail 9224 into contact with bodily fluids.

The sensor control device 9102 may provide a sealed subassembly that includes, among other component parts, portions of the shell 9106, the sensor 9112, the sharp 9114, the seal 9208, the collar 9212, and the sensor cap 9120. The sealed subassembly may help isolate the sensor 9112 and the sharp 9114 within the inner chamber 9124 (FIG. 32A) of the sensor cap 9120. In assembling the sealed subassembly, the sharp tip 9226 is advanced through the electronics housing 9104 until the sharp hub 9116 engages the seal 9208 and, more particularly, the first seal element 9210*a*. The mating member 9118 provided at the bottom of the sharp hub 9116 may extend out the second aperture 9202*b* in the bottom of the mount 9108, and the sensor cap 9120 may be coupled to the sharp hub 9116 at the mating member 9118. Coupling the sensor cap 9120 to the sharp hub 9116 at the mating member 9118 may urge the first end 9122*a* of the sensor cap 9120 into sealed engagement with the seal 9208 and, more particularly, into sealed engagement with the second seal element 9210*b* on the bottom of the mount 9108. In some embodiments, as the sensor cap 9120 is coupled to the sharp hub 9116, a portion of the first end 9122*a* of the sensor cap 9120 may bottom out (engage) against the bottom of the mount 9108, and the sealed engagement between the sensor hub 9116 and the first seal element 9210*a* may be able to assume any tolerance variation between features.

Figure 33:
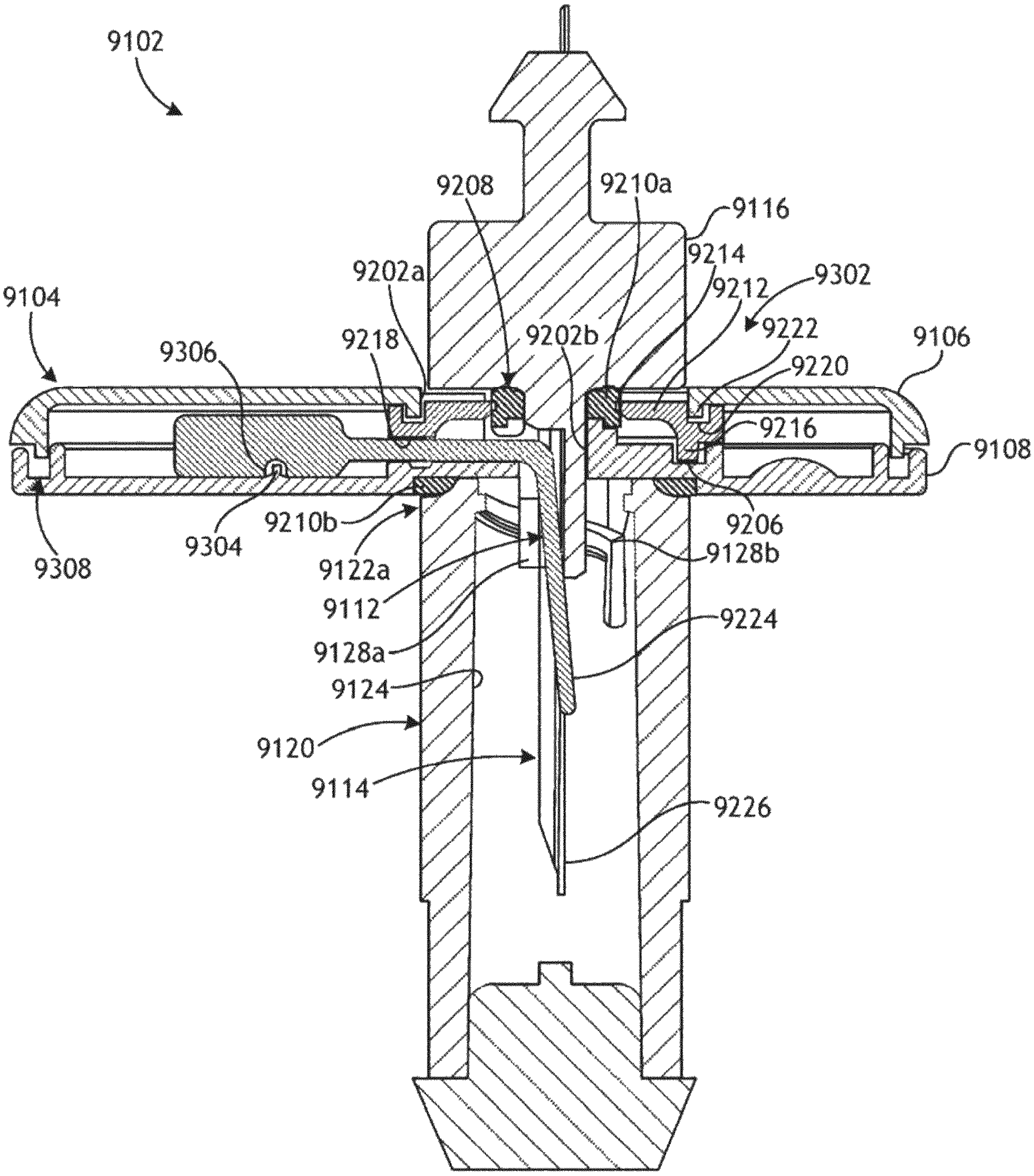
FIG. 33 is a cross-sectional side view of the sensor control device of FIGS. 31A-31B and 32A-32B, according to one or more embodiments.

FIG. 33 is a cross-sectional side view of the sensor control device 9102, according to one or more embodiments. As indicated above, the sensor control device 9102 may include or otherwise incorporate a sealed subassembly 9302, which may be useful in isolating the sensor 9112 and the sharp 9114 within the inner chamber 9124 of the sensor cap 9120. To assemble the sealed subassembly 9302, the sensor 9112 may be located within the mount 9108 such that the tail 9224 extends through the second aperture 9202*b* at the bottom of the mount 9108. In at least one embodiment, a locating feature 9304 may be defined on the inner surface of the mount 9108, and the sensor 9112 may define a groove 9306 that is matable with the locating feature 9304 to properly locate the sensor 9112 within the mount 9108.

Once the sensor 9112 is properly located, the collar 9212 may be installed on the mount 9108. More specifically, the collar 9212 may be positioned such that the first seal element 9210*a* of the seal 9208 is received within the central aperture 9214 defined by the collar 9212 and the first seal element 9210*a* generates a radial seal against the collar 9212 at the central aperture 9214. Moreover, the annular lip 9216 defined on the collar 9212 may be received within the channel 9206 defined on the mount 9108, and the groove 9218 defined through the annular lip 9216 may be aligned to receive the portion of the sensor 9112 that traverses the channel 9206 laterally within the mount 9108. In some embodiments, an adhesive may be injected into the channel 9206 to secure the collar 9212 to the mount 9108. The adhesive may also facilitate a sealed interface between the two components and generate a seal around the sensor 9112 at the groove 9218, which may isolate the tail 9224 from the interior of the electronics housing 9104.

The shell 9106 may then be mated with or otherwise coupled to the mount 9108. In some embodiments, as illustrated, the shell 9106 may mate with the mount 9108 via a tongue-and-groove engagement 9308 at the outer periphery of the electronics housing 9104. An adhesive may be injected (applied) into the groove portion of the engagement 9308 to secure the shell 9106 to the mount 9108, and also to create a sealed engagement interface. Mating the shell 9106 to the mount 9108 may also cause the annular ridge 9222 defined on the inner surface of the shell 9106 to be received within the collar channel 9220 defined on the upper surface of the collar 9212. In some embodiments, an adhesive may be injected into the collar channel 9220 to secure the shell 9106 to the collar 9212, and also to facilitate a sealed interface between the two components at that location. When the shell 9106 mates with the mount 9108, the first seal element 9210*a* may extend at least partially through (into) the first aperture 9202*a* defined in the shell 9106.

The sharp 9114 may then be coupled to the sensor control device 9102 by extending the sharp tip 9226 through the aligned first and second apertures 9202*a,b* defined in the shell 9106 and the mount 9108, respectively. The sharp 9114 may be advanced until the sharp hub 9116 engages the seal 9208 and, more particularly, engages the first seal element 9210*a*. The mating member 9118 may extend (protrude) out the second aperture 9202*b* at the bottom of the mount 9108 when the sharp hub 9116 engages the first seal element 9210*a*.

The sensor cap 9120 may then be removably coupled to the sensor control device 9102 by threadably mating the internal threads 9128*b* of the sensor cap 9120 with the external threads 9128*a* of the mating member 9118. The inner chamber 9124 may be sized and otherwise configured to receive the tail 9224 and the sharp tip 9226 extending from the bottom of the mount 9108. Moreover, the inner chamber 9124 may be sealed to isolate the tail 9224 and the sharp tip 9226 from substances that might adversely interact with the chemistry of the tail 9224. In some embodiments, a desiccant (not shown) may be present within the inner chamber 9124 to maintain proper humidity levels.

Tightening (rotating) the mated engagement between the sensor cap 9120 and the mating member 9118 may urge the first end 9122*a* of the sensor cap 9120 into sealed engagement with the second seal element 9210*b* in an axial direction (e.g., along the centerline of the apertures 9202*a, b*), and may further enhance the sealed interface between the sharp hub 9116 and the first seal element 9210*a* in the axial direction. Moreover, tightening the mated engagement between the sensor cap 9120 and the mating member 9118 may compress the first seal element 9210*a*, which may result in an enhanced radial sealed engagement between the first seal element 9210*a* and the collar 9212 at the central aperture 9214. Accordingly, in at least one embodiment, the first seal element 9210*a* may help facilitate axial and radial sealed engagements.

As mentioned above, the first and second seal elements 9210*a,b* may be overmolded onto the mount 9108 and may be physically linked or otherwise interconnected. Consequently, a single injection molding shot may flow through the second aperture 9202*b* of the mount 9108 to create both ends of the seal 9208. This may prove advantageous in being able to generate multiple sealed interfaces with only a single injection molded shot. An additional advantage of a two-shot molded design, as opposed to using separate elastomeric components (e.g., O-rings, gaskets, etc.), is that the interface between the first and second shots is a reliable bond rather than a mechanical seal. Hence, the effective number of mechanical sealing barriers is effectively cut in half. Moreover, a two-shot component with a single elastomeric shot also has implications to minimizing the number of two-shot components needed to achieve all the necessary sterile barriers. Once properly assembled, the sealed subassembly 9302 may be subjected to a radiation sterilization process to sterilize the sensor 9112 and the sharp 9114. The sealed subassembly 9302 may be subjected to the radiation sterilization prior to or after coupling the sensor cap 9120 to the sharp hub 9116. When sterilized after coupling the sensor cap 9120 to the sharp hub 9116, the sensor cap 9120 may be made of a material that permits the propagation of radiation therethrough. In some embodiments, the sensor cap 9120 may be transparent or translucent, but can otherwise be opaque, without departing from the scope of the disclosure.

Figure 33A:
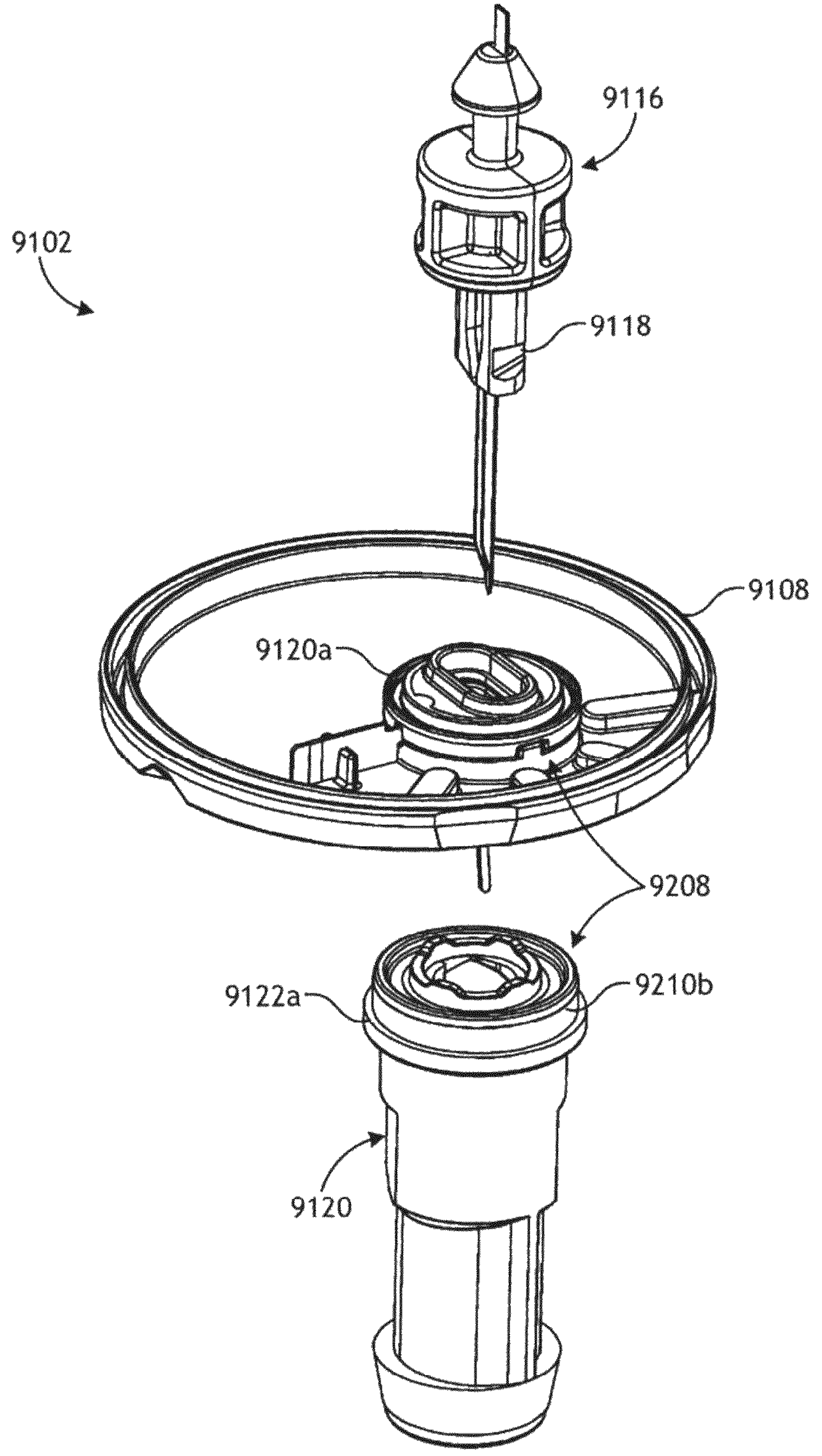
FIG. 33A is an exploded isometric view of a portion of another embodiment of the sensor control device of FIGS. 31A-31B and 32A-32B.
Figure 33B:
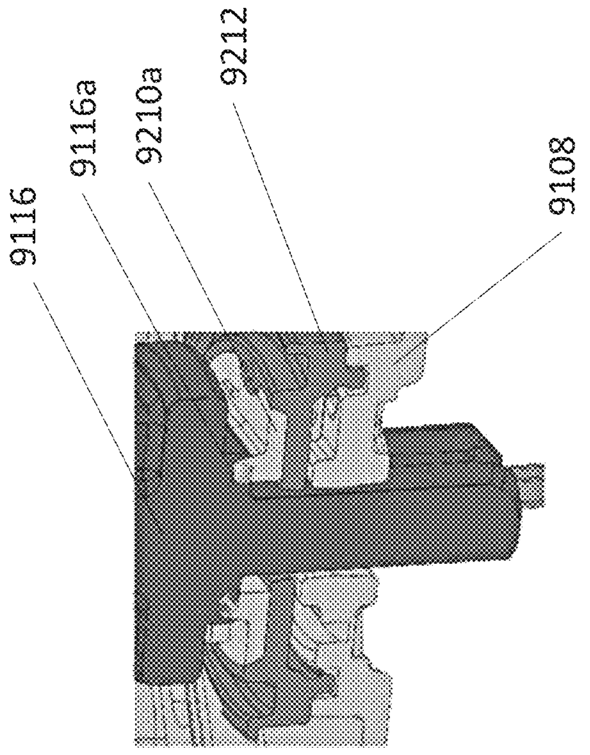
FIG. 33B is a cross-sectional view of the sharp hub and the mount of FIG. 33A, according to one or more embodiments.

FIG. 33A is an exploded isometric view of a portion of another embodiment of the sensor control device 9102 of FIGS. 31A-31B and 32A-32B. Embodiments included above describe the mount 9108 and the seal 9208 being manufactured via a two-shot injection molding process. In other embodiments, however, as briefly mentioned above, one or both of the seal elements 9210*a,b* of the seal 9208 may comprise an elastomeric component part independent of the mount 9208. In the illustrated embodiment, for example, the first seal element 9210*a* may be overmolded onto the collar 9212 and the second seal element 9210*b* may be overmolded onto the sensor cap 9120. Alternatively, the first and second seal elements 9210*a,b* may comprise a separate component part, such as a gasket or O-ring 9210*a* positioned on the upper surface of the collar 9212 (FIGS. 32C and 33A) and the sensor cap 9120, respectively. Tightening (rotating) the mated engagement between the sensor cap 9120 and the mating member 9118 may urge the second seal element 9210*b* into sealed engagement with the bottom of the mount 9108 in an axial direction, and may enhance a sealed interface between the sharp hub 9116 and the first seal element 9210*a* in the axial direction. In some embodiments, as shown in FIG. 33B, sharp hub 9116 may include a raised mating surface 9116*a* (e.g., a ledge) configured to mate with seal element 9210*a*. As such, tightening (rotating) the mated engagement between the sensor cap 9120 and the mating member 9118 may enhance a sealed interface between the mating surface 9116*a* and the first seal element 9210*a* in the axial direction.

Figure 34A:
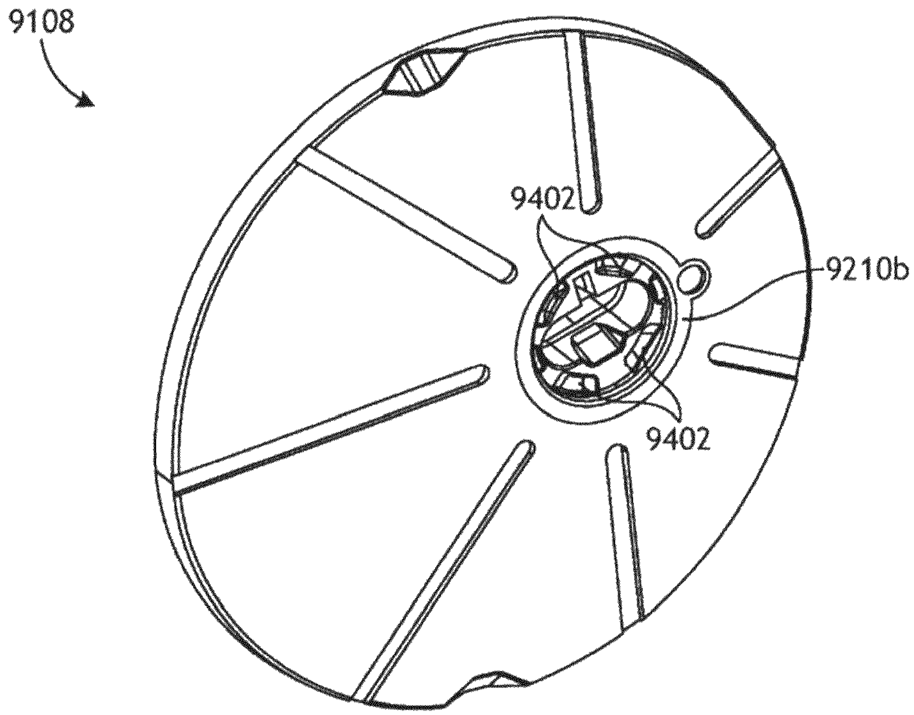
FIG. 34A is an isometric bottom view of the mount of FIGS. 31A-31B and 32A-32B.
Figure 34B:
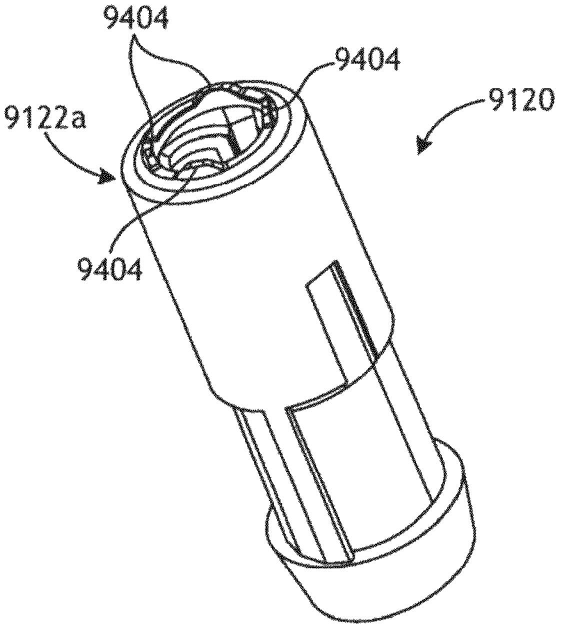
FIG. 34B is an isometric top view of the sensor cap of FIGS. 31A-31B and 32A-32B.

FIG. 34A is an isometric bottom view of the mount 9108, and FIG. 34B is an isometric top view of the sensor cap 9120, according to one or more embodiments. As shown in FIG. 34A, the mount 9108 may provide or otherwise define one or more indentations or pockets 9402 at or near the opening to the second aperture 9202*b*. As shown in FIG. 34B, the sensor cap 9120 may provide or otherwise define one or more projections 9404 at or near the first end 9122*a* of the sensor cap 9120. The projections 9404 may be received within the pockets 9402 when the sensor cap 9120 is coupled to the sharp hub 9116 (FIGS. 32A-32B and 93). More specifically, as described above, as the sensor cap 9120 is coupled to the mating member 9118 (FIGS. 32A-32B and 93) of the sensor hub 9116, the first end 9122*a* of the sensor cap 9120 is brought into sealed engagement with the second seal element 9210*b*. In this process, the projections 9404 may also be received within the pockets 9402, which may help prevent premature unthreading of the sensor cap 9120 from the sharp hub 9116.

Figure 35B:
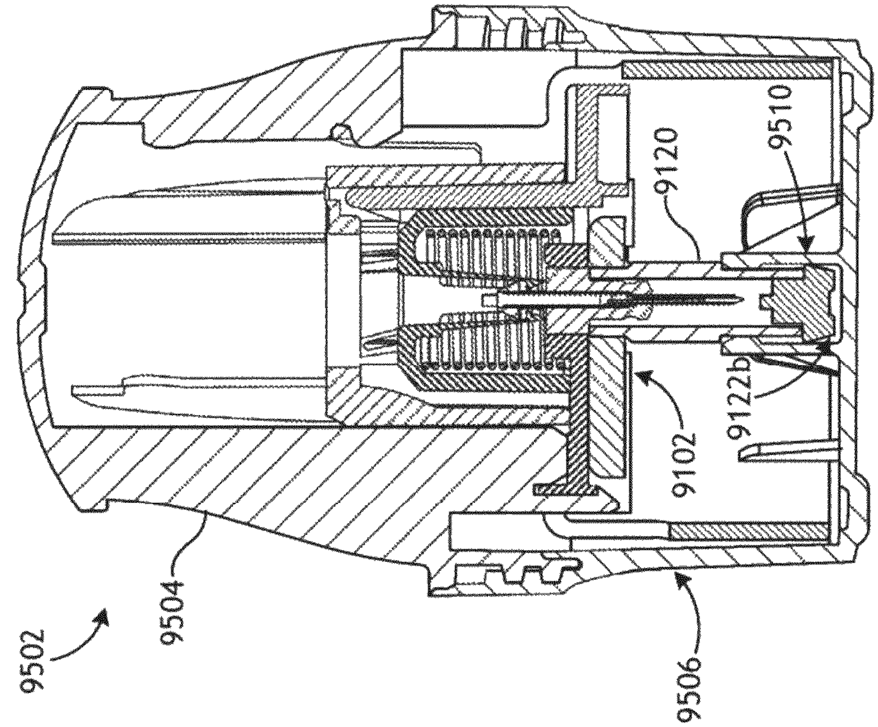
FIGS. 35A and 35B are side and cross-sectional side views, respectively, of an example sensor applicator, according to one or more embodiments.
Figure 35A:
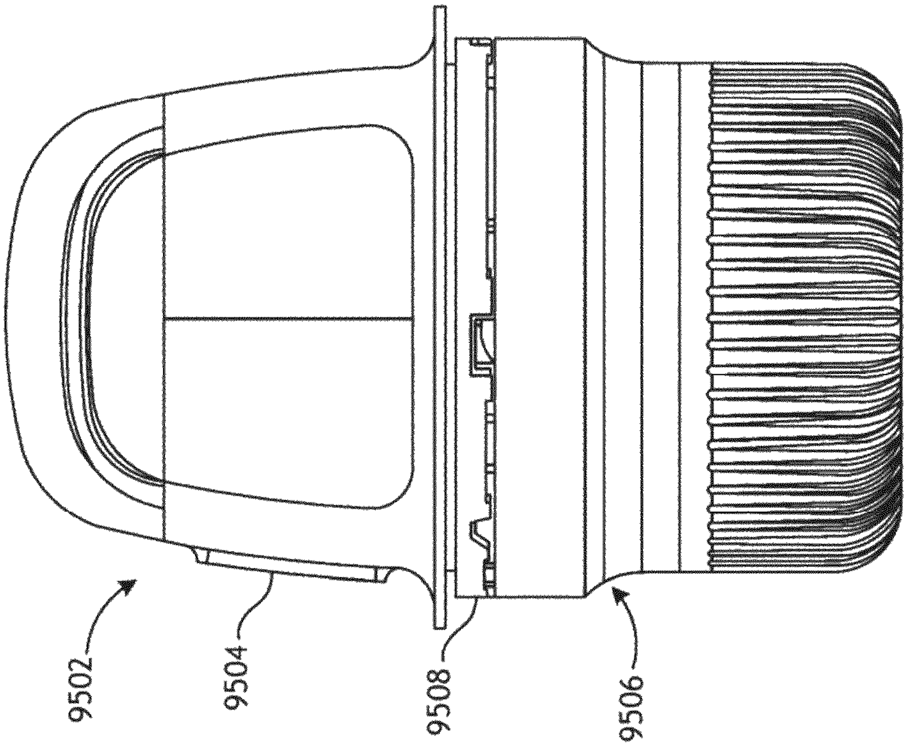

FIGS. 35A and 35B are side and cross-sectional side views, respectively, of an example sensor applicator 9502, according to one or more embodiments. The sensor applicator 9502 may be similar in some respects to the sensor applicator 102 of FIG. 1 and, therefore, may be designed to deliver (fire) a sensor control device, such as the sensor control device 9102. FIG. 35A depicts how the sensor applicator 9502 might be shipped to and received by a user, and FIG. 35B depicts the sensor control device 9102 arranged within the interior of the sensor applicator 9502.

As shown in FIG. 35A, the sensor applicator 9502 includes a housing 9504 and an applicator cap 9506 removably coupled to the housing 9504. In some embodiments, the applicator cap 9506 may be threaded to the housing 9504 and include a tamper ring 9508. Upon rotating (e.g., unscrewing) the applicator cap 9506 relative to the housing 9504, the tamper ring 9508 may shear and thereby free the applicator cap 9506 from the sensor applicator 9502.

In FIG. 35B, the sensor control device 9102 is positioned within the sensor applicator 9502. Once the sensor control device 9102 is fully assembled, it may then be loaded into the sensor applicator 9502 and the applicator cap 9506 may be coupled to the sensor applicator 9502. In some embodiments, the applicator cap 9506 and the housing 9504 may have opposing, matable sets of threads that enable the applicator cap 9506 to be screwed onto the housing 9504 in a clockwise (or counter-clockwise) direction and thereby secure the applicator cap 9506 to the sensor applicator 9502.

Securing the applicator cap 9506 to the housing 9504 may also cause the second end 9122*b* of the sensor cap 9120 to be received within a cap post 9510 located within the interior of the applicator cap 9506 and extending proximally from the bottom thereof. The cap post 9510 may be configured to receive at least a portion of the sensor cap 9120 as the applicator cap 9506 is coupled to the housing 9504.

Figure 36A:
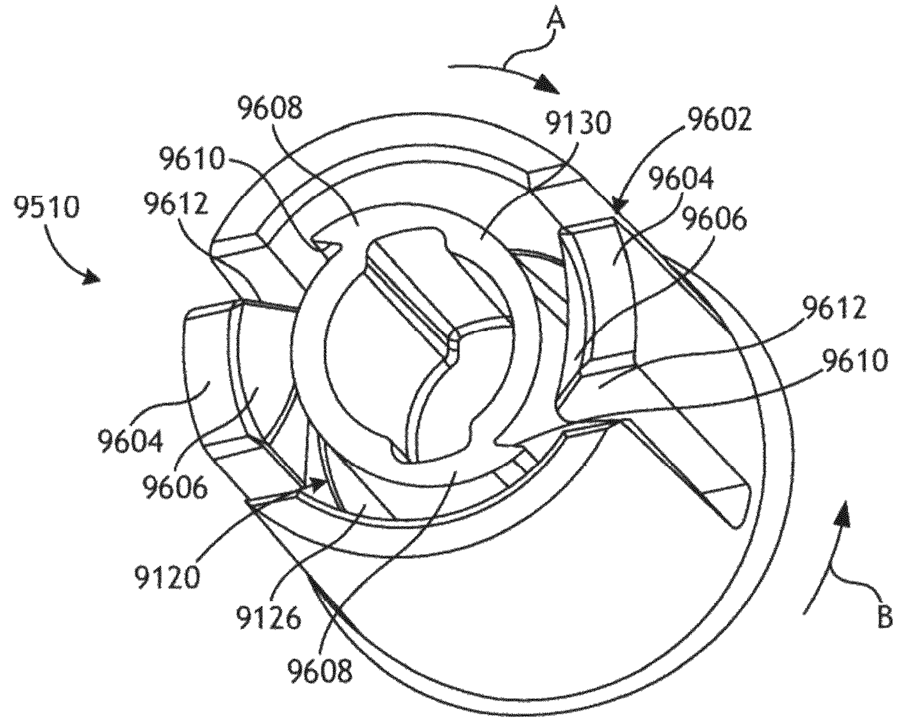
FIGS. 36A and 36B are perspective and top views, respectively, of the cap post of FIG. 35B, according to one or more embodiments.
Figure 36B:
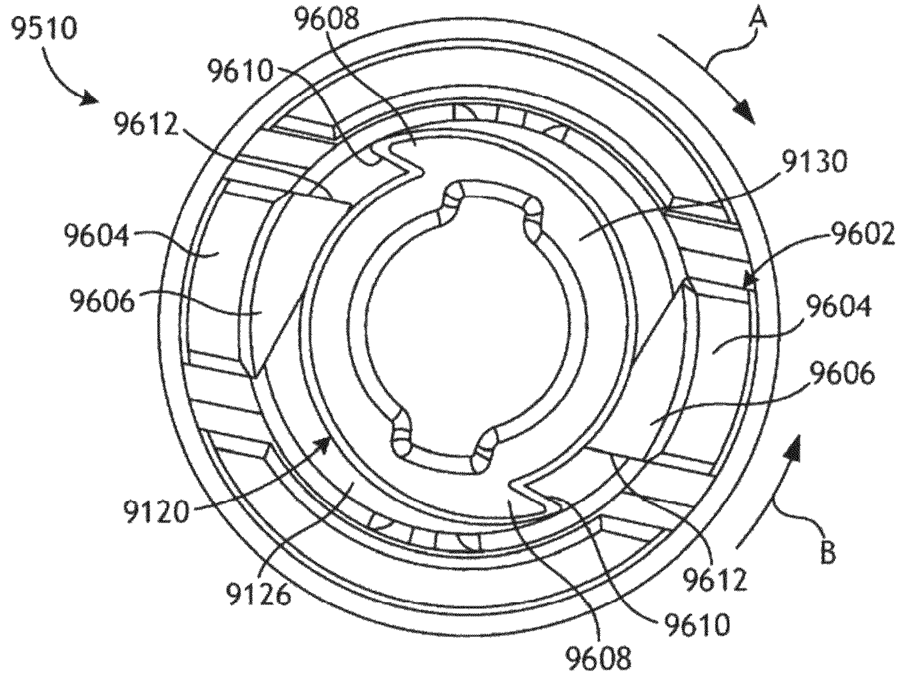

FIGS. 36A and 36B are perspective and top views, respectively, of the cap post 9510, according to one or more additional embodiments. In the illustrated depiction, a portion of the sensor cap 9120 is received within the cap post 9510 and, more specifically, the desiccant cap 9130 of the sensor cap 9120 is arranged within cap post 9510. The cap post 9510 may define a receiver feature 9602 configured to receive the engagement feature 9126 of the sensor cap 9120 upon coupling (e.g., threading) the applicator cap 9506 (FIG. 35B) to the sensor applicator 9502 (FIGS. 35A-35B). Upon removing the applicator cap 9506 from the sensor applicator 9502, however, the receiver feature 9602 may prevent the engagement feature 9126 from reversing direction and thus prevent the sensor cap 9120 from separating from the cap post 9510. Instead, removing the applicator cap 9506 from the sensor applicator 9502 will simultaneously detach the sensor cap 9120 from the sensor control device 9102 (FIGS. 31A-31B and 32A-32B), and thereby expose the distal portions of the sensor 9112 (FIGS. 32A-32B) and the sharp 9114 (FIGS. 32A-32B).

Many design variations of the receiver feature 9602 may be employed, without departing from the scope of the disclosure. In the illustrated embodiment, the receiver feature 9602 includes one or more compliant members 9604 (two shown) that are expandable or flexible to receive the engagement feature 9126. The engagement feature 9126 may comprise, for example, an enlarged head and the compliant member(s) 9604 may comprise a collet-type device that includes a plurality of compliant fingers configured to flex radially outward to receive the enlarged head.

The compliant member(s) 9604 may further provide or otherwise define corresponding ramped surfaces 9606 configured to interact with one or more opposing camming surfaces 9608 provided on the outer wall of the engagement feature 9126. The configuration and alignment of the ramped surface(s) 9606 and the opposing camming surface(s) 9608 is such that the applicator cap 9506 is able to rotate relative to the sensor cap 9120 in a first direction A (e.g., clockwise), but the cap post 9510 binds against the sensor cap 9120 when the applicator cap 9506 is rotated in a second direction B (e.g., counter clockwise). More particularly, as the applicator cap 9506 (and thus the cap post 9510) rotates in the first direction A, the camming surfaces 9608 engage the ramped surfaces 9606, which urge the compliant members 9604 to flex or otherwise deflect radially outward and results in a ratcheting effect. Rotating the applicator cap 9506 (and thus the cap post 9510) in the second direction B, however, will drive angled surfaces 9610 of the camming surfaces 9608 into opposing angled surfaces 9612 of the ramped surfaces 9606, which results in the sensor cap 9120 binding against the compliant member(s) 9604.

Figure 37:
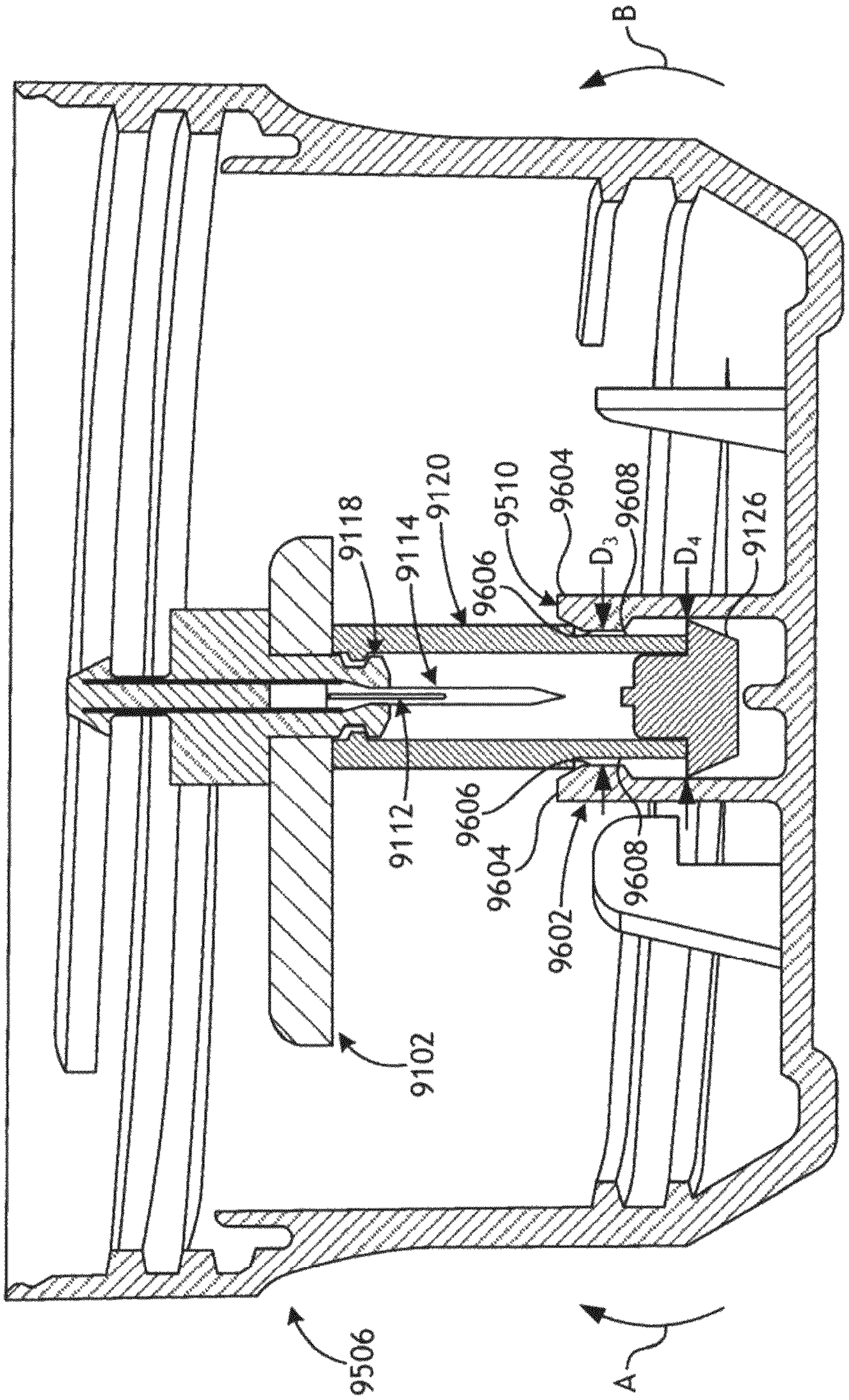
FIG. 37 is a cross-sectional side view of the sensor control device positioned within the applicator cap, according to one or more embodiments.

FIG. 37 is a cross-sectional side view of the sensor control device 9102 positioned within the applicator cap 9506, according to one or more embodiments. As illustrated, the opening to the receiver feature 9602 exhibits a first diameter $D_3$, while the engagement feature 9126 of the sensor cap 9120 exhibits a second diameter $D_4$ that is larger than the first diameter $D_3$ and greater than the outer diameter of the remaining portions of the sensor cap 9120. As the sensor cap 9120 is extended into the cap post 9510, the compliant member(s) 9604 of the receiver feature 9602 may flex (expand) radially outward to receive the engagement feature 9126. In some embodiments, as illustrated, the engagement feature 9126 may provide or otherwise define an angled outer surface that helps bias the compliant member(s) 9604 radially outward. Once the engagement feature 9126 bypasses the receiver feature 9602, the compliant member(s) 9604 are able to flex back to (or towards) their natural state and thus lock the sensor cap 9120 within the cap post 9510.

As the applicator cap 9506 is threaded to (screwed onto) the housing 9504 (FIGS. 35A-35B) in the first direction A, the cap post 9510 correspondingly rotates in the same direction and the sensor cap 9120 is progressively introduced into the cap post 9510. As the cap post 9510 rotates, the ramped surfaces 9606 of the compliant members 9604 ratchet against the opposing camming surfaces 9608 of the sensor cap 9120. This continues until the applicator cap 9506 is fully threaded onto (screwed onto) the housing 9504. In some embodiments, the ratcheting action may occur over two full revolutions of the applicator cap 9506 before the applicator cap 9506 reaches its final position.

To remove the applicator cap 9506, the applicator cap 9506 is rotated in the second direction B, which correspondingly rotates the cap post 9510 in the same direction and causes the camming surfaces 9608 (i.e., the angled surfaces 9610 of FIGS. 36A-36B) to bind against the ramped surfaces 9606 (i.e., the angled surfaces 9612 of FIGS. 36A-36B). Consequently, continued rotation of the applicator cap 9506 in the second direction B causes the sensor cap 9120 to correspondingly rotate in the same direction and thereby unthread from the mating member 9118 to allow the sensor cap 9120 to detach from the sensor control device 9102. Detaching the sensor cap 9120 from the sensor control device 9102 exposes the distal portions of the sensor 9112 and the sharp 9114, and thus places the sensor control device 9102 in position for firing (use).

Figure 38A:
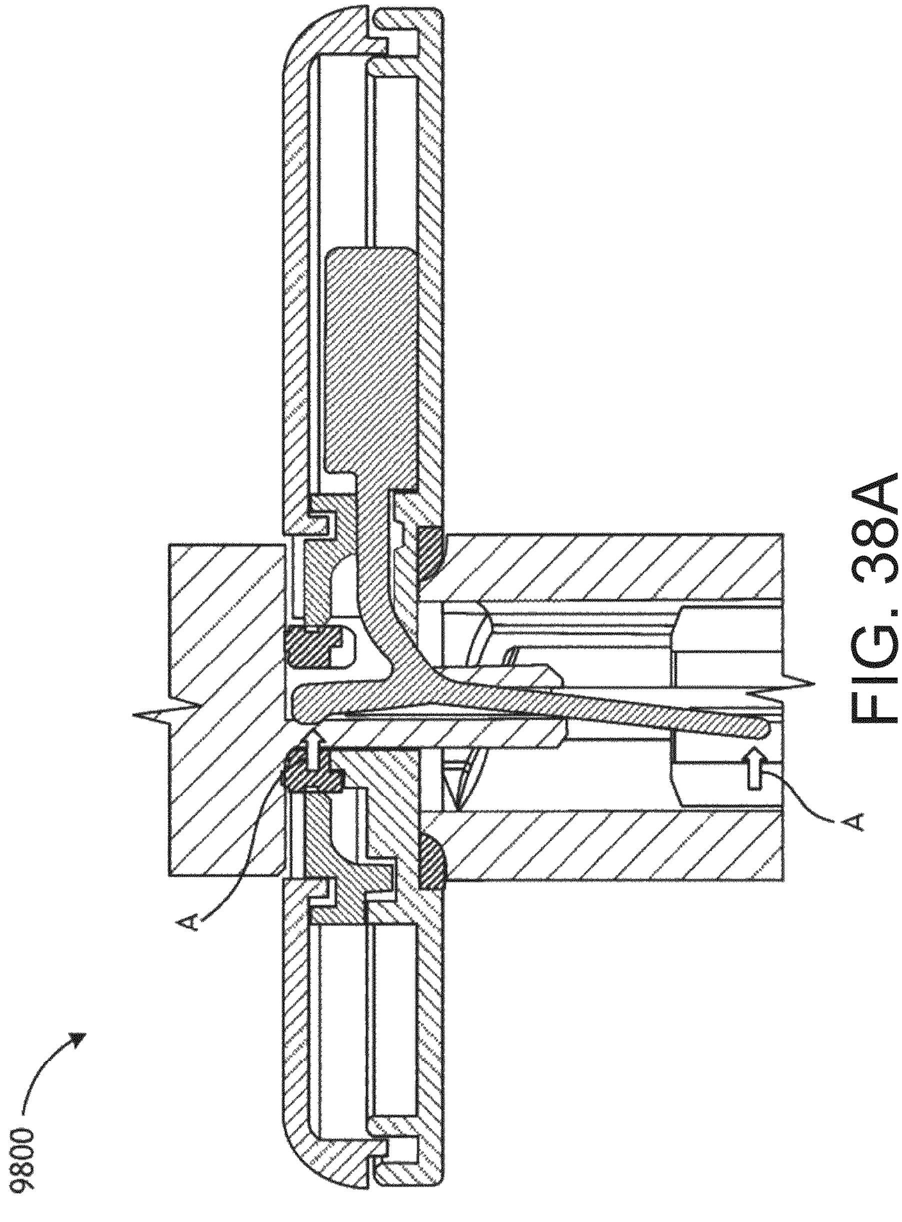
FIG. 38A is a cross-sectional view of a sensor control device showing example interaction between the sensor and the sharp.

FIG. 38A is a cross-sectional view of a sensor control device 9800 showing example interaction between the sensor and the sharp. After assembly of the sharp, the sensor should sit in a channel defined by the sharp. The sensor control device in FIG. 9 does not show the sensor deflected inwards and otherwise aligned fully with the sharp, but such may be the case upon full assembly as slight bias forces may be assumed by the sensor at the locations indicated by the two arrows A. Biasing the sensor against the sharp may be advantageous so that any relative motion between the sensor and the sharp during subcutaneous insertion does not expose the sensor tip (i.e., the tail) outside the sharp channel, which could potentially cause an insertion failure.

Figure 38B:
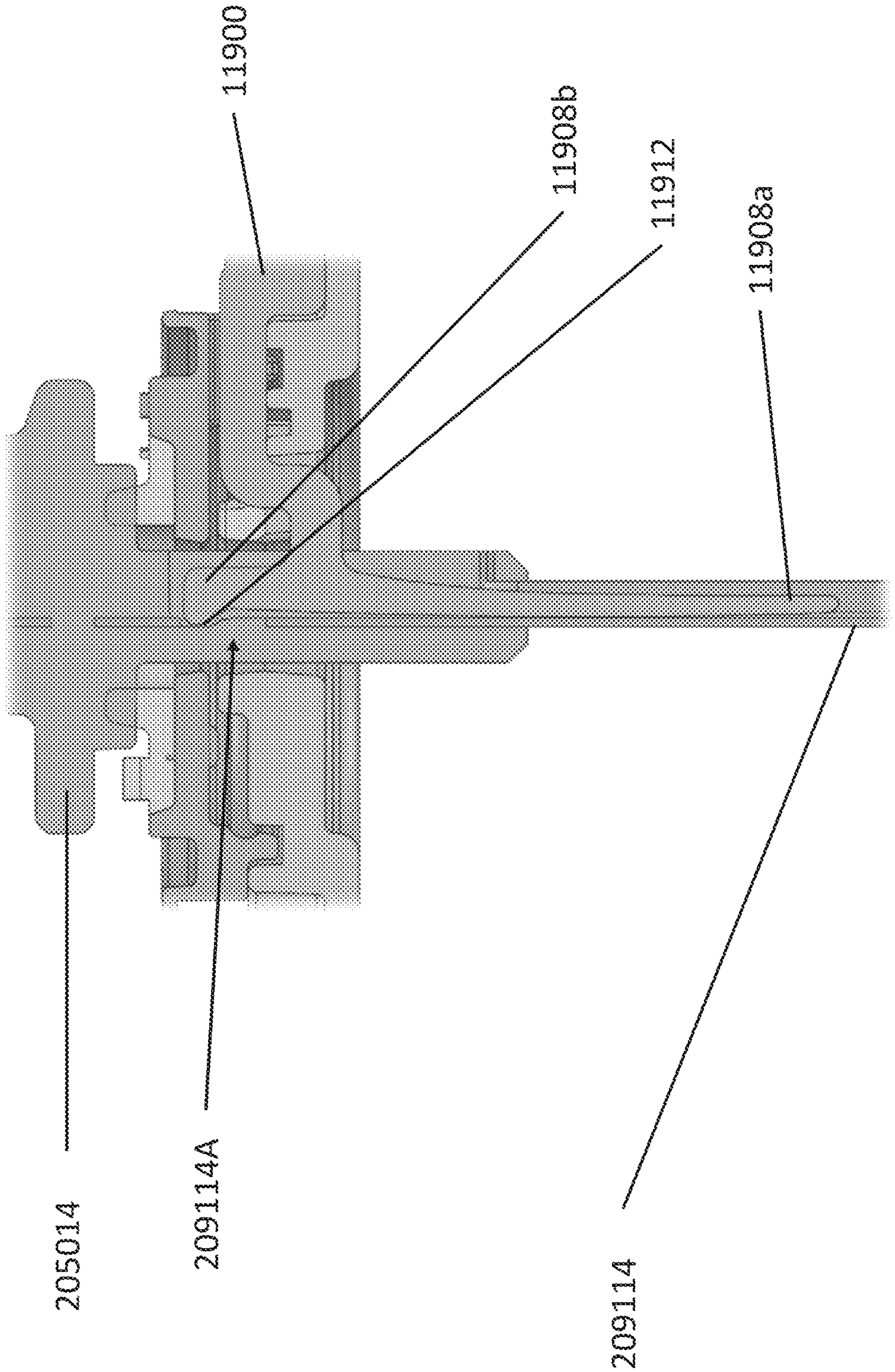
FIG. 38B is a side cross-sectional view of a sharp hub, sharp, and sensor, with the sensor in an unbiased position, in accordance with the disclosed subject matter.
Figure 38C:
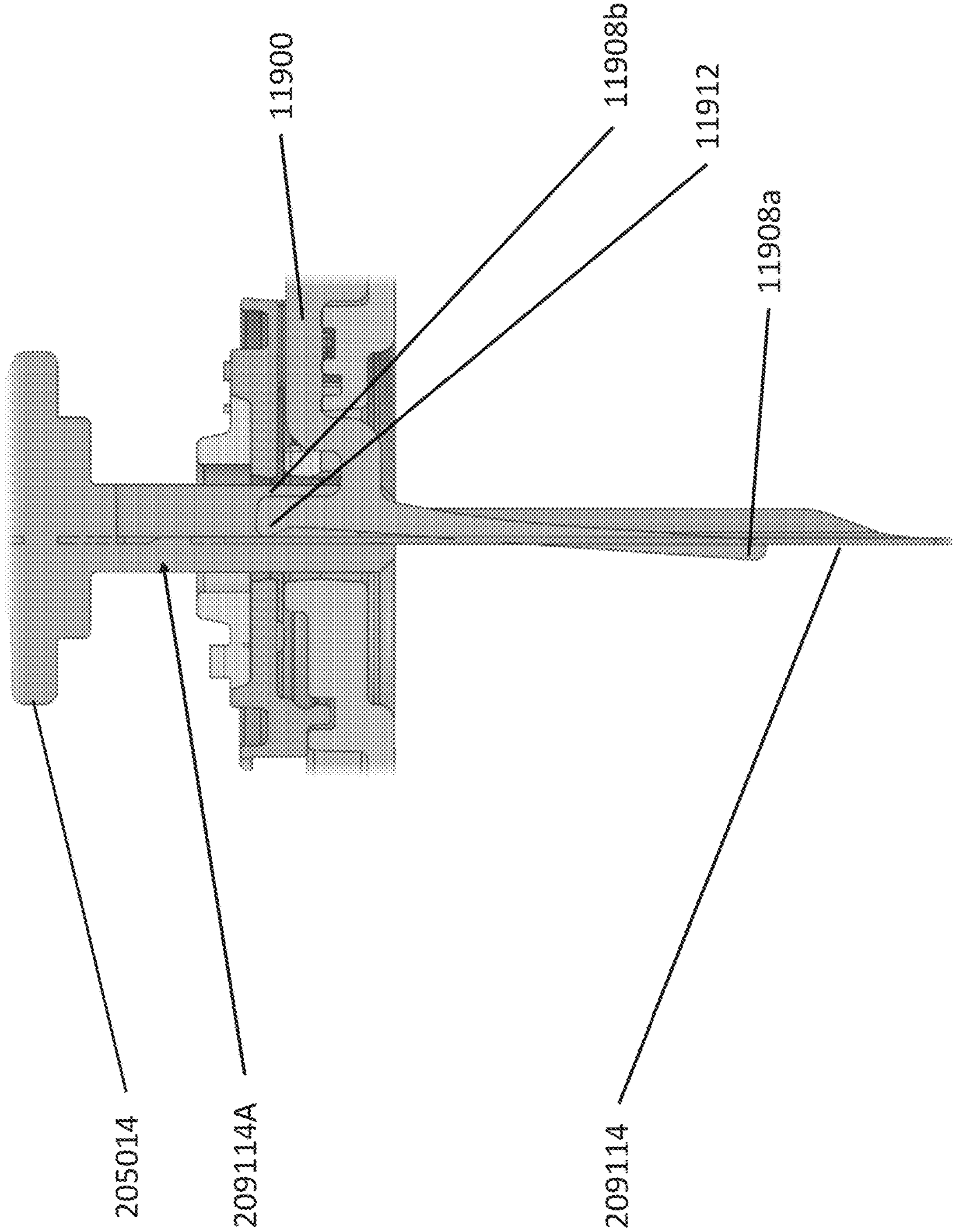
FIG. 38C is a side cross-sectional view of a sharp hub, sharp, and sensor, with the sensor in a biased position, in accordance with the disclosed subject matter.
Figure 38D:
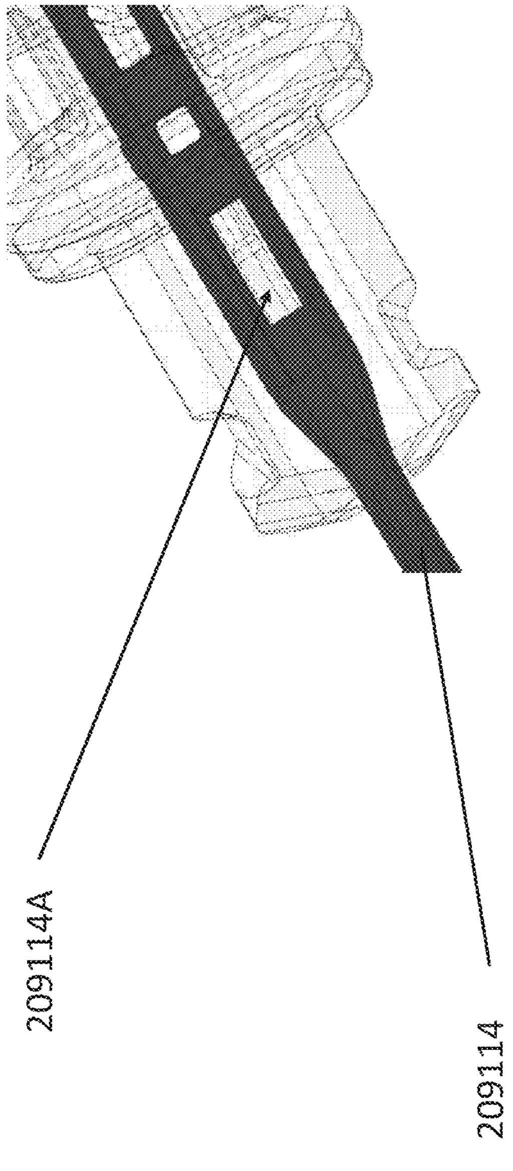
FIG. 38D is a closeup of a portion of a sharp in accordance with the disclosed subject matter.

FIGS. 38B-38D illustrates an exemplary sharp hub 205014 and sharp 209114 configured to not bias the sensor 11900 prior to delivery, for example, during shipping and storage (FIG. 15B) and bias the sensor 11900 during delivery of the sensor (FIG. 38C). By storing and shipping the sensor in the unbiased (relaxed or unstressed) position, the sensor can have increased shelf life and lower overall stress. Furthermore, by storing and shipping the sensor in the unbiased position, stress relaxation over shelf life can be reduced and therefore loss in bias force due to stress relaxation can be limited. Accordingly, bias forces during delivery of the sensor can more predictable and biasing during delivery can be as designed. The sharp 209114 can include a window 209114A. Prior to use, window 209114A can be aligned with protrusion 11912 on top end 11908*b* of the sensor 11900, and protrusion 11912 can extend through window 209114. In such a configuration, bottom end 11908*a* is not biased toward the sharp, and accordingly, sensor 11900 can be in a relaxed state. During firing, needle carrier 201102 can be partially retracted, thereby pulling sharp 209114 into a partially retracted position. Partial retraction can occur as the sheath 20704 initially moves proximally relative the sensor carrier 20710 during firing. Each sharp carrier lock arm 20710K of the sensor carrier 20710 (see FIG. 9D) can extend radially outward as the rib 20710M of the retention arm 20710L engages a respective slot 20704Q of sheath 20704 (see FIG. 8M) which can allow sharp carrier retention feature 20710L to clear the pre-partial retraction retention face 201102A and engage the post-partial retraction retention face 201102B of the sharp carrier 201102 (see FIG. 10C). In the partially retracted position, window 209114A no longer receives protrusion 11912, and sharp 209114 engages protrusion 11912 to thereby biases the bottom end 11908*a* toward the sharp 209114 and into a proper position for delivery, as described above.

Embodiments disclosed herein include:

D. A sensor control device that includes an electronics housing including a shell that defines a first aperture and a mount that defines a second aperture alignable with the first aperture when the shell is coupled to the mount, a seal overmolded onto the mount at the second aperture and comprising a first seal element overmolded onto a pedestal protruding from an inner surface of the mount, and a second seal element interconnected with the first seal element and overmolded onto a bottom of the mount, a sensor arranged within the electronics housing and having a tail extending through the second aperture and past the bottom of the mount, and a sharp that extends through the first and second apertures and past the bottom of the electronics housing.

E. An assembly that includes a sensor applicator, a sensor control device positioned within the sensor applicator and including an electronics housing including a shell that defines a first aperture and a mount that defines a second aperture alignable with the first aperture when the shell is mated to the mount, a seal overmolded onto the mount at the second aperture and comprising a first seal element overmolded onto a pedestal protruding from an inner surface of the mount, and a second seal element interconnected with the first seal element and overmolded onto a bottom of the mount, a sensor arranged within the electronics housing and having a tail extending through the second aperture and past the bottom of the mount, and a sharp that extends through the first and second apertures and past the bottom of the electronics housing. The assembly further including a sensor cap removably coupled to the sensor control device at the bottom of the mount and defining a sealed inner chamber that receives the tail and the sharp, and an applicator cap coupled to the sensor applicator.

Each of embodiments D and E may have one or more of the following additional elements in any combination: Element 1: wherein the mount comprises a first injection molded part molded in a first shot, and the seal comprises a second injection molded part overmolded onto the first injection molded part in a second shot. Element 2: further comprising a sharp hub that carries the sharp and sealingly engages the first seal element, and a sensor cap removably coupled to the sharp hub at the bottom of the mount and sealingly engaging the second seal element, wherein the sensor cap defines an inner chamber that receives the tail and the sharp. Element 3: wherein the sharp hub provides a mating member that extends past the bottom of the mount and the sensor cap is removably coupled to the mating member. Element 4: further comprising one or more pockets defined on the bottom of the mount at the second aperture, and one or more projections defined on an end of the sensor cap and receivable within the one or more pockets when the sensor cap is coupled to the sharp hub. Element 5: further comprising a collar positioned within the electronics housing and defining a central aperture that receives and sealingly engages the first seal element in a radial direction. Element 6: further comprising a channel defined on the inner surface of the mount and circumscribing the pedestal, an annular lip defined on an underside of the collar and matable with the channel, and an adhesive provided in the channel to secure and seal the collar to the mount at the channel. Element 7: further comprising a groove defined through the annular lip to accommodate a portion of the sensor extending laterally within the mount, wherein the adhesive seals about the sensor at the groove. Element 8: further comprising a collar channel defined on an upper surface of the collar, an annular ridge defined on an inner surface of the shell and matable with the collar channel, and an adhesive provided in the collar channel to secure and seal the shell to the collar. Element 9: wherein one or both of the first and second seal elements define at least a portion of the second aperture. Element 10: wherein the first seal element extends at least partially through the first aperture when the shell is coupled to the mount.

Element 11: wherein the sensor control device further includes a sharp hub that carries the sharp and sealingly engages the first seal element, and wherein the sensor cap is removably coupled to the sharp hub at the bottom of the mount and sealingly engages the second seal element. Element 12: wherein the sensor control device further includes one or more pockets defined on the bottom of the mount at the second aperture, and one or more projections defined on an end of the sensor cap and receivable within the one or more pockets when the sensor cap is coupled to the sharp hub. Element 13: wherein the sensor control device further includes a collar positioned within the electronics housing and defining a central aperture that receives and sealingly engages the first seal element in a radial direction. Element 14: wherein the sensor control device further includes a channel defined on the inner surface of the mount and circumscribing the pedestal, an annular lip defined on an underside of the collar and matable with the channel, and an adhesive provided in the channel to secure and seal the collar to the mount at the channel. Element 15: wherein the sensor control device further includes a groove defined through the annular lip to accommodate a portion of the sensor extending laterally within the mount, and wherein the adhesive seals about the sensor at the groove. Element 16: wherein the sensor control device further includes a collar channel defined on an upper surface of the collar, an annular ridge defined on an inner surface of the shell and matable with the collar channel, and an adhesive provided in the collar channel to secure and seal the shell to the collar. Element 17: wherein one or both of the first and second seal elements define at least a portion of the second aperture. Element 18: wherein the first seal element extends at least partially through the first aperture.

By way of non-limiting example, exemplary combinations applicable to D and E include: Element 2 with Element 3; Element 2 with Element 4; Element 5 with Element 6; Element 6 with Element 7; Element 5 with Element 8; Element 11 with Element 12; Element 13 with Element 14; Element 14 with Element 15; and Element 13 with Element 16.

Exemplary Firing Mechanism of One-Piece and Two-Piece Applicators

FIGS. 39A-39F illustrate example details of embodiments of the internal device mechanics of "firing" the applicator 216 to apply sensor control device 222 to a user and including retracting sharp 1030 safely back into used applicator 216. All together, these drawings represent an example sequence of driving sharp 1030 (supporting a sensor coupled to sensor control device 222) into the skin of a user, withdrawing the sharp while leaving the sensor behind in operative contact with interstitial fluid of the user, and adhering the sensor control device to the skin of the user with an adhesive. Modification of such activity for use with the alternative applicator assembly embodiments and components can be appreciated in reference to the same by those with skill in the art. Moreover, applicator 216 may be a sensor applicator having one-piece architecture or a two-piece architecture as disclosed herein.

Figure 39A:
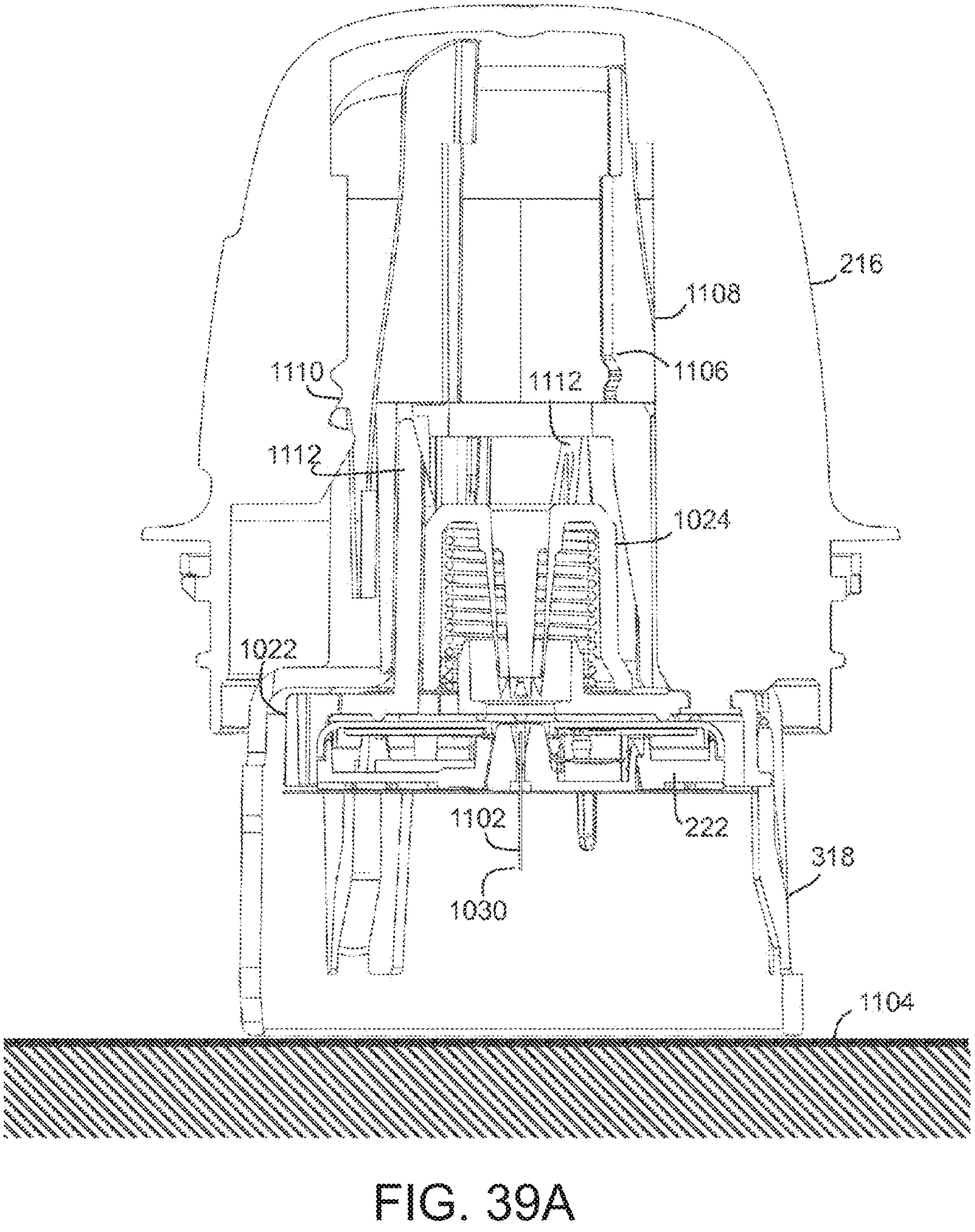
FIGS. 39A-39F illustrate cross-sectional views depicting an example embodiment of an applicator during a stage of deployment.

Turning now to FIG. 39A, a sensor 1102 is supported within sharp 1030, just above the skin 1104 of the user. Rails 1106 (optionally three of them) of an upper guide section 1108 may be provided to control applicator 216 motion relative to sheath 318. The sheath 318 is held by detent features 1110 within the applicator 216 such that appropriate downward force along the longitudinal axis of the applicator 216 will cause the resistance provided by the detent features 1110 to be overcome so that sharp 1030 and sensor control device 222 can translate along the longitudinal axis into (and onto) skin 1104 of the user. In addition, catch arms 1112 of sensor carrier 1022 engage the sharp retraction assembly 1024 to maintain the sharp 1030 in a position relative to the sensor control device 222.

Figure 39B:
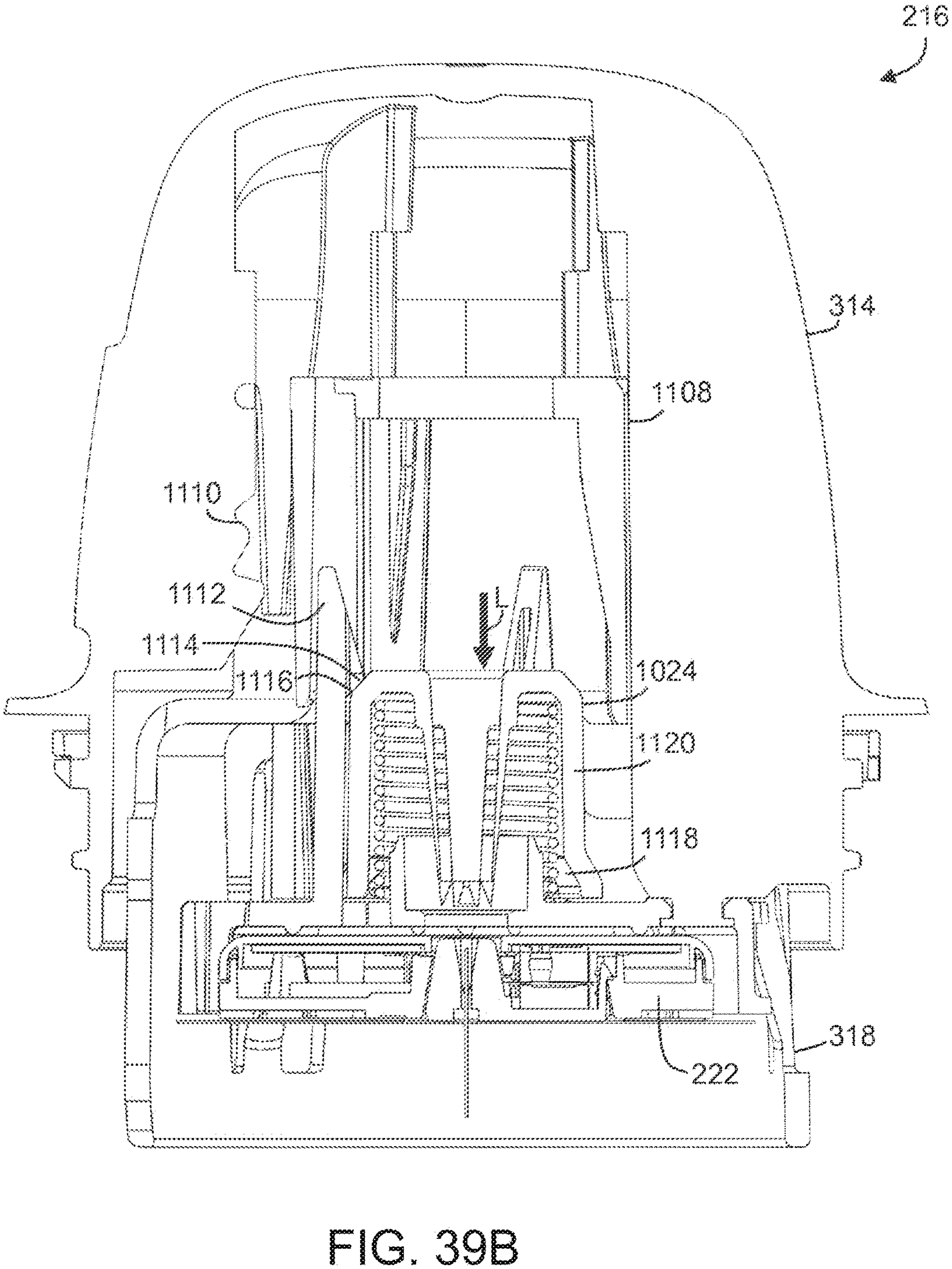

In FIG. 39B, user force is applied to overcome or override detent features 1110 and sheath 318 collapses into housing 314 driving the sensor control device 222 (with associated parts) to translate down as indicated by the arrow L along the longitudinal axis. An inner diameter of the upper guide section 1108 of the sheath 318 constrains the position of carrier arms 1112 through the full stroke of the sensor/sharp insertion process. The retention of the stop surfaces 1114 of carrier arms 1112 against the complimentary faces 1116 of the sharp retraction assembly 1024 maintains the position of the members with return spring 1118 fully energized.

Figure 39C:
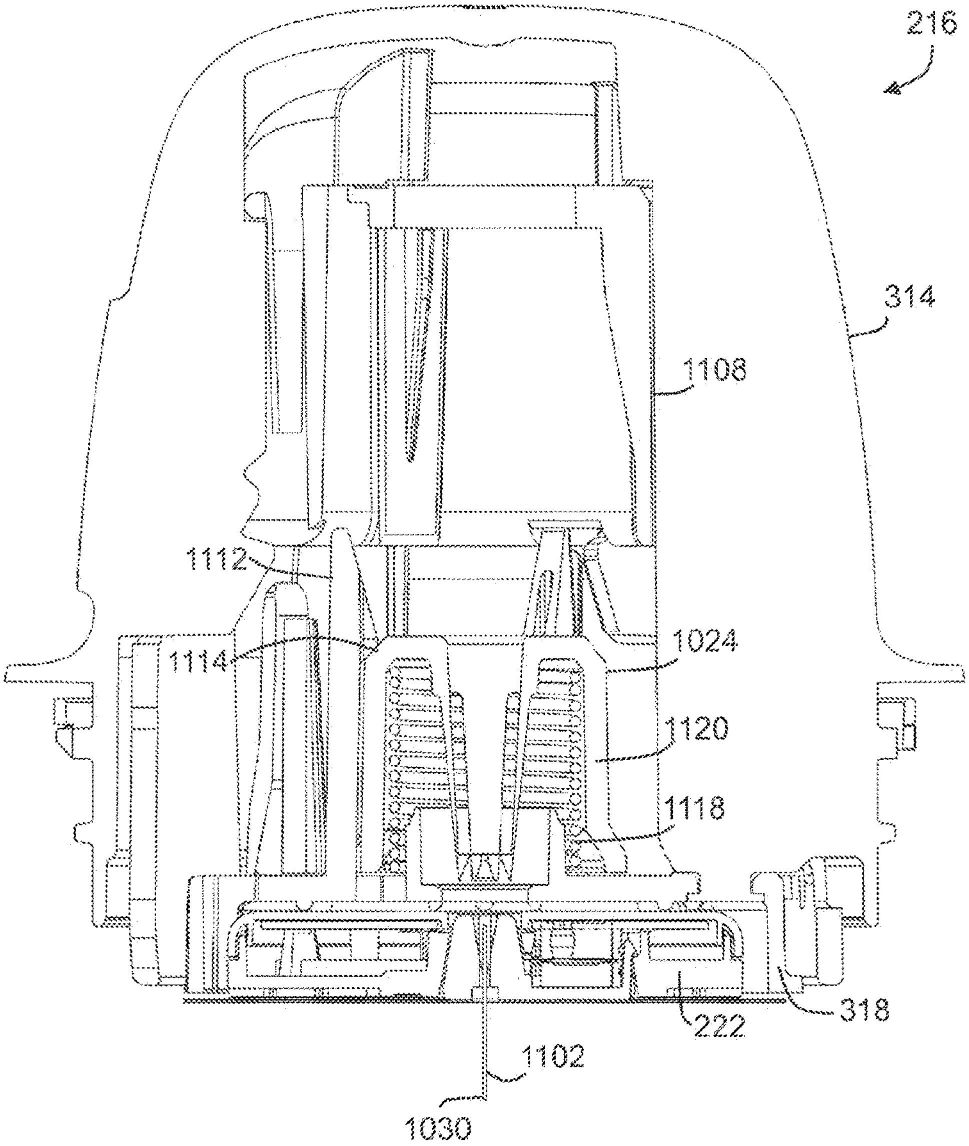
Figure 39D:
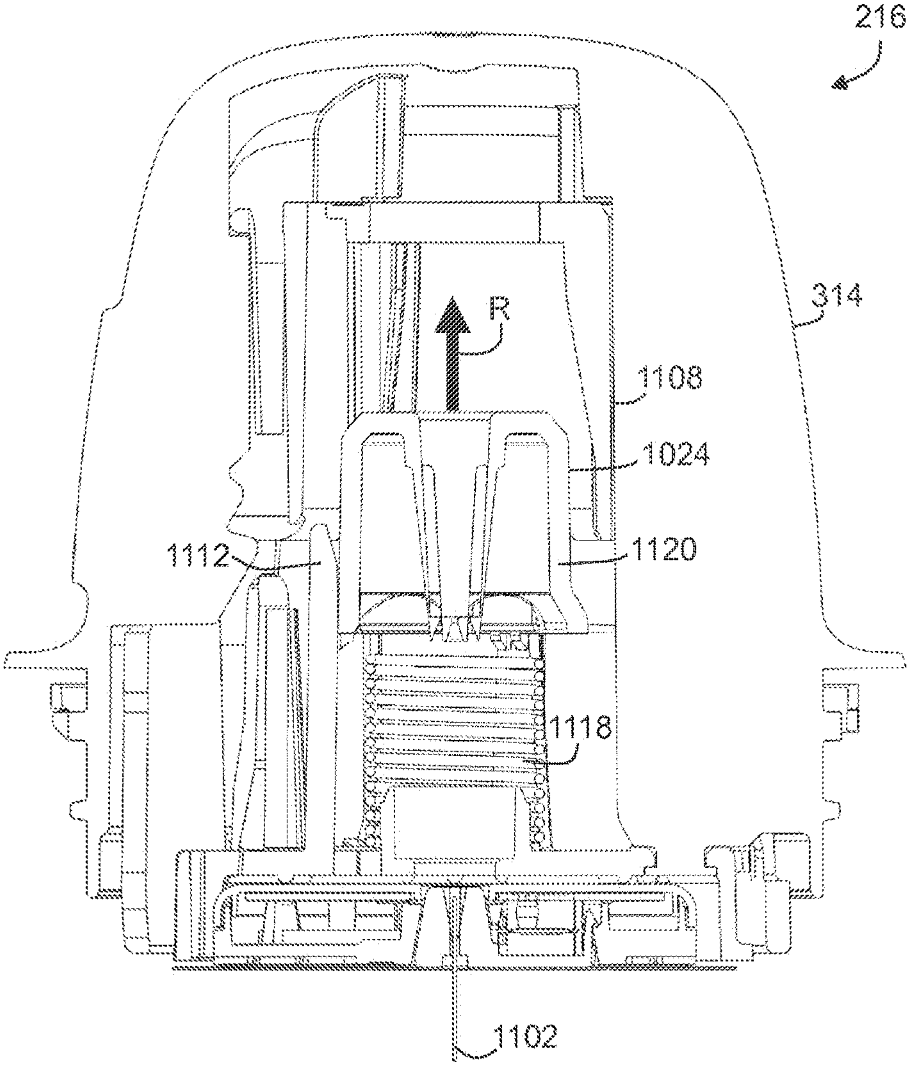

In FIG. 39C, sensor 1102 and sharp 1030 have reached full insertion depth. In so doing, the carrier arms 1112 clear the upper guide section 1108 inner diameter. Then, the compressed force of the coil return spring 1118 drives angled stop surfaces 1114 radially outward, releasing force to drive the sharp carrier 1102 of the sharp retraction assembly 1024 to pull the (slotted or otherwise configured) sharp 1030 out of the user and off of the sensor 1102 as indicated by the arrow R in FIG. 39D.

Figure 39E:
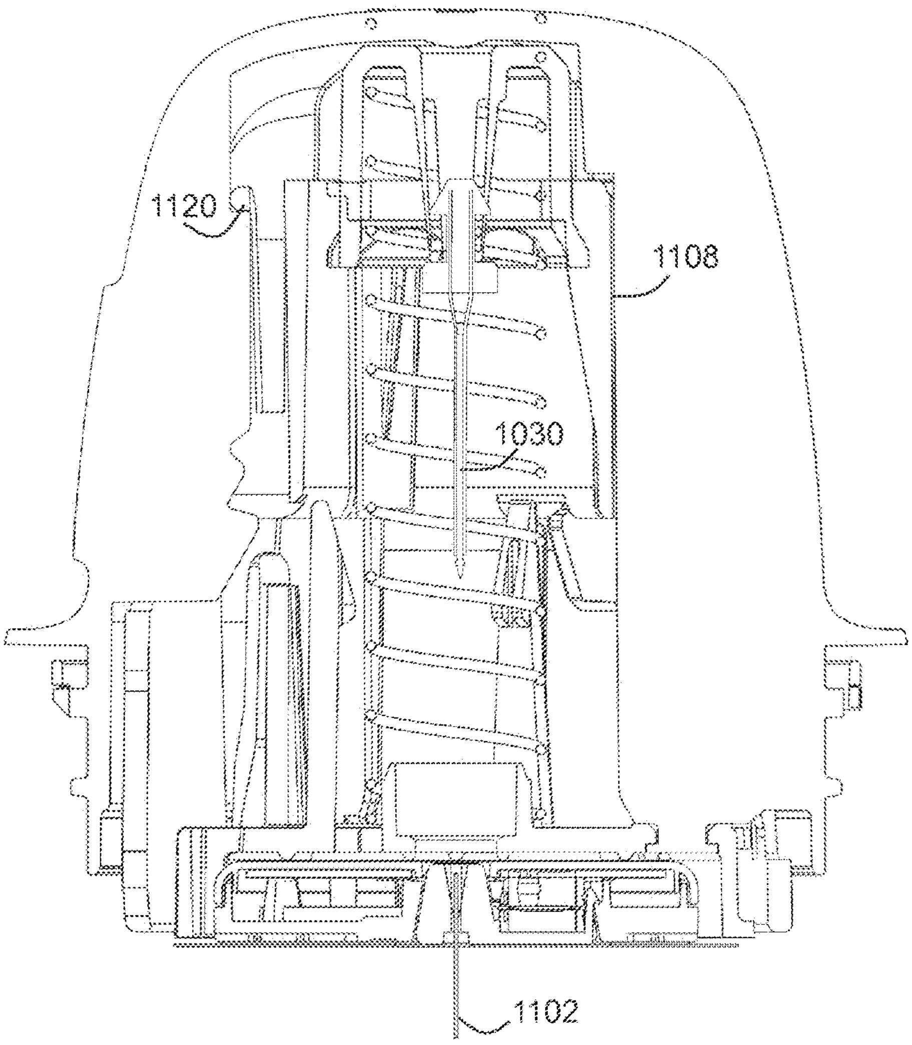
Figure 39F:
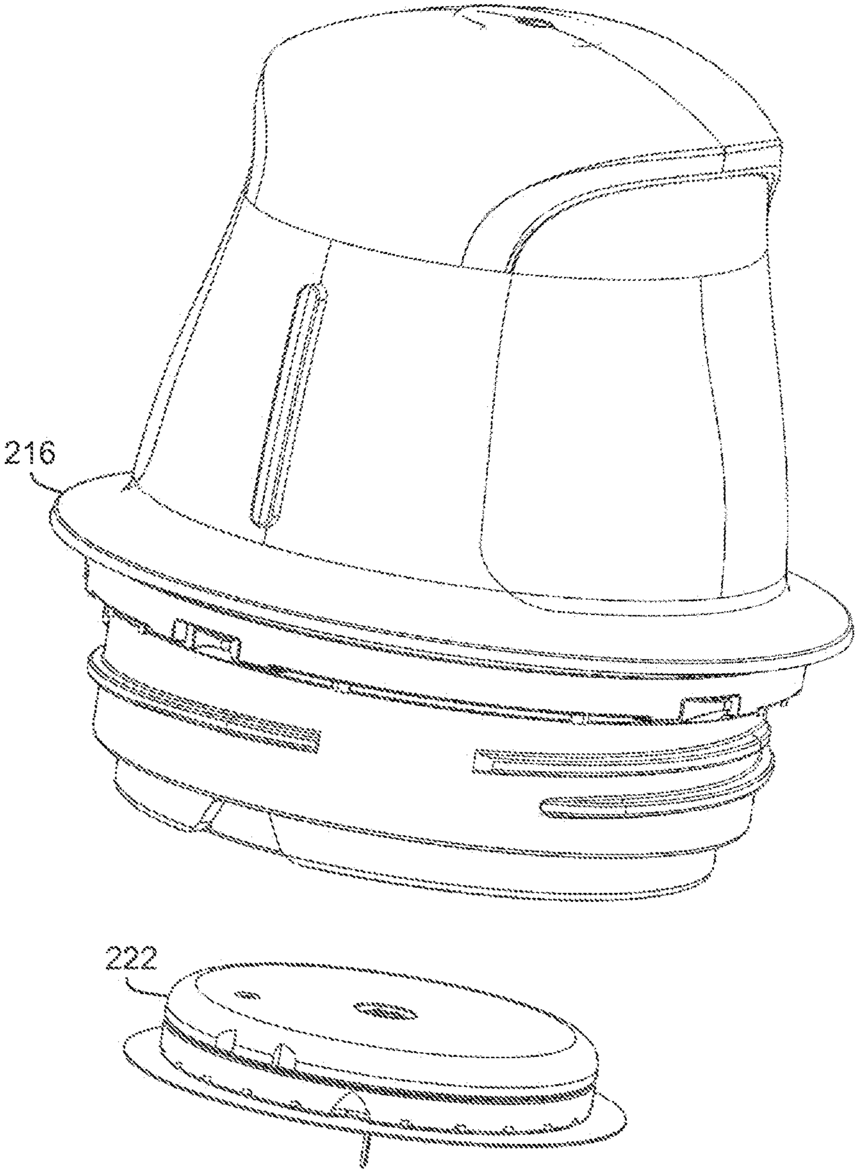

With the sharp 1030 fully retracted as shown in FIG. 39E, the upper guide section 1108 of the sheath 318 is set with a final locking feature 1120. As shown in FIG. 39F, the spent applicator assembly 216 is removed from the insertion site, leaving behind the sensor control device 222, and with the sharp 1030 secured safely inside the applicator assembly 216. The spent applicator assembly 216 is now ready for disposal.

Operation of the applicator 216 when applying the sensor control device 222 is designed to provide the user with a sensation that both the insertion and retraction of the sharp 1030 is performed automatically by the internal mechanisms of the applicator 216. In other words, the present invention avoids the user experiencing the sensation that he is manually driving the sharp 1030 into his skin. Thus, once the user applies sufficient force to overcome the resistance from the detent features of the applicator 216, the resulting actions of the applicator 216 are perceived to be an automated response to the applicator being "triggered." The user does not perceive that he is supplying additional force to drive the sharp 1030 to pierce his skin despite that all the driving force is provided by the user and no additional biasing/driving means are used to insert the sharp 1030. As detailed above in FIG. 39C, the retraction of the sharp 1030 is automated by the coil return spring 1118 of the applicator 216.

With respect to any of the applicator embodiments described herein, as well as any of the components thereof, including but not limited to the sharp, sharp module and sensor module embodiments, those of skill in the art will understand that said embodiments can be dimensioned and configured for use with sensors configured to sense an analyte level in a bodily fluid in the epidermis, dermis, or subcutaneous tissue of a subject. In some embodiments, for example, sharps and distal portions of analyte sensors disclosed herein can both be dimensioned and configured to be positioned at a particular end-depth (i.e., the furthest point of penetration in a tissue or layer of the subject's body, e.g., in the epidermis, dermis, or subcutaneous tissue). With respect to some applicator embodiments, those of skill in the art will appreciate that certain embodiments of sharps can be dimensioned and configured to be positioned at a different end-depth in the subject's body relative to the final end-depth of the analyte sensor. In some embodiments, for example, a sharp can be positioned at a first end-depth in the subject's epidermis prior to retraction, while a distal portion of an analyte sensor can be positioned at a second end-depth in the subject's dermis. In other embodiments, a sharp can be positioned at a first end-depth in the subject's dermis prior to retraction, while a distal portion of an analyte sensor can be positioned at a second end-depth in the subject's subcutaneous tissue. In still other embodiments, a sharp can be positioned at a first end-depth prior to retraction and the analyte sensor can be positioned at a second end-depth, wherein the first end-depth and second end-depths are both in the same layer or tissue of the subject's body.

Additionally, with respect to any of the applicator embodiments described herein, those of skill in the art will understand that an analyte sensor, as well as one or more structural components coupled thereto, including but not limited to one or more spring-mechanisms, can be disposed within the applicator in an off-center position relative to one or more axes of the applicator. In some applicator embodiments, for example, an analyte sensor and a spring mechanism can be disposed in a first off-center position relative to an axis of the applicator on a first side of the applicator, and the sensor electronics can be disposed in a second off-center position relative to the axis of the applicator on a second side of the applicator. In other applicator embodiments, the analyte sensor, spring mechanism, and sensor electronics can be disposed in an off-center position relative to an axis of the applicator on the same side. Those of skill in the art will appreciate that other permutations and configurations in which any or all of the analyte sensor, spring mechanism, sensor electronics, and other components of the applicator are disposed in a centered or off-centered position relative to one or more axes of the applicator are possible and fully within the scope of the present disclosure.

A number of deflectable structures are described herein, including but not limited to deflectable detent snaps 1402, deflectable locking arms 1412, sharp carrier lock arms 1524, sharp retention arms 1618, and module snaps 2202. These deflectable structures are composed of a resilient material such as plastic or metal (or others) and operate in a manner well known to those of ordinary skill in the art. The deflectable structures each has a resting state or position that the resilient material is biased towards. If a force is applied that causes the structure to deflect or move from this resting state or position, then the bias of the resilient material will cause the structure to return to the resting state or position once the force is removed (or lessened). In many instances these structures are configured as arms with detents, or snaps, but other structures or configurations can be used that retain the same characteristics of deflectability and ability to return to a resting position, including but not limited to a leg, a clip, a catch, an abutment on a deflectable member, and the like.

Additional details of suitable devices, systems, methods, components and the operation thereof along with related features are set forth in International Publication No. WO2018/136898 to Rao et. al., International Publication No. WO2019/236850 to Thomas et. al., International Publication No. WO2019/236859 to Thomas et. al., International Publication No. WO2019/236876 to Thomas et. al., and U.S. Patent Publication No. 2020/0196919, filed Jun. 6, 2019, each of which is incorporated by reference in its entirety herein. Further details regarding embodiments of applicators, their components, and variants thereof, are described in U.S. Patent Publication Nos. 2013/0150691, 2016/0331283, and 2018/0235520, all of which are incorporated by reference herein in their entireties and for all purposes. Further details regarding embodiments of sharp modules, sharps, their components, and variants thereof, are described in U.S. Patent Publication No. 2014/0171771, which is incorporated by reference herein in its entirety and for all purposes.

Exemplary embodiments of the devices described herein are set out in the following numbered clauses.

Clause 1. An analyte measurement device, comprising:
- an electronics housing including:
  - a shell having an upper surface with a first aperture defined therein;
  - a mount mated to the shell and having an underside with a second aperture defined therein aligned with the first aperture;
  - a collar disposed between the shell and the mount and including:

a third aperture aligned with the first aperture and the second aperture, and a plurality of tabs on an outer periphery of the collar;

a circuit board disposed within the electronics housing and including a plurality of electronic modules, wherein the circuit board is mounted within the electronics housing on the plurality of tabs on the outer periphery; and an analyte sensor including a tail portion extending through an aperture in the mount and configured to measure an analyte level, a flag portion including a plurality of electrical contacts coupled with the circuit board, and a neck portion interconnecting the tail portion and the flag portion.

Clause 2. The device of clause 1, wherein the circuit board includes a first portion foldable over a second portion, the second portion mounted on the mount and the first portion mounted on the plurality of tabs on the outer periphery.

Clause 3. The device of clause 1 or 2, wherein the plurality of tabs includes three tabs.

Clause 4. The device of any of clauses 1 to 3, wherein the collar further includes:

a collar channel on an upper surface mated with an annular ridge defined on an inner surface of the shell, an annular lip on a bottom surface received within a channel defined on an inner surface of the mount, and a seal on the upper surface of the collar.

Clause 5. The device of clause 4, wherein the seal comprises an elastomeric seal.

Clause 6. The device of clause 4 or 5, further comprising a sharp hub including a sharp extending through the first, second, and third apertures and a mating surface mated with the seal.

Clause 7. The device of any of clauses 4-6, wherein the mating surface includes a ledge.

Clause 8. The device of any of clauses 1 to 7, whether the circuit board further includes a battery.

Clause 9. The device of clause 8, wherein the circuit board further includes a battery aperture to position the battery and to eliminate electrical interference between the battery and the circuit board.

Clause 10. An assembly for delivery of an analyte sensor comprising:

a sensor control device including:

an electronics housing including a shell and a mount mounted to the shell;

a circuit board disposed within the electronics housing and including a plurality of electronic modules;

an analyte sensor including a tail portion extending through an aperture in the mount and configured to measure an analyte level, a flag portion including a plurality of electrical contacts coupled with the circuit board, and a neck portion interconnecting the tail portion and the flag portion; and a sensor cap having a first end, a second end, and an inner chamber, wherein the inner chamber receives the tail portion of the analyte sensor and wherein the first end is removably coupled to the mount to seal the inner chamber; and an applicator for delivery of the analyte sensor including:

a housing including a sensor carrier configured to secure the sensor control device within an interior of the applicator;

an applicator cap removably coupled to the housing to seal the interior of the applicator and including:

a desiccant including a plurality of retention snaps, one or more retention clips engaged to the plurality of retention snaps to retain the desiccant in the cap and to limit rotation of the desiccant, and a cap post engaged with an engagement feature on the second end of the sensor cap.

Clause 11. The assembly of clause 10, wherein the desiccant includes an internal bore and the engagement feature on the second end of the sensor cap passes through the internal bore of desiccant and engages the applicator cap.

Clause 12. The assembly of clause 10 or 11, wherein the desiccant is substantially cylindrical in shape.

Clause 13. The assembly of any of clauses 10 to 12, wherein the first end is removably coupled to the mount to seal the inner chamber Clause 14. The assembly of any of clauses 10 to 13, wherein the sensor control device further comprises an elastomeric plug arranged at the second end of the sensor cap.

Clause 15. The assembly of clause 14, wherein the elastomeric plug includes a seal bead in an interference fit arrangement with the sensor cap.

Clause 16. The assembly of clause 14 or 15, wherein the elastomeric plug defines the engagement feature of the sensor cap.

Clause 17. The assembly of any of clauses 10 to 16, wherein the applicator for delivery of the analyte sensor further includes:

a sharp carrier coupled to a sharp extending through the aperture in the mount, the sharp configured to penetrate a user's skin to position the analyte sensor into contact with bodily fluid;

a sensor carrier to releasably hold the sensor control device within the interior space; and a spring biasing the sharp carrier to move upward within the housing.

Clause 18. The assembly of clause 17, wherein the spring includes a spring having a spring constant of about 0.12.

Clause 19. The assembly of clause 17 or 18, wherein the spring includes a spring having a wire diameter of about 0.65 millimeters, an inner diameter of about 9.6 millimeter, and an outer diameter of about 11.1 millimeters Clause 20. The assembly of any of clauses 17 to 19, wherein the spring includes a spring having a maximum solid strength of about 11 millimeters.

In summary, an analyte measurement device including an electronics housing including a shell having an upper surface with a first aperture defined therein; a mount mated to the shell and having an underside with a second aperture defined therein aligned with the first aperture; a collar disposed between the shell and the mount and including: a third aperture aligned with the first aperture and the second aperture, and a plurality of tabs on an outer periphery of the collar; a circuit board disposed within the electronics housing and including a plurality of electronic modules, wherein the circuit board is mounted within the electronics housing on the plurality of tabs on the outer periphery; and an analyte sensor including a tail portion extending through the first aperture and the second aperture and configured to measure an analyte level and a flag portion including a plurality of electrical contacts coupled with the circuit board, and a neck portion interconnecting the tail portion and the flag portion. An assembly for delivery of an analyte sensor is also disclosed.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. Thus, the foregoing description of specific embodiments of the disclosed subject matter has been presented for purposes of illustration and description. It is explicitly acknowledged that express recitation of every possible combination and substitution is overly burdensome, especially given that the permissibility of each and every such combination and substitution will be readily recognized by those of ordinary skill in the art.

While the embodiments are susceptible to various modifications and alternative forms, specific examples thereof have been shown in the drawings and are herein described in detail. It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents. Furthermore, any features, functions, steps, or elements of the embodiments may be recited in or added to the claims, as well as negative limitations that define the inventive scope of the claims by features, functions, steps, or elements that are not within that scope.

The invention claimed is:

1. An analyte measurement device, comprising:

an electronics housing including:

a shell having an upper surface with a first aperture defined therein;

a mount mated to the shell and having an underside with a second aperture defined therein aligned with the first aperture;

a collar disposed between the shell and the mount and including:

a third aperture aligned with the first aperture and the second aperture, and a plurality of tabs on an outermost periphery of the collar, wherein the plurality of tabs extend radially outward from the outermost periphery of the collar to define a shelf for a circuit board;

the circuit board disposed within the electronics housing and including a plurality of electronic modules, wherein the circuit board is mounted within the electronics housing on the shelf defined by the plurality of tabs on the outermost periphery of the collar; and an analyte sensor including a tail portion extending through the second aperture in the mount and configured to sense an analyte level, a flag portion including a plurality of electrical contacts coupled with the circuit board, and a neck portion interconnecting the tail portion and the flag portion.

2. The device of claim 1, wherein the circuit board includes a first portion foldable over a second portion, the second portion mounted on the mount and the first portion mounted on the shelf created by the plurality of tabs on the outermost periphery of the collar.

3. The device of claim 2, wherein the circuit board comprises a flexible printed circuit board.

4. The device of claim 2, wherein the first portion of the circuit board is positioned beneath the plurality of tabs and the second portion of the circuit board is folded over the first portion and supported by the plurality of tabs.

5. The device of claim 1, wherein the plurality of tabs includes three tabs.

6. The device of claim 1, wherein the collar further includes:

a collar channel on an upper surface mated with an annular ridge defined on an inner surface of the shell, an annular lip on a bottom surface received within a channel defined on an inner surface of the mount, and a seal on the upper surface of the collar.

7. The device of claim 6, wherein the seal comprises an elastomeric seal.

8. The device of claim 6, further comprising a sharp hub including a sharp extending through the first, second, and third apertures and a mating surface mated with the seal.

9. The device of claim 8, wherein the mating surface includes a ledge.

10. The device of claim 1, wherein the circuit board further includes a battery.

11. The device of claim 10, wherein the circuit board further includes a battery aperture to position the battery and to eliminate electrical interference between the battery and the circuit board.

12. The device of claim 1, wherein the plurality of tabs are equally spaced along the outermost periphery of the collar.

13. The device of claim 1, wherein the plurality of tabs are of different sizes.

14. The device of claim 13, wherein two of the plurality of tabs have a first length along the outermost periphery of the collar and a third tab has a second length different from the first length.

15. The device of claim 1, wherein the plurality of tabs extend radially outward from a top surface of the collar.

16. The device of claim 1, wherein the plurality of tabs extend radially outward from a bottom surface of the collar.

17. The device of claim 1, wherein the plurality of tabs extend radially outward from an intermediate location between a top surface and a bottom surface of the collar.

18. The device of claim 1, wherein the circuit board includes one or more circuit board tabs configured to correspond with and mate with the plurality of tabs on the outermost periphery of the collar.

19. The device of claim 18, wherein the one or more circuit board tabs are fixed to the plurality of tabs on the outermost periphery of the collar.

20. The device of claim 19, wherein the one or more circuit board tabs are configured to mate with the plurality of tabs on the outermost periphery of the collar.

* * * * *